US007470797B2

(12) United States Patent
Salvati et al.

(10) Patent No.: US 7,470,797 B2

(45) Date of Patent: Dec. 30, 2008

(54) FUSED HETEROCYCLIC IMIDO AND AMIDO COMPOUNDS

(75) Inventors: Mark E. Salvati, Lawrenceville, NJ (US); Raj N. Misra, Hopewell, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 449 days.

(21) Appl. No.: 10/917,031

(22) Filed: Aug. 12, 2004

(65) Prior Publication Data

US 2006/0223832 A1 Oct. 5, 2006

Related U.S. Application Data

(60) Division of application No. 10/322,077, filed on Dec. 18, 2002, now abandoned, which is a continuation-in-part of application No. 10/025,116, filed on Dec. 19, 2001, now abandoned, which is a continuation-in-part of application No. 09/885,381, filed on Jun. 20, 2001, now abandoned, and a continuation-in-part of application No. 09/885,827, filed on Jun. 20, 2001, now Pat. No. 6,960,474.

(51) Int. Cl.
*C07D 313/06* (2006.01)

(52) U.S. Cl. ...................................................... 549/355

(58) Field of Classification Search .................. 549/355
See application file for complete search history.

(56) References Cited

U.S. PATENT DOCUMENTS

| | | | | |
|---|---|---|---|---|
| 3,215,597 | A * | 11/1965 | Stevenson | 514/411 |
| 3,261,845 | A | 7/1966 | Bockstahler | |
| 3,320,270 | A | 5/1967 | Grogan et al. | |
| 3,343,940 | A | 9/1967 | Popoff et al. | |
| 3,428,538 | A | 2/1969 | Scheiner | |
| 3,717,634 | A | 2/1973 | Wu et al. | |
| 3,821,232 | A | 6/1974 | Redmore | |
| 3,906,102 | A | 9/1975 | Tottori et al. | |
| 3,907,801 | A | 9/1975 | Wu et al. | |
| 3,923,490 | A | 12/1975 | Redmore | |
| 3,925,554 | A | 12/1975 | Tottori et al. | |
| 3,965,264 | A | 6/1976 | Redmore | |
| 3,997,293 | A | 12/1976 | Redmore | |
| 3,998,833 | A | 12/1976 | Redmore | |
| 4,089,650 | A | 5/1978 | Redmore | |
| 4,092,413 | A | 5/1978 | Arth et al. | |
| 4,097,578 | A | 6/1978 | Perronnet | |
| 4,191,775 | A | 3/1980 | Glen | |
| 4,234,736 | A | 11/1980 | Bernauer et al. | |
| 4,239,776 | A | 12/1980 | Glen et al. | |
| 4,305,944 | A | 12/1981 | Temple, Jr. et al. | |
| 4,367,335 | A | 1/1983 | Temple, Jr. et al. | |
| 4,397,857 | A | 8/1983 | Vincent et al. | |
| 4,472,382 | A | 9/1984 | Labrie et al. | |
| 4,473,393 | A | 9/1984 | Nagpal | |
| 4,476,184 | A | 10/1984 | Lubowitz et al. | |
| 4,507,303 | A | 3/1985 | Ishizumi et al. | |
| 4,533,737 | A | 8/1985 | Ryang | |
| 4,536,559 | A | 8/1985 | Lubowitz et al. | |
| 4,543,355 | A | 9/1985 | Ishizumi et al. | |
| 4,562,255 | A | 12/1985 | Freed et al. | |
| 4,582,886 | A | 4/1986 | Ryang | |
| 4,584,364 | A | 4/1986 | Lubowitz et al. | |
| 4,598,072 | A | 7/1986 | Schweikert et al. | |
| 4,656,235 | A | 4/1987 | Tesoro et al. | |
| 4,659,695 | A | 4/1987 | Labrie | |

(Continued)

FOREIGN PATENT DOCUMENTS

AU A-16993-83 1/1984

(Continued)

OTHER PUBLICATIONS

Caplus Abstract of: Some derivatives of 4,5-dichloro-3,6-endooxyhexahydrophthalic acid. Mel'nikov, N.N.; Kraft, V. A.; Zhurnal Obshchei Khimii (1959), 29, 968-71. Accession # 1960:7143.*

(Continued)

*Primary Examiner*—Rebecca L Anderson
*Assistant Examiner*—Robert Havlin
(74) *Attorney, Agent, or Firm*—Gary D. Greenblatt; Anastasia P. Winslow

(57) ABSTRACT

Disclosed are fused cyclic compounds, method of using such compounds in the treatment of nuclear hormone receptor-associated conditions such as cancer and immune disorders, and pharmaceutical compositions containing such compounds of formula

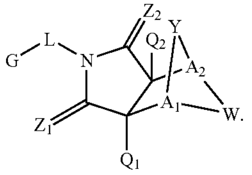

Also disclosed are fused heterocyclic imido and amido compounds of formula

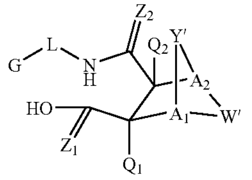

and stereoisomers thereof. The groups G, L, $Z_1$, $Z_2$, $Q_1$, $Q_2$, $A_1$, $A_2$, Y', and W' are defined herein.

11 Claims, No Drawings

U.S. PATENT DOCUMENTS

| | | | | |
|---|---|---|---|---|
| 4,666,885 | A | 5/1987 | Labrie | |
| 4,673,748 | A | 6/1987 | Rock et al. | |
| 4,677,104 | A | 6/1987 | New et al. | |
| 4,739,075 | A | 4/1988 | Odagiri et al. | |
| 4,753,957 | A | 6/1988 | Chan | |
| 4,760,053 | A | 7/1988 | Labrie | |
| 4,775,660 | A | 10/1988 | Labrie et al. | |
| 4,775,661 | A | 10/1988 | Labrie | |
| 4,833,249 | A | 5/1989 | Abou-Gharbia et al. | |
| 4,851,495 | A | 7/1989 | Sheppard et al. | |
| 4,873,256 | A | 10/1989 | Coussediere et al. | |
| 4,892,578 | A | 1/1990 | Chang et al. | |
| 4,892,943 | A | 1/1990 | Abou-Gharbia | |
| 4,944,791 | A | 7/1990 | Schroder et al. | |
| 4,980,481 | A | 12/1990 | Lubowitz et al. | |
| 5,084,472 | A | 1/1992 | Moguilewsky et al. | |
| 5,093,500 | A | 3/1992 | Wang | |
| 5,098,888 | A | 3/1992 | Vincent et al. | |
| 5,104,967 | A | 4/1992 | Sheppard et al. | |
| 5,112,939 | A | 5/1992 | Lubowitz et al. | |
| 5,114,612 | A | 5/1992 | Benicewicz et al. | |
| 5,116,935 | A | 5/1992 | Lubowitz et al. | |
| 5,151,487 | A | 9/1992 | Lubowitz et al. | |
| 5,155,206 | A | 10/1992 | Lubowitz et al. | |
| 5,210,213 | A | 5/1993 | Sheppard et al. | |
| 5,239,046 | A | 8/1993 | Lubowitz et al. | |
| 5,367,083 | A | 11/1994 | Sheppard et al. | |
| 5,399,725 | A | 3/1995 | Poss et al. | |
| 5,403,666 | A | 4/1995 | Lubowitz et al. | |
| 5,434,176 | A | 7/1995 | Claussner et al. | |
| 5,446,120 | A | 8/1995 | Lubowitz et al. | |
| 5,455,115 | A | 10/1995 | Lubowitz et al. | |
| 5,463,076 | A | 10/1995 | Sheppard et al. | |
| 5,482,921 | A | 1/1996 | Secking et al. | |
| 5,512,676 | A | 4/1996 | Sheppard et al. | |
| 5,516,876 | A | 5/1996 | Lubowitz et al. | |
| 5,530,089 | A | 6/1996 | Sheppard et al. | |
| 5,532,372 | A | 7/1996 | Saji et al. | |
| 5,550,107 | A | 8/1996 | Labrie | |
| 5,556,983 | A | 9/1996 | Claussner et al. | |
| 5,573,854 | A | 11/1996 | Sheppard et al. | |
| 5,587,105 | A | 12/1996 | Sheppard et al. | |
| 5,589,497 | A | 12/1996 | Claussner et al. | |
| 5,594,089 | A | 1/1997 | Lubowitz et al. | |
| 5,595,985 | A | 1/1997 | Labrie | |
| 5,610,317 | A | 3/1997 | Lubowitz et al. | |
| 5,627,201 | A | 5/1997 | Gaillard-Kelly et al. | |
| 5,643,855 | A | 7/1997 | Kilama | |
| 5,645,925 | A | 7/1997 | Sheppard et al. | |
| 5,693,741 | A | 12/1997 | Sheppard et al. | |
| 5,714,566 | A | 2/1998 | Lubowitz et al. | |
| 5,750,553 | A | 5/1998 | Claussner et al. | |
| 5,780,583 | A | 7/1998 | Lubowitz et al. | |
| 5,817,649 | A | 10/1998 | Labrie | |
| 5,817,744 | A | 10/1998 | Sheppard et al. | |
| RE35,956 | E | 11/1998 | Gaillard-Kelly et al. | |
| 5,929,146 | A | 7/1999 | Amos et al. | |
| 6,017,924 | A | 1/2000 | Edwards et al. | |
| 6,020,327 | A | 2/2000 | Messenger | |
| 6,054,487 | A | 4/2000 | Sekut et al. | |
| 6,071,957 | A | 6/2000 | Miller et al. | |
| 6,090,837 | A | 7/2000 | Lavielle et al. | |
| 6,124,460 | A | 9/2000 | Tomiyama et al. | |
| 6,162,444 | A | 12/2000 | Dubois | |
| 6,200,573 | B1 | 3/2001 | Locke | |
| 6,242,611 | B1 | 6/2001 | Claussner et al. | |
| 6,384,050 | B1 | 5/2002 | Takemura et al. | |
| 6,448,284 | B1 | 9/2002 | Bach et al. | |
| 6,482,861 | B2 | 11/2002 | Miller et al. | |
| 6,573,218 | B1 | 6/2003 | Tsukamoto et al. | |
| 6,638,933 | B2 * | 10/2003 | Gerlach et al. | 514/249 |
| 6,642,230 | B2 * | 11/2003 | Wilde et al. | 514/234.2 |
| 6,653,320 | B2 * | 11/2003 | Hayakawa et al. | 514/300 |
| 6,670,389 | B2 | 12/2003 | Sun et al. | |
| 6,673,810 | B2 * | 1/2004 | Lam et al. | 514/300 |
| 6,673,927 | B2 * | 1/2004 | Gordon et al. | 544/350 |
| 6,686,358 | B2 * | 2/2004 | De Nanteuil et al. | 514/249 |
| 6,686,471 | B2 * | 2/2004 | Chiu et al. | 544/350 |
| 6,696,464 | B2 * | 2/2004 | McClure et al. | 514/303 |
| 6,706,750 | B1 | 3/2004 | Bentley et al. | |
| 6,710,048 | B2 * | 3/2004 | Kuo et al. | 514/252.11 |
| 6,720,334 | B2 * | 4/2004 | Dellaria et al. | 514/303 |
| 6,723,735 | B1 * | 4/2004 | Hallett et al. | 514/303 |
| 6,750,225 | B2 * | 6/2004 | Pinto et al. | 514/303 |
| 6,800,625 | B2 | 10/2004 | Jiang et al. | |
| 6,953,679 | B2 | 10/2005 | Salvati et al. | |
| 6,960,474 | B2 | 11/2005 | Salvati et al. | |
| 7,001,911 | B2 | 2/2006 | Salvati et al. | |
| 2001/0012839 | A1 | 8/2001 | Miller et al. | |
| 2001/0020002 | A1 | 9/2001 | Lederman et al. | |
| 2002/0173445 | A1 | 11/2002 | Salvati et al. | |
| 2003/0181728 | A1 | 9/2003 | Salvati et al. | |
| 2004/0019063 | A1 | 1/2004 | Sun et al. | |
| 2004/0077605 | A1 | 4/2004 | Salvati et al. | |
| 2004/0077606 | A1 | 4/2004 | Salvati et al. | |
| 2004/0087548 | A1 | 5/2004 | Salvati et al. | |
| 2004/0176324 | A1 | 9/2004 | Salvati et al. | |
| 2004/0181064 | A1 | 9/2004 | Sun et al. | |
| 2005/0187273 | A1 | 8/2005 | Salvati et al. | |
| 2005/0192253 | A1 | 9/2005 | Salvati et al. | |
| 2005/0272799 | A1 | 12/2005 | Salvati et al. | |
| 2005/0282813 | A1 | 12/2005 | Salvati et al. | |
| 2006/0020002 | A1 | 1/2006 | Salvati et al. | |

FOREIGN PATENT DOCUMENTS

| | | | |
|---|---|---|---|
| CN | 1050877 | | 4/1991 |
| DE | 2365677 | | 11/1975 |
| DE | 3227055 | A1 | 7/1982 |
| EP | 0001813 | A1 | 10/1978 |
| EP | 0082402 | B1 | 6/1982 |
| EP | 0091596 | A2 | 3/1983 |
| EP | 0051020 | A1 | 8/1984 |
| EP | 0253503 | B1 | 6/1987 |
| EP | 0277476 | A2 | 1/1988 |
| EP | 0436426 | A1 | 12/1990 |
| EP | 0494819 | A1 | 1/1992 |
| EP | 0406119 | B1 | 1/1994 |
| EP | 0 626 384 | | 11/1994 |
| EP | 0678507 | | 10/1995 |
| EP | 1008457 | A1 | 6/2000 |
| FR | 2075751 | | 1/1971 |
| FR | 2329276 | | 11/1975 |
| GB | 1039020 | | 8/1964 |
| GB | 2 133 006 | | 10/1986 |
| GB | 2133066 | B | 10/1986 |
| GB | 2174703 | | 11/1986 |
| GB | 2290296 | | 12/1995 |
| JP | 51088631 | | 8/1976 |
| JP | 53-86035 | | 7/1978 |
| JP | 56-63961 | | 5/1981 |
| JP | 63-170383 | | 7/1988 |
| JP | 64-6258 | | 1/1989 |
| JP | 1-125381 | | 5/1989 |
| JP | 7-144477 | | 6/1995 |
| WO | WO 91/06297 | | 5/1991 |
| WO | WO95/18794 | | 7/1995 |
| WO | WO 96/06093 | | 2/1996 |
| WO | WO96/19458 | | 6/1996 |
| WO | WO 97/21993 | | 6/1997 |
| WO | WO97/49709 | | 12/1997 |
| WO | WO98/16830 | | 4/1998 |
| WO | WO98/ 29495 | | 7/1998 |
| WO | WO98/32439 | | 7/1998 |

| | | |
|---|---|---|
| WO | WO 98/39303 | 9/1998 |
| WO | WO98/49555 | 11/1998 |
| WO | WO99/27365 | 6/1999 |
| WO | WO99/32463 | 7/1999 |
| WO | WO02/00653 | 1/2000 |
| WO | WO00/06525 | 2/2000 |
| WO | WO00/37430 | 6/2000 |
| WO | WO01/07052 | 2/2001 |
| WO | WO01/16108 | 3/2001 |
| WO | WO01/16133 | 3/2001 |
| WO | WO01/16139 | 3/2001 |
| WO | WO01/19831 | 3/2001 |
| WO | WO 01/27622 | 4/2001 |
| WO | WO01/30781 | 5/2001 |
| WO | WO02/00617 | 1/2002 |
| WO | WO02/00653 | 1/2002 |
| WO | WO01/16139 | 3/2002 |
| WO | WO02/24702 | 3/2002 |
| WO | WO 02/067939 | 9/2002 |
| WO | WO 03/053354 | 7/2003 |
| WO | WO 03/053358 | 7/2003 |
| WO | WO 03/062241 | 7/2003 |

OTHER PUBLICATIONS

Alekperov, N.A. et al., "Effect of the Nature of the Groups at the Bridging Carbon Atom on the Formation of Endo,Endo- and Endo,Exo-Anhydrides and Imides of the 3,6-Epoxytricyclo[6.2.1.0$^2$, $^7$]-undecene Series", Zhurnal Organicheskoi Khimii, vol. 16, No. 4, pp. 675-682 (1980) (English language version).

Benítez, A. et al., "Site Selectivity of the Diels-Alder Reactions of 3-[1-(*tert*-Butyldimethylsilyloxy)vin-1-yl]furan and 3-(Proren-2-yl)furan. Synthesis of 4-Substituted Benzofurans", J. Org. Chem., vol. 61, No. 4, pp. 1487-1492 (1996).

Berson, J. A. et al., "*cis*-Addition in the Bromination of Bicyclic Olefins. The Structure and Stereochemistry of the Dibromides of *exo-cis*-3,6-Endoxo-—$^4$- tetrahydrophthalic Anhydride and *endo-cis*-3,6-Endomethylene-—$^4$-tetrahydrophthalic Anhydride", J. Amer. Chem. Soc., vol. 76, pp. 4060-4069 (1954).

Chen, G et al., "N-Mannich Bases of Norcantharidinimide and Analogs", Chemical Journal of Chinese Universities, vol. 4, No. 2, pp. 201-206 (1983).

Fuhrmann, U. et al., "Stable Transfection of Androgen Receptor and MMTV-CAT into Mammalian Cells: Inhibition of CAT Expression by Anti-Androgens", J. Steriod Biochem. Molec. Biol., vol. 42, No. 8, pp. 787-793 (1992).

Gribble, G.W. et al., "Syntheses and Diels-Alder Cycloaddition Reactions of 4*H*-Furo[3,4-*b*]indoles. A Regiospecific Diels-Alder Synthesis of Ellipticine", J. Org. Chem., vol. 57, No. 22, pp. 5878-5891 (1992).

Grondin, A. et al., "Benxotriazole malemide as a bifunctional reactant for SERS", J. Chem. Soc., Perkin Trans. 2, pp. 2136-2141 (2001).

Kaplan, F. A. et al., "Annelation of Tricarbonyliron Complexes of Ortho-Disubstituted Annules. Synthesis of Tricarbonyliron Complexes of Derivatives of Bicyclo[6.2.0]decapentaene via Wittig Cyclooefination", Journal of the American Chemical Society, vol. 99, No. 2, pp. 513-517 (1977).

Kobayashi, T. et al., "Norbornadiene-Fused Heterocycles: Synthesis and Cycloaddition Reactions of 2-Aryl-4,7-dihydro-4,7-methan-2*H*-isonidoles and 4,7- Dihydro-4,7-methanoisobenzofuran", Bull. Chem. Soc. Jpn., vol. 68, pp. 3269-3275 (1995).

Kovtunenko, V.A. et al., "1-Ethylthio-2R-isoindoles. An Example of Nonsynchronous Addition in the Diels-Alder Reaction", Khimiya Geterotsiklicheskikh Soedinenii, No. 9, pp. 978-983 (1984) (English language version).

Kovtunenko, V. A. et al., "Criteria for Establishment of Three-Dimensional Structures of Diels-Alder Adducts in the Isoindoles Series. 2. Reaction of 1,2-Disubstituted Isoindoles with Maleinimide Derivatives", Khimiya Geterotsiklicheskikh Soedinenii, No., 2, pp. 161-172 (1990) (English language version).

Liu, J. et al., "A Study on Antitumor Chemotherapeutic Agents - Synthesis of Cantharidine Derivatives", Acta Pharmaceutica Sinica, vol. 15, No. 5, pp. 271-277 (1980).

Matias, P.M. et al., "Structural Evidence for Ligand Specificity in the Binding Domain of the Human Androgen Receptor: Implications for Pathogenic Gene Mutations", The Journal of Biological Chemistry, vol. 275, No. 34, pp. 26164-26171 (2000).

Matsuki, K. et al., "Enantioselective Reduction of *meso*-Cyclic-1,2-dicarboxylic Anhydrides and 1,2-Dicarboximides: Asymmetric Synthesis of Bicyclic Lactones and Hydroxylactams", Chem. Pharm. Bull., vol. 42, No.1, pp. 9-18 (1994).

Mel'nikow, N.N. et al., "Some Derivatives of 4,5-Dichloro-3,6-endoxohexahydrophthalic Acid", Zh. Obshch. Khim., vol. 29, pp. 949-952 (1959) ( English language version).

Mikhailyuchenko, N. G. et al., "Polyfural(aryl)alkanes and Theis Derivatives. 9. Polyfuryl(aryl)methanes in the Diels-Alder Reaction", Khimiya Geterotsiklicheskikh Soedinenii, No. 6, pp. 642-649 (1993) (English language version).

Mishiev, R. D. et al., "Diels-Alder synthesis based on furan and its adducts", Vses. Nauchn. konf. Khim. Tekhnol. Furanovykh Soedin. (Tezisy Dokl.) 3rd, Sumgait. Filial, Inst. Neftekhim. Protsessov, Sumgait, USSR, Stradyn, Ya. P., ed., pp. 142-143 (1978).

Mueller, R.H. et al., "Diastereoselective Reaction of a Grignard Reagent with Chiral Imides: A Practical Preparation of a Key Intermediate in the Synthesis of Ifetroban Sodium", Organic Process Research & Development, vol. 1, No. 1, pp. 14-19 (1997).

Padwa, A et al., "Cyclic Carbonyl Ylide Formation from the Rhodium (II) Actetate Catalyzed Reaction of 1-Diazoalkanediones", Tetrahedron Letters, vol. 30, No. 3, pp. 301-304 (1989).

Sack, J.S. et al. "Crystallographic structures of the ligand-binding domains of the androgen receptor and its T877A mutant complexed with the natural agonist dihydrotestosterone", Proc. Natl. Acad. Sci. USA, vol. 98, No. 9, pp. 4904-4909 (2001).

Salakhov, M.S. et al., "Stereochemistry of the Adducts of Some Polychlorocyclopentadienes with the Anhydride and N-Phenylimide of 3,6-Epoxy-4-cyclohexene-1,2-dicarboxylic Acid", Zhurnal Organicheskoi Khimii, vol. 14, No. 6, pp. 1116-1118 (1978) (English language version).

Salakhov, M.S. et al., "Synthesis and some conversions of diene adducts of 5,5-di(substituted-oxy)tetrachlorocyclopentadienes with 3,6-endo-oxa-4-cyclohexene-1,2-dicarboxylic andhdride and -N-phenylimide", Azerb. Khim. Zh., No., 3, pp. 53-57 (1978).

SciFinder Search Results (Aug. 16, 2000).

SciFinder Search Results, Registry No. 10487-45-3 (Aug. 16, 2000).

SciFinder Search Results, Registry No. 99542-17-3 (Jun. 20, 2001).

SciFinder Search Results, Registry No. 107919-15-3.

SciFinder Search Results, Registry No. 146797-53-7 (Sep. 11, 2000).

Térouanne, B. et al., "A stable prostatic bioluminescent cell line to investigate androgen and antiandrogen effects", Molecular and Cellular Endocrinology, vol. 160, pp. 39-49 (2000).

Tosunyan, D. É. et al., "Benzopyrylium Salts. 44. Formation of 4-Acyl-3,4-dihydroisoquinolinium Salts from the Reaction of 2-Benzopyrylium Salts with Azomethines and the Cycloaddition of Maleimides to the Product of tTheir Deprotonation, the 2,3-Dihydroisoquinolines", Khimiya Geterotsiklicheskikh Soedinenii, No. 11, pp. 1249-1254 (1992) (English language version).

Walter, C.J. et al., "Free- Energy Profile for a Host-Accelerated Diels-Alder Reaction: The Sources of *exo* Selectivity", Agnew. Chem. Intl. Ed. Engl., vol. 34, No. 2, pp. 217-219 (1995).

Ward, D. E. et al., "Diels-Alder Reactions of 2H-Thiopyrans", Tetrahedron Letters, vol. 31, No. 6, pp. 845-848 (1990).

Yarbrough, W.G. et al., "A Single Base Mutation in the Androgen Receptor Gene Causes Androgen Insensitivity in the Testicular Feminized Rat", The Journal of Biological Chemistry, vol. 265, No. 15, pp. 8893-8900 (1990).

Zhang, S., "A Study on Antitumor Chemotherapeutic Agents - Synthesis of N-Cantharidine Derivatives", Acta Pharmaceutica Sinica, vol. 16, No. 10, pp. 784-786 (1981).

Zhou, Q. et al., "Comparison of the Sensitivity of Murine Hemopoietic and $P_{388}$ Leukemic Stem Cells to Five Antitumor Drugs", Acta Pharmaceutica Sinica, vol. 18, No. 10, pp. 725-730 (1983).

Lin et al., Synthesis of Novel N-Pyridylcantharidinimides by Using High Pressure, Journal of Chinese Chemical Society, vol. 48, pp. 49-53, 2001.
Dominianni et al., J. Med. Chem., Some Derivatives of 7-Oxabicyclo[2.2.1]Heptane-exo-cis-2,3-Dicarboxylic Acid, vol. 14, p. 175, 1971.
Krow et al, Tetrahedron, vol. 30, p. 2977-2981 (1974).
Kucharczyk et al., J. Med. Chem., vol. 36, p. 1645-1661 (1993).
Ben-Ishai et al., Tetrahedron, vol. 27, p. 3119-3127 (1971).
Vincent et al., Tetrahedron Letters, vol. 33, No. 48, p. 7369-7372 (1992).
Goldstein et al., Tetrahedron Letters, vol. 31, p. 2631-2634 (1969).
Evnin et al., J. Org. Che., vol. 35, No. 9, p. 3097-3106 (1970).
Kobayashi et al., Bull. Chem. Soc. Jpn., vol. 67, No. 11, p. 3082-3087 (1994).
Kobayashi et al., Bull. Chem. Soc. Jpn., vol. 65, p. 61-65 (1992).
Pons et al., Eur. J. Org. Chem., p. 853-859 (1998).
Pons et al., Pept. Proc. Am. Pept. Symp., 15th p. 176-177 (1999).
Reyniers et al., Bull. Soc. Chim. Belg. vol. 94(6), p. 413-419 (1985).
Anteunis et al., Tetrahedron Lett., vol. 22(32), p. 3101-3104 (1981).
Mauger et al., J. Chem. Soc., Perkin Trans. 1, vol. 17, p. 2146-2148 (1972).
Mauger , J. Chem. Soc. d, vol. 1, p. 39-40 (1971).
Lee et al., Tetrahedron Lett., vol. 37(34), p. 6053-6056 (1996).
Verbruggen et al., Acta Crystallogr., Sect. C: Cryst. Struct. Commun., vol. C49(6), p. 1113-1116 (1993).
Shalati et al., Journal of Polymer Science: Polm. Chem. Ed., vol. 22(1), p. 107-120 (1984).
Van Poucke et al., Bull. Soc. Chim. Belg., vol. 91(3), p. 213-218 (1982).
Schrooten et al., Bull. Soc. Chim. Belg., vol. 89(8), p. 615-628 (1980).
Hausler et al., Chem. Ber. vol. 107(9), p. 2804-2815 (1974).
Vicar et al., Collect. Czech. Chem. Commun. vol. 38(7), p. 1940-1956 (1973).
Vicar et al., Collect. Czech. Chem. Commun. vol. 37(12), p. 4060-4071 (1972).
Kovtunenko et al., Ukr. Khim. Zh. (Russ. Ed), vol. 58(11), p. 1035-1040 (1992).
Kovtunenko et al., Ukr. Khim. Zh. (Russ. Ed), vol. 58(7), p. 588-592 (1992).
Kreher et al., Chem. Ber., vol. 125(1), p. 183-189 (1992).
Kovtunenko et al., Ukr. Khim. Zh. (Russ. Ed), vol. 57(1), p. 71-77 (1991).
Kovtunenko et al., Khim. Geterotsikl. Soedin., vol. (2), p. 190-202 (1990).
Kreher et al., Chem. Ber., vol. 123(2), p. 381-390 (1990).
Kreher et al., Chem.-Ztg., vol. 112(11), p. 335-342 (1988).
Kovtunenko et al., Ukr. Khim. Zh. (Russ. ed.), vol. 55(1), p. 64-69 (1989).
Kovtunenko et al., Ukr. Khim. Zh. (Russ. ed.), vol. 54(11), p. 1186-1190 (1988).
Kovtunenko et al., Ukr. Khim. Zh., vol. 54(2), p. 186-190 (1988).
Kreher et al., Chem.-Ztg., vol. 111(12), p. 349-356 (1987).
Kreher et al., Chem. Ber., vol. 121(5), p. 927-934 (1988).
Kreher et al., Chem.-Ztg., vol. 110(10), p. 363-367 (1986).
Kovtunenko et al., Khim. Geterotsikl. Soedin., vol. 20(9), p. 1200-1205 (1984).
Kreher et al., Angew Chem., vol. 96(7), p. 507-508 (1984).
Kovtunenko et al., Ukr. Khim. Zh., vol. 49(12), p. 1287-1293 (1983).
Kreher et al., Angew. Chem., vol. 94(8), p. 634-635 (1982).
Munoz et al., Biotechnol. Bioeng., vol. 71(1), p. 78-84 (2000).
Chen et al., Tetrahedron Lett., vol. 40(18), p. 3491-3494 (1999).
Srivastav et al., Natl. Acad. Sci. Lett., vol. 19(1&2), p. 16-18 (1996).
Tosunyan et al., Khim. Geterotsikl. Soedin., vol. (11), p. 1465-1471 (1992).
Kirby et al., J. Chem. Res., Synop., vol. (9), p. 273 (1985).
Krow et al., J. Heterocycl. Chem., vol. 22(1), p. 131-135 (1985).
Krow et al., J. Org. Chem., vol. 47(11), p. 1989-1993 (1982).
Knaus et al., J. Heterocycl. Chem., vol. 13(3), p. 481-486 (1976).
Lyle et al., J. Org. Chem., vol. 39(25), p. 3708-3711 (1974).
Kirby et al., J. Chem. Res. Miniprint, vol. 9, p. 3089-3097 (1985).
Xu, Trends in Pharmacological Science, vol. 2(10), p. 271-272 (1981).
Li et al., J. Pharm. Biomed. Anal. vol. 7(12), p. 1635-1639 (1989).
Cheng et al., Huaxue Shiji, vol. 15(1), p. 1-4 (1993).
Liu et al., Yaoxue Xuebao, vol. 18(10), p. 752-759 (1983).
Bockstahler et al., J. Med. Chem., vol. 11(3), p. 603-606 (1968).
Srivastava et al., Natl. Acad. Sci. Lett., vol. 15(2), p. 41-44 (1992).
Joshi et al., Indian J. Chem., Sect. B, vol. 22B(2), p. 131-135 (1983).
Fisera et al., Chem. Pap., vol. 49(4), p. 186-191 (1995).
Fang et al., Huaxue Tongbao, vol. (1), p. 27-30 (1994).
Wijnberg et al., Tetrahedron, vol. 38, p. 209-217 (1982).
Grogan et al., J. Med. Chem., vol. 6, p. 802-805 (1963).
Gringauz et al., J. Med. Chem., vol. 11, p. 611-612 (1968).
Chem. Abstr., vol. 65 p. 15325h (1966).
Chem. Abstr., vol. 57, p. 16561f (1962).
Jolivet, Ann. Chim., vol. 5, p. 1165-1217 (1960).
Maruyama et al., J. Org. Chem., vol. 46, p. 27-34 (1981).
Chem. Abstr., vol. 68, p. 39458j (1964).
Kwart, J. Amer. Chem. Soc., vol. 74 p. 3094-3097 (1952).
Berson et al., J. Amer. Chem. Soc., vol. 76, p. 4060-4067 (1954).
Yur'ev et al., J. Gen. Chem. (Engl. Transl.), vol. 30, p. 869-872 (1960).
Jolivet, C.R. Hebd. Seances Acad. Sci., vol. 243, p. 2085-2086 (1956).
Lin et al., Bioorganic Chemistry, vol. 28, p. 266-272 (2000).
Mel'nikow, Zh. Obshch. Khim., vol. 26, p. 227-232 (1956).
Mel'nikow, Zh. Obshch. Khim., vol. 29, p. 968,970 (1956).
CA 54:1480g.
CA 65:15326c.
Fisera et al., Chem. Pap., vol. 49(4), p. 186-191 (1995).
Warrener et al., Tetrahedron Lett., vol. 36(42), p. 7753-7756 (1995).
Qimin et al., J. Pharm. Biomed. Anal., vol. 7(12), p. 1635-1639 (1989).
Maruyama et al., J. Org. Chem., vol. 46(1), p. 27-34 (1981).
Zawadowski et al., Rocz. Chem., vol. 51(3), p. 557-560 (1977).
Liu et al., Eur. J. Canada, vol. 31A, (6), p. 953-963 (1995).
Lin, Journal of Natural Toxins, vol. 4 (2), p. 147-153 (1995).
Walter et al., Biochemica et Biophysica Acta, 1155, p. 207-0226 (1993).
Walter, J. Pharm. Sci., vol. 78 (1), p. 66-67 (1989).
Yin et al., Chem. Chinese Chemical Society, No. 1, p. 27-30 (1994).
Bockstahler et al., J. Med. Chem., vol. 11 (3), p. 603-606 (1968).
Dominianni et al., J. Med. Chem., vol. 14 (2), p. 175 (1971).
Zhou et al., Acta Pharm. Sinica, vol. 18 (10), p. 725-729 (1983).
Wang, J. Ethnopharm., vol. 26, p. 147-162 (1989).
Honkanen, FEBS Letters, vol. 330 (3), p. 283-286 (1993).
Waller, Toxicol. Appl. Pharmacol., vol. 137 (2), p. 219-227 (1996).
Search Report "A" (Scifinder Jun. 23, 2000).
Search Report "B" (Scifinder Jun. 5, 2001).
Search Report "C" (Scifinder, Jun. 20, 2001).
Search Report "D" (Scifinder, Jun. 20, 2001).
Search Report "E" (Scifinder, Jun. 20, 2001).
Search Report "F" (Scifinder, Aug. 16, 2000).
Search Report "G" (Scifinder, Aug. 22, 2000).
Search Report "H" (Scifinder, Sep. 12, 2000).
Search Report "I".
Search Report "J".
Search Report "K" (Scifinder, Sep. 11, 2000).
Search Report "L" (Scifinder, Sep. 11, 2000).
Search Report "M" (Scifinder, Sep. 11, 2000).
Search Report "N" (Scifinder, Sep. 11, 2000).
Search Report "O" (Scifinder, Sep. 11, 2000).
Search Report "P" (Scifinder, Sep. 11, 2000).
Search Report "Q" (Scifinder, Sep. 11, 2000).
Search Report "R" (Scifinder, Sep. 11, 2000).
Search Report "S" (Scifinder, Sep. 11, 2000).
Search Report "T" (Scifinder, Sep. 11, 2000).
Search Report "U" (Scifinder, Sep. 11, 2000).
Search Report "V" (Scifinder, Sep. 11, 2000).
Search Report "W".
Search Report "X".
Search Report "Y" (Scifinder, Sep. 11, 2000).
Search Report "Z".

Search Report "AA".
Search Report "BB" (Scifinder, Sep. 11, 2000).
Tanaka et al., Tetrahedron, Elsevier Science Publishers, Amsterdam, NL, vol. 54 (34), p. 10029-10042 (1998).
Rosen et al., J. Med. Chem., vol. 31 (8), p. 1598-1611 (1988).
Remuzon et al., Journal of Medicinal Chemistry, American Chemical Society, vol. 35, (15), p. 2989-2909, 1992.
Evans, American Association for the Advancement of Science, vol. 240, No. 4854, p. 889-895 (1988).
Denison, J. Biol. Chem., vol. 270 (31), p. 18175-18178 (1995).
Furr, Eur. Urol., vol. 29 (Suppl. 2), 83-95 (1996).
Negro-Vilar, Journal of Clinical Endocrinology & Metabolism, vol. 84, No. 10, 3459-3462 (1999).
Reid et al., Investigational New Drugs, vol. 17, 271-284 (1999).
Avolos et al., Tetra. Ltrs., vol. 39, 9301-9304 (1998).
Rui et al., ACTA Pharmaceuticals Sinica, vol. 10, 783-786 (1981).
Tsuchiya et al., Tetra., vol. 29, No. 18, 2747-2751 (1973).
Ca113:40505(1990).
Furr, Eur. Urol., vol. 29 (Suppl. 2), 83-95 (1996).
Negro-Vilar, Journal of Clinical Endocrinology & Metabolism, vol. 84, No. 10, 3459-3462 (1999).
Reid et al., Investigational New Drugs, vol. 17, 271-284 (1999).
Avolos et al., Tetra. Ltrs., vol. 39, 9301-9304 (1998).
Rui et al., ACTA Pharmaceutica Sinica, vol. 10, 783-786 (1981).
Tsuchiya et al., Tetra., vol. 29, No. 18, 2747-2751 (1973).

* cited by examiner

FUSED HETEROCYCLIC IMIDO AND AMIDO COMPOUNDS

This application is a divisional application of U.S. application Ser. No. 10/322,077, filed Dec. 18, 2002, now abandoned, which is a continuation-in-part of U.S. application Ser. No. 10/025,116, filed Dec. 19, 2001, now abandoned, which is a continuation-in-part of U.S. application Ser. No. 09/885,381, filed Jun. 20, 2001, now abandoned, and also a continuation-in-part of U.S. application Ser. No. 09/885,827, filed Jun. 20, 2001, now U.S. Pat. No. 6,960,474, which applications are incorporated herein by reference in their entirety, wherein U.S. application Ser. No. 09/885,381 further claims the benefit of provisional Application No. 60/233,519, filed Sep. 19, 2000, and provisional Application No. 60/284,730, filed Apr. 18, 2001, and provisional Application No. 60/284,438, filed Apr. 18, 2001, which provisional applications are incorporated herein by reference in their entirety.

FIELD OF THE INVENTION

The present invention relates to fused cyclic compounds, to methods of using such compounds in the treatment of nuclear hormone receptor-associated conditions such as cancer, and to pharmaceutical compositions containing such compounds.

BACKGROUND OF THE INVENTION

Nuclear hormone receptors (NHR's) constitute a large super-family of ligand-dependent and sequence-specific transcription factors. Members of this family influence transcription either directly, through specific binding to the promoter target genes (Evans, in *Science* 240: 889-895 (1988)), or indirectly, via protein-protein interactions with other transcription factors (Jonat et al., *Cell* 62: 1189-1204 (1990), Schuele et al., *Cell* 62: 1217-1226 (1990), and Yang-Yen et al., *Cell* 62: 1205-1215 (1990)). The nuclear hormone receptor super-family (also known in the art as the "steroid/thyroid hormone receptor super-family") includes receptors for a variety of hydrophobic ligands, including cortisol, aldosterone, estrogen, progesterone, testosterone, vitamin D3, thyroid hormone and retinoic acid (Evans, 1988, supra). In addition to these conventional nuclear hormone receptors, the super-family contains a number of proteins that have no known ligands, termed orphan nuclear hormone receptors (Mangelsdorf et al., *Cell* 83: 835-839 (1995), O'Malley et al., *Mol. Endocrinol.* 10: 1293 (1996), Enmark et al., *Mol. Endocrinol.* 10, 1293-1307 (1996) and Giguere, *Endocrin. Rev.* 20, 689-725 (1999)). The conventional nuclear hormone receptors are generally transactivators in the presence of ligand, and can either be active repressors or transcriptionally inert in the absence of ligand. Some of the orphan receptors behave as if they are transcriptionally inert in the absence of ligand. Others, however, behave as either constitutive activators or repressors. These orphan nuclear hormone receptors are either under the control of ubiquitous ligands that have not been identified, or do not need to bind ligand to exert these activities.

In common with other transcription factors, the nuclear hormone receptors have a modular structure, being comprised of three distinct domains: an N-terminal domain of variable size containing a transcriptional activation function AF-1, a highly conserved DNA binding domain and a moderately conserved ligand-binding domain. The ligand-binding domain is not only responsible for binding the specific ligand but also contains a transcriptional activation function called AF-2 and a dimerisation domain (Wurtz et al., *Nature Struc. Biol.* 3, 87-94 (1996), Parker et al., *Nature Struc. Biol.* 3, 113-115 (1996) and Kumar et al., *Steroids* 64, 310-319 (1999)). Although the overall protein sequence of these receptors can vary significantly, all share both a common structural arrangement indicative of divergence from an ancestral archetype, and substantial homology (especially, sequence identity) at the ligand-binding domain.

The steroid binding nuclear hormone receptors (SB-NHR's) comprise a sub-family of nuclear hormone receptors. These receptors are related in that they share a stronger sequence homology to one another, particularly in the ligand binding domain (LBD), than to the other members of the NHR super-family (Evans, 1988, supra) and they all utilize steroid based ligands. Some examples of this sub-family of NHR's are the androgen receptor (AR), the estrogen receptor (ER), the progesterone receptor (PR), the glucocorticoid receptor (GR), the mineralocorticoid receptor (MR), the aldosterone receptor (ALDR) and the steroid and xenobiotic receptor (SXR) (Evans et al., WO 99/35246). Based on the strong sequence homology in the LBD, several orphan receptors may also be members of the SB-NHR sub-family.

Consistent with the high sequence homology found in the LBD for each of the SB-NHR's, the natural ligands for each is derived from a common steroid core. Examples of some of the steroid based ligands utilized by members of the SB-NHR's include cortisol, aldosterone, estrogen, progesterone, testosterone and dihydrotestosterone. Specificity of a particular steroid based ligand for one SB-NHR versus another is obtained by differential substitution about the steroid core. High affinity binding to a particular SB-NHR, coupled with high level specificity for that particular SB-NHR, can be achieved with only minor structural changes about the steroid core (e.g., Waller et al., *Toxicol. Appl. Pharmacol.* 137, 219-227 (1996) and Mekenyan et al., *Environ. Sci. Technol.* 31, 3702-3711 (1997), binding affinity for progesterone towards the androgen receptor as compared to testosterone).

Numerous synthetically derived steroidal and non-steroidal agonists and antagonists have been described for the members of the SB-NHR family. Many of these agonist and antagonist ligands are used clinically in man to treat a variety of medical conditions. RU486 is an example of a synthetic agonist of the PR, which is utilized as a birth control agent (Vegeto et al., *Cell* 69: 703-713 (1992)), and Flutamide is an example of an antagonist of the AR, which is utilized for the treatment of prostate cancer (Neri et al, *Endo.* 91, 427-437 (1972)). Tamoxifen is an example of a tissues specific modulator of the ER function, that is used in the treatment of breast cancer (Smigel, *J. Natl. Cancer Inst.* 90, 647-648 (1998)). Tamoxifen can function as an antagonist of the ER in breast tissue while acting as an agonist of the ER in bone (Grese et al., *Proc. Natl. Acad. Sci. USA* 94, 14105-14110 (1997)). Because of the tissue selective effects seen for Tamoxifen, this agent and agents like it are referred to as "partial-agonist" or partial-antagonist". In addition to synthetically derived non-endogenous ligands, non-endogenous ligands for NHR's can be obtained from food sources (Regal et al., *Proc. Soc. Exp. Biol. Med.* 223, 372-378 (2000) and Hempstock et al., *J. Med. Food* 2, 267-269 (1999)). The falconoid phytoestrogens are an example of an unnatural ligand for SB-NHR's that are readily obtained from a food source such as soy (Quella et al., *J. Clin. Oncol.* 18, 1068-1074 (2000) and Banz et al., *J. Med. Food* 2, 271-273 (1999)). The ability to modulate the transcriptional activity of individual NHR by the addition of a small molecule ligand, makes them ideal targets for the development of pharmaceutical agents for a variety of disease states.

As mentioned above, non-natural ligands can be synthetically engineered to serve as modulators of the function of NHR's. In the case of SB-NHR's, engineering of an unnatural ligand can include the identification of a core structure which mimics the natural steroid core system. This can be achieved by random screening against several SB-NHR's or through directed approaches using the available crystal structures of a variety of NHR ligand binding domains (Bourguet et al., *Nature* 375, 377-382 (1995), Brzozowski, et al., *Nature* 389, 753-758 (1997), Shiau et al., *Cell* 95, 927-937 (1998) and Tanenbaum et al., *Proc. Natl. Acad. Sci. USA* 95, 5998-6003 (1998)). Differential substitution about such a steroid mimic core can provide agents with selectivity for one receptor versus another. In addition, such modifications can be employed to obtain agents with agonist or antagonist activity for a particular SB-NHR. Differential substitution about the steroid mimic core can result in the formation of a series of high affinity agonists and antagonists with specificity for, for example, ER versus PR versus AR versus GR versus MR. Such an approach of differential substitution has been reported, for example, for quinoline based modulators of steroid NHR in *J. Med. Chem.,* 41, 623 (1999); WO 9749709; U.S. Pat. No. 5,696,133; U.S. Pat. No. 5,696,130; U.S. Pat. No. 5,696,127; U.S. Pat. No. 5,693,647; U.S. Pat. No. 5,693,646; U.S. Pat. No. 5,688,810; U.S. Pat. No. 5,688,808 and WO 9619458, all incorporated herein by reference.

The compounds of the present invention comprise a core which serves as a steroid mimic, and are useful as modulators of the function of steroid binding nuclear hormone receptors, as well as other NHR as described following.

SUMMARY OF THE INVENTION

The present invention provides fused cyclic compounds of the following formula I and salts thereof, which compounds are especially useful as modulators of nuclear hormone receptor function:

(I)

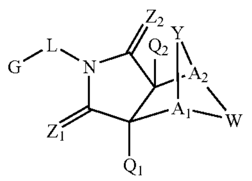

As used in formula I, and throughout the specification, the symbols have the following meanings unless otherwise indicated, and are, for each occurrence, independently selected:

G is an aryl or heterocyclo (e.g., heteroaryl) group, where said group is mono- or polycyclic, and which is optionally substituted at one or more positions, preferably with hydrogen, alkyl or substituted alkyl, alkenyl or substituted alkenyl, alkynyl or substituted alkynyl, halo, cycloalkyl or substituted cycloalkyl, cycloalkenyl or substituted cycloalkenyl, aryl or substituted aryl, heterocyclo or substituted heterocyclo, arylalkyl or substituted arylalkyl, heterocycloalkyl or substituted heterocycloalkyl, CN, $R^1OC—O$, $R^1C=O$, $R^1C=S$, $R^1HNC=O$, $R^1R^2NC—O$, $HOCR^3R^3$, nitro, $R^1OCH_2$, $R^1O$, $NH_2$, $NR^4R^5$, $SR^1$, $S=OR^1$, $SO_2R^1$, $SO_2OR^1$, $SO_2NR^1R^{1''}$, $(R^1O)(R^{1'}O)P=O$, oxo, $(R^1)(R^{1''})P=O$, or $(R^{1''})(NHR^1)P=O$;

$Z_1$ is O, S, NH, or $NR^6$;

$Z_2$ is O, S, NH, or $NR^6$;

$A_1$ is $CR^7$ or N;

$A_2$ is $CR^7$ or N;

Y is J—J'—J" where J is $(CR^7R^{7'})n$ and n=0-3, J' is a bond or O, S, S=O, $SO_2$, NH, $NR^7$, C=O, OC=O, $NR^1C=O$, $CR^7R^{7'}$, $C=CR^8R^{8'}$, $R^2P=O$, $R^2P=S$, $R^2OP=O$, $R^2NHP=O$, $OP=OOR^2$, $OP=ONHR^2$, $OP=OR^2$, $OSO_2$, $C=NR^7$, NHNH, $NHNR^6$, $NR^6NH$, N=N, cycloalkyl or substituted cycloalkyl, cycloalkenyl or substituted cycloalkenyl, heterocyclo or substituted heterocyclo or aryl or substituted aryl, and J" is $(CR^7R^{7'})n$ and n=0-3, where Y is not a bond (i.e., if J' is a bond, then in at least one of J or J" (each defined as $(CR^7R^{7'})n$), n is not zero);

W is $CR^7R^{7'}—CR^7R^{7'}$, $CR^8=CR^{8'}$, $CR^7R^{7'}—C=O$, C=O—C=O, $CR^7R^{7'}—C=CH_2$, $C=CH_2—C=CH_2$, $CR^7R^{7'}—C=NR^1$, $C=NR^1—C=NR^1$, $NR^9—CR^7R^{7'}$, $N=CR^8$, N=N, $NR^9—NR^{9'}$, $S—CR^7R^{7'}$, $SO—CR^7R^{7'}$, $SO_2—CR^7R^{7'}$, cycloalkyl or substituted cycloalkyl, cycloalkenyl or substituted cycloalkenyl, heterocyclo or substituted heterocyclo, or aryl or substituted aryl, wherein when W is not $NR^9—R^7R^{7'}$, $N=CR^8$, N=N, $NR^9—NR^{9'}$, $S—CR^7R^{7'}$, $SO—CR^7R^{7'}$, $SO_2—CR^7R^{7'}$, or heterocyclo or substituted heterocyclo, then J' must be O, S, S=O, $SO_2$, NH, $NR^7$, OC=O, $NR^1C=O$, $OP=OOR^2$, $OP=ONHR^2$, $OSO_2$, NHNH, $NHNR^6$, $NR^6NH$, or N=N; or when W is $CR^7R^{7'}—CR^7R^{7'}$, the $R^7$ and $R^7$ substituents in each occurrence may be taken together to form a substituted or unsubstituted carbocyclic or substituted or unsubstituted heterocyclic ring system which can be formed by any combination of $R^7$ and $R^{7'}$ attached to the same carbon atom;

$Q_1$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^1OC=O$, $R^4C=O$, $R^5R^6NC=O$, $HOCR^7R^{7'}$, nitro, $R^1OCH_2$, $R^1O$, $NH_2$, $C=OSR^1$, $SO_2R^1$ or $NR^4R^5$;

$Q_2$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^1OC=O$, $R^4C=O$, $R^5R^6NC=O$, $HOCR^7R^{7'}$, nitro, $R^1OCH_2$, $R^1O$, $NH_2$, $C=OSR^1$, $SO_2R^1$ or $NR^4R^5$;

L is a bond, $(CR^7R^{7'})n$, NH, $NR^5$, $NH(CR^7R^{7'})n$, or $NR^5(CR^7R^{7'})n$, where n=0-3;

$R^1$ and $R^{1'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkalkyl, cycloalkenylalkyl or substituted cycloalkenylalkyl, heterocycloalkyl or substituted heterocycloalkyl, aryl or substituted aryl, arylalkyl or substituted arylalkyl;

$R^2$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

$R^3$ and $R^{3'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, hydroxylamine, hydroxamide, alkoxy or substituted alkoxy, amino, $NR^1R^2$, thiol, alkylthio or substituted alkylthio;

$R^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C{=}O$, $R^1OC{=}O$, $R^1NHC{=}O$, $SO_2OR^1$, $SO_2R^1$ or $SO_2NR^1R^{1'}$;

$R^5$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C{=}O$, $R^1NHC{=}O$, $SO_2R^1$, $SO_2OR^1$, or $SO_2NR^1R^{1'}$;

$R^6$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, $OR^1$, $R^1C{=}O$, $R^1NHC{=}O$, $SO_2R^1$, $SO_2OR^1$, or $SO_2NR^1R^{1'}$;

$R^7$ and $R^{7'}$ are each independently H, alkyl or substituted alkyl, alkenyl or substituted alkenyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, $OR^4$, nitro, hydroxylamine, hydroxylamide, amino, $NHR^4$, $NR^2R^5$, $NR^5R^5$, $NOR^1$, thiol, alkylthio or substituted alkylthio, $HOC{=}O$, $R^1C{=}O$, $R^1(C{=}O)O$, $R^1OC{=}O$, $R^1NHC{=}O$, $NH_2C{=}O$, $SO_2R^1$, $SOR^1$, $PO_3R^1R^{1'}$, $R^1R^{1'}NC{=}O$, $C{=}OSR^1$, $SO_2R^1$, $SO_2OR^1$, or $SO_2NR^1R^{1'}$, or, wherein $A_1$ or $A_2$ contains a group $R^7$ and W contains a group $R^7$, said $R^7$ groups of $A_1$ or $A_2$ and W together form a heterocyclic ring;

$R^8$ and $R^{8'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, nitro, halo, CN, $OR^1$, amino, $NHR^4$, $NR^2R^5$, $NOR^1$, alkylthio or substituted alkylthio, $C{=}OSR^1$, $R^1OC{=}O$, $R^1C{=}O$, $R^1NHC{=}O$, $R^1R^{1'}NC{=}O$, $SO_2OR^1$, $S{=}OR^1$, $SO_2R^1$, $PO_3R^1R^{1'}$, or $SO_2NR^1R^{1'}$; and $R^9$ and $R^{9'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, $OR^1$, $R^1C{=}O$, $R^1OC{=}O$, $R^1NHC{=}O$, $SO_2R^1$, $SO_2OR^1$, or $SO_2NR^1R^{1'}$.

Compounds within formula I are novel, a preferred subgenus of which is the following formula Ia:

(Ia)

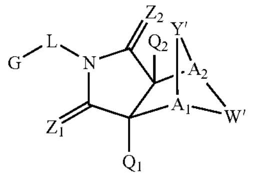

where G, L, $Z_1$, $Z_2$, $A_1$, $A_2$, $Q_1$ and $Q_2$ are as defined above;

Y' is J—J'—J" where J is $(CR^7R^{7'})$n and n=0-3, J' is a bond or O, S, S=O, $SO_2$, NH, $NR^7$, $CR^7R^{7'}$, $R^2P{=}O$, $R^2P{=}S$, $R^2OP{=}O$, $R^2NHP{=}O$, $OP{=}OOR^2$, $OP{=}ONHR^2$, $OSO_2$, NHNH, $NHNR^6$, $NR^6NH$, N=N, cycloalkyl or substituted cycloalkyl, cycloalkenyl or substituted cycloalkenyl, or heterocyclo or substituted heterocyclo, and J" is $(CR^7R^{7'})$n and n=0-3, where Y is not a bond; and W' is $CR^7R^{7'}$—$CR^7R^{7'}$, $CR^7R^{7'}$—C=O, C=O—C=O, $CR^7R^{7'}$—$C{=}CH_2$, $C{=}CH_2$—$C{=}CH_2$, $CR^7R^{7'}$—$C{=}NR^1$, $C{=}NR^1$—$C{=}NR^1$, $NR^9$—$CR^7R^{7'}$, $N{=}CR^8$, N=N, $NR^9$—$NR^{9'}$, cycloalkyl or substituted cycloalkyl, cycloalkenyl or substituted cycloalkenyl, heterocyclo or substituted heterocyclo, or aryl or substituted aryl, wherein when W' is not $NR^9$—$CR^7R^{7'}$, $N{=}CR^1$, N=N, $NR^9$—$NR^{9'}$, or heterocyclo or substituted heterocyclo, then J' must be O, S, S=O, $SO_2$, NH, $NR^7$, $OP{=}OOR^2$, $OP{=}ONHR^2$, $OSO_2$, NHNH, $NHNR^6$, $NR^6NH$, or N=N; or when W' is $CR^7R^{7'}$—$CR^7R^{7'}$, the $R^7$ and $R^7$ substituents in each occurrence may be taken together to form a substituted or unsubstituted carbocyclic or substituted or unsubstituted heterocyclic ring system which can be formed by any combination of $R^7$ and $R^{7'}$ attached to the same carbon atom; or alternatively, Y' is $NR^7$—$CR^7R^{7'}$ and W' is $CR^8{=}CR^8$; or, alternatively, Y' is $CR^7R^{7'}$—C=O and W' is $NR^9$—$CR^7R^{7'}$;

where $R^2$, $R^6$, $R^7$, $R^{7'}$, $R^8$, $R^9$ and $R^{9'}$ are as defined above and with the provisos that (1) when Y' is —O—, $Q_1$ and $Q_2$ are hydrogen, $Z_1$ and $Z_2$ are O, W' is —$CH_2$—$CH_2$—, and $A_1$ and $A_2$ are CH, then G—L is not phenyl, monosubstituted phenyl or phenyl which is substituted with two or more of the following groups: methoxy, halo, $NO_2$, methyl, $CH_3$—S—, OH, $CO_2H$, trifluoromethyl, —C(O)—$C_6H_5$, $NH_2$, 4-7-epoxy, hexahydro-1H-isoindole-1,3(2H)dione, or —C(O)—$CH_3$;

(2) when Y' is —O—, $Q_1$ and $Q_2$ are hydrogen, $Z_1$ and $Z_2$ are O, W' is $CH_2$—$CH_2$, and one of $A_1$ and $A_2$ is CH and the other is $CR^7$, then G—L is not unsubstituted phenyl;

(3) when Y' is —O—, $Q_1$ and $Q_2$ are hydrogen, $Z_1$ and $Z_2$ are O, W' is $CH_2$—$CH_2$, and one of $A_1$ and $A_2$ is CH and the other is C—$CH_3$, then G—L is not phenyl substituted with chloro and/or methyl;

(4) when Y' is —O— or —S—, $Q_1$ and $Q_2$ are hydrogen, $Z_1$ and $Z_2$ are O, W' is $CH_2$—$CH_2$, and one of $A_1$ and $A_2$ is CH and the other is CH or C-alkyl, then G—L is not N-substituted piperazine-alkyl- or N-substituted imidazolidine-alkyl-;

(5) when Y' is —O—; $Q_1$ and $Q_2$ are hydrogen, $Z_1$ and $Z_2$ are O, W' is $CH_2$—$CH_2$, and $A_1$ and $A_2$ are CH, then G—L is not oxazole or triazole;

(6) when Y' is —O—; $Q_1$ and $Q_2$ are hydrogen or methyl, $Z_1$ and $Z_2$ are O, W' is $CH_2$—$CH_2$, and $A_1$ and $A_2$ are CH or C—$CH_3$, then G—L is not thiazole or substituted thiazole (in addition such compounds where G—L is optionally substituted thiadiazole or partially saturated thiazole are optionally removed by proviso where $A_1$ and $A_2$ are both CH);

(7) when Y' contains a group J' selected from S, S═O, $SO_2$, NH, $NR^7$, $R^2P$═O, $R^2P$═S, $R^2OP$═O, $R^2NHP$═O, OP═$OOR^2$, OP═$ONHR^2$, $OSO_2$, NHNH, $NHR^6$, $NR^6NH$ or N═N, W' is $CR^7R^{7'}$—$CR^7R^{7'}$, and $Z_1$ and $Z_2$ are 0, then G—L is not unsubstituted phenyl;

(8) when Y' is $NR^7$, W' is unsubstituted or substituted phenyl, and $Q_1$ and $Q_2$ are hydrogen, then $Z_1$ and $Z_2$ are not O;

(9) when Y' is —O—, $Q_1$ and $Q_2$ are hydrogen, $Z_1$ and $Z_2$ are O, W' is dihydroisoxazole bearing an optionally substituted phenyl group, and $A_1$ and $A_2$ are CH, then G—L is not unsubstituted phenyl or dichlorophenyl;

(10) when Y' is O, $Q_1$ and $Q_2$ are hydrogen, $Z_1$ and $Z_2$ are O, W' is ethylene oxide, and $A_1$ and $A_2$ are CH, then G—L is not methylphenyl or chlorophenyl;

(11) when Y' is $NR^7$—$CR^7R^{7'}$, W' is $CR^8$═$CR^{8'}$, $Q_1$ and $Q_2$ are hydrogen, $A_1$ and $A_2$ are CH, C—$CH_3$, C—$CH_2$—$C_6H_5$ or C—$CH_2$—$CH_3$, and $Z_1$ and $Z_2$ are O, then G—L is not unsubstituted phenyl, monosubstituted phenyl or methylpyridinyl;

(12) when Y' is $CR^7R^{7'}$—C═O, W' is $NR^9$—$CR^7R^{7'}$, $Q_1$ and $Q_2$ are hydrogen, $A_1$ and $A_2$ are CH, and $Z_1$ and $Z_2$ are O, then G—L is not unsubstituted phenyl;

(13) when Y' is $CHR^{7'}$—$NR^7$ where $R^{7'}$ is unsubstituted phenyl, methoxy or ethoxy and $R^7$ is unsubstituted phenyl, methyl or —C(O)—$C_6H_5$, W' is dimethoxyphenylene or unsubstituted phenylene, $Z_1$ and $Z_2$ are O, $Q_1$ and $Q_2$ are hydrogen, and $A_1$ and $A_2$ are CH, C—CN, C—C(O)—$C_6H_5$, or —C(O)— dimethoxyphenyl, then G—L is not unsubstituted phenyl;

(14) the compound of formula Ia is not 6,10-epithio-4H-thieno-[3',4':5,6]cyclooct[1,2-f]isoindole-7,9(5H,8H)-dione, 8-(3,5-dichlorophenyl)-6,6a,9a, 10,11,12,-hexahydro-1,3,6,10-tetramethyl-2,2,13-trioxide, (6R, 6aR,9aS,10S);

(15) when Y' is O, W' is —$CH_2$—$CH_2$—, $Q_1$ and $Q_2$ are methyl, $Z_1$ and $Z_2$ are O, and $A_1$ and $A_2$ are CH, then G—L is not unsubstituted phenyl, phenyl substituted with methoxy, phenyl-alkyl-, or morpholine-alkyl, nor is the compound bridged to itself through a group L which is alkylene to form a bis compound;

(16) when Y' is —O—, $Q_1$ and $Q_2$ are hydrogen, $Z_1$ and $Z_2$ are O, W' is $CR^7R^{7'}$—$CR^7R^{7'}$, and $A_1$ and $A_2$ are CH, then G—L is not an unsubstituted phenyl group; and

(17) when Y' is —O—, $Q_1$ and $Q_2$ are hydrogen, $Z_1$ and $Z_2$ are O, W' is cyclopentyl, cyclohexyl, 3-phenyl-2-isoxazoline or $CR^7R^{7'}$—$CR^7R^{7'}$ where $R^7$ and $R^{7'}$ are each independently defined as Cl, Br, H and 4-butyrolactone and $R^7$ and $R^{7'}$ are not all simultaneously H, and $A_1$ and $A_2$ are CH, then G—L is not an unsubstituted naphthyl ring or a monosubstituted phenyl ring, where said substituent is methoxy, Br, Cl, $NO_2$, methyl, ethyl, $CH_2$-phenyl, S-phenyl, or O-phenyl.

Preferably, compounds of formula I are monomeric, and are not comprised within other oligomers or polymers.

Another preferred novel subgenus is that of the following formula Ib:

Ib

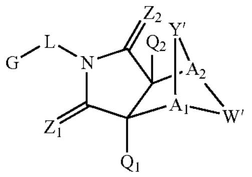

where G, $Z_1$, $Z_2$, $Q_1$ and $Q_2$ are as defined above;

Y' is J—J'—J" where J is $(CR^7R^{7'})$n and n=0-3, J' is a bond or O, S, S═O, $SO_2$, NH, $NR^7$, $CR^7R^{7'}$, $R^2P$═O, $R^2P$═S, $R^2OP$═O, $R^2NHP$═O, OP═$OOR^2$, OP═$ONHR^2$, $OSO_2$, NHNH, $NHNR^6$, $NR^6NH$, N═N, cycloalkyl or substituted cycloalkyl, cycloalkenyl or substituted cycloalkenyl, or heterocyclo or substituted heterocyclo, and J" is $(CR^7R^{7'})$n and n=0-3, where Y is not a bond; and W' is $CR^7R^{7'}$—$R^7R^{7'}$, $CR^7R^{7'}$—C═O, C═O—C═O, $CR^7R^{7'}$—C═$CH_2$, C═$CH_2$—C═$CH_2$, $CR^7R^{7'}$—C═$NR^1$, C═$NR^1$—C═$NR^1$, $NR^9$—$CR^7R^{7'}$, N═$CR^8$, N═N, $NR^9$—$NR^{9'}$, cycloalkyl or substituted cycloalkyl, cycloalkenyl or substituted cycloalkenyl, heterocyclo or substituted heterocyclo, or aryl or substituted aryl, wherein when W' is not $NR^9$—$CR^7R^{7'}$, N═$CR^8$, N═N, $NR^9$—$NR^{9'}$, or heterocyclo or substituted heterocyclo, then J' must be O, S, S═O, $SO_2$, NH, $NR^7$, OP═$OOR^2$, OP═$ONHR^2$, $OSO_2$, NHNH, $NHNR^6$, $NR^6NH$, or N═N; or when W' is $CR^7R^{7'}$—$CR^7R^{7'}$, the $R^7$ and $R^{7'}$ substituents in each occurrence may be taken together to form a substituted or unsubstituted carbocyclic or substituted or unsubstituted heterocyclic ring system which can be formed by any combination of $R^7$ and $R^{7'}$ attached to the same carbon atom; or alternatively, Y' is $CR^7R^{7'}$—C═O and W' is $NR^9$— $CR^7R^{7'}$;

L is a bond; and $A_1$ and $A_2$ are as defined above, especially where $A_1$ and/or $A_2$ are alkyl or optionally substituted alkyl (preferred such optional substituents being one or more groups $V^1$ defined below), with the proviso that, when Y'=O and W'=—$CH_2$—$CH_2$—, then at least one of $A_1$ or $A_2$ is not CH;

with the further provisos (2), (3), (6), (7) and (8) above.

The compounds of formula I and salts thereof comprise a core which can serve as a steroid mimic (and do not require the presence of a steroid-type (e.g., cyclopentanoperhydrophenanthrene analog) structure).

FURTHER DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary such groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. "Substituted alkyl" refers to an alkyl group substituted with one or more substituents, preferably 1 to 4 substituents, at any available point of attachment. Exemplary substituents include but are not limited to one or more of the following groups: halo (e.g., a single halo substituent or multiple halo substitutents forming, in the latter case, groups such as a perfluoroalkyl group or an alkyl group bearing $Cl_3$ or $CF_3$), alkoxy, alkylthio, hydroxy, carboxy (i.e., —COOH), alkoxycarbonyl, alkylcarbonyloxy, amino (i.e., $—NH_2$), carbamoyl or substituted carbamoyl, carbamate or substituted carbamate, urea or substituted urea, amidinyl or substituted amidinyl, thiol (i.e., —SH), aryl, heterocycle, cycloalkyl, heterocycloalkyl, —S-aryl, —S-heterocycle, —S═O-aryl, —S═O-heterocycle, arylalkyl-O—, $—S(O)_2$-aryl, $—S(O)_2$-heterocycle, $—NHS(O)_2$-aryl, $—NHS(O)_2$-heterocycle, $—NHS(O)_2NH$-aryl, $—NHS(O)_2NH$-heterocycle, $—P(O)_2$-aryl, $—P(O)_2$-heterocycle, $—NHP(O)_2$-aryl, $—NHP(O)_2$-heterocycle, $—NHP(O)_2NH$-aryl, $—NHP(O)_2NH$-heterocycle, —O-aryl, —O-heterocycle, —NH-aryl, —NH-heterocycle, —NHC═O-aryl, —NHC═O-alkyl, —NHC═O-heterocycle, —OC═O-aryl, —OC═O-heterocycle, —NHC═ONH-aryl, —NHC═ONH-heterocycle, —OC═OO-aryl, —OC═OO-heterocycle, —OC═ONH-aryl, —OC═ONH-heterocycle, —NHC═OO-aryl, —NHC═OO-heterocycle, —NHC═OO-alkyl, —C═ONH-aryl, —C═ONH-heterocycle, —C═OO-aryl, —C═OO-heterocycle, $—N(alkyl)S(O)_2$-aryl, $—N(alkyl)S(O)_2$-heterocycle, $—N(alkyl)S(O)_2NH$-aryl, $—N(alkyl)S(O)_2NH$-heterocycle, $—N(alkyl)P(O)_2$-aryl, $—N(alkyl)P(O)_2$-heterocycle, $—N(alkyl)P(O)_2NH$-aryl, $—N(alkyl)P(O)_2NH$-heterocycle, —N(alkyl)-aryl, —N(alkyl)-heterocycle, —N(alkyl)C═O-aryl, —N(alkyl)C═O-heterocycle, —N(alkyl)C—ONH-aryl, —N(alkyl)C═ONH-heterocycle, —OC═ON(alkyl)-aryl, —OC═ON(alkyl)-heterocycle, —N(alkyl)C═OO-aryl, —N(alkyl)C═OO-heterocycle, —C═ON(alkyl)-aryl, —C═ON(alkyl)-heterocycle, $—NHS(O)_2N(alkyl)$-aryl, $—NHS(O)_2N(alkyl)$-heterocycle, $—NHP(O)_2N(alkyl)$-aryl, $NHP(O)_2N(alkyl)$-heterocycle, —NHC═ON(alkyl)-aryl, —NHC═ON(alkyl)-heterocycle, $—N(alkyl)S(O)_2N(alkyl)$-aryl, $—N(alkyl)S(O)_2N(alkyl)$-heterocycle, $—N(alkyl)P(O)_2N(alkyl)$-aryl, $—N(alkyl)P(O)_2N(alkyl)$-heterocycle, —N(alkyl)C═ON(alkyl)-aryl, and —N(alkyl)C═ON(alkyl)-heterocycle. In the aforementioned exemplary substitutents, in each instance, groups such as "alkyl", "aryl" and "heterocycle" can themselves be optionally substituted; for example, "alkyl" in the group "NCH═OO-alkyl" recited above can be optionally substituted so that both "NHC═OO-alkyl" and "NHC═OO-substituted alkyl" are exemplary substitutents. Exemplary alkyl substituents also include groups such as "T" and "T-$R^{12}$" (which are defined below), especially for substituted alkyl groups within $A_1$ or $A_2$.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents, and as previously mentioned as preferred aryl substituents in the definition for G. Exemplary substituents also include spiro-attached or fused cyclic substituents, especially cycloalkenyl or substituted cycloalkenyl.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents, and as previously mentioned as preferred aryl substituents in the definition for G. Exemplary substituents also include spiro-attached or fused cyclic substituents, especially cycloalkyl or substituted cycloalkyl.

The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively.

The term "alkoxycarbonyl" refers to an alkoxy group bonded through a carbonyl group.

The term "alkylcarbonyl" refers to an alkyl group bonded through a carbonyl group. The term "alkylcarbonyloxy" refers to an alkylcarbonyl group bonded through an oxygen linkage.

The terms "arylalkyl", "substituted arylalkyl," "cycloalkylalkyl," "substituted cycloalkylalkyl," "cycloalkenylalkyl", "substituted cycloalkenylalkyl", "heterocycloalkyl" and "substituted heterocycloalkyl" refer to aryl, cycloalkyl, cycloalkenyl and heterocyclo groups bonded through an alkyl group, substituted on the aryl, cycloalkyl, cycloalkenyl or heterocyclo and/or the alkyl group where indicated as "substituted."

The term "aryl" refers to cyclic, aromatic hydrocarbon groups which have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1, 2, 3, 4 or 5 substituents, at any point of attachment. Exemplary substituents include, but are not limited to, nitro, cycloalkyl or substituted cycloalkyl, cycloalkenyl or substituted cycloalkenyl, cyano, alkyl-$S(O)_m$— (m=0, 1 or 2), alkyl or substituted alkyl, as well as those groups recited above as exemplary alkyl substituents and as previously mentioned as preferred aryl substituents in the definition for G. Exemplary substituents also include fused cyclic substituents, such as heterocyclo or cycloalkenyl, or substituted heterocyclo or cycloalkenyl, groups (e.g., thereby forming a fluoroenyl, tetrahydronapthalenyl, or dihydroindenyl group).

"Carbamoyl" refers to the group —CONH— which is bonded on one end to the remainder of the molecule and on the other to hydrogen or an organic moiety (such as alkyl, substituted alkyl, aryl, substituted aryl, heterocycle, alkylcarbonyl, hydroxyl and substituted nitrogen). "Carbamate" refers to the group —O—CO—NH— which is bonded on one end to the remainder of the molecule and on the other to hydrogen or an organic moiety (such as those listed above). "Urea" refers to the group —NH—CO—NH— which is bonded on one end to the remainder of the molecule and on the other to hydrogen or an organic moiety (such as those listed above). "Amidinyl" refers to the group —C(=NH)($NH_2$). "Substituted carbamoyl," "substituted carbamate," "substituted urea" and "substituted amidinyl" refer to carbamoyl, carbamate, urea or amidinyl groups as described above in which one more of the hydrogen groups are replaced by an organic moiety (such as those listed above).

The terms "heterocycle", heterocyclic" and "heterocyclo" refer to fully saturated, or partially or fully unsaturated, including aromatic (i.e., "heteroaryl") cyclic groups (for example, 3 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. It is understood that, where W or W' are cycloalkyl or substituted cycloalkyl, cycloalkenyl or substituted cycloalkenyl, heterocyclo or substituted heterocyclo, or aryl or substituted aryl, that A1 and A2 can be separately bonded to different (such as adjacent) ring atoms on said groups. Exemplary monocyclic heterocyclic groups include ethylene oxide, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, dibenzofuranyl, acridinyl, phenanthridinyl, xanthenyl and the like.

"Substituted heterocycle," "substituted heterocyclic," and "substituted heterocyclo" (such as "substituted heteroaryl") refer to heterocycle, heterocyclic or heterocyclo groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl-$S(O)_m$— (m=0, 1 or 2), alkyl or substituted alkyl, as well as those groups recited above as exemplary alkyl substituents, and as previously mentioned as preferred heterocyclo substituents in the definition for G.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethylhydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The terms "halogen" or "halo" refer to chlorine, bromine, fluorine or iodine.

The terms "hydroxylamine" and "hydroxylamide" refer to the groups OH—NH— and OH—NH—CO—, respectively.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991).

When a term such as "(CRR)n" is used, it denotes an optionally substituted alkyl chain existing between the two fragments to which it is bonded, the length of which chain is defined by the range described for the term n. An example of this is n=0-3, implying from zero to three (CRR) units existing between the two fragments, which are attached to the primary and terminal (CRR) units. In the situation where the term n is set to zero (n=0) then a bond exists between the two fragments attached to (CRR).

Unless otherwise indicated, any heteroatom with unsatisfied valences is assumed to have hydrogen atoms sufficient to satisfy the valences.

Divalent groups, such as those in the definition of W (e.g., $NR^9$—$CR^7R^{7'}$), may be bonded in either direction to the remainder of the molecule (e.g.,

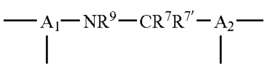
or,
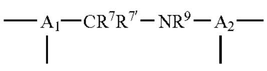

for the aforementioned group within the definition of W).

Carboxylate anion refers to a negatively charged group —$COO^-$.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings. In certain cases, for example, the exo or endo conformation can be preferred for the fused ring system bonded to G—L in formula I. For example, for androgen receptor antagonists (or selective androgen receptor modulators), where Y is O or $NR^7$, the exo configuration can be preferred, while for most other definitions of Y, the endo configuration can be preferred. As can be appreciated, the preferred configuration can be a function of the particular compound and its preferred activity. Separation of configurational isomers can be achieved by any suitable method, such as column chromatography.

Throughout the specifications, groups and substituents thereof may be chosen to provide stable moieties and compounds.

Embodiments indicated herein as exemplary or preferred are intended to be illustrative and not limiting.

Methods of Preparation

The compounds of the present invention may be prepared by methods such as those illustrated in the following Schemes I to XI. Solvents, temperatures, pressures, and other reaction conditions may readily be selected by one of ordinary skill in the art. Starting materials are commercially available or readily prepared by one of ordinary skill in the art. Combinatorial techniques may be employed in the preparation of compounds, for example, where the intermediates possess groups suitable for these techniques. See the following which describe other methods which may be employed in the preparation of compounds of the present invention: Li, et al., *Eur. J. Org. Chem.* 9, 1841-1850 (1998); Li, Y-Q, *Synlett.* 5, 461-464 (1996); Thiemann, et al., *Bull. Chem. Soc. Jpn.* 67, 1886-1893 (1994); Tsuge et al., *Heterocycles* 14, 423-428 (1980); Ward et al., *Can J. Chem.* 75, 681-693 (1997); Ward et al., *Can J. Chem.* 69, 1487-1497 (1991); Ward et al., *Tetrahedron Lett.* 31, 845-848 (1990); Fleming et al., *J. Org. Chem.* 44, 2280-2282 (1979); Jankowski et al., *J. Organomet. Chem.* 595, 109-113 (2000); Keglevich et al., *J. Organomet. Chem.* 579, 182-189 (1999); Keglevich et al., *J. Organomet. Chem.* 570, 49-539 (1998); Jankowski et al., *Hetroat. Chem.* 7, 369-374 (1996); Jankowski et al., *J. Am. Chem. Soc.* 113, 7011-7017 (1991); Quin et al., *Tetrahedron Lett.* 31, 6473-6476 (1990); Quin et al., *J. Org. Chem.* 59, 120-129 (1994); Quin et al., *J. Org. Chem.* 58, 6212-6216 (1993); Quin et al., *Phosphorous, Sulfur Silicon Relat. Elem.* 63, 349-362 (1991); Quin et al., *Hetroat. Chem.* 2, 359-367 (1991); Hussong et al., *Phosphorus Sulfur.* 25, 201-212 (1985); Quin et al., *J. Org. Chem.* 51, 3341-3347 (1986); Myers et al., *J. Am. Chem. Soc.* 114, 5684-5692 (1992); Myers et al., *J. Am. Chem. Soc.* 113, 6682-6683 (1991); Shen et al., U.S. Pat. No. 5,817,679; Cordone et al., *J. Am. Chem. Soc.* 111, 5969-5970 (1989); Jung et al., *J. Chem. Soc. Commun.* 630-632 (1984); Lay et al., *J. Am. Chem. Soc.* 104, 7658-7659 (1982); Gonzalez et al., *J. Am. Chem. Soc.* 117, 3405-3421 (1995); Kreher et al., *Chem. Ber.* 125, 183-189 (1992); Simig et al., *Synlett.* 7, 425-426 (1990); Sha et al., *J. Org. Chem.* 55, 2446-2450 (1990); Drew et al., *J. Chem. Soc., Perkin Trans.* 17, 1277-1284 (1985); Kreher et al., *Anorg. Chem., Org. Chem.* 31B, 599-604 (1976); Avalos et al., *Tetrahedron Lett.* 39, 9301-9304 (1998); Gousse et al., *Macromolecules* 31, 314-321 (1998); Mikhailyuchenko et al., *Khim. Geterotsikl. Soedin.* 6, 751-758 (1993); Lubowitz et al., U.S. Pat. No. 4,476,184; Padwa et al., *J. Org. Chem.* 61, 3706-3714 (1996); Schlessinger et al., *J. Org. Chem.* 59, 3246-3247 (1994); Buchrneiser et al., WO Publication No. 9827423; Tanabe et al., Japanese Patent Document JP 07144477; Mochizucki et al., Japanese Patent Document JP 63170383; Hosoda et al., Japanese Patent Document JP 62053963; Onaka et al., Japanese Patent Document JP 62053964; Kato et al., Japanese Patent Document JP 53086035; Kato et al., Japanese Patent Document JP 51088631; Tottori et al., Japanese Patent Document JP 49124225; Augustin et al., German Patent Document DD101271; Title et al., French Patent Document FR 2031538; Gousse et al., *Polym. Int.* 48, 723-731 (1999); Padwa et al., *J. Org. Chem.* 62, 4088-4096 (1997); Theurillat-Moritz et al., *Tetrahedron: Asymmetry* 7, 3163-3168 (1996); Mathews et al., *J. Carbohydr. Chem.* 14, 287-97 (1995); Srivastava et al., *Natl. Acad. Sci. Lett.* (*India*) 15, 41-44 (1992); Mayorga et al., *Rev. Cubana Quim.* 4, 1-6 (1988); Kondoli et al., *J. Chem. Res., Synop.* 3, 76 (1987); Primelles et al., *Cent. Azucar* 7-14 (1985); Solov'eva et al., *Khim. Geterotsikl. Soedin.* 5, 613-15 (1984); Liu et al., *Yaoxue Xuebao* 18, 752-759 (1983); Joshi et al., *Indian J. Chem, Sect. B.* 22B, 131-135 (1983); Amos et al., WO Publication No. 9829495; Odagiri et al., U.S. Pat. No. 4,670,536; Gallucci et al., European Patent Document EP 355435; Redmore, D. U.S. Pat. No. 3,821,232; Nakano et al., *Heterocycles* 35, 37-40 (1993); Tomisawa et al., *Chem. Pharm. Bull.* 36, 1692-1697 (1988); Krow et al., *J. HeterocycL Chem.* 22, 131-135 (1985); Krow et al., *J. Org. Chem.* 47, 1989-1993 (1982); Liu et al., *Yaoxue Xuebao* 18, 752-759 (1983); Nishikawa et al., *Yaoxue Xuebao* JP 01061457; and/or Rice et al., *J. Med. Chem.* 11, 183-185 (1968).

All documents cited in the present specification, such as those cited in this "Methods of Preparation" as well as other sections herein, are incorporated herein by reference in their entirety. Reference to any document herein is not to be construed as an admission that such document is prior art.

Scheme I

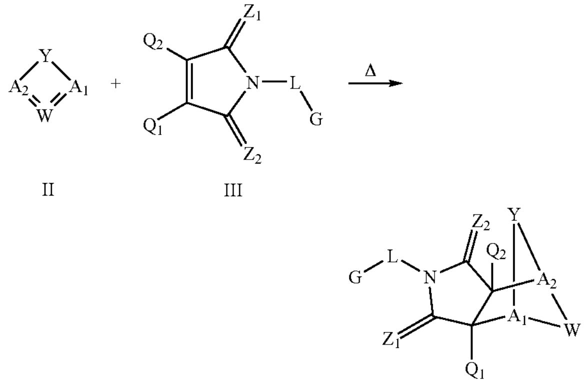

II III IV

As illustrated in Scheme I, a diene of formula II can be reacted with a dienophile of formula III, under conditions readily selected by one skilled in the art (such as by the addition of heat ("Δ")), to obtain a compound of formula IV, which is a compound of formula I. An intermediate diene of formula II can be obtained from commercial sources or readily made by one skilled in the art, for example, in accordance with the following literature documents and the references found therein: Hofman et al., *J. Agric. Food Chem.* 45, 898-906 (1997); Baciocchi et al., *J. Chem. Soc., Perkin Trans.* 2 8, 821-824 (1975); Wu et al., *J. Heterocycles* 38, 1507-1518 (1994); Yin et al., *Tetrahedron Lett.* 38, 5953-5954 (1997); Mic'ovic' et al., *Tetrahedron* 20, 2279-2287 (1964); Gorbunova et al., *J. Org. Chem.* 35, 1557-1566 (1999); Rassu et al., *Chem. Soc. Rev.* 29, 109-118 (2000); Kaberdin et al., *Russ. Chem. Rev.* 68, 765-779 (1999); Barluenga et al., *Aldrichimica Acta* 32, 4-15 (1999); Bogdanowicz-Szwed et al., *Pol. Wiad. Chem.* 52, 821-842 (1998); Casiraghi et al., *Adv. Asymmetric Synth.* 3, 113-189 (1998); and/or Baeckvall et al., *Chem. Rev.* 98, 2291-2312 (1998). An intermediate dienophile of formula III can be obtained from commercial sources or readily made by one skilled in the art, for example, in accordance with the following literature references and the references found therein: Deshpande et al., *Heterocycles* 51, 2159-2162 (1999); Seijas et al., *J. Chem. Res., Synop.* 7, 420-421 (1999); Langer et al., *Eur. J. Org. Chem.* 7, 1467-1470 (1998); Kita et al., Japanese Patent Document JP 09194458; Lopez-Alvarado et al., *J. Org. Chem.* 61, 5865-5870 (1996); Condon et al., U.S. Pat. No. 5,523,277; Sasakihara et al., Japanese Patent Document JP 04290868; Igarashi et al., Japanese Patent Document JP 04149173; Aoyama et al., Japanese Patent Document JP 04134063; Aoyama et al., Japanese Patent Document JP 04134062; Pastor et al., *J. Org. Chem.* 53, 5776-5779 (1988); and/or Takahashi et al., *Chem. Lett.* 6, 1229-1232 (1987).

Scheme II

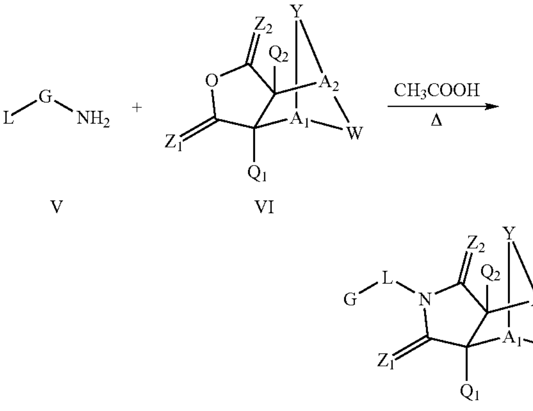

V VI IV

As illustrated in Scheme II, compounds of formula I can be obtained by reaction of a primary amine of formula V with a substituted anhydride-like intermediate of formula VI, for example, in a solvent such as acetic acid with or without heating, to yield a compound of formula IV, which is a compound of formula I. Primary amines of formula V can be obtained from commercial sources or readily synthesized by one skilled in the art. Anhydride-like agents of formula VI can be obtained from commercial sources or readily synthesized by one skilled in the art. The documents listed following describe exemplary approaches for the synthesis of intermediates of formula VI as well as synthetic approaches which can be applied to the synthesis of compounds of formula IV (all incorporated herein by reference in their entirety): Kohler, E. P.; Tishler, M.; Potter, H.; Thompson, H. T. *J. Am.*

*Chem. Soc.* 1939, 1057-1061; Yurxev, Y. K.; Zefirov, N. S. *J. Gen. Chem. U.S.S.R.* (*Engl. Transl.*) 1961, 31, 772-5; Norman G. Gaylord U.S. Pat. No. 3,995,099; Schueler, P. E.; Rhodes, Y. E. *J. Org. Chem.* 1974, 39, 2063-9; Ishitobi, H.; Tanida, H; Tsuji, T. *Bull. Chem. Soc. Japan* 1971, 44, 2993-3000; Stájer, G.; Virág, M.; Szabó, A. E.; Bernáth, G.; Sohár, P.; Sillanpää, R. *Acta. Chem. Scand.* 1996, 50, 922-30; Hart, H.; Ghosh, T. *Tetrahedron Lett.* 1988,29,881-884; Kato, M.; Yamamoto, S.; Yoshihara, T.; Furuichi, K; Miwa, T. *Chem. Lett.* 1987, 1823-1826; Kottwitz, J.; Vorbrüggen, H. *Synthesis* 1995, 636-637; Creary, X. *J. Org. Chem.* 1975, 40, 3326-3331; Alder, K.; Ache, H.-J.; Flock, F. H. *Chem. Ber.* 1960, 93, 1888-1895; Toder, B. H.; Branca, S. J.; Dieter, R. K.; Smith, A. B. III *Synth. Commun.* 1975, 5, 435-439; Sprague, P. W.; Heikes, J. E.; Gougoutas, J. Z.; Malley, M. F.; Harris, D. N.; and/or Greenberg, R. *J. Med. Chem.* 1985, 28, 1580-1590.

The aforementioned approach(es) can be applied in a combinatorial fashion, for example, by utilizing a multi-well reaction block such as is described in Waldemar Ruediger, Wen-Jeng Li, John W., Allen Jr., and Harold N. Weller III, U.S. Pat. No. 5,961,925, Apparatus for Synthesis of Multiple Organic Compounds With Pinch Valve Block (incorporated herein by reference in its entirety). By utilizing the above-mentioned multi-well reaction block, one can, for example, perform multiples of 96 reactions at a time. Solvent can then be removed from the reaction tubes without removal from the reaction block and the crude products can be precipitated using a base such as sodium bicarbonate. The precipitates can be collected by filtration of the reaction block and then the desired products can be transferred directly to 96 well plates for screening. In this fashion, a large array of compounds of formula I can be synthesized, and tests conducted as desired by an automated approach.

Scheme III

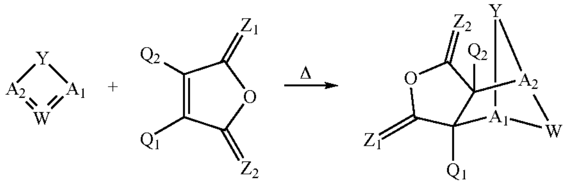

II VII VI

Scheme III describes a method for preparing an intermediate compound of formula VI which can be used to synthesize a compound of formula I, as described in Scheme II. As described in Scheme III, a diene of formula II can be reacted with a dieneophile of formula VII to yield the intermediate of formula VI. The methods applied to obtain such a transformation are analogous to those described in Scheme I.

Scheme IV

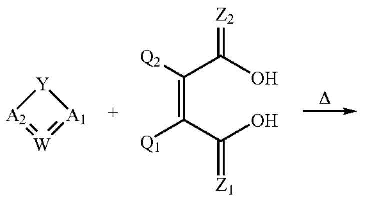

II VIII

-continued

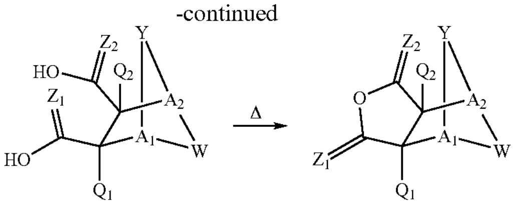

IX VI

Scheme IV describes a method for preparing an intermediate compound of formula VI which can be used to synthesize a compound of formula I, as described in Scheme II. As shown in Scheme IV, a diene of formula II can be reacted with a dieneophile of formula VIII to yield the intermediate of formula IX. The intermediate of formula IX can be dehydrated to an anhydride-like intermediate of formula VI. Dehydration of the bis-acid intermediate of formula IX to can be achieved by a variety of methods, such as those known to one skilled in the art and described in the following documents and the references embodied therein: Sprague et al., *J. Med. Chem.* 28, 1580-1590 (1985); and/or Retemi et al., *J. Org. Chem.* 61, 6296-6301 (1996).

Schemes I to IV describe general methods for the synthesis of compounds of formula I, and intermediates thereof, in which substitution about the ring system is incorporated directly, for example, at the level of the intermediate diene, dienophile, anhydride-like intermediate and amine groups. In addition to these approaches, additional substitution can be incorporated onto an already-prepared compound of formula I by a variety of approaches to prepare other compounds of the formula I. Exemplary methods for further substitution are described in Schemes V to XI.

Scheme V

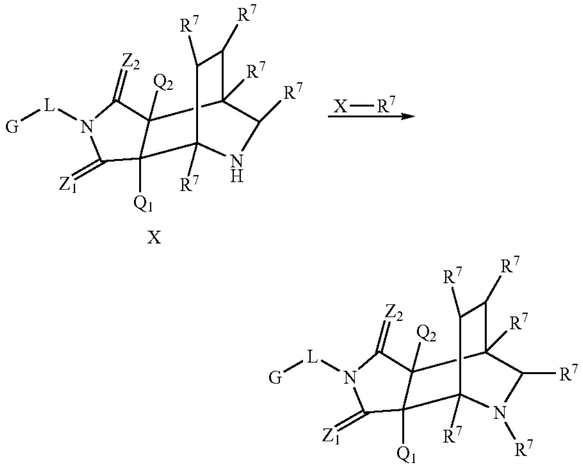

X

XI

Scheme V describes one such approach to incorporating additional substitution into a structure of formula I. As illustrated in Scheme V, a compound of formula X, which is a compound of formula I where $A_1$ and $A_2$ are $CR^7$, W is NH—$CHR^7$ and Y is $CHR^7$—$CHR^7$, can be functionalized at the free amine of the group W by reaction with any of a variety of electrophilic agents such as acid halides or alkyl halides in the presence of base, for example, by methods known by one skilled in the art. In Scheme V, X is a leaving group, and a compound of formula XI is a compound of formula I where $A_1$ and $A_2$ are $CR^7$, W is $NR^7$—$HR^7$ and Y is $CHR^7$—$CHR^7$.

Scheme VI

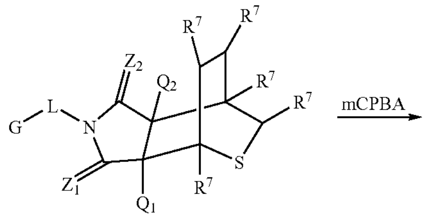

XII

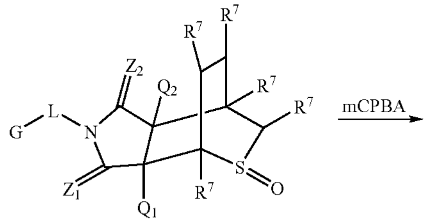

XIII

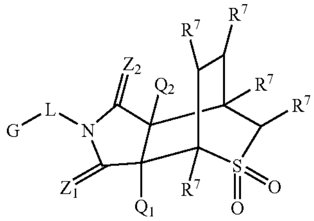

XIV

Scheme VI describes an additional approach for further incorporating substitution onto a compound of formula I. As illustrated in Scheme VI, a compound of formula XII, which is a compound of formula I where $A_1$ and $A_2$ are $CR^7$, W is S—$CHR^7$ and Y is $CHR^7$—$CHR^7$, can be partially oxidized with an oxidizing agent such as mCPBA or other agents such as those known to one skilled in the art, to give the sulfoxide analog of formula XIII, which is a compound of formula I where $A_1$ and $A_2$ are $CR^7$, W is SO—$CHR^7$ and Y is $CHR^7$—$CHR^7$. Further treatment of a compound of formula XIII with an oxidizing agent such as mCPBA or other agents such as those known to one skilled in the art, can yield the sulphone analog of formula XIV, which is a compound of formula I where $A_1$ and $A_2$ are $CR^7$, W is $SO_2$—$CHR^7$ and Y is $CHR^7$—$CHR^7$. Alternatively, a compound of formula XII can be converted directly to a compound of formula XIV by prolonged treatment with an oxidizing agent, such as mCPBA, or with other agents such as those known to one skilled in the art.

Scheme VII

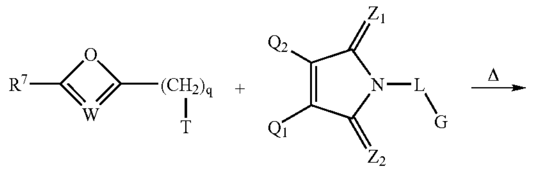

IIa III

-continued

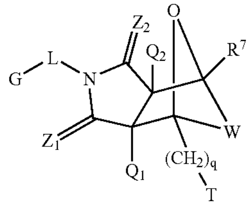

IVa

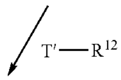

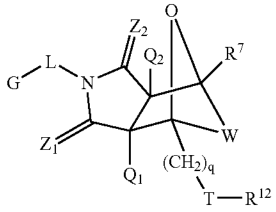

IVc

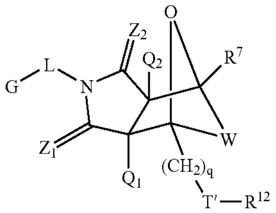

IVb

Scheme VII describes another approach to incorporating additional substitution onto a compound of formula I. As illustrated in Scheme VII, a diene of formula IIa can be reacted with a dienophile of formula III, as described in Scheme I, to yield a compound of formula IVa, which is a compound of formula I where Y is O, $A_2$ is $CR^7$ and $A_1$ is $C+CH_2)_q$—T. The compound of formula IVa can be reacted with a reagent of formula $R^{12}$—T' to obtain a compound of formula IVb or IVc which are compounds of formula I where Y is O, $A_2$ is $CR^7$ and $A_1$ is C—$(CH_2)_q$—T'—$R^{12}$ or C—$(CH_2)_q$—T—$R^{12}$, respectively. The reagent $R^{12}$—T' can be obtained from commercial sources or can readily be prepared by one skilled in the art.

In the above Scheme, $R^{12}$ has the same definition as $R^7$ defined earlier, q is zero or an integer from 0-8, and T is defined either as (1) a nucleophilic center such as, but not limited, to a nitrogen, oxygen or sulfur-containing group, capable of undergoing a nucleophilic substitution reaction with the leaving group T' or (2) a leaving group capable undergoing a nucleophilic substitution reaction with a nucleophilic group T' (such as, but not limited, to a nitrogen, oxygen or sulfur-containing nucleophilic group). T' has the same definition as T. In the present case, for example, a nucleophilic substitution reaction occurs when the attacking reagent (the nucleophile) brings an electron pair to the substrate, using this pair to form the new bond, and the leaving group (the nucleofuge) comes away with the electron pair, leaving as an anionic intermediate. For a detailed discussion of the mechanism of aliphatic nucleophilic substitutions and a review of specific aliphatic nucleophilic substitution reactions see *Advanced Organic Chemistry, Reactions, Mechanisms, and Structure, 4th Addition*. Jerry March (Ed.), John Wiley & Sons, New York (1992) 293-500 and the references therein. Compounds of the formulae IVa, IVb, or IVc may, of course, be employed in the methods described herein (especially, in the treatment of nuclear hormone receptor-associated conditions) without undergoing further reaction of T or T'.

Scheme VIII

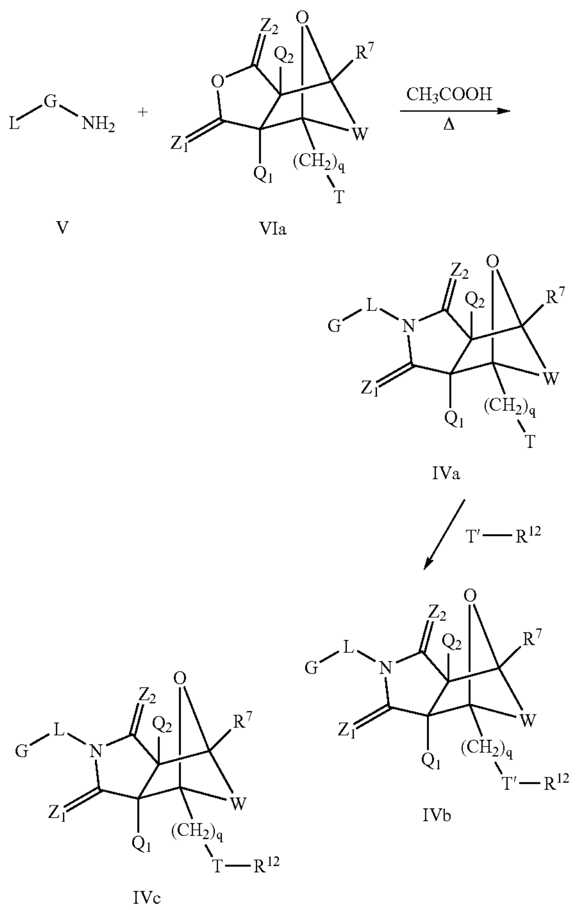

An alternate approach to compounds of formula IVa, IVb and IVc is illustrated in Scheme VIII. For this approach, techniques such as those described in Schemes II, III and IV can be applied to the preparation of an intermediate of formula VIa, where T and q are as defined in Scheme VII. The intermediate of formula VIa can be reacted with a substituted amine of formula V, as described in Scheme II, to yield the compound of formula IVa, which is a compound of formula I where Y is O, $A_2$ is $CR^7$ and $A_1$ is C—$(CH_2)_q$—T. The compound of formula IVa can be treated in the manner described in Scheme VII to obtain compounds of formula IVb or IVc which are compounds of formula I where Y is O, $A_2$ is $CR^7$ and $A_1$ is C—$(CH_2)_q$—T'—$R^{12}$ or C—$(CH_2)_q$—T—$R^{12}$, respectively.

Scheme IX

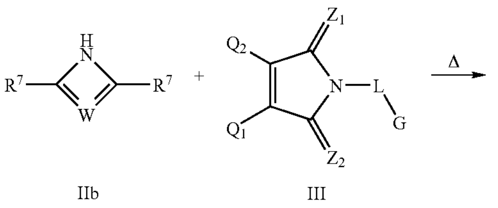

-continued

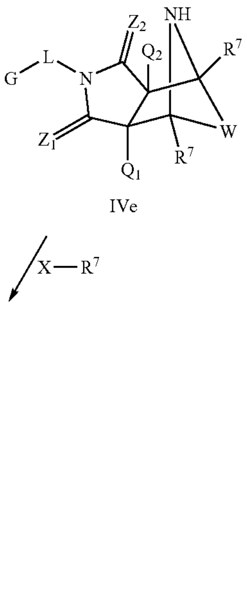

Scheme IX describes another approach to incorporating further substitution onto a compound of formula I. As illustrated in Scheme IX (where X is a leaving group), a diene of formula IIb can be reacted with a dienophile of formula III, as described in Scheme I, to yield a compound of formula IVe, which is a compound of formula I where Y is NH, and $A_1$ and $A_2$ are $CR^7$. The compound of formula IVe can be functionalized at the free amine by reacting with a variety of electrophilic agents such as acid halides or alkyl halides in the presence of base, for example by methods known by one skilled in the art and described in Scheme V, to yield a compound of formula IVf, which is a compound of formula I where Y is $NR^7$ and $A_1$ and $A_2$ are $CR^7$.

Scheme X

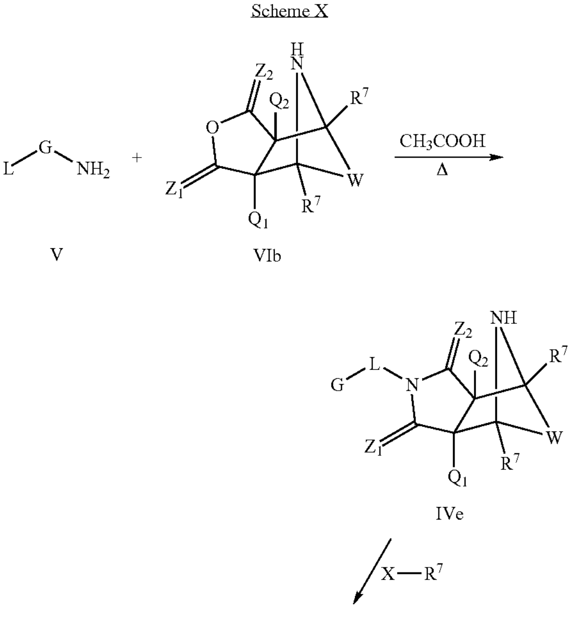

-continued

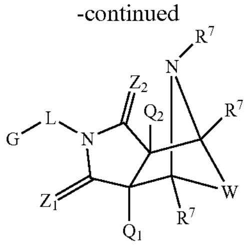

IVf

An alternate approach to compounds of formula IVe and IVf is illustrated in Scheme X. For this approach, techniques as described in Schemes II, III and IV can be applied to the preparation of an intermediate of formula VIb. The intermediate of formula VIb can be reacted with a substituted amine of formula V, as described in Scheme II, to yield a compound of formula IVe, which is a compound of formula I where Y is NH, and $A_1$ and $A_2$ are $CR^7$. The latter intermediate can be treated in the manner described in Scheme V to obtain a compound of formula IVf, which is a compound of formula I where Y is $NR^7$, and $A_1$ and $A_2$ are $CR^7$.

Scheme XI

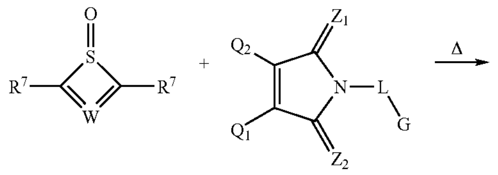

IIc III

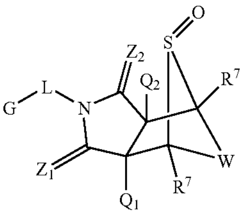

IVg

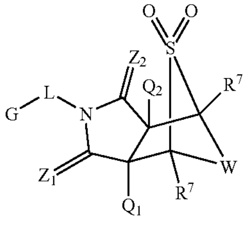

IVh

Scheme XI describes another approach to incorporating additional substitution onto a compound of formula I. As illustrated in Scheme XI, a diene of formula IIc can be reacted with a dienophile of formula III, as described in Scheme I, to yield a compound of formula IVg, which is a compound of formula I where Y is SO and $A_1$ and $A_2$ are $CR^7$. A compound of formula IVg can be treated with an oxidizing agent such as mCPBA, as described in Scheme VI, to yield a compound of formula IVh, which is a compound of formula I where Y is $SO_2$ and $A_1$ and $A_2$ are $CR^7$.

Scheme XII

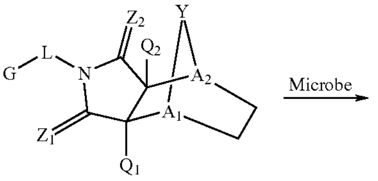

XV

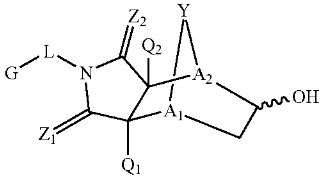

XVI

Scheme XII describes another approach to incorporating additional substitution onto a compound of formula I. As illustrated in Scheme XII, a compound of formula XV, which can be prepared in accordance with the above Schemes, can be incubated in the presence of a suitable enzyme or microorganism resulting in the formation of a hydroxylated analog of formula XVI. Such a process can be employed to yield regiospecific as well as enantiospecific incorporation of a hydroxyl group into a molecule of formula XV by a specific microorganism or by a series of different microorganisms. Such microorganisms can, for example, be bacterial, yeast or fungal in nature and can be obtained from distributors such as ATCC or identified for use in this method such as by methods known to one skilled in the art. Compound XVI is a compound of formula I where Y is as described above and $A_1$ and $A_2$ are preferably $CR^7$.

Scheme XIII

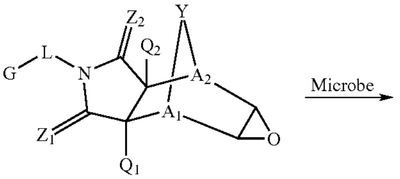

XVII

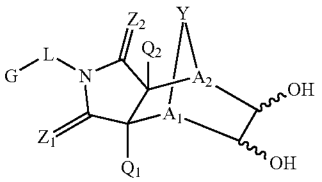

XVIII

Scheme XIII describes another approach to incorporating additional substitution onto a compound of formula I. As illustrated in Scheme XIII, a compound of formula XVII, which can be prepared in accordance with the above Schemes, can be incubated in the presence of a suitable enzyme or microorganism resulting in the formation of a diol analog of formula XVIII. Such a process can be employed to yield regiospecific as well as enantiospecific transformation of a compound of formula XVII to a 1-2 diol of formula XVIII by a specific microorganism or by a series of different microorganisms. Such microorganisms can, for example, be bacterial, yeast or fungal in nature and can be obtained from distributors such as ATCC or identified for use in this method such as by methods known to one skilled in the art. Compound XVIII is a compound of formula I where Y is as described above and $A_1$ and $A_2$ are preferably $CR^7$.

The present invention also provides the methods of Schemes XII and XIII.

Thus, in one embodiment, the present invention provides a method for preparation of a compound of the following formula XVI, or salt thereof:

XVI

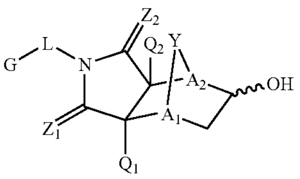

where the symbols are as defined herein, comprising the steps of contacting a compound of the following formula XV, or salt thereof:

XV

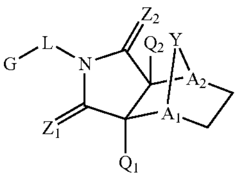

where the symbols are as defined above;

with an enzyme or microorganism capable of catalyzing the hydroxylation of said compound XV to form said compound XVI, and effecting said hydroxylation.

In another preferred embodiment, the present invention provides a method for preparation of a compound of the following formula XVIII, or salt thereof:

XVIII

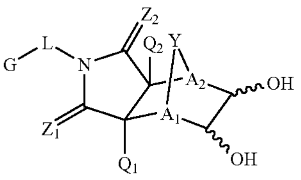

where the symbols are as defined herein, comprising the steps of contacting a compound of the following formula XVII, or salt thereof:

XVII

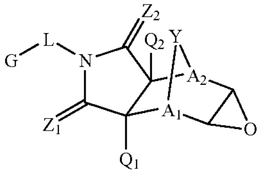

where the symbols are as defined above;

with an enzyme or microorganism capable of catalyzing the opening of the epoxide ring of compound XVII to form the diol of said compound XVIII, and effecting said ring opening and diol formation.

All stereoconfigurations of the unspecified chiral centers of the compounds of the formulae XV, XVI, XVII and XVIII are contemplated in the methods of the present invention, either alone (that is, substantially free of other stereoisomers) or in admixture with other stereoisomeric forms. Conversion of one isomer selectively (e.g., hydroxylation of the exo isomer preferentially to hydroxylation of the endo isomer) when contacting an isomeric mixture is a preferred embodiment of the invention. Conversion to one isomer selectively (e.g., hydroxylation on the exo face "exo isomer" preferentially to the endo face "endo isomer" or regioselective opening of an epoxide to form only one of two possible regioisomers of a trans diol) is a preferred embodiment of the invention. Hydroxylation of an achiral intermediate to form a single optical isomer of the hydroxylated product is also a preferred embodiment of the invention. Resolution of a recemic mixture of an intermediate by selective hydroxylation, or epoxide ring opening and diol formation, to generate one of the two possible optical isomers is also a preferred embodiment of the invention. The term "resolution" as used herein denotes partial, as well as, preferably, complete resolution.

The terms "enzymatic process" or "enzymatic method", as used herein, denote a process or method of the present invention employing an enzyme or microorganism. The term "hydroxylation", as used herein, denotes the addition of a hydroxyl group to a methylene group as described above. Hydroxylation can be achieved, for example, by contact with molecular oxygen according to the methods of the present invention. Diol formation can be achieved, for example, by contact with water according to the methods of the present invention. Use of "an enzyme or microorganism" in the present methods includes use of two or more, as well as a single, enzyme or microorganism.

The enzyme or microorganism employed in the present invention can be any enzyme or microorganism capable of catalyzing the enzymatic conversions described herein. The enzymatic or microbial materials, regardless of origin or purity, can be employed in the free state or immobilized on a support such as by physical adsorption or entrapment. Microorganisms or enzymes suitable for use in the present invention can be selected by screening for the desired activity, for example, by contacting a candidate microorganism or enzyme with a starting compound XV or XVII or salt thereof, and noting conversion to the corresponding compound XVI or XVIII or salt thereof. The enzyme may, for example, be in the form of animal or plant enzymes or mixtures thereof, cells of microorganisms, crushed cells, extracts of cells, or of synthetic origin.

Exemplary microorganisms include those within the genera: *Streptomyces* or *Amycolatopsis*. Particularly preferred microorganisms are those within the species *Streptomyces griseus*, especially *Streptomyces griseus* ATCC 10137, and *Amycolatopsis orientalis* such as ATCC 14930, ATCC 21425, ATCC 35165, ATCC 39444, ATCC 43333, ATCC 43490, ATCC 53550, ATCC 53630, and especially ATCC 43491. The term "ATCC" as used herein refers to the accession number of the American Type Culture Collection, 10801 University Blvd., Manassas Va. 20110-2209, the depository for the organism referred to. It should be understood that mutants of these organisms are also contemplated by the present invention, for use in the methods described herein, such as those modified by the use of chemical, physical (for example, X-rays) or biological means (for example, by molecular biology techniques).

Preferred enzymes include those derived from microorganisms, particularly those microorganisms described above. Enzymes may be isolated, for example, by extraction and purification methods such as by methods known to those of ordinary skill in the art. An enzyme may, for example, be used in its free state or in immobilized form. One embodiment of the invention is that where an enzyme is adsorbed onto a suitable carrier, e.g., diatomaceous earth (porous Celite Hyflo Supercel), microporous polypropylene (Enka Accurel® polypropylene powder), or a nonionic polymeric adsorbent such as Amberlite® XAD-2 (polystyrene) or XAD-7 (polyacrylate) from Rohm and Haas Co. When employed to immobilize an enzyme, a carrier may control the enzyme particle size and prevent aggregation of the enzyme particles when used in an organic solvent. Immobilization can be accomplished, for example, by precipitating an aqueous solution of the enzyme with cold acetone in the presence of the Celite Hyflo Supercel followed by vacuum drying, or in the case of a nonionic polymeric adsorbent, incubating enzyme solutions with adsorbent on a shaker, removing excess solution and drying enzyme-adsorbent resins under vacuum. While it is desirable to use the least amount of enzyme possible, the amount of enzyme required will vary depending upon the specific activity of the enzyme used.

Hydroxylation as described above can occur in vivo. For example, liver enzyme can selectively, relative to the endo isomer, hydroxylate the exo isomer of a compound of the present invention. In conducting the methods of the present invention outside the body, liver microsomal hydroxylase can be employed as the enzyme for catalysis.

These processes may also be carried out using microbial cells containing an enzyme having the ability to catalyze the conversions. When using a microorganism to perform the conversion, these procedures are conveniently carried out by adding the cells and the starting material to the desired reaction medium.

Where microorganisms are employed, the cells may be used in the form of intact wet cells or dried cells such as lyophilized, spray-dried or heat-dried cells, or in the form of treated cell material such as ruptured cells or cell extracts. Cell extracts immobilized on Celite® or Accurel® polypropylene as described earlier may also be employed. The use of genetically engineered organisms is also contemplated. The host cell may be any cell, e.g. *Escherichia coli*, modified to contain a gene or genes for expressing one or more enzymes capable of catalysis as described herein.

Where one or more microorganisms are employed, the enzymatic methods of the present invention may be carried out subsequent to the fermentation of the microorganism (two-stage fermentation and conversion), or concurrently therewith, that is, in the latter case, by in situ fermentation and conversion (single-stage fermentation and conversion).

Growth of the microorganisms can be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and elements (e.g. in trace amounts). Inducers may also be added. The term "inducer", as used herein, includes any compound enhancing formation of the desired enzymatic activity within the microbial cell.

Carbon sources can include sugars such as maltose, lactose, glucose, fructose, glycerol, sorbitol, sucrose, starch, mannitol, propylene glycol, and the like; organic acids such as sodium acetate, sodium citrate, and the like; and alcohols such as ethanol, propanol and the like.

Nitrogen sources can include N—Z amine A, corn steep liquor, soy bean meal, beef extracts, yeast extracts, molasses, baker's yeast, tryptone, nutrisoy, peptone, yeastamin, amino acids such as sodium glutamate and the like, sodium nitrate, ammonium sulfate and the like.

Trace elements can include magnesium, manganese, calcium, cobalt, nickel, iron, sodium and potassium salts. Phosphates may also be added in trace or, preferably, greater than trace amounts.

The medium employed can include more than one carbon or nitrogen source or other nutrient.

Preferred media for growth include aqueous media.

The agitation and aeration of the reaction mixture affects the amount of oxygen available during the conversion process when conducted, for example, in shake-flask cultures or fermentor tanks during growth of microorganisms.

Incubation of the reaction medium is preferably at a temperature between about 4 and about 60° C. The reaction time can be appropriately varied depending upon the amount of enzyme used and its specific activity. Reaction times may be reduced by increasing the reaction temperature and/or increasing the amount of enzyme added to the reaction solution.

It is also preferred to employ an aqueous liquid as the reaction medium, although an organic liquid, or a miscible or immiscible (biphasic) organic/aqueous liquid mixture, may also be employed. The amount of enzyme or microorganism employed relative to the starting material is selected to allow catalysis of the enzymatic conversions of the present invention.

Solvents for the organic phase of a biphasic solvent system may be any organic solvent immiscible in water, such as toluene, cyclohexane, xylene, trichlorotrifluoroethane and the like. The aqueous phase is conveniently of water, preferably deionized water, or a suitable aqueous buffer solution, especially a phosphate buffer solution. The biphasic solvent system preferably comprises between about 10 to 90 percent by volume of organic phase and between about 90 to 10 percent by volume of aqueous phase, and most preferably contains at or about 20 percent by volume of organic phase and at or about 80 percent by volume of the aqueous phase.

An exemplary embodiment of such processes starts with preparation of an aqueous solution of the enzyme(s) or microbes to be used. For example, the preferred enzyme(s) or microbes can be added to a suitable amount of an aqueous solvent, such as phosphate buffer or the like. This mixture is preferably adjusted to and maintained at a desired pH.

The compounds XVI and XVIII produced by the processes of the present invention can be isolated and purified, for example, by methods such as extraction, distillation, crystallization, and column chromatography.

Preferred Compounds

A preferred subgenus of the compounds of the present invention includes compounds of the formula I or salts thereof wherein one or more, preferably all, of the following substituents are as defined below:

G is an aryl or heterocyclo (e.g., heteroaryl) group, where said group is mono- or polycyclic, and which is optionally substituted at one or more positions, preferably with hydrogen, alkyl or substituted alkyl, alkenyl or substituted alkenyl, alkynyl or substituted alkynyl, halo, cycloalkyl or substituted cycloalkyl, cycloalkenyl or substituted cycloalkenyl, aryl or substituted aryl, heterocyclo or substituted heterocyclo, arylalkyl or substituted arylalkyl, heterocycloalkyl or substituted heterocycloalkyl, CN, $R^1OC{=}O$, $R^1C{=}O$, $R^1HNC{=}O$, $R^1R^2NC{=}O$, $HOCR^3R^{3'}$, nitro, $R^1OCH_2$, $R^1O$, $NH_2$, $NR^4R^5$, $S{=}OR^1$, $SO_2R^1$, $SO_2NR^1R^{1'}$, $(R^1)(R^{1'})P{=}O$, or $(R^{1'})(NHR^1)P{=}O$;

$Z_1$ is O, S, NH, or $NR^6$;

$Z_2$ is O, S, NH, or $NR^6$;

$A_1$ is $CR^7$ or N;

$A_2$ is $CR^7$ or N;

Y is J—J'—J" where J is $(CR^7R^{7'})n$ and n=0-3, J' is a bond or O, S, S═O, $SO_2$, NH, OC═O, C═O, $NR^7$, $CR^7R^{7'}$, $R^2P{=}O$, $R^2P{=}S$, $R^2P{=}O$, $R^2NHP{=}O$, $OP{=}OOR^2$, $OP{=}ONHR^2$, $OP{=}OR^2$, $OSO_2$, NHNH, $NHNR^6$, $NR^6NH$, N═N, cycloalkyl or substituted cycloalkyl, cycloalkenyl or substituted cycloalkenyl, or heterocyclo or substituted heterocyclo, and J" is $(CR^7R^{7'})n$ and n=0-3, where Y is not a bond;

W is $CR^7R^{7'}$—$R^7R^{7'}$, $CR^7R^{7'}$—C═O, $NR^9$—$CR^7R^{7'}$, $N{=}CR^8$, N═N, $NR^9$—$NR^{9'}$, cycloalkyl or substituted cycloalkyl, cycloalkenyl or substituted cycloalkenyl, heterocyclo or substituted heterocyclo, or aryl or substituted aryl, wherein, when W is not $NR^9$—$CR^7R^{7'}$, $N{=}CR^8$, N═N, $NR^9$—$NR^{9'}$, or heterocyclo or substituted heterocyclo, then J' must be O, S, S═O, $SO_2$, NH, $NR^7$, $OP{=}OOR^2$, $OP{=}ONHR^2$, $OSO_2$, NHNH, $NHNR^6$, $NR^6NH$, or N═N;

$Q_1$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^1OC{=}O$, $R^4C{=}O$, $R^5R^6NC{=}O$, $HOCR^7R^{7'}$, nitro, $R^1OCH_2$, $R^1O$, $NH_2$, or $NR^4R^5$;

$Q_2$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^1OC{=}O$, $R^4C{=}O$, $R^5R^6NC{=}O$, $HOCR^7R^{7'}$, nitro, $R^1OCH_2$, $R^1O$, $NH_2$, or $NR^4R^5$;

L is a bond, $(CR^7R^{7'})n$, NH, $NR^5$ or $NR^5(CR^7R^{7'})n$, where n=0-3;

$R^1$ and $R^{1'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl;

$R^2$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

$R^3$ and $R^{3'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, hydroxylamine, hydroxamide, alkoxy or substituted alkoxy, amino, $NR^1R^2$, thiol, alkylthio or substituted alkylthio;

$R^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C{=}O$, $R^1NHC{=}O$, or $SO_2NR^1R^{1'}$;

$R^5$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C{=}O$, $R^1NHC{=}O$, $SO_2R^1$, or $SO_2NR^1R^{1'}$;

$R^6$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, $OR^1$, $R^1C{=}O$, $R^1NHC{=}O$, $SO_2R^1$, or $SO_2NR^1R^{1'}$;

$R^7$ and $R^{7'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, $OR^4$, nitro, hydroxylamine, hydroxylamide, amino, $NHR^4$, $NR^2R^5$, $NOR^1$, thiol, alkylthio or substituted alkylthio, $R^1C{=}O$, $R^1(C{=}O)O$, $R^1OC{=}O$, $R^1NHC{=}O$, $SOR^1$, $PO_3R^1R^{1'}$, $R^1R^{1'}NC{=}O$, $C{=}OSR^1$, $SO_2R^1$, or $SO_2NR^1R^{1'}$;

$R^8$ and $R^{8'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, nitro, halo, CN, $OR^1$, amino, $NHR^4$, $NR^2R^5$, $NOR^1$, alkylthio or substituted alkylthio, $C{=}OSR^1$, $R^1OC{=}O$, $R^1C{=}O$, $R^1NHC{=}O$, $R^1R^{1'}NC{=}O$, $S{=}OR^1$, $SO_2R^1$, $PO_3R^1R^{1'}$, or $SO_2NR^1R^{1'}$;

$R^9$ and $R^{9'}$ are each independently H, alkyl or substituted alkyl, alkenyl or substituted alkenyl, alkynyl or substituted alkynyl; cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, $OR^1$, $R^1C{=}O$, $R^1OC{=}O$, $R^1NHC{=}O$, or $SO_2NR^1R^{1'}$;

especially where the groups W and Y of this preferred subgenus are also within the definitions of W' and Y' of formula Ia, with the provisos (1) to (14) of said formula Ia where appropriate to this subgenus, and most preferably where (i) when Y' is —O— and W' is $CR^7R^{7'}$—$CR^7R^{7'}$, $A_1$ and $A_2$ are not simultaneously CH; and (ii) when L is a bond, G is not an unsubstituted phenyl group.

Another, more preferred subgenus of the compounds of the invention includes compounds of the formula I or salts thereof wherein one or more, preferably all, of the following substituents are as defined below:

G is an aryl or heterocyclo (e.g., heteroaryl) group, where said group is mono- or polycyclic, and which is optionally substituted at one or more positions, preferably with hydrogen, alkyl or substituted alkyl, alkenyl or substituted alkenyl, alkynyl or substituted alkynyl, halo, cycloalkyl or substituted cycloalkyl, cycloalkenyl or substituted cycloalkenyl, aryl or substituted aryl, heterocyclo or substituted heterocyclo, arylalkyl or substituted arylalkyl, heterocycloalkyl or substituted heterocycloalkyl, CN, $R^1C{=}O$, $R^1HNC{=}O$, $R^1R^2NC{=}O$, $HOCR^3R^{3'}$, nitro, $R^1OCH_2$, $R^1O$, $NH_2$, $NR^4R^5$, $SO_2R^1$, or $SO_2NR^1R^{1'}$;

$Z_1$ is O;

$Z_2$ is O;

$A_1$ is $CR^7$;

$A_2$ is $CR^7$;

Y is J—J'—J" where J is $(CR^7R^{7'})n$ and n=0-3, J' is a bond or O, S, S=O, $SO_2$, NH, $NR^7$, $CR^7R^{7'}$, $R^2P{=}O$, $R^2P{=}S$, $R^2OP{-}O$, $R^2NHP{=}O$, $OP{=}OOR^2$, $OP{=}ONHR^2$, $OP{=}OR^2$, $OSO_2$, NHNH, $NHNR^6$, $NR^6NH$, N=N, cycloalkyl or substituted cycloalkyl, cycloalkenyl or substituted cycloalkenyl, or heterocyclo or substituted heterocyclo, and J" is $(CR^7R^{7'})n$ and n=0-3, where Y is not a bond;

W is $CR^7R^{7'}$—$CR^7R^{7'}$, $CR^7R^{7'}$—C=O, $NR^9$—$CR^7R^{7'}$, $N{=}CR^8$, N=N, $NR^9$—$NR^{9'}$, cycloalkyl or substituted cycloalkyl, cycloalkenyl or substituted cycloalkenyl, heterocyclo or substituted heterocyclo, or aryl or substituted aryl, wherein, when W is not $NR^9$—$CR^7R^{7'}$, $N{=}CR^8$, N=N, $NR^9$—$NR^{9'}$, or heterocyclo or substituted heterocyclo, then J' must be O, S, S=O, $SO_2$, NH, $NR^7$, $OP{=}OOR^2$, $OP{=}ONHR^2$, $OSO_2$, NHNH, $NHNR^6$, $NR^6NH$, or N=N;

$Q_1$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^4C{=}O$, $R^5R^6NC{=}O$, $HOCR^7R^{7'}$, nitro, $R^1OCH_2$, $R^1O$, $NH_2$, or $NR^4R^5$;

$Q_2$ is H, alkyl or substituted alkyl, alkenyl or substituted alkenyl, cycloalkyl or substituted cycloalkyl, cycloalkenyl or substituted cycloalkenyl, heterocycloalkyl or substituted heterocycloalkyl, arylalkyl or substituted arylalkyl, alkynyl or substituted alkynyl, aryl or substituted aryl, heterocyclo (e.g., heteroaryl) or substituted heterocyclo (e.g., substituted heteroaryl), halo, CN, $R^4C{=}O$, $R^5R^6NC{=}O$, $HOCR^7R^{7'}$, nitro, $R^1OCH_2$, $R^1O$, $NH_2$, or $NR^4R^5$;

L is a bond;

$R^1$ and $R^{1'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl;

$R^2$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl;

$R^3$ and $R^{3'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, alkoxy or substituted alkoxy, amino, $NR^1R^2$, alkylthio or substituted alkylthio;

$R^4$ is H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C{=}O$, $R^1NHC{=}O$, or $SO_2NR^1R^{1'}$;

$R^5$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, $R^1C{=}O$, $R^1NHC{=}O$, $SO_2R^1$, or $SO_2NR^1R^{1'}$;

$R^6$ is alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, $OR^1$, $R^1C{=}O$, $R^1NHC{=}O$, $SO_2R^1$, or $SO_2NR^1R^{1'}$;

$R^7$ and $R^{7'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, halo, CN, $OR^4$, nitro, amino, $NHR^4$, $NR^2R^5$, alkylthio or substituted alkylthio, $R^1C{=}O$, $R^1(C{=}O)O$, R1NHC=O, $SO_2R^1$, $R^1R^{1'}NC{=}O$, or $SO_2NR^1R^{1'}$;

$R^8$ and $R^{8'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkyalkyl, cycloalkenylalkyl or substituted cycloalkenylalkyl, heterocycloalkyl or substituted heterocycloalkyl, aryl or substituted aryl, arylalkyl or substituted arylalkyl, nitro, halo, CN, $OR^1$, amino, $NHR^4$, $NR^2R^5$, alkylthio or substituted alkylthio, $R^1C{=}O$, $R^1NHC{=}O$, $R^1R^{1'}NC{=}O$, $SO_2R^1$, or $SO_2NR^1R^{1'}$; and $R^9$ and $R^{9'}$ are each independently H, alkyl or substituted alkyl, alkenyl or substituted alkenyl, alkynyl or substituted alkynyl, cycloalkyl or substituted cycloalkyl, cycloalkenyl or substituted cycloalkenyl, heterocyclo or substituted heterocyclo, cycloalkylalkyl or substituted cycloalkylalkyl, cycloalkenylalkyl or substituted cycloalkenylalkyl, heterocycloalkyl or substituted heterocycloalkyl, aryl or substituted aryl, arylalkyl or substituted arylalkyl, CN, OH, $OR^1$, $R^1C{=}O$, $R^1NHC{=}O$, or $SO_2NR^1R^{1'}$;

especially where the groups W and Y of this preferred subgenus are also within the definitions of W' and Y'of formula Ia, with the provisos (1) to (14) of said formula Ia where appropriate to this subgenus, and most preferably where (i) when Y' is —O— and W' is $CR^7R^{7'}$—$CR^7R^{7'}$, $A_1$ and $A_2$ are not simultaneously CH; and (ii) when L is a bond, G is not an unsubstituted phenyl group.

A particularly preferred subgenus of the compounds of the invention includes compounds of the formula I or salts thereof wherein one or more, preferably all, of the substituents are as defined below:

G is an aryl (especially, phenyl or naphthyl) or heterocyclo (especially those heterocyclo groups G of the compounds of the Examples herein) group, where said group is mono- or polycyclic, and which is optionally substituted at one or more positions, preferably with substituents as exemplified in any of the compounds of the Examples herein;

L is a bond, $(CR^7R^{7'})$n (where n is 1 and $R^7$ and $R^{7'}$ are each independently H, alkyl or substituted alkyl), or —$CH_2$—NH—;

$A_1$ and $A_2$ are each independently $CR^7$ where $R^7$ (i) is hydrogen, alkyl or substituted alkyl, arylalkyl or substituted arylalkyl, alkenyl or substituted alkenyl (for example, alkenyl substituted with aryl (especially, phenyl or naphthyl) or substituted aryl, or alkenyl substituted with heterocyclo or substituted heterocyclo), aryl or substituted aryl, heterocyclo or substituted heterocyclo, heterocycloalkyl or substituted heterocycloalkyl, where, for each, preferred substituents are one or more groups selected from $V^1$ (especially $A_1$ and $A_2$ groups of the formula $CR^7$ where $R^7$ for each of $A_1$ and/or $A_2$ is independently selected from unsubstituted $C_{1-4}$ alkyl, or $C_{1-4}$ alkyl which alkyl is substituted by one or more groups $V_1$), or (ii) forms, together with $R^7$ of a group W (especially where W is $CR^7R^{7'}$—$CR^7R^{7'}$), a heterocyclic ring;

$V^1$ is OH, CN, halo, —O-aryl, —O-substituted aryl, —O-heterocyclo (e.g., —O— (optionally substituted pyridinyl) or —O-(optionally substituted pyrimidinyl)), —O-substituted heterocyclo, —O—CO-alkyl, —O—CO-substituted alkyl, —O-(alkylsilyl), —O-arylalkyl, —O-substituted arylalkyl, —O—CO-alkyl, —O—CO-substituted alkyl, —O—CO-arylalkyl, —O—CO-substituted arylalkyl, —O—CO-aryl, —O—CO-substituted aryl, —O—CO-heterocyclo, —O—CO-substituted heterocyclo, —S-(optionally substituted aryl)-NH—CO-(optionally substituted alkyl), —SO-(optionally substituted aryl)-NH—CO-(optionally substituted alkyl), —SO2-(optionally substituted aryl)-NH—CO-(optionally substituted alkyl), —NH—$SO_2$-aryl, —NH—$SO_2$-substituted aryl, —NH—CO—O-(optionally substituted arylalkyl), —NH—CO—O-alkyl, —NH—CO—O-substituted alkyl, —NH—CO-alkyl, —NH—CO-substituted alkyl, —NH—CO-aryl, —NH—CO-substituted aryl, —NH—CO-(optionally substituted arylalkyl), —NH—CO-(optionally substituted alkyl)-O-(optionally substituted aryl), —N(optionally substituted alkyl)(optionally substituted aryl), —N(optionally substituted alkyl)(optionally substituted arylalkyl), —COH, —COOH, —CO—O-alkyl, —CO—O-substituted alkyl, —CO—O-optionally substituted arylalkyl, —CO-aryl, —CO-substituted aryl, —O—CO—NH-aryl, —O—CO—NH-substituted aryl, —CO—NH-aryl, —CO—NH-substituted aryl, —CO—NH-arylalkyl, —CO—NH-substituted arylalkyl, —O-(optionally substituted aryl)-NH—CO-(optionally substituted alkyl);

Y is —O—, —SO—, —$N(V^2)$—, —$CH_2$—$N(V^2)$—, —CO—N(alkyl)-, —$CH_2$—S—, —$CH_2$—$SO_2$—;

$V^2$ is hydrogen, alkyl, arylalkyl, —CO-alkyl, —CO—O-aryl, —CO—O-arylalkyl;

W is $CR^7R^{7'}$—$CR^7R^{7'}$ (where $R^7$ and $R^{7'}$ are each independently selected from H, OH, alkyl or substituted alkyl (such as hydroxyalkyl), or where $R^7$ forms a heterocyclic ring together with $R^7$ of $A_1$ or $A_2$), $CR^8{=}CR^{8'}$ (where $R^8$ and $R^{8'}$ are each independently selected from H, alkyl or substituted alkyl (such as hydroxyalkyl)), $CR^7R^{7'}$—C=O (where $R^7$ and $R^{7'}$ are each hydrogen, or where $R^7$ forms a heterocyclic ring together with $R^7$ of $A_1$ or $A_2$), $N{=}CR^8$ (where $R^8$ is alkyl), cycloalkyl or substituted cyclalkyl, or heterocyclo or substituted heterocyclo;

$Z_1$ and $Z_2$ are O; and $Q_1$ and $Q_2$ are H.

Preferred G—L groups are optionally substituted phenyl, optionally substituted naphthyl and optionally substituted fused bicyclic heterocyclic groups such as optionally substituted benzo-fused heterocyclic groups (e.g., bonded to the remainder of the molecule through the benzene portion), especially such groups wherein the heterocyclic ring bonded to benzene has 5 members exemplified by benzoxazole, benzothiazole, benzothiadiazole, benzoxadiazole or benzothiophene, for example:

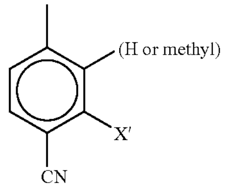

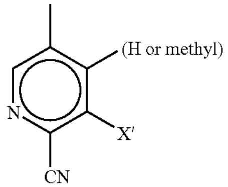

-continued

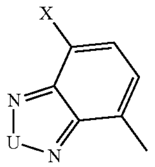

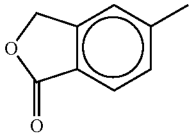

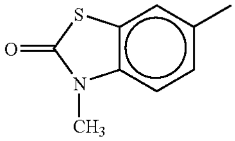

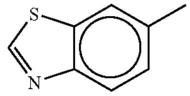

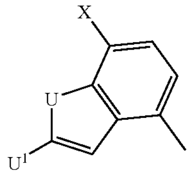

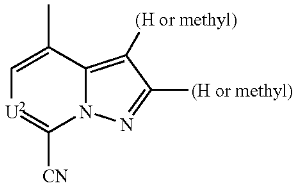

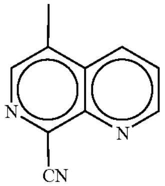

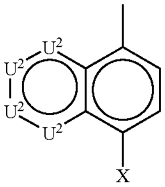

(e.g., 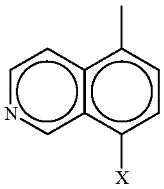 where X is OH or CN) or

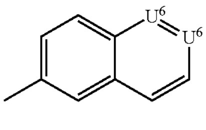

-continued

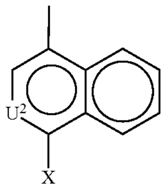

(e.g., 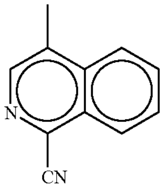 ) or

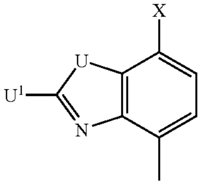

where

X=halo (especially F), OH, CN, $NO_2$ or

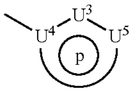

(e.g., 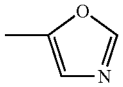 , 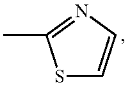 , or 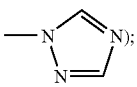);

X'=halo (especially Cl, F, or I), $CH_3$, $CF_3$, CN or $OCH_3$;

U is O or S (where S can optionally be oxygenated, e.g., to SO);

$U^1$ is $CH_3$ or $CF_3$;

each $U^2$ is independently N, CH or CF;

$U^3$ is N, O or S;

$U^4$ and $U^5$, together with the atoms to which they are bonded, form an optionally substituted 5-membered heterocyclic ring which can be partially unsaturated or aromatic and which contains 1 to 3 ring heteroatoms;

each $U^6$ is independently CH or N; and

denotes optional double bond(s) within the ring formed by $U^3$, $U^4$ and $U^5$.

An especially preferred subgenus includes compounds of the formula I having the following structure, or salts thereof:

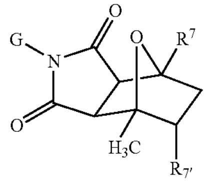

where G is an optionally substituted phenyl, naphthyl or benzo-fused bicyclic heterocyclic group, $R^7$ is $CH_3$ or $C_{1-4}$alkyl substituted by $V^1$, and one $R^{7'}$ is H or hydroxyl and the other is H.

Preferred compounds of the invention include:

[3aS-(3aα,4β,6β,7β,7aα)]-4-(Octahydro-6-hydroxy-4-methyl-1,3-dioxo-4,7-epoxy-2H-isoindol-2-yl)-2-(trifluoromethyl)benzonitrile;

[3aR-(3aα,4β,6β,7β,7aα)]-4-(Octahydro-6-hydroxy-4-methyl-1,3-dioxo-4,7-epoxy-2H-isoindol-2-yl)-2-(trifluoromethyl)benzonitrile;

[3aS-(3aα,4β,5β,6α,7β,7aα)]-4-(Octahydro-5,6-dihydroxy-4,7-dimethyl-1,3-dioxo-4,7-epoxy-2H-isoindol-2-yl)-2-(trifluoromethyl)benzonitrile;

[3aS-(3aα,4β,5β,7β,7aα)]-5-(Octahydro-5-hydroxy-4,7-dimethyl-1,3-dioxo-4,7-epoxy-2H-isoindol-2-yl)-3-methyl-2-pyridinecarbonitrile;

[3aS-(3aα,4β,5β,7β,7aα)]-2-(2,1,3-Benzoxadiazol-5-yl)hexahydro-5-hydroxy-4,7-dimethyl-4,7-epoxy-1H-isoindole-1,3(2H)-dione;

[3aS-(3aα,4β,5β,7β,7aα)]-5-(Octahydro-5-hydroxy-4,7-dimethyl-1,3-dioxo-4,7-epoxy-2H-isoindol-2-yl)-3,4-dimethyl-2-pyridinecarbonitrile;

[3aR-(3aα,4β,5β,7β,7aα)]-5-(Octahydro-5-hydroxy-4,7-dimethyl-1,3-dioxo-4,7-epoxy-2H-isoindol-2-yl)-3,4-dimethyl-2-pyridinecarbonitrile;

[3aS-(3aα,4β,5β,7β,7aα)]-2-(6-Benzothiazolyl)hexahydro-5-hydroxy-4,7-dimethyl-4,7-epoxy-1H-isoindole-1,3(2H)-dione;

[3aR-(3aα,4β,5β,7β,7aα)]-2-(7-Chloro-2,1,3-benzoxadiazol-4-yl)hexahydro-5-hydroxy-4,7-dimethyl-4,7-epoxy-1H-isoindole-1,3(2H)-dione;

[3aR-(3aα,4β,5α,7β,7aα)]-5-(Octahydro-5-hydroxy-4,7-dimethyl-1,3-dioxo-4,7-epoxy-2H-isoindol-2-yl)-3-(trifluoromethyl)-2-pyridinecarbonitrile;

[3aR-(3aα,4β,5α,7β,7aα)]-4-(Octahydro-5-hydroxy-4,7-dimethyl-1,3-dioxo-4,7-epoxy-2H-isoindol-2-yl)-2-iodobenzonitrile;

(3aα,4β,5α,6β,7β,7aα)-2-(4-Cyano-3-(trifluoromethyl)phenyl)hexahydro-6-cyano-4,7-dimethyl-1,3-dioxo-4,7-epoxy-1H-isoindole-5-carboxylic acid, methyl ester;

(3aα,4β,7β,7aα)-4-(Octahydro-4,7,8-trimethyl-1,3-dioxo-4,7-imino-2H-isoindol-2-yl)-2-(trifluoromethyl)benzonitrile;

[3aR-(3aα,4β,5β,6α,7β,7aα)]-4-(Octahydro-5,6-dichloro-4,7-dimethyl-1,3-dioxo-4,7-epoxy-2H-isoindol-2-yl)-2-(trifluoromethyl)benzonitrile;

[3aS-(3aα,4β,5β,6α,7β,7aα)]-4-(Octahydro-5,6-dichloro-4,7-dimethyl-1,3-dioxo-4,7-epoxy-2H-isoindol-2-yl)-2-(trifluoromethyl)benzonitrile;

(3aα,4β,7β,7aα)-4-(Octahydro-4,7-dimethyl-1,3,5-trioxo-4,7-epoxy-2H-isoindol-2-yl)-2-iodobenzonitrile;

(3aα,4β,5α,7β,7aα)-4-(Octahydro-5-[[[difluoromethyl]oxy]methyl]-4,7-dimethyl-1,3-dioxo-4,7-epoxy-2H-isoindol-2-yl)-2-(trifluoromethyl)benzonitrile;

(3aα,4β,5α,7β,7aα)-4-(Octahydro-5-[[phenylmethoxycarbonyl]amino]-4,7-dimethyl-1,3-dioxo-4,7-epoxy-2H-isoindol-2-yl)-2-(trifluoromethyl)benzonitrile;

(3aα,4β,5α,7β,7aα)-4-(Octahydro-5-[[propyloxycarbonyl]amino]-4,7-dimethyl-1,3-dioxo-4,7-epoxy-2H-isoindol-2-yl)-2-(trifluoromethyl)benzonitrile;

(3aα,4β,5α,7β,7aα)-4-(Octahydro-5-[[[cyclopropylmethyloxy]carbonyl]amino]-4,7-dimethyl-1,3-dioxo-4,7-epoxy-2H-isoindol-2-yl)-2-(trifluoromethyl)benzonitrile;

(3aα,4β,5α,7β,7aα)-4-(Octahydro-5-[[methoxycarbonyl]amino]-4,7-dimethyl-1,3-dioxo-4,7-epoxy-2H-isoindol-2-yl)-2-(trifluoromethyl)benzonitrile;

[3aR-(3aα,4β,5β,7β,7aα)]-4-(Octahydro-5-hydroxy-4,7-dimethyl-1,3-dioxo-4,7-epoxy-2H-isoindol-2-yl)-2,3-dichlorobenzonitrile;

[3aR-(3aα,4β,4aα,5aα,6β,7aα)]-4-(Octahydro-4a-hydroxy-4,6-dimethyl-1,3-dioxo-4,6-epoxycycloprop[f]isoindol-2(1H)-yl)-2-(trifluoromethyl)benzonitrile;

(3aα,4β,5α,7β,7aα)-2-(4-Cyano-3-(trifluoromethyl)phenyl)hexahydro-5-hydroxy-4,7-dimethyl-1,3-dioxo-4,7-epoxy-N,N-dimethyl-1H-isoindole-5-carboxamide;

[3aR-(3aα,4β,5β,6β,7β,7aα)]-4-(Octahydro-5-chloro-6-hydroxy-4,7-dimethyl-1,3-dioxo-4,7-epoxy-2H-isoindol-2-yl)-2-(trifluoromethyl)benzonitrile;

[3aS-(3aα,4β,5β,6β,7β,7aα)]-4-(Octahydro-5-chloro-6-hydroxy-4,7-dimethyl-1,3-dioxo-4,7-epoxy-2H-isoindol-2-yl)-2-(trifluoromethyl)benzonitrile;

(3aα,4β,5α,7β,7aα)-4-(Octahydro-5-[[[6-(trifluoromethyl)-4-pyrimidinyl]oxy]methyl]-4,7-dimethyl-1,3-dioxo-4,7-epoxy-2H-isoindol-2-yl)-2-(trifluoromethyl)benzonitrile;

(3aα,4β,5α,7β,7aα)-4-(Octahydro-5-[[[5-chloro-2-pyridinyl]oxy]methyl]-4,7-dimethyl-1,3-dioxo-4,7-epoxy-2H-isoindol-2-yl)-2-(trifluoromethyl)benzonitrile;

[3aR-(3aα,4β,5α,7β,7aα)]-4-(Octahydro-5-[[[phenylamino]carbonyl]amino]-4,7-dimethyl-1,3-dioxo-4,7-epoxy-2H-isoindol-2-yl)-2-(trifluoromethyl)benzonitrile;

[3aR-(3aα,4β,5a,7β,7aα)]-4-(Octahydro-5-[[(1-methylethyloxy)carbonyl]amino]-4,7-dimethyl-1,3-dioxo-4,7-epoxy-2H-isoindol-2-yl)-2-(trifluoromethyl)benzonitrile;

(3aα,4β,5α,7β,7aα)-4-(Octahydro-5-[[[5-fluoro-4-pyrimidinyl]oxy]methyl]-4,7-dimethyl-1,3-dioxo-4,7-epoxy-2H-isoindol-2-yl)-2-(trifluoromethyl)benzonitrile;

[3aR-(3aα,4β,5α,7β,7aα)]-4-(Octahydro-5-[[ethyloxycarbonyl]amino]-4,7-dimethyl-1,3-dioxo-4,7-epoxy-2H-isoindol-2-yl)-2-(trifluoromethyl)benzonitrile;

[3aR-(3aα,4β,5α,7β,7aα)]-2-(4-Cyano-3-(trifluoromethyl)phenyl)-hexahydro-4,7-dimethyl-1,3-dioxo-4,7-epoxy-1H-isoindole-5-carboxylic acid, 4-pyridinylmethyl ester;

[3aR-(3aα,4β,5α,7β,7aα)]-4-(Octahydro-5-[[4-pyridinylmethoxycarbonyl]amino]-4,7-dimethyl-1,3-dioxo-4,7-epoxy-2H-isoindol-2-yl)-2-(trifluoromethyl)benzonitrile;

3aα,4β,5β,7β,7aα)-4-(Octahydro-5-[[[2-methyl-5-(trifluoromethyl)-2H-pyrazol-3-yl]oxy]methyl]-5-hydroxy-4,7-dimethyl-1,3-dioxo-4,7-epoxy-2H-isoindol-2-yl)-2-(trifluoromethyl)benzonitrile;

(3aα,4β,5α,7β,7aα)-2-(4-Cyano-3-(trifluoromethyl)phenyl)hexahydro-4,7-dimethyl-1,3-dioxo-4,7-epoxy-1H-isoindole-5-carboxylic acid, methyl ester;

[3aR-(3aα,4β,5β,7β,7aα)]-4-(Octahydro-5-cyclopropylmethoxy-4,7-dimethyl-1,3-dioxo-4,7-epoxy-2H-isoindol-2-yl)-2-(trifluoromethyl)benzonitrile;

(3aα,4β,5α,7β,7aα)-4-(Octahydro-5-[[((phenylmethyl)amino)carbonyl]oxy]-4,7-dimethyl-1,3-dioxo-4,7-epoxy-2H-isoindol-2-yl)-2-(trifluoromethyl)benzonitrile; and

[3aR-(3aα,4β,5β,7β,7aα)]-4-(Octahydro-5-cyclopropyloxy-4,7-dimethyl-1,3-dioxo-4,7-epoxy-2H-isoindol-2-yl)-2-(trifluoromethyl)benzonitrile;

or pharmaceutically acceptable salts, solvates, prodrugs or stereoisomers thereof.

More preferred compounds of the invention include:

[3aR-(3aα,4β,5β,7β,7aα)]-5-(Octahydro-5-hydroxy-4,7-dimethyl-1,3-dioxo-4,7-epoxy-2H-isoindol-2-yl)-3-(trifluoromethyl)-2-pyridinecarbonitrile;

[3aS-(3aα,4β,5β,7β,7aα)]-5-(Octahydro-5-hydroxy-4,7-dimethyl-1,3-dioxo-4,7-epoxy-2H-isoindol-2-yl)-3-(trifluoromethyl)-2-pyridinecarbonitrile;

[3aR-(3aαx,4β,5β,7β,7aα)]-2-(4-Chloro-3-iodophenyl)hexahydro-5-hydroxy-4,7-dimethyl-4,7-epoxy-1H-isoindole-1,3(2H)-dione;

[3aS-(3aα,4β,5β,6α,7β,7aα)]-4-(Octahydro-5,6-dihydroxy-4,7-dimethyl-1,3-dioxo-4,7-epoxy-2H-isoindol-2-yl)-2-(trifluoromethyl)benzonitrile;

[3aR-(3aα,4β,7β,7aα)]-4-(Octahydro-4,7-dimethyl-1,3,5-trioxo-4,7-epoxy-2H-isoindol-2-yl)-2-(trifluoromethyl)benzonitrile;

[3aR-(3aα,4β,5α,7β,7aα)]-4-(Octahydro-5-hydroxy-4,7-dimethyl-1,3-dioxo-4,7-epoxy-2H-isoindol-2-yl)-2-(trifluoromethyl)benzonitrile;

[3aS-(3aα,4β,5α,7β,7aα)]-4-(Octahydro-5-hydroxy-4,7-dimethyl-1,3-dioxo-4,7-epoxy-2H-isoindol-2-yl)-2-(trifluoromethyl)benzonitrile;

[3aS-(3aα,4β,6β,7β,7aα)]-4-(Octahydro-6-hydroxy-4-methyl-1,3-dioxo-4,7-epoxy-2H-isoindol-2-yl)-2-(trifluoromethyl)benzonitrile;

[3aR-(3aα,4β,5β,7β,7aα)]-2-(4-Chloro-3-(trifluoromethyl)phenyl)hexahydro-5-hydroxy-4,7-dimethyl-4,7-epoxy-1H-isoindole-1,3(2H)-dione;

[3aS-(3aα,4β,5β,7β,7aα)]-4-(Octahydro-5-hydroxy-4,7-dimethyl-1,3-dioxo-4,7-epoxy-2H-isoindol-2-yl)-2-iodobenzonitrile;

[3aR-(3aα,4β,5β,7β,7aα)]-4-(Octahydro-5-hydroxy-4,7-dimethyl-1,3-dioxo-4,7-epoxy-2H-isoindol-2-yl)-2-iodobenzonitrile;

[3aS-(3aα,4β,5β,7β,7aα)]-2-(4-Chloro-3-(trifluoromethyl)pyridinyl)hexahydro-5-hydroxy-4,7-dimethyl-4,7-epoxy-1H-isoindole-1,3(2H)-dione;

[3aR-(3aα,4β,5β,7β,7aα)]-4-(Octahydro-5-hydroxy-4,7-dimethyl-1,3-dioxo-4,7-epoxy-2H-isoindol-2-yl)-3-methyl-2-(trifluoromethyl)benzonitrile;

[3aR-(3aα,4β,5β,7β,7aα)]-4-(Octahydro-5-methoxy-4,7-dimethyl-1,3-dioxo-4,7-epoxy-2H-isoindol-2-yl)-2-(trifluoromethyl)benzonitrile;

[3aR-(3aα,4β,5α,7β,7aα)]-5-(Octahydro-5-hydroxy-4,7-dimethyl-1,3-dioxo-4,7-epoxy-2H-isoindol-2-yl)-3-(trifluoromethyl)-2-pyridinecarbonitrile;

[3aS-(3aα,4β,5β7β,7aα)]-4-(Octahydro-5-methoxy-4,7-dimethyl-1,3-dioxo-4,7-epoxy-2H-isoindol-2-yl)-2-(trifluoromethyl)benzonitrile;

[3aS-(3aα,4β,6β,7β,7aα)]-4-(Octahydro-6-fluoro-5,5-dihydroxy-4,7-dimethyl-1,3-dioxo-4,7-epoxy-2H-isoindol-2-yl)-2-(trifluoromethyl)benzonitrile;

[3aR-(3aα,4β,7β,7aα)]-5-(Octahydro-4,7-dimethyl-1,3,5-trioxo-4,7-epoxy-2H-isoindol-2-yl)-3-(trifluoromethyl)-2-pyridinecarbonitrile;

[3aS-(3aα,4β,5β,7β,7aα)]-2-(4-Chloro-2-methyl-3-(trifluoromethyl)phenyl)hexahydro-5-hydroxy-4,7-dimethyl-4,7-epoxy-1H-isoindole-1,3(2H)-dione;

[3aR-(3aα,4β,5β,7β,7aα)]-2-(4-Chloro-2-methyl-3-(trifluoromethyl)phenyl)hexahydro-5-hydroxy-4,7-dimethyl-4,7-epoxy-1H-isoindole-1,3(2H)-dione;

(3aα,4β,6β,7β,7aα)-4-(Octahydro-6-fluoro-5,5-dihydroxy-4,7-dimethyl-1,3-dioxo-4,7-epoxy-2H-isoindol-2-yl)-2-iodobenzonitrile;

(3aα,4β,5α,7β,7aα)-2-(4-Cyano-3-(trifluoromethyl)phenyl)-hexahydro-5-hydroxy-4,7-dimethyl-1,3-dioxo-4,7-epoxy-1H-isoindole-5-carboxylic acid, methyl ester;

[3aS-(3aα,4β,6β,7β,7aα)]-4-(Octahydro-6-fluoro-5,5-dihydroxy-4,7-dimethyl-1,3-dioxo-4,7-epoxy-2H-isoindol-2-yl)-2-iodobenzonitrile;

(3aα,4β,5α,7β,7aα)-4-(Octahydro-5-ethylsulfonamido-4,7-dimethyl-1,3-dioxo-4,7-epoxy-2H-isoindol-2-yl)-2-(trifluoromethyl)benzonitrile;

[3aR-(3aα,4β,5α,7β,7aα)]-4-(Octahydro-5-[[(4-fluorophenylamino)carbonyl]oxy]-4,7-dimethyl-1,3-dioxo-4,7-epoxy-2H-isoindol-2-yl)-2-(trifluoromethyl)benzonitrile;

[3aR-(3aα,4β,5α,7β,7aα)]-4-(Octahydro-5-[[(1-methylethylamino)carbonyl]oxy]-4,7-dimethyl-1,3-dioxo-4,7-epoxy-2H-isoindol-2-yl)-2-(trifluoromethyl)benzonitrile;

[3aS-(3aα,4β,5α,7β,7aα)]-4-(Octahydro-5-[[(1-methylethoxy)carbonyl]amino]-4,7-dimethyl-1,3-dioxo-4,7-epoxy-2H-isoindol-2-yl)-2-(trifluoromethyl)benzonitrile;

[3aR-(3aα,4β,6β,7β,7aα)]-4-(Octahydro-6-fluoro-5,5-dihydroxy-4,7-dimethyl-1,3-dioxo-4,7-epoxy-2H-isoindol-2-yl)-2-iodobenzonitrile;

[3aR-(3aα,4β,5α,7β,7aα)]-2-(4-Cyano-3-(trifluoromethyl)phenyl)hexahydro-4,7-dimethyl-1,3-dioxo-4,7-epoxy-N-methyl-N-phenyl-1H-isoindole-5-carboxamide;

[3aR-(3aα,4β,5β,7β,7aα)]-4-(Octahydro-5-hydroxy-4,7-dimethyl-1,3-dioxo-4,7-epoxy-2H-isoindol-2-yl)-2-chloro-3-methylbenzonitrile;

[3aR-(3aα,4β,5α,7β,7aα)]-4-(Octahydro-5-[[ethoxycarbonyl]amino]-4,7-dimethyl-1,3-dioxo-4,7-epoxy-2H-isoindol-2-yl)-2-(trifluoromethyl)benzonitrile;

(3aα,4β,5α,7β,7aα)-4-(Octahydro-5-[[[2-methyl-5-(trifluoromethyl)-2H-pyrazol-3-yl]oxy]methyl]-4,7-dimethyl-1,3-dioxo-4,7-epoxy-2H-isoindol-2-yl)-2-(trifluoromethyl)benzonitrile;

[3aS-(3aα,4β,5α,6β,7β,7aα)]-2-(4-Cyano-3-(trifluoromethyl)phenyl)-hexahydro-6-hydroxy-4,7-dimethyl-1,3-dioxo-4,7-epoxy-1H-isoindole-5-carboxylic acid, methyl ester;

(3aα,4β,5α,7β,7aα)-4-(Octahydro-5-[[[6-(trifluoromethyl)-4-pyrimidinyl]oxy]methyl]-4,7-dimethyl-1,3-dioxo-4,7-epoxy-2H-isoindol-2-yl)-2-(trifluoromethyl)benzonitrile;

[3aR-(3aα,4β,5α,7β,7aα)]-4-(Octahydro-5-methoxy-4,7-dimethyl-1,3-dioxo-4,7-epoxy-2H-isoindol-2-yl)-2-(trifluoromethyl)benzonitrile;

(3aα,4β,5α,7β,7aα)-2-(4-Cyano-3-(trifluoromethyl)phenyl)-hexahydro-4,7-dimethyl-1,3-dioxo-4,7-epoxy-1H-isoindole-5-carbonitrile;

[3aR-(3aα,4β,5β,6α,7β,7aα)]-4-(Octahydro-5,6-dihydroxy-4,7-dimethyl-1,3-dioxo-4,7-epoxy-2H-isoindol-2-yl)-3-methyl-2-(trifluoromethyl)benzonitrile;

[3aR-(3aα,4β,5α,7β,7aα)]-4-(Octahydro-5-[[[(cyclopropylmethyl)amino]carbonyl]amino]-4,7-dimethyl-1,3-dioxo-4,7-epoxy-2H-isoindol-2-yl)-2-(trifluoromethyl)benzonitrile;

[3aR-(3aα,4β,5α,7β,7aα)]-4-(Octahydro-5-[[(dimethylamino)sulfonyl]amino]-4,7-dimethyl-1,3-dioxo-4,7-epoxy-2H-isoindol-2-yl)-2-(trifluoromethyl)benzonitrile;

(3aα,4β,5α,7β,7aα)-4-(Octahydro-5-benzenesulfonamido-4,7-dimethyl-1,3-dioxo-4,7-epoxy-2H-isoindol-2-yl)-2-(trifluoromethyl)benzonitrile;

[3aR-(3aα,4β,6β,7β,7aα)]-4-(Octahydro-6-fluoro-5,5-dihydroxy-4,7-dimethyl-1,3-dioxo-4,7-epoxy-2H-isoindol-2-yl)-2-(trifluoromethyl)benzonitrile;

[3aR-(3aα,4β,5α,6β,7β,7aα)]-2-(4-Cyano-3-(trifluoromethyl)phenyl)-hexahydro-6-hydroxy-4,7-dimethyl-1,3-dioxo-4,7-epoxy-1H-isoindole-5-carboxylic acid, methyl ester; and

[3aR-(3aα,4β,5α,7β,7aα)]-4-(Octahydro-5-[[(dimethylamino)sulfonyl]amino]-4,7-dimethyl-1,3-dioxo-4,7-epoxy-2H-isoindol-2-yl)-2-(trifluoromethyl)benzonitrile;

or pharmaceutically acceptable salts, solvates, prodrugs or stereoisomers thereof.

Compounds where $R^{7'}$ is hydroxyl can provide enhanced water solubility and metabolic stability, relative to the corresponding compounds where $R^{7'}$ is H, in addition to having good permeability and high systemic blood levels. These hydroxyl-bearing compounds can be obtained in vivo by metabolism of the corresponding compound where $R^{7'}$ is H, as well as by synthetic preparative methods such as those described herein.

Use and Utility

The compounds of the present invention modulate the function of nuclear hormone receptors (NHR), and include compounds which are, for example, agonists, partial agonists, antagonists or partial antagonists of the androgen receptor (AR), the estrogen receptor (ER), the progesterone receptor (PR), the glucocorticoid receptor (GR), the mineralocorticoid receptor (MR), the steroid and xenobiotic receptor (SXR), other steroid binding NHR's, the Orphan receptors or other NHR's. Selective modulation of one such NHR relative to others within the NHR family is preferred. "Modulation" includes, for example, activation (e.g., agonist activity such as selective androgen receptor agonist activity) or inhibition (e.g., antagonist activity).

The present compounds are thus useful in the treatment of NHR-associated conditions. A "NHR-associated condition", as used herein, denotes a condition or disorder which can be treated by modulating the function of a NHR in a subject, wherein treatment comprises prevention (e.g., prophylactic treatment), partial alleviation or cure of the condition or disorder. Modulation may occur locally, for example, within certain tissues of the subject, or more extensively throughout a subject being treated for such a condition disorder.

The compounds of the present invention are useful for the treatment of a variety of conditions and disorders including, but not limited to, those described following:

Compounds of formula I can be applied as agonists, partial agonists, antagonists, or partial antagonists of the estrogen receptor, preferably selectively to that receptor, in an array of medical conditions which involve modulation of the estrogen receptor pathway. Applications of said compounds include but are not limited to: osteoporosis, hot flushes, vaginal dryness, prostate cancer, breast cancer, endometrial cancer, cancers expressing the estrogen receptor such as the aforementioned cancers and others, contraception, pregnancy termination, menopause, amennoreahea, and dysmennoreahea.

Compounds of formula I can be applied as agonists, partial agonists, antagonists or partial antagonists of the progesterone receptor, preferably selectively to that receptor, in an array of medical conditions which involve modulation of the progesterone receptor pathway. Applications of said compounds include but are not limited to: breast cancer, other cancers containing the progesterone receptor, endometriosis, cachexia, contraception, menopause, cyclesynchrony, meniginoma, dysmennoreahea, fibroids, pregnancy termination, labor induction and osteoporosis.

Compounds of formula I can be applied as agonists, partial agonists, antagonists or partial antagonists of the glucocorticoid receptor, preferably selectively to that receptor, in an array of medical conditions which involve modulation of the glucocorticoid receptor pathway. Applications of said compounds include but are not limited to: inflammatory diseases, autoimmune diseases, prostate cancer, breast cancer, Alzheimer's disease, psychotic disorders, drug dependence, non-insulin dependent Diabetes Mellitus, and as dopamine receptor blocking agents or otherwise as agents for the treatment of dopamine receptor mediated disorders.

Compounds of formula I can be applied as agonists, partial agonists, antagonists or partial antagonists of the mineralocorticoid receptor, preferably selectively to that receptor, in an array of medical conditions which involve modulation of the mineralocorticoid receptor pathway. Applications of said compounds include but are not limited to: drug withdrawal syndrome and inflammatory diseases.

Compounds of formula I can be applied as agonists, partial agonists, antagonists or partial antagonists of the aldosterone receptor, preferably selectively to that receptor, in an array of medical conditions which involve modulation of the aldosterone receptor pathway. One application of said compounds includes but is not limited to: congestive heart failure.

Compounds of formula I can be applied as agonists, partial agonists, antagonists or partial antagonists of the androgen receptor, preferably selectively to that receptor, in an array of medical conditions which involve modulation of the androgen receptor pathway. Applications of said compounds include but are not limited to: hirsutism, acne, seborrhea, Alzheimer's disease, androgenic alopecia, hypogonadism, hyperpilosity, benign prostate hypertrophia, adenomas and neoplasies of the prostate (such as advanced metastatic prostate cancer), treatment of benign or malignant tumor cells containing the androgen receptor such as is the case for breast, brain, skin, ovarian, bladder, lymphatic, liver and kidney cancers, pancreatic cancers modulation of VCAM expression and applications therein for the treatment of heart disease, inflammation and immune modulations, modulation of VEGF expression and the applications therein for use as antiangiogenic agents, osteoporosis, suppressing spermatogenesis, libido, cachexia, endometriosis, polycystic ovary syndrome, anorexia, androgen supplement for age related decreased testosterone levels in men, male menopause, male hormone replacement, male and female sexual dysfunction, and inhibition of muscular atrophy in ambulatory patients. For example, pan AR modulation is contemplated, with prostate selective AR modulation ("SARM") being particularly preferred, such as for the treatment of early stage prostate cancers.

Compounds of formula I can be applied as (preferably, selective) antagonists of the mutated androgen receptor, for example, found in many tumor lines. Examples of such mutants are those found in representative prostate tumor cell lines such as LNCap, (T877A mutation, Biophys. Acta, 187, 1052 (1990)), PCa2b, (L701H & T877A mutations, J. Urol., 162, 2192 (1999)) and CWR22, (H874Y mutation, Mol. Endo., 11, 450 (1997)). Applications of said compounds include but are not limited to: adenomas and neoplasies of the prostate, breast cancer and endometrial cancer.

Compounds of formula I can be applied as agonists, partial agonists, antagonists or partial antagonists of the steroid and xenobiotic receptor, preferably selectively to that receptor, in an array of medical conditions which involve modulation of the steroid and xenobiotic receptor pathway. Applications of said compounds include but are not limited to: treatment of disregulation of cholesterol homeostasis, attenuation of metabolism of pharmaceutical agents by co-administration of an agent (compound of the present invention) which modulates the P450 regulator effects of SXR.

Along with the aforementioned NHR, there also exist a number of NHR for which the activating or deactivating ligands may not be characterized. These proteins are classified as NHR due to strong sequence homology to other NHR, and are known as the Orphan receptors. Because the Orphan receptors demonstrate strong sequence homology to other NHR, compounds of formula I include those which serve as modulators of the function of the Orphan NHR. Orphan receptors which are modulated by NHR modulators such as compounds within the scope of formula I are exemplified, but not limited to, those listed in Table 1. Exemplary therapeutic applications of modulators of said Orphan receptors are also listed in Table 1, but are not limited to the examples therein.

TABLE 1

Exemplary Orphan nuclear hormone receptors, form (M = monomeric, D = heterodimeric, H = homodimeric), tissue expression and target therapeutic applications. (CNS = central nervous system)

| Receptor | Form | Tissue Expression | Target Therapeutic Application |
|---|---|---|---|
| NURR1 | M/D | Dopaminergic Neurons | Parkinson's Disease |
| RZRβ | M | Brain (Pituitary), Muscle | Sleep Disorders |
| RORα | M | Cerebellum, Purkinje Cells | Arthritis, Cerebellar Ataxia |
| NOR-1 | M | Brain, Muscle, Heart, Adrenal, Thymus | CNS Disorders, Cancer |
| NGFI-Bβ | M/D | Brain | CNS Disorders |
| COUP-Tfα | H | Brain | CNS Disorders |
| COUP-TFβ | H | Brain | CNS Disorders |
| COUP-TFγχ | H | Brain | CNS Disorders |
| Nur77 | H | Brain, Thymus, Adrenals | CNS Disorders |
| Rev-ErbAα | H | Muscle, Brain (Ubiquitous) | Obesity |
| HNF4α | H | Liver, Kidney, Intestine | Diabetes |
| SF-1 | M | Gonads, Pituitary | Metabolic Disorders |
| LXRα, β | D | Kidney (Ubiquitous) | Metabolic Disorders |
| GCNF | M/H | Testes, Ovary | Infertility |
| ERRα, β | M | Placenta, Bone | Infertility, Osteoporosis |
| FXR | D | Liver, Kidney | Metabolic Disorders |
| CARα | H | Liver, Kidney | Metabolic Disorders |
| PXR | H | Liver, Intestine | Metabolic Disorders |
| COUP-TF2 (ARP1) | D | Testis | Oncology/angiogenesis |
| RORbeta | M | CNS, retina, pineal gland | Metabolic Disorders |

The present invention thus provides methods for the treatment of NHR-associated conditions, comprising the step of administering to a subject in need thereof at least one compound of formula I in an amount effective therefor. Other therapeutic agents such as those described below may be employed with the inventive compounds in the present methods (for example, separately, or formulated together as a fixed dose). In the methods of the present invention, such other therapeutic agent(s) can be administered prior to, simultaneously with or following the administration of the compound(s) of the present invention.

The present invention also provides pharmaceutical compositions comprising at least one of the compounds of the formula I capable of treating a NHR-associated condition in an amount effective therefor, and a pharmaceutically acceptable carrier (vehicle or diluent). The compositions of the present invention can contain other therapeutic agents as described below, and can be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

It should be noted that the compounds of the present invention are, without limitation as to their mechanism of action, useful in treating any of the conditions or disorders listed or described herein such as inflammatory diseases or cancers, or other proliferate diseases, and in compositions for treating such conditions or disorders. Such conditions and disorders include, without limitation, any of those described previously, as well as those described following such as: maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic malagia; treatment of acute fatigue syndrome and muscle loss following elective surgery (e.g., post-surgical rehabilitation); acceleration of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olfaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength; and the conditions, diseases, and maladies collectively referenced to as "Syndrome X" or Metabolic Syndrome as detailed in Johannsson *J. Clin. Endocrinol. Metab.,* 82, 727-34 (1997).

The present compounds have therapeutic utility in the modulation of immune cell activation/proliferation, e.g., as competitive inhibitors of intercellular ligand/receptor binding reactions involving CAMs (Cellular Adhesion Molecules) and Leukointegrins. For example, the present compounds modulate LFA-ICAM 1, and are particularly useful as LFA-ICAM 1 antagonists, and in the treatment of all conditions associated with LFA-ICAM 1 such as immunological disorders. Preferred utilities for the present compounds include, but are not limited to: inflammatory conditions such as those resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukopheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The present compounds can be used in treating asthma or as an adjunct to minimize toxicity with cytokine therapy in the treatment of cancers. The present compounds can be employed in the treatment of all diseases currently treatable through steroid therapy. The present compounds may be employed for the treatment of these and other disorders alone or with other immunosuppressive or antiinflammatory agents. In accordance with the invention, a compound of the formula I can be administered prior to the onset of inflammation (so as to suppress an anticipated inflammation) or after the initiation of inflammation. When provided prophylactically, the immunosuppressive compound(s) are preferably provided in advance of any inflammatory response or symptom (for example, prior to, at, or shortly after the time of an organ or tissue transplant but in advance of any symptoms or organ rejection). The prophylactic administration of a compound of the formula I prevents or attenuates any subsequent inflammatory response (such as, for example, rejection of a transplanted organ or tissue, etc.) Administration of a compound of the formula I attenuates any actual inflammation (such as, for example, the rejection of a transplanted organ or tissue).

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for an adult human of from about 1 to 100 (for example, 15 or lower, especially 1 to 3 or less) mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

As mentioned above, the compounds of the present invention can be employed alone or in combination with each other and/or other suitable therapeutic agents useful in the treatment of NHR-associated conditions, e.g., an antibiotic or other pharmaceutically active material.

For example, the compounds of the present invention can be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention can also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-$HT_D$ agonists, such as sumatriptan, or agents which inhibit somatostatin or its release, such as physostigmine and pyridostigmine. A still further use of the disclosed compounds of the invention is in combination with parathyroid hormone, PTH(1-34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.*, 9, 1003-1008 (1999) and Hamann, L. G. et al., *J. Med. Chem.*, 42, 210-212 (1999).

A further use of the compounds of this invention is in combination with progesterone receptor agonists ("PRA"), such as levonorgestrel, medroxyprogesterone acetate (MPA).

The compounds of the present invention can be employed alone or in combination with each other and/or other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phosphodiesterase inhibitors; protein tyrosine kinase inhibitors; thyroid mimetics (including thyroid receptor agonists); anabolic agents; HIV or AIDS therapies; therapies useful in the treatment of Alzheimer's disease and other cognitive disorders; therapies useful in the treatment of sleeping disorders; anti-proliferative agents; and anti-tumor agents.

Examples of suitable anti-diabetic agents for use in combination with the compounds of the present invention include biguanides (e.g., metformin), glucosidase inhibitors (e.g., acarbose), insulins (including insulin secretagogues or insulin sensitizers), meglitinides (e.g., repaglinide), sulfonylureas (e.g., glimepiride, glyburide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonin, steroidal or non-steroidal progesterone receptor agonists, RANK ligand antagonists, calcium sensing receptor antagonists, TRAP inhibitors, selective estrogen receptor modulators (SERM), estrogen and AP-1 inhibitors.

Examples of suitable anti-obesity agents for use in combination with the compounds of the present invention include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993 (U. Cal SF), WO 99/00353 (KaroBio) and GB98/284425 (KaroBio), and/or an anorectic agent, such as dexamphetamine, phentermine, phenylpropanolamine or mazindol.

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®) integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), rennin inhibitors, ACE inhibitors (e.g., captopril, zofenopril, fosinopril, enalapril, ceranopril, cilazapril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phosphodiesterase inhibitors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

Examples of suitable HIV or AIDS therapies for use in combination with the compounds of the present invention include indinavir sulfate, saquinavir, saquinavir mesylate, ritonavir, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, paclitaxel, FK 506, and adriamycin.

Examples of suitable anti-tumor agents for use in combination with the compounds of the present invention include paclitaxel, adriamycin, epothilones, cisplatin and carboplatin.

Compounds of the present invention can further be used in combination with nutritional supplements such as those described in U.S. Pat. No. 5,179,080, especially in combination with whey protein or casin, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatine, and coenzyme Q-10.

In addition, compounds of the present invention can be used in combination with therapeutic agents used in the treatment of sexual dysfunction, including but not limited to PDE5 inhibitors, such as sildenafil or IC-351; with an antiresorptive agent, hormone replacement therapies, vitamin D analogues, calcitonins, elemental calcium and calcium supplements, cathepsin K inhibitors, MMP inhibitors, vitronectin receptor antagonists, Src $SH_2$ antagonists, vacular —$H^+$-ATPase inhibitors, progesterone receptor agonists, ipriflavone, fluoride, RANK antagonists, PTH and its analogues and fragments, Tibolone, HMG-CoA reductase inhibitors, SERM's, p38 inhibitors, prostanoids, 17-beta hydroxysteroid dehydrogenase inhibitors and Src kinase inhibitors.

Compounds of the present invention can be used in combination with male contraceptives, such as nonoxynol 9 or therapeutic agents for the treatment of hair loss, such as minoxidil and finasteride or chemotherapeutic agents, such as with LHRH agonists.

For their preferred anticancer or antiangiogenic use, the compounds of the present invention can be administered either alone or in combination with other anti-cancer and cytotoxic agents and treatments useful in the treatment of cancer or other proliferative diseases, for example, where the second drug has the same or different mechanism of action than the present compounds of formula I. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; EGFR inhibitors such as small molecule EGFR inhibitors, EGFR antibodies such as C225 (Erbitux); antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3 or type 1; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, caminomycin, daunorubicin, aminopterin, methotrexate, methopterin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. patent can be employed together with any NHR modulators (including, but not limited to, those of present invention) such as AR modulators, ER modulators, with LHRH modulators, or with surgical castration, especially in the treatment of cancer).

The combinations of the present invention can also be formulated or co-administered with other therapeutic agents that are selected for their particular usefulness in administering therapies associated with the aforementioned conditions. For example, the compounds of the invention may be formulated with agents to prevent nausea, hypersensitivity and gastric irritation, such as antiemetics, and $H_1$ and $H_2$ antihistaminics.

As it pertains to the treatment of cancer, the compounds of this invention are most preferably used alone or in combination with anti-cancer treatments such as radiation therapy and/or with cytostatic and/or cytotoxic agents, such as, but not limited to, DNA interactive agents, such as cisplatin or doxorubicin; inhibitors of farnesyl protein transferase, such as those described in U.S. Pat. No. 6,011,029; topoisomerase II inhibitors, such as etoposide; topoisomerase I inhibitors, such as CPT-11 or topotecan; tubulin stabilizing agents, such as paclitaxel, docetaxel, other taxanes, or epothilones; hormonal agents, such as tamoxifen; thymidilate synthase inhibitors, such as 5-fluorouracil; antimetabolites, such as methoxtrexate; antiangiogenic agents, such as angiostatin, ZD6474, ZD6126 and comberstatin A2; kinase inhibitors, such as her2 specific antibodies, Iressa and CDK inhibitors; histone deacetylase inhibitors, such as CI-994 and MS-27-275. Such compounds may also be combined with agents which suppress the production of circulating testosterone such as LHRH agonists or antagonists or with surgical castration. Exemplary combination therapies (e.g., for the treatment of prostate cancer) for use with a compound of the present invention include an LHRH modulator or prednisone.

The present invention also contemplates kits, for example, for the treatment of prostate cancer, comprising a first container (such as a vial) containing a pharmaceutical formulation comprising a compound of the present invention, said compound optionally in a pharmaceutically acceptable carrier, and a second container (such as a vial) containing a pharmaceutical formulation comprising one or more agents (such as an LHRH modulator) to be used in combination with said compound of the present invention, said agent(s) optionally in a pharmaceutically acceptable carrier.

For example, known therapies for advanced metastatic prostate cancer include "complete androgen ablation therapy" wherein tumor growth is inhibited by controlling the supply of androgen to the prostate tissues via chemical castration (castration serves to inhibit the production of circulating testosterone (T) and dihydrotestosterone (DHT)) followed by the administration of androgen receptor (AR) antagonists (which inhibit the function T/DHT derived from the conversion of circulating androgen precursors to T/DHT by the prostate tissue). The compounds of the present invention can be employed as AR antagonists in complete ablation therapy, alone or in combination with other AR antagonists such as Flutamide, Casodex, Nilutamide, or Cyproterone acetate.

The present invention provides compounds which can be used to treat patients suffering from prostate cancer resistant to androgen receptor antagonists which are not within formula I of the invention (or salts thereof), such as bicalutamide. The invention thus further contemplates a method of treating prostate cancer resistant to an androgen receptor antagonist other than those of formula I or salts thereof, comprising the step of administering to a patient in need thereof a compound capable of reducing the growth rate of the tumor mass of said cancer in an amount effective therefor. The term "reducing the growth rate of said tumor mass" denotes reduction in the growth rate (including, of course, stabilization or reduction in size) of said tumor mass upon treatment relative to the growth rate upon treatment with said androgen receptor antagonist other than those of formula I or salts thereof. Compounds of the formula I and pharmaceutically acceptable salts thereof of the present invention are preferred such compounds.

The present invention also contemplates use of an antiestrogen and/or aromatase inhibitor in combination with a compound of the present invention, for example, to assist in mitigating side effects associated with antiandrogen therapy such as gynecomastia. Exemplary antiestrogen and/or aromatase inhibitors include anastrozole (Arimidex), tamoxifen citrate (Nolvadex), exemestane (Aromasin), toremifene citrate (Fareston), letrozole (Femara), raloxifene hydrochloride (Evista), Faslodex, or 923 (Wyeth Ayerst).

The compounds of the present invention may be employed adjuvant to surgery.

Another application of the present compounds is in combination with antibody therapy such as but not limited to antibody therapy against PSCA. An additional application is in concert with vaccine/immune modulating agents for the treatment of cancer.

Compounds of the present invention can be employed in accordance with the methods described in U.S. Provisional Patent Application Ser. No. 60/284,438, entitled "Selective Androgen Receptor Modulators and Methods for Their Identification, Design and Use" filed Apr. 18, 2001 by Mark E. Salvati et al., which Provisional Patent Application is incorporated herein by reference in its entirety (including, but not limited to, reference to all specific compounds within formula I of the present invention), and U.S. patent application Ser. No. 09/885,827, entitled "Selective Androgen Receptor Modulators and Methods for Their Identification, Design and Use" filed Jun. 20, 2001 by Mark E. Salvati et al., which patent application is incorporated herein by reference in its entirety (including, but not limited to, reference to all specific compounds within formula I of the present invention).

For racemates of compounds of the present invention, one enantiomer can, for example be a full AR antagonist while the other can be an AR antagonist in tumor tissue while having no activity or agonist activity in nontumor tissue containing the androgen receptor.

The above other therapeutic agents, when employed in combination with the compounds of the present invention, can be used, for example, in those amounts indicated in the Physicians' Desk Reference (PDR) or as otherwise determined by one of ordinary skill in the art.

The following assays can be employed in ascertaining the activity of a compound as a NHR modulator. Preferred are those compounds with an activity greater than 20 μm for binding or transactivation in any of these assays. Various compounds of the present invention were determined to have AR modulator activity utilizing the transactivation assay, and standard AR binding assays as described following.

Transactivation Assays:

AR Specific Assay:

Compounds of the present invention were tested in transactivation assays of a transfected reporter construct and using the endogenous androgen receptor of the host cells. The transactivation assay provides a method for identifying functional agonists and partial agonists that mimic, or antagonists that inhibit, the effect of native hormones, in this case, dihydrotestosterone (DHT). This assay can be used to predict in vivo activity as there is a good correlation in both series of data. See, e.g. T. Berger et al., *J. Steroid Biochem. Molec. Biol.* 773 (1992), the disclosure of which is herein incorporated by reference.

For the transactivation assay a reporter plasmid is introduced by transfection (a procedure to induce cells to take foreign genes) into the respective cells. This reporter plasmid, comprising the cDNA for a reporter protein, such as secreted alkaline phosphatase (SEAP), controlled by prostate specific antigen (PSA) upstream sequences containing androgen response elements (AREs). This reporter plasmid functions as a reporter for the transcription-modulating activity of the AR. Thus, the reporter acts as a surrogate for the products (mRNA then protein) normally expressed by a gene under control of the AR and its native hormone. In order to detect antagonists, the transactivation assay is carried out in the presence of constant concentration of the natural AR hormone (DHT) known to induce a defined reporter signal. Increasing concentrations of a suspected antagonist will decrease the reporter signal (e.g., SEAP production). On the other hand, exposing the transfected cells to increasing concentrations of a suspected agonist will increase the production of the reporter signal.

For this assay, LNCaP and MDA 453 cells were obtained from the American Type Culture Collection (Rockville, Md.), and maintained in RPMI 1640 or DMEM medium supplemented with 10% fetal bovine serum (FBS; Gibco) respectively. The respective cells were transiently transfected by electroporation according to the optimized procedure described by Heiser, 130 Methods Mol. Biol., 117 (2000), with the pSEAP2/PSA540/Enhancer reporter plasmid. The reporter plasmid, was constructed as follows: commercial human placental genomic DNA was used to generate by Polymerase Cycle Reaction (PCR) a fragment containing the BglII site (position 5284) and the Hind III site at position 5831 of the human prostate specific antigen promoter (Accession # U37672), Schuur, et al., *J. Biol. Chem.,* 271 (12): 7043-51 (1996). This fragment was subcloned into the pSEAP2/basic (Clontech) previously digested with BglII and HindIII to generate the pSEAP2/PSA540 construct. Then a fragment bearing the fragment of human PSA upstream sequence between positions −5322 and −3873 was amplified by PCR from human placental genomic DNA. A XhoI and a BglII sites were introduced with the primers. The resulting fragment was subcloned into pSEAP2/PSA540 digested with XhoI and BglII respectively, to generate the pSEAP2/PSA540/Enhancer construct. LNCaP and MDA 453 cells were collected in media containing 10% charcoal stripped FBS. Each cell suspension was distributed into two Gene Pulser Cuvetts (Bio-Rad) which then received 8 μg of the reporter construct, and electoporated using a Bio-Rad Gene Pulser at 210 volts and 960 μFaraday. Following the transfections the cells were washed and incubated with media containing charcoal stripped fetal bovine serum in the absence (blank) or presence (control) of 1 nM dihydrotestosterone (DHT; Sigma Chemical) and in the presence or absence of the standard anti-androgen bicalutamide or compounds of the present invention in concentrations ranging from 10-10 to 10-5 M (sample). Duplicates were used for each sample. The compound dilutions were performed on a Biomek 2000 laboratory workstation.

After 48 hours, a fraction of the supernatant was assayed for SEAP activity using the Phospha-Light Chemiluminescent Reporter Gene Assay System (Tropix, Inc). Viability of the remaining cells was determined using the CellTiter 96 Aqueous Non-Radioactive Cell Proliferation Assay (MTS Assay, Promega). Briefly, a mix of a tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS) are added to the cells. MTS (Owen's reagent) is bioreduced by cells into a formazan that is soluble in tissue culture medium, and therefore its absorbance at 490 nm can be measured directly from 96 well assay plates without additional processing. The quantity of formazan product as measured by the amount of 490 nm absorbance is directly proportional to the number of living cells in culture. For each replicate the SEAP reading was normalized by the Abs490 value derived from the MTS assay. For the antagonist mode, the % Inhibition was calculated as:

% Inhibition=100×(1−[average control−average blank/average sample−average blank])

Data was plotted and the concentration of compound that inhibited 50% of the normalized SEAP was quantified ($IC_{50}$).

For the agonist mode % Control was referred as the effect of the tested compound compared to the maximal effect observed with the natural hormone, in this case DHT, and was calculated as:

% Control=100×average sample−average blank/average control−average blank

Data was plotted and the concentration of compound that activates to levels 50% of the normalized SEAP for the control was quantified ($EC_{50}$).

GR Specificity Assay:

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR see, e.g. G. Chalepakis et al., *Cell,* 53(3), 371 (1988). This plasmid was transfected into A549 cells, which expresses endogenous GR, to obtain a GR specific transactivation assay. A549 cells were obtained from the American Type Culture Collection (Rockville, Md.), and maintained in RPMI 1640 supplemented with 10% fetal bovine serum (FBS; Gibco). Determination of the GR specific antagonist activity of the compounds of the present invention was identical to that described for the AR specific transactivation assay, except that the DHT was replaced with 5 nM dexamethasone (Sigma Chemicals), a specific agonist for GR. Determination of the GR specific agonist activity of the compounds of the present invention was performed as described for the AR transactivation assay, wherein one measures the activation of the GR specific reporter system by the addition of a test compound, in the absence of a known GR specific agonists ligand.

PR Specific Assay:

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR. This plasmid was transfected into T47D, which expresses endogenous PR, to obtain a PR specific transactivation assay. T47D cells were obtained from the American Type Culture Collection (Rockville, Md.), and maintained in DMEM medium supplemented with 10% fetal bovine serum (FBS; Gibco). Determination of the PR specific antagonist activity of the compounds of the present invention was identical to that described for the AR specific transactivation assay, except that the DHT was replaced with 1 nM Promegastone (NEN), a specific agonist for PR. Determination of the PR specific agonist activity of the compounds of the present invention was performed as described for the AR transactivation assay, wherein one measures the activation of the PR specific reporter system by the addition of a test compound, in the absence of a known PR specific agonists ligand.

AR Binding Assay:

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, were incubated at 37° C. to remove any endogenous ligand that might be complexed with the receptor in the cells. After 48 hours, either a saturation analysis to determine the $K_d$ for tritiated dihydrotestosterone, [$^3$H]-DHT, or a competitive binding assay to evaluate the ability of test compounds to compete with [$^3$H]-DHT were performed. For the saturation analysis, media (RPMI 1640 or DMEM-0.2% CA-FBS) containing [$^3$H]-DHT (in concentrations ranging from 0.11 nM to 16 nM) in the absence (total binding) or presence (non-specific binding) of a 500-fold molar excess of unlabeled DHT were added to the cells. After 4 hours at 37° C., an aliquot of the total binding media at each concentration of [$^3$H]-DHT was removed to estimate the amount of free [$^3$H]-DHT. The remaining media was removed, cells were washed three times with PBS and harvested onto UniFilter GF/B plates (Packard), Microscint (Packard) was added and plates counted in a Top-Counter (Packard) to evaluate the amount of bound [$^3$H]-DHT.

For the saturation analysis, the difference between the total binding and the non-specific binding, was defined as specific binding. The specific binding was evaluated by Scatchard analysis to determine the $K_d$ for [$^3$H]-DHT. See e.g. D. Rodbard, Mathematics and statistics of ligand assays: an illustrated guide: In: J. Langon and J. J. Clapp, eds., Ligand Assay, Masson Publishing U.S.A., Inc., New York, pp. 45-99, (1981), the disclosure of which is herein incorporated by reference.

For the competition studies, media containing 1 nM [$^3$H]-DHT and compounds of the invention ("test compounds") in concentrations ranging from $10^{-10}$ to $10^{-5}$ M were added to the cells. Two replicates were used for each sample. After 4 hours at 37° C., cells were washed, harvested and counted as described above. The data was plotted as the amount of [$^3$H]-DHT (% of control in the absence of test compound) remaining over the range of the dose response curve for a given compound. The concentration of test compound that inhibited 50% of the amount of [$^3$H]-DHT bound in the absence of competing ligand was quantified ($IC_{50}$) after log-logit transformation. The $K_I$ values were determined by application of the Cheng-Prusoff equation to the $IC_{50}$ values, where:

$$K_t = \frac{IC_{50}}{(1 + (^3H\text{-}DHT)/K_d \text{ for } ^3H\text{-}DHT)}.$$

After correcting for non-specific binding, $IC_{50}$ values were determined. The $IC_{50}$ is defined as the concentration of competing ligand needed to reduce specific binding by 50%. The $K_d$s for [$^3$H]-DHT for MDA 453 and LNCaP were 0.7 and 0.2 nM respectively.

Human Prostate Cell Proliferation Assay:

Compounds of the present invention were tested ("test compounds") on the proliferation of human prostate cancer cell lines. For that, MDA PCa2b cells, a cell line derived from the metastasis of a patient that failed castration, Navone et al., *Clin. Cancer Res.*, 3, 2493-500 (1997), were incubated with or without the test compounds for 72 hours and the amount of [$^3$H]-thymidine incorporated into DNA was quantified as a way to assess number of cells and therefore proliferation. The MDA PCa2b cell line was maintained in BRFF-HPC1 media (Biological Research Faculty & Facility Inc., MD) supplemented with 10% FBS. For the assay, cells were plated in Biocoated 96-well microplates and incubated at 37° C. in 10% FBS (charcoal-stripped)/BRFF-BMZERO (without androgens). After 24 hours, the cells were treated in the absence (blank) or presence of 1 nM DHT (control) or with test compounds (sample) of the present invention in concentrations ranging from $10^{-1}$ to $10^{-5}$ M. Duplicates were used for each sample. The compound dilutions were performed on a Biomek 2000 laboratory work station. Seventy two hours later 0.44 uCi. of [$^3$H]-Thymidine (Amersham) was added per well and incubated for another 24 h followed by tripsinization, harvesting of the cells onto GF/B filters. Micro-scint PS were added to the filters before counting them on a Beckman TopCount.

The % Inhibition was calculated as:

% Inhibition=100×(1−[average$_{control}$−average$_{blank}$/average$_{sample}$−average$_{blank}$])

Data was plotted and the concentration of compound that inhibited 50% of the [$^3$H]-Thymidine incorporation was quantified ($IC_{50}$).

C2C12 Mouse Mvoblast Transactivation Assay:

Two functional transactivation assays were developed to assess the efficacy of androgen agonists in a muscle cell background using a luciferase reporter. The first assay (ARTA Stable 1) uses a cell line, Stable 1 (clone #72), which stably expresses the full length rat androgen receptor but requires the transient transfection of an enhancer/reporter. This cell line was derived from C2C12 mouse moyoblast cells. The second assay (ARTA Stable 2) uses a cell line, Stable 2 (clone #133), derived from Stable 1 which stably expresses both rAR and the enhancer/luciferase reporter.

The enhancer/reporter construct used in this system is pGL3/2XDR-1/luciferase. 2×DR-1 was reported to be an AR specific response element in CV-1 cells, Brown et. al. *The Journal of Biological Chemisty* 272, 8227-8235, (1997). It was developed by random mutagenesis of an AR/GR consensus enhancer sequence.

ARTA Stable 1:
1. Stable 1 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5× Antibiotic-Antimycotic, and 800 µg/ml Geneticin (Gibco BRL, Cat. No.: 10131-035).
2. 48 hours later, cells are transfected with pGL3/2XDR-1/luciferase using LipofectAMINE Plus™ Reagent (Gibco BRL, Cat. No.: 10964-013). Specifically, 5 ng/well pGL3/2XDR-1/luciferase DNA and 50 ng/well Salmon Sperm DNA (as carrier) are diluted with 5 µl/well Opti-MEMem media (Gibco BRL, Cat. No.: 31985-070). To this, 0.5 µl/well Plus reagent is added. This mixture is incubated for 15 minutes at room temperature. In a separate vessel, 0.385 µl/well LipofectAMINE reagent is diluted with 5 µl/well Opti-MEM. The DNA mixture is then combined with the LipofectAMINE mixture and incubated for an additional 15 minutes at room temperature. During this time, the media from the cells is removed and replaced with 60 µl/well of Opti-MEM. To this is added 10 µl/well of the DNA/LipofectAMINE transfection mixture. The cells are incubated for 4 hours.
3. The transfection mixture is removed from the cells and replaced with 90 µl of media as in #1 above.
4. 10 µl/well of appropriate drug dilution is placed in each well.
5. 24 hours later, the Steady-Glo™ Luciferase Assay System is used to detect activity according to the manufacturer's instructions (Promega, Cat. No.: E2520).

ARTA Stable 2
1. Stable 2 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5× Antibiotic-Antimycotic, 800 µg/ml Geneticin (Gibco BRL, Cat. No.: 10131-035) and 800 µg/ml Hygromycin β (Gibco BRL, Cat. No.: 10687-010).
2. 48 hours later, the media on the cells is removed and replaced with 90 µl fresh. 10 µl/well of appropriate drug dilution is placed in each well.
3. 24 hours later, the Steady-Glo™ Luciferase Assay System is used to detect activity according to the manufacturer's instructions (Promega, Cat. No.: E2520).

See U.S. patent application Ser. No. 09/885,831, entitled "Cell Lines and Cell-BasedAssays for Identification of Androgen Receptor Modulators" filed Jun. 20, 2001 by Jacek Ostrowski et al., which patent application is incorporated herein by reference in its entirety.

Proliferation Assays

Murine Breast Cell Proliferation Assay:

The ability of compounds of the present invention ("test compounds") to modulate the function of the AR was determined by testing said compounds in a proliferation assay using the androgen responsive murine breast cell line derived from the Shionogi tumor, Hiraoka et al., *Cancer Res.*, 47, 6560-6564 (1987). Stable AR dependent clones of the parental Shionogi line were established by passing tumor fragments under the general procedures originally described in Tetuo, et. al., *Cancer Research* 25, 1168-1175 (1965). From the above procedure, one stable line, SC114, was isolated, characterized and utilized for the testing of example compounds. SC114 cells were incubated with or without the test compounds for 72 hours and the amount of [3H]-thymidine incorporated into DNA was quantified as a surrogate endpoint to assess the number of cells and therefore the proliferation rate as described in Suzuki et. al., *J. Steroid Biochem. Mol. Biol.* 37, 559-567 (1990). The SC114 cell line was maintained in MEM containing $10^{-8}$ M testosterone and 2% DCC-treated FCS. For the assay, cells were plated in 96-well microplates in the maintenance media and incubated at 37° C. On the following day, the medium was changed to serum free medium [Ham's F-12:MEM (1:1, v/v) containing 0.1% BSA] with (antagonist mode) or without (agonist mode) $10^{-8}$ M testosterone and the test compounds of the present invention in concentrations ranging from $10^{-10}$ to $10^{-5}$ M. Duplicates were used for each sample. The compound dilutions were performed on a Biomek 2000 laboratory work station. Seventy two hours later 0.44uCi of [3H]-Thymidine (Amersham) was added per well and incubated for another 2 hr followed by tripsinization, and harvesting of the cells onto GF/B filters. Micro-scint PS were added to the filters before counting them on a Beckman TopCount.

For the antagonist mode, the % Inhibition was calculated as:

$$\% \text{ Inhibition}=100\times(1-[\text{average}_{sample}-\text{average}_{blank}/\text{average}_{control}-\text{average}_{blank}])$$

Data was plotted and the concentration of compound that inhibited 50% of the [$^3$H]-Thymidine incorporation was quantified ($IC_{50}$).

For the agonist mode % Control was referred as the effect of the tested compound compared to the maximal effect observed with the natural hormone, in this case DHT, and was calculated as:

$$\% \text{ Control}=100\times(\text{average}_{sample}-\text{average}_{blank})/(\text{average}_{control}-\text{average}_{blank})$$

Data was plotted and the concentration of compound that inhibited 50% of the [$^3$H]-Thymidine incorporation was quantified ($EC_{50}$).

In Vitro Assay to Measure GR Induced AP-1 Transrepression:

The AP-1 assay is a cell based luciferase reporter assay. A549 cells, which contain endogenous glucocorticoid receptor, were stably transfected with an AP-1 DNA binding site attached to the luciferase gene. Cells are then grown in RPMI+10% fetal calf serum (charcoal-treated)+Penicillin/Streptomycin with 0.5 mg/ml geneticin. Cells are plated the day before the assay at approximately 40000 cells/well. On assay day, the media is removed by aspiration and 20 μl assay buffer (RPMI without phenol red+10%-FCS (charcoal-treated)+Pen/Strep) is added to each well. At this point either 20 μl assay buffer (control experiments), the compounds of the present invention ("test compounds") (dissolved in DMSO and added at varying concentrations) or dexamethasome (100 nM in DMSO, positive control) are added to each well. The plates are then pre-incubated for 15 minutes at 37° C., followed by stimulation of the cells with 10 ng/ml PMA. The plates are then incubated for 7 hrs at 37° C. after which 40 μl luciferase substrate reagent is added to each well. Activity is measured by analysis in a luminometer as compared to control experiments treated with buffer or dexamethasome. Activity is designated as % inhibition of the reporter system as compared to the buffer control with 10 ng/ml PMA alone. The control, dexamethasone, at a concentration of ≦10 μM typically suppresses activity by 65%. Test compounds which demonstrate an inhibition of PMA induction of 50% or greater at a concentration of test compound of ≦10 μM are deemed active.

Wet Prostate Weight Assay AR Antagonist Assay:

The activity of compounds of the present invention as AR antagonists was investigated in an immature male rat model, a standard, recognized test of antiandrogen activity of a given compound, as described in L. G. Hershberger et al., *Proc. Soc. Expt. Biol. Med.,* 83, 175 (1953); P. C. Walsh and R. F. Gittes, "Inhibition of extratesticular stimuli to prostate growth in the castrated rat by antiandrogens", *Endocrinology,* 86, 624 (1970); and B. J. Furr et al., "ICI 176,334: A novel non-steroid, peripherally selective antiandrogen", *J. Endocrinol.,* 113, R7-9 (1987), the disclosures of which are herein incorporated by reference.

The basis of this assay is the fact that male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et al. Clin. Invest. Med., 16, 475-492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues. M. C. Luke and D. S. Coffey, "*The Physiology of Reproduction*" ed. By E. Knobil and J. D. Neill, 1, 1435-1487 (1994). Since the male sex organs are the tissues most responsive to modulation of the androgen activity, this model is used to determine the androgen dependent growth of the sex accessory organs in immature castrated rats.

Male immature rats (19-20 days old Sprague-Dawley, Harlan Sprague-Dawely) were castrated under metofane ansestesia. Five days after surgery these castrated rats (60-70 g, 23-25 day-old) were dosed for 3 days. Animals were dosed sub-cutaneously (s.c.) 1 mg/kg with Testosterone Proprionate (TP) in arachis oil vehicle and anti-androgen test compounds (compounds of the present invention) were dosed orally by gavage (p.o.) in dissolved/suspensions of 80% PEG 400 and 20% Tween 80 (PEGTW). Animals were dosed (v/w) at 0.5 ml of vehicle/100 g body weight. Experimental groups were as follows:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 3-day treatment, the animals were sacrificed, and the ventral prostate weighed. To compare data from different experiments, the sexual organs weights were first standardized as mg per 100 g of body weight, and the increase in organ weight induced by TP was considered as the maximum increase (100%). ANOVA followed by one-tailed Student or Fischer's exact test was used for statistical analysis.

The gain and loss of sexual organ weight reflect the changes of the cell number (DNA content) and cell mass (protein content), depending upon the serum androgen concentration. See Y. Okuda et al., *J. Urol.,* 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases seminal vesicles (SV) and the ventral prostate (VP) in a dose dependent manner.

The maximum increase in organ weight was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10-30-fold higher potency than free T.

In this immature castrated rat model, a known AR antagonist (Casodex) was also administered simultaneously with 0.1 mg of TP ($ED_{80}$), inhibiting the testosterone-mediated increase in the weights of the VP and SV in a dose dependent manner. The antagonist effects were similar when dosing orally or subcutaneously. Compounds of the invention also exhibited AR antagonist activity by suppressing the testosterone-mediated increase in the weights of VP and SV.

Levator Ani & Wet Prostate Weight Assay AR Agonist Assay:

The activity of compounds of the present invention as AR agonists was investigated in an immature male rat model, a recognized test of anabolic effects in muscle and sustaining effects in sex organs for a given compound, as described in L. G. Hershberger et al., *Proc. Soc. Expt. Biol. Med.,* 83, 175 (1953); B. L. Beyler et al, "Methods for evaluating anabolic and catabolic agents in laboratory animals", *J. Amer. Med. Women's Ass.,* 23, 708 (1968); H. Fukuda et al., "Investigations of the levator ani muscle as an anabolic steroid assay", *Nago Dai. Yak. Ken. Nem.* 14, 84 (1966) the disclosures of which are herein incorporated by reference.

The basis of this assay lies in the well-defined action of androgenic agents on the maintenance and growth of muscle tissues and sexual accessory organs in animals and man. Androgenic steroids, such as testosterone (T), have been well characterized for their ability to maintain muscle mass. Treatment of animals or humans after castrations with an exogenous source of T results in a reversal of muscular atrophy. The effects of T on muscular atrophy in the rat levator ani muscle have been well characterized. M. Masuoka et al., "Constant cell population in normal, testosterone deprived and testosterone stimulated levator ani muscles" *Am. J. Anat.* 119, 263 (1966); Z. Gori et al., "Testosterone hypertrophy of levator ani muscle of castrated rats. I. Quantitative data" *Boll.-Soc. Ital. Biol. Sper.* 42, 1596 (1966); Z. Gori et al., "Testosterone hypertrophy of levator ani muscle of castrated rats. II. Electron-microscopic observations" *Boll.-Soc. Ital. Biol. Sper.* 42, 1600 (1966); A. Boris et al., *Steroids* 15, 61 (1970). As described above, the effects of androgens on maintenance of male sexual accessory organs, such as the prostate and seminal vesicles, is well described. Castration results in rapid involution and atrophy of the prostate and seminal vesicles. This effect can be reversed by exogenous addition of androgens. Since both the levator ani muscle and the male sex organs are the tissues most responsive to the effects of androgenic agents, this model is used to determine the androgen dependent reversal of atrophy in the levator ani muscle and the sex accessory organs in immature castrated rats. Sexually mature rats (200-250 g, 6-8 weeks-old, Sprague-Dawley, Harlan) were acquired castrated from the vendor (Taconic). The rats were divided into groups and treated daily for 7 to 14 days with one of the following:

1. Control vehicle
2. Testosterone Propionate (TP) (3 mg/rat/day, subcutaneous)
3. TP plus Casodex (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 7-14-day treatment, the animals were sacrificed by carbon dioxide, and the levator ani, seminal vesicle and ventral prostate weighed. To compare data from different experiments, the levator ani muscle and sexual organ weights were first standardized as mg per 100 g of body weight, and the increase in organ weight induced by TP was considered as the maximum increase (100%). Super-anova (one factor) was used for statistical analysis.

The gain and loss of sexual organ weight reflect the changes of the cell number (DNA content) and cell mass (protein content), depending upon the serum androgen concentration. See Y. Okuda et al., *J. Urol.,* 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases levator ani, seminal vesicles (SV) and prostate in a dose dependent manner.

The maximum increase in organ weight was 4 to 5-fold when dosing 3 mg/rat/day of testosterone (T) or 1 mg/rat/day of testosterone propionate (TP) for 3 days. The $EC_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 hours after subcutaneous injection than that of TP, thereafter, these high levels declined very rapidly. In contrast, the serum concentrations of T and DHT in TP-treated animals were fairly consistent during the 24 hours, and therefore, TP showed about 10-30-fold higher potency than free T.

MDA PCa2b Human Prostate Zenograft Assay:

In Vivo Antitumor Testing: MDA-PCa-2b human prostate tumors were maintained in Balb/c nu/nu nude mice. Tumors were propagated as subcutaneous transplants in adult male nude mice (4-6 weeks old) using tumor fragments obtained from donor mice. Tumor passage occurred every 5-6 weeks.

For antitumor efficacy trial, the required number of animals needed to detect a meaningful response were pooled at the start of the experiment and each was given a subcutaneous implant of a tumor fragment (~50 mg) with a 13-gauge trocar. Tumors were allowed to grow to approx. 100-200 mg (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2-Wt1) provides a measure of treatment-related toxicity.

Tumor response was determined by measurement of tumors with a caliper twice a week, until the tumors reach a predetermined "target" size of 0.5 gm. Tumor weights (mg) were estimated from the formula: Tumor weight=(length×width2)÷2

Tumor response end-point was expressed in terms of tumor growth inhibition (% T/C), defined as the ratio of median tumor weights of the treated tumors (T) to that of the control group (C).

To estimate tumor cell kill, the tumor volume doubling time was first calculated with the formula:

$TVDT$=Median time (days) for control tumors to reach target size–Median time (days) for control tumors to reach half the target size s And, Log cell kill=$(T-C)+(3.32\times TVDT)$ Statistical evaluations of data were performed using Gehan's generalized Wilcoxon test.

Dunning Prostate Tumor:

Dunning R3327H prostate tumor is a spontaneously derived, well differentiated androgen responsive adenocarcinoma of the prostate (Smolev J K, Heston W D, Scott W W, and Coffey D S, Cancer Treat Rep. 61, 273-287 (1977)). The growth of the R3327H subline has been selected for its highly androgen-dependent and reproducible growth in intact male rats. Therefore, this model and other sublines of this tumor have been widely used to evaluate in vivo antitumor activities of antiandrogens such as flutamide and bacilutamide/Casodex (Maucher A., and von Angerer, *J. Cancer Res. Clin. Oncol.*, 119, 669-674 (1993), Furr B. J. A. Euro. URL. 18 (suppl. 3), 2-9 (1990), Shain S. A. and Huot R I. *J. Steroid Biochem.* 31, 711-718 (1988)).

At the beginning of the study, the Dunning tumor pieces (about 4×4 mm) are transplanted subcutaneously to the flank of mature male Copenhagen rats (6-7 weeks old, Harlan-Sprague Dawley, Indianapolis, Md.). About 6 weeks after the implantation, the animals with tumors of measurable size (about 80-120 mm$^2$) are randomized into treatment groups (8-10 rats/group) and the treatments are initiated. One group of the rats are castrated to serve as the negative control of tumor growth. Animals are treated daily with compounds of the current invention, standard antiandrogens such as bacilutamide or vehicle (control) for an average of 10 to 14 weeks. Test compounds are dissolved in a vehicle of (2.5 ml/kg of body weight) 10% polyethylene glycol and 0.05% Tween-80 in 1% carboxymethyl cellulose, PEG/CMC, (Sigma, St Louis, Mo.). Typical therapeutic experiments would include three groups of three escalating doses for each standard or test compound (in a range of 300-3 mg/kg).

Tumors in the vehicle (control) group reach a size of 1500 to 2500 mm$^3$, whereas the castrated animal group typically shows tumor stasis over the 14 weeks of observation. Animals treated orally with 20 mg/kg of bicalutamide or flutamide would be expected to show a 40% reduction in tumor volumes compared to control after 14 weeks of treatment. The size of tumors are measured weekly by vernier caliper (Froboz, Switzerland), taking perpendicular measurements of length and width. Tumor volumes are measured in mm using the formula: Length×Width×Height=Volume. Statistical differences between treatment groups and control are evaluated using multiple ANOVA analysis followed by one tail non-parametric Student t test.

Mature Rat Prostate Weight Assay:

The activity of compounds of the present invention were investigated in a mature male rat model, which is a variation of the Levator ani & wet prostate weight assay described above. The above in vivo assays are recognized assays for determining the anabolic effects in muscle and sustaining effects in sex organs for a given compound, as described in L. G. Hershberger et al., 83 *Proc. Soc. Expt. Biol. Med.*, 175 (1953); B. L. Beyler et al, "Methods for evaluating anabolic and catabolic agents in laboratory animals", 23 *J. Amer. Med. Women's Ass.*, 708 (1968); H. Fukuda et al., "Investigations of the levator ani muscle as an anabolic steroid assay", 14 *Nago Dai. Yak. Ken. Nem.* 84 (1966) the disclosures of which are herein incorporated by reference. The basis of this assay lies in the well-defined action of androgenic agents on the maintenance and growth of muscle tissues and sexual accessory organs in animals and man.

The male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et. al. 16 *Clin. Invest. Med.*, 475-492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues, M. C. Luke and D. S. Coffey, "The Physiology of Reproduction" ed. By E. Knobil and J. D. Neill, 1, 1435-1487 (1994). Since the male sex organs and the levator ani are the tissues most responsive to modulation of the androgen activity, this model is used to determine the activity of compounds that modulate the androgen receptor pathway in mature rats.

Along with its mitogenic activity on tissues such as prostate, seminal vesicle and muscle, testosterone also serves as a negative regulator for its own biosynthesis. Testosterone production in the Leydig cells of the testis is controlled by the level of circulating LH released from the pituitary gland. LH levels are themselves controlled by the level of LHRH produced in the hypothalmic region. Testosterone levels in the blood serve to inhibit the secretion of LHRH and subsequently reduce levels of LH and ultimately the levels of circulating testosterone levels. By measuring blood levels of LH as they are effected by compounds of the present invention ("test compounds"), it is possible to determine the level of agonist or antagonist activity of said compounds at the hypothalamic axis of this endocrine cycle.

Matched sets of Harlan Sprague-Dawely rats (40-42 days old, 180-220 g), were dosed orally by gavage (p.o.) with the test compounds in dissolved/suspensions of 80% PEG 400 and 20% Tween 20 (PEGTW) for 14 days. Two control groups, one intact and one castrated were dose orally only with the PEGTW vehicle. Animals were dosed (v/w) at 0.5 ml of vehicle/100 g body weight. Experimental groups were as follows:

1. Intact vehicle (p.o., PEGTW, QD)

2. Control vehicle (p.o., PEGTW, QD)

3. Bicalutamide (Casodex, a recognized antiandrogen, as a reference compound) or a compound of the present invention, p.o. in PEGTW QD. (in a range of doses). At the end of the 14-day treatment, the animals were sacrificed, and the ventral prostate, the seminal vesicles, and the levator ani were removed surgically and weighed. To compare data from different experiments, the organs weights were first standardized as mg per 100 g of body weight, and expressed as a percentage of the value of the respective organ in the intact group.

Rat luteinizing hormone (rLH) is quantitatively determined with the Biotrak [125 I] kit (Amersham Pharmacia Biotek), following the manufacturer directions. The assay is based on the competition by the LH present in the serum of the binding of [$^{125}$I] rLH to an Amerlex-M bead/antibody suspension. The radioactivity that remains after incubation with the serum and subsequent washes is extrapolated into a standard curve to obtain a reading in ng/ml.

The gain and loss of sexual organ and levator ani weight reflect the changes of the cell number (DNA content) and cell mass (protein content), depending upon the serum androgen concentration, see Y. Okuda et al., *J. Urol.,* 145, 188-191 (1991), the disclosure of which in herein incorporated by reference. Therefore, measurement of organ wet weight is sufficient to indicate the bioactivity of androgens and androgen antagonist. In the mature rats assay, active agonist agents will have no effect or will increase the weight of one or more of the androgen responsive organs (levator ani, prostate, seminal vessicle) and will have no effect or a suppressive effect on LH secretion. Compounds with antagonist activity will decrease the weight of one or more of the androgen responsive organs (levator ani, prostate, seminal vesicle) and will have no effect or a reduced suppressive effect on LH secretion.

CWR22 Human Prostate Zenograft Assay:

In Vivo Antitumor Testing: CWR22 human prostate tumors were maintained in Balb/c nu/nu nude mice. Tumors were propagated as subcutaneous transplants in adult male nude mice (4-6 weeks old) using tumor fragments obtained from donor mice. Tumor passage occurred every 5-6 weeks.

For antitumor efficacy trial, the required number of animals needed to detect a meaningful response were pooled at the start of the experiment and each was given a subcutaneous implant of a tumor fragment (~50 mg) with a 13-gauge trocar. Tumors were allowed to grow to approx. 100-200 mg (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2-Wt1) provides a measure of treatment-related toxicity.

Tumor response was determined by measurement of tumors with a caliper twice a week, until the tumors reach a predetermined "target" size of 0.5 gm. Tumor weights (mg) were estimated from the formula: Tumor weight=(length× width2)÷2.

Tumor response end-point was expressed in terms of tumor growth inhibition (% T/C), defined as the ratio of median tumor weights of the treated tumors (T) to that of the control group (C).

To estimate tumor cell kill, the tumor volume doubling time was first calculated with the formula:

$$TVDT = \text{Median time (days) for control tumors to reach target size} - \text{Median time (days) for control tumors to reach half the target size}$$

$$\text{And, Log cell kill} = (T-C) \div (3.32 \times TVDT)$$

Statistical evaluations of data were performed using Gehan's generalized Wilcoxon test.

The following Examples illustrate embodiments of the present invention, and are not intended to limit the scope of the claims. Within certain Examples, one compound of the formula I is prepared and then employed to further prepare one or more additional compounds of the formula I or salts thereof. Methods employed to prepare one compound of the formula I or salt thereof as described herein can be employed as appropriate to prepare other compounds of the invention.

Abbreviations

The following abbreviations are used herein:

DBU=1,8-diazabicyclo[5.4.0]undec-7-ene
4-DMAP=4-dimethylaminopyridine
ee=enantiomeric excess
DMF=dimethylformamide
EtOAc=ethyl acetate
LDA=lithium diisopropylamide
Hünig's Base=N,N-diisopropylethylamine
Me=methyl
RT=retention time
TFA=trifluoroacetic acid
THF=tetrahydrofuran
TLC=thin layer chromatography
TMS=trimethylsilyl
pTSA=para-toluenesulfonic acid
Δ=heat
t-Bu=tert-butyl
$PhCH_3$=toluene
Pd/C=palladium on activated charcoal
TsCl=tosyl chloride
TBSOTf=tert-butyldimethylsilyl trifluoromethane sulfonate
TBS=tert-butyldimethylsilane
MeI=methyl iodide
$(BOC)_2O$=di-tert-butyl dicarbonate
TEA=triethylamine
n-BuLi=n-butyllithium
rt=room temperature
LC=liquid chromatography
Ts=tosyl
Ph=phenyl
EtOH=ethanol
DCE=dichloroethane
DMSO=dimethylsulfoxide
Ra—Ni=Raney Nickel
MS=molecular sieves
MS(ES)=Electro-Spray Mass Spectrometry
mCPBA=m-chloroperoxybenzoic acid
sat=saturated
AcOH=acetic acid
MeOH=methanol
$Et_2O$=diethyl ether
Ac=acetyl
DEAD=diethyl azodicarboxylate
h=hours
Et=ethyl
WSDCC=water soluble dicarbonyl diimide, 1-(3-dimethylaminopropyl)-3-ethylcarbodiimide hydrochloride
TBAF=tetrabutylammonium fluoride
DBAD=di-terbutylazodicarboxylate
DCC=Dicyclohexylcarbodiimide
Wilkinson's catalyst=RhCl(PPh3)3
ADDP=1,1-[azodicarbonyl]dipiperidine
DMA=dimethylacetamide
DME=1,2-dimethoxyethane
BOP=benzotriazol-1-yloxytris(dimethylamino)-phosphonium hexafluorophosphate
HRMS=high resolution mass spectrometry
TBME=MTBE=methyl tert-butyl ether (i.e., 2-methoxy-2-methyl-propane)
$TiCl_2\ Cp_2$=bis(cyclopentadienyl)titanium dichloride
DPPA=diphenylphosphoryl azide
HMPA=hexamethylphosphoryl amide
V %=volume percent
$BH_3$.MS=borane dimethylsulfate
vvm=volume gas per volume liquid per minute

EXAMPLE 1

(3aα,4α,7α,7aα)-2-(4-Bromo-3-methylphenyl)tetrahydro-4,7-ethanothiopyrano[3,4-c]pyrrole-1,3,8 (2H,4H)-trione (1C)

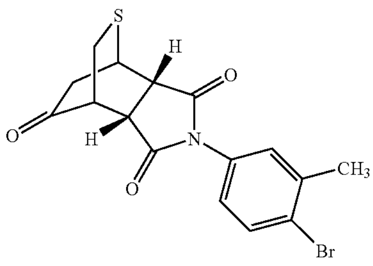

A. 4-(tert-Butyldimethylsiloxy)-2H-thiopyran (1A)

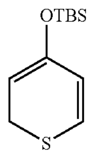

2,3-Dihydro-4H-thiopyran-4-one (1.50 g, 13.1 mmol, synthesized as described in Richards et al. *J. Org. Chem.* 46, 4836-4842 (1981)) was dissolved in $CH_2Cl_2$ (130 mL) and triethylamine (5.47 mL, 39.4 mmol) was added. tert-Butyldimethylsilyl trifluoromethanesulfonate (3.62 mL, 15.8 mmol) was then added. After 10 minutes, the volatiles were removed in vacuo at 25° C. The resulting yellow oil was passed through a short column of $SiO_2$ eluting with 3% TEA in hexanes to yield 1.82 g (7.97 mmol, 61%) of compound 1A as an orange oil.

B. 1-[4-bromo-3-methylphenyl]-1H-pyrrole-2,5-dione (1B)

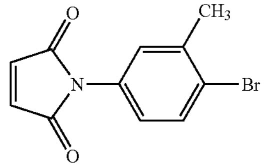

4-Bromo-3-methylaniline (1.55 g, 8.33 mmol) and maleic anhydride (0.898 g, 9.16 mmol) were dissolved in acetic acid (10 mL) and heated at 115° C. for 12 h. The reaction was then cooled to 25° C. and the acetic acid was removed in vacuo. The resulting residue was suspended in 5% $K_2CO_3$ (100 mL), stirred for 25 minutes, filtered and rinsed with water. The material was then dried in vacuo to give 1.65 g (6.20 mmol, 74%) of compound 1B as a light brown solid. HPLC: 100% at 2.96 min (retention time) (YMC S5 ODS column 4.6×50 mm eluting with 10-90% aqueous methanol over 4 minutes containing 0.1% TFA, 4 mL/min, monitoring at 220 nm).

C. (3aα,4α,7α,7a α)-2-(4-Bromo-3-methylphenyl) tetrahydro-4,7-ethanothiopyrano[3,4-c]pyrrole-1,3,8 (2H,4H)-trione (1C)

Compound 1A (0.313 g, 1.41 mmol) and compound 1B (0.250 g, 0.940 mmol) were dissolved in toluene and heated to reflux for 5 h. The toluene was then removed by passing a stream of argon through the reaction flask. The residue was then purified by flash chromatography on $SiO_2$ eluting with 20% hexane in chloroform. This gave 0.168 g of the enol ether intermediate as a yellow solid. The enol ether intermediate was dissolved in dichloroethane (2.0 mL) and TFA (0.25 mL) was added. After 0.5 h, the reaction was quenched with saturated aqueous $NaHCO_3$ and extracted with $CH_2Cl_2$ (2×30 mL). The organics were dried over anhydrous sodium sulfate and evaporated to give 0.079 g (0.21 mmol, 22%) of compound 1C as a white solid. HPLC: 99% at 3.010 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 396.9 $[M+NH_4]^+$.

EXAMPLE 2

(3aα,4α,7α,7aα)-2-(4-Bromo-3-methylphenyl)tetrahydro-4,7-ethanothiopyrano[3,4-c]pyrrole-1,3,8 (2H,4H)-trione 5,5-dioxide (2)

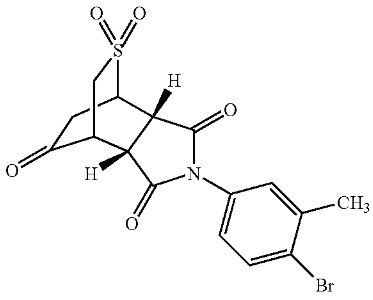

Compound 1C (0.040 g, 0.11 mmol) was dissolved in $CH_2Cl_2$ (4.0 mL) and cooled to 0° C. m-CPBA (60% purity, 0.061 g, 0.21 mmol) was added and the reaction was then warmed to 25° C. After 1 h, a 1:1 mixture of saturated $NaHCO_3$ and saturated sodium sulfite (20 mL) was added with vigorous stirring. After 15 minutes, the mixture was extracted with $CH_2Cl_2$ (2×30 mL) and the organics were dried over anhydrous sodium sulfate to yield 0.031 g (0.075 mmol, 71%) of compound 2 as a white solid. No purification was necessary. HPLC: 78% at 2.290 min (retention time) (YMC S5 ODS column 4.6×50 mm eluting with 10-90% aqueous methanol over 4 minutes containing 0.1% TFA, 41n L/min, monitoring at 220 nm). MS (ES): m/z 429.8 $[M+NH_4]^+$.

EXAMPLE 3

(3aα,4β,7β,7aα)-2-(3-Chlorophenyl)hexahydro-4-methyl-4,7-epoxy-1H-isoindole-1,3(2H)-dione (3)

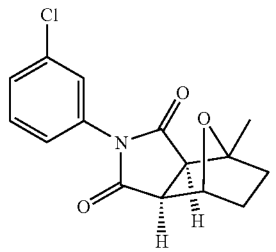

3-Chloroaniline (0.100 g, 0.787 mmol) and 3,6-endoxo-3-methylhexahydrophthalic anhydride (0.172 g, 0.945 mmol) were dissolved in AcOH (2.0 mL) and heated at 110° C. for 11 h. The reaction was then cooled to 25° C., poured into cold saturated aq. $K_2CO_3$ and stirred vigorously for 10 min. The solution was then filtered and rinsed with water. The resulting filtrate was dried in vacuo to give 0.118 g (0.404 mmol, 51%) of compound 3 as a white solid. No further purification was needed. HPLC: 99% at 2.510 min (retention time) (YMC S5

ODS column 4.6×50 mm eluting with 10-90% aqueous methanol over 4 minutes containing 0.1% TFA, 4 mL/min, monitoring at 220 nm). MS (ES): m/z 292.32 $[M+H]^+$.

EXAMPLE 4

(3aα,4α,7α,7aα)- and (3aα,4β,7β,7aα)-4-[(Acetyloxy)methyl]-3a,4,7,7a-tetrahydro-2-[3-(trifluoromethyl)phenyl]-4,7-epoxy-1H-isoindole-1,3(2H)-dione (4i and 4ii, respectively)

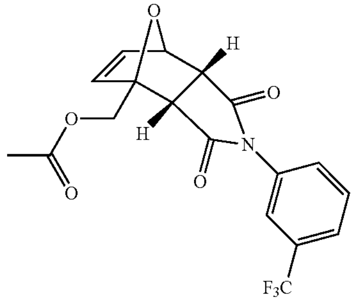

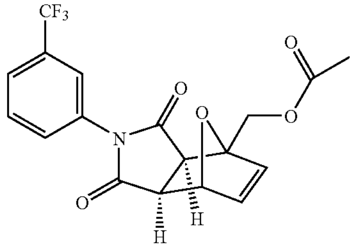

2-Acetoxymethylfuran (0.599 mL, 4.78 mmol) and 1-[3-(trifluoromethyl)-phenyl]-1H-pyrrole-2,5-dione (0.500 g, 2.39 mmol, prepared as described in Example 1B) were dissolved in methylene chloride (3.0 mL) at 25° C. After 22 h, the volatiles were removed in vacuo and the resulting residue was purified by flash chromatography on $SiO_2$ eluting with 0-15% acetone in methylene chloride to give 0.438 g (1.15 mmol, 48%) of a yellow oil as a 2:1 mixture of compound 4i and compound 4ii, which was not separated. HPLC: 100% at 3.093 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 398.9 $[M+NH_4]^+$.

EXAMPLE 5

(3aα,4α,7α,7aα)- and (3aα,4β,7β,7aα)-4-[(Acetyloxy)methyl]-Hexahydro-2-[3-(trifluoromethyl)phenyl]-4,7-epoxy-1H-isoindole-1,3(2H)-dione (5i and 5ii, respectively)

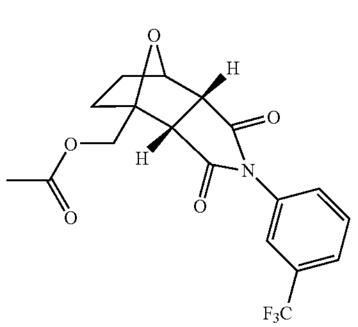

-continued

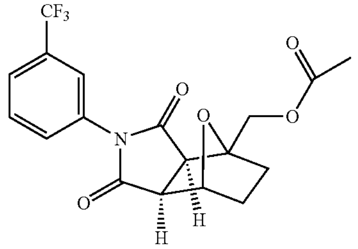

The 2:1 mixture of compounds 4i and 4ii (0.361 g, 0.948 mmol) was dissolved in ethyl acetate (25 mL) and Pd/C (10% Pd, 0.2 g) was added. Hydrogen was introduced via a balloon and the reaction was stirred at 25° C. for 4 h, followed by filtration through Celite and rinsing with ethyl acetate. Concentration in vacuo gave 0.348 g (0.908 mmol, 96%) of a yellow oil that was determined to be a 2:1 mixture of compound 5i and compound 5ii (which was not separated). HPLC: 100% at 2.900 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 401.0 $[M+NH_4]^+$.

EXAMPLE 6

(3aα,4α,7α,7aα)- and (3aα,4β,7β,7aα)-3a,4,7,7a-Tetrahydro-5-(hydroxymethyl)-2-[3-(trifluoromethyl)phenyl]4,7-epoxy-1H-isoindole-1,3(2H)-dione (6i and 6ii, respectively)

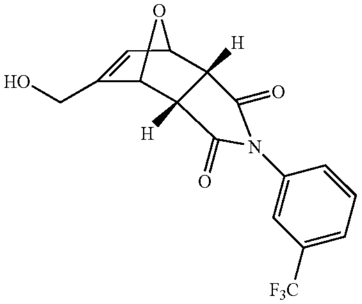

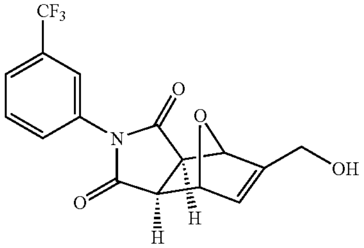

1-[3-(Trifluoromethyl)phenyl]-1H-pyrrole-2,5-dione (0.500 g, 2.39 mmol, prepared as described in Example 1B) and 3-furanmethanol (0.412 mL, 4.78 mmol) were dissolved in methylene chloride (3.0 mL) and stirred at 25° C. for 20 h. The volatiles were then removed in vacuo and the resulting material purified by flash chromatography on $SiO_2$ eluting with chloroform/acetone to give 0.379 g (1.12 mmol, 47%) of compound 6i and 0.220 g of compound 6ii, both as white solids. Compound 61: HPLC: 100% at 2.197 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 338.0 $[M-H]^-$. Compound 6ii: HPLC: 100% at 2.477 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 338.0 $[M-H]^-$.

EXAMPLE 7

(3aα,4α,7α,7aα)-3a,4,7,7a-Tetrahydro-5-(hydroxymethyl)-4-methyl-2-[3-(trifluoromethyl)phenyl]-4,7-epoxy-1H-isoindole-1,3(2H)-dione (7)

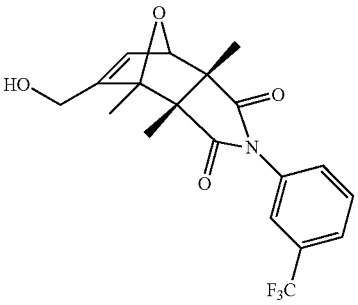

2-Methyl-3-furanmethanol (0.537 g, 4.78 mmol) and 1-[3-(trifluoromethyl)-phenyl]-1H-pyrrole-2,5-dione (0.500 g, 2.39 mmol, prepared as described in Example 1B) were dissolved in dichloroethane (2.0 mL) and stirred at 25° C. for 20 h. The reaction was then concentrated in vacuo and purified by flash chromatography in $SiO_2$ eluting with ethyl acetate/methylene chloride to give 0.317 g (0.897 mmol, 37.5%) of compound 7 as a white solid. No other possible isomer was isolated after chromatography. HPLC: 100% at 2.197 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 351.9 $[M-H]^-$.

EXAMPLE 8

(3aα,4β,7β,7aα)-2-[3,5-Bis(trifluoromethyl)phenyl]hexahydro-4,7-epoxy-1H-isoindole-1,3(2H)-dione (8)

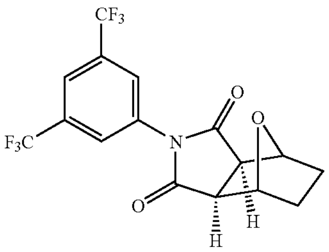

3,5-Bis(trifluoromethyl)aniline (0.017 g, 0.075 mmol) was dissolved in acetic acid (0.300 mL) and transferred to a 1.5 mL conical vial with a septa cap. Stock solutions of an additional 95 amines were prepared as described above. To each of the above vials was added 0.40 mL (0.12 mmol) of a stock solution of exo-7-oxabicyclo[2.2.1]heptane-2,-3-dicarboxylic anhydride in acetic acid. The vials were then sealed and heated at 110° C. for 11 h. Upon cooling to 25° C., the caps were removed from the vials and the acetic acid was removed in vacuo. To each vial was added 1 mL of 2:1 acetone/methylene chloride and the vials were heated at 40° C. for 1 h. Once all products were in solution, they were transferred via robot to filter tubes with coarse frits pre-wetted with 0.2 mL of water. Nitrogen was blown through each tube until the volatile organics were removed. 1.5 mL of 10% aq. $K_2CO_3$ was then added to each tube followed by vigorous shaking at 25° C. for 15 min. The tubes were then drained, resealed and 1.0 mL of water was added to each tube followed by shaking. The tubes were drained again and washed with water a second time. The resulting residues in each tube were then dried in vacuo for 48 h. After drying, 1.0 mL of 20% TFA in methylene chloride was added to each tube and the racks were shaken for 30 min. The tubes were then drained into a 96-well plate with pre-tared custom micro-tubes present. Each tube was assayed for product purity (analytical LC) and identity (LC-MS). The tubes were then concentrated in vacuo and weighed for yields. The tube containing the reaction of 3,5-bistrifluoromethylaniline and exo-7-oxabicyclo[2.2.1]heptane-2,3-dicarboxylic anhydride, yielded 0.022 g (0.058 mmol, 77%) of compound 8 as a white solid. HPLC: 94% at 4.03 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 434.2 $[M+Na^+ MeOH]^+$. Of the remaining 95 additional reactions run, a total of 80 final compounds were obtained in >70% purity and >5 mg yield. Several samples needed further purification which was performed by short $SiO_2$ column eluting with methylene chloride/acetone. See Table 2 below.

EXAMPLE 9

(3aα,4α,7α,7aα)-2-(4-Bromophenyl)octahydro-1,3-dioxo-4,7-etheno-5H-pyrrolo[3,4-c]pyridine-5-carboxylic acid phenyl ester (9)

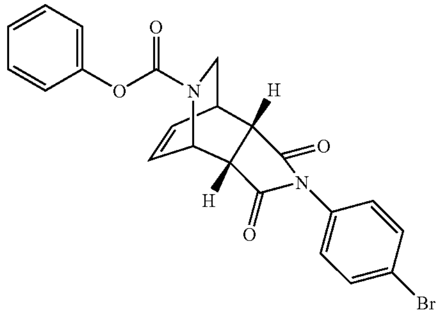

1-[4-Bromophenyl]-1H-pyrrole-2,5-dione (0.250 g, 0.992 mmol, prepared as described in Example 1B) and 1(2H)-pyridinecarboxylic acid phenylmethyl ester (0.299 g, 1.49 mmol, synthesized as described in Richard et al. *J. Org. Chem.* 46, 4836-4842 (1981)) were dissolved in toluene and heated at 85° C. for 1 h. Upon cooling to 25° C., the toluene was removed in vacuo. The resulting residue was dissolved in a minimum amount of chloroform and the product was precipitated by addition of hexanes. After 1 h at 25° C., the product was filtered and rinsed with cold 20% hexanes in chloroform giving 0.243 g (0.536 mmol, 54%) of compound 9 as a white solid (single isomer). HPLC: 100% at 3.393 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 454.98 $[M+H]^+$.

EXAMPLE 10

(3aα,4α,7α,7aα)-2-(4-Bromophenyl)octahydro-1,3-dioxo-4,7-etheno-5H-Pyrrolo[3,4-c]pyridine-5-carboxylic acid phenylmethyl ester (10)

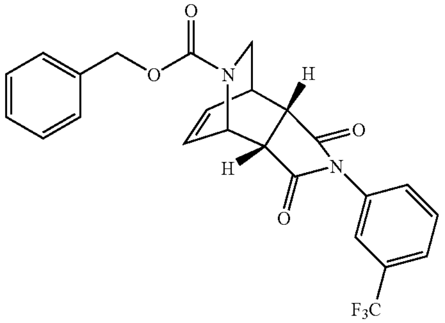

1-[3-(Trifluoromethyl)phenyl]-1H-pyrrole-2,5-dione (3.78 g, 15.7 mmol, prepared as described in Example 1B) and 1(2H)-pyridinecarboxylic acid phenylmethyl ester (4.00 g, 18.8 mmol, synthesized as described in Richard et al. *J. Org. Chem.* 46, 4836-4842 (1981)) were dissolved in toluene and heated at 80° C. for 3 h. After cooling to 25° C., the toluene was removed in vacuo and the resulting residue was purified by flash chromatography on $SiO_2$ eluting with methanol/methylene chloride to give 3.20 g (7.01 mmol, 45%) of compound 10 as a yellow oil. HPLC: 95% at 3.510 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 457.2 $[M+H]^+$.

EXAMPLE 11

(3aα,4α,7α,7aα)-Hexahydro-2-[3-(trifluoromethyl)phenyl]-4,7-ethano-1H-Pyrrolo[3,4-c]pyridine-1,3(2H)-dione trifluoroacetate (11)

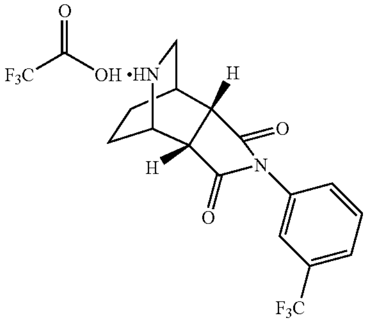

Compound 10 (3.20 g, 7.01 mmol) was dissolved in 100 mL of MeOH and 10% Pd/C Degussa catalyst (2.00 g, cat.) was added. Hydrogen was then introduced via a balloon. After 1 h, the reaction was filtered through Celite and rinsed with MeOH. The volatiles were removed in vacuo and the resulting crude material was purified by reverse phase preparative HPLC to yield 2.50 g (5.70 mmol, 81%) of compound 11 as the TFA salt (white solid). HPLC: 99% at 1.843 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 325.12 $[M+H]^+$.

EXAMPLE 12

(3aα,4α,7α,7aα)-5-Acetylhexahydro-2-[3-(trifluoromethyl)phenyl]-4,7-ethano-1H-pyrrolo[3,4-c]pyridine-1,3(2H)-dione (12)

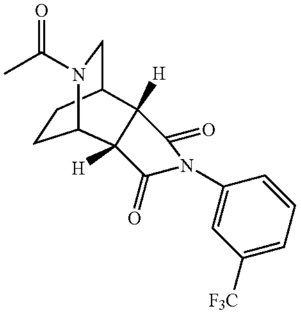

Compound 11 (0.10 g, 0.23 mmol) was suspended in THF (5.0 mL) and TEA (0.097 mL, 0.46 mmol) was added resulting in a homogeneous solution. Acetyl chloride (0.033 mL, 0.46 mmol) was then added. After 2 h, the reaction was quenched with saturated aqueous $NaHCO_3$ and extracted with methylene chloride (3×15 mL). The crude material was purified by preparative TLC eluting with chloroform/acetone to give 0.067 g (0.18 mmol, 79%) of compound 12 as a colorless oil. HPLC: 99% at 2.66 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 367.0 $[M+H]^+$.

EXAMPLE 13

(3aα,4α,7α,7aα)-5-Benzoylhexahydro-2-[3-(trifluoromethyl)phenyl]-4,7-ethano-1H-pyrrolo[3,4-c]pyridine-1,3(2H)-dione (13)

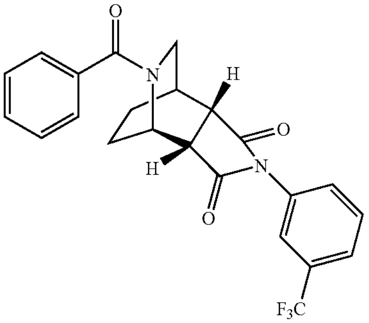

Compound 11 (0.10 g, 0.23 mmol) was suspended in THF (5.0 mL) and TEA (0.097 mL, 0.46 mmol) was added resulting in a homogeneous solution. Benzoyl chloride (0.053 mL, 0.46 mmol) was then added. After 2 h, the reaction was quenched with saturated aqueous $NaHCO_3$ and extracted with methylene chloride (3×15 mL). The crude material was purified by reverse phase preparative HPLC to give 0.020 g (0.047 mmol, 20%) of compound 13 as a white foam. HPLC: 99% at 3.183 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 429.1 $[M+H]^+$.

EXAMPLE 14

(3aα,4α,7α,7aα)-Hexahydro-5-methyl-2-[3-(trifluoromethyl)phenyl]-4,7-ethano-1H-pyrrolo[3,4-c]pyridine-1,3(21)-dione (14)

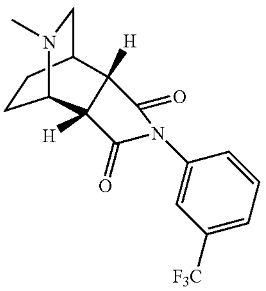

Compound 11 (0.10 g, 0.23 mmol) was suspended in THF (5.0 mL) and TEA (0.097 mL, 0.46 mmol) was added resulting in a homogeneous solution. Dimethyl sulfate (0.043 mL, 0.46 mmol) was added and the reaction was stirred at 25° C. After 14 h, the reaction was concentrated in vacuo and the crude material was purified by preparative TLC eluting with 10% MeOH in methylene chloride to give 0.030 g (0.088 mmol, 39%) of compound 14 as a white solid. HPLC: 100% at 1.797 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 339.21 $[M+H]^+$.

EXAMPLE 15

(3aα,4α,7α,7aα)-Hexahydro-5-(Phenylmethyl)-2-[3-(trifluoromethyl)phenyl]-4,7-ethano-1H-pyrrolo[3,4-c]pyridine-1,3(2H)-dione trifluoroacetate (15)

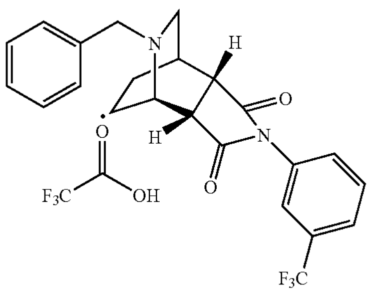

Compound 11 (0.10 g, 0.23 mmol) was dissolved in DMF (5.0 mL) and $K_2CO_3$ (0.063 g, 0.46 mmol) was added. Benzyl bromide (0.041 mL, 0.35 mmol) was then added. The reaction was stirred at 25° C. for 1 h, filtered and concentrated in vacuo. The crude material was purified by reverse phase preparative HPLC to give 0.055 g (0.10 mmol, 43%) of compound 15 as a white solid. HPLC: 100% at 2.31 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 415.36 $[M+H]^+$.

EXAMPLE 16

(3aα,4α,7α,7aα)-Hexahydro-5-propyl-2-[3-(trifluoromethyl)phenyl]-4,7-ethano-1H-pyrrolo[3,4-c]pyridine-1,3(2H)-dione trifluoroacetate (16)

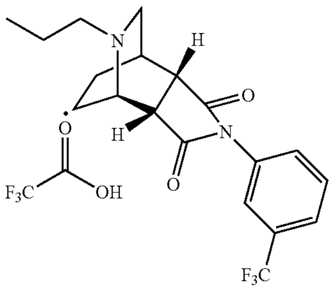

Compound 11 (0.10 g, 0.23 mmol) was dissolved in DMF (5.0 mL) and $K_2CO_3$ (0.079 g, 0.57 mmol) was added, followed by 1-bromopropane (0.031 mL, 0.34 mmol). The reaction was stirred at 25° C. for 6 h, then filtered and concentrated in vacuo. The crude material was purified by reverse phase preparative HPLC to give 0.070 g (0.15 mmol, 63%) of compound 16 as a white solid. HPLC: 100% at 1.907 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 340.22 $[M+H]^+$.

EXAMPLE 17

(3aα,4α,4aβ,5aβ,6α,6aα)-2-[4-Cyano-3-(trifluoromethyl)phenyl]decahydro-1,3-dioxo-4,6-(iminomethano)cycloprop[f]isoindole-7-carboxylic acid phenylmethyl ester (17)

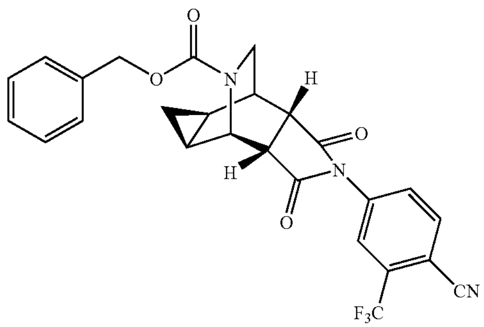

1-Methyl-3-nitro-1-nitrosoguanidine (2.5 g, 17 mmol) was added portionwise to a solution of 40% KOH/$H_2O$ (15 mL) and $Et_2O$ (25 mL) at 0° C. The ether layer turned yellow once addition was complete. After 30 min at 0° C., the ether layer was poured into a solution of (3aα,4α,7α,7aα)-2-[4-cyano-3-(trifluoromethyl)phenyl]-octahydro-1,3-dioxo-4,7-etheno-5H-pyrrolo[3,4-c]pyridine-5-carboxylic acid phenylmethyl ester (0.500 g, 1.09 mmol, prepared as described in Example 10) and $Pd(OAc)_2$ (0.010 g) in THF (10 mL) at 0° C. The reaction was then warmed slowly to 25° C., stirred for 24 h and then filtered through Celite rinsing with THF. The crude material was then purified by flash chromatography on $SiO_2$ eluting with MeOH/$CH_2Cl_2$ to give 0.34 g (0.69 mmol, 63%) of compound 17 as a white solid and a single isomer. HPLC: 100% at 3.61 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 496.25 $[M+H]^+$.

EXAMPLE 18

(3aα,4α,4aβ,5aβ,6α,6aα)-4-[Decahydro-1,3-dioxo-4,6-(iminomethano)cycloprop[f]isoindol-2-yl]-2-(trifluoromethyl)benzonitrile (18)

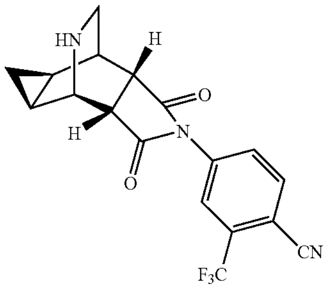

Compound 17 (0.200 g, 0.404 mmol) was dissolved in MeOH (20 mL) and 5% Pd/C (0.200 g) was added. Hydrogen was then introduced via balloon. After 3 h, the reaction was filtered through Celite, rinsed with MeOH and the volatiles were removed in vacuo to yield 0.130 g (0.360 mmol, 89%) compound 18 as a white solid. HPLC: 100% at 1.80 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 362.09 $[M+H]^+$.

EXAMPLE 19

(3aα,4α,4aβ,5aβ,6α,6aα)-4-[Decahydro-7-methyl-1,3-dioxo-4,6-(iminomethano)cycloprop[f]isoindol-2-yl]-2-(trifluoromethyl)benzonitrile (19)

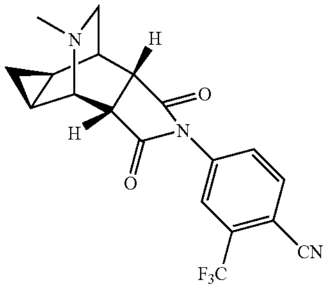

Compound 18 (0.100 g, 0.277 mmol) was dissolved in $CH_3CN$ (2.0 mL). TEA (0.19 mL, 1.4 mmol) and MeI (0.052 mL, 0.83 mmol) were then added and the reaction was stirred at 25° C. for 14 h. The reaction was concentrated under reduced pressure and the crude material was partioned between $CH_2Cl_2$/water and the aqueous layer was extracted with $CH_2Cl_2$ (3×15 mL). The combined organics were dried over anhydrous $Na_2SO_4$. The crude material was purified by flash chromatography eluting with 3% MeOH/$CH_2Cl_2$ to give 0.030 g (0.080 mmol, 29%) of compound 19 as a light yellow solid. HPLC: 100% at 1.720 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 376.11 $[M+H]^+$.

EXAMPLE 20

(3aα,4β,7β,7aα)-4-(Octahydro-4,7-dimethyl-1,3-dioxo-4,7-epoxy-2H-isoindol-2-yl)-2-(trifluoromethyl)benzonitrile (20B)

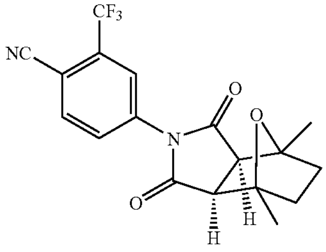

A. (3aα,4β,7β,7aα)-Hexahydro-4,7-epoxyisobenzofuran-1,3-dione (20A)

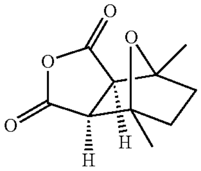

Freshly distilled dimethyl furan (1.60 mL, 15.3 mmol) was dissolved in $CH_2Cl_2$ (2.0 mL) and maleic anhydride (1.00 g, 10.2 mmol) was added. The reaction was stirred at 25° C. for 16 h and was then concentrated in vacuo to give a yellow solid. This solid was dissolved in ethyl acetate (30 mL) and 10% Pd/C (0.200 g, cat.) was added. Hydrogen was then introduced via a balloon and the reaction stirred for 24 h. The reaction mixture was filtered through Celite rinsing with EtOAc followed by concentration in vacuo to give 1.69 g (8.61 mmol, 84%) of compound 20A as a white solid. 2-Dimensional NOE experiments confirmed the structural assignment to be that of compound 20A.

B. (3aα,4β,7β,7aα)-4-(Octahydro-4,7-dimethyl-1,3-dioxo-4,7-epoxy-2H-isoindol-2-yl)-2-(trifluoromethyl)benzonitrile (20B)

A solution of compound 20A (603 mg, 3.21 mmol), 5-amino-2-cyanobenzotrifluoride (640 mg, 3.44 mmol) and TsOH (10 mg, cat.) in toluene (5 mL) was heated in a sealed tube for 2 days. The reaction mixture was cooled to room temperature and then concentrated under reduced pressure.

Purification by flash chromatography on silica gel eluting with 50% EtOAc/hexanes gave 400 mg (1.10 mmol, 34%) of compound 20B as a white solid. HPLC: 99% at 3.04 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 382.2 $[M+NH_4]^+$.

EXAMPLE 21

(3aα,4β,7β,7aα)-N-[4-[[2-[2-[4-Cyano-3-(trifluoromethyl)phenyl]octahydro-7-methyl-1,3-dioxo-4,7-epoxy-4H-isoindol-4-yl]ethyl]thio]phenyl]acetamide (21E)

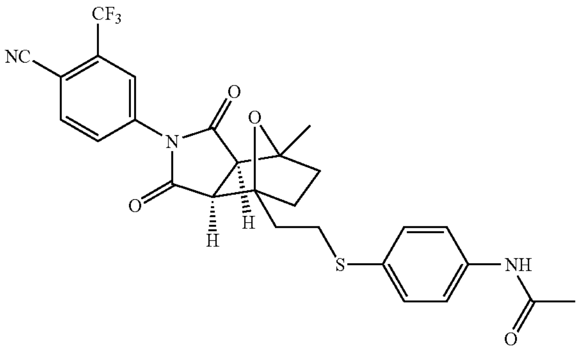

A. 5-Methyl-2-furanethanol (21A)

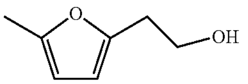

A solution of n-BuLi (83.0 mL, 133 mmol, 1.6 M in hexanes) was added to a stirred solution of 2-methylfuran (10.0 mL, 111 mmol) in THF (85 mL) at 0° C. under inert atmosphere. The reaction mixture was stirred for 4 h at room temperature then cooled to 0° C. Ethylene oxide (8.30 mL, 166 mmol) was added dropwise and the reaction mixture was allowed to warm to room temperature overnight. After quenching with saturated aqueous $NH_4Cl$, the resulting layers were separated and the aqueous layer was extracted with $Et_2O$ (2×250 mL). The combined organic layers were dried over $Na_2SO_4$ and concentrated under reduced pressure. Distillation at atmospheric pressure (170-185° C.) gave 10.1 g (80.3 mmol, 72%) of compound 21A as a light yellow oil.

B. 2-(2-Bromoethyl)-5-methylfuran (21B)

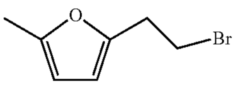

$Ph_3Br_2$ (3.68 g, 8.72 mmol) was added to a solution of compound 21A (1.00 g, 7.93 mmol) in DMF (8 mL) and the reaction mixture was stirred at room temperature for 1 h. The reaction mixture was added to $H_2O$ and extracted with EtOAc (3×). The combined organic layers were washed with $H_2O$ (2×), dried over $Na_2SO_4$ and concentrated under reduced pressure. Purification by flash chromatography on silica gel eluting with 10% EtOAc/hexanes gave 0.507 g (2.68 mmol, 34%) of compound 21B.

C. N-[4-[[2-(5-Methyl-2-furanyl)ethyl]thio]phenyl]acetamide (21C)

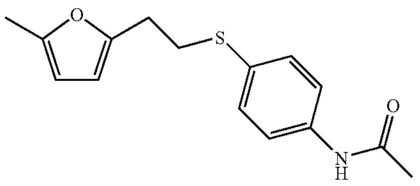

To a solution of 4-acetamidothiophenol (442 mg, 2.64 mmol) in THF (1 mL) at 0° C. under inert atmosphere was added a solution of n-BuLi (2.00 mL, 3.17 mmol, 1.6 M in hexanes) in THF (1 mL). The reaction solution was stirred at room temperature for 10 min then a solution of compound 21B (500 mg, 2.64 mmol) in THF (3 mL) was added. After the starting material was consumed (as determined by TLC), the reaction was quenched with $H_2O$ and the mixture was extracted with EtOAc (2×), dried over $Na_2SO_4$ and concentrated under reduced pressure. Purification by flash chromatography on silica gel eluting with 50% EtOAc/hexanes gave 0.644 g (2.34 mmol, 88%) of compound 21C. MS (ESI): m/z 276.09 $[M+H]^+$.

D. (3aα,4β,7β,7aα)-N-[4-[[2-[2-[4-Cyano-3-(trifluoromethyl)phenyl]-1,2,3,3a,7,7a-hexahydro-7-methyl-1,3-dioxo-4,7-epoxy-4H-isoindol-4-yl]ethyl]thio]phenyl]acetamide (21D)

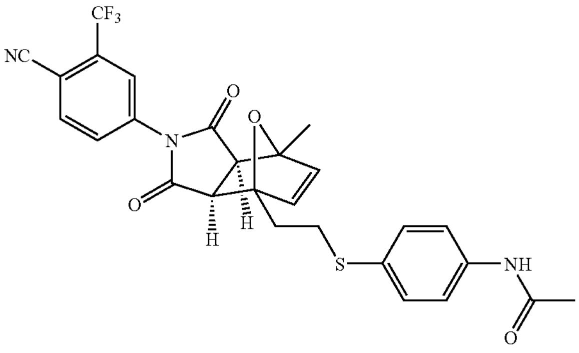

A solution of compound 21C (195 mg, 0.708 mmol) and 4-(2,5-dihydro-2,5-dioxo-1H-pyrrol-1-yl)-2-trifluoromethylbenzonitrile (377 mg, 1.416 mmol, prepared as described for Example 1B) in $CH_2Cl_2$ (1.5 mL) was stirred at room temperature for two days. The reaction mixture was concentrated under reduced pressure to yield compound 21D as determined by NMR analysis. Compound 21D was used directly in the next step without purification.

E. (3aα,4β,7β,7aα)-N-[4-[[2-[2-[4-Cyano-3-(trifluoromethyl)phenyl]-octahydro-7-methyl-1,3-dioxo-4,7-epoxy-4H-isoindol-4-yl]ethyl]thio]-phenyl]acetamide (21E)

A solution of crude compound 21D (0.708 mmol) and 10% Pd/C (200 mg) in MeOH (20 mL) was stirred under a hydrogen atmosphere overnight. Purification by reverse phase HPLC [34.4 min (retention time) (YMC S5 ODS column 20×250 mm, 0-100% aqueous methanol over 30 minutes containing 0.1% TFA, 10 mL/min, monitoring at 220 nm)] followed by flash chromatography on silica gel eluting with 1% MeOH/$CH_2Cl_2$ gave 29 mg (0.053 mmol, 7.5%) of compound 21E as a yellow powder. HPLC: 99% at 3.44 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 544.01 $[M+H]^+$.

EXAMPLE 22

(3aα,4β,7β,7aα)-N-[4-[[2-[2-[4-Cyano-3-(trifluoromethyl)phenyl]octahydro-7-methyl-1,3-dioxo-4,7-epoxy-4H-isoindol-4-yl]ethyl]sulfinyl]phenyl]acetamide (22)

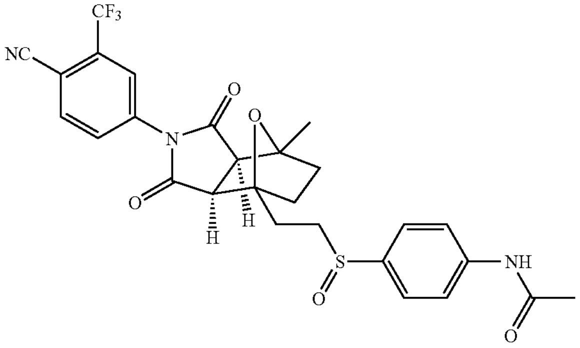

mCPBA (12 mg, 0.050 mmol) was added portionwise to a solution of crude compound 21E (65 mg, 0.12 mmol) in $CH_2Cl_2$ (6 mL) until the starting material was consumed. Purification by reverse phase HPLC [30.5 min (retention time) (YMC S5 ODS column 30×250 mm, 0-100% aqueous methanol over 30 minutes containing 0.1% TFA, 25 mL/min, monitoring at 220 nm)] gave 27.5 mg (0.0491 mmol, 41%) of compound 22 as a tan solid (~1:1 mixture of diastereomers). HPLC: 96% at 2.88 min (retention time) (YMC S5 ODS column 4.6×50 mm eluting with 10-90% aqueous methanol over 4 minutes containing 0.1% TFA, 4 mL/min, monitoring at 220 nm). MS (ESI): m/z 559.97 $[M+H]^+$.

EXAMPLE 23

(3aα,4β,7β,7aα)-N-[4-[[2-[2-[4-Cyano-3-(trifluoromethyl)phenyl]octahydro-7-methyl-1,3-dioxo-4,7-epoxy-4H-isoindol-4-yl]ethyl]sulfonyl]phenyl]acetamide (23)

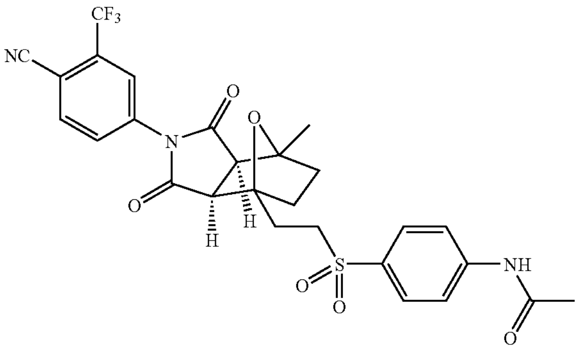

mCPBA (26 mg, 0.11 mmol) was added to a solution of compound 21E (19 mg, 0.035 mmol) in $CH_2Cl_2$ (6 mL) and the reaction was stirred at rt until starting material and the intermediate sulfoxide (compound 22) were consumed as was apparent by TLC. Purification by reverse phase preparative HPLC [53.3 min (retention time) (YMC S5 ODS column 30×250 mm, 0-70% aqueous methanol over 45 minutes containing 0.1% TFA, 25 mL/min, monitoring at 220 nm)] gave 8.0 mg mg (0.014 mmol, 40%) of compound 23 as a white solid. HPLC: 99% at 2.94 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 575.95 $[M+H]^+$.

EXAMPLE 24

(3aα,4β,7β,7aα)- and (3aα,4α,7α,7aα)-N-[2-[2-[4-Cyano-3-(trifluoromethyl)phenyl]octahydro-7-methyl-1,3-dioxo-4,7-epoxy-4H-isoindol-4-yl]ethyl]benzenesulfonamide (24Ci and 24Cii, respectively)

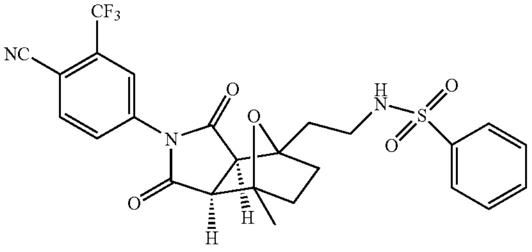

-continued

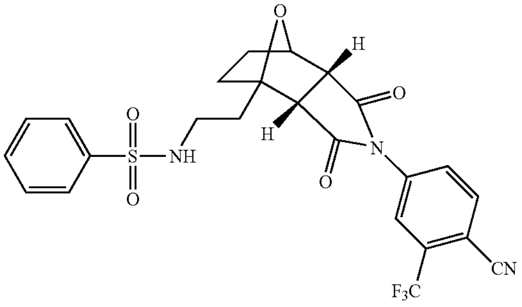

A. 5-Methyl-2-furanethanol 4-methylbenzenesulfonate (24A)

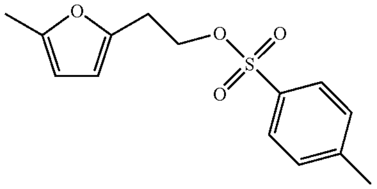

4-Methylbenzenesulfonyl chloride (907 mg, 4.76 mmol) was added to a solution of compound 21A (500 mg, 3.96 mmol) in 6 mL of dry pyridine. The reaction was stirred at room temperature for 4 h and then quenched with ice. The reaction mixture was extracted with $CH_2Cl_2$ and the combined organic layers were washed with saturated aqueous sodium bicarbonate and water, dried and concentrated under reduced pressure to give 900 mg (81%) of compound 24A as a yellow oil.

B. N-[2-(5-Methyl-2-furanyl)ethyl] benzenesulfonamide (24B)

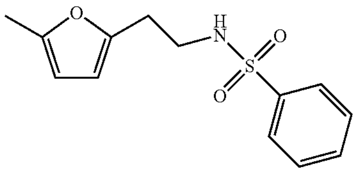

Benzenesulfonamide (157 mg, 1.00 mmol) was added to a 10% aqueous solution of sodium hydroxide (0.40 mL, 1.0 mmol). A solution of compound 24A (280 mg, 1.00 mmol) in acetone (1 mL) was then added. The reaction mixture was heated at 90° C. for 8 h then cooled to room temperature. Ice was added and the mixture was extracted with $CH_2Cl_2$. The combined organic layers were washed with water, dried and concentrated under reduced pressure. Purification by flash chromatography on silica gel, eluting with $CH_2Cl_2$ gave 60 mg (0.23 mmol, 23%) of compound 24B as yellow oil.

C. (3aα,4β,7β,7aα)- and (3aα,4α,7α,7aα)-N-[2-[2-[4-Cyano-3-(trifluoromethyl)phenyl]octahydro-7-methyl-1,3-dioxo-4,7-epoxy-4H-isoindol-4-yl]ethyl] benzenesulfonamide (24Ci and 24Cii, respectively)

4-(2,5-Dihydro-2,5-dioxo-1H-pyrrol-1-yl)-2-trifluoromethylbenzonitrile (129 mg, 0.485 mmol, prepared as described in Example 1B) was added to a solution of compound 24B (60 mg, 0.23 mmol) in $CH_2Cl_2$ (2 mL). The reaction mixture was stirred at room temperature for 2 days, concentrated under reduced pressure and purified by flash chromatography on silica gel, eluting with 70% EtOAc/hexanes, to give 20 mg (0.038 mmol, 16%) of the unsaturated Diels-Alder product. The unsaturated product (20 mg) was immediately dissolved in ethanol (2 mL) and 10% Pd/C (10 mg, cat.) was added. The solution was stirred at room temperature overnight under a hydrogen atmosphere. The mixture was filtered and the filtrate was concentrated under reduced pressure. Purification by reverse phase preparative HPLC gave 7.0 mg (0.013 mmol, 34%) of compound 24Ci and 2.0 mg (0.0037 mmol, 10%) of compound 24Cii. Compound 24Ci: HPLC: 96% at 3.17 min (retention time) (YMC ODSA S5 C18 4.6×50 mm, 10%-90% aqueous methanol over 4 min gradient with 0.1% TFA, monitoring at 220 nm). MS (ES): m/z: 533.99 $[M+H]^+$. Compound 24Cii: HPLC: 99% at 38.95 min (retention time) (YMC ODS S5 20×250 mm, 10%-90% aqueous methanol over 40 min gradient with 0.1% TFA, monitoring at 220 nm). MS (ES): m/z 533.99 $[M+H]^+$.

EXAMPLE 25

(3aα,4β,7β,7aα)-4-[Octahydro-4-(2-hydroxyethyl)-7-methyl-1,3-dioxo-4,7-epoxy-2H-isoindol-2-yl]-2-(trifluoromethyl)benzonitrile (25B)

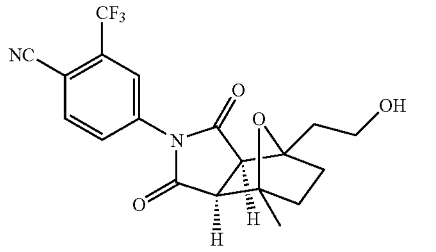

A. (3aα,4β,7β,7aα)- and (3aα,4α,7α,7aα)-4-[1,3,3a,4,7,7a-Hexahydro-4-(2-hydroxyethyl)-7-methyl-1,3-dioxo-4,7-epoxy-2H-isoindol-2-yl]-2-(trifluoromethyl)benzonitrile (25Ai and 25Aii, respectively)

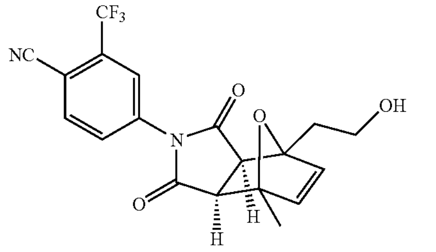

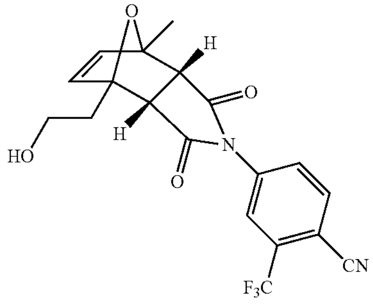

A solution of compound 21A (252 mg, 2.00 mmol) and 4-(2,5-dihydro-2,5-dioxo-1H-pyrrol-1-yl)-2-trifluoromethylbenzonitrile (798 mg, 3.00 mmol) in $CH_2Cl_2$ (10 mL) was stirred at room temperature for 2 days. The reaction mixture was concentrated under reduced pressure. Purification by flash chromatography on silica gel eluting with 65% EtOAc/hexanes gave 217 mg of pure compound 25Ai, 73 mg of pure compound 25Aii and 310 mg of a mixture of both compound 25Ai and 25Aii. All three fractions were isolated as white solids with a total isolated yield of 600 mg (1.53 mmol, 76.5%). Compound 25Ai: HPLC: 90% at 2.56 min (retention time) (YMC S5 ODS column 4.6×50 mm, 10-90% aqueous methanol over 4 minutes containing 0.2% phosphoric acid, 4 mL/min, monitoring at 220 nm). Compound 25Aii: HPLC: 90% at 2.56 min (retention time) (YMC S5 ODS column 4.6×50 mm, 10-90% aqueous methanol over 4 minutes containing 0.2% phosphoric acid, 4 mL/min, monitoring at 220 nm).

B. (3aα,4β,7β,7aα)-4-[Octahydro-4-(2-hydroxyethyl)-7-methyl-1,3-dioxo-4,7-epoxy-2H-isoindol-2-yl]-2-(trifluoromethyl)benzonitrile (25B)

A solution of compound 25Ai (0.20 g, 0.51 mmol) and 10% Pd/C (43 mg, cat.) in EtOH (12 mL) was stirred under a hydrogen atmosphere at room temperature for 2 h. The reaction mixture was filtered through Celite and concentrated under reduced pressure to give 0.20 g (0.51 mmol, 100%) of compound 25B as a white solid. HPLC: 95% at 2.59 min (retention time) (YMC S5 ODS column 4.6×50 mm eluting with 10-90% aqueous methanol over 4 minutes containing 0.1% TFA, 4 mL/min, monitoring at 220 nm). MS (ESI): m/z 394.97 $[M+H]^+$.

EXAMPLE 26

(3aα,4β,7β,7aα)- and (3aα,4α,7α,7aα)-N-[4-[2-[2-[4-Cyano-3-(trifluoromethyl)phenyl]octahydro-7-methyl-1,3-dioxo-4,7-eyoxy-4H-isoindol-4-yl]ethoxy]phenyl]acetamide (26Ci and 26Cii, respectively)

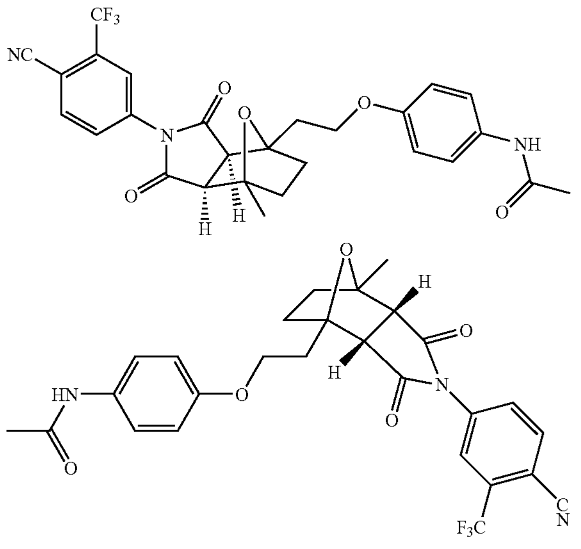

A. 2-[4-[2-(5-Methyl-2-furanyl)ethoxy]phenyl]acetamide (26A)

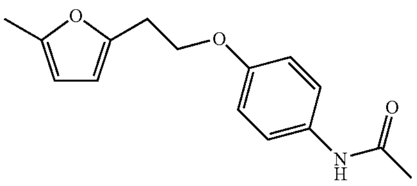

Triphenylphosphine (681 mg, 2.60 mmol) was added to a solution of compound 21A (252 mg, 2.00 mmol) and 4-acetamidophenol (302 mg, 2.00 mmol) in $CH_2Cl_2$ (4 mL). THF (5 mL) was added to make the reaction mixture homogeneous and the mixture was then cooled to 0° C. DEAD (0.41 mL, 2.6 mmol) was added dropwise and the reaction mixture was stirred at room temperature overnight, then concentrated under reduced pressure. Purification by flash chromatography on silica gel eluting with 60% EtOAc/hexanes followed by reverse phase preparative HPLC gave 270 mg (1.04 mmol, 52%) of compound 26A as a light brown solid. MS (ESI): m/z 260.09 $[M+H]^+$.

B. (3aα,4β,7β,7aα)- and (3aα,4α,7α,7aα)-N-[4-[2-[2-[4-Cyano-3-(trifluoromethyl)phenyl]-1,2,3,3a,7,7a-hexahydro-7-methyl-1,3-dioxo-4,7-epoxy-4H-isoindol-4-yl]ethoxy]phenyl]acetamide (26Bi and 26Bii, respectively)

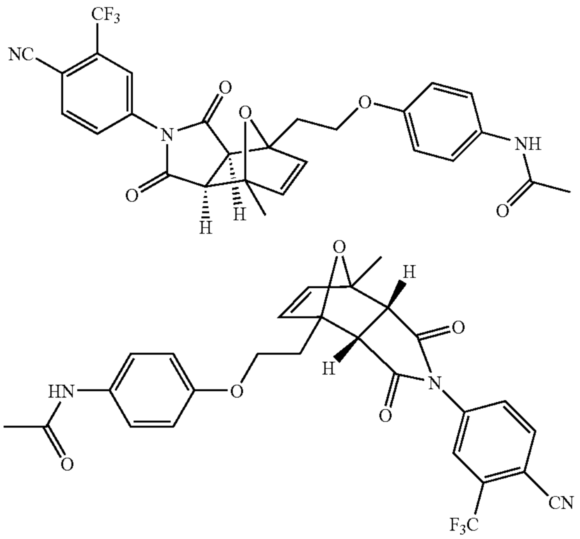

A solution of compound 26A (40 mg, 0.15 mmol) and 4-(2,5-dihydro-2,5-dioxo-1H-pyrrol-1-yl)-2-trifluoromethylbenzonitrile (88 mg, 0.31 mmol) in $CH_2Cl_2$ (2 mL) was stirred at room temperature for 2 days. The reaction mixture was concentrated under reduced pressure. Purification by flash chromatography on silica gel eluting with 75% EtOAc/hexanes gave 55 mg (0.105 mmol, 68%) of a 5:1 mixture of compounds 26Bi and 26Bii as a white solid, which was used directly in the next step. HPLC: 90% at 3.28 min (retention time) (YMC S5 ODS column 4.6×50 mm, 10-90% aqueous methanol over 4 minutes containing 0.2% phosphoric acid, 4 mL/min, monitoring at 220 nm).

C. (3aα,4β,7β,7aα)- and (3aα,4α,7α,7aα)-N-[4-[2-[2-[4-Cyano-3-(trifluoromethyl)phenyl]octahydro-7-methyl-1,3-dioxo-4,7-epoxy-4H-isoindol-4-yl]ethoxy]phenyl]acetamide (26Ci and 26Cii, respectively)

A solution of a mixture of compounds 26Bi and 26Bii (55 mg, 0.105 mmol) and 10% Pd/C (12 mg, cat.) in EtOH (3 mL)

was stirred under a hydrogen atmosphere at room temperature overnight. The reaction mixture was filtered through Celite and concentrated under reduced pressure to give 50 mg of crude product. Purification by flash chromatography on silica gel eluting with 70% EtOAc/hexanes gave 18 mg (0.034 mmol, 32%) of compound 26Ci [HPLC: 96% at 3.33 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 528.01 $[M+H]^+$]; and 2.3 mg (0.0044 mmols, 4%) of an 85:15 mixture of 26Cii and 26Ci respectively as determined by $^1$H NMR. HPLC: 90% at 3.35 min (retention time) (YMC S5 ODS column 4.6×50 mm, 10-90% aqueous methanol over 4 minutes containing 0.2% phosphoric acid, 4 mL/min, monitoring at 220 nm). MS (ESI): nl/z 528.12 $[M+H]^+$.

EXAMPLE 27

(3aα,4α,7α,7aα)-Hexahydro-2-(2-naphthalenyl)-4,7-epoxy-1H-isoindole-1,3(2H)-dione (27D)

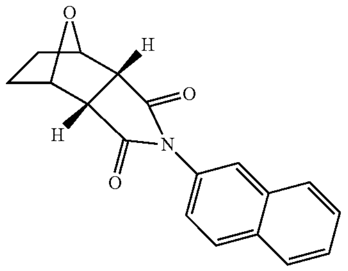

A. (endo, endo)-7-Oxabicyclo[2.2.1]hept-5-ene-2,3-dicarboxylic acid (27A)

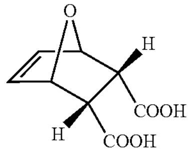

Compounds 27A, 27B and 27C were synthesized in accordance with the approaches described in Sprague et al. *J. Med. Chem.* 28, 1580-1590 (1985). A mixture of furan (100 mL, 1.38 mol) and maleic acid (160 g, 1.38 mol) in $H_2O$ (340 mL) was stirred at room temperature for 5 days. The mixture was placed in a separatory funnel and the aqueous layer was separated from the layer containing the unreacted furan. The aqueous layer was treated with charcoal, filtered through Celite and placed in the refrigerator. The desired product crystallized from solution upon seeding, was filtered, washed with cold water and dried over $P_2O_5$ to give 70 g (0.38 mol, 28%) of compound 27A as a white solid.

B. (endo, endo)-7-Oxabicyclo[2.2.1]heptane-2,3-dicarboxylic acid (27B)

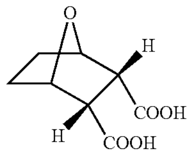

To a solution of compound 27A (69.0 g, 0.375 mol) in EtOH (700 mL) was added 10% Pd/C (4.5 g, cat.) and the mixture was shaken under a hydrogen atmosphere at 55 psi until gas uptake ceased. The mixture was filtered through Celite and concentrated in vacuo to give 66.0 g (0.355 mol, 95%) of compound 27B as a white solid.

C. (3aα,4α,7α,7aα)-Hexahydro-4,7-epoxyisobenzofuran-1,3-dione (27C)

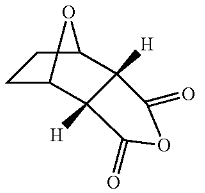

A solution of compound 27B (66.0 g, 355 mol) in acetyl chloride (300 mL) was refluxed for 1 h. The reaction solution was concentrated in vacuo and the resulting residue was recrystallized from benzene to give 49.2 g (0.292 mol, 82%) of compound 27C as a white solid (>99% endo by H NMR).

D. (3aα,4α,7α,7aα)-Hexahydro-2-(2-naphthalenyl)-4,7-epoxy-1H-isoindole-1,3(2H)-dione (27D)

Compound 27C (45 mg, 0.30 mmol) was combined with 2-aminonaphthalene (47 mg, 0.33 mmol) in acetic acid (1 mL) and heated at 115° C. overnight. After the reaction was cooled to rt, a drop of water was added, and the resulting precipitate was filtered. The material was washed with methanol and dried to provide 65.7 mg (0.224 mmol, 74.7%) of compound 27D as a white crystalline solid. HPLC: 99% at 2.68 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 294.0 $[M+H]^+$.

EXAMPLE 28

(1aα,2β,2aα,5aα,6β,6aα)-Hexahydro-4-(2-naphthalenyl)-2,6-epoxy-3H-oxireno[f]isoindole-3,5(4H)-dione (28B)

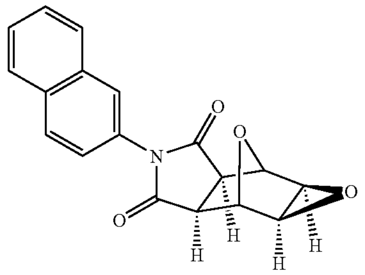

A. (1aα,2β,2aα,5aα,6β,6aα)-Tetrahydro-2,6-epoxy-oxireno[f]isobenzofuran-3,5(2aH,5aH)-dione (28A)

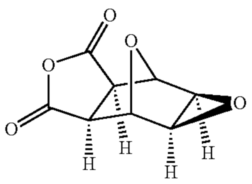

As described in Yur'ev et al. *J. Gen. Chem. U.S.S.R.* (*Engl. Transl.*) 31, 772-775 (1961), a solution of exo-7-oxabicyclo [2.2.1]heptane-2,3-dicarboxylic anhydride (5.00 g, 30.1 mmol), formic acid (10 mL) and hydrogen peroxide (6 mL) was stirred at room temperature. After 30 min, the reaction was placed in an ice bath (it became exothermic along with gas evolution) and was allowed to warm to room temperature slowly. After stirring overnight, the resulting precipitate was collected by filtration and washed with glacial acetic acid and dried to yield 3.02 g of a white powder. The crude solid was boiled in acetyl chloride (100 mL) for 10 hours and the mixture was concentrated to ~20 mL under reduced pressure. The resulting precipitate was filtered, washed with dioxanes and dried to give 2.37 g (13.0 mmol, 43%) of compound 28A as a white powder.

B. (1aα,2β,2aα,5aα,6β,6aα)-Hexahydro-4-(2-naphthalenyl)-2,6-epoxy-3H-oxireno[f]isoindole-3,5(4H)-dione (28B)

Compound 28A (100 mg, 0.520 mmol) was combined with 2-aminonaphthalene (62.1 mg, 0.434 mmol) in acetic acid (2 mL) and heated at 115° C. overnight. After the reaction was allowed to cool to rt, water was added, and the resulting precipitate was filtered. The material was washed sequentially with aqueous $K_2CO_3$ and water and then dried in a vacuum oven to provide 113.7 mg (0.371 mmol, 85.5%) of compound 28B as an off-white crystalline solid. HPLC: 99% at 1.76 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 308.0 $[M+H]^+$.

EXAMPLE 29

(3aα,4α,7α,7aα)-2-[4-Bromo-3-(trifluoromethyl)phenyl]-3a,4,7,7a-tetrahydro-4,7-dimethyl-4,7-epithio-1H-isoindole-1,3(2H)-dione 8-oxide (29)

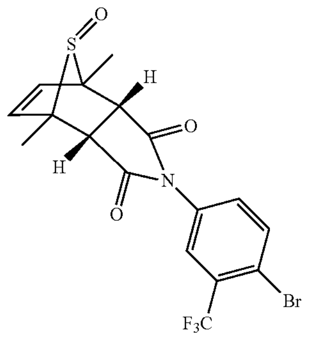

2,5-Dimethylthiophene (0.048 mL, 0.42 mmol) and 4-(2,5-dihydro-2,5-dioxo-1H-pyrrol-1-yl)-2-trifluoromethylbenzonitrile (0.290 g, 0.625 mmol, prepared as described for Example 1B) were dissolved in $CH_2Cl_2$ (8.0 mL) and cooled to −20° C. $BF_3.Et_2O$ (0.412 mL, 3.36 mmol) was added slowly followed by addition of mCPBA (~50%, 0.29 g, 0.84 mmol). After 2 h at −20° C., the reaction mixture was poured into saturated aq. $NaHCO_3$ and extracted with $CH_2Cl_2$ (3×20 mL) and the organics dried over anhydrous $Na_2SO_4$. The crude product was purified by flash chromatography on $SiO_2$ eluting with 5%-10%-20% EtOAc in $CH_2Cl_2$ to give 0.119 g (0.265 mmol, 63%) of compound 29 as a white solid. HPLC: 91% at 3.303 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 480.2 $[M+H]^+$.

EXAMPLE 30

(3aα,4α,7α,7aα)-2-[4-Bromo-3-(trifluoromethyl)phenyl]-3a,4,7,7a-tetrahydro-4,7-epithio-1H-isoindole-1,3(2H)-dione 8-oxide (30)

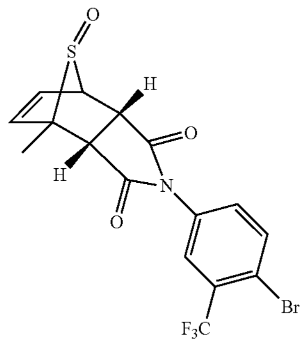

Thiophene (0.375 mL, 4.69 mmol) and 4-(2,5-dihydro-2,5-dioxo-1H-pyrrol-1-yl)-2-trifluoromethylbenzonitrile (0.100 g, 0.313 mmol, prepared as described for Example 1B) were dissolved in $CH_2Cl_2$ (50 mL), mCPBA (~50%, 1.62 g, 4.69 mmol) was added and the resulting mixture was stirred at 25° C. for 3 h. Triphenylphosphine (2.0 g) was then added. After 15 min, the volatiles were removed in vacuo and the resulting residue was dissolved in $CH_2Cl_2$ (200 mL) and washed with saturated aq. $NaHCO_3$ (3×50 mL) and dried over $Na_2SO_4$. The crude material was then purified by flash chromatography on $SiO_2$ eluting with 1%-3%-5% methanol in $CH_2Cl_2$ to give 0.059 g (0.14 mmol, 45%) compound 30 as a white powder. NMR and LC analysis showed a single diastereomer. HPLC: 100% at 3.437 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 443.2 $[M+H]^+$.

EXAMPLE 31

(3aα,4α,7α,7aα)-Hexahydro-2-[3-(trifluoromethyl)phenyl]-4,7-imino-1H-isoindole-1,3(2H)-dione (31D)

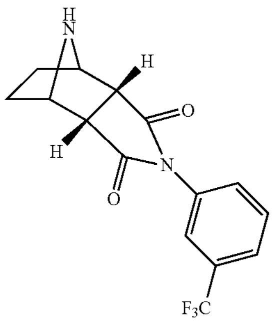

A. 7-Azabicyclo[2.2.1]hepta-2,5-diene-2,3,7-tricarboxylic acid 2,3-dimethyl 7-(1,1-dimethylethyl) ester (31A)

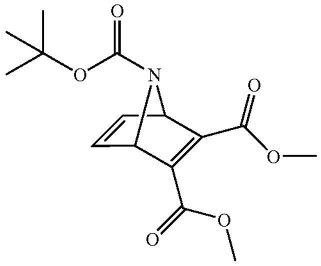

Freshly distilled acetylenedicarboxylic acid dimethyl ester (6.7 mL, 54 mmol) and N-(tert-butyloxycarbonyl)-1H-pyrrole (9.0 mL, 54 mmol) were combined and heated at 120° C. for 3 h. Purification by flash chromatography on $SiO_2$ eluting with EtOAc/$CH_2Cl_2$ gave 8.3 g (27 mmol, 50%) of compound 31A as a yellow solid.

B. (exo,endo)-7-Azabicyclo[2.2.1]hept-2,5-diene-2,3,7-tricarboxylic acid 7-(1,1-dimethylethyl) ester (31B)

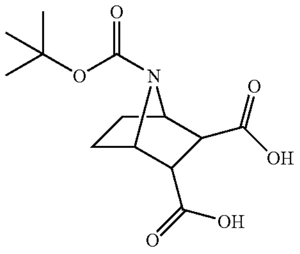

Compound 31A (1.0 g, 3.5 mmol) was dissolved in MeOH (2.0 mL) and aq. KOH (1 g in 5 mL $H_2O$) was added. The reaction was heated at 50° C. for 1 h. The reaction was then cooled to 25° C. and 10% Pd/C (0.5 g, cat.) was added and the mixture was placed in a Parr apparatus for 14 h at 25° C. The reaction was then filtered through Celite rinsing with water. The aqueous solution was acidified to pH 2 by addition of 1 N HCl and then extracted with EtOAc (2×100 mL). Concentration of the organics gave the compound 31B as a pale yellow solid.

C. (3aα,4α,7α,7aα)-Hexahydro-1,3-dioxo-4,7-iminoisobenzofuran-8-carboxylic acid 1,1-dimethylethyl ester (31C)

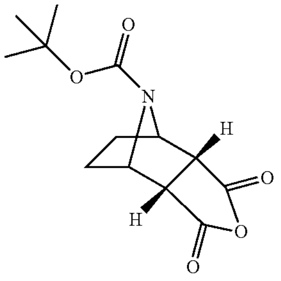

Crude compound, 31B, was heated to 120° C. in vacuo in a sublimation chamber, resulting in sublimation of 0.051 g (0.19 mmol, 5.4%) of compound 31C as a white solid, which was collected directly and used in the next step without further purification.

D. (3aα,4α,7α,7aα)-Hexahydro-2-[3-(trifluoromethyl)phenyl]-4,7-imino-1H-isoindole-1,3(2H)-dione (31D)

Compound 31C (0.050 g, 0.19 mmol) and the 1-amino-3-(trifluoromethyl)benzene (0.030 g, 0.19 mmol) were dissolved in AcOH (2.5 mL) and heated at 115° C. for 4.5 h. The reaction was quenched by addition of saturated aqueous $NaHCO_3$ and the mixture was extracted with methylene chloride (3×15 mL). The crude material was purified by reverse phase preparative HPLC to give 0.030 g (0.097 mmol, 51%) of compound 31D as a white solid. HPLC: 99% at 2.33 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 311.15 $[M+H]^+$.

EXAMPLE 32

(3aα,4β,7β,7aα)- and (3aα,4α,7α,7aα)-3a,4,7,7a-Tetrahydro-4,7-dimethyl-2-[3-(trifluoromethyl)phenyl]-4,7-epoxy-1H-isoindole-1,3(2H)-dione (32i and 32ii, respectively)

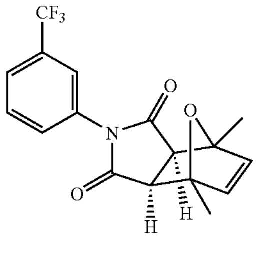

-continued

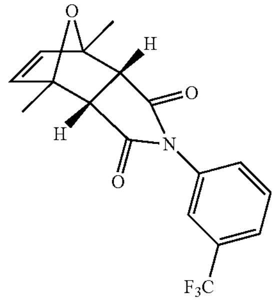

Freshly distilled 2,5-dimethylfuran (0.32 mL, 2.6 mmol) was dissolved in $CH_2Cl_2$ (2.0 mL) and 1-[3-(trifluoromethyl)phenyl]-1H-pyrrole-2,5-dione (0.5 g, 2.5 mmol, prepared as described in Example 1B) was added. The reaction was stirred at 25° C. for 16 h and was then concentrated under reduced pressure. Purification by flash chromatography on silica gel eluting with 0.5% $MeOH/CH_2Cl_2$ gave 250 mg (0.741 mmol, 30%) of compound 32i, and 50 mg (0.15 mmol, 6%) of compound 32ii as white solids. Compound 32i: HPLC: 98% at 3.080 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 338.30, $[M+H]^+$. Compound 32ii: HPLC: 92% at 3.047 min (retention time) (YMC S5 ODS column 4.6×50 mm, 10-90% aqueous methanol over 4 minutes containing 0.2% phosphoric acid, 4 mL/min, monitoring at 220 nm), MS (ES): m/z: 338.15 $[M+H]^+$.

EXAMPLE 33

(3aα,4β,7β,7aα)-Hexahydro-4,7-dimethyl-2-[3-(trifluoromethyl)phenyl]-4,7-epoxy-1H-isoindole-1,3(2H)-dione (33)

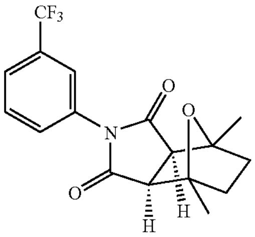

Compound 32i (0.080 g, 0.24 mmol) was dissolved in EtOAc (2 mL) and EtOH (1 mL) and 10% Pd/C (0.050 g, cat.) was added. Hydrogen was then introduced by a balloon and the reaction was stirred for 24 h. The mixture was filtered through Celite, rinsed with EtOAc and concentrated in vacuo to give 0.075 g (0.22 mmol, 93%) of compound 33 as a white solid. No further purification was needed. HPLC: 90% at 3.233 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 340.40 $[M+H]^+$.

EXAMPLE 34

(3aα,4β,7β,7aα)-Tetrahydro-5-methyl-2-(4-nitro-1-naphthalenyl)-4,7-etheno-1H-pyrrolo[3,4-c]pyridine-1,3,6(2H,5H)-trione (34B)

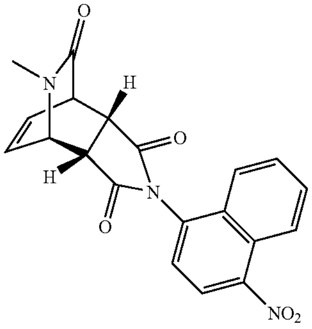

A. 4,5,7,7a-Tetrahydro-5-methyl-4,7-ethenofuro[3,4-c]pyridine-1,3,6(3aH)-trione (34A)

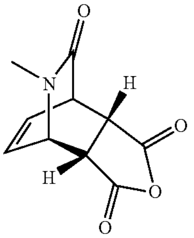

Compound 34A was synthesized by a modification of the methods described by Tomisawa et al. *Heterocycles* 6, 1765-1766 (1977) & *Tetrahedron Lett.* 29, 2465-2468 (1969). Maleic anhydride (2.00 g, 20.4 mmol) and 1-methyl-2-pyridone (2.22 g, 20.4 mmol) were suspended in 30 mL of anhydrous toluene. The reaction vessel was fitted with a Dean Stark trap and refluxed for 48 hours. The dark colored solution was allowed to cool to rt and then the volatiles were removed in vacuo. The resulting brown paste (4 g) was dissolved in 10 mL of boiling toluene and the hot solution was filtered under a nitrogen flow to remove particulates. On standing at 25° C. the desired product precipitated from solution. The solid was isolated by filtration and washed with cold toluene to give 1.0 g (4.8 mmol, 24%) of compound 34A, which was used without further purification.

B. (3aα,4α,7α,7aα)-Tetrahydro-5-methyl-2-(4-nitro-1-naphthalenyl)-4,7-etheno-1H-pyrrolo[3,4-c]pyridine-1,3,6(2H,5H)-trione (34B)

1-Amino-4-nitronaphthalene (0.094 g, 0.50 mmol) and compound 34A (0.130 g, 0.627 mmol) were dissolved in AcOH (2.0 mL) and heated at 110° C. for 11 h. The reaction was then cooled to 25° C. and poured into cold saturated aqueous $K_2CO_3$ and stirred vigorously for 10 min. The solution was filtered and rinsed with water. The resulting filtrate was concentrated in vacuo and purified by flash chromatography on silica gel eluting with 4:6 EtOAc/hexanes to give 0.172 g (0.456 mmol, 91%) of compound 34B as a white solid. HPLC: 92% at 2.472 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 378.29 $[M+H]^+$.

EXAMPLE 35

(3aα,4β,7β,7aα)-4-[4-[2-(4-Fluorophenoxy)ethyl]octahydro-7-methyl-1,3-dioxo-4,7-epoxy-2H-isoindol-2-yl]-2-(trifluoromethyl)benzonitrile (35)

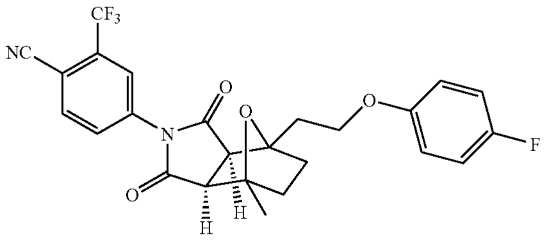

DEAD (0.060 mL, 0.38 mmol) was added to a solution of triphenylphosphine (100 mg, 0.380 mmol) in THF (1.3 mL) at room temperature under an inert atmosphere. After stirring for 10 min, 4-fluorophenol (43 mg, 0.380 mmol) was added in one portion. The reaction mixture was stirred for 5 min, compound 25B (100 mg, 0.254 mmol) was added and stirring was continued for 3.5 h. Purification by flash chromatography on silica gel eluting with 50% EtOAc/hexanes followed by reverse phase preparative HPLC [11.93 min (retention time) (YMC S5 ODS column 20×100 mm, 0-100% aqueous methanol over 10 minutes containing 0.1% TFA, 20 mL/min, monitoring at 220 nm)] gave 72 mg (58%) of compound 35 as a solid. HPLC: 99% at 3.74 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 487.1 $[M-H]^-$.

EXAMPLE 36

(3aα,4β,7β,7aα)-4-[4-(2-Bromoethyl]octahydro-7-methyl-1,3-dioxo-4,7-epoxy-2H-isoindol-2-yl]-2-(trifluoromethyl)benzonitrile (36)

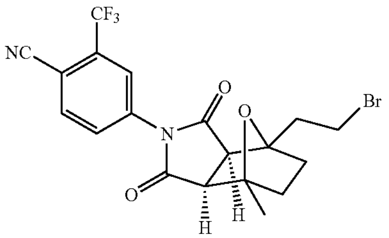

A solution of 25B (495 mg, 1.26 mmol) and pyridine (100 μL, 1.26 mmol) in $CH_2Cl_2$ (2 mL) was added to a solution of $Ph_3PBr_2$ (636 mg, 1.51 mmol) in $CH_2Cl_2$ (2 mL) at 0° C. The reaction mixture was stirred at room temperature for 3 hr, then the solvent was removed under reduced pressure. The resulting residue was washed 2× with 10 mL portions of EtOAc-hexane (6:4) and the combined washings were purified by flash chromatography on silica gel eluting with 60% EtOAc/hexane to give 390 mg (0.853 mmol, 67.7%) of compound 36 as a white solid. HPLC: 99% at 3.51 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 456.7 $[M-H]^-$.

EXAMPLE 37

(3aα,4β,7β,7aα)-Hexahydro-4,7-dimethyl-2-(3-methyl-4-nitrophenyl)-4,7-epoxy-1H-isoindole-1,3(2H)-dione (37)

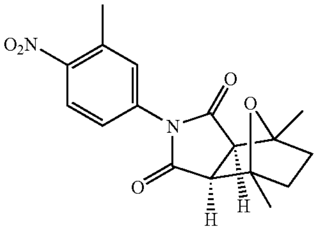

A combination of 4-nitro-3-methylaniline (0.050 g, 0.33 mmol), compound 20A (0.083 g, 0.43 mmol), TEA (0.2 mL), $MgSO_4$ (0.075 g) and toluene (0.8 mL) were combined in a sealed tube and the mixture was heated at 120° C. for 14 h. After cooling to 25° C., the reaction was filtered, rinsed with $CH_2Cl_2$ and concentrated under reduced pressure. The crude product was purified by preparative TLC on $SiO_2$ eluting with $CH_2Cl_2$ to give 0.075 g (0.23 mmol, 69%) of compound 37 as a pale yellow solid. HPLC: 100% at 2.733 min (retention time) (YMC S5 ODS column, 4.6×50 mm; 10-90% MeOH/$H_2O$ gradient,+0.1% TFA; 4 mL/min, 220 nm detection). MS (ES): m/z 348.2 $[M+NH_4]^+$.

EXAMPLES 38 TO 121

Additional compounds of the present invention were prepared by procedures analogous to those described above. The compounds of Examples 38 to 121 have the following structure (L is a bond):

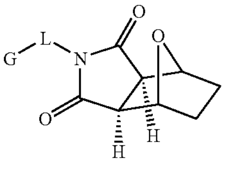

where G, the compound name, retention time, molecular mass, and the procedure employed, are set forth in Table 2. The chromatography techniques used to determine the compound retention times of Table 2 are as follows: LCMS=YMC S5 ODS column, 4.6×50 mm eluting with 10-90% MeOH/$H_2O$ over 4 minutes containing 0.10% TFA; 4 mL/min, monitoring at 220 nm. The molecular mass of the compounds listed in Table 2, where provided, were determined by MS (ES) by the formula m/z.

TABLE 2

| Ex. No. | G | Compound Name | Retention Time (Min.)/Molecular Mass | Pro. of Ex. |
|---|---|---|---|---|
| 38 | 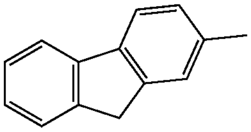 | (3aα,4β,7β,7aα)-2-(2-Fluorenyl)hexahydro-4,7-epoxy-1H-isoindole-1,3(2H)-dione | 3.72 LCMS/ 332.20 $[M + H]^+$ | 8 |
| 39 | 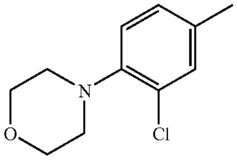 | (3aα,4β,7β,7aα)-2-[3-Chloro-4-(4-morpholinyl)phenyl]hexahydro-4,7-epoxy-1H-isoindole-1,3(2H)-dione | 3.20 LCMS/ 363.20 $[M + H]^+$ | 8 |
| 40 | 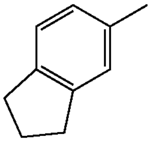 | (3aα,4β,7β,7aα)-2-(2,3-Dihydro-1H-inden-5-yl)hexahydro-4,7-epoxy-1H-isoindole-1,3(2H)-dione | 3.26 LCMS/ 284.22 $[M + H]^+$ | 8 |
| 41 | 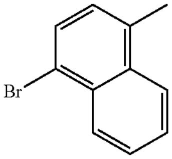 | (3aα,4β,7β,7aα)-2-(4-Bromo-1-naphthalenyl)hexahydro-4,7-epoxy-1H-isoindole-1,3(2H)-dione | 3.73 LCMS/ 404.11 $[M + CH_3OH + H]^+$ | 8 |
| 42 | 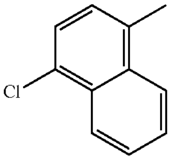 | (3aα,4β,7β,7aα)-2-(4-Chloro-1-naphthalenyl)hexahydro-4,7-epoxy-1H-isoindole-1,3(2H)-dione | 3.63 LCMS/ 328.14 $[M + H]^+$ | 8 |
| 43 | 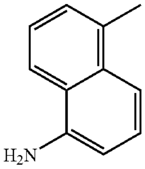 | (3aα,4β,7β,7aα)-2-(5-Amino-1-naphthalenyl)hexahydro-4,7-epoxy-1H-isoindole-1,3(2H)-dione | 1.64 LCMS/ | 8 |
| 44 | 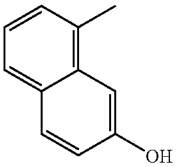 | (3aα,4β,7β,7aα)-Hexahydro-2-(7-hydroxy-1-naphthalenyl)-4,7-epoxy-1H-isoindole-1,3(2H)-dione | 2.54 LCMS/ 308.23 $[M - H]^-$ | 8 |
| 45 | 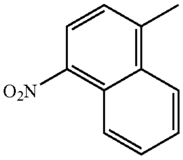 | (3aα,4β,7β,7aα)-Hexahydro-2-(4-nitro-1-naphthalenyl)-4,7-epoxy-1H-isoindole-1,3(2H)-dione | 3.117 LCMS/ 404.11 $[M + CH_3OH + H]^+$ | 8 |
| 46 | 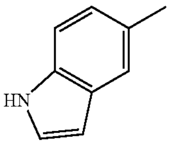 | (3aα,4β,7β,7aα)-Hexahydro-2-(1H-indol-5-yl)-4,7-epoxy-1H-isoindole-1,3(2H)-dione | 2.39 LCMS/ 283.23 $[M + H]^+$ | 8 |

TABLE 2-continued

| Ex. No. | G | Compound Name | Retention Time (Min.)/Molecular Mass | Pro. of Ex. |
|---|---|---|---|---|
| 47 | 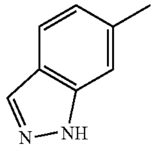 | (3aα,4β,7β,7aα)-Hexahydro-2-(1H-indazol-6-yl)-4,7-epoxy-1H-isoindole-1,3(2H)-dione | 2.35 LCMS/ 282.23 $[M-H]^-$ | 8 |
| 48 | 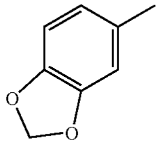 | (3aα,4β,7β,7aα)-2-(1,3-Benzodioxol-5-yl)hexahydro-4,7-epoxy-1H-isoindole-1,3(2H)-dione | 2.47 LCMS/ 288.20 $[M+H]^+$ | 8 |
| 49 | 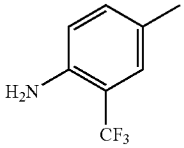 | (3aα,4β,7β,7aα)-2-[4-Amino-3-(trifluoromethyl)phenyl]hexahydro-4,7-epoxy-1H-isoindole-1,3(2H)-dione | 2.71 LCMS/ 327.20 $[M+H]^+$ | 8 |
| 50 | 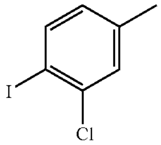 | (3aα,4β,7β,7aα)-2-(3-Chloro-4-iodophenyl)hexahydro-4,7-epoxy-1H-isoindole-1,3(2H)-dione | 3.70 LCMS/ 435.2 $[M+CH_3OH]^+$ | 8 |
| 51 | 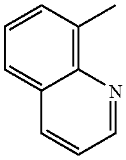 | (3aα,4β,7β,7aα)-Hexahydro-2-(8-quinolinyl)-4,7-epoxy-1H-isoindole-1,3(2H)-dione | 2.28 LCMS/ 295.22 $[M+H]^+$ | 8 |
| 52 | 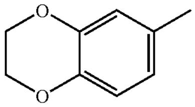 | (3aα,4β,7β,7aα)-2-(2,3-Dihydro-1,4-benzodioxin-6-yl)hexahydro-4,7-epoxy-1H-isoindole-1,3(2H)-dione | 2.55 LCMS/ 302.23 $[M+H]^+$ | 8 |
| 53 | 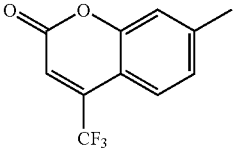 | (3aα,4β,7β,7aα)-Hexahydro-2-[2-oxo-4-(trifluoromethyl)-2H-1-benzopyran-7-yl]-4,7-epoxy-1H-isoindole-1,3(2H)-dione | 3.38 LCMS/ 412.17 $[M+CH_3OH+H]^+$ | 8 |
| 54 | 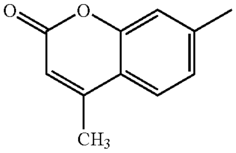 | (3aα,4β,7β,7aα)-Hexahydro-2-(4-methyl-2-oxo-2H-1-benzopyran-7-yl)-4,7-epoxy-1H-isoindole-1,3(2H)-dione | 2.74 LCMS/ 326.20 $[M+H]^+$ | 8 |
| 55 | 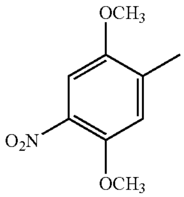 | (3aα,4β,7β,7aα)-2-(2,5-Dimethoxy-4-nitrophenyl)hexahydro-4,7-epoxy-1H-isoindole-1,3(2H)-dione | 2.70 LCMS/ 349.23 $[M+H]^+$ | 8 |

TABLE 2-continued

| Ex. No. | G | Compound Name | Retention Time (Min.)/Molecular Mass | Pro. of Ex. |
|---|---|---|---|---|
| 56 | 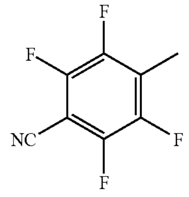 | (3aα,4β,7β,7aα)-2,3,5,6-Tetrafluoro-4-(octahydro-1,3-dioxo-4,7-epoxy-2H-isoindol-2-yl)benzonitrile | 2.97 LCMS | 8 |
| 57 | 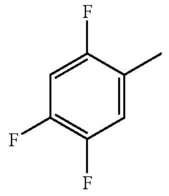 | (3aα,4β,7β,7aα)-Hexahydro-2-(2,4,5-trifluorophenyl)-4,7-epoxy-1H-isoindole-1,3(2H)-dione | 2.90 LCMS | 8 |
| 58 | 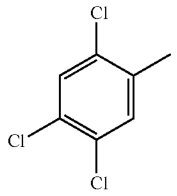 | (3aα,4β,7β,7aα)-Hexahydro-2-(2,4,5-trichlorophenyl)-4,7-epoxy-1H-isoindole-1,3(2H)-dione | 3.64 LCMS/ 346.39 $[M]^+$ | 8 |
| 59 | 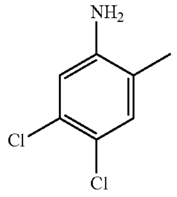 | (3aα,4β,7β,7aα)-2-(2-Amino-4,5-dichlorophenyl)hexahydro-4,7-epoxy-1H-isoindole-1,3(2H)-dione | 3.23 LCMS | 8 |
| 60 | 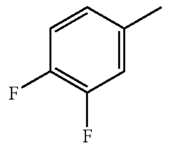 | (3aα,4β,7β,7aα)-2-(3,4-Difluorophenyl)hexahydro-4,7-epoxy-1H-isoindole-1,3(2H)-dione | 2.91 LCMS/ 280.23 $[M + H]^+$ | 8 |
| 61 | 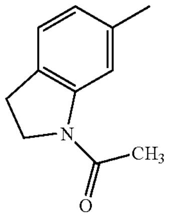 | (3aα,4β,7β,7aα)-1-Acetyl-2,3-dihydro-6-(octahydro-1,3-dioxo-4,7-epoxy-2H-isoindol-2-yl)-1H-indole | 2.43 LCMS/ 359.26 $[M + CH_3OH + H]^+$ | 8 |
| 62 | 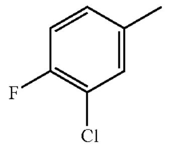 | (3aα,4β,7β7aα)-2-(3-Chloro-4-fluorophenyl)hexahydro-4,7-epoxy-1H-isoindole-1,3(2H)-dione | 3.21 LCMS/ 328.14 $[M + CH_3OH + H]^+$ | 8 |
| 63 | 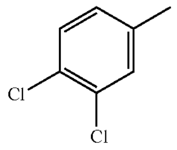 | (3aα,4β,7β,7aα)-2-(3,4-Dichlorophenyl)hexahydro-4,7-epoxy-1H-isoindole-1,3(2H)-dione | 3.54 LCMS/ 311.79 $[M - H]^-$ | 8 |

TABLE 2-continued

| Ex. No. | G | Compound Name | Retention Time (Min.)/Molecular Mass | Pro. of Ex. |
|---|---|---|---|---|
| 64 | 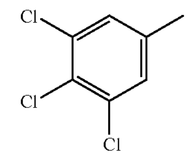 | (3aα,4β,7β,7aα)-Hexahydro-2-(3,4,5-trichlorophenyl)-4,7-epoxy-1H-isoindole-1,3(2H)-dione | 4.05 LCMS/ 378.10 $[M + CH_3OH + H]^+$ | 8 |
| 65 | 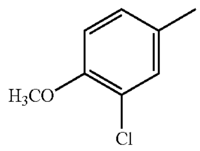 | (3aα,4β,7β,7aα)-2-(3-Chloro-4-methoxyphenyl)hexahydro-4,7-epoxy-1H-isoindole-1,3(2H)-dione | 2.99 LCMS/ 308.11 $[M + H]^+$ | 8 |
| 66 | 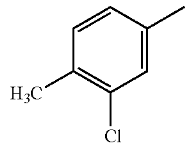 | (3aα,4β,7β,7aα)-2-(3-Chloro-4-methylphenyl)hexahydro-4,7-epoxy-1H-isoindole-1,3(2H)-dione | 3.39 LCMS/ 292.20 $[M + H]^+$ | 8 |
| 67 | 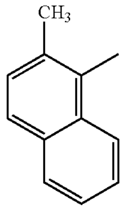 | (3aα,4β,7β,7aα)-Hexahydro-2-(2-methyl-1-naphthalenyl)-4,7-epoxy-1H-isoindole-1,3(2H)-dione | 3.28 LCMS/ 308.23 $[M + H]^+$ | 8 |
| 68 | 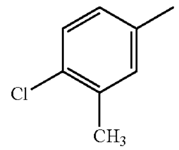 | (3aα,4β,7β,7aα)-2-(4-Chloro-3-methylphenyl)hexahydro-4,7-epoxy-1H-isoindole-1,3(2H)-dione | 3.40 LCMS/ 292.20 $[M + H]^+$ | 8 |
| 69 | 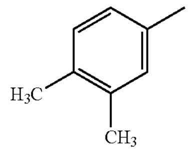 | (3aα,4β,7β,7aα)-2-(3,4-Dimethylphenyl)hexahydro-4,7-epoxy-1H-isoindole-1,3(2H)-dione | 3.11 LCMS/ 272.23 $[M + H]^+$ | 8 |
| 70 | 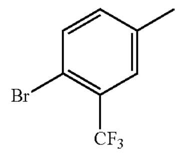 | (3aα,4β,7β,7aα)-2-[4-Bromo-3-(trifluoromethyl)phenyl]hexahydro-4,7-epoxy-1H-isoindole-1,3(2H)-dione | 3.76 LCMS/ 421.98 $[M + CH_3OH + H]^+$ | 8 |
| 71 | 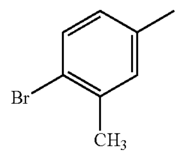 | (3aα,4β,7β,7aα)-2-(4-Bromo-3-methylphenyl)hexahydro-4,7-epoxy-1H-isoindole-1,3(2H)-dione | 3.50 LCMS/ 336.05 $[M + H]^+$ | 8 |
| 72 | 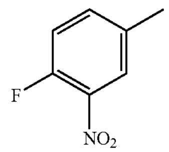 | (3aα,4β,7β,7aα)-2-(4-Fluoro-3-nitrophenyl)hexahydro-4,7-epoxy-1H-isoindole-1,3(2H)-dione | 2.80 LCMS/ 305.25 $[M - H]^-$ | 8 |

TABLE 2-continued

| Ex. No. | G | Compound Name | Retention Time (Min.)/Molecular Mass | Pro. of Ex. |
|---|---|---|---|---|
| 73 | 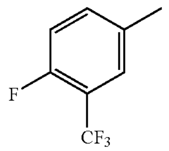 | (3aα,4β,7β,7aα)-2-[4-Fluoro-3-(trifluoromethyl)phenyl]hexahydro-4,7-epoxy-1H-isoindole-1,3(2H)-dione | 3.45 LCMS/ 362.26 $[M + CH_3OH + H]^+$ | 8 |
| 74 | 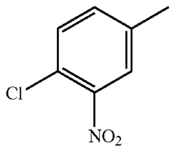 | (3aα,4β,7β,7aα)-2-(4-Chloro-3-nitrophenyl)hexahydro-4,7-epoxy-1H-isoindole-1,3(2H)-dione | 3.19 LCMS/ 322.86 $[M]^+$ | 8 |
| 75 | 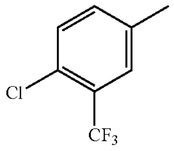 | (3aα,4β,7β,7aα)-2-[4-Chloro-3-(trifluoromethyl)phenyl]hexahydro-4,7-epoxy-1H-isoindole-1,3(2H)-dione | 3.68 LCMS/ 345.83 $[M]^+$ | 8 |
| 76 | 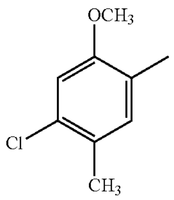 | (3aα,4β,7β,7aα)-2-(4-Chloro-2-methoxy-5-methylphenyl)hexahydro-4,7-epoxy-1H-isoindole-1,3(2H)-dione | 3.31 LCMS/ 322.20 $[M + H]^+$ | 8 |
| 77 | 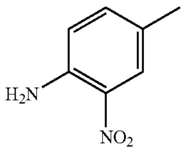 | (3aα,4β,7β,7aα)-2-(4-Amino-3-nitrophenyl)hexahydro-4,7-epoxy-1H-isoindole-1,3(2H)-dione | 2.34 LCMS/ 302.27 $[M - H]^-$ | 8 |
| 78 | 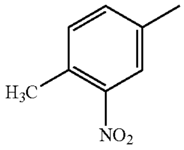 | (3aα,4β,7β,7aα)-Hexahydro-2-(4-methyl-3-nitrophenyl)-4,7-epoxy-1H-isoindole-1,3(2H)-dione | 3.02 LCMS/ 335.20 $[M + CH_3OH + H]^+$ | 8 |
| 79 | 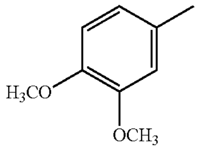 | (3aα,4β,7β,7aα)-2-(3,4-Dimethoxyphenyl)hexahydro-4,7-epoxy-1H-isoindole-1,3(2H)-dione | 2.35 LCMS/ 304.25 $[M + H]^+$ | 8 |
| 80 | 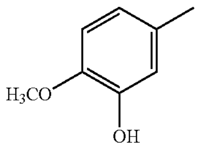 | (3aα,4β,7β,7aα)-Hexahydro-2-(3-hydroxy-4-methoxyphenyl)-4,7-epoxy-1H-isoindole-1,3(2H)-dione | 0.98 LCMS/ 321.19 $[M + CH_3OH]^+$ | 8 |
| 81 | 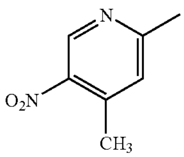 | (3aα,4β,7β,7aα)-Hexahydro-2-(4-methyl-5-nitro-2-pyridinyl)-4,7-epoxy-1H-isoindole-1,3(2H)-dione | 0.54 LCMS/ 304.20 $[M + H]^+$ | 8 |

TABLE 2-continued

| Ex. No. | G | Compound Name | Retention Time (Min.)/Molecular Mass | Pro. of Ex. |
| --- | --- | --- | --- | --- |
| 82 | 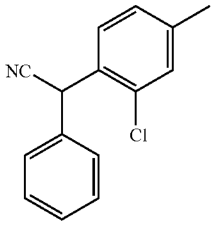 | (3aα,4β,7β,7aα)-2-Chloro-4-(octahydro-1,3-dioxo-4,7-epoxy-2H-isoindol-2-yl)-α-phenylbenzeneacetonitrile | 3.67 LCMS/ 423.8 $[M + CH_3OH]^+$ | 8 |
| 83 | 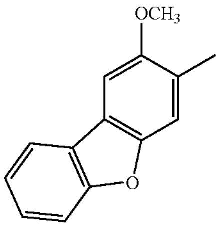 | (3aα,4β,7β,7aα)-Hexahydro-2-(2-methoxy-3-dibenzofuranyl)-4,7-epoxy-1H-isoindole-1,3(2H)-dione | 3.66 LCMS/ 364.25 $[M + H]^+$ | 8 |
| 84 | 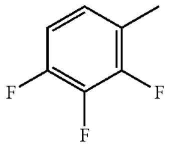 | (3aα,4β,7β,7aα)-Hexahydro-2-(2,3,4-trifluorophenyl)-4,7-epoxy-1H-isoindole-1,3(2H)-dione | 3.06 LCMS/ 298.14 $[M + H]^+$ | 8 |
| 85 | 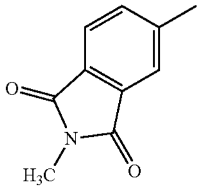 | (3aα,4β,7β,7aα)-2-(2,3-Dihydro-2-methyl-1,3-dioxo-1H-isoindol-5-yl)hexahydro-4,7-epoxy-1H-isoindole-1,3(2H)-dione | 2.70 LCMS/ 359.22 $[M + CH_3OH + H]^+$ | 8 |
| 86 | 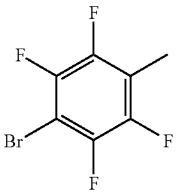 | (3a,4β,7β,7aα)-2-(4-Bromo-2,3,5,6-tetrafluorophenyl)hexahydro-4,7-epoxy-1H-isoindole-1,3(2H)-dione | 3.72 LCMS/ 426.07 $[M + CH_3OH + H]^+$ | 8 |
| 87 | 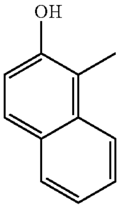 | (3aα,4β,7β,7aα)-Hexahydro-2-(2-hydroxy-1-naphthalenyl)-4,7-epoxy-1H-isoindole-1,3(2H)-dione | 2.52 LCMS/ 308.26 $[M - H]^-$ | 8 |
| 88 | 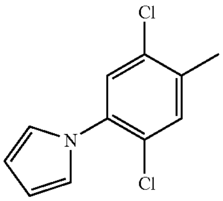 | (3aα,4β,7β,7aα)-2-[2,5-Dichloro-4-(1H-pyrrol-1-yl)phenyl]hexahydro-4,7-epoxy-1H-isoindole-1,3(2H)-dione | 3.70 LCMS/ 376.64 $[M - H]^-$ | 8 |

TABLE 2-continued

| Ex. No. | G | Compound Name | Retention Time (Min.)/Molecular Mass | Pro. of Ex. |
|---|---|---|---|---|
| 89 | 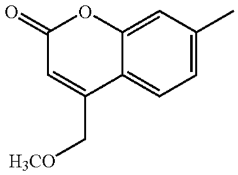 | (3aα,4β,7β,7aα)-Hexahydro-2-[4-(methoxymethyl)-2-oxo-2H-1-benzopyran-7-yl]-4,7-epoxy-1H-isoindole-1,3(2H)-dione | 2.79 LCMS/ 356.26 $[M + H]^+$ | 8 |
| 90 | 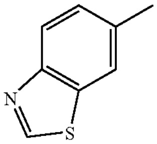 | (3aα,4β,7β,7aα)-2-(6-Benzothiazolyl)hexahydro-4,7-epoxy-1H-isoindole-1,3(2H)-dione | 2.46 LCMS/ 301.19 $[M + H]^+$ | 8 |
| 91 | 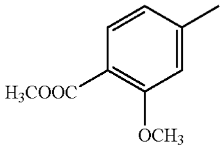 | (3aα,4β,7β,7aα)-2-Methoxy-4-(octahydro-1,3-dioxo-4,7-epoxy-2H-isoindol-2-yl)benzoic acid methyl ester | 2.75 LCMS/ 332.25 $[M + H]^+$ | 8 |
| 92 | 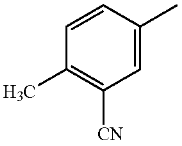 | (3aα,4β,7β,7aα)-2-Methyl-5-(octahydro-1,3-dioxo-4,7-epoxy-2H-isoindol-2-yl)benzonitrile | 2.80 LCMS/ 315.26 $[M + CH_3OH + H]^+$ | 8 |
| 93 | 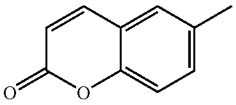 | (3aα,4β,7β,7aα)-Hexahydro-2-(2-oxo-2H-1-benzopyran-6-yl)-4,7-epoxy-1H-isoindole-1,3(2H)-dione | 2.45 LCMS/ 312.20 $[M + H]^+$ | 8 |
| 94 | 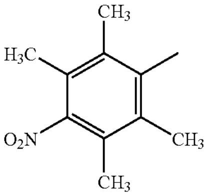 | (3aα,4β,7β,7aα)-Hexahydro-2-(2,3,5,6-tetramethyl-4-nitrophenyl)-4,7-epoxy-1H-isoindole-1,3(2H)-dione | 3.59 LCMS/ 377.25 $[M + CH_3OH + H]^+$ | 8 |
| 95 | 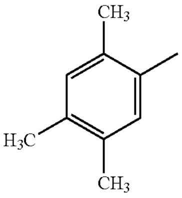 | (3aα,4β,7β,7aα)-Hexahydro-2-(2,4,5-trimethylphenyl)-4,7-epoxy-1H-isoindole-1,3(2H)-dione | 3.33 LCMS/ 286.30 $[M + H]^+$ | 8 |
| 96 | 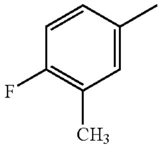 | (3aα,4β,7β,7aα)-2-(4-Fluoro-3-methylphenyl)hexahydro-4,7-epoxy-1H-isoindole-1,3(2H)-dione | 3.00 LCMS/ 276.23 $[M + H]^+$ | 8 |
| 97 | 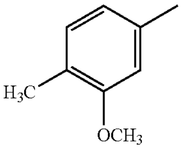 | (3aα,4β,7β,7aα)-Hexahydro-2-(3-methoxy-4-methylphenyl)-4,7-epoxy-1H-isoindole-1,3(2H)-dione | 3.05 LCMS/ 288.23 $[M + H]^+$ | 8 |

TABLE 2-continued

| Ex. No. | G | Compound Name | Retention Time (Min.)/Molecular Mass | Pro. of Ex. |
|---|---|---|---|---|
| 98 | 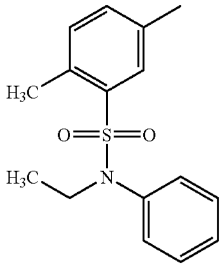 | (3aα,4β,7β,7aα)-N-Ethyl-2-methyl-5-(octahydro-1,3-dioxo-4,7-epoxy-2H-isoindol-2-yl)-N-phenylbenzenesulfonamide | 3.56 LCMS/ 441.26 $[M + H]^+$ | 8 |
| 99 | 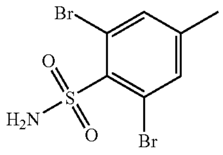 | (3aα,4β,7β,7aα)-2,6-Dibromo-4-(octahydro-1,3-dioxo-4,7-epoxy-2H-isoindol-2-yl)benzenesulfonamide | 2.25 LCMS | 8 |
| 100 | 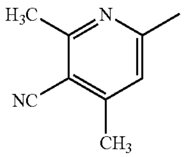 | (3aα,4β,7β,7aα)-2,4-Dimethyl-6-(octahydro-1,3-dioxo-4,7-epoxy-2H-isoindol-2-yl)-3-pyridinecarbonitrile | 2.75 LCMS/ 298.23 $[M + H]^+$ | 8 |
| 101 | 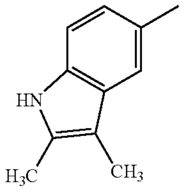 | (3aα,4β,7β,7aα)-2-(2,3-Dimethyl-1H-indol-5-yl)hexahydro-4,7-epoxy-1H-isoindole-1,3(2H)-dione | 3.00 LCMS/ 311.26 $[M + H]^+$ | 8 |
| 102 | 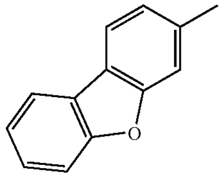 | (3aα,4β,7β,7aα)-2-(3-Dibenzofuranyl)hexahydro-4,7-epoxy-1H-isoindole-1,3(2H)-dione | 3.72 LCMS/ 366.23 $[M + CH_3OH + H]^+$ | 8 |
| 103 | 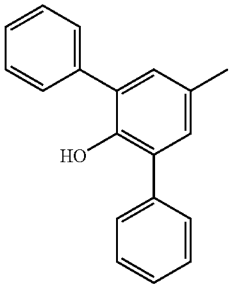 | (3aα,4β,7β,7aα)-Hexahydro-2-(2'-hydroxy[1,1':3',1"-terphenyl]-5'-yl)-4,7-epoxy-1H-isoindole-1,3(2H)-dione | 3.70 LCMS/ 412.23 $[M + H]^+$ | 8 |
| 104 | 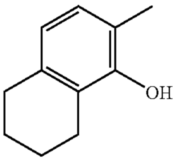 | (3aα,4β,7β,7aα)-Hexahydro-2-(5,6,7,8-tetrahydro-3-hydroxy-2-naphthalenyl)-4,7-epoxy-1H-isoindole-1,3(2H)-dione | 3.24 LCMS/ 312.32 $[M + H]^+$ | 8 |

TABLE 2-continued

| Ex. No. | G | Compound Name | Retention Time (Min.)/Molecular Mass | Pro. of Ex. |
|---|---|---|---|---|
| 105 | 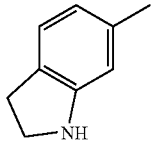 | (3aα,4β,7β,7aα)-2-(2,3-Dihydro-1H-indol-6-yl)hexahydro-4,7-epoxy-1H-isoindole-1,3(2H)-dione | 2.42 LCMS/ 285.29 $[M + H]^+$ | 8 |
| 106 | 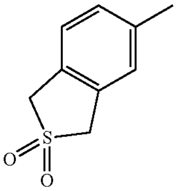 | (3aα,4β,7β,7aα)-2-(1,3-Dihydro-2,2-dioxidobenzo[c]thiophen-5-yl)hexahydro-4,7-epoxy-1H-isoindole-1,3(2H)-dione | 1.99 LCMS/ 366.26 $[M + CH_3OH + H]^+$ | 8 |
| 107 | 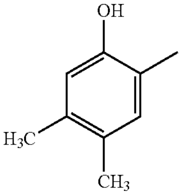 | (3aα,4β,7β,7aα)-Hexahydro-2-(2-hydroxy-4,5-dimethylphenyl)-4,7-epoxy-1H-isoindole-1,3(2H)-dione | 2.78 LCMS/ 286.32 $[M - H]^-$ | 8 |
| 108 | 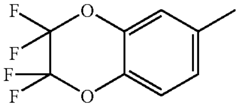 | (3aα,4β,7β,7aα)-2-(2,3-Dihydro-2,2,3,3-tetrafluoro-1,4-benzodioxin-6-yl)hexahydro-4,7-epoxy-1H-isoindole-1,3(2H)-dione | 3.82 LCMS/ 406.19 $[M + CH_3OH + H]^+$ | 8 |
| 109 | 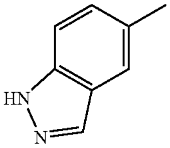 | (3aα,4β,7β,7aα)-Hexahydro-2-(1H-indazol-5-yl)-4,7-epoxy-1H-isoindole-1,3(2H)-dione | 2.13 LCMS/ 284.23 $[M + H]^+$ | 8 |
| 110 | 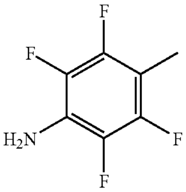 | (3aα,4β,7β,7aα)-2-(4-Amino-2,3,5,6-tetrafluorophenyl)-hexahydro-4,7-epoxy-1H-isoindole-1,3(2H)-dione | 2.60 LCMS/ 363.22 $[M + CH_3OH + H]^+$ | 8 |
| 111 | 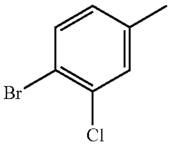 | (3aα,4β,7β,7aα)-2-(4-Bromo-3-chlorophenyl)hexahydro-4,7-epoxy-1H-isoindole-1,3(2H)-dione | 3.64 LCMS/ 389.64 $[M + CH_3OH + H]^+$ | 8 |
| 112 | 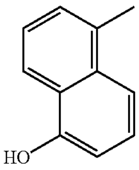 | (3aα,4β,7β,7aα)-Hexahydro-2-(5-hydroxy-1-naphthalenyl)-4,7-epoxy-1H-isoindole-1,3(2H)-dione | 2.48 LCMS/ 308.27 $[M - H]^-$ | 8 |
| 113 | 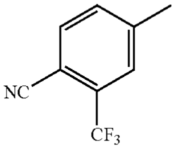 | (3aα,4β,7β,7aα)-4-(Octahydro-1,3-dioxo-4,7-epoxy-2H-isoindol-2-yl)-2-(trifluoromethyl)benzonitrile | 3.28 LCMS/ 337.16 $[M + H]^+$ | 8 |

TABLE 2-continued

| Ex. No. | G | Compound Name | Retention Time (Min.)/Molecular Mass | Pro. of Ex. |
|---|---|---|---|---|
| 114 | 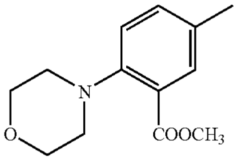 | (3aα,4β,7β,7aα)-2-(4-Morpholinyl)-5-(octahydro-1,3-dioxo-4,7-epoxy-2H-isoindol-2-yl)benzoic acid methyl ester | 2.72 LCMS/ 387.17 $[M + H]^+$ | 8 |
| 115 | 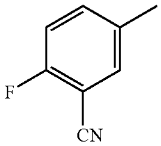 | (3aα,4β,7β,7aα)-2-Fluoro-5-(octahydro-1,3-dioxo-4,7-epoxy-2H-isoindol-2-yl)benzonitrile | 2.69 LCMS/ 319.26 $[M + CH_3OH + H]^+$ | 8 |
| 116 | 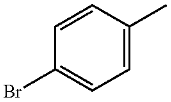 | (3aα,4β,7β,7aα)-2-(4-Bromophenyl)hexahydro-4,7-epoxy-1H-isoindole-1,3(2H)-dione | 5.80 LCMS/ 393.0 $[M + H]^+$ | 8 |
| 117 | 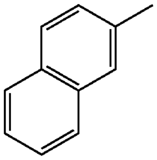 | (3aα,4β,7β,7aα)-Hexahydro-2-(2-naphthalenyl)-4,7-epoxy-1H-isoindole-1,3(2H)-dione | 6.92 LCMS/ 333.7 $[M + H]^+$ | 8 |
| 118 | 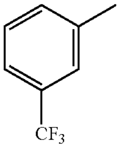 | (3aα,4β,7β,7aα)-Hexahydro-2-[3-(trifluoromethyl)phenyl]-4,7-epoxy-1H-isoindole-1,3(2H)-dione | 3.27 LCMS/ 312.2 $[M + H]^+$ | 8 |
| 119 | 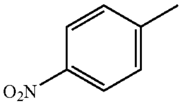 | (3aα,4β,7β,7aα)-Hexahydro-2-(4-nitrophenyl)-4,7-epoxy-1H-isoindole-1,3(2H)-dione | 2.88 LCMS/ 343.2 $[M + H]^+$ | 8 |
| 120 | 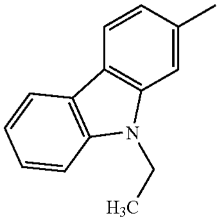 | (3aα,4β,7β,7aα)-2-(9-Ethyl-9H-carbazol-3-yl)hexahydro-4,7-epoxy-1H-isoindole-1,3(2H)-dione | 3.73 LCMS/ 360.1 $[M + H]^+$ | 8 |
| 121 | 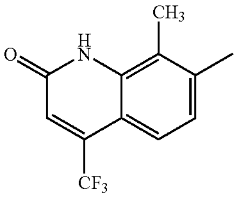 | (3aα,4β,7β,7aα)-2-[1,2-Dihydro-8-methyl-2-oxo-4-(trifluoromethyl)-7-quinolinyl]hexahydro-4,7-epoxy-1H-isoindole-1,3(2H)-dione | 3.11 LCMS/ 393.0 $[M + H]^+$ | 8 |

EXAMPLES 122 TO 164

Further compounds of the present invention were prepared by procedures analogous to those described above. Table 3 provides the compound name and structure, retention time, as well as the Example number of the procedure on which the preparation of Table 3 was based, for the compounds of Examples 122 to 164. The chromatography techniques used to determine the compound retention times of Table 3 are as follows:

LCMS=YMC S5 ODS column, 4.6×50 mm eluting with 10-90% $MeOH/H_2O$ over 4 minutes containing 0.1% TFA; 4 mL/min, monitoring at 220 nm.

LC=YMC S5 ODS column 4.6×50 mm eluting with 10-90% MeOH/$H_2O$ over 4 minutes containing 0.2% phosphoric acid, 4 mL/min, monitoring at 220 nm

TABLE 3

| Ex. No. | Compound Structure | Compound Name | Retention Time Min./Molecular Mass | Pro. of Ex. |
|---|---|---|---|---|
| 122 | 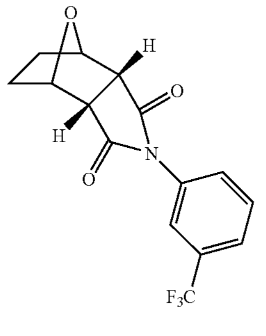 | (3aα,4α,7α,7aα)-Hexahydro-2-[3-(trifluoromethyl)phenyl]-4,7-epoxy-1H-isoindole-1,3(2H)-dione | 2.66 LCMS | 27 |
| 123 | 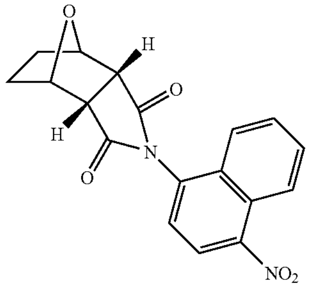 | (3aα,4α,7α,7aα)-Hexahydro-2-(4-nitro-1-naphthalenyl)-4,7-epoxy-1H-isoindole-1,3(2H)-dione | 2.76 LCMS | 27 |
| 124 | 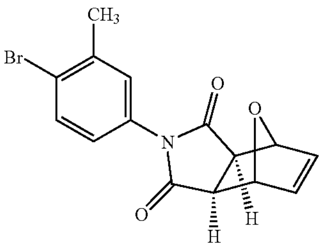 | (3aα,4β,7β,7aα)-2-(4-Bromo-3-methylphenyl)-3a,4,7,7a-tetrahydro-4,7-epoxy-1H-isoindole-1,3(2H)-dione | 6.36 LCMS | 8 |
| 125 | 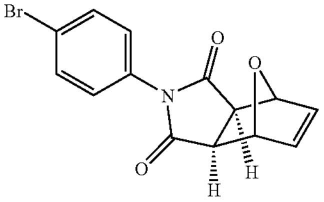 | (3aα,4β,7β,7aα)-2-(4-Bromophenyl)-3a,4,7,7a-tetrahydro-4,7-epoxy-1H-isoindole-1,3(2H)-dione | 5.72 LCMS | 8 |
| 126 | 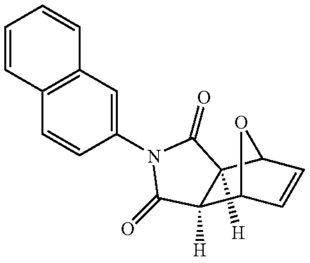 | (3aα,4β,7β,7aα)-3a,4,7,7a-Tetrahydro-2-(2-naphthalenyl)-4,7-epoxy-1H-isoindole-1,3(2H)-dione | 5.92 LCMS | 8 |

TABLE 3-continued

| Ex. No. | Compound Structure | Compound Name | Retention Time Min./Molecular Mass | Pro. of Ex. |
|---|---|---|---|---|
| 127 | 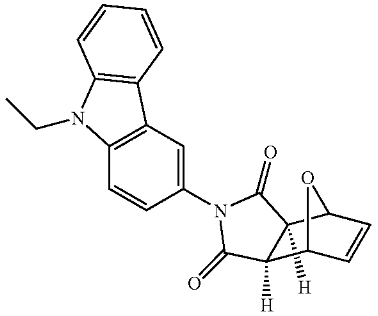 | (3aα,4β,7β,7aα)-2-(9-Ethyl-9H-carbazol-3-yl)-3a,4,7,7a-tetrahydro-4,7-epoxy-1H-isoindole-1,3(2H)-dione | 3.73 LCMS | 8 |
| 128 | 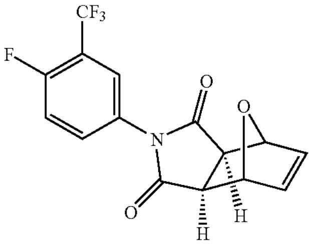 | (3aα,4β,7β,7aα)-2-[4-Fluoro-3-(trifluoromethyl)phenyl]-3a,4,7,7a-tetrahydro-4,7-epoxy-1H-isoindole-1,3(2H)-dione | 3.40 LCMS | 8 |
| 129 | 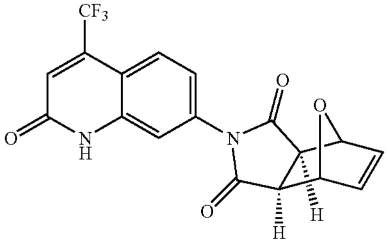 | (3aα,4β,7β,7aα)-2-[1,2-Dihydro-8-methyl-2-oxo-4-(trifluoromethyl)-7-quinolinyl]-3a,4,7,7a-tetrahydro-4,7-epoxy-1H-isoindole-1,3(2H)-dione | 3.14 LCMS | 8 |
| 130 | 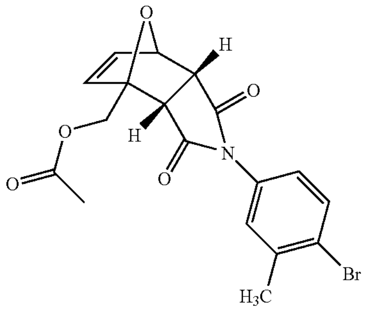 | (3aα,4α,7α,7aα)-4-[(Acetyloxy)methyl]-2-(4-bromo-3-methylphenyl)-3a,4,7,7a-tetrahydro-4,7-epoxy-1H-isoindole-1,3(2H)-dione | 2.95 LC | 4 |
| 131 | 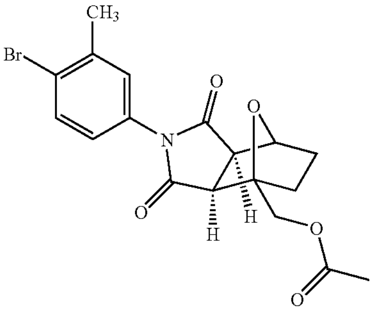 | (3aα,4β,7β,7aα)-4-[(Acetyloxy)methyl]-2-(4-bromo-3-methylphenyl)-3a,47,7a-tetrahydro-4,7-epoxy-1H-isoindole-1,3(2H)-dione. | 2.97 LCMS | 5 |

TABLE 3-continued

| Ex. No. | Compound Structure | Compound Name | Retention Time Min./Molecular Mass | Pro. of Ex. |
|---|---|---|---|---|
| 132 | 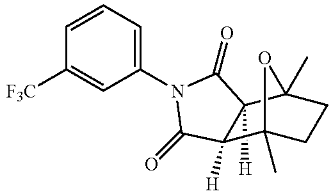 | (3aα,4β,7β,7aα)-Hexahydro-4,7-dimethyl-2-[3-(trifluoromethyl)phenyl]-4,7-epoxy-1H-isoindole-1,3(2H)-dione | 3.08 LC | 20 |
| 133 | 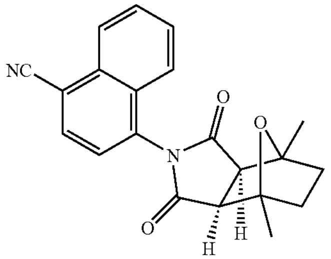 | (3aα,4β,7β,7aα)-4-(Octahydro-4,7-dimethyl-1,3-dioxo-4,7-epoxy-2H-isoindol-2-yl)-1-naphthalenecarbonitrile | 3.00 LC | 20 |
| 134 | 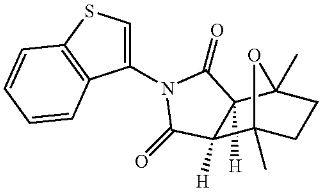 | (3aα,4β,7β,7aα)-(Benzo[b]thiophen-3-yl)hexahydro-4,7-dimethyl-4,7-epoxy-1H-isoindole-1,3(2H)-dione | 3.61 LC | 20 |
| 135 | 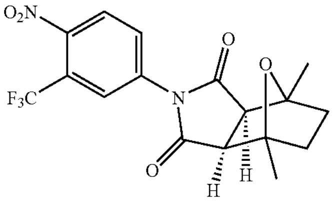 | (3aα,4β,7β,7aα)-Hexahydro-4,7-dimethyl-2-[4-nitro-3-(trifluoromethyl)phenyl]-4,7-epoxy-1H-isoindole-1,3(2H)-dione | 3.21 LC | 20 |
| 136 | 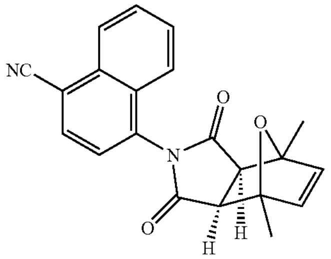 | (3aα,4β,7β,7aα)-4-(1,3,3a,4,7,7a-Hexahydro-4,7-dimethyl-1,3-dioxo-4,7-epoxy-2H-isoindol-2-yl)-1-naphthalenecarbonitrile | 2.94 LC | 32 |
| 137 | 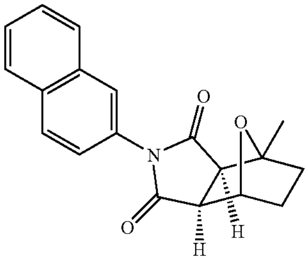 | (3aα,4α,7α,7aα)-Hexahydro-4-methyl-2-(2-naphthalenyl)-4,7-epoxy-1H-isoindole-1,3(2H)-dione | 2.88 LC | 3 |

TABLE 3-continued

| Ex. No. | Compound Structure | Compound Name | Retention Time Min./Molecular Mass | Pro. of Ex. |
|---|---|---|---|---|
| 138 | 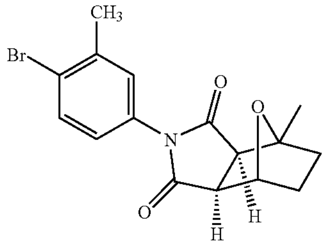 | (3aα,4β,7β,7aα)-2-(4-Bromo-3-methylphenyl)hexahydro-4-methyl-4,7-epoxy-1H-isoindole-1,3(2H)-dione | 3.11 LC | 3 |
| 139 | 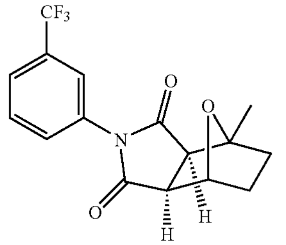 | (3aα,4β,7β,7aα)-Hexahydro-4-methyl-2-[3-(trifluoromethyl)phenyl]-4,7-epoxy-1H-isoindole-1,3(2H)-dione | 2.90 LC | 3 |
| 140 | 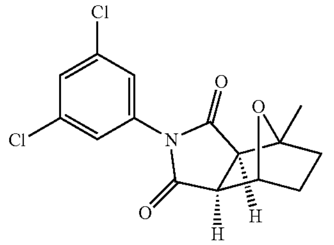 | (3aα,4β,7β,7aα)-2-(3,5-Dichlorophenyl)hexahydro-4-methyl-4,7-epoxy-1H-isoindole-1,3(2H)-dione | 3.31 LC | 3 |
| 141 | 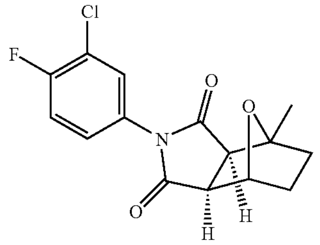 | (3aα,4β,7β,7aα)-2-(3-Chloro-4-fluorophenyl)-hexahydro-4-methyl-4,7-epoxy-1H-isoindole-1,3(2H)-dione | 2.72 LC | 3 |
| 142 | 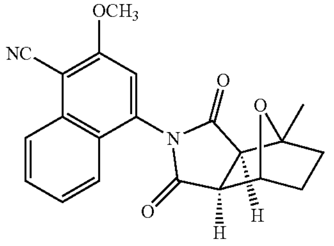 | (3aα,4β,7β,7aα)-2-Methoxy-4-(octahydro-1,3-dioxo-4-methyl-4,7-epoxy-2H-isoindol-2-yl)-1-naphthalenecarbonitrile | 2.72 LC | 3 |
| 143 | 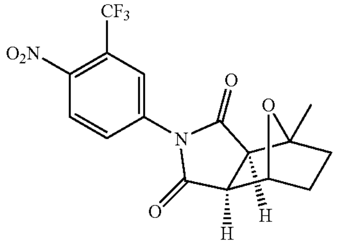 | (3aα,4β,7β,7aα)-Hexahydro-4-methyl-2-[4-nitro-3-(trifluoromethyl)phenyl]-4,7-epoxy-1H-isoindole-1,3(2H)-dione | 3.10 LC | 3 |

TABLE 3-continued

| Ex. No. | Compound Structure | Compound Name | Retention Time Min./Molecular Mass | Pro. of Ex. |
|---|---|---|---|---|
| 144 | 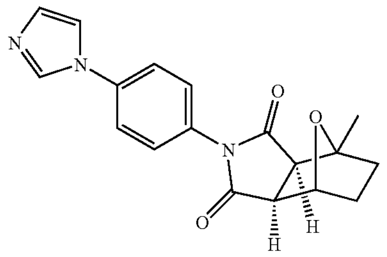 | (3aα,4β,7β,7aα)-Hexahydro-2-[4-(1H-imidazol-1-yl)phenyl]-4-methyl-4,7-epoxy-1H-isoindole-1,3(2H)-dione | 1.16 LC | 3 |
| 145 | 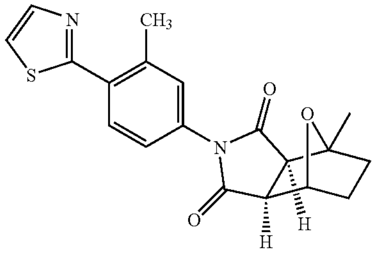 | (3aα,4β,7β,7aα)-2-[3-Chloro-4-(2-thiazolyl)phenyl]hexahydro-4-methyl-4,7-epoxy-1H-isoindole-1,3(2H)-dione | 2.81 LC | 3 |
| 146 | 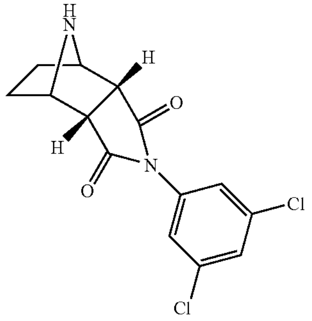 | (3aα,4α,7α,7aα)-2-(3,5-Dichlorophenyl)hexahydro-4,7-imino-1H-isoindole-1,3(2H)-dione | 2.72 LC | 31 |
| 147 | 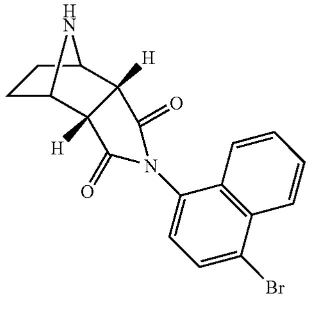 | (3aα,4α,7α,7aα)-2-(4-Bromo-1-naphthalenyl)hexahydro-4,7-imino-1H-isoindole-1,3(2H)-dione | 2.95 LC | 31 |
| 148 | 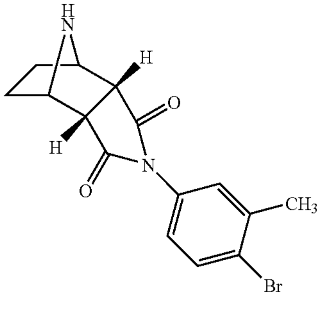 | (3aα,4α,7α,7aα)-2-(4-Bromo-3-methylphenyl)hexahydro-4,7-imino-1H-isoindole-1,3(2H)-dione | 2.65 LC | 31 |

TABLE 3-continued

| Ex. No. | Compound Structure | Compound Name | Retention Time Min./Molecular Mass | Pro. of Ex. |
|---|---|---|---|---|
| 149 | 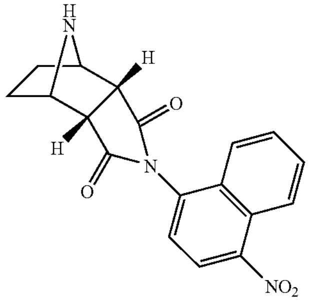 | (3aα,4α,7α,7aα)-Hexahydro-2-(4-nitro-1-naphthalenyl)-4,7-imino-1H-isoindole-1,3(2H)-dione | 2.49 LC | 31 |
| 150 | 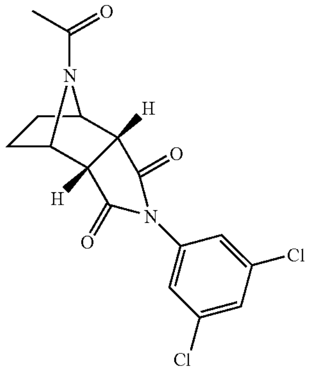 | (3aα,4α,7α,7aα)-8-Acetyl-2-(3,5-dichlorophenyl)hexahydro-4,7-imino-1H-isoindole-1,3(2H)-dione | 3.53 LC | 31, 12 |
| 151 | 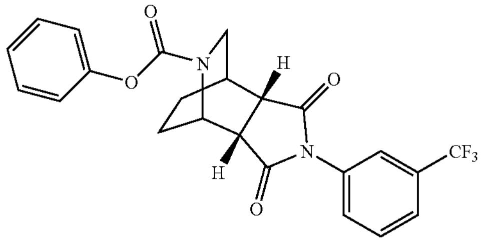 | (3aα,4α,7α,7aα)-Octahydro-1,3-dioxo-2-[3-(trifluoromethyl)phenyl]-4,7-ethano-5H-pyrrolo[3,4-c]pyridine-5-carboxylic acid phenyl ester | 3.397 LC | 9 |
| 152 | 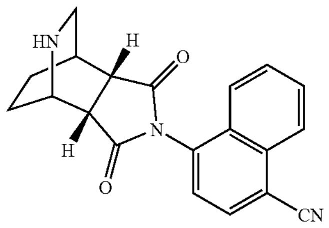 | (3aα,4α,7α,7aα)-4-(Octahydro-1,3-dioxo-4,7-ethano-2H-pyrrolo[3,4-naphthalenecarbonitrile | 1.74 LC | 11 |
| 153 | 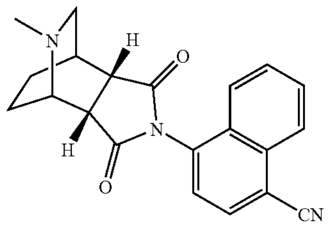 | (3aα,4α,7α,7aα)-4-(Octahydro-5-methyl-1,3-dioxo-4,7-ethano-2H-pyrrolo[3,4-c]pyridin-2-yl)-1-naphthalenecarbonitrile | 1.71 LC | 14 |

TABLE 3-continued

| Ex. No. | Compound Structure | Compound Name | Retention Time Min./Molecular Mass | Pro. of Ex. |
|---|---|---|---|---|
| 154 | 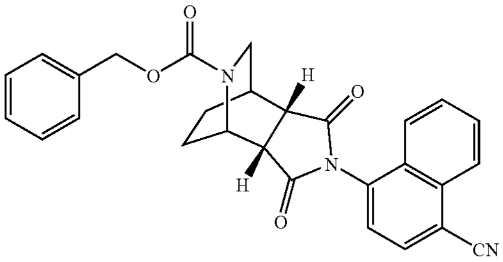 | (3aα,4α,7α,7aα)-2-(4-Cyano-1-naphthalenyl)octahydro-1,3-dioxo-4,7-etheno-5H-pyrrolo[3,4-c]pyridine-5-carboxylic acid phenylmethyl ester | 3.40 LC | 10 |
| 155 | 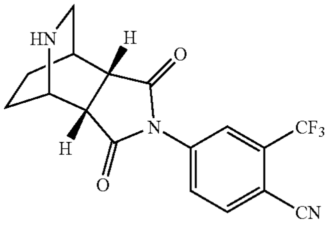 | (3aα,4α,7α,7aα)-4-(Octahydro-1,3-dioxo-4,7-ethano-2H-pyrrolo[3,4-c]pyridin-2-yl)-2-(trifluoromethyl)benzonitrile | 1.74 LC | 11 |
| 156 | 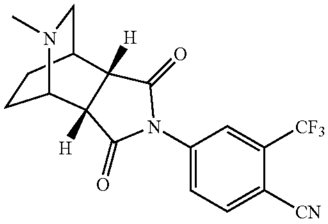 | (3aα,4α,7α,7aα)-4-(Octahydro-5-methyl-1,3-dioxo-4,7-ethano-2H-pyrrolo[3,4-c]pyridin-2-yl)-2-(trifluoromethyl)benzonitrile | 1.65 LC | 14 |
| 157 | 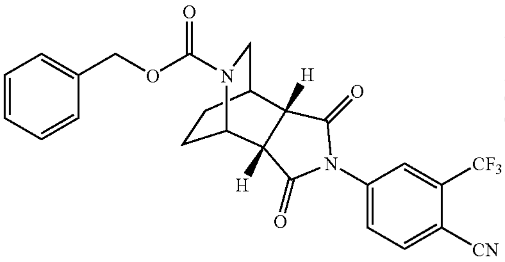 | (3aα,4α,7α,7aα)-2-[4-Cyano-3-(trifluoromethyl)phenyl]octahydro-1,3-dioxo-4,7-etheno-5H-pyrrolo[3,4-c]pyridine-5-carboxylic acid phenylmethyl ester | 3.53 LC | 10 |
| 158 | 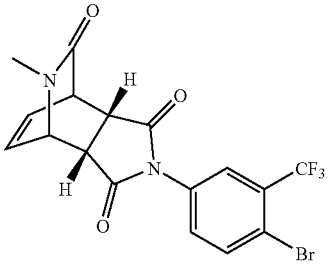 | (3aα,4α,7α,7aα)-2-[4-Bromo-3-(trifluoromethyl)phenyl]tetrahydro-5-methyl-4,7-etheno-1H-pyrrolo[3,4-c]pyridine-1,3,6(2H,5H)-trione | 2.95 LCMS | 34 |
| 159 | 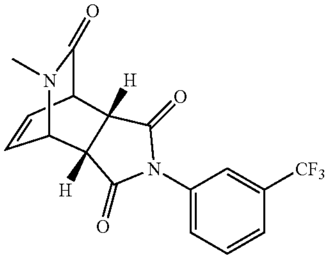 | (3aα,4α,7α,7aα)-Tetrahydro-5-methyl-2-[3-(trifluoromethyl)phenyl]-4,7-etheno-1H-pyrrolo[3,4-c]pyridine-1,3,6(2H,5H)-trione | 2.53 LCMS | 34 |

TABLE 3-continued

| Ex. No. | Compound Structure | Compound Name | Retention Time Min./Molecular Mass | Pro. of Ex. |
|---|---|---|---|---|
| 160 | 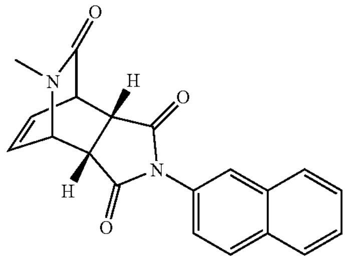 | (3aα,4α,7α,7aα)-Tetrahydro-5-methyl-2-(2-naphthalenyl)-4,7-etheno-1H-pyrrolo[3,4-c]pyridine-1,3,6(2H,5H)-trione | 2.58 LCMS | 34 |
| 161 | 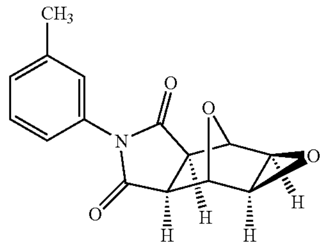 | (1aα,2β,2aα,5aα,6β,6aα)-Hexahydro-4-[3-(trifluoromethyl)phenyl]-2,6-epoxy-3H-oxireno[f]iso-indole-3,5(4H)-dione | 1.80 LCMS | 28 |
| 162 | 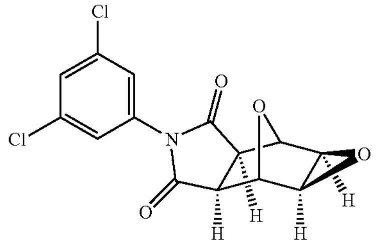 | (1aα,2β,2aα,5aα,6β,6aα)-4-(3,5-Dichlorophenyl)-hexahydro-2,6-epoxy-3H-oxireno[f]isoindole-3,5(4H)-dione | 1.45 LCMS | 28 |
| 163 | 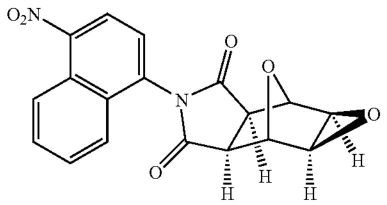 | (1aα,2β,2aα,5aα,6β,6aα)-Hexahydro-4-(4-nitro-1-naphthalenyl)-2,6-epoxy-3H-oxireno[f]isoindole-3,5(4H)-dione | 1.52 LCMS | 28 |
| 164 | 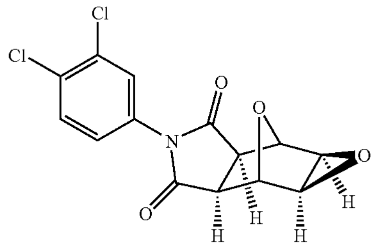 | (1aα,2β,2aα,5aα,6β,6aα)-4-(3,4-Dichlorophenyl)-hexahydro-2,6-epoxy-3H-oxireno[f]isoindole-3,5(4H)-dione | 3.21 LCMS | 28 |

EXAMPLES 165 TO 203

Additional compounds of the present invention were prepared and are described further below in Table 4. Table 4 sets forth the compound name and structure, as well as the Example number of the procedure on which the preparation of Table 4 was based, for the compounds of Examples 165 to 203.

TABLE 4

| Ex. No. | Compound Structure | Compound Name | Pro. of Ex. |
|---|---|---|---|
| 165 | 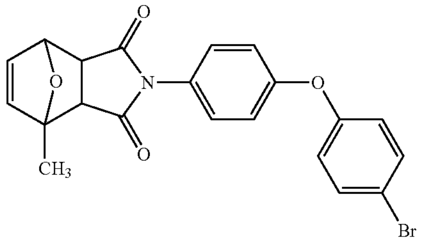 | 2-[4-(4-Bromo-phenoxy)phenyl]-3a,4,7,7a-tetrahydro-4-methyl-4,7-epoxy-1H-isoindole-1,3(2H)-dione | 32 |
| 166 | 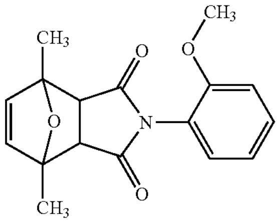 | 3a,4,7,7a-Tetrahydro-2-(2-methoxyphenyl)-4,7-dimethyl-4,7-epoxy-1H-isoindole-1,3(2H)-dione | 32 |
| 167 | 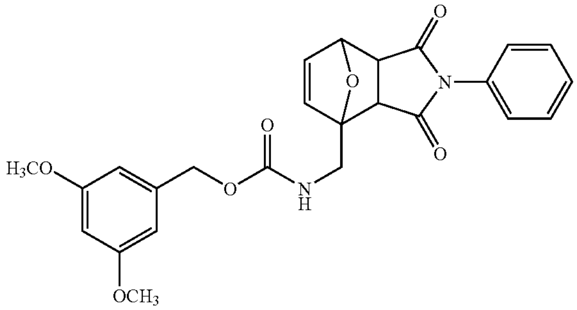 | [(1,2,3,3a,7,7a-Hexahydro-2-phenyl-4,7-epoxy-4H-isoindol-4-yl)methyl]carbamic acid (3,5-dimethoxyphenyl)methyl ester | 21-26 |
| 168 | 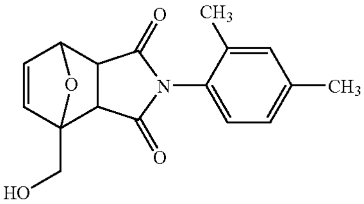 | 2-(2,4-Dimethylphenyl)-3a,4,7,7a-tetrahydro-4-(hydroxymethyl)-4,7-epoxy-1H-isoindole-1,3(2H)-dione | 21-26 |
| 169 | 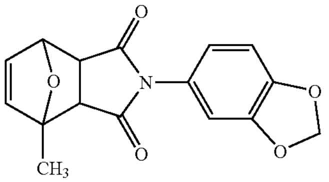 | 2-(1,3-Benzodioxol-5-yl)-3a,4,7,7a-tetrahydro-4-methyl-4,7-epoxy-1H-isoindole-1,3(2H)-dione | 32 |
| 170 | 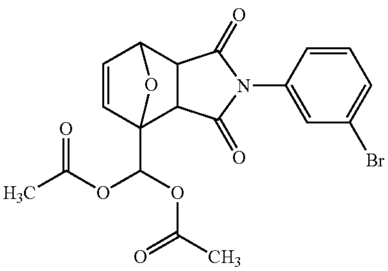 | 4-[Bis(acetyloxy)methyl]-2-(3-bromophenyl)-3a,4,7,7a-tetrahydro-4,7-epoxy-1H-isoindole-1,3(2H)-dione | 21-26 |

TABLE 4-continued

| Ex. No. | Compound Structure | Compound Name | Pro. of Ex. |
| --- | --- | --- | --- |
| 171 | 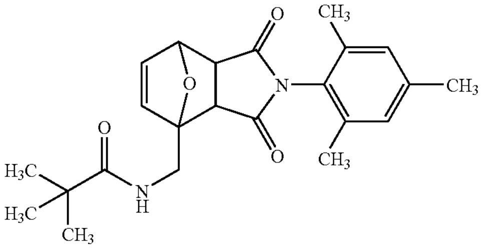 | N-[[1,2,3,3a,7,7a-Hexahydro-2-(2,4,6-trimethylphenyl)-4,7-epoxy-4H-isoindol-4-yl]methyl]-2,2-dimethylpropanamide | 21-26 |
| 172 | 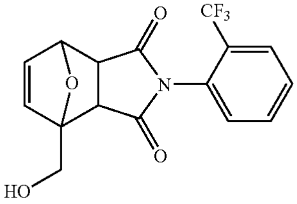 | 3a,4,7,7a-Tetrahydro-4-(hydroxymethyl)-2-[2-(trifluoromethyl)phenyl]-4,7-epoxy-1H-isoindole-1,3(2H)-dione | 21-26 |
| 173 | 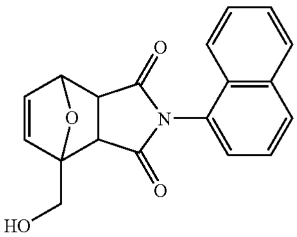 | 3a,4,7,7a-Tetrahydro-4-(hydroxymethyl)-2-(1-naphthalenyl)-4,7-epoxy-1H-isoindole-1,3(2H)-dione | 21-26 |
| 174 | 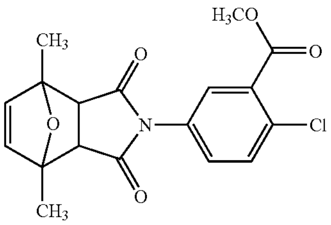 | 2-Chloro-5-(1,3,3a,4,7,7a-hexahydro-4,7-dimethyl-4,7-epoxy-2H-isoindol-2-yl)benzoic acid methyl ester | 32 |
| 175 | 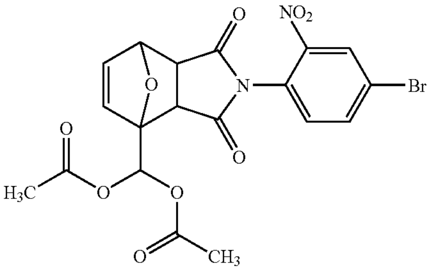 | 4-[Bis(acetyloxy)methyl]-2-(4-bromo-2-nitrophenyl)-3a,4,7,7a-tetrahydro-4,7-epoxy-1H-isoindole-1,3(2H)-dione | 21-26 |
| 176 | 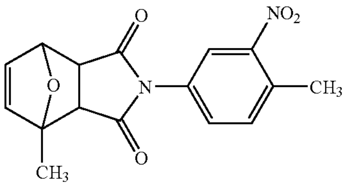 | 3a,4,7,7a-Tetrahydro-4-methyl-2-(4-methyl-3-nitrophenyl)-4,7-epoxy-1H-isoindole-1,3(2H)-dione | 32 |

TABLE 4-continued

| Ex. No. | Compound Structure | Compound Name | Pro. of Ex. |
|---|---|---|---|
| 177 | 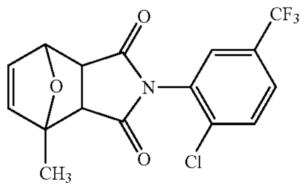 | 2-[2-Chloro-5-(trifluoromethyl)phenyl]-3a,4,7,7a-tetrahydro-4-methyl-4,7-epoxy-1H-isoindole-1,3(2H)-dione | 32 |
| 178 | 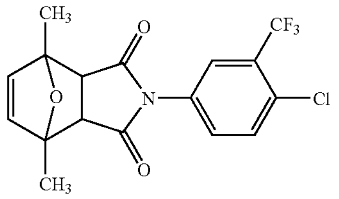 | 2-[4-Chloro-3-(trifluoromethyl)phenyl]-3a,4,7,7a-tetrahydro-4,7-dimethyl-4,7-epoxy-1H-isoindole-1,3(2H)-dione | 32 |
| 179 | 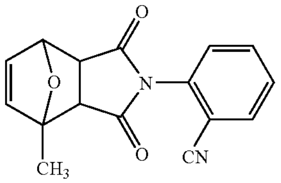 | 2-(1,3,3a,4,7,7a-Hexahydro-4-methyl-4,7-epoxy-2H-isoindol-2-yl)benzonitrile | 32 |
| 180 | 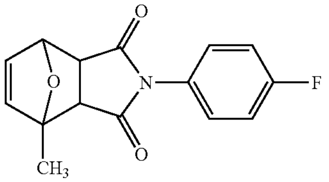 | 2-(4-Fluorophenyl)-3a,4,7,7a-tetrahydro-4-methyl-4,7-epoxy-1H-isoindole-1,3(2H)-dione | 32 |
| 181 | 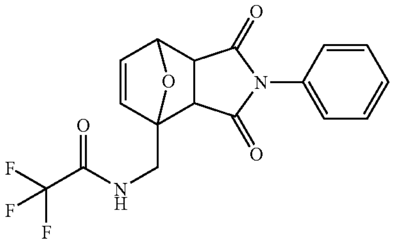 | 2,2,2-Trifluoro-N-[(1,2,3,3a,7,7a-hexahydro-2-phenyl-4,7-epoxy-4H-isoindol-4-yl)methyl]acetamide | 21-26 |
| 182 | 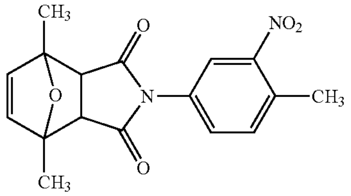 | 3a,4,7,7a-Tetrahydro-4,7-dimethyl-2-(4-methyl-3-nitrophenyl)-4,7-epoxy-1H-isoindole-1,3(2H)-dione | 32 |
| 183 | 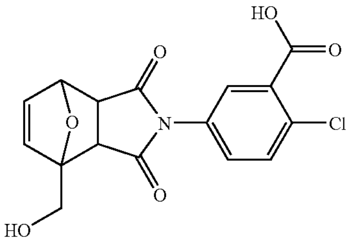 | 2-Chloro-5-[1,3,3a,4,7,7a-hexahydro-4-(hydroxymethyl)-4,7-epoxy-2H-isoindol-2-yl]benzoic acid | 21-26 |

TABLE 4-continued

| Ex. No. | Compound Structure | Compound Name | Pro. of Ex. |
|---|---|---|---|
| 184 | 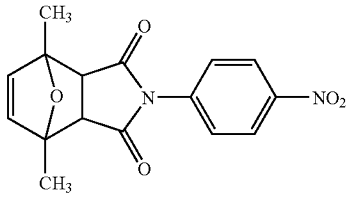 | 3a,4,7,7a-Tetrahydro-4,7-dimethyl-2-(4-nitrophenyl)-4,7-epoxy-1H-isoindole-1,3(2H)-dione | 32 |
| 185 | 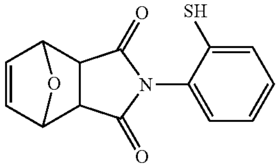 | 3a,4,7,7a-Tetrahydro-2-(2-mercaptophenyl)-4,7-epoxy-1H-isoindole-1,3(2H)-dione | 32 |
| 186 | 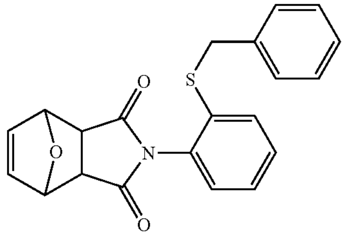 | 3a,4,7,7a-Tetrahydro-2-[2-[(phenylmethyl)thio]phenyl]-4,7-epoxy-1H-isoindole-1,3(2H)-dione | 32 |
| 187 | 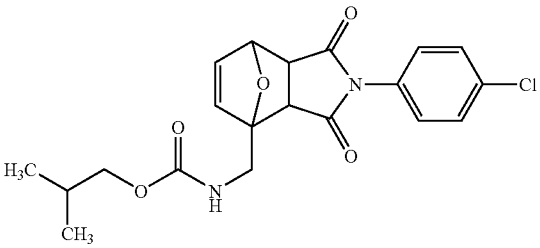 | [[2-(4-Chlorophenyl)-1,2,3,3a,7,7a-hexahydro-4,7-epoxy-4H-isoindol-4-yl]methyl]carbamic acid 2-methylpropyl ester | 21-26 |
| 188 | 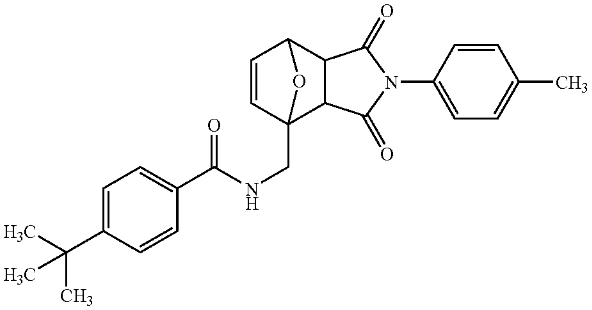 | 4-(1,1-Dimethylethyl)-N-[[1,2,3,3a,7,7a-hexahydro-2-(4-methylphenyl)-4,7-epoxy-4H-isoindol-4-yl]methyl]benzamide | 21-26 |
| 189 | 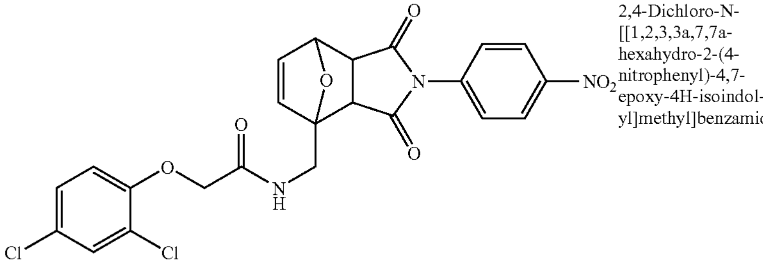 | 2,4-Dichloro-N-[[1,2,3,3a,7,7a-hexahydro-2-(4-nitrophenyl)-4,7-epoxy-4H-isoindol-4-yl]methyl]benzamide | 21-26 |

TABLE 4-continued

| Ex. No. | Compound Structure | Compound Name | Pro. of Ex. |
|---|---|---|---|
| 190 | 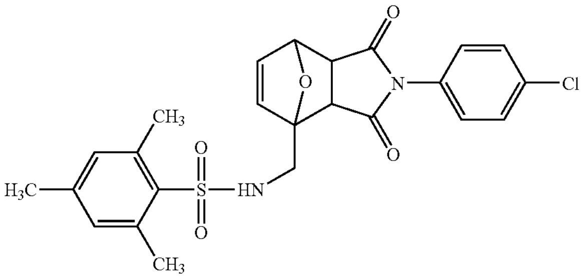 | N-[[2-(4-Chlorophenyl)-1,2,3,3a,7,7a-hexahydro-4,7-epoxy-4H-isoindol-4-yl]methyl]-2,4,6-trimethylbenzenesulfonamide | 21-26 |
| 191 | 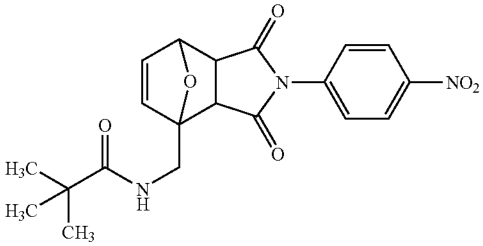 | N-[[1,2,3,3a,7,7a-Hexahydro-2-(4-nitrophenyl)-4,7-epoxy-4H-isoindol-4-yl]methyl]-2,2-dimethylpropanamide | 21-26 |
| 192 | 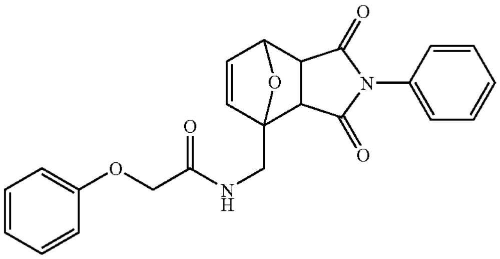 | N-[(1,2,3,3a,7,7a-Hexahydro-2-phenyl-4,7-epoxy-4H-isoindol-4-yl)methyl]-2-phenoxyacetamide | 21-26 |
| 193 | 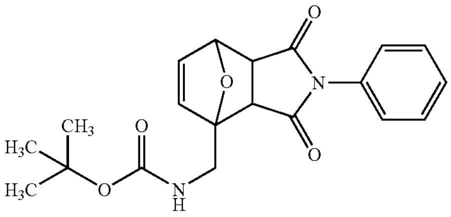 | [(1,2,3,3a7,7a-Hexahydro-2-phenyl-4,7-epoxy-4H-isoindol-4-yl)methyl]carbamic acid 1,1-dimethylethyl ester | 21-26 |
| 194 | 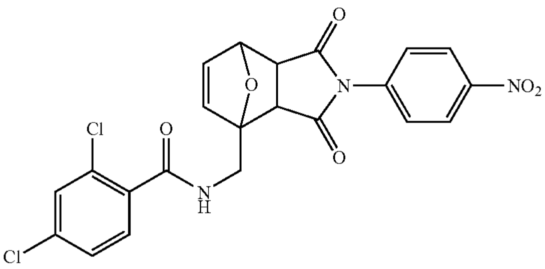 | 2-(2,4-Dichlorophenoxy)-N-[[1,2,3,3a,7,7a-hexahydro-2-(4-nitrophenyl)-4,7-epoxy-4H-isoindol-4-yl]methyl]acetamide | 21-26 |

TABLE 4-continued

| Ex. No. | Compound Structure | Compound Name | Pro. of Ex. |
| --- | --- | --- | --- |
| 195 | 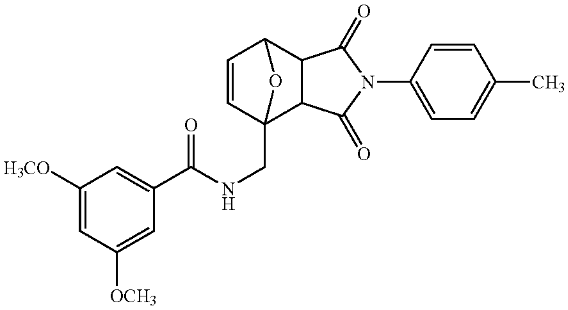 | N-[[1,2,3,3a,7,7a-Hexahydro-2-(4-methylphenyl)-4,7-epoxy-4H-isoindol-4-yl]methyl]-3,5-dimethoxybenzamide | 21-26 |
| 196 | 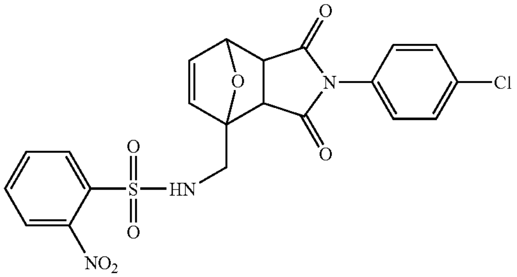 | N-[[2-(4-Chlorophenyl)-1,2,3,3a,7,7a-hexahydro-4,7-epoxy-4H-isoindol-4-yl]methyl]-2-nitrobenzenesulfonamide | 21-26 |
| 197 | 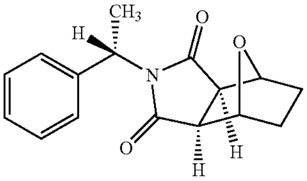 | (3aα,4β,7β,7aα)-Hexahydro-2-[(1S)-1-epoxy-1H-isoindole-1,3(2H)-dione. | 8 |
| 198 | 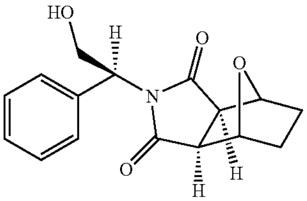 | (3aα,4β,7β,7aα)-Hexahydro-2-[(1S)-2-hydroxy-1-phenylethyl]-4,7-epoxy-1H-isoindole-1,3(2H)-dione. | 8 |
| 199 | 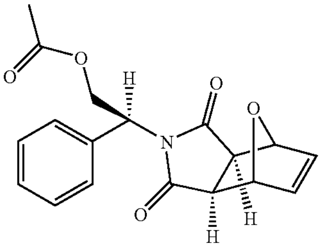 | (3aα,4β,7β,7aα)-2-[(1S)-2-(Acetyloxy)-1-phenylethyl]-3a,4,7,7a-tetrahydro-4,7-epoxy-1H-isoindole-1,3(2H)-dione. | 8 |
| 200 | 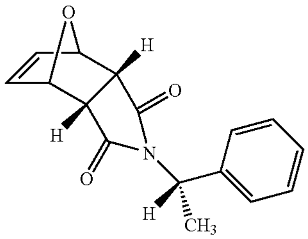 | (3aα,4α,7α,7aα)-3a,4,7,7a-Tetrahydro-2-[(1S)-1-phenylethyl]-4,7-epoxy-1H-isoindole-1,3(2H)-dione. | 8 |

TABLE 4-continued

| Ex. No. | Compound Structure | Compound Name | Pro. of Ex. |
|---|---|---|---|
| 201 | 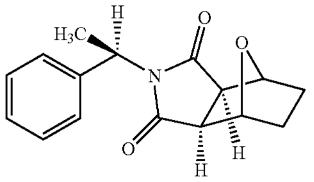 | (3aα,4β,7β,7aα)-Hexahydro-2-[(1R)-1-phenylethyl]-4,7-epoxy-1H-isoindole-1,3(2H)-dione. | 8 |
| 202 | 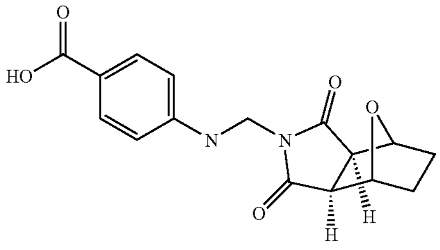 | (3aα,4β,7β,7aα)-4-[[[(Octahydro-1,3-dioxo-4,7-epoxy-2H-isoindol-2-yl)methyl]amino]benzoic acid. | 8 |
| 203 | 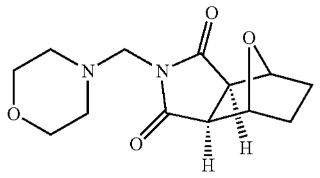 | (3aα,4β,7β,7aα)-Hexahydro-2-(4-morpholinylmethyl)-4,7-epoxy-1H-isoindole-1,3(2H)-dione. | 8 |

EXAMPLE 204

(3aα,4β,7β,7aα)-4-[Octahydro-4-(2-hydroxyethyl)-7-methyl-1,3-dioxo-4,7-epoxy-2H-isoindol-2-yl]-2-(trifluoromethyl)benzonitrile (204D/25B)

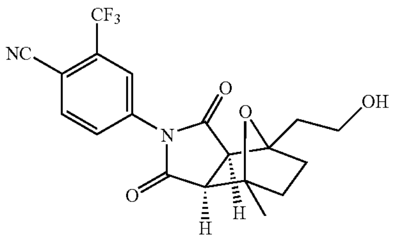

A. 2-[2-[[(1,1-Dimethylethyl)dimethylsilyl]oxy]ethyl]-5-methylfuran (204A)

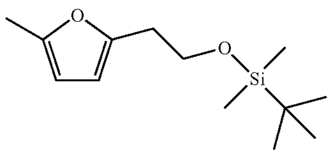

To a solution of compound 21A (2.00 g, 15.9 mmol) in DMF (50 mL) was added imidazole (1.62 g, 23.9 mmol), followed by tert-butyldimethylsilyl chloride (2.63 g, 17.5 mmol). After 2 h at 25° C., the reaction was poured into diethyl ether (300 mL) and washed with water (1×100 mL), 1 N HCl (1×100 mL), water (1×100 mL), brine (1×50 mL) and dried over anhydrous $MgSO_4$. Crude compound 204A was analyzed by LCMS and NMR and determined to be pure enough to be carried on directly to the next step. HPLC: 100% at 4.347 min (retention time) (YMC S5 ODS column 4.6×50 mm eluting with 10-90% aqueous methanol over 4 minutes containing 0.1% TFA, 4 mL/min, monitoring at 220 nm).

B. (3aα,4β,7β,7aα)-4-[2-[[(1,1-Dimethylethyl)dimethylsilyl]-oxy]ethyl]hexahydro-7-methyl-4,7-epoxy-1H-isobenzofuran-1,3(2H)-dione (204B)

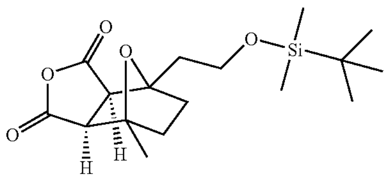

Compound 204A (4.0 g, 18.9 mmol) and maleic anhydride (1.42 g, 14.5 mmol) were dissolved in dichloroethane (10 mL) and stirred at 25° C. for 60 hours. The volatiles were then removed in vacuo and the resulting orange oil was dissolved in absolute ethanol (50 mL) and 10% Pd/C (1.00 g, cat.) was added. Hydrogen was then introduced via a balloon. After 3 h, the reaction was filtered through Celite rinsing with EtOAc and concentrated in vacuo. The crude anhydride was purified by rapid flash chromatography on $SiO_2$ eluting with acetone/chloroform (0-2-4% acetone) to give 1.30 g (3.82 mmol, 20%) of compound 204B as a clear oil, in addition to 3.00 g (12.5 mmol, 66%) of the starting compound 204A. Characterization by proton NMR spectroscopy showed only the exo isomer. $^1H$ NMR (400 MHz, $CDCl_3$) δ=3.83 (2H, t, J=6.0 Hz), 3.22 (1H, d, J=8.2 Hz), 3.06 (1H, d, J=8.2 Hz), 1.70-2.25 (6H, m), 1.55 (3H, s), 0.82 (9H, s), 0.00 (6H, s).

C. (3aα,4β,7β,7aα)-4-[4-[2-[[(1,1-Dimethylethyl)dimethylsilyl]-oxy]ethyl]octahydro-7-methyl-1,3-dioxo-4,7-epoxy-2H-isoindol-2-yl]-2-(trifluoromethyl)benzonitrile (204C)

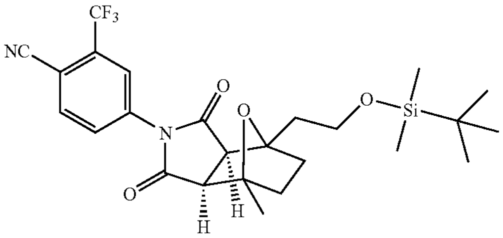

Compound 204B (0.250 g, 0.734 mmol) and 4-amino-2-trifluoromethylbenzonitrile (0.124 g, 0.668 mmol) were suspended in dry toluene (2.0 mL) in a sealed tube. $MgSO_4$ (0.200 g) and triethylamine (0.5 mL) were then added and the tube was sealed and placed in a oil bath at 125° C. After 40 h, the reaction was cooled to 25° C., filtered and concentrated in vacuo. The crude material was purified by flash chromatography on $SiO_2$ eluting with $CH_2Cl_2$ to give 0.111 g (0.281 mmol, 30%) of compound 204C as a yellow solid. HPLC: 92% at 4.203 min (retention time) (YMC S5 ODS column 4.6×50 mm eluting with 10-90% aqueous methanol over 4 minutes containing 0.1% TFA, 4 mL/min, monitoring at 220 nm). MS (ESI): m/z 531.1 $[M+Na]^+$.

D. (3aα,4β,7β,7aα)-4-[Octahydro-4-(2-hydroxyethyl)-7-methyl-1,3-dioxo-4,7-epoxy-2H-isoindol-2-yl]-2-(trifluoromethyl)benzonitrile (204D)

Compound 204C (0.031 g, 0.061 mmol) was dissolved in THF (0.5 mL) and transferred to a polypropylene container followed by cooling to 0° C. HF.pyridine (~47% HF, 0.1 mL) was then added. After 15 min, the reaction was complete as determined by LC and was poured into cold sat. aqueous $NaHCO_3$. The mixture was extracted with $CH_2Cl_2$ (3×10 mL). The combined organic layers were washed with 1 N HCl (1×20 mL) and dried over anhydrous $Na_2SO_4$. Compound 204D was isolated as a yellow oil and compared to the material prepared in Example 25. No purification was necessary.

EXAMPLE 205

(3aα,4β,7β,7aα)- and (3aα,4α,7α,7aα)-4-[Octahydro-4-methyl-1,3-dioxo-7-(phenylmethyl)-4,7-epoxy-2H-isoindol-2-yl]-2-(trifluoromethyl)benzonitrile (205Ci and 205Cii, respectively)

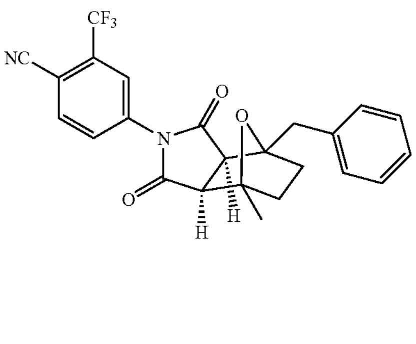

-continued

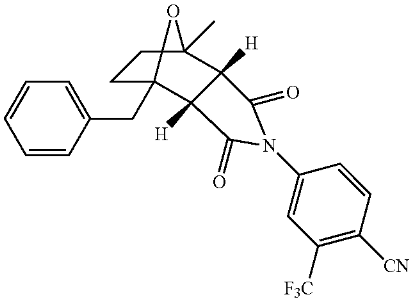

A. 2-Methyl-5-(phenylmethyl)-furan (205A)

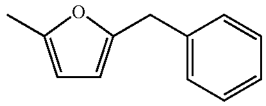

n-BuLi (1.8 mL, 4.51 mmol, 2.5 M in hexane) was added to a solution of 2-methylfuran (0.37 mL, 4.10 mmol) in anhydrous THF (3 mL) at −25° C. The resulting solution was stirred at room temperature for 3 h and then cooled to −15° C. Benzyl bromide (0.59 mL, 4.92 mmol), which was passed through a plug of aluminum oxide, was added and the solution was warmed to rt and stirred overnight. Saturated $NH_4Cl$ solution (5 mL) was added and the mixture was stirred for 1 h. The reaction mixture was then extracted with ether (2×5 mL) and the combined organic extracts were dried and concentrated under reduced pressure. Purification by flash chromatography on silica gel eluting with hexanes gave 323 mg (1.88 mmol, 46%) of compound 205A as colorless oil. HPLC: 95% at 3.72 min (retention time) (YMC S5 ODS column 4.6×50 mm, 10-90% aqueous methanol over 4 minutes containing 0.2% phosphoric acid, 4 mL/min, monitoring at 220 nm) and about 400 mg mixture of product and benzyl bromide (~2:1 by HPLC).

B. (3aα,4β,7β,7aα)- and (3aα,4α,7α,7aα)-4-[Octahydro-4-methyl-1,3-dioxo-7-(phenylmethyl)-4,7-epoxy-2H-isoindol-2-yl]-2-(trifluoromethyl)benzonitrile (205Bi and 205Bii, respectively)

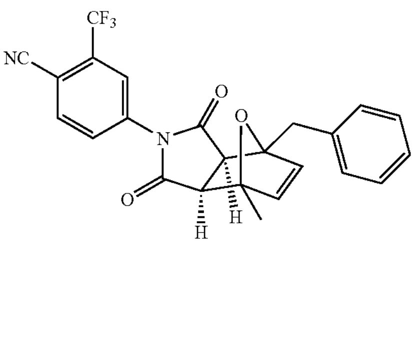

-continued

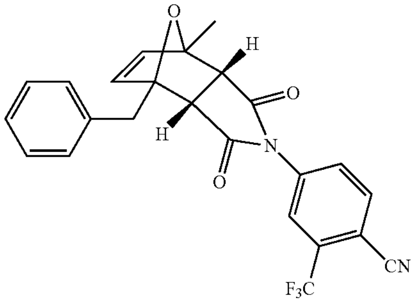

A solution of compound 205A (124 mg, 0.72 mmol) and 4-(2,5-dihydro-2,5-dioxo-1H-pyrrol-1-yl)-2-trifluoromethylbenzonitrile (290 mg, 1.09 mmol) in $CH_2Cl_2$ (2 mL) was stirred at room temperature. After 4 days, the reaction mixture was concentrated under reduced pressure. Purification by flash chromatography on silica gel eluting with $CH_2Cl_2$ gave 62 mg (0.14 mmol, 20%) of a mixture of compounds 205Bi and 205Bii as a white solid, which was used directly in the next step. HPLC: 93% at 3.69 min (retention time) (YMC S5 ODS column 4.6×50 mm, 10-90% aqueous methanol over 4 minutes containing 0.2% phosphoric acid, 4 mL/min, monitoring at 220 nm).

C. (3aα,4β,7β,7aα)- and (3aα,4α,7α,7aα)-4-[Octahydro-4-methyl-1,3-dioxo-7-(phenylmethyl)-4,7-epoxy-2H-isoindol-2-yl]-2-(trifluoromethyl)-benzonitrile (205Ci and 205Cii, respectively)

A solution of a mixture of compounds 205Bi and 205Bii (62 mg, 0.14 mmol) and 10% Pd/C (12 mg, cat.) in EtOH (3.5 mL) was stirred under a hydrogen atmosphere at room temperature for 2 h. The reaction mixture was filtered through Celite and concentrated under reduced pressure. Purification by flash chromatography on silica gel eluting with 35% EtOAc/hexanes gave 22 mg (0.05 mmol, 35%) of compound 205Ci and 12 mg (0.027 mmols, 19%) of compound 205Cii. Compound 205Ci: HPLC: 98% at 3.75 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 458.2 $[M+NH_4]^+$. Compound 205Cii: HPLC: 97% at 3.78 min (retention time) (YMC S5 ODS column 4.6×50 mm, 10-90% aqueous methanol over 4 minutes containing 0.2% phosphoric acid, 4 mL/min, monitoring at 220 nm). MS (ESI): m/z 473.45 $[M+CH_3OH]^+$.

EXAMPLE 206

(3aα,4β,7β,7aα)-2-[4-Cyano-3-(trifluoromethyl)phenyl]octahydro-7-methyl-1,3-dioxo-4,7-epoxy-4H-isoindole-4-propanenitrile (206)

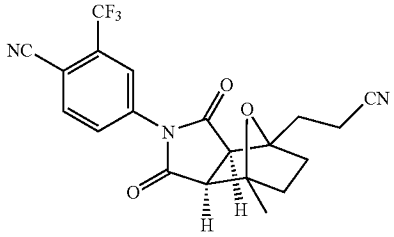

A solution of compound 36 (34 mg, 0.074 mmol) and NaCN (24 mg, 0.49 mmol) in DMSO (1 mL) was heated at 100° C. for 0.5 h. After cooling, the reaction mixture was poured into $H_2O$ (5 mL) and the aqueous layer was extracted with EtOAc (2×5 mL). The combined organic layers were washed with $H_2O$ (2×5 mL), dried over $Na_2SO_4$ and concentrated under reduced pressure. Purification by flash chromatography on $SiO_2$ eluting with 50% EtOAc/hexanes followed by reverse phase preparative HPLC [30.41 min (retention time) (YMC S5 ODS 30×250 mm, 10-90% aqueous methanol over 30 minutes containing 0.1% TFA, 25 mL/min, monitoring at 220 nm)] gave 6.6 mg (0.016 mmol, 22%) of compound 206 as a white solid. HPLC: 99% at 2.89 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 402.1 $[M-H]^-$.

EXAMPLE 207

(3aα,4β,7β,7aα)-4-[Octahydro-4-methyl-7-[2-(4-morpholinyl)ethyl]-1,3-dioxo-4,7-epoxy-2H-isoindol-2-yl]-2-(trifluoromethyl)benzonitrile, trifluoroacetate (1:1) (207)

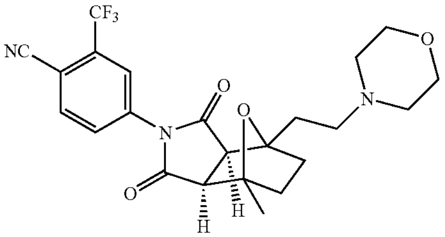

A solution of compound 36 (15.6 mg, 0.0341 mmol) and morpholine (6.0 μL, 0.068 mmol) in toluene (1 mL) was heated at 100° C. overnight. After cooling, the reaction mixture was concentrated under reduced pressure. Purification by flash chromatography on $SiO_2$ eluting with 10% MeOH/$CH_2Cl_2$ followed by reverse phase preparative HPLC [23.96 min (retention time) (YMC S5 ODS 30×250 mm, 10-90% aqueous methanol over 30 minutes containing 0.1% TFA, 25 mL/min, monitoring at 220 nm)] gave 8.7 mg (0.015 mmol, 44%) of compound 207 (TFA salt) as a white solid. HPLC: 99% at 2.02 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 464.3 $[M+H]^+$.

EXAMPLE 208

(3aα,4β,7β,7aα)-2-(5-Fluoro-1-naphthalenyl)hexahydro-4,7-dimethyl-4,7-epoxy-1H-isoindole-1,3(2H)-dione (208C)

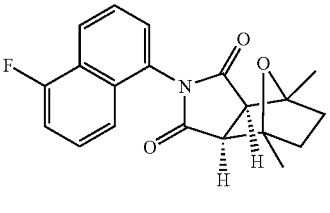

A. 1-Fluoro-5-nitronaphthalene (208A)

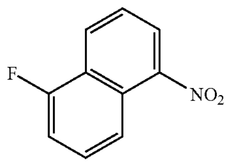

To a solution of 6 N HCl (12 mL) was added 1.47 g (7.83 mmol) of finely powdered 5-nitro-1-naphthylamine, as described in *J. Chem. Soc.* 1187 (1949). The mixture was cooled to 0° C. and a cold solution of $NaNO_2$ (547 mg, 7.93 mmol) in 2 mL $H_2O$ was added slowly so that the temperature was kept near 0° C. After the addition was complete, the reaction mixture was stirred for 30 min and filtered. The filtrate was cooled to 0° C. and treated with cold 4.5 M $NaBF_4$ solution (5 mL) to give complete precipitation of the diazonium borofluoride. The mixture was kept at 0° C. for 30 min before it was filtered and the precipitates were washed with cold 4.5 M $NaBF_4$ solution (5 mL), ice-cold ethanol (10 mL) and $Et_2O$ (20 mL). The obtained solids were air dried to yield 1.74 g (77%) of the corresponding diazonium salt.

To 1.70 g (5.92 mmol) of the above diazonium borofluoride was added 5 g of sand and the components were thoroughly mixed. The reaction mixture was heated cautiously under reduced pressure until decomposition set in. Toward the end of the reaction the flask was further heated for 30 min to 130° C. to assure complete conversion. After cooling the reaction mixture was dissolved in acetone and the contents were pre-absorbed on silica gel. Purification was achieved by flash chromatography on silica gel, eluting with 0 to 10% EtOAc in hexanes to give 449 mg (2.35 mmol, 40%) of compound 208A as a white solid.

B. 1-Amino-5-fluoronaphthalene (208B)

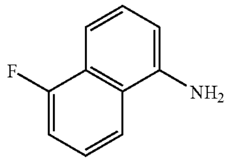

A solution of compound 208A (62 mg, 0.32 mmol) in 1 mL EtOH containing 0.1 mL 12 N HCl was heated to reflux. Iron powder (62 mg, 1.11 mmol) was added in small portions and heating was continued for 2 h. The mixture was cooled, neutralized with 1 N NaOH solution and the aqueous layer was extracted with $CH_2Cl_2$. The combined organic phases were dried over $MgSO_4$ and concentrated in vacuo to leave a residue which was purified by flash chromatography on silica gel eluting with 40 to 80% EtOAc in hexanes to give 42 mg (0.26 mmol, 80%) of compound 208B as a yellow solid.

C. (3aα,4β,7β,7aα)-2-(5-Fluoro-1-naphthalenyl) hexahydro-4,7-dimethyl-4,7-epoxy-1H-isoindole-1,3 (2H)-dione (208C)

Compound 208B (42 mg, 0.26 mmol), compound 20A (54 mg, 0.27 mmol), $MgSO_4$ (69 mg, 0.58 mmol) and triethylamine (191 μL, 1.37 mmol) were taken up in 2 mL of toluene and placed in a sealed tube. The sealed tube was heated at 135° C. for 14 h. The cooled reaction mixture was filtered through a short pad of Celite eluting with $CH_2Cl_2$ and the solvent was removed under reduced pressure. The residue was purified by reverse phase preparative HPLC (YMC S5 ODS 20×100 mm eluting with 30-100% aqueous methanol over 10 mincontaining 0.1% TFA, 20 mL/min) to give 15 mg (0.044 mmol, 17%) of compound 208C as a light yellow solid. HPLC: 16% at 2.96 min & 77% at 3.06 min (atropisomers, retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 340.2 $[M+H]^+$.

EXAMPLE 209

(3aα,4β,7β,7aα)-2-(5-Fluoro-4-nitro-1-naphthalenyl)hexahydro-4,7-dimethyl-4,7-epoxy-1H-isoindole-1,3(2H)-dione (209C)

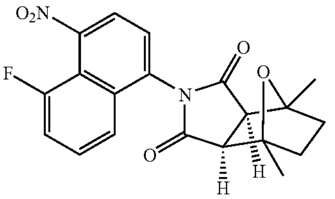

A. N-(5-Fluoro-1-naphthalenyl)acetamide (209A)

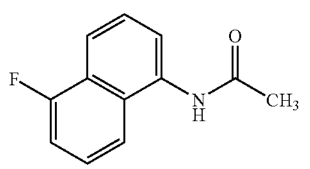

A solution of 141 mg (0.74 mmol) of compound 208A in 2 mL of AcOH was heated to reflux and treated with small portions of iron powder (118 mg, 2.11 mmol). The mixture was kept at reflux for 15 min before 73 μL (0.78 mmol) of $Ac_2O$ was added. After an additional 15 min at reflux, the mixture was cooled and filtered eluting with $CH_2Cl_2$. The filtrate was then concentrated under reduced pressure and the residue was purified by flash chromatography on silica gel eluting with 20 to 50% EtOAc in to give 145 mg (0.71 mmol, 97%) of compound 209A as a white solid.

B. 1-Amino-5-fluoro-4-nitronaphthalene (209B)

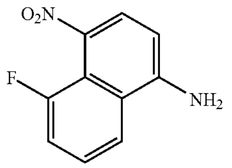

Compound 209A (133 mg, 0.645 mmol) was dissolved in 1 mL AcOH and the resulting solution was cooled to 10° C. At this temperature, 80.0 μL (2.00 mmol) of red fuming $HNO_3$ was added and stirring was continued for 15 min before the reaction was quenched by the addition of crushed ice. The aqueous layer was extracted with $CH_2Cl_2$ and the combined organic phases were dried over $MgSO_4$ and concentrated in vacuo. The resulting residue was dissolved in 3 mL EtOH, heated to reflux and treated with 0.5 mL of 40% aqueous NaOH solution. Stirring was continued for 15 min before the reaction was cooled and diluted with $H_2O$. The aqueous layer was extracted with $CH_2Cl_2$ and the combined organic phases were dried over $MgSO_4$ and concentrated in vacuo. The resulting residue was purified by flash chromatography on silica gel, eluting with 40 to 70% EtOAc in hexane to afford 36 mg (0.17 mmol, 27%) of compound 209B as a yellow solid.

C. 3aα,4β,7β,7aα)-2-(5-Fluoro-4-nitro-1-naphthalenyl)hexahydro-4,7-dimethyl-4,7-epoxy-1H-isoindole-1,3(2H)-dione (209C)

Compound 209B (36 mg, 0.18 mmol) was reacted in a sealed tube with compound 20A (38 mg, 0.19 mmol), $MgSO_4$ (46 mg, 0.39 mmol) and $Et_3N$ (128 μL, 0.920 mmol) in 250 μL toluene according to the above procedure described in example 208C to give, after purification by reverse phase preparative HPLC (YMC S5 ODS 20×100 mm eluting with 30-100% aqueous methanol over 10 mincontaining 0.1% TFA, 20 mL/min), 27 mg (0.070 mmol, 39%) of compound 209C as a yellow solid. HPLC: 8% at 2.88 min & 84% at 3.06 min (atropisomers, retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 402.0 $[M+H]^+$.

EXAMPLE 210

(3aα,4β,7β,7aα)-2-(1,1-Dioxidobenzo[b]thiophen-3-yl)hexahydro-4,7-dimethyl-4,7-epoxy-1H-isoindole-1,3(2H)-dione (210)

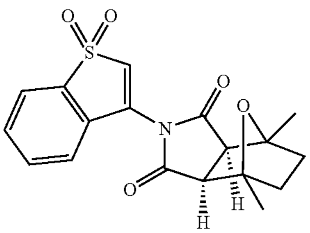

mCPBA (160 mg, 0.641 mmol, 70% pure) was added to a solution of compound 134 (70.0 mg, 0.214 mmol) in $CH_2CL_2$ (2 mL) at rt. After the starting material was consumed, the reaction was quenched with sat. $NaHCO_3$, and extracted with $CH_2Cl_2$. The organic layer was washed with 1 N NaOH, dried over $Na_2SO_4$ and concentrated under reduced pressure to give 63.9 mg (0.178 mmol, 83%) of compound 210 as a white solid. HPLC: 99% at 3.81 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 360.0 $[M+H]^+$.

EXAMPLE 211

4-(1,3,3a,4,7,7a-Hexahydro-4,6,7-trimethyl-1,3-dioxo-4,7-epoxy-2H-pyrrolo[3,4-c]pyridin-2-yl)-2-(trifluoromethyl)benzonitrile (211)

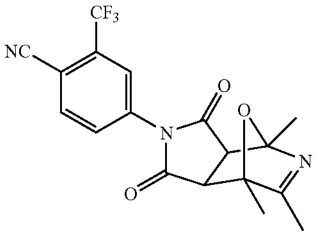

2,4,5-Trimethyl oxazole (0.48 mL, 4.14 mmol) was dissolved in toluene (2.0 mL) and 4-(2,5-dihydro-2,5-dioxo-1H-pyrrol-1-yl)-2-trifluoromethylbenzonitrile (1.00 g, 3.76 mmol) was added. The reaction mixture was stirred at 75° C. under nitrogen for 2.5 hrs. The solution was cooled to room temperature and the resulting precipitate was filtered and rinsed with toluene to give 0.51 g (35%) of compound 211 as a light grey solid. NMR analysis revelaed that compound 211 was one isomer (exo/endo) however the identity of the isomer could not be determined by NMR analysis. HPLC: 100% at 2.85 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 378.42 $[M+H]^+$.

EXAMPLE 212

(3aα,4β,7β,7aα)-Tetrahydro-4,7-dimethyl-2-[3-(trifluoromethyl)phenyl]-4,7-epoxy-1H-isoindole-1,3,5(2H,4H)-trione & (3aα,4α,7α,7aα)-Tetrahydro-4,7-dimethyl-2-[3-(trifluoromethyl)phenyl]-4,7-epoxy-1H-isoindole-1,3,5(2H,4H)-trione (212i & 212ii, respectively)

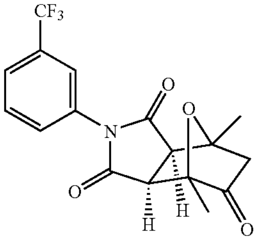

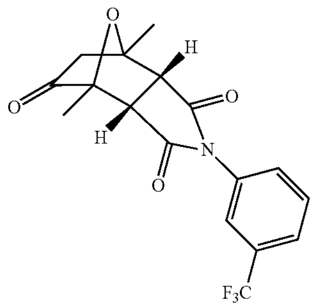

2,2-Dimethyl-3(H)-furanone (0.500 g, 4.46 mmol) and 1-[3-(trifluoromethyl)phenyl]-1H-pyrrole-2,5-dione (1.07 g, 4.46 mmol, prepared as described in Example 1B) were suspended in toluene (20 mL) in a sealed tube. The mixture was heated at 110° C. for 4 h and then cooled to 25° C. followed by concentration in vacuo. The resulting residue was purified by flash chromatography on $SiO_2$ eluting with methylene chloride to yield 0.411 g (26%) of compound 212i as a white solid and 0.193 g (12%) of compound 212ii as a white solid. The structural assignments were confirmed by 1-D NOE proton NMR experiments. Compound 212i: HPLC: 100% at 2.817 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 376.0 $[M+Na]^+$. Compound 212ii: HPLC: 100% at 3.013 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 354.02 $[M+H]^+$.

EXAMPLE 213

(3aα,4β,7β,7aα)-2-(5-Chloro-1-naphthalenyl)hexahydro-4,7-dimethyl-4,7-epoxy-1H-isoindole-1,3(2H)-dione (213B)

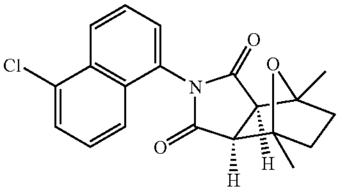

A. 1-Amino-5-chloronaphthalene (213A)

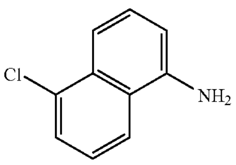

To a solution of 1.74 g (6.06 mmol) of the diazonium borofluoride (described in Example 208A) in acetone (7 mL) was added 693 mg (7.00 mmol) of CuCl in small portions. After the evolution of nitrogen had ceased the acetone was removed under reduced pressure and the residue was taken up in $CH_2Cl_2$ (30 mL). The organic phase was washed with $H_2O$ (30 mL), dried over $MgSO_4$, concentrated in vacuo and finally purified by flash chromatography (silica gel, EtOAc in hexane 0 to 15%) to give 754 mg (70%) of 1-chloro-5-nitronaphthalene.

The above synthesized 1-chloro-5-nitronaphthalene (540 mg, 2.6 mmol) was dissolved in 10 mL AcOH, followed by treatment with 415 mg (7.43 mmol) iron powder and subsequently acylated with $Ac_2O$ (0.26 mL, 2.73 mmol) according to the procedure described in Example 209A to give 543 mg (95%) of 1-acetamino-5-chloronaphthalene.

A solution of the above synthesized 1-acetamino-5-chloronaphthalene (52 mg, 0.24 mmol) in 3 mL EtOH was heated to reflux and treated with 0.5 mL 40% aqueous NaOH solution. The mixture was refluxed until no more starting material could be detected, cooled and concentrated under reduced pressure. The residue was taken up in $CH_2Cl_2$ (50 mL) and was washed with $H_2O$ (25 mL). The organic layer was dried over $MgSO_4$ and concentrated in vacuo to leave 41 mg (98%) of compound 213A as a white solid.

B. (3aα,4β,7β,7aα)-2-(5-Chloro-1-naphthalenyl)hexahydro-4,7-dimethyl-4,7-epoxy-1H-isoindole-1,3(2H)-dione (213B)

Compound 213A (24 mg, 0.14 mmol) was reacted in a sealed tube with compound 20A (29 mg, 0.15 mmol), $MgSO_4$ (36 mg, 0.30 mmol) and $Et_3N$ (100 μL, 0.710 mmol) in 250 μL toluene according to the procedure described in Example 208C to give, after purification by reverse phase preparative HPLC (YMC S5 ODS 20×100 mm eluting with 30-100% aqueous methanol over 10 mincontaining 0.1% TFA, 20 mL/min), 27 mg (40%) of compound 213B as a white solid. HPLC: 98% at 1.82 min (retention time) (YMC S5 TurboPack Pro column 4.6×33 mm eluting with 10-90% aqueous methanol over 2 minutes containing 0.2% phosphoric acid, 4 mL/min, monitoring at 220 nm). MS (ES): m/z 356.4 $[M+H]^+$.

EXAMPLE 214

(3aα,4β,7β,7aα)-2-(5-Chloro-4-nitro-1-naphthalenyl)hexahydro-4,7-dimethyl-4,7-epoxy-1H-isoindole-1,3(2H)-dione (214B)

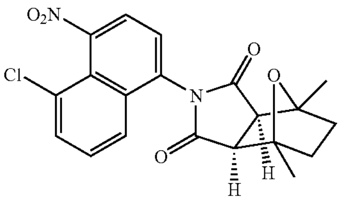

A. 1-Amino-5-chloro-4-nitronaphthalene (214A)

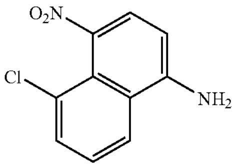

1-Acetamino-5-chloronaphthalene (150 mg, 0.68 mmol, prepared as described in Example 213A) was dissolved in 1 mL AcOH and treated with 82 μL of red fuming $HNO_3$ and subsequently deacylated with 1 mL 40% aqueous NaOH solution in 3 mL EtOH according to the procedure described in Example 209A to yield 49 mg (32%) of compound 214A as a yellow solid.

B. (3aα,4β,7β,7aα)-2-(5-Chloro-4-nitro-1-naphthalenyl)hexahydro-4,7-dimethyl-4,7-epoxy-1H-isoindole-1,3(2H)-dione (214B)

Compound 214A (27 mg, 0.12 mmol) was reacted in a sealed tube with compound 20A (26 mg, 0.13 mmol), $MgSO_4$ (32 mg, 0.27 mmol) and $Et_3N$ (88 μL, 0.63 mmol) in 250 μL toluene according to the procedure described in Example 208C to give, after purification by reverse phase preparative HPLC (YMC S5 ODS 20×100 mm eluting with 30-100% aqueous methanol over 10 mincontaining 0.1% TFA, 20 mL/min) 22 mg (45%) of compound 214B as a yellow solid. HPLC: 24% at 3.06 min & 76% at 3.25 min (atropisomers, retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 418.0 $[M+NH_4]^+$.

EXAMPLE 215

(3aα,4β,7β,7aα)-4-Ethylhexahydro-7-methyl-2-(4-nitro-1-naphthalenyl)-4,7-epoxy-1H-isoindole-1,3 (2H)-dione (215B)

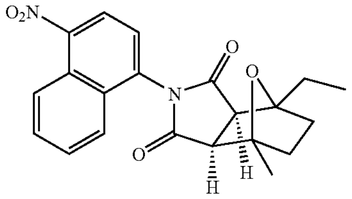

A. (3aα,4β,7β,7aα)-4-Ethylhexahydro-7-methyl-4,7-epoxyisobenzofuran-1,3-dione (215A)

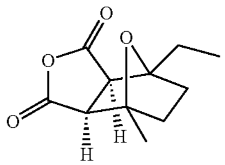

2-Ethyl-5-methylfuran (1.89 mL, 15.3 mmol) was dissolved in methylene chloride (10 mL) and maleic anhydride (1.00 g, 10.2 mmol) was added. The reaction was stirred at 25° C. for 18 h and then concentrated in vacuo. The resulting crude bicycle was dissolved in EtOAc (50 mL) and 10% Pd/C (0.40 g) was added. Hydrogen was then introduced via a balloon. After 4 h, the reaction was filtered through Celite, rinsing with EtOAc. Concentration in vacuo gave the crude compound 215A (1.93 g) as a white solid. This material was taken on directly to the next reaction without purification.

B. (3aα,4β,7β,7aα)-4-Ethylhexahydro-7-methyl-2-(4-nitro-1-naphthalenyl)-4,7-epoxy-1H-isoindole-1,3 (2H)-dione (215B)

Compound 215A (0.168 g, 0.798 mmol) and 1-amino-4-nitronaphthalene (0.10 g, 0.53 mmol) were suspended in toluene (0.8 mL) and TEA (0.2 mL) and magnesium sulfate (0.1 g) were added. The mixture was heated at 135° C. in a sealed tube for 18 h. The reaction was then cooled to rt and filtered, rinsing with chloroform. Concentration gave the crude product which was purified by preparative TLC on $SiO_2$ eluting with methylene chloride. This gave 0.077 g (0.20 mmol, 38%) of compound 215B as a yellow solid. HPLC: 100% at 3.260 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 381.05 $[M+H]^+$.

EXAMPLE 216

(3aα,4β,7β,7aα)-2-(4-Cyano-1-naphthalenyl)-N-(4-fluorophenyl)octahydro-7-methyl-1,3-dioxo-4,7-epoxy-4H-isoindole-4-acetamide (216B)

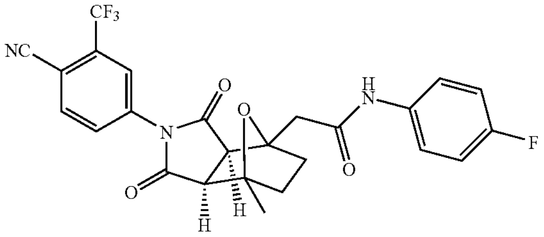

A. N-(4-Fluorophenyl)-5-methyl-2-furanacetamide (216A)

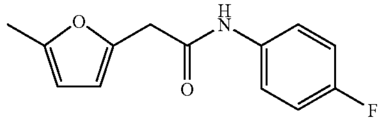

5-Methyl-2-furanacetic acid (1.00 g, 7.14 mmol, synthesized as described WO 9507893, Example 19) was dissolved in $CH_3CN$/DMF (4:1, 25 mL), 1-[3-(dimethylamino)propyl]-3-ethylcarbodiimide (1.37 g, 7.14 mmol) and 1-hydroxy-7-azabenzotriazole (0.972 g, 7.14 mmol) were then added followed by 4-fluoroaniline (0.676 mL, 7.14 mmol). After 3 h, the reaction was diluted with EtOAc (150 mL) and washed with 1 N HCl (1×30 mL), sat. aq. $NaHCO_3$ (1×30 mL), brine (1×40 mL) and dried over sodium sulfate. Compound 216A (1.58 g, 95%)) was isolated as a yellow foam after concentration in vacuo. No further purification was necessary. HPLC: 78% at 2.647 min (retention time) (YMC S5 ODS column 4.6×50 mm eluting with 10-90% aqueous methanol over 4 minutes containing 0.2% phosphoric acid, 4 mL/min, monitoring at 220 nm).

B. 3aα,4β,7β,7aα)-2-(4-Cyano-1-naphthalenyl)-N-(4-fluorophenyl)octahydro-7-methyl-1,3-dioxo-4,7-epoxy-4H-isoindole-4-acetamide (216B)

Compound 216A (0.200 g, 0.858 mmol) and 4-(2,5-dihydro-2,5-dioxo-1H-pyrrol-1-yl)-2-trifluoromethylbenzonitrile (0.164 g, 0.616 mmol) were dissolved in benzene and heated at 60° C. for 14 h. The reaction was then cooled and concentrated in vacuo. The resulting orange oil was dissolved in EtOAc (15 mL) and 10% Pd/C (0.050 g) was added. Hydrogen was then introduced via a balloon. After 3 h, the reaction was filtered through Celite rinsing with EtOAc and concentrated in vacuo. The resulting crude material was purified by preparative TLC on silica eluting with 5% acetone in methylene chloride to give 0.166 g (54%) of compound 216B as a white solid. NMR spectroscopy showed only a single isomer which was determined to be exo by NOE experiments. HPLC:

95% at 3.200 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 484.0 $[M+H]^+$.

EXAMPLE 217

(3aα,4β,7β,7aα)-Hexahydro-4-methyl-2-(2-naphthalenyl)-4,7-epoxy-1H-isoindole-1,3(2H)-dione, faster eluting enantiomer & (3aα,4β,7β,7aα)-Hexahydro-4-methyl-2-(2-naphthalenyl)-4,7-epoxy-1H-isoindole-1,3(2H)-dione, slower eluting enantiomer (217i & 217ii, respectively)

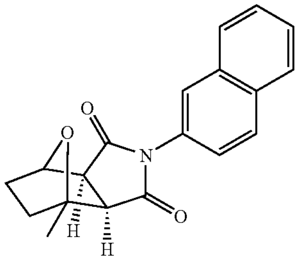

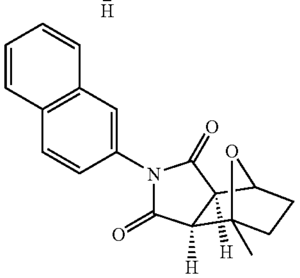

Racemic compound 137 was separated into the individual antipodes by chiral reverse phase liquid chromatography. A Chiralpak AD-R column (4.6×250 mm) was used eluting with 70% acetonitrile/30% water at 1 mL/min. UV detection at 220 nm was used. The faster eluting isomer, compound 217i (retention time=15.66 min), was found to be 99.9% ee and the slower eluting isomer, compound 217ii (retention time=15.66 min) was 99.6% ee by analytical chiral reverse phase chromatography.

EXAMPLE 218

(3aα,4β,7β,7aα)-4-[4-[2-[[(4-Fluorophenyl)methyl]methylamino]ethyl]octahydro-7-methyl-1,3-dioxo-4,7-epoxy-2H-isoindol-2-yl]-2-(trifluoromethyl)benzonitrile (218B)

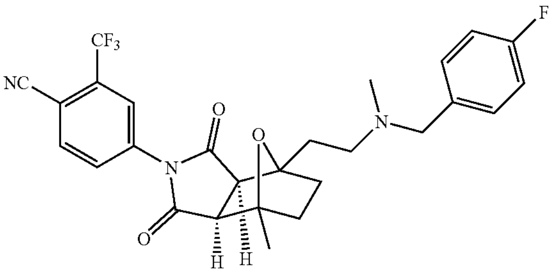

A. (4-Fluorobenzyl)methylamine & Bis(4-fluorobenzyl)methylamine (218A & 218A')

218A

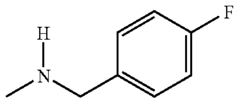

218A'

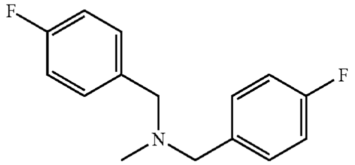

Compounds 218A & 218A' were made in accordance with the procedure described by Singer et al. *J. Med. Chem.* 29, 40-44 (1986). 4-Fluorobenzyl bromide (189 mg, 1.00 mmol) was refluxed in a solution of ethanol (1.5 mL) and methylamine (5 mL, 2 M solution in MeOH) for 3 h. An additional portion of methylamine (2 mL) was added and the mixture was refluxed for an additional hour. The solution was cooled and concentrated in vacuo, and the residue was dissolved in a mixture of 2 N HCl (3 mL) and ether (1.5 mL). The layers were separated and the aqueous layer was extracted with an additional portion of ether. The aqueous solution was chilled to 0° C., titrated to pH 11 with NaOH and extracted with $CH_2Cl_2$. The extracts were dried over $MgSO_4$ and concentrated in vacuo to give 120 mg of a 2.5:1 mixture of compounds 218A and compound 218A' respectively. The crude mixture was taken on without further purification.

B. (3aα,4β,7β,7aα)-4-[4-[2-[[(4-Fluorophenyl)methyl]-methylamino]ethyl]octahydro-7-methyl-1,3-dioxo-4,7-epoxy-2H-isoindol-2-yl]-2-(trifluoromethyl)benzonitrile (218B)

A solution of compound 36 (34.3 mg, 0.075 mmol) and compounds 218A & 218A' (21 mg, ~0.088 mmol (of 218A)) in toluene (0.4 mL) was heated at 100° C. overnight. The reaction mixture was cooled to room temperature and then concentrated under reduced pressure. Purification by flash chromatography on silica gel eluting with 25% acetone/75% $CH_2Cl_2$ gave 30 mg (0.058 mmol, 78%) of 218B as a yellow solid. HPLC: 99% at 2.46 min (retention time) (YMC S5 ODS 4.6×50 mm, 10-90% aqueous methanol over 4 minutes containing 0.2% phosphoric acid, monitoring at 220 nm). MS (ES): m/z 516.26 $[M+H]^+$.

EXAMPLE 219

(3aα,4β,5β,6β,7β,7aα)-4-(Octahydro-4,5,6,7-tetramethyl-1,3-dioxo-4,7-epoxy-2H-isoindol-2-yl)-2-(trifluoromethyl)benzonitrile (219D)

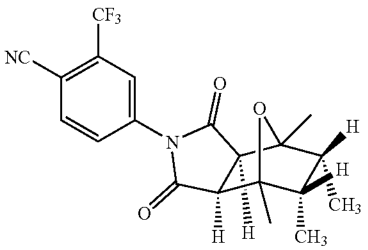

A. 2,3,4,5-Tetramethylfuran (219A)

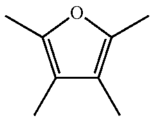

Compound 219A was made in accordance with the procedures described in Hancock et al. *J. Org. Chem.* 42, 1850-1856 (1977) & Amarnath et al. *J. Org. Chem.*, 60, 301-307 (1995). 2-Propanone (100 mL, 1.1 mol) was refluxed over $PbO_2$ (26.7 g, 0.112 mol) for 28 h. After cooling to rt, the reaction mixture was filtered and the residue was washed with acetone. The filtrate was concentrated under reduced pressure to remove the acetone and then distilled at 20 Torr. The fraction that came over between 100-120° C. was collected to give 6.75 g (42.5%) of 3,4-dimethylhexane-2,5-dione as a light yellow oil.

A solution of 3,4-dimethylhexane-2,5-dione (3.00 g, 21.1 mmol) and p-toluenesulfonic acid (401 mg, 2.11 mmol) in benzene (30,mL) was heated to reflux in a Dean-Stark trap overnight. The reaction mixture was distilled at atmospheric pressure to remove the excess benzene. The remaining mixture was transferred to a smaller flask and distilled at atmospheric pressure. The fraction that came over between 80-100° C. was collected to give 509 mg (19%) of compound 219A as a light yellow oil.

B. (3aα,4β,7β,7aα)-4-Ethyl-3a,4,7,7a-tetrahydro-4,5,6,7-tetramethyl-4,7-epoxyisobenzofuran-1,3-dione (219B)

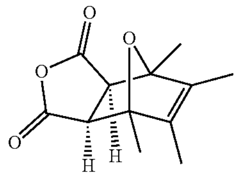

A solution of compound 219A (400 mg, 3.22 mmol) and maleic anhydride (442 mg, 4.51 mmol) in $Et_2O$ (1.5 mL) was stirred at rt overnight. The reaction mixture was then placed in freezer for 5 days, after which time the resulting crystals were collected and dried to give 0.26 g (37%) of compound 219B as tan crystals. The crude compound 219B was taken on to the next step without further purification.

C. (3aα,4β,5α,6α,7β,7aα)-4-Ethylhexahydro-4,5,6,7-tetramethyl-4,7-epoxyisobenzofuran-1,3-dione (219C)

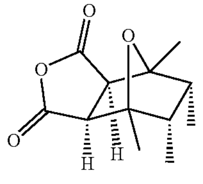

A solution of compound 219B (120 mg, 0.545 mmol) and 10% Pd/C (24 mg, cat.) in EtOAc (2 mL) was stirred under a balloon of hydrogen at room temperature overnight. The reaction mixture was filtered through Celite and concentrated under reduced pressure to give 100 mg (0.446 mmol, 82%) of compound 219C as a white solid, which was carried on with no further purification.

D. (3aα,4β,5β,6β,7β,7aα)-4-(Octahydro-4,5,6,7-tetramethyl-1,3-dioxo-4,7-epoxy-2H-isoindol-2-yl)-2-(trifluoromethyl)benzonitrile (219D)

A solution of compound 219C (44.4 mg, 0.2 mmol), 5-amino-2-cyanobenzotrifluoride (45 mg, 0.24 mmol), TEA (0.04 mL) and $MgSO_4$ (20 mg) in toluene (0.2 mL) was heated at 135° C. overnight. The reaction mixture was cooled to room temperature, filtered and then concentrated under reduced pressure. Purification by flash chromatography on silica gel eluting with 40% EtOAc/hexanes followed by washing the resulting solid with MeOH gave 17 mg (0.043 mmol, 22%) of compound 219D as a white solid. HPLC: 90% at 3.11 min (retention time) (YMC S5 ODS 4.6×50 mm, 10-90% aqueous methanol over 4 minutes containing 0.2% phosphoric acid, monitoring at 220 nm). MS (ES): m/z 391.2 $[M-H]^-$.

EXAMPLE 220

(3aα,4β,7β,7aα)-4-[Octahydro-4-methyl-1,3-dioxo-7-[2-[4-(trifluoromethyl)phenoxy]ethyl]-4,7-epoxy-2H-isoindol-2-yl]-2-(trifluoromethyl)benzonitrile, faster eluting antipode & (3aα,4β,7β,7aα)-4-[Octahydro-4-methyl-1,3-dioxo-7-[2-[4-(trifluoromethyl)phenoxy]ethyl]-4,7-epoxy-2H-isoindol-2-yl]-2-(trifluoromethyl)benzonitrile, slower eluting enantiomer (220i & 220ii, respectively)

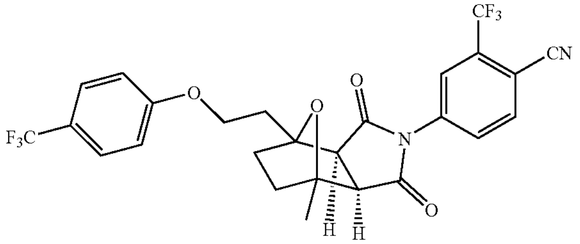

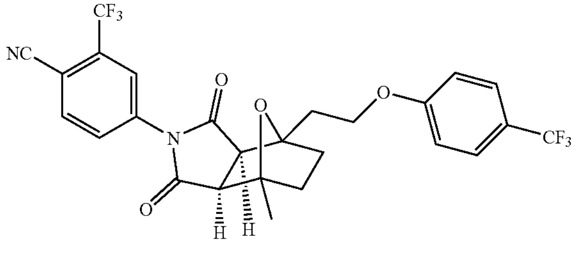

Racemic compound 35 was separated into the individual antipodes by chiral normal phase liquid chromatography. A Chiralpak AD column (50×500 mm) was used eluting with 85% hexanes/7.5% methanol/7.5% ethanol, at 50 mL/min. UV detection at 220 nm was used. The faster eluting isomer compound 220i (retention time=55.86 min) was found to have 95.8% ee ($[\alpha]_D^{25}$=−53.02°, C=3.134 mg/cc in $CH_2Cl_2$) and the slower eluting isomer compound 220ii (retention time=62.86 min) was 86% ee ([α]D$^{25}$=+48.740, C=2.242 mg/cc in $CH_2Cl_2$) by analytical chiral normal phase chromatography.

EXAMPLE 221

(3aα,4β,5β,7β,7aα)-4-(Octahydro-5-hydroxy-4,7-dimethyl-1,3-dioxo=4,7-epoxy-2H-isoindol-2-yl)-2-(trifluoromethyl)benzonitrile (221B)

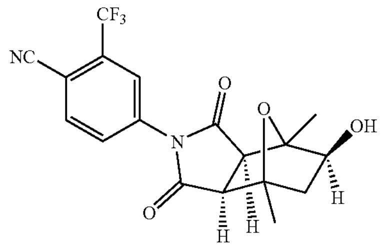

A. (3aα,4β,7β,7aα)-4-(hexahydro-4,7-dimethyl-1,3-dioxo-4,7-epoxy-2H-isoindol-2-yl)-2-(trifluoromethyl)benzonitrile (221Ai) & (3aα,4α,7α,7aα)-4-(hexahydro-4,7-dimethyl-1,3-dioxo-4,7-epoxy-2H-isoindol-2-yl)-2-(trifluoromethyl)benzonitrile (221Aii)

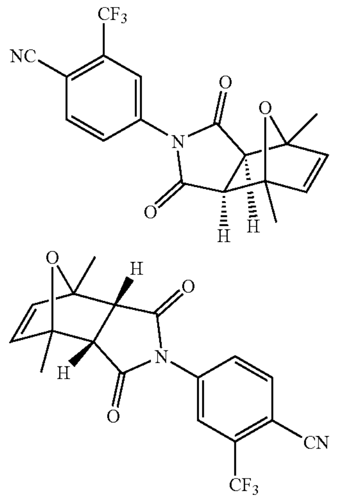

A solution of 2,5-dimethylfuran (0.800 mL, 7.51 mmol) and 4-(2,5-dihydro-2,5-dioxo-1H-pyrrol-1-yl)-2-trifluoromethylbenzonitrile (synthesized as described in Example 1B, using 4-cyano-3-trifluoromethylaniline in place of 4-bromo-3-methylaniline) (1.00 g, 3.75 mmol) in benzene (4 mL) was heated at 60° C. overnight. The reaction mixture was concentrated under reduced pressure and placed on a high vacuum pump until the oil solidified to give a 3:1 mixture (determined by LC and NMR) of compounds 221Ai & 221Aii, respectively, as a brown solid, which was used directly in the next step without further purification.

B. (3aα,4β,5β,7β,7aα)-4-(Octahydro-5-hydroxy-4,7-dimethyl-1,3-dioxo-4,7-epoxy-2H-isoindol-2-yl)-2-(trifluoromethyl)benzonitrile (221B)

$BH_3$.THF (3.75 mL, 3.75 mmol, 1M in THF) was added to a solution of crude compounds 221Ai & 221Aii (3.75 mmol) in THF (12.5 mL) at 0° C. After the starting material was consumed the reaction mixture was concentrated under reduced pressure. The resulting residue was then dissolved in toluene (12.5 mL), $Me_3NO$ (845 mg, 11.2 mmol) was added and the mixture was heated to reflux overnight. The reaction mixture was then cooled to rt, added to $H_2O$ and extracted with EtOAc (3×). The combined organic layers were dried over $MgSO_4$ and concentrated under reduced pressure. Purification by flash chromatography on $SiO_2$ eluting with 75% EtOAc/hexanes gave 0.354 g (25%) of compound 221B as a tan powder. HPLC: 90% at 2.45 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 381.11 $[M+H]^+$.

EXAMPLE 222

(3aα,4β,5α,7β,7aα)-4-(Octahydro-5-hydroxy-4,7-dimethyl-1,3-dioxo-4,7-epoxy-2H-isoindol-2-yl)-2-(trifluoromethyl)benzonitrile (222D)

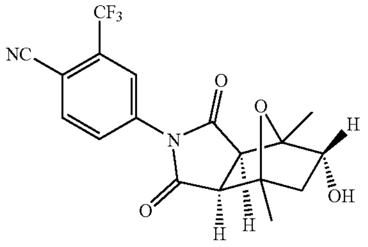

A. 3-[[(1,1-Dimethylethyl)dimethylsilyl]oxy]-2,5-dimethylfuran (222A)

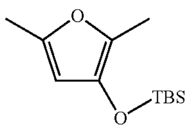

2,5-Dimethyl-3(3H)-furanone (2.00 g, 17.8 mmol) was dissolved in methylene chloride (180 mL). TEA (7.43 mL, 53.5 mmol) was added followed by TBSOTf (4.92 mL, 21.4 mmol) at 25° C. After 1 h, the reaction was concentrated in vacuo and the resulting slurry was run through a silica gel column conditioned with 3% TEA in hexanes. The product was eluted with 3% TEA/hexanes to give 3.6 g (89%) of compound 222A as an orange oil which was used directly in subsequent reactions.

B. (3aα,4β,7β,7aα)-4-[5-[[(1,1-Dimethylethyl)dimethylsilyl]oxy]-1,3,3a,4,7,7a-hexahydro-4,7-dimethyl-1,3-dioxo-4,7-epoxy-2H-isoindol-2-yl]-2-(trifluoromethyl)benzonitrile (222B)

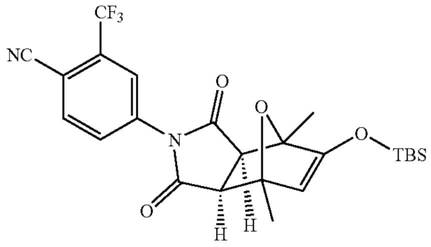

4-(2,5-Dihydro-2,5-dioxo-1H-pyrrol-1-yl)-2-trifluoromethylbenzonitrile (1.00 g, 3.85 mmol) was dissolved in benzene (5.0 mL) and the compound 222A (1.30 g, 5.77 mmol) was added. The reaction mixture was warmed to 60° C. for 2 h and then cooled to 25° C. The solution was then concentrated in vacuo to give compound 222B as a yellow oil which was carried on to the next reaction without purification. HPLC: 60% at 4.013 min (retention time) (YMC S5 ODS column 4.6×50 mm eluting with 10-90% aqueous methanol over 4 minutes containing 0.2% phosphoric acid, 4 mL/min, monitoring at 220 nm).

C. (3aα,4β,5α,7β,7aα)-4-[5-[[(1,1-Dimethylethyl)dimethylsilyl]oxy]octahydro-4,7-dimethyl-1,3-dioxo-4,7-epoxy-2H-isoindol-2-yl]-2-(trifluoromethyl)benzonitrile (222C)

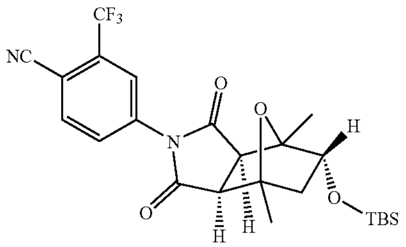

Crude compound 222B (3.85 mmol) was dissolved in ethyl acetate (75 mL) and 10% Pd/C (1.20 g) was added. Hydrogen was then introduced via a balloon. After 24 h, the reaction was filtered through Celite rinsing with ethyl acetate and concentrated in vacuo to give a yellow oil. The crude product was purified by flash chromatography on silica gel eluting with methylene chloride/acetone (0%-1%-2% acetone) to give 0.710 g (35%) compound 222C as a yellow solid. HPLC: 100% at 4.160 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 517.6 $[M+Na]^+$.

D. (3aα,4β,5α,7β,7aα)-4-(Octahydro-5-hydroxy-4,7-dimethyl-1,3-dioxo-4,7-epoxy-2H-isoindol-2-yl)-2-(trifluoromethyl)benzonitrile (222D)

Compound 222C (0.040 g, 0.081 mmol) was dissolved in THF (1.0 mL) and HFoPyridine (0.5 mL) was added. After 2 h, the reaction was carefully poured into cold saturated aq. $NaHCO_3$. The mixture was then extracted with methylene chloride (3×10 mL). The combined organics were washed with 1 N HCl (1×10 mL) and dried over anhydrous sodium sulfate. Concentration in vacuo gave 0.031 g (10%) compound 222D as a yellow solid. NOE experiments confirmed the assigned isomer. HPLC: 98% at 2.777 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 403.06 $[M+Na]^+$.

EXAMPLE 223

(αR)-α-Methoxybenzeneacetic acid, 2-[(3aα,4β,7β,7aα)-2-(4-cyano-1-naphthalenyl)octahydro-7-methyl-1,3-dioxo-4,7-epoxy-4H-isoindol-4-y]ethyl ester (223C)

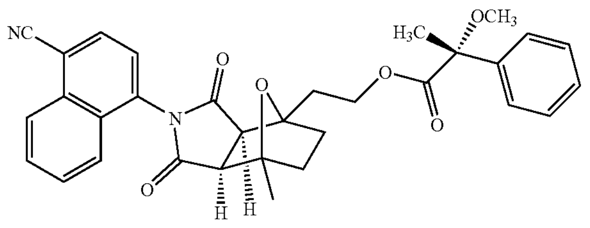

A. (3aα,4β,7β,7aα)-4-[4-[2-[[(1,1-Dimethylethyl)dimethylsilyl]oxy]ethyl]octahydro-7-methyl-1,3-dioxo-4,7-epoxy-2H-isoindol-2-yl]-1-naphthalenecarbonitrile (223A)

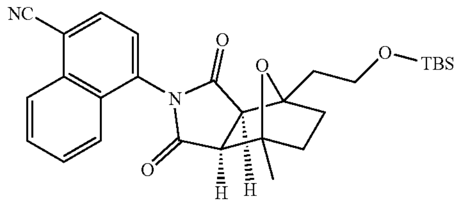

A solution of 4-amino-1-naphthalenecarbonitrile (19.2 g, 114 mmol) and maleic anhydride (14.0 g, 113 mmol) in AcOH (230 mL) was heated at 115° C. for 12 h. After cooling to rt, the reaction mixture was concentrated under reduced pressure then diluted with $CH_2Cl_2$ (2.5 L). The organic layer was washed 3× with $H_2O$ (3 L), 1× with sat. aq. $Na_2CO_3$ (1 L) and 1× with brine (1 L), dried over $MgSO_4$ and concentrated to ~200 mL under reduced pressure. Purification by flash chromatography on cation exchange resin (60 g, CUBX13M6 from United Chemical Technologies) eluting with $CH_2Cl_2$ gave 25.0 g (88%) of 4-(2,5-dihydro-2,5-dioxo-1H-1-yl)-1-naphthalenecarbonitrile as a yellow solid. HPLC: 96% at 2.48 min (retention time) (Phenomenex-prime S5-C18 column 4.6×50 mm, 10-90% aqueous methanol over 4 minutes containing 0.2% phosphoric acid, 4 mL/min, monitoring at 220 nm). MS (ES): m/z 249.25 $[M+H]^+$.

4-(2,5-Dihydro-2,5-dioxo-1H-1-yl)-1-naphthalenecarbonitrile (1.00 g, 4.03 mmol) was suspended in benzene (6.0 mL) in a sealed tube and compound 204A (1.11 g, 5.24 mmol) was added. The reaction was heated at 60° C. for 16 h and then cooled to 25° C. The benzene was removed in vacuo to give a yellow solid. The solid was dissolved in ethyl acetate (40 mL) and Pd/C (10% Pd, 0.300 g) was added. Hydrogen was then introduced via a balloon. After 4 h, the reaction was filtered through Celite rinsing with ethyl acetate. Concentration in vacuo gave a pale yellow solid which was purified by flash chromatography on silica gel eluting with acetone/chloroform (0%-1.5%-3% acetone) to give 1.53 g (77%) compound 223A as a yellow foam. HPLC: 86% at 4.173 min (retention time) (YMC S5 ODS column 4.6×50 mm eluting with 10-90% aqueous methanol over 4 minutes containing 0.2% phosphoric acid, 4 mL/min, monitoring at 220 nm).

B. (3aα,4β,7β,7aα)-4-[Octahydro-4-(2-hydroxy-ethyl)-7-methyl-1,3-dioxo-4,7-epoxy-2H-isoindol-2-yl]-1-naphthalenecarbonitrile (223B)

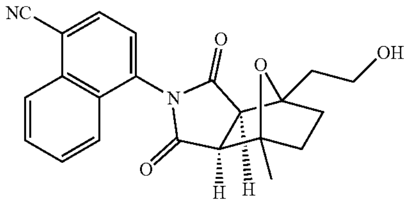

Compound 223A (1.37 g, 2.97 mmol) was dissolved in THF (8.0 mL) and transferred to a polypropylene bottle and cooled to 0° C. HFoPyridine (2.0 mL) was then added. After 20 min, the reaction was carefully poured into cold sat. aq. sodium bicarbonate and extracted with methylene chloride (3×30 mL). The organics were then washed with 1 N HCl and dried over anhydrous sodium sulfate. Concentration in vacuo gave 0.99 g (89%) the compound 223B as a yellow foam which was not purified further. HPLC: 96% at 2.443 and 2.597 min (atropisomers, retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 399.02 $[M+Na]^+$.

C. (αR)-α-Methoxybenzeneacetic acid, 2-[(3aα,4β,7β,7aα)-2-(4-cyano-1-naphthalenyl)octahydro-7-methyl-1,3-dioxo-4,7-epoxy-4H-isoindol-4-y]ethyl ester (223C)

Compound 223B (0.200 g, 0.575 mmol) was added to a solution of WSDCC (0.138 g, 0.719 mmol) and (R)-mandelic acid (0.096 g, 0.57 mmol) in dichloromethane (6.0 mL). 4-DMAP (0.005 g) was then added and the reaction was stirred at 25° C. for 4 h. The mixture was then diluted with dichloromethane, washed with 1 N HCl (2×10 mL) followed by sodium bicarbonate (1×10 mL) and dried over anhydrous sodium sulfate. Concentration in vacuo gave 0.220 g (71%) compound 223C as a yellow solid which was not purified further. HPLC: 100% at 3.283 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 547.26 $[M+Na]^+$.

EXAMPLE 224

(3aα,4β,7β,7aα)-2-(Methylthio)-4-(octahydro-4,7-dimethyl-1,3-dioxo-4,7-epoxy-2H-isoindol-2-yl) benzonitrile (224)

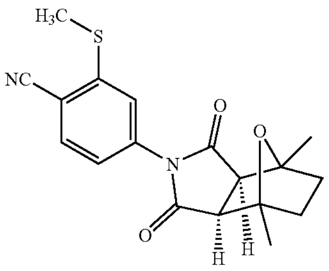

4-Amino-2-(methylthio)benzonitrile (100 mg, 0.609 mmol, synthesized as described in EP 40931 A1) was reacted in a sealed tube with compound 20A (131 mg, 0.668 mmol), $MgSO_4$ (161 mg, 1.34 mmol) and $Et_3N$ (0.440 mL, 3.17 mmol) in 0.50 mL toluene according to the procedure described in Example 208C to give, after purification by reverse phase preparative HPLC (YMC S5 ODS 20×100 mm eluting with 30-100% aqueous methanol over 10 mincontaining 0.1% TFA, 20 mL/min), 137 mg (0.400 mmol, 66%) of compound 224 as a white solid. HPLC: 100% at 2.73 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 401.0 $[M-H+OAc]^-$.

EXAMPLE 225

(3aα,4β,7β,7aα)-2-(Methylsulfinyl)-4-(octahydro-4,7-dimethyl-1,3-dioxo-4,7-epoxy-2H-isoindol-2-yl) benzonitrile (225)

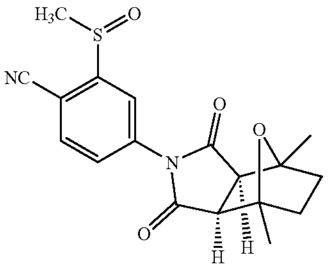

To an ice-cold suspension of compound 224 (30 mg, 0.088 mmol) in 2 mL of $H_2O$/MeOH (1:1) was added oxone (80 mg, 0.26 mmol) in one solid portion. The resulting mixture was stirred for 4 h at 0° C. before it was diluted with $H_2O$ (10 mL) and extracted with $CH_2Cl_2$ (2×20 mL). The combined organic layers were dried and concentrated in vacuo to leave a residue which was purified by filtering the material through a short pad of silica gel eluting with $CH_2Cl_2$ to yield 32 mg (0.088 mmol, 100%) of compound 225 as a colorless oil. HPLC: 99% at 2.01 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 376.0 $[M+NH_4]^+$.

EXAMPLE 226

(3aα,4β,7β,7aα)-2-(Methylsulfonyl)-4-(octahydro-4,7-dimethyl-1,3-dioxo-4,7-epoxy-2H-isoindol-2-yl) benzonitrile (226)

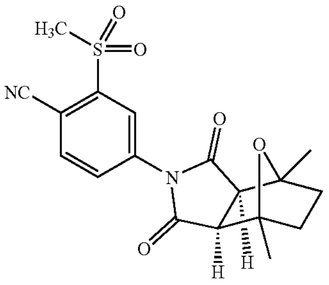

To a solution of compound 225 (48 mg, 0.14 mmol) in $CH_2Cl_2$ (2 mL) was added mCPBA (145 mg, 50% mixture, 0.420 mmol) in one solid portion. The resulting mixture was allowed to warm to room temperature and was stirred for 60 h at which time no more starting material could be detected by HPLC. The reaction was quenched by the addition of sat. $NaHCO_3$ solution (5 mL), the layers were separated and the aqueous layer was extracted with $CH_2Cl_2$ (20 mL). The combined organic phases were dried over $MgSO_4$ and concentrated in vacuo. The remaining residue was purified by reverse phase preparative HPLC (YMC S5 ODS 20×100 mm eluting with 30-100% aqueous methanol over 10 mincontaining 0.1% TFA, 20 mL/min) to afford 48 mg (0.13 mmol, 92%) of compound 226 as a white solid. HPLC: 100% at 2.07 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 392.0 $[M+NH_4]^+$.

EXAMPLE 227

(3aα,4β,5β,7β,7aα)-7-[2-[[(1,1-Dimethylethyl)dimethylsilyl]oxy]ethyl]hexahydro-5-hydroxy-4-methyl-2-(4-nitro-1-naphthalenyl)-4,7-epoxy-1H-isoindole-1,3(2H)-dione (227B)

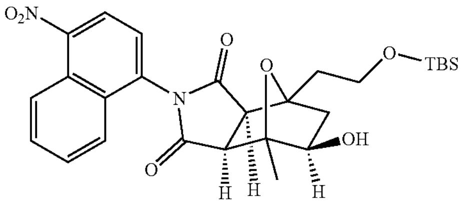

A. (3aα,4β,7β,7aα)-4-[2-[[(1,1-Dimethylethyl)dimethylsilyl]oxy]ethyl]-3a,4,7,7a-tetrahydro-7-methyl-2-(4-nitro-1-naphthalenyl)-4,7-epoxy-1H-isoindole-1,3(2H)-dione (227A)

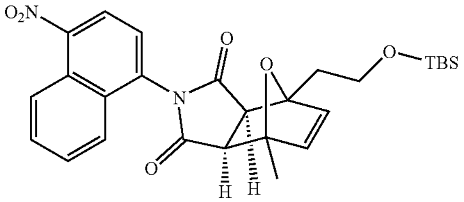

A solution of compound 204A (455 mg, 1.89 mmol) and 1-[4-nitronaphthalene]-1H-pyrrole-2,5-dione (254 mg, 0.947 mmol, prepared as described for 4-(2,5-dihydro-2,5-dioxo-1H-1-yl)-1'-naphthalenecarbonitrile, Example 223A) in benzene (2 mL) was heated at 60° C. overnight. The reaction mixture was concentrated under reduced pressure to give crude compound 227A as a brown solid, which was used directly in the next step without further purification.

B. (3aα,4β,5β,7β,7aα)-7-[2-[[(1,1-Dimethylethyl)dimethylsilyl]oxy]ethyl]hexahydro-5-hydroxy-4-methyl-2-(4-nitro-1-naphthalenyl)-4,7-epoxy-1H-isoindole-1,3(2H)-dione (227B)

$BH_3$.THF (0.95 mL, 0.95 mmol, 1M in THF) was added to a solution of crude compound 227A (0.48 g, 0.95 mmol) in THF (2 mL) at 0° C. After compound 227A was consumed, as was evident by HPLC, the reaction mixture was concentrated under reduced pressure. The resulting residue was then dissolved in toluene (2 mL), $Me_3NO$ (71.0 mg, 2.84 mmol) was added and the mixture was heated to reflux overnight. The reaction mixture was then cooled to rt, added to $H_2O$ and extracted with EtOAc (3×). The combined organic layers were dried over $MgSO_4$ and concentrated under reduced pressure. Purification by flash chromatography on $SiO_2$ eluting with 75% EtOAc/hexanes, gave 130 mg (26%) of compound 227B as a brown solid. HPLC: 94% at 3.92 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 527.5 $[M+H]^+$.

EXAMPLE 228

(3aα,4β,5β,7β,7aα)-Hexahydro-5-hydroxU-7-(2-hydroxyethyl)-4-methyl-2-(4-nitro-1-naphthalenyl)-4,7-epoxy-1H-isoindole-1,3(2H)-dione (228)

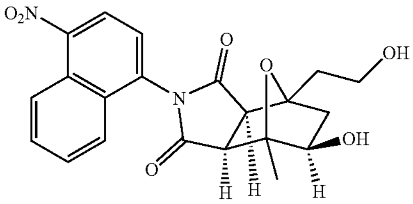

A mixture of TBAF (0.3 mL, 0.3 mmol, 1 M solution in THF) and HF (0.3 mL, 50% in $H_2O$) in $CH_3CN$ (6 mL) was added to a solution of 227B (104 mg, 0.197 mmol) in THF (2 mL) at 0° C. The reaction mixture was stirred overnight at rt. After the starting material was consumed, as was evident by TLC, $H_2O$ and EtOAc were added and the layers were separated. The aqueous layer was extracted with EtOAc (1×) and the combined organic layers were washed with $H_2O$ (1×) and brine (1×), dried over $Na_2SO_4$ and concentrated under reduced pressure. Purification by flash chromatography on $SiO_2$ eluting with 5% $MeOH/CH_2Cl_2$ gave 61 mg (75%) of compound 228 as a yellow solid. HPLC: 99% at 2.47 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 411.2 $[M-H]^-$.

EXAMPLE 229

(3aα,4β,5β,7β,7aα)-7-[2-(4-Fluorophenoxy)ethyl]hexahydro-5-hydroxy-4-methyl-2-(4-nitro-1-naphthalenyl)-4,7-epoxy-1H-isoindole-1,3(2H)-dione (229)

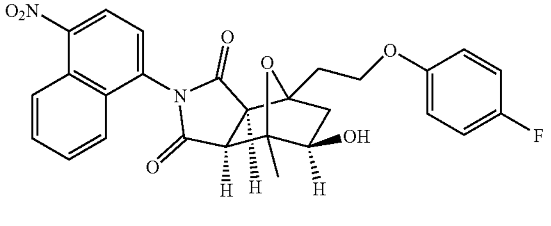

DBAD (37.7 mg, 0.164 mmol) was added to a solution of $PPh_3$ (43.0 mg, 0.164 mmol) in THF (1 mL). After stirring for 10 min, 4-fluorophenol (18.3 mg, 0.164 mmol) was added and the reaction mixture was stirred for a further 5 min. A solution of compound 228 (45.0 mg, 0.109 mmol) in THF (1 mL) was added and the mixture was stirred at rt overnight. HPLC showed the crude reaction mixture to contain mostly starting diol (compound 228), so this mixture was added to a preformed mixture as before of $PPh_3$ (86 mg), DBAD (75.4 mg) and phenol (36.6 mg) in THF (4 mL) at rt. Stirring was continued until all of compound 228 was consumed. The reaction was then concentrated under reduced pressure. Purification by reverse phase preparative HPLC [15.2 min (retention time) (YMC S5 ODS A column 20×100 mm, 10-90% aqueous methanol over 15 minutes containing 0.1%. TFA, 20 mL/min, monitoring at 220 nm)] gave 25.0 mg (45%) of compound 229 as a light yellow solid. HPLC: 99% at 3.53 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 505.2 $[M-H]^-$.

EXAMPLE 230

(3aα,4β,5β,6β,7β,7aα)-4-(Octahydro-5,6-dihydroxy-4,7-dimethyl-1,3-dioxo-4,7-epoxy-2H-isoindol-2-yl)-2-(trifluoromethyl)benzonitrile & (3aα,4β,5α,6α,7β,7aα)-4-(Octahydro-5,6-dihydroxy-4,7-dimethyl-1,3-dioxo-4,7-epoxy-2H-isoindol-2-yl)-2-(trifluoromethyl)benzonitrile (230Bi & 230Bii. Respectively)

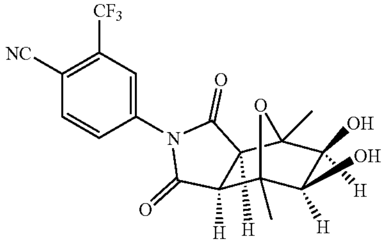

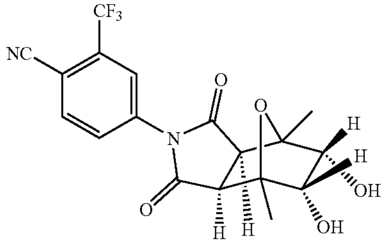

A. (3aα,4β,7β,7aα)-4-(1,3,3a,4,7,7a-Hexahydro-4,7-dimethyl-1,3-dioxo-4,7-epoxy-2H-isoindol-2-yl)-2-(trifluoromethyl)benzonitrile (230A)

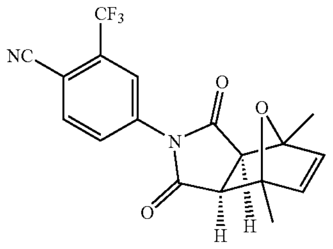

2,5-Dimethyl furan (1.23 mL, 11.5 mmol) and 4-(2,5-dihydro-2,5-dioxo-1H-pyrrol-1-yl)-2-trifluoromethylbenzonitrile (2.00 g, 7.69 mmol) were dissolved in benzene (10 mL) and heated at 60° C. for 18 h. The volatile organics were then removed in vacuo. The resulting crude compound 230A was carried on without purification. HPLC: 71% at 3.007 min (retention time) (YMC S5 ODS column 4.6×50 mm eluting with 10-90% aqueous methanol over 4 minutes containing 0.2% phosphoric acid, 4 mL/min, monitoring at 220 nm).

B. (3aα,4β,5β,6β,7β,7aα)-4-(Octahydro-5,6-dihydroxy-4,7-dimethyl-1,3-dioxo-4,7-epoxy-2H-isoindol-2-yl)-2-(trifluoromethyl)benzonitrile & (3aα,4β,5α,6α,7β,7aα)-4-(Octahydro-5,6-dihydroxy-4,7-dimethyl-1,3-dioxo-4,7-epoxy-2H-isoindol-2-yl)-2-(trifluoromethyl)benzonitrile (230Bi & 230Bii)

Compound 230A (0.100 g, 0.281 mmol) was dissolved in acetone and N-methylmorpholine-N-oxide (50% aq. solution, 0.10 mL, 0.42 mmol) was added. $OsO_4$ (4% aq. solution, 0.014 mmol) was then added. After 3 h at 25° C., the reaction was complete and sodium sulfite (0.250 g) was added with vigorous stirring. After 15 min, brine (10 mL) was added and the solution was extracted with EtOAc (3×15 mL). The organics were dried over anhydrous sodium sulfate and then concentrated in vacuo. The crude diol mixture was purified by preparative TLC eluting with 18% acetone in chloroform to give 0.038 g (34%) of compound 230Bi (beta face) and 0.012 g (11%) of compound 230Bii (alpha face) as pale yellow solids. Compound 230Bi: HPLC: 100% at 2.567 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 397.08 $[M+H]^+$. Compound 230Bii: HPLC: 100% at 2.417 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 397.08 $[M+H]^+$.

EXAMPLE 231

(3aα,4β,5β,6β,7β,7aα)-4-[Octahydro-5,6-dihydroxy-4-(hydroxyethyl)-7-methyl-1,3-dioxo-4,7-epoxy-2H-isoindol-2-yl]-1-naphthalenecarbonitrile, (231C)

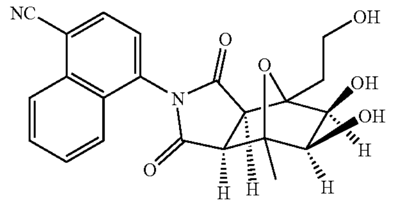

A. (3aα,4β,7β,7aα)-4-[4-[2-[[(1,1-Dimethylethyl)dimethylsilyl]oxy]ethyl]-1,3,3a,4,7,7a-hexahydro-7-methyl-1,3-dioxo-4,7-epoxy-2H-isoindol-2-yl]-1-naphthalenecarbonitrile (231A)

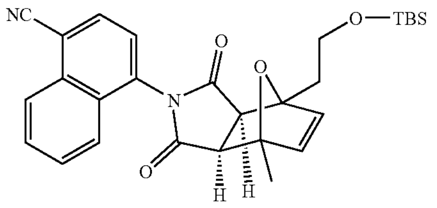

Compound 204A (29.0 g, 120 mmol) and 4-(2,5-dihydro-2,5-dioxo-1H-1-yl)-1-naphthalenecarbonitrile (20.0 g, 80.6 mmol) were suspended in benzene (80 mL) and heated at 60° C. for 14 h. The mixture was then concentrated in vacuo at 40° C. for 40 min. The resulting slurry was cooled to 25° C. and then suspended in MeOH (200 mL) and stirred at rt for 30 min. The solution was then cooled to 0° C. for 30 min and then filtered rinsing with cold MeOH. The resulting solid was dried in vacuo to give 26.1 g (55%) of crude compound 231A as a white solid. The methanol solution was concentrated in vacuo and resuspended in MeOH (50 mL) and cooled to −20° C. for 4 h. The solution was then filtered rinsing with cold MeOH. The resulting solid was dried in vacuo to give 3.8 g (10%) of compound 231A as a white solid. HPLC: 95% at 4.227 min (retention time) (YMC S5 ODS column 4.6×50 mm eluting with 10-90% aqueous methanol over 4 minutes containing 0.2% phosphoric acid, 4 mL/min, monitoring at 220 nm)

B. (3aα,4β,5β,6β,7β,7aα)-4-[4-[2-[[(1,1-Dimethylethyl)dimethylsilyl]oxy]ethyl]octahydro-5,6-dihydroxy-7-methyl-1,3-dioxo-4,7-epoxy-2H-isoindol-2-yl]-1-naphthalenecarbonitrile (231B)

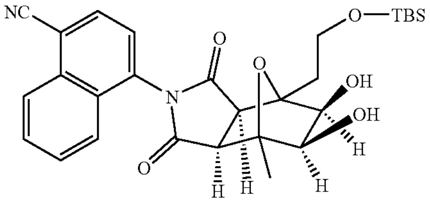

Compound 231A (0.400 g, 0.851 mmol) was dissolved in acetone (9.0 mL) and N-methylmorpholine-N-oxide (50% aq. solution, 0.150 mL, 1.28 mmol) was added. $OsO_4$ (4% aq. solution, 0.043 mmol) was then added. After 3 h at 25° C., the reaction was complete and sodium sulfite (1.0 g) was added with vigorous stirring. After 15 minutes, brine (30 mL) was added and the solution extracted with EtOAc (3×50 mL). The organics were dried over anhydrous sodium sulfate and then concentrated in vacuo. The crude diol was purified by flash chromatography on silica eluting with 5-25% acetone in chloroform to give 0.355 g (80%) of compound 231B as a yellow solid. HPLC: 93% at 3.903 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 522.00 $[M+H]^+$.

C. (3aα,4β,5β,6β,7β,7aα)-4-[Octahydro-5,6-dihydroxy-4-(hydroxyethyl)-7-methyl-1,3-dioxo-4,7-epoxy-2H-isoindol-2-yl]-1-naphthalenecarbonitrile (231C)

Compound 231B (0.400 g, 0.766 mmol) was dissolved in THF (5.0 mL) and transferred to a polypropylene bottle and cooled to 0° C. HFoPyridine (1.0 mL) was then added. After 20 min, the reaction was carefully poured into cold sat. aq. sodium bicarbonate and extracted with methylene chloride (3×30 mL). The organics were then washed once with 1 N HCl and dried over anhydrous sodium sulfate. Concentration in vacuo gave 0.290 g (93%) compound 231C (0.290 g) as a yellow foam which was not purified further. HPLC: 92% at 2.273 and 2.423 min (atropisomers, retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 409.10 $[M+H]^+$.

EXAMPLE 232

(3aα,4β,5β,6β,7β,7aα)-4-[Octahydro-5,6-dihydroxy-4-methyl-1,3-dioxo-7-[2-[4-(trifluoromethyl)phenoxy]ethyl]-4,7-epoxy-2H-isoindol-2-yl]-2-(trifluoromethyl)benzonitrile, (232C)

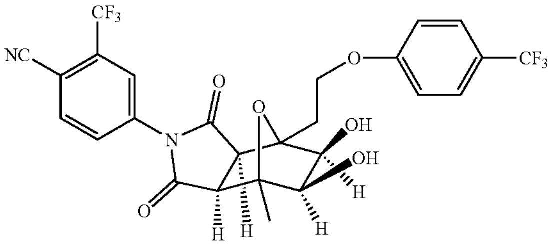

A. 2-Methyl-5-[2-[4-(trifluoromethyl)phenoxy]ethyl]furan (232A)

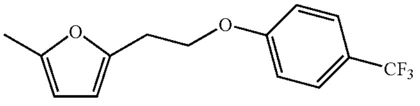

To a solution of triphenylphosphine (1.56 g, 5.95 mmol) in THF (40 mL) was added DBAD (1.37 g, 5.95 mmol). After 10 min, 4-trifluoromethylphenol (0.964 g, 5.95 mmol) was added. After 10 additional minutes, compound 21A (0.500 g, 3.97 mmol) was added. After 14 h at 25° C., the reaction was concentrated in vacuo and purified by flash chromatography on silica eluting with chloroform to give 0.713 g (44%) of compound 232A as a clear oil.

B. (3aα,4β,7β,7aα)-4-[1,3,3a,4,7,7a-hexahydro-4-methyl-1,3-dioxo-7-[2-[4-(trifluoromethyl)phenoxy]ethyl]-4,7-epoxy-2H-isoindol-2-yl]-2-(trifluoromethyl)benzonitrile (232B)

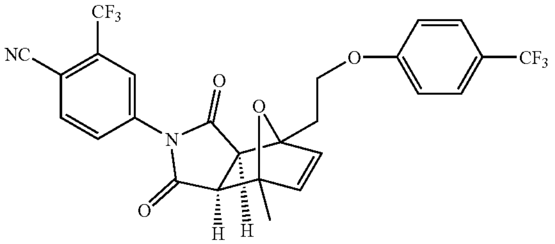

Compound 232A (0.301 g, 1.15 mmol) and 4-(2,5-dihydro-2,5-dioxo-1H-pyrrol-1-yl)-2-trifluoromethylbenzonitrile (0.220 g, 0.846 mmol) were suspended in benzene (1.5 mL) and heated at 60° C. for 14 h. The mixture was then concentrated in vacuo at 40° C. for 40 minutes. The crude product was purified by flash chromatography on silica eluting with 10-0% hexanes in methylene chloride to give 0.199 g (44%) of compound 232B as a yellow solid. Compound 232B was characterized as the exo diastereomer by NOE experiments. HPLC: 94% at 3.993 min (retention time)

(YMC S5 ODS column 4.6×50 mm eluting with 10-90% aqueous methanol over 4 minutes containing 0.2% phosphoric acid, 4 mL/min, monitoring at 220 nm).

C. (3aα,4β,5β,6β,7β,7aα)-4-[Octahydro-5,6-dihydroxy-4-methyl-1,3-dioxo-7-[2-[4-(trifluoromethyl)phenoxy]ethyl]-4,7-epoxy-2H-isoindol-2-yl]-2-(trifluoromethyl)benzonitrile, (232C)

Compound 232B (0.075 g, 0.14 mmol) was dissolved in acetone (2.0 mL) and N-methylmorpholine-N-oxide (50% aq. solution, 0.025 mL, 0.21 mmol) was added. $OsO_4$ (4% aq. solution, 0.007 mmol) was then added. After 3 h at 25° C., the reaction was complete and sodium sulfite (0.25 g) was added with vigorous stirring. After 15 minutes, brine (5 mL) was added and the solution extracted with EtOAc (3×10 mL). The organics were dried over anhydrous sodium sulfate and then concentrated in vacuo. The crude diol was purified by preparative TLC on silica gel, eluting with 10% acetone in chloroform to give 0.038 g (48%) of compound 232C as a yellow solid. HPLC: 98% at 3.747 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 593.08 $[M+Na]^+$.

EXAMPLE 233

(3aα,4β,5β,5aβ,8aβ,8bα)-4-(Decahydro-5-hydroxy-4-methyl-1,3-dioxo-4,8a-epoxy-2H-furo[3,2-e]isoindol-2-yl)-1-naphthalenecarbonitrile, (233)

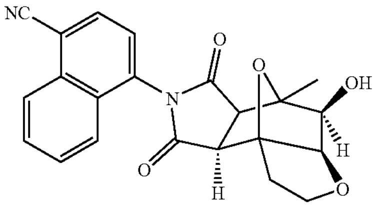

To a solution of triphenylphosphine (0.072 g, 0.28 mmol) in THF (3.0 mL) was added DBAD (0.063 g, 0.28 mmol). After 10 min, 4-cyanophenol (0.033 g, 0.28 mmol) was added. After 10 additional minutes, compound 231C (0.075 g, 0.18 mmol) was added. After 3 h at 25° C., the reaction was concentrated in vacuo and purified by preparative TLC on silica gel, eluting with 15% acetone in chloroform to give 0.068 g (95%) of compound 233 as a white solid. HPLC: 95% at 2.430 and 2.560 min (atropisomers, retention time) (YMC S5 ODS column 4.6×50 mm, 10-90% aqueous methanol over 4 minutes containing 0.2% phosphoric acid, 4 mL/min, monitoring at 220 nm). MS (ES): m/z 391.09 $[M+H]^+$.

EXAMPLE 234

(3aα,4β,7β,7aα)-2-(4-Cyano-1-naphthalenyl)octahydro-7-methyl-1,3-dioxo-4,7-epoxy-4H-isoindole-4-acetic acid. (234B)

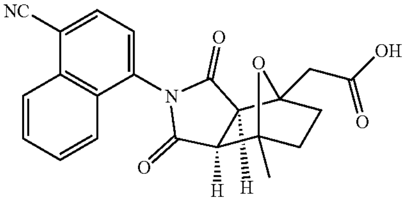

A. (3aα,4β,7β,7aα)-2-(4-Cyano-1-naphthalenyl)-1,2,3,3a,7,7a-hexahydro-7-methyl-1,3-dioxo-4,7-epoxy-4H-isoindole-4-acetic acid (234A)

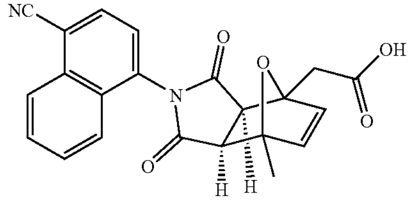

5-Methyl-2-furanacetic acid (0.500 g, 3.57 mmol) and 4-(2,5-dihydro-2,5-dioxo-1H-1-yl)-1-naphthalenecarbonitrile (0.899 g, 3.57 mmol) were dissolved in benzene (3.0 mL) and heated at 60° C. for 2 h and then cooled to 25° C. After 12 h, a white solid precipitated out of solution which was collected and rinsed with diethyl ether to yield 1.20 g (87%) of compound 234A as a light yellow solid. NMR analysis showed only one diastereomer. HPLC: 86% at 2.767 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 389.45 $[M+H]^+$.

B (3aα,4β,7β,7aα)-2-(4-Cyano-1-naphthalenyl)octahydro-7-methyl-1,3-dioxo-4,7-epoxy-4H-isoindole-4-acetic acid, (234B)

Compound 234A (1.10 g, 2.82 mmol) was dissolved in EtOH/EtOAc (1:1, 50 mL) and 10% Pd/C (0.4 g, cat.) was added. $H_2$ was introduced via a balloon. After 5 h at 25° C., the reaction was filtered through Celite rinsing with EtOAc and concentrated in vacuo to yield 1.00 g (91%) of compound 234B as a yellow solid. HPLC: 80% at 2.84 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 391.1 $[M+H]^+$.

EXAMPLE 235

(3aα,4β,7β,7aα)-2-(4-Cyano-1-naphthalenyl)octahydro-7-methyl-1,3-dioxo-4,7-epoxy-4H-isoindole-4-acetic acid, methyl ester, (235)

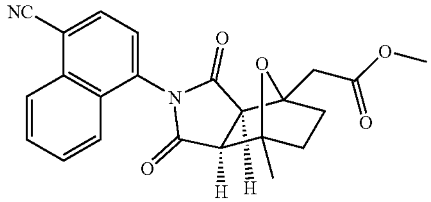

Compound 234B (0.050 g, 0.13 mmol) was dissolved in acetonitrile (2.0 mL), then DCC (0.025 g, 0.13 mmol) was added followed by HOAc (0.018 g, 0.13 mmol). 4-Fluorobenzyl alcohol (0.014 mL, 0.13 mmol) was then added and the reaction was stirred for 3 h. The reaction mixture was concentrated in vacuo and purified by reverse phase preparative HPLC (YMC S5 ODS 20×100 mm, 10-90% aqueous methanol over 15 min containing 0.1% TFA, 20 mL/min, monitoring at 220 nm). Purification yielded 0.040 g (82%) of compound 235 as a white solid, rather than the expected benzyl ester. None of the anticipated benzyl ester was observed by NMR or LC-MS. HPLC: 100% at 3.033 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 405.51 $[M+H]^+$.

EXAMPLE 236

(3aα,4β,7β,7aα)-2-(4-Cyano-1-naphthalenyl)-N-[(4-fluorophenyl)methyl]octahydro-7-methyl-1,3-dioxo-4,7-epoxy-4H-isoindole-4-acetamide, (236)

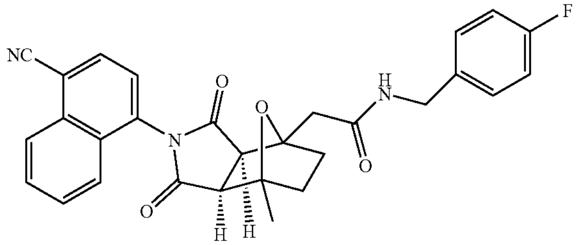

Compound 234B (0.10 g, 0.27 mmol) was dissolved in acetonitrile (4.0 mL). HOAc (0.035 g, 0.27 mmol) and DCC (0.049 g, 0.27 mmol) were then added followed by 4-fluorobenzylamine (0.030 mL, 0.27 mmol). After 4 h at 25° C., the reaction was concentrated in vacuo and purified by reverse phase preparative HPLC (YMC S5 ODS 20×100 mm, 10-90% aqueous methanol over 15 minutes containing 0.1% TFA, 20 mL/min, monitoring at 220 nm) to yield 0.085 g (67%) of compound 236 as a white solid. HPLC: 100% at 3.277 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 498.43 $[M+H)^+$.

EXAMPLE 237

(3aα,4β,7β,7aα)-N-[2-[2-(4-Cyano-1-naphthalenyl) octahydro-7-methyl-1,3-dioxo-4,7-epoxy-4H-isoindol-4-yl]ethyl]-4-fluorobenzamide, (237B)

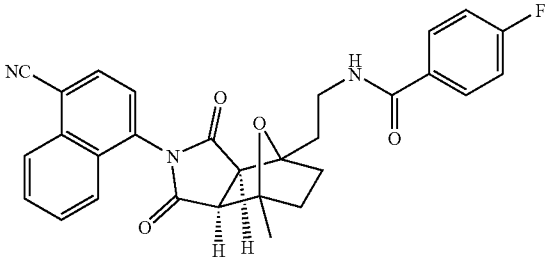

A. 4-Fluoro-N-[2-(5-methyl-2-furanyl)ethyl]benzamide (237A)

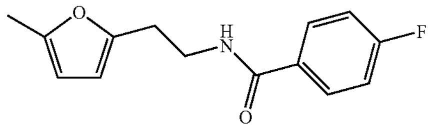

4-Fluorophenylacetyl chloride (0.290 mL, 2.44 mmol) was added dropwise to a solution of β-(5-methyl-2-furanyl)ethanamine (300 mg, 2.44 mmol, made according to the procedure of Yur'ev et al. *J. Gen. Chem. USSR* (*Engl. Transl.*) 33, 3444-8 (1963)) in THF (2.5 mL) at rt, followed by the dropwise addition of $Et_3N$ (0.340 mL, 2.44 mmol). Once the starting material was consumed, as was evident by HPLC, the reaction was quenched with $H_2O$ and extracted with $CH_2Cl_2$. The combined organic layers were dried over $MgSO_4$ and concentrated under reduced pressure. Purification by flash chromatography on silica gel eluting with a gradient of 0-50% EtOAc/hexane gave 523 mg (95%) of compound 237A as a white solid. HPLC: 99% at 2.84 min (retention time) (Phenomenex-prime S5-C18 column 4.6×50 mm eluting with 10-90% aqueous methanol over 4 minutes containing 0.2% phosphoric acid, 4 mL/min, monitoring at 220 nm). MS (ES): m/z 248.15 $[M+H]^+$.

B. (3aα,4β,7β,7aα)-N-[2-[2-(4-Cyano-1-naphthalenyl)octahydro-7-methyl-1,3-dioxo-4,7-epoxy-4H-isoindol-4-yl]ethyl]-4-fluorobenzamide, (237B)

A solution of compound 237A (221 mg, 0.896 mmol) and 4-(2,5-dihydro-2,5-dioxo-1H-1-yl)-1-naphthalenecarbonitrile (222 mg, 0.896 mmol) in benzene (4 mL) was heated at 60° C. overnight. The reaction mixture was concentrated under reduced pressure and dissolved in EtOAc (30 mL). 10% Pd/C (50 mg) was added and the mixture was stirred under a hydrogen balloon overnight. The reaction mixture was filtered through a pad of Celite and concentrated under reduced pressure. Purification by flash chromatography on silica gel eluting with 25%-75% EtOAc/hexane (gradient) gave 160 mg (36%) of compound 237B as an off-white solid. HPLC: 97% at 3.13 & 3.23 min (atropisomers, retention time) (Phenomenex-prime S5-C18 column 4.6×50 mm eluting with 10-90% aqueous methanol over 4 minutes containing 0.2% phosphoric acid, 4 mL/min, monitoring at 220 nm). MS (ES): m/z 498.11 $[M+H]^+$.

EXAMPLE 238

[3aR-(3aα,4β,7β,7aα)]-4-[Octahydro-4-(2-hydroxyethyl)-7-methyl-1,3-dioxo-4,7-epoxy-2H-isoindol-2-yl]-1-naphthalenecarbonitrile & [3aS-(3aα,4β,7β,7aα)]-4-[Octahydro-4-(2-hydroxyethyl)-7-methyl-1,3-dioxo-4,7-epoxy-2H-isoindol-2-yl]-1-naphthalenecarbonitrile. (238i & 238ii)

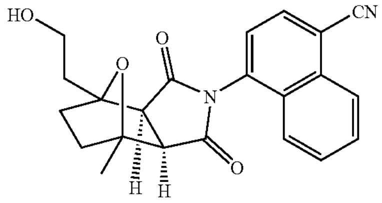

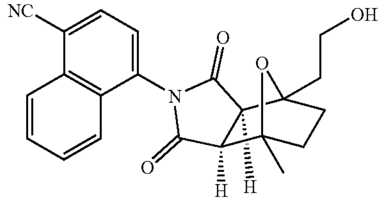

Racemic compound 223B was separated into its enantiomers by normal phase preparative chiral HPLC (CHIRALPAK AD 5×50 cm column; eluting with 20% MeOH/EtOH (1:1) in heptane (isocratic) at 50 mL/min, monitoring at 220 nm) to give the faster eluting compound 238i (Chiral HPLC: 13.54 min; CHIRALPAK AD 4.6×250 mm column; eluting with 20% MeOH/EtOH (1:1) in heptane at 1 mL/min) and the slower eluting compound 238ii (Chiral HPLC: 14.99 min; CHIRALPAK AD 4.6×250 mm column; eluting with 20% MeOH/EtOH (1:1) in heptane at 1 mL/min). The absolute conformation for compounds 238i & 238ii was not established. For simplicity in nomenclature, compound 238i is designated herein as having an "R" configuration and compound 238ii as having an "S" configuration. Enantiomerically pure products derived from compound 238i are designated herein as having a "R" configuration and enantiomerically pure products derived from compound 238ii are designated herein as having an "S" configuration.

EXAMPLE 239

[3aR-(3aα,4β,7β,7aα)]-4-[4-[2-(3-Fluorophenoxy)ethyl]octahydro-7-methyl-1,3-dioxo-4,7-epoxy-2H-isoindol-2-yl]-1-naphthalenecarbonitrile & [3aS-(-(3aα,4β,7β,7aα)]-4-[4-[2-(3-Fluorophenoxy)ethyl]octahydro-7-methyl-1,3-dioxo-4,7-epoxy-2H-isoindol-2-yl]-1-naphthalenecarbonitrile. (239i & 239ii)

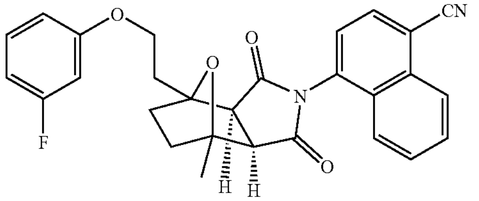

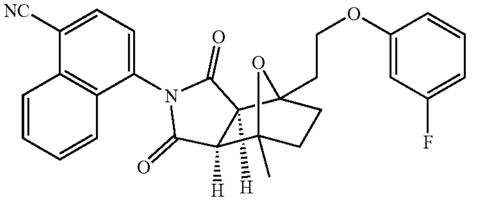

To a solution of triphenylphosphine (0.052 g, 0.20 mmol) in THF (2.0 mL) was added DBAD (0.046 g, 0.20 mmol). After 10 min, 3-fluorophenol (0.018 mL, 0.20 mmol) was added. After 10 additional minutes, compound 238i (0.050 g, 0.13 mmol) was added. After 3 h at 25° C., the reaction was concentrated in vacuo and purified by reverse phase preparative HPLC (YMC S5 ODS 20×100 mm, 10-90% aqueous methanol over 15 minutes containing 0.2% TFA, 20 mL/min, monitoring at 220 nm) to give 0.031 g (33%) of compound 239i as a white solid. This process was repeated with compound 238ii to yield compound 239ii. Compound 239i: HPLC: 100% at 3.80 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 471.65 $[M+H]^+$, $[\alpha]_D^{25}$=−47.371 (c=4.412 mg/cc, $CH_2Cl_2$). Compound 239ii: HPLC: 100% at 3.80 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 471.65 $[M+H]^+$, $[\alpha]_D^{25}$=+24.3 (c=4.165 mg/cc, $CH_2Cl_2$).

EXAMPLE 240

(4-Fluorophenyl)carbamic acid, 2-[(3aα,4β,7β,7aα)-2-(4-cyano-1-naphthalenyl)octahydro-7-methyl-1,3-dioxo-4,7-epoxy-4H-isoindol-4-y]ethyl ester, (240)

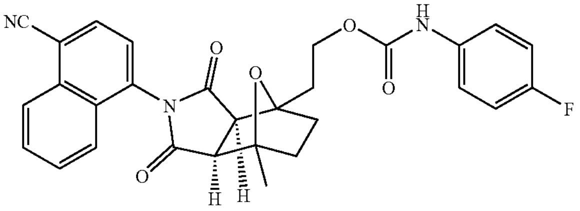

Compound 223B (0.100 g, 0.279 mmol) was dissolved in dichloroethane (3.0 mL) and 4-fluorophenylisocyanate (0.048 mL, 0.42 mmol) was added followed by heating to 60° C. After 2 h, the reaction was cooled to 25° C. and diluted with methylene chloride. The mixture was washed once with sat. aq. sodium bicarbonate (20 mL) and then the organics were dried over anhydrous sodium sulfate. The crude material was purified by flash chromatography on silica gel eluting with 15% acetone in chloroform to give 0.098 g (68%) of compound 240 as a yellow foam. HPLC: 98% at 3.320 & 3.457 min (atropisomers, retention time) (YMC S5 ODS column 4.6×50 mm, 10-90% aqueous methanol over 4 minutes containing 0.2% phosphoric acid, 4 mL/min, monitoring at 220 nm). MS (ES): m/z 514.13 $[M+H]^+$.

EXAMPLE 241

(3aα,4β,7β,7aα)-4-[Octahydro-4-(2-hydroxyethyl)-1,3-dioxo-4,7-epoxy-2H-isoindol-2-yl]-1-naphthalenecarbonitrile, (241D)

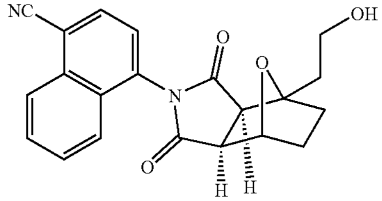

A. 2-[2-[[(1,1-Dimethylethyl)dimethylsilyl]oxy]ethyl]furan (241A)

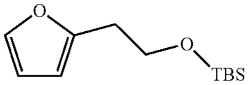

2-(2-Hydroxyethyl)furan (1.00 g, 8.93 mmol, Example 255A) was dissolved in DMF at 25° C. and imidazole (0.790 g, 11.6 mmol) was added. TBSCl (1.35 g, 8.93 mmol) was then added in portions over 5 minutes. After 2 h, the reaction was poured into diethyl ether (300 mL) and washed sequentially with water (1×100 mL), 1 N HCl (1×100 mL), and brine (1×100 mL). The combined organics were then dried over magnesium sulfate and concentrated in vacuo. Compound 241A was isolated as a clear oil (1.77 g) and was taken on without purification. HPLC: 100% at 4.233 min (retention time) (YMC S5 ODS column 4.6×50 mm, 10-90% aqueous methanol over 4 minutes containing 0.2% phosphoric acid, 4 mL/min, monitoring at 220 nm).

B. (3aα,4β,7β,7aα)-4-[4-[2-[[(1,1-Dimethylethyl) dimethylsilyl]oxy]ethyl]-1,3,3a,4,7,7a-hexahydro-1, 3-dioxo-4,7-epoxy-2H-isoindol-2-yl]-1-naphthalenecarbonitrile (241B)

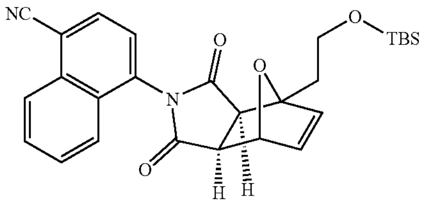

4-(2,5-Dihydro-2,5-dioxo-1H-1-yl)-1-naphthalenecarbonitrile (0.721 g, 3.40 mmol) was suspended in benzene (5.0 mL) in a sealed tube and compound 241A (1.00 g, 4.42 mmol) was added. The reaction was heated at 60° C. for 16 h and then cooled to 25° C. The benzene was removed in vacuo to give a yellow solid. The crude material was purified by flash chromatography on silica gel eluting with 1-5% acetone in chloroform to give 1.37 g (85%) of compound 241B as a yellow solid. NMR experiments confirmed the exo isomer assignment. HPLC: 100% at 4.030 & 4.110 min (atropsiomers, retention time) (YMC S5 ODS column 4.6×50 mm, 10-90% aqueous methanol over 4 minutes containing 0.2% phosphoric acid, 4 mL/min, monitoring at 220 nm).

C. (3aα,4β,7β,7aα)-4-[4-[2-[[(1,1-Dimethylethyl) dimethylsilyl]oxy]ethyl]octahydro-1,3-dioxo-4,7-epoxy-2H-isoindol-2-yl]-1-naphthalenecarbonitrile (241C)

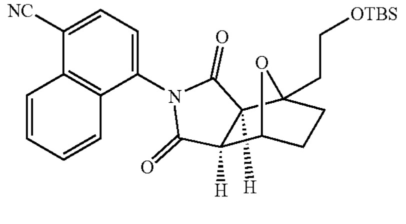

Compound 241B (0.500 g, 1.14 mmol) was dissolved in ethyl acetate (40 mL) and 10% Pd/C (0.200 g) was added. Hydrogen was then introduced via a balloon. After 4 h, the reaction was filtered through Celite, rinsed with ethyl acetate and concentrated in vacuo to yield a pale yellow solid, which was purified by flash chromatography on silica gel eluting with acetone/chloroform (0%-1.5%-3% acetone) to give 0.450 g (83%) of compound 241C as a yellow foam.

D. (3aα,4β,7β,7aα)-4-[Octahydro-4-(2-hydroxyethyl)-1,3-dioxo-4,7-epoxy-2H-isoindol-2-yl]-1-naphthalenecarbonitrile, (241D)

Compound 241C (0.283 g, 0.594 mmol) was dissolved in a solution of 2% conc. HCl in absolute ethanol (10 mL). After 1 h, the reaction was quenched with sat. aq. sodium bicarbonate and extracted with methylene chloride (4×20 mL). The combined organics were dried over sodium sulfate and concentrated in vacuo to give 0.211 g (98%) of compound 241D as a white solid. HPLC: 100% at 2.14 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 363.45 $[M+H]^+$.

EXAMPLE 242

(3aα,4β,6β,7β,7aα)-4-[4-[2-(4-Cyanophenoxy) ethyl]octahydro-6-hydroxy-1,3-dioxo-4,7-epoxy-2H-isoindol-2-yl]-1-naphthalenecarbonitrile, (242C)

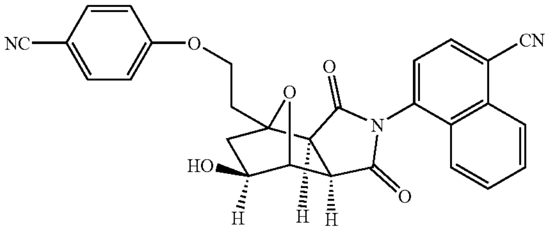

A. (3aα,4β,6β,7β,7aα)-4-[4-[2-[[(1,1-Dimethylethyl)dimethylsilyl]oxy]ethyl]octahydro-6-hydroxy-1,3-dioxo-4,7-epoxy-2H-isoindol-2-yl]-1-naphthalenecarbonitrile (242A)

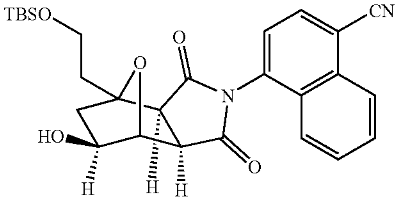

Compound 241B (1.00 g, 2.28 mmol) and Wilkinson's catalyst (0.105 g, 0.114 mmol) were stirred rapidly under vacuum at 25° C. for 1 h and then purged with $N_2$. THF (30 mL) was then added followed by catecholborane (0.487 mL, 4.57 mmol) after the olefin was completely dissolved. After 1 h, the reaction was cooled to 0° C. and a pH 7.2 phosphate buffer (33 mL) was added followed by EtOH (13 mL) and $H_2O_2$ (30% aq. soln, 3.0 g). After 3 h at 0° C. the reaction was complete by LC and the mixture was extracted with methylene chloride (3×50 mL). The combined organics were washed with a 1:1 mixture of 10% sodium sulfite/1 N NaOH (50 mL) and once with brine (50 mL). All aqueous phases were combined and extracted with methylene chloride (50 mL) and the organic phase combined with the previous extractions. All the organics were then dried over anhydrous sodium sulfate and then concentrated in vacuo. The crude material was purified by flash chromatography on silica gel eluting with 10-20% acetone in chloroform to give 0.634 g of compound 242A as a white foam. HPLC: 96% at 3.797 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 493.13 $[M+H]^+$.

B. (3aα,4β,6β,7β,7aα)-4-[Octahydro-6-hydroxy-4-(2-hydroxyethyl)-1,3-dioxo-4,7-epoxy-2H-isoindol-2-yl]-1-naphthalenecarbonitrile (242B)

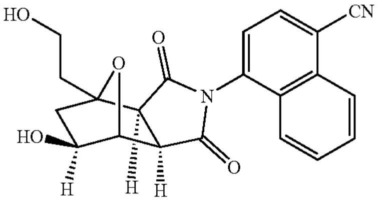

Compound 242A (0.400 g, 0.813 mmol) was dissolved in a solution of 2% 12 N HCl in absolute ethanol (10 mL). After 1 h, the reaction was quenched with sat. aq. sodium bicarbonate and extracted with EtOAc (4×20 mL). The combined organics were dried over sodium sulfate and concentrated in vacuo to give 0.305 g of compound 242B as a white solid. HPLC: 90% at 2.043 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 379.09 $[M+H]^+$.

C. (3aα,4β,5β,7β,7aα)-4-[4-[2-(4-Cyanophenoxy)ethyl]octahydro-6-hydroxy-1,3-dioxo-4,7-epoxy-2H-isoindol-2-yl]-1-naphthalenecarbonitrile, (242C)

To a solution of triphenylphosphine (0.054 g, 0.207 mmol) in THF (2.0 mL) was added DBAD (0.048 g, 0.207 mmol). After 10 min, 4-cyanophenol (0.025 g, 0.207 mmol) was added. After 10 additional minutes, compound 242B (0.050 g, 0.138 mmol) was added. After 3 h at 25° C., the reaction was concentrated in vacuo and purified by preparative TLC on silica eluting with 25% acetone/chloroform to give 0.056 g of compound 242C as a white solid. HPLC: 90% at 2.987 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 480.10 $[M+H]^+$.

EXAMPLE 243

[3aS-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile & [3aR-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile. (243Di & 243Dii)

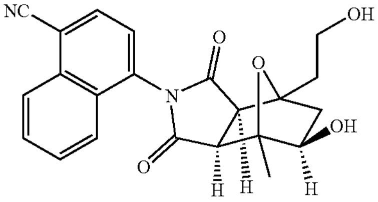

-continued

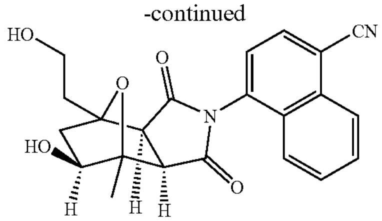

A. (3aα,4β,7β,7aα)-4-[4-[2-[[(1,1-Dimethylethyl)dimethylsilyl]oxy]ethyl]-1,3,3a,4,7,7a-hexahydro-1,3-dioxo-4,7-epoxy-2H-isoindol-2-yl]-1-naphthalenecarbonitrile (243A)

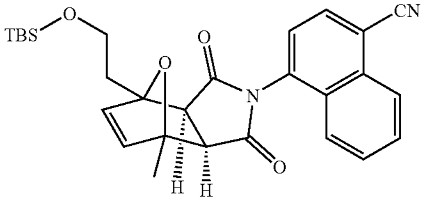

4-(2,5-Dihydro-2,5-dioxo-1H-1-yl)-1-naphthalenecarbonitrile (18.3 g, 68.7 mmol) was added to a solution of compound 204A (26.6 g, 110.6 mmol) in benzene (75 mL) and heated at 60° C. overnight. After cooling to rt, the reaction mixture was concentrated under reduced pressure. The residue was treated with MeOH (250 mL) with stirring at 0° C. for 10 min. The resulting solid was filtered, washed with cold MeOH (2×10 mL) and dried to give 26.7 g (79.5%) of compound 243A as a yellow solid. HPLC analysis of the above solid revealed it to be 95% pure (HPLC conditions: 95% at 2.48 min (retention time) (Phenomenex-prime S5-C18 column, 4.6×50 mm, 10%-90% aqueous methanol over 4 minute gradient with 0.2% $H_3PO_4$, detecting at 220 nm)). The filtrate was then concentrated under reduced pressure and the resulting solid was chromatographed, eluting with 3% acetone/$CHCl_3$, to give an additional 4.36 g of compound 243A (13%), giving a total final yield of 92.5%.

B. (3aα,4β,5β,7β,7aα)-4-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-1-naphthalenecarbonitrile (243B)

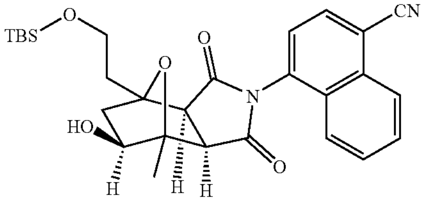

A mixture of 243A (10 g, 20.46 mmol) and $RhCl(PPh_3)_3$ (0.947 mg, 1.02 mmol) was evacuated and filled with argon (3×). THF (200 mL) was added and once all particulates had dissolved, catecholborane (4.4 mL, 40.93 mmol) was slowly added dropwise. When the formation of product ceased, as was determined by HPLC, the reaction mixture was cooled to 0° C. and quenched with phosphate buffer (330 mL, pH 7.2) then EtOH (130 mL) and $H_2O_2$ (300 mL, 30% aq. sol) were added. Once boronate was consumed, the mixture was extracted with $CH_2Cl_2$ (3×) and the combined organic layers were washed with 1 N NaOH, 10% aq. $NaHSO_3$ (1:1, 1×) and brine (1×). The combined washes was extracted with $CH_2Cl_2$ (1×) and the combined organic layers were dried over $Na_2SO_4$. Purification by flash chromatography on silica gel eluting with 10% to 30% acetone/$CHCl_3$ gradient over 25 min gave 7.1 g (68%) of 243B as a light yellow solid. HPLC conditions: 98% at 3.82 min (retention time) (Phenomenex-prime S5-C18 column 4.6×50 mm, 10%-90% aqueous methanol over 4 minute gradient with 0.2% $H_3PO_4$, detecting at 220 nm).

C. [3aR-(3aα,4β,5β,7β,7aα)]-4-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-1-naphthalenecarbonitrile & [3aS-(3aα,4β,5β,7β,7aα)]-4-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-1-naphthalenecarbonitrile (243Ci & 243Cii)

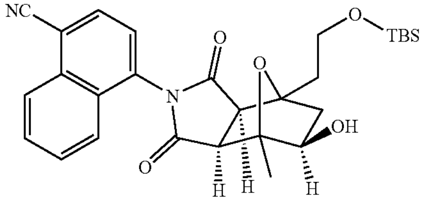

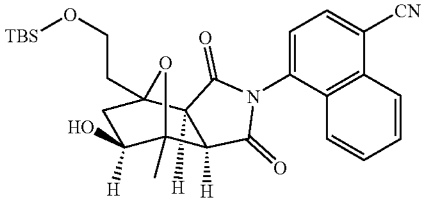

The racemic compound 243B was separated into the individual enantiomers by chiral normal phase liquid chromatography. A Chiralpak OD column (50×500 mm) was used, eluting with 13% EtOH/hexanes over 99 min at 50 mL/min detecting at 220 nm. The faster eluting isomer compound 243Ci had a retention time=45 min and the slower eluting isomer compound 243Cii had a retention time=66 min.

D. [3aS-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile & [3aR-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile, (243Di & 243Dii)

Compound 243Ci (0.84 g, 2.14 mmol) was dissolved in 2% 12 N HCl/EtOH (20 mL), stirred for 5 minutes and concentrated under reduced pressure. Purification by flash chromatography on silica gel eluting with 5-10% MeOH/$CH_2Cl_2$ gave 0.57 g (88%) of 243Di. Compound 243Di which came from the faster eluting isomer (243Ci) was found to be 99.7% ee by analytical normal phase chiral chromatography. HPLC conditions: 99.7% at 2.17 min (retention time) (Chiralcel OJ 44.6×250 mm, 10 micron, 40° C., isocratic 80% Heptane/20% EtOH/MeOH (1:1), 1.0 mL/min., detection at 288 nm).

Compound 243Cii (0.86 g, 2.19 mmol) was dissolved in 2% 12 N HCl/EtOH (20 mL), stirred for 5 minutes and concentrated under reduced pressure. Purification by flash chromatography on silica gel eluting with 5-10% MeOH/$CH_2Cl_2$ gave 0.60 g (90%) of 243Dii. Compound 243Dii which came from the slower eluting isomer (243Cii) was found to have 87.1% ee by analytical chiral phase chiral chromatography. HPLC conditions: 87.1% at 18.4 min (retention time) (Chiralcel OJ 44.6×250 mm, 10 micron, 40° C., isocratic 80% heptane/20% EtOH/MeOH (1:1), 1.0 mL/min., detection at 288 nm).

The absolute conformation for compounds 243Di & 243Dii was not determined. For simplicity in nomenclature, compound 243Di is designated herein as having an "S" configuration and compound 243Dii as having an "R" configuration. Enantiomerically pure products derived from compound 243Di are designated herein as having an "S" configuration and enantiomerically pure products derived from compound 243Dii are designated herein as having an "R" configuration

EXAMPLE 244

[3aS-(3aα,4β,5β,7β,7aα)]-4-[7-[2-(4-Cyanophenoxy)ethyl]octahydro-5-hydroxy-4-methyl-1,3-dioxo-4,7-epoxy-2H-isoindol-2-yl]-1-naphthalenecarbonitrile & [3aR-(3aα,4β,5β,7β,7aα)]-4-[7-[2-(4-Cyanophenoxy)ethyl]octahydro-5-hydroxy-4-methyl-1,3-dioxo-4,7-epoxy-2H-isoindol-2-yl]-1-naphthalenecarbonitrile, (244i & 244ii)

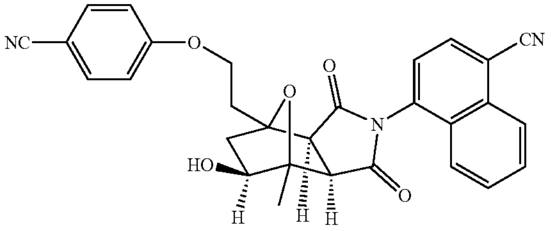

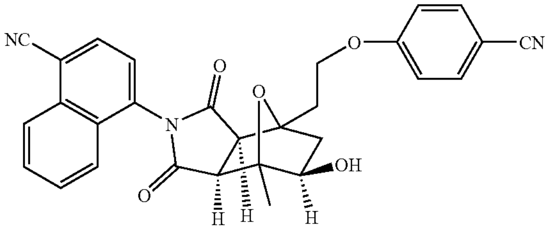

DBAD (26 mg, 0.115 mmol) was added to a solution of $PPh_3$ (30 mg, 0.115 mmol) in THF (0.65 mL). After stirring for 10 min, 4-cyanophenol (13.6 mg, 0.115 mmol) was added and the reaction mixture was stirred for a further 5 min. Compound 243Di (30 mg, 0.076 mmol) was added and the mixture was stirred at rt for 1 h. The reaction was concentrated under reduced pressure. Purification by flash chromatography on silica gel eluting with 30% acetone/70% $CHCl_3$ gave 23.1 mg (0.047 mmol, 61.7%) of compound 244i. HPLC conditions: 95% at 3.06 min (retention time) (YMC S5 ODS 4.6×50 mm, 10%-90% aqueous methanol over 4 minute gradient with 0.2% $H_3PO_4$, detecting at 220 nm). MS (ES): m/z 494.09 $[M+H]^+$. $[\alpha]_D$=53.30°, C=4.5 mg/cc in THF, @589 nm)

DBAD (26 mg, 0.115 mmol) was added to a solution of $PPh_3$ (30 mg, 0.115 mmol) in THF (0.65 mL). After stirring for 10 min, 4-cyanophenol (13.6 mg, 0.115 mmol) was added and the reaction mixture was stirred for a further 5 min. Compound 243Dii (30 mg, 0.076 mmol) was added and the mixture was stirred at rt for 1 h. The reaction was concentrated under reduced pressure. Purification by flash chromatography on silica gel eluting with 30% acetone/70% $CHCl_3$ gave 20.3 mg (0.041 mmol, 54.2%) of compound 244ii. HPLC conditions: 90% at 3.07 min (retention time) (YMC S5 ODS 4.6×50 mm, 10%-90% aqueous methanol over 4 minute gradient with 0.2% $H_3PO_4$, detecting at 220 nm). MS (ES): m/z 494.09 $[M+H]^+$. $[\alpha]_D$=−42.87°, C=6.6 mg/cc in THF, @589 nm)

EXAMPLE 245

(3aα,4β,7β,7aα)-4-[4-[2-(4-Cyanophenoxy)ethyl]-7-ethyloctahydro-1,3-dioxo-4,7-epoxy-2H-isoindol-2-yl]-1-naphthalenecarbonitrile, (245D)

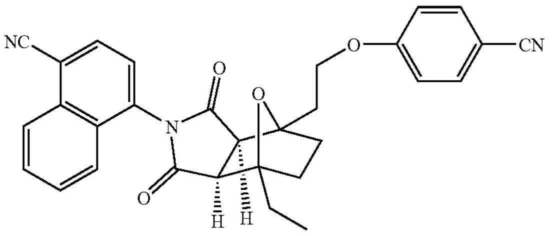

A. 2-Ethyl-5-(2-hydroxyethyl)furan (245A)

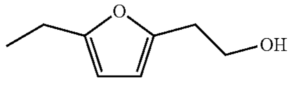

n-BuLi (2.5 M in hexane, 4.4 mL, 11 mmol) was added to a solution of 2-ethylfuran (1.05 mL, 10 mmol) in THF (10 mL) at −25° C. The solution was warmed to rt and stirred for 3 h. Ethylene oxide (0.75 mL) was added at −78° C. The reaction was stirred for 0.5 h at −15° C. and overnight at rt. Aqueous sat. $NH_4Cl$ was added and the mixture was extracted with ether (3×). The combined extracts were washed with water (1×) and brine (1×) and dried over $Na_2SO_4$. Purification by flash chromatography on silica gel eluting with 30% EtOAc/70% hexane gave 1.12 g (8.02 mmol, 80.2%) of compound 245A as a yellow oil.

B. (3aα,4β,7β,7aα)-4-[4-Ethyl-1,3,3a,4,7,7a-hexahydro-7-(2-hydroxyethyl)-1,3-dioxo-4,7-epoxy-2H-isoindol-2-yl]-1-naphthalenecarbonitrile (245B)

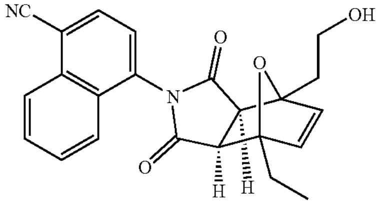

A solution of compound 245A (280 mg, 2.00 mmol) and the 4-(2,5-dihydro-2,5-dioxo-1H-1-yl)-1-naphthalenecarbonitrile (496 mg, 2.00 mmol) in benzene (2 mL) was stirred at 60° C. for 2 h. The reaction mixture was concentrated under reduced pressure. The yellow solid, compound 245B, was used directly in the next step.

C. (3aα,4β,7β,7aα)-4-[4-Ethyloctahydro-7-(2-hydroxyethyl)-1,3-dioxo-4,7-epoxy-2H-isoindol-2-yl]-1-naphthalenecarbonitrile (245C)

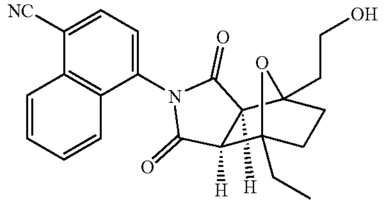

A mixture of compound 245B (764 mg, 1.97 mmol) and 10% Pd/C (115 mg, cat.) in EtOAc (36 mL) was stirred under a hydrogen atmosphere at rt for 2 h. The reaction mixture was filtered through Celite and concentrated under reduced pressure to give 779 mg of crude compound 245C. Purification of this crude product by flash chromatography on silica gel eluting with 70% EtOAc/30% hexane gave 235 mg (0.6 mmol, 30.1%) of compound 245C. HPLC conditions: 99% at 2.84 min (retention time) (YMC S5 ODS 4.6×50 mm, 10%-90% aqueous methanol over 4 minute gradient with 0.2% $H_3PO_4$, detecting at 220 nm). MS (ES): m/z 391.12 $[M+H]^+$.

D. (3aα,4β,7β,7aα)-4-[4-[2-(4-Cyanophenoxy)ethyl]-7-ethyloctahydro-1,3-dioxo-4,7-epoxy-2H-isoindol-2-yl]-1-naphthalenecarbonitrile (245D)

DBAD (44.2 mg, 0.192 mmol) was added to a solution of $PPh_3$ (50.4 mg, 0.192 mmol) in THF (1 mL). After stirring for 10 min, 4-cyanophenol (23 mg, 0.192 mmol) was added and the reaction mixture was stirred for an additional 5 min. Compound 245C (50 mg, 0.128 mmol) was added and the mixture was stirred at rt for 2 h. The reaction was concentrated under reduced pressure. Purification by flash chromatography on silica gel eluting with 40% EtOAc/60% hexane gave 43 mg (0.087 mmol, 68.4%) of compound 245D as a white solid. HPLC conditions: 99% at 3.65 min (retention time) (YMC S5 ODS 4.6×50 mm, 10%-90% aqueous methanol over 4 minute gradient with 0.2% $H_3PO_4$, detecting at 220 nm). MS (ES): m/z 492.16 $[M+H]^+$.

EXAMPLE 246

(3aα,4β,7β,7aα)-4-[2-(Acetyloxy)ethyl]-2-(4-cyano-1-naphthalenyl)hexahydro-7-methyl-4,7-epoxy-1H-isoindole-1,3(2H)-dione, (246)

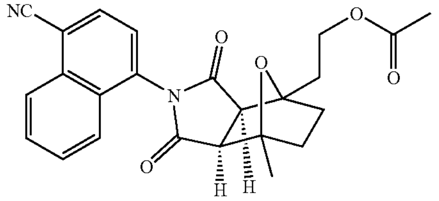

Compound 223B (0.100 g, 0.279 mmol) was dissolved in methylene chloride (3.0 mL) at 25° C. and pyridine (0.071 mL, 0.837 mmol) and 4-DMAP (1.0 mg) were added. Acetic anhydride (0.053 mL, 0.559 mmol) was then added and the reaction was stirred for 20 h at 25° C. After 20 h, sat. aq. sodium bicarbonate was added and the reaction was stirred for 30 min. The mixture was then extracted with methylene chloride (2×20 mL). The organics were then washed once with 1 N HCl (10 mL) and then dried over anhydrous sodium sulfate. After concentration in vacuo, the crude material was purified by preparative TLC on silica eluting with 12% acetone in chloroform to give 0.073 g of compound 246 as a yellow foam. HPLC: 95% at 2.837 and 3.027 min (atropisomers, retention time) (YMC S5 ODS column 4.6×50 mm, 10-90% aqueous methanol over 4 minutes containing 0.2% phosphoric acid, 4 mL/min, monitoring at 220 nm). MS (ES): m/z 441.10 [M+Na]$^+$.

EXAMPLE 247

(3aα,4β,7β,7aα)-4-[Octahydro-4-methyl-1,3-dioxo-7-(2-oxoethyl)-4,7-epoxy-2H-isoindol-2-yl]-1-naphthalenecarbonitrile, (247)

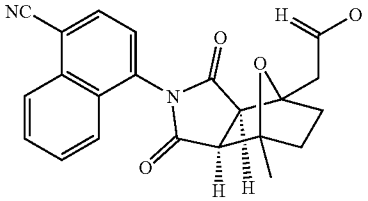

Oxalyl chloride (2.0 M soln, 1.73 mL, 3.5 mmol) was added to dry methylene chloride (10 mL) and cooled to −78° C. DMSO (0.283 mL, 3.99 mmol) was then added dropwise with the evolution of gas. After 15 min, compound 223B (1.00 g, 2.66 mmol) was then added in methylene chloride (10 mL). After 15 min, TEA (1.10 mL, 7.98 mmol) was added and the reaction was slowly warmed to 25° C. Water (30 mL) was then added and the mixture was diluted with methylene chloride (100 mL). The organics were then washed once with 1 N HCl (30 mL), once with water (30 mL) and once with brine (30 mL) and then dried over anhydrous sodium sulfate. The crude product was isolated by concentration in vacuo to yield compound 247 as an orange foam. Crude compound 247 was taken on directly to the next reaction. HPLC: 100% at 2.70 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 483.65 [M+H]$^+$.

EXAMPLE 248

[3aα,4β(E),7β,7aα]-4-[4-[3-(4-Cyanophenyl)-2-propenyl]octahydro-7-methyl-1,3-dioxo-4,7-epoxy-2H-isoindol-2-yl]-1-naphthalenecarbonitrile & [3aα,4β(Z),7β,7aα]-4-[4-[3-(4-Cyanophenyl)-2-propenyl]octahydro-7-methyl-1,3-dioxo-4,7-epoxy-2H-isoindol-2-yl]-1-naphthalenecarbonitrile (248i & 248ii)

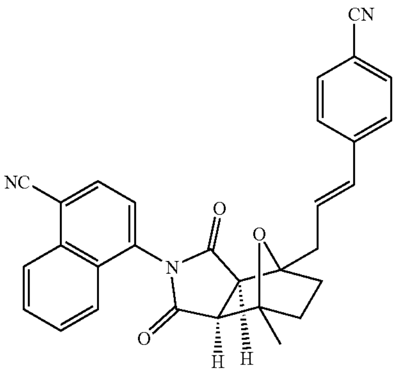

-continued

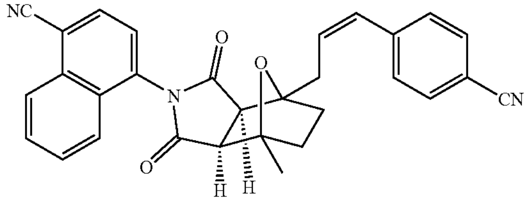

(4-cyanobenzyl)-triphenylphosphonium chloride (0.072 g, 0.174 mmol) was suspended in THF (2.0 mL) and cooled to 0° C. n-BuLi (1.6 M soln, 0.092 mL, 0.147 mmol) was then added dropwise resulting in a homogenous solution. The solution warmed to 25° C. for 15 min and then cooled to 0° C. Compound 247 (0.050 g, 0.134 mmol) was then added in THF. After 1 h, the reaction was quenched with sat. aq. ammonium chloride and then extracted with methylene chloride (3×20 mL). The combined organics were dried over anhydrous sodium sulfate and then concentrated in vacuo. The crude material was purified by preparative TLC eluting with 5% acetone in chloroform to give 0.010 g of a mixture of compounds 248i & 248ii as a white solid. A 1:1 mixture of E and Z olefin isomers characterized by NMR spectroscopy. HPLC: 100% at 3.517 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 474.2 [M+H]$^+$.

EXAMPLE 249

(3aα,4β,7β,7aα)-4-[4-[3-(4-Cyanophenyl)propyl]octahydro-7-methyl-1,3-dioxo-4,7-epoxy-2H-isoindol-2-yl]-1-naphthalenecarbonitrile, (249)

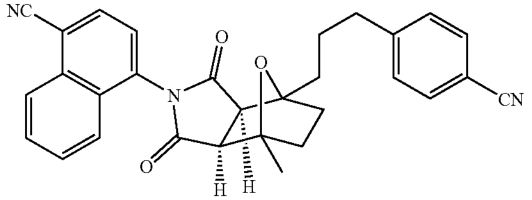

The mixture of compounds 248i & 248ii (0.008 g, 0.017 mmol) was dissolved in EtOH (3.0 mL) and Pd/C (10% Pd, 0.008 g) was added. $H_2$ was then introduced via a balloon. After 18 h, the reaction was filtered through Celite, eluting with EtOAc, followed by concentration in vacuo. Compound 249 was isolated as a white solid (0.007 g). HPLC: 90% at 3.520 min (retention time) (YMC S5 ODS column 4.6×50 mm, 10-90% aqueous methanol over 4 minutes containing 0.2% phosphoric acid, 4 mL/min, monitoring at 220 nm). MS (ES): m/z 476.13 [M+H]$^+$.

EXAMPLE 250

(3aα,4β,7β,7aα)-4-[4-[2-[(6-Chloro-1,2-benzisoxazol-3-yl)oxy]ethyl]octahydro-7-methyl-1,3-dioxo-4,7-epoxy-2H-isoindol-2-yl]-1-naphthalenecarbonitrile, (250)

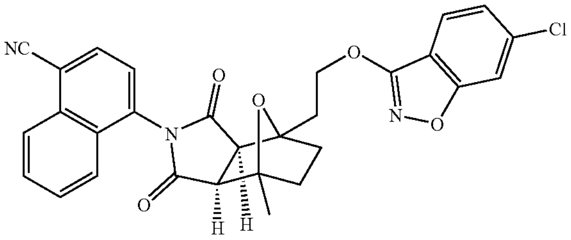

To a solution of $PPh_3$ (52 mg, 0.20 mmol) in 0.5 mL THF was added DBAD (46 mg, 0.20 mmol) as one solid portion. The resulting mixture was stirred for 10 min before 6-chloro-3-hydroxy-1,2-benzisoxazole (34 mg, 0.20 mmol) was added. Stirring was continued for 10 min before a solution of compound 223B (50 mg, 0.13 mmol) in 0.5 mL THF was introduced via canula. The resulting mixture was stirred at ambient temperature for 24 h, concentrated in vacuo and purified by reverse phase preparative HPLC (YMC S5 ODS 20×100 mm column; eluting with 30-100% aqueous MeOH containing 0.1% TFA over 10 min at 20 mL/min) to yield a white solid. The obtained solids were dissolved in $CH_2Cl_2$, washed with sat. $NaHCO_3$ solution, dried over $Na_2SO_4$ and concentrated in vacuo to yield 50 mg (71%) of compound 250 as a colorless oil. HPLC: 3.89 min & 4.02 min (atropisomers, retention time) (YMC S5 ODS column 4.6×50 mm Ballistic, 10-90% aqueous methanol over 4 minutes containing 0.2% $H3PO_4$, 4 mL/min, monitoring at 220 nm). MS (ES): m/z 528.4 $[M+H]^+$.

EXAMPLE 251

(3aα,4β,7β,7aα)-4-[Octahydro-4-methyl-7-[2-[(6-nitro-1H-indazol-3-yl)oxy]ethyl]-1,3-dioxo-4,7-epoxy-2H-isoindol-2-yl]-1-naphthalenecarbonitrile, (251)

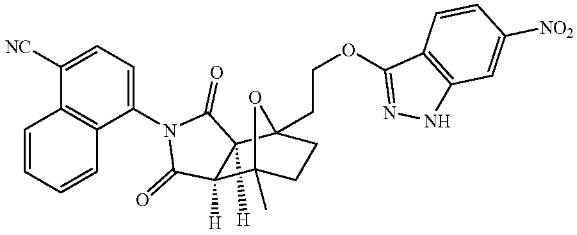

To a solution of compound 223B (50 mg, 0.13 mmol) in toluene (1 mL) was added ADDP (50 mg, 0.20 mmol), 6-nitro-3-indazolinone (36 mg, 0.20 mmol) and $n-Bu_3P$ (50 μL, 0.2 mmol). The resulting mixture was heated at 80° C. for 24 h, concentrated in vacuo and purified by a combination of reverse phase preparative HPLC (YMC S5 ODS 20×100 mm column; eluting with 30-100% aqueous MeOH containing 0.1% TFA over 10 min at 20 mL/min) and flash chromatography (silica gel, 25% acetone in $CHCl_3$) to give 17 mg (25%) of compound 251 as a yellow solid. HPLC: 3.60 min & 3.74 min (atropisomers, retention time) (YMC S5 ODS column 4.6×50 mm Ballistic, 10-90% aqueous methanol over 4 minutes containing 0.2% $H_3PO_4$, 4 mL/min, monitoring at 220 nm). MS (ES): m/z 537.6 $[M+H]^+$.

EXAMPLE 252

[3aS-(3aα,4β,5β,7β,7aα)]-4-[7-[2-(1,2-Benzisoxazol-3-yloxy)ethyl]octahydro-5-hydroxy-4-methyl-1,3-dioxo-4,7-epoxy-2H-isoindol-2-yl]-1-naphthalenecarbonitrile, (252)

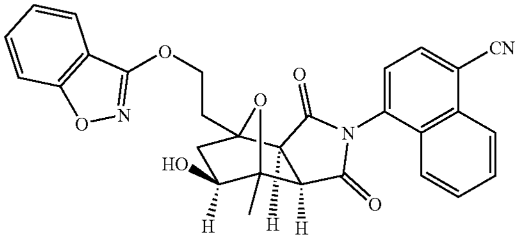

$PPh_3$ (47 mg, 0.18 mmol), DBAD (41 mg, 0.18 mmol), 3-hydroxy-1,2-benzisoxazole (24 mg, 0.18 mmol) and compound 243Di (35 mg, 0.09 mmol) were reacted according to the procedure given for compound 250. Purification was achieved by reverse phase HPLC (YMC S5 ODS 20×100 mm column; eluting with 30-100% aqueous MeOH containing 0.1% TFA over 10 min at 20 mL/min) to yield a white solid. The obtained solids were dissolved in $CH_2Cl_2$, washed with sat. $NaHCO_3$ solution, dried over $Na_2SO_4$ and concentrated under reduced pressure to furnish 29 mg (64%) of compound 252 as a colorless oil. HPLC: 96% at 3.29 min (atropisomers, retention time) (YMC S5 ODS column 4.6×50 mm Ballistic, 0-100% aqueous methanol over 4 minutes containing 0.2% $H_3PO_4$, 4 mL/min, monitoring at 220 nm). MS (ES): m/z 510.2 $[M+H]^+$.

EXAMPLE 253

[3aR-(3aα,4β,5β,7β,7aα)]-4-[7-[2-(1,2-Benzisoxazol-3-yloxy)ethyl]octahydro-5-hydroxy-4-methyl-1,3-dioxo-4,7-epoxy-2H-isoindol-2-yl]-1-naphthalenecarbonitrile, (253)

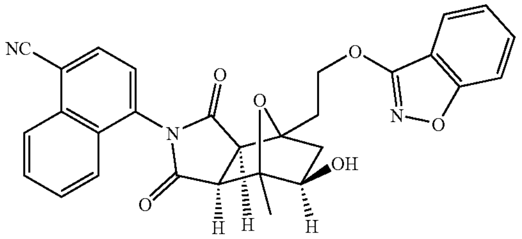

$PPh_3$ (47 mg, 0.18 mmol), DBAD (41 mg, 0.18 mmol), 3-hydroxy-1,2-benzisoxazole (24 mg, 0.18 mmol) and compound 243Dii (35 mg, 0.09 mmol) were reacted according to the procedure given for compound 250. Purification was achieved by reverse phase HPLC (YMC S5 ODS 20×100 mm column; eluting with 30-100% aqueous MeOH containing 0.1% TFA over 10 min at 20 mL/min) to yield a white solid. The obtained solids were dissolved in $CH_2Cl_2$, washed with sat. $NaHCO_3$ solution, dried over $Na_2SO_4$ and concentrated under reduced pressure to furnish 23 mg (51%) of compound 253 as a colorless oil. HPLC: 95% at 3.29 min (atropisomers, retention time) (YMC S5 ODS column 4.6×50 mm Ballistic, 0-100% aqueous methanol over 4 minutes containing 0.2% $H_3PO_4$, 4 mL/min, monitoring at 220 nm). MS (ES): m/z 510.4 $[M+H]^+$.

EXAMPLE 254

[3aR-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile & [3aS-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile, (254i & 254ii)

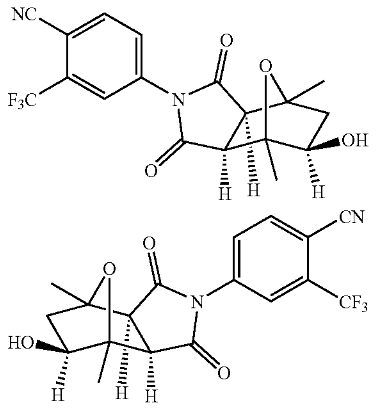

Racemic compound 221B was separated into its enantiomers by normal phase preparative chiral HPLC (CHIRALPAK AD 5×50 cm column; eluting with 20% MeOH/EtOH (1:1) in heptane (isocratic) at 50 mL/min) to give the faster eluting compound 254i (Chiral HPLC: 10.02 min; CHIRALPAK AD 4.6×250 mm column; eluting with 20% MeOH/EtOH (1:1) in heptane at 1 mL/min) and the slower eluting 254ii (Chiral HPLC: 14.74 min; CHIRALPAK AD 4.6×250 mm column; eluting with 20% MeOH/EtOH (1:1) in heptane at 1 mL/min). (Names of title compounds based on absolute stereochemistry determination).

EXAMPLE 255

(3aα,4β,7β,7aα)-2-(4-Cyano-1-naphthalenyl)octahydro-1,3-dioxo-7-[2-(phenylmethoxy)ethyl]-4,7-epoxy-4H-isoindole-4-propanenitrile & (3aα,4α,7α,7aα)-2-(4-Cyano-1-naphthalenyl)octahydro-1,3-dioxo-7-[2-(phenylmethoxy)ethyl]-4,7-epoxy-4H-isoindole-4-propanenitrile, (255Hi & 255Hii)

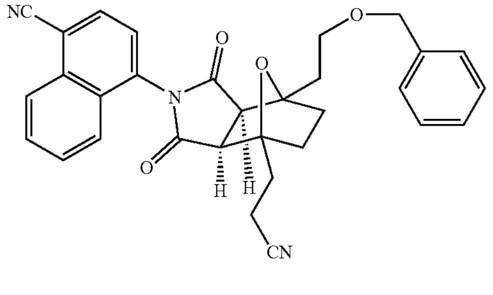

-continued

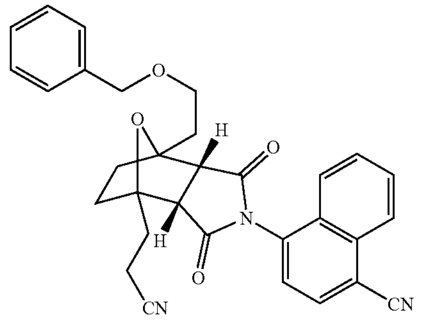

A. 2-(2-Hydroxyethyl)furan (255A)

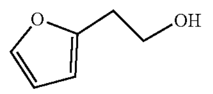

2-(2-Hydroxyethyl)furan was made in accordance with the following reference: Harmata, M, et al. *J. Org. Chem.* 60, 5077-5092 (1995). n-BuLi (2.5 M in hexane, 44 mL, 110 mmol) was added to a solution of furan (8 mL, 110 mmol) in 100 mL of THF at −78° C. The solution was stirred at 0° C. for 4 h and then ethylene oxide (7.5 mL) was added at −78° C. The reaction mixture was stirred at −15° C. for 1 h and then overnight at rt. The reaction was quenched with sat. $NH_4Cl$ and extracted with ether (3×). The combined extracts were washed with water (1×) and brine (1×). The ether solution was dried over $Na_2SO_4$ and concentrated under reduced pressure. Purification by flash chromatography on silica gel eluting with 40% EtOAc/60% hexane gave 5.4 g (48.2 mmol, 43.8%) of compound 255A as a light brown oil.

B. 2-[2-[[(1,1-Dimethlethyl)dimethylsilyl]oxy]ethyl]furan (255B)

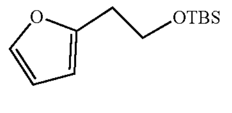

Imidazole (3.65 g, 53.6 mmol) and TBSCl (6.47 g, 42.9 mmol) were added to the solution of compound 255A (4.00 g, 35.7 mmol) in 50 mL of DMF. The mixture was stirred at rt for 2 h and then the reaction mixture was poured into ether. The ether solution was washed with water (1×), 1 N HCl (1×), water (1×) and brine (1×). The organic layer was dried over $Na_2SO_4$ and concentrated under reduced pressure. Purification by flash chromatography on silica gel eluting with 30% $CH_2Cl_2$/70% hexane gave 7.4 g (32.7 mmol, 91.7%) of 255B as a colorless oil.

C. 2-[2-[[(1,1-Dimethlethyl)dimethylsilyl]oxy]ethyl]-5-(2-hydroxyethyl)furan (255C)

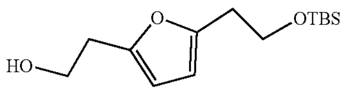

t-BuLi (1.2 M in pentane, 10 mL, 16.99 mmol) was added to a stirred solution of 255B (3.49 g, 15.44 mmol) in 13 mL of THF at −78° C. dropwise. The mixture was stirred for an additional 4 h at 0° C. Ethylene oxide (1.05 mL) was added at −78° C. to the reaction solution. The mixture was warmed to rt and stirred overnight. Aqueous sat. $NH_4Cl$ was added and most of the THF was removed under reduced pressure. The mixture was extracted with ether (3×) and the combined organic layers were washed with water (1×) and brine (1×) and dried over $Na_2SO_4$. Purification by flash chromatography on silica gel eluting with 5% EtOAc/95% $CH_2Cl_2$ gave 2.8 g (10.4 mmol, 67%) of compound 255C as a yellow oil.

D. 2-[2-[[(1,1-Dimethlethyl)dimethylsilyl]oxy]ethyl]-5-[2-(phenylmethoxy)ethyl]furan (255D)

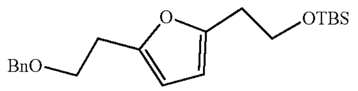

The alcohol 255C (1.00 g, 3.7 mmol) in 12 mL of THF was treated with 60% NaH (177.8 mg, 4.44 mmol), benzyl bromide (0.53 mL, 4.44 mmol) and tetrabutylammonium iodide (50 mg, 5%) for 3 h at rt. Water was added and the mixture was extracted with EtOAc (3×). The combined extracts were washed with water (1×) and brine (1×) and dried over $Na_2SO_4$. Purification by flash chromatography on silica gel eluting with 20% hexane/80% $CH_2Cl_2$ gave 1.10 g (3.05 mmol, 82.6%) of compound 255D as a yellow oil.

E. 2-(2-Hydroxyethyl)-5-[2-(phenylmethoxy)ethyl]furan (255E)

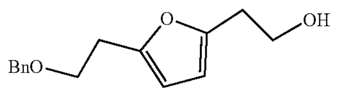

Tetrabutylammonium fluoride (1.0M in THF, 3.06 mL, 3.06 mmol) was added to the solution of compound 255D (1.1 g, 3.06 mmol) in 10 mL of THF at 0° C. The reaction mixture was stirred at rt for 10 minutes, quenched by sat. $NH_4Cl$ and extracted with ether (3×). The combined extracts were dried over $Na_2SO_4$. Purification by flash chromatography on silica gel eluting with 10% EtOAc/90% $CH_2Cl_2$ gave 750 mg (3.05 mmol, 99.6%) of compound 255E as a light yellow oil.

F. 5-[2-(Phenylmethoxy)ethyl]furan-2-propanenitrile (255F)

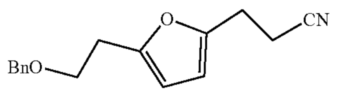

DEAD (1.285 mL, 8.17 mmol) was added to a stirred solution of $Ph_3P$ (2.14 g, 8.17 mmol) in 12 mL of dry THF at 0° C. The solution was stirred for 30 min at rt and compound 255E (670 mg, 2.72 mmol) was added. The reaction was stirred for 15 min and acetone cyanohydrin (0.745 mL, 8.17 mmol) was added at −15° C. The reaction was stirred for 30 min at −15° C., then at rt overnight. The mixture was then concentrated under reduced pressure. Purification by flash chromatography on silica gel eluting with 100% $CH_2Cl_2$ gave 180 mg (0.705 mmol, 26%) of compound 255F as a colorless oil.

G. (3aα,4β,7β,7aα)-2-(4-Cyano-1-naphthalenyl)-1,2,3,3a,7,7a-hexahydro-1,3-dioxo-7-[2-(phenylmethoxy)ethyl]-4,7-epoxy-4H-isoindole-4-propanenitrile (255G)

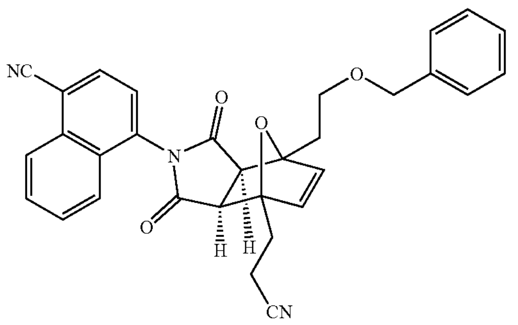

A solution of compound 255F (180 mg, 0.706 mmol) and 4-(2,5-dihydro-2,5-dioxo-1H-1-yl)-1-naphthalenecarbonitrile (263 mg, 1.06 mmol) in $CH_2Cl_2$ (3 mL) was stirred at rt for 3 days. The reaction mixture was concentrated under reduced pressure. Purification by flash chromatography on silica gel eluting with 5% EtOAc/$CH_2Cl_2$ gave 318 mg (0.63 mmol, 89.6%) of compound 255G as a light gray solid which was used directly in the next step.

H. (3aα,4β,7β,7aα)-2-(4-Cyano-1-naphthalenyl)octahydro-1,3-dioxo-7-[2-(phenylmethoxy)ethyl]-4,7-epoxy-4H-isoindole-4-propanenitrile & (3aα,4α,7α,7aα)-2-(4-Cyano-1-naphthalenyl)octahydro-1,3-dioxo-7-[2-(phenylmethoxy)ethyl]-4,7-epoxy-4H-isoindole-4-propanenitrile (255Hi & 255Hii)

A mixture of compound 255G (318 mg, 0.63 mmol) and 10% Pd/C (64 mg) in EtOH (10 mL) and EtOAc (5 mL) was stirred under a hydrogen atmosphere at rt overnight. The reaction mixture was filtered through Celite and concentrated under reduced pressure to give 320 mg of crude compounds 255Hi & 255Hii. Purification of 25 mg of this crude product by flash chromatography on silica gel eluting with 55% EtOAc/hexane gave 6.5 mg (0.013 mmol, 26% (based on 25 mg)) of compound 255Hi & 8.1 mg (0.016 mmol, 32.4% (based on 25 mg)) of compound 255Hii. Compound 255Hi: HPLC conditions: 98% at 3.57 min (retention time) (YMC S5 ODS 4.6×50 mm, 10%-90% aqueous methanol over 4 minute gradient with 0.2% $H_3PO_4$, detecting at 220 nm, MS (ES): m/z 506.15 $[M+H]^+$. Compound 255Hii: HPLC conditions: 98% at 3.51 min (retention time) (YMC S5 ODS 4.6×50 mm, 10%-90% aqueous methanol over 4 minute gradient with 0.2% $H_3PO_4$, detecting at 220 nm). MS (ES): m/z 506.15 $[M+H]^+$.

EXAMPLE 256

(3aα,4β,7β,7aα)-2-(4-Cyano-1-naphthalenyl)octahydro-7-(2-hydroxyethyl)-1,3-dioxo-4,7-epoxy-4H-isoindole-4-propanenitrile & (3aα,4α,7α,7aα)-2-(4-Cyano-1-naphthalenyl)octahydro-7-(2-hydroxyethyl)-1,3-dioxo-4,7-epoxy-4H-isoindole-4-propanenitrile, (256i & 256ii)

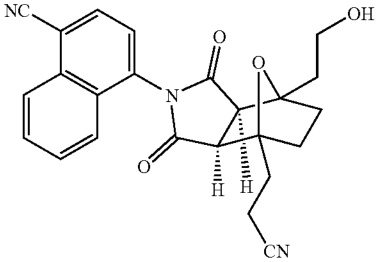

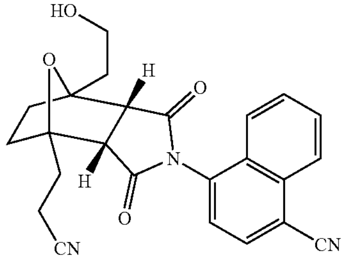

A mixture of compounds 255Hi & 255Hii (200 mg, 0.396 mmol) and $PdCl_2$ (8.4 mg, cat.) in EtOH (1 mL) and EtOAc (3 mL) was stirred under a hydrogen atmosphere (30 psi) at rt overnight. The reaction mixture was filtered through Celite and concentrated under reduced pressure. Purification by flash chromatography on silica gel eluting with 5% MeOH/$CH_2Cl_2$ followed by a second column eluting with 100% EtOAc gave 28.9 mg (0.0696 mmol, 17.6%) of compound 256ii and 26.5 mg (0.0639 mmol, 16.1%) of compound 256i. Compound 256ii: HPLC conditions: 90% at 2.44 min (retention time) (YMC S5 ODS 4.6×50 mm, 10%-90% aqueous methanol over 4 minute gradient with 0.2% $H_3PO_4$, detecting at 220 nm.). MS (ES): m/z 416.11 $[M+H]^+$. Compound 256i: HPLC conditions: 99% at 2.47 min (retention time) (YMC S5 ODS 4.6×50 mm, 10%-90% aqueous methanol over 4 minute gradient with 0.2% $H_3PO_4$, detecting at 220 nm). MS (ES): m/z 416.11 $[M+H]^+$.

EXAMPLE 257

(3aα,4β,7β,7aα)-2-(4-Cyano-1-naphthalenyl)-7-[2-(4-fluorophenoxy)ethyl]octahydro-1,3-dioxo-4,7-epoxy-4H-isoindole-4-propanenitrile, (257)

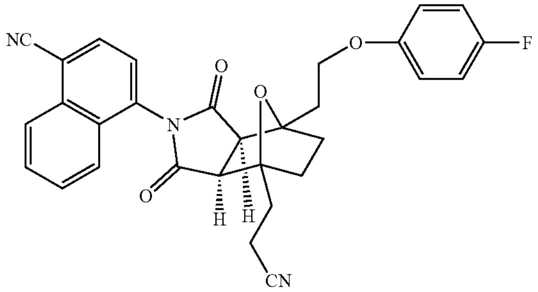

DBAD (15 mg, 0.065 mmol) was added to a solution of $PPh_3$ (17 mg, 0.065 mmol) in THF (0.3 mL). After stirring for 10 min, 4-fluorophenol (7.33 mg, 0.065 mmol) was added and the reaction mixture was stirred for a further 5 min. Compound 256i (18.1 mg, 0.044 mmol) was added and the mixture was stirred at rt for 3 h. The reaction was concentrated under reduced pressure. Purification by flash chromatography on silica gel eluting with 60% EtOAc/30% hexane gave 5.9 mg (0.0116 mmol, 26.34%) of compound 257. HPLC conditions: 98% at 3.59 min (retention time) (YMC S5 ODS 4.6×50 mm, 10%-90% aqueous methanol over 4 minute gradient with 0.2% $H_3PO_4$, detecting at 220 nm). MS (ES): m/z 510.14 $[M+H]^+$.

EXAMPLE 258

(3aα,4β,7β,7aα)-2-(7-Chloro-2,1,3-benzoxadiazol-4-yl)hexahydro-4,7-dimethyl-4,7-epoxy-1H-isoindole-1,3(2H)-dione, (258)

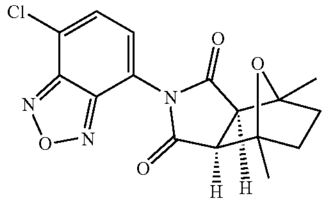

A. 4-Amino-7-chloro-2,1,3-benzoxadiazole (258A)

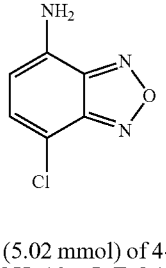

A solution of 1.0 g (5.02 mmol) of 4-chloro-7-nitrobenzofurazan in 20 mL AcOH, 10 mL EtOAc and 2 mL $H_2O$ was heated at 50° C. and treated with iron powder (1.4 g, 251 mmol). The mixture was heated at 80° C. for 30 min and then allowed to cool to rt. The mixture was filtered through Celite eluting with EtOAc. The filtrate was washed with sat. aq. $NaHCO_3$, dried over $MgSO_4$, and concentrated under reduced pressure to give compound 258A (0.80 g, 94%) as a red solid.

B. (3aα,4β,7β,7aα)-2-(7-Chloro-2,1,3-benzoxadiazol-4-yl)hexahydro-4,7-dimethyl-4,7-epoxy-1H-isoindole-1,3(2H)-dione, (258B)

Compound 258A (42 mg, 0.25 mmol) was reacted in a sealed tube with compound 20A (73.5 mg, 0.375 mmol), $MgSO_4$ (75 mg, 0.625 mmol) and $Et_3N$ (170 μL, 1.25 mmol) in 250 μL toluene according to the above procedure described in example 208C to give after purification by reverse phase preparative HPLC (YMC S5 ODS 20×100 mm eluting with 30-100% aqueous methanol containing 0.1% TFA over 12 min, 20 mL/min) 23 mg (26%) of compound 258B as a yellow solid. HPLC: 97.6% at 2.87 min (retention time) (YMC S5 ODS column 4.6×50 mm eluting with 10-90% aqueous methanol containing 0.2% phosphoric acid over 4 minutes, 4 mL/min, monitoring at 220 nm). MS (DCI): m/z 347.9 $[M]^+$.

EXAMPLE 259

(3aα,4β,7β,7aα)-2-(7-Chloro-2-methyl-4-benzofuranyl)hexahydro-4,7-dimethyl-4,7-epoxy-1H-isoindole-1,3(2H)-dione, (259)

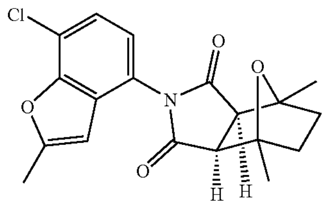

7-Chloro-2-methyl-4-benzofuranamine (38 mg, 0.25 mmol, prepared in accordance with the procedure described by Enomoto and Takemura in EP 0476697 A1) was reacted in a sealed tube with compound 20A (73.5 mg, 0.375 mmol), $MgSO_4$ (75 mg, 0.625 mmol) and $Et_3N$ (170 μL, 1.25 mmol) in 250 μL toluene according to the procedure described in example 208C to give, after purification by reverse phase preparative HPLC (YMC S5 ODS 20×100 mm eluting with 30-100 aqueous methanol containing 0.1% TFA over 12 min, 20 mL/min), 42 mg (47%) of compound 259 as a white solid. HPLC: 98% at 3.45 min (retention time) (YMC S5 ODS column 4.6×50 mm eluting with 10-90% aqueous methanol over 4 minutes containing 0.2% phosphoric acid, 4 mL/min, monitoring at 220 nm). MS (DCI): m/z 359.9 $[M]^+$.

EXAMPLE 260

(3aα,4β,7β,7aα)-2-(7-Chloro-2-methylbenzo[b]thiophen-4-yl)hexahydro-4,7-dimethyl-4,7-epoxy-1H-isoindole-1,3(2H)-dione, (260)

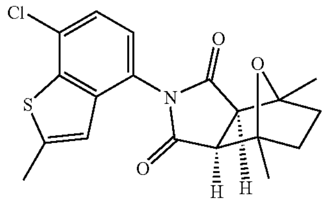

A. 1-Chloro-2-(2-chloro-allylsulfanyl)-4-nitro-benzene (260A)

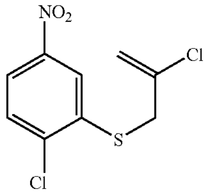

A solution of 2-chloro-5-nitro-benzenethiol (1.0 g, 5.27 mmol, prepared in accordance with the procedure described by Still et al. *Synth. Comm.* 13, 1181 (1983)) in 15 mL DMF was treated with 2,3-dichloropropene (693 μL, 7.52 mmol) and $K_2CO_3$ (433 mg, 3.13 mmol). The mixture was heated at 80° C. for 2 h and then allowed to cool to rt. EtOAc (200 mL) and $H_2O$ (100 mL) were added. The organic phase was washed with $H_2O$ (2×250 mL), saturated aqueous NaCl (100 mL), dried over $MgSO_4$, and concentrated in vacuo. The crude material was purified by flash column chromatography on silica gel eluting with 20% EtOAc in hexanes to give compound 260A (1.09 g, 89%) as an orange oil.

B. 4-Amino-7-chloro-2-methylbenzo[b]thiophene (260B)

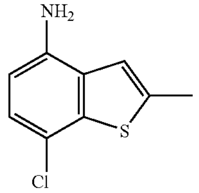

A solution of 1.09 g (4.67 mmol) of compound 260A in 20 mL AcOH with 10 mL EtOAc and 2 mL $H_2O$ was heated to 80° C. and treated with iron powder (1.3 g, 23.4 mmol). The mixture was heated at 80° C. for 40 min and then allowed to cool to rt. The mixture was filtered through Celite eluting with EtOAc. The filtrate was washed with sat. aq. $NaHCO_3$, dried over $MgSO_4$, and concentrated in vacuo. N,N-diethylaniline (10 mL) was added, and the reaction was heated at 215° C. for 6 h. After cooling to rt, 1 N aqueous HCl (20 mL) was added, and the reaction was stirred at room temperature for 2 h. The mixture was extracted with EtOAc (3×30 mL). The organic phase was washed with saturated aqueous $NaHCO_3$, dried over $MgSO_4$, and concentrated in vacuo. The crude material was purified by flash column chromatography on silica gel eluting with 25% EtOAc in hexanes to give compound 260B (320 mg, 35%) as a beige solid.

C. (3aα,4β,7β,7aα)-2-(7-Chloro-2-methylbenzo[b]thiophen-4-yl)hexahydro-4,7-dimethyl-4,7-epoxy-1H-isoindole-1,3(2H)-dione, (260C)

Compound 260B (49 mg, 0.25 mmol) was reacted in a sealed tube with compound 20A (73.5 mg, 0.38 mmol), $MgSO_4$ (75 mg, 0.63 mmol) and $Et_3N$ (170 μL, 1.25 mmol) in 250 μL toluene according to the procedure described in example 208C to give, after purification by reverse phase preparative HPLC (YMC S5 ODS 20×100 mm eluting with 30-100% aqueous methanol over 12 mincontaining 0.1% TFA, 20 mL/min), 28 mg (30%) of compound 260C as a pale yellow solid. HPLC: 96% at 3.18 min (retention time) (YMC S5 ODS column 4.6×50 mm eluting with 10-90% aqueous methanol over 4 minutes containing 0.2% phosphoric acid, 4 mL/min, monitoring at 220 nm). MS (DCI): m/z 376.0 $[M]^+$.

EXAMPLE 261

[3aα,4β(E),7β,7aα]-4-[2-(4-Cyano-1-naphthalenyl) octahydro-7-methyl-1,3-dioxo-4,7-epoxy-4H-isoindol-4-yl]-2-butenoic acid, phenylmethyl ester, (261)

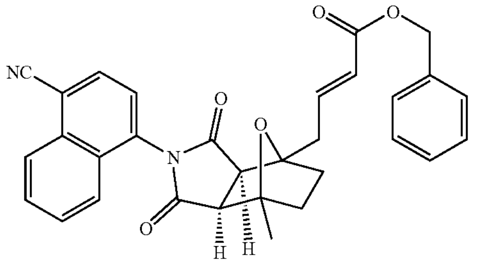

Compound 247 (0.500 g, 1.34 mmol) was dissolved in THF (20 mL) and benzyl(triphenylphosphoranylidene) (0.55 g, 1.34 mmol) was added. The reaction mixture was stirred at 67° C. for 2 h and then concentrated under reduced pressure. Purification by flash chromatography on $SiO_2$ eluting with 5% acetone/95% $CHCl_3$ gave 0.65 g of compound 261 as a yellow solid. HPLC: 99% at 3.717 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 507.1 $[M+H]^+$.

EXAMPLE 262

(3aα,4β,7β,7aα)-2-(4-Cyano-1-naphthalenyl)octahydro-7-methyl-1,3-dioxo-4,7-epoxy-4H-isoindole-4-butanoic acid, (262)

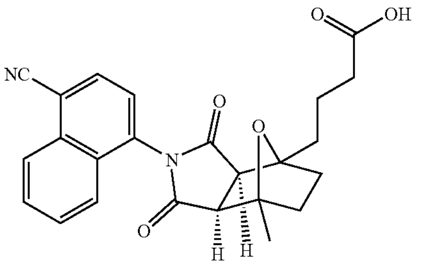

Compound 261 (0.60 g, 1.19 mmol) was dissolved in EtOH/EtOAc (5 mL/5 mL) and 10% Pd/C (0.30 g) was added. Hydrogen was then introduced via a balloon. After 8 h the reaction was filtered through Celite and then concentrated under reduced pressure to give compound 262 (0.47 g) as a white solid. HPLC: 98% at 2.81 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 419.1 $[M+H]^+$.

EXAMPLE 263

(3aα,4β,7β,7aα)-2-(4-Cyano-1-naphthalenyl)-N-(4-fluorophenyl)octahydro-7-methyl-1,3-dioxo-4,7-epoxy-4H-isoindole-4-butanamide (263)

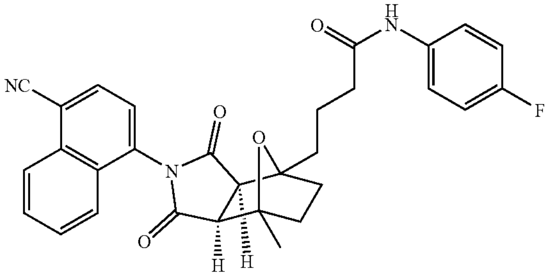

Compound 262 (0.030 g, 0.072 mmol) was dissolved in $CH_3CN$ (1 mL). DCC (0.014 g, 0.072 mmol) and HOAc (0.0098 g, 0.072 mmol) were then added, followed by 4-fluoroaniline (0.007 mL, 0.072 mmol). The reaction mixture was stirred under argon for 14 h and the crude material was dissolved in MeOH, purified by reverse phase preparative HPLC (YMC VP-ODS column, 20×100 mm, eluting with 20% B to 100% B in 15 minutes and hold @ 100% B for 10 minutes). Compound 263 (0.020 g) was isolated as white solid. HPLC: 100% at 3.217 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 512.1 $[M+H]^+$.

EXAMPLE 264

[3aS-(3aα,4β,5β,7β,7aα)]-4-[7-[2-(Acetyloxy)ethyl] octahydro-5-hydroxy-4-methyl-1,3-dioxo-4,7-epoxy-2H-isoindol-2-yl]-1-naphthalenecarbonitrile & [3aR-(3α,4β,5β,7β,7aα)]-4-[Octahydro-5-hydroxy-7-(2-hydroxyethyl)-4-methyl-1,3-dioxo-4,7-epoxy-2H-isoindol-2-yl]-1-naphthalenecarbonitrile, (264 & 243Dii)

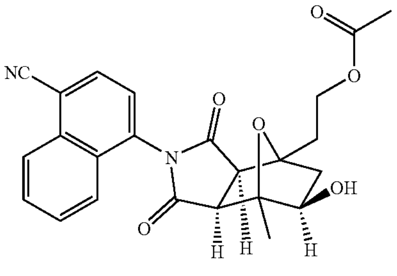

-continued

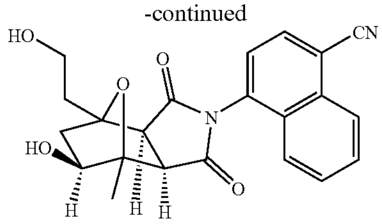

A racemic mixture of compounds 243Di & 243Dii (1.90 gram) were dissolved in 100 mL of anhydrous THF in a 2 L flask. Anhydrous tert-butyl-methyl ether (900 mL) and vinyl acetate (40 mL) were transferred into the flask with stirring and lipase (20 g, typeII, crude, from porcine pancreas; Sigma, Cat# L3126) was added. The reaction mixture was stirred for 21 hr at rt at which point an additional 5 grams of the lipase and 20 mL of vinyl acetate were added. The reaction was stirred at rt for an additional 19 h, stored at 4° C. without stirring for 36 h and then stirred at rt for another 22 h (until the desired % ee was apparent by chiral HPLC). To monitor the reaction, 200 uL of the mixture was withdrawn and centrifuged. The supernatant (100 uL) was dried under nitrogen and the resulting residue was dissolved in 100 uL of EtOH and subjected to HPLC analysis:

1) Reverse phase HPLC: Column, YMC-ODS AQ 150×4.6; flow rate, 1.2 mL/min; sample size, 10 uL solvent A,: 1 mM HCl in water; solvent B, MeCN; monitored at 300 nm

| Gradient: | | | | | | |
|---|---|---|---|---|---|---|
| Time(min) | 0 | 8 | 8.5 | 9.5 | 10 | 12 |
| B % | 30 | 60 | 85 | 85 | 30 | 30 |

2) Chiral-HPLC: Column, CHIRALCEL OJ 4.6×250 mm mobile phase, hexanes/MeOH/EtOH (8:1:1) flow rate, 1 mL/min; sample size, 20 uL monitored at both 220 and 300 nm performed at 25° C. & 40° C. (for ee % determination of reaction mixture)

The enzyme was removed by filtration and filtrate was concentrated under reduced pressure. The resulting mixture was dissolved in $CHCl_3$ and adsorbed onto silica gel (63-200 microns). These solids were applied to a VLC funnel (3 cm I.D., VLC is vacuum liquid chromatography using glass funnels having 24/40 joints at the bottom) containing a 5 cm bed height of silica gel (25-40 microns) and a step gradient was carried out. The gradient was 100% $CHCl_3$ in the first 3 fractions, followed by $CHCl_3$-1% MeOH (3 fractions), $CHCl_3$-2% MeOH (3 fractions), $CHCl_3$-3% MeOH (3 fractions), $CHCl_3$-4% MeOH (3 fractions), and finally with $CHCl_3$-5% MeOH (3 fractions). The volume of the fractions was 100 mL until reaching $CHCl_3$-3% MeOH and from that point on it was 200 mL. Compound 264 elutes in the last two fractions of 100% $CHCl_3$ and until the first fraction of $CHCl_3$-2% MeOH. Compound 243Dii elutes starting with the second fraction of $CHCl_3$-2% MeOH, and continues to the first fraction of $CHCl_3$-5% MeOH. The crude compound 243Dii contained a small amount of a colored impurity which was removed by a Sephadex column [LH-20 swollen in $CHCl_3$-MeOH (2:1), column (2.5 cm I.D. & 90 cm long) to yield 632 mg of compound 243Dii. Compound 264: HPLC conditions: 98% at 7.2 min (retention time) (method 1), chiral HPLC conditions: 29.0 min @ 25° C. (method 2). Compound 243Dii: HPLC conditions: 98% at 4.6 min (retention time) (method 1), chiral HPLC conditions: 96% ee at 25.7 min (retention time) (@ 25° C.) & 19.8 min (retention time) (@ 40° C.) (method 2).

EXAMPLE 265

(3aα,4β,7β,7aα(E)]-4-[Octahydro-4-methyl-1,3-dioxo-7-(4-oxo-4-phenyl-2-butenyl)-4,7-epoxy-2H-isoindol-2-yl]-1-naphthalenecarbonitrile, (265)

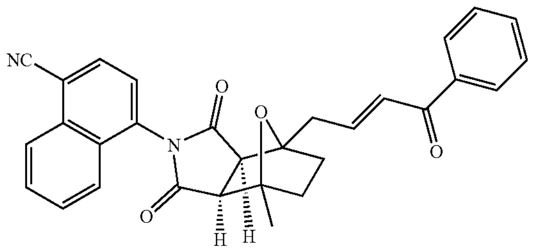

The compound 247 (0.050 g, 0.134 mmol) was dissolved in THF (1.5 mL) and (phenacylidene)triphenylphosphorane (0.051 g, 0.134 mmol) was added. The reaction mixture was stirred at 67° C. for 24 h and then cooled to 23° C. and concentrated in vacuo. The crude material was then purified by reverse phase preparative HPLC. (YMC VP-ODS column, 20×100 mm, eluting with 20% B to 100% B in 15 minutes and hold @ 100% B for 10 minutes.) to give compound 265 (0.040 g) as white solid. HPLC: 100% at 3.503 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 477.1 $[M+H]^+$.

EXAMPLE 266

(3aα,4β,7β,7aα(E)]-4-[Octahydro-4-methyl-1,3-dioxo-7-(4-hydroxy-4-phenyl-2-butyl)-4,7-epoxy-2H-isoindol-2-yl]-1-naphthalenecarbonitrile, (266)

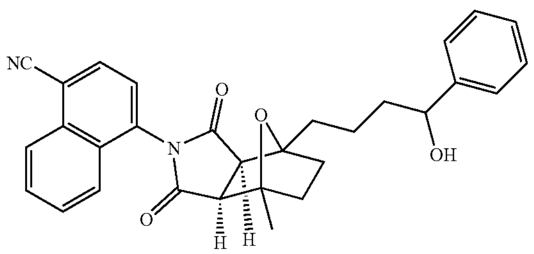

Compound 265 (0.010 g, 0.021 mmol) was dissolved in EtOH (2.0 mL) and Pd/C (10% Pd, 0.005 g) was added. Hydrogen was then introduced via a balloon and the reaction was stirred at 25° C. for 3 h. The reaction was then filtered through Celite rinsing with EtOAc and concentrated in vacuo to give compound 266 as a tan solid (0.009 g). No purification was necessary. HPLC: 100% at 3.38 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 503.2 [M+Na]$^+$. (Where this reaction was run for 1 hour, the resulting product was compound 455.)

EXAMPLES 267 TO 378

Additional compounds of the present invention were prepared by procedures analogous to those described above. The compounds of Examples 267 to 378 have the following structure (L is a bond):

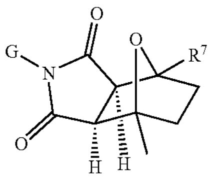

where G, $R^7$, the compound name, retention time, molecular mass, and the procedure employed, are set forth in Table 5.

The absolute configuration for the following compounds was not determined. For simplicity in nomenclature, compound 238i is designated herein as having an "R" configuration and compound 238ii as having an "S" configuration. Enantiomerically pure products derived from compound 238i are designated herein as having an "R" configuration and enantiomerically pure products derived from compound 238ii are designated herein as having an "S" configuration.

The chromatography techniques used to determine the compound retention times of Table 5 are as follows: LCMS=YMC S5 ODS column, 4.6x50 mm eluting with 10-90% MeOH/$H_2O$ over 4 minutes containing 0.1% TFA; 4 mL/min, monitoring at 220 nm. LCMS*=YMC S5 ODS column, 4.6x50 mm eluting with 10-90% MeOH/$H_2O$ over 2 minutes containing 0.1% TFA; 4 mL/min, monitoring at 220 nm. LC=YMC S5 ODS column 4.6x50 mm eluting with 10-90% MeOH/$H_2O$ over 4 minutes containing 0.2% phosphoric acid, 4 mL/min, monitoring at 220 nm. The molecular mass of the compounds listed in Table 5 were determined by MS (ES) by the formula m/z.

TABLE 5

| Ex. No | G | $R^7$ | Compound Name | Retention Time Min./ Molecular Mass | Procedure of Ex. |
|---|---|---|---|---|---|
| 267 | 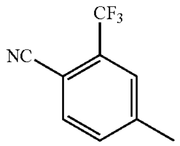 | 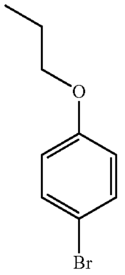 | (3aα,4β,7β,7aα)-(4-[7-[2-(4-Bromophenoxy) ethyl]octahydro-4-methyl-1,3-dioxo-4,7-epoxy-2H-isoindol-2-yl]-2-(trifluoromethyl) benzonitrile.. | 3.97 LCMS 549.0 [M + H]$^+$ | 204, 35 |
| 268 | 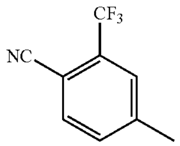 | 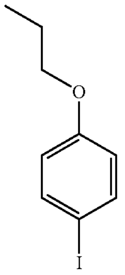 | (3aα,4β,7β,7aα)-4-[Octahydro-7-[2-(4-iodophenoxy) ethyl]-4-methyl-1,3-dioxo-4,7-epoxy-2H-isoindol-2-yl]-2-(trifluoromethyl) benzonitrile. | 4.09 LCMS 597.0 [M + H]$^+$ | 204, 35 |
| 269 | 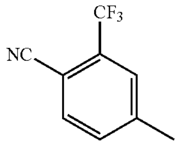 | 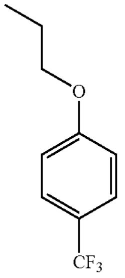 | (3aα,4β,7β,7aα)-4-[Octahydro-4-methyl-1,3-dioxo-7-[2-[4-(trifluoromethyl) phenoxy]ethyl]-4,7-epoxy-2H-isoindol-2-yl]-2-(trifluoromethyl) benzonitrile. | 3.95 LC | 204, 35 |

TABLE 5-continued

| Ex. No | G | R7 | Compound Name | Retention Time Min./ Molecular Mass | Procedure of Ex. |
|---|---|---|---|---|---|
| 270 | 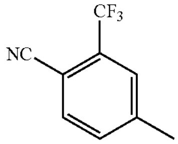 | 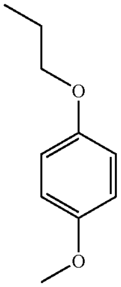 | (3aα,4β,7β,7aα)-4-[Octahydro-7-[2-(4-methoxyphenoxy) ethyl]-4-methyl-1,3-dioxo-4,7-epoxy-2H-isoindol-2-yl]-2-(trifluoromethyl) benzonitrile. | 3.66 LC | 204, 35 |
| 271 | 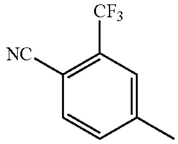 | 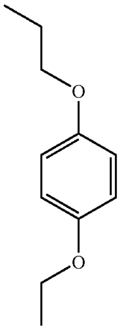 | (3aα,4β,7β,7aα)-4-[7-[2-(4-Ethoxyphenoxy) ethyl]octahydro-4-methyl-1,3-dioxo-4,7-epoxy-2H-isoindol-2-yl]-2-(trifluoromethyl) benzonitrile. | 3.81 LC | 204, 35 |
| 272 | 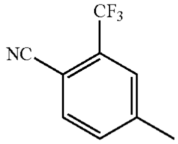 | 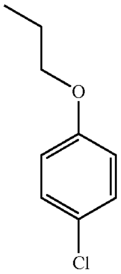 | (3aα,4β,7β,7aα)-4-[7-[2-(4-Chlorophenoxy) ethyl]octahydro-4-methyl-1,3-dioxo-4,7-epoxy-2H-isoindol-2-yl]-2-(trifluoromethyl) benzonitrile. | 3.97 LCMS 522.2 $[M + H]^+$ | 204, 35 |
| 273 | 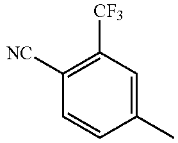 | 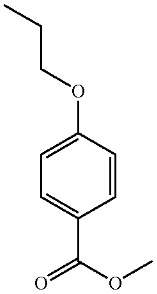 | (3aα,4β,7β,7aα)-4-[2-[2-[4-Cyano-3-(trifluoromethyl) phenyl]octahydro-7-methyl-1,3-dioxo-4,7-epoxy-4H-isoindol-4-yl]ethoxy]benzoic acid, methyl ester. | 3.77 LCMS 529.12 $[M + H]^+$ | 204, 35 |
| 274 | 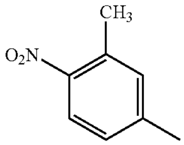 | 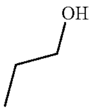 | (3aα,4β,7β,7aα)-Hexahydro-4-(2-hydroxyethyl)-7-methyl-2-(3-methyl-4-nitrophenyl)-4,7-epoxy-1H-isoindole-1,3(2H)-dione. | 2.44 LC | 204, 35 |

TABLE 5-continued

| Ex. No | G | $R^7$ | Compound Name | Retention Time Min./ Molecular Mass | Procedure of Ex. |
|---|---|---|---|---|---|
| 275 | 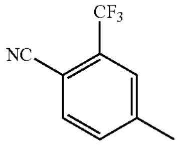 | 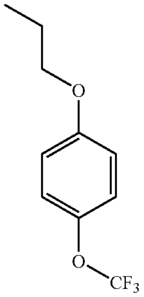 | (3aα,4β,7β,7aα)-4-[Octahydro-4-methyl-1,3-dioxo-7-[2-[4-(trifluoromethoxy)phenoxy]ethyl]-4,7-epoxy-2H-isoindol-2-yl]-2-(trifluoromethyl)benzonitrile. | 3.97 LC | 204, 35 |
| 276 | 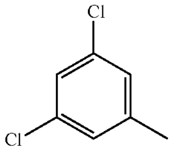 | $CH_3$ | (3aα,4β,7β,7aα)-2-(3,5-Dichlorophenyl)hexahydro-4,7-dimethyl-4,7-epoxy-1H-isoindole-1,3(2H)-dione. | 3.31 LCMS 341.2 $[M + H]^+$ | 20 |
| 277 | 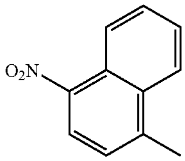 | $CH_3$ | (3aα,4β,7β,7aα)-Hexahydro-4,7-dimethyl-2-(4-nitro-1-naphthalenyl)-4,7-epoxy-1H-isoindole-1,3(2H)-dione. | 3.04 LCMS | 20 |
| 278 | 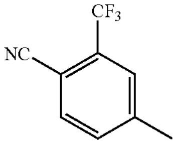 | 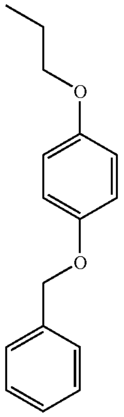 | (3aα,4β,7β,7aα)-4-[Octahydro-4-methyl-1,3-dioxo-7-[2-[4-(phenylmethoxy)phenoxy]ethyl]-4,7-epoxy-2H-isoindol-2-yl]-2-(trifluoromethyl)benzonitrile. | 4.06 LC | 204, 35 |
| 279 | 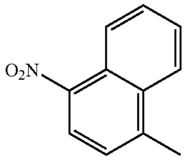 | 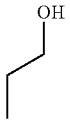 | (3aα,4β,7β,7aα)-Hexahydro-4-(2-hydroxyethyl)-7-methyl-2-(4-nitro-1-naphthalenyl)-4,7-epoxy-1H-isoindole-1,3(2H)-dione. | 2.607 & 2.743 rotational isomers LC | 204, 35 |
| 280 | 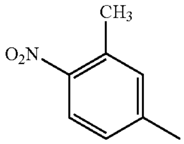 | 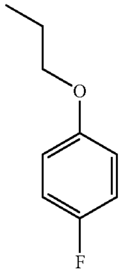 | (3aα,4β,7β,7aα)-4-[2-(4-Fluorophenoxy)ethyl]hexahydro-7-methyl-2-(3-methyl-4-nitrophenyl)-4,7-epoxy-1H-isoindole-1,3(2H)-dione. | 3.68 LC | 204, 35 |

TABLE 5-continued

| Ex. No | G | $R^7$ | Compound Name | Retention Time Min./ Molecular Mass | Procedure of Ex. |
|---|---|---|---|---|---|
| 281 | 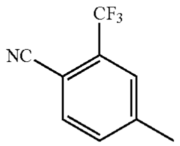 | 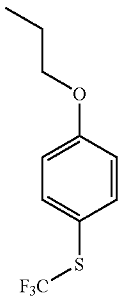 | (3aα,4β,7β,7aα)-4-[Octahydro-4-methyl-1,3-dioxo-7-[2-[4-[(trifluoromethyl)thio]phenoxy]ethyl]-4,7-epoxy-2H-isoindol-2-yl]-2-(trifluoromethyl)benzonitrile. | 4.11 LC | 204, 35 |
| 282 | 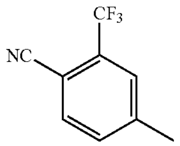 | 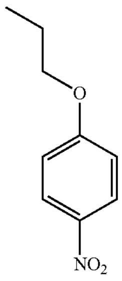 | (3aα,4β,7β,7aα)-4-[Octahydro-4-methyl-7-[2-(4-nitrophenoxy)ethyl]-1,3-dioxo-4,7-epoxy-2H-isoindol-2-yl]-2-(trifluoromethyl)benzonitrile. | 3.68 LC | 204, 35 |
| 283 | 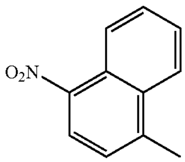 | 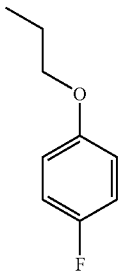 | (3aα,4β,7β,7aα)-4-[2-(4-Fluorophenoxy)ethyl]hexahydro-7-methyl-2-(4-nitro-1-naphthalenyl)-4,7-epoxy-1H-isoindole-1,3(2H)-dione. | 3.68 & 3.80 rotational isomers LC | 204, 35 |
| 284 | 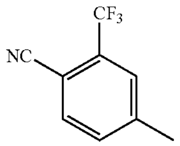 | 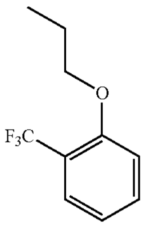 | (3aα,4β,7β,7aα)-4-[Octahydro-7-methyl-1,3-dioxo-7-[2-[2-(trifluoromethyl)phenoxy]ethyl]-4,7-epoxy-2H-isoindol-2-yl]-2-(trifluoromethyl)benzonitrile. | 3.89 LC | 204, 35 |
| 285 | 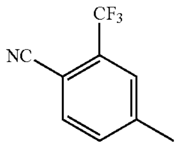 | 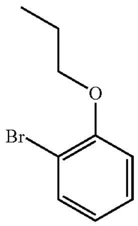 | (3aα,4β,7β,7aα)-4-[4-[2-(2-Bromophenoxy)ethyl]octahydro-7-methyl-1,3-dioxo-4,7-epoxy-2H-isoindol-2-yl]-2-(trifluoromethyl)benzonitrile. | 3.91 LC | 204, 35 |

TABLE 5-continued

| Ex. No | G | $R^7$ | Compound Name | Retention Time Min./ Molecular Mass | Procedure of Ex. |
|---|---|---|---|---|---|
| 286 | 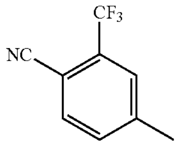 | 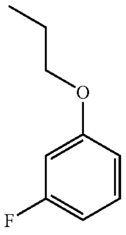 | (3aα,4β,7β,7aα)-4-[4-[2-(3-Fluorophenoxy) ethyl]octahydro-7-methyl-1,3-dioxo-4,7-epoxy-2H-isoindol-2-yl]-2-(trifluoromethyl) benzonitrile. | 3.78 LC | 204, 35 |
| 287 | 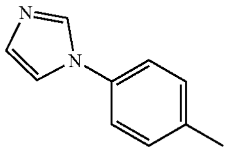 | H | (3aα,4β,7β,7aα)-Hexahydro-2-[4-(1H-imidazol-1-yl)phenyl]-4-methyl-4,7-epoxy-1H-isoindole-1,3(2H)-dione. | 1.16 LC | 3 |
| 288 | 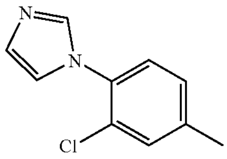 | H | (3aα,4β,7β,7aα)-2-[3-Chloro-4-(2-thiazolyl)phenyl] hexahydro-4-methyl-4,7-epoxy-1H-isoindole-1,3(2H)-dione. | 2.81 LC | 3 |
| 289 | 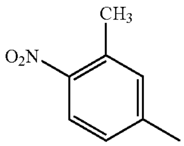 | $CH_3$ | (3aα,4β,7β,7aα)-Hexahydro-4,7-dimethyl-2-(3-methyl-4-nitrophenyl)-4,7-epoxy-1H-isoindole-1,3(2H)-dione. | 2.74 LC | 20 |
| 290 | 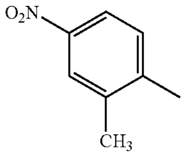 | $CH_3$ | (3aα,4β,7β,7aα)-Hexahydro-4,7-dimethyl-2-(2-methyl-4-nitrophenyl)-4,7-epoxy-1H-isoindole-1,3(2H)-dione. | 2.71 LC | 20 |
| 291 | 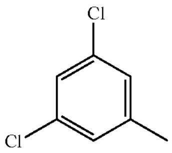 | 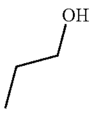 | (3aα,4β,7β,7aα)-2-(3,5-Dichlorophenyl) hexahydro-4-(2-hydroxyethyl)-7-methyl-4,7-epoxy-1H-isoindole-1,3(2H)-dione. | 2.98 LC | 204 |
| 292 | 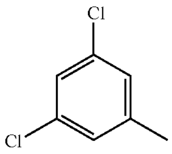 | 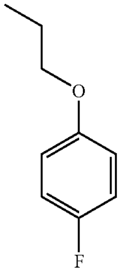 | (3aα,4β,7β,7aα)-2-(3,5-Dichlorophenyl)-4-[2-(4-fluorophenoxy) ethyl]hexahydro-7-methyl-4,7-epoxy-1H-isoindole-1,3(2H)-dione. | 4.03 LC | 204, 35 |

TABLE 5-continued

| Ex. No | G | $R^7$ | Compound Name | Retention Time Min./ Molecular Mass | Procedure of Ex. |
|---|---|---|---|---|---|
| 293 | 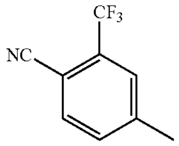 | 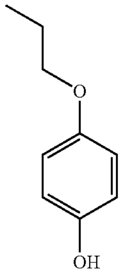 | (3aα,4β,7β,7aα)-4-[Octahydro-4-[2-(4-hydroxyphenoxy)ethyl]-7-methyl-1,3-dioxo-4,7-epoxy-2H-isoindol-2-yl]-2-(trifluoromethyl)benzonitrile. | 3.25 LC | 204, 35 |
| 294 | 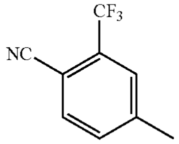 | 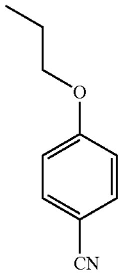 | (3aα,4β,7β,7aα)-4-[4-[2-(4-Cyanophenoxy)ethyl]octahydro-7-methyl-1,3-dioxo-4,7-epoxy-2H-isoindol-2-yl]-2-(trifluoromethyl)benzonitrile. | 3.51 LC | 204, 35 |
| 295 | 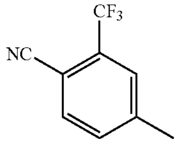 | 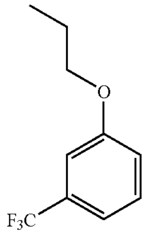 | (3aα,4β,7β,7aα)-4-[Octahydro-4-methyl-1,3-dioxo-7-[2-[3-(trifluoromethyl)phenoxy]ethyl]-4,7-epoxy-2H-isoindol-2-yl]-2-(trifluoromethyl)benzonitrile. | 3.85 LC | 204, 35 |
| 296 | 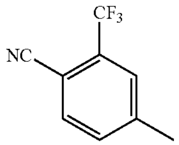 | 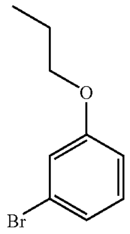 | (3aα,4β,7β,7aα)-4-[4-[2-(3-Bromophenoxy)ethyl]octahydro-7-methyl-1,3-dioxo-4,7-epoxy-2H-isoindol-2-yl]-2-(trifluoromethyl)benzonitrile. | 3.84 LC | 204, 35 |
| 297 | 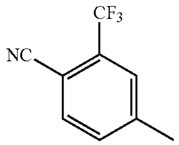 | 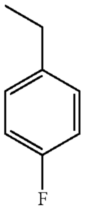 | (3aα,4β,7β,7aα)-4-[4-[(4-Fluorophenyl)methyl]octahydro-7-methyl-1,3-dioxo-4,7-epoxy-2H-isoindol-2-yl]-2-(trifluoromethyl)benzonitrile. | 3.73 LC | 205 |
| 298 | 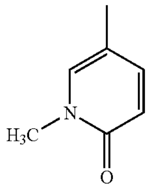 | $CH_3$ | (3aα,4β,7β,7aα)-2-(1,6-Dihydro-1-methyl-6-oxo-3-pyridinyl)hexahydro-4,7-dimethyl-4,7-epoxy-1H-isoindole 1,3(2H)-dione. | 1.61 LC | 20 |

TABLE 5-continued

| Ex. No | G | $R^7$ | Compound Name | Retention Time Min./ Molecular Mass | Procedure of Ex. |
|---|---|---|---|---|---|
| 299 | 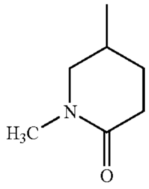 | $CH_3$ | (3aα,4β,7β,7aα)-Hexahydro-4,7-dimethyl-2-(1-methyl-6-oxo-3-piperidinyl)-4,7-epoxy-1H-isoindole-1,3(2H)-dione. | 1.73 LC | 20 |
| 300 | 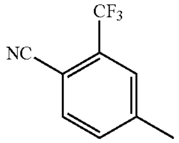 | 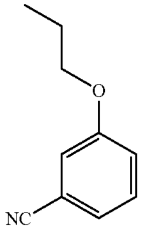 | (3aα,4β,7β,7aα)-4-[4-[2-(3-Cyanophenoxy) ethyl]octahydro-7-methyl-1,3-dioxo-4,7-epoxy-2H-isoindol-2-yl]-2-(trifluoromethyl) benzonitrile. | 3.46 LC | 204, 35 |
| 301 | 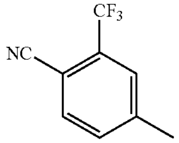 | 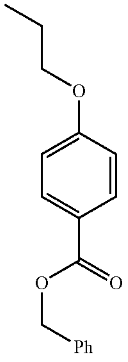 | (3aα,4β,7β,7aα)-4-[2-[4-Cyano-3-(trifluoromethyl) phenyl]octahydro-7-methyl-1,3-dioxo-4,7-epoxy-4H-isoindol-4-yl]ethoxy]benzoic acid, phenylmethyl ester. | 4.01 LC | 204, 35 |
| 302 | 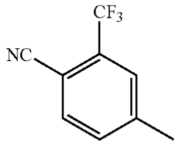 | 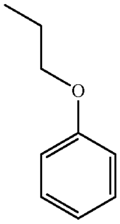 | (3aα,4β,7β,7aα)-4-[Octahydro-4-methyl-1,3-dioxo-7-(2-phenoxyethyl)-4,7-epoxy-2H-isoindol-2-yl]-2-(trifluoromethyl) benzonitrile. | 3.57 LC | 204, 35 |
| 303 | 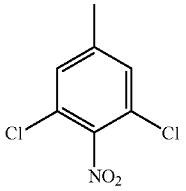 | $CH_3$ | (3aα,4β,7β,7aα)-2-(3,5-Dichloro-4-nitrophenyl) hexahydro-4,7-dimethyl-4,7-epoxy-1H-isoindole-1,3(2H)-dione. | 3.40 LC | 20 |
| 304 | 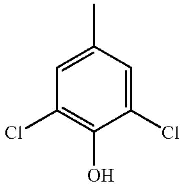 | $CH_3$ | (3aα,4β,7β,7aα)-2-(3,5-Dichloro-4-hydroxyphenyl) hexahydro-4,7-dimethyl-4,7-epoxy-1H-isoindole-1,3(2H)-dione. | 2.58 LC | 20 |

TABLE 5-continued

| Ex. No | G | $R^7$ | Compound Name | Retention Time Min./ Molecular Mass | Procedure of Ex. |
|---|---|---|---|---|---|
| 305 | 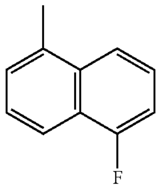 | $CH_3$ | (3aα,4β,7β,7aα)-2-(5-Fluoro-1-naphthalenyl) hexahydro-4,7-dimethyl-4,7-epoxy-1H-isoindole-1,3(2H)-dione. | 2.96 & 3.06 rotational isomers LC | 20 |
| 306 | 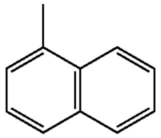 | $CH_3$ | (3aα,4β,7β,7aα)-Hexahydro-4,7-dimethyl-2-(1-naphthalenyl)-4,7-epoxy-1H-isoindole-1,3(2H)-dione. | 2.60 & 2.73 rotational isomers LC | 20 |
| 307 | 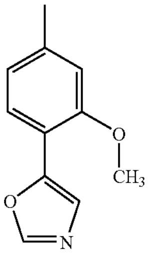 | $CH_3$ | (3aα,4β,7β,7aα)-Hexahydro-2-[3-methoxy-4-(5-oxazolyl)phenyl]-4,7-dimethyl-4,7-epoxy-1H-isoindole-1,3(2H)-dione. | 2.62 LC | 20 |
| 308 | 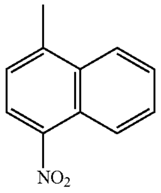 | 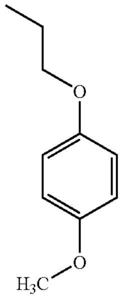 | (3aα,4β,7β,7aα)-Hexahydro-4-[2-(4-methoxyphenoxy) ethyl]-7-methyl-2-(4-nitro-1-naphthalenyl)-4,7-epoxy-1H-isoindole-1,3(2H)-dione. | 3.42 & 3.55 rotational isomers LC | 204, 35 |
| 309 | 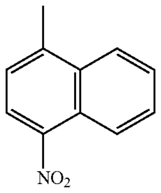 | 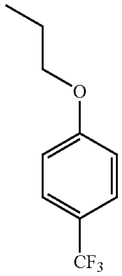 | (3aα,4β,7β,7aα)-Hexahydro-4-methyl-2-(4-nitro-1-naphthalenyl)-7-[2-[4-(trifluoromethyl) phenoxy]ethyl]-4,7-epoxy-1H-isoindole-1,3(2H)-dione. | 3.81 & 3.93 rotational isomers LC | 204, 35 |
| 310 | 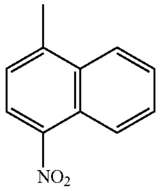 | 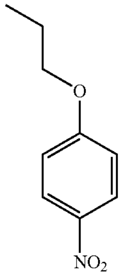 | (3aα,4β,7β,7aα)-Hexahydro-4-methyl-2-(4-nitro-1-naphthalenyl)-7-[2-(4-nitrophenoxy) ethyl]-4,7-epoxy-1H-isoindole-1,3(2H)-dione. | 3.48 & 3.61 rotational isomers LC | 204, 35 |

TABLE 5-continued

| Ex. No | G | $R^7$ | Compound Name | Retention Time Min./ Molecular Mass | Procedure of Ex. |
|---|---|---|---|---|---|
| 311 | 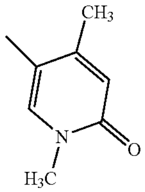 | $CH_3$ | (3aα,4β,7β,7aα)-2-(1,6-Dihydro-1,4-dimethyl-6-oxo-3-pyridinyl)hexahydro-4,7-dimethyl-4,7-epoxy-1H-isoindole 1,3(2H)-dione. | 1.89 LC | 20 |
| 312 | 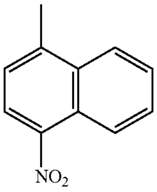 | 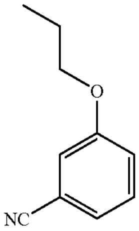 | (3aα,4β,7β,7aα)-4-[Octahydro-7-methyl-2-(4-nitro-1-naphthalenyl)-1,3-dioxo-4,7-epoxy-4H-isoindol-4-yl]ethoxy]benzonitrile. | 3.63 LC | 204, 35 |
| 313 | 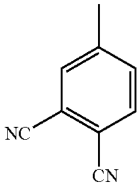 | $CH_3$ | (3aα,4β,7β,7aα)-4-(Octahydro-4,7-dimethyl-1,3-dioxo-4,7-epoxy-2H-isoindol-2-yl)-1,2-benzenedicarbonitrile. | 2.38 LC | 20 |
| 314 | 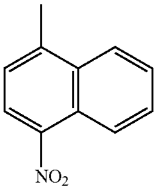 | 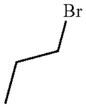 | (3aα,4β,7β,7aα)-4-(2-Bromoethyl) hexahydro-7-methyl-2-(4-nitro-1-naphthalenyl)-4,7-epoxy-1H-isoindole-1,3(2H)-dione. | 3.52 LC | 36 |
| 315 | 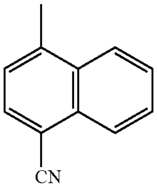 | 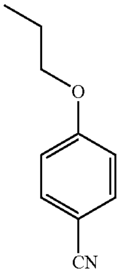 | (3aα,4β,7β,7aα)-4-[4-[2-(4-Cyanophenoxy) ethyl]octahydro-7-methyl-1,3-dioxo-4,7-epoxy-2H-isoindol-2-yl]-1-naphthalenecarbonitrile. | 3.19 & 3.35 rotational isomers LC | 223, 35 |
| 316 | 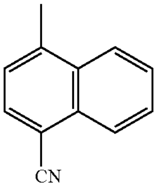 | 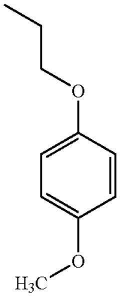 | (3aα,4β,7β,7aα)-4-[Octahydro-4-[2-(4-methoxyphenoxy) ethyl]-7-methyl-1,3-dioxo-4,7-epoxy-2H-isoindol-2-yl]-1-naphthalenecarbonitrile. | 3.34 & 3.50 rotational isomers LC | 223, 35 |

TABLE 5-continued

| Ex. No | G | R7 | Compound Name | Retention Time Min./ Molecular Mass | Procedure of Ex. |
|---|---|---|---|---|---|
| 317 | 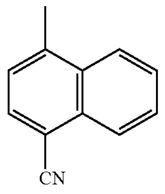 | 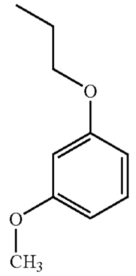 | (3aα,4β,7β,7aα)-4-[Octahydro-4-[2-(3-methoxyphenoxy)ethyl]-7-methyl-1,3-dioxo-4,7-epoxy-2H-isoindol-2-yl]-1-naphthalenecarbonitrile. | 3.34 & 3.50 rotational isomers LC | 223, 35 |
| 318 | 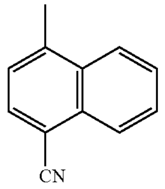 | 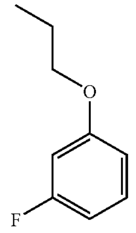 | (3aα,4β,7β,7aα)-4-[4-[2-(3-Fluorophenoxy)ethyl]octahydro-7-methyl-1,3-dioxo-4,7-epoxy-2H-isoindol-2-yl]-1-naphthalenecarbonitrile. | 3.46 & 3.61 rotational isomers LC | 223, 35 |
| 319 | 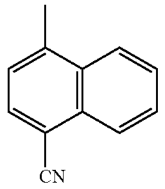 | 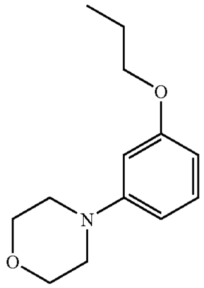 | (3aα,4β,7β,7aα)-4-[Octahydro-4-methyl-7-[2-[3-(4-morpholinyl)phenoxy]ethyl]-1,3-dioxo-4,7-epoxy-2H-isoindol-2-yl]-1-naphthalenecarbonitrile. | 3.01 & 3.18 rotational isomers LC | 223,35 |
| 320 | 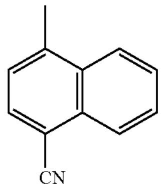 | 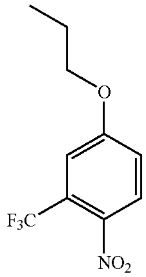 | (3aα,4β,7β,7aα)-4-[Octahydro-4-methyl-7-[2-[4-nitro-3-(triflouoromethyl)phenoxy]ethyl]-1,3-dioxo-4,7-epoxy-2H-isoindol-2-yl]-1-naphthalenecarbonitrile. | 3.70 & 3.83 rotational isomers LC | 223, 35 |
| 321 | 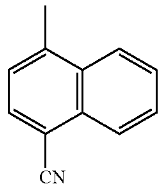 | 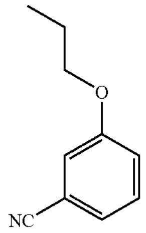 | (3aα,4β,7β,7aα)-4-[4-[2-(3-Cyanophenoxy)ethyl]octahydro-7-methyl-1,3-dioxo-4,7-epoxy-2H-isoindol-2-yl]-1-naphthalenecarbonitrile. | 3.39 & 3.55 rotational isomers LC | 223, 35 |

TABLE 5-continued

| Ex. No | G | $R^7$ | Compound Name | Retention Time Min./ Molecular Mass | Procedure of Ex. |
|---|---|---|---|---|---|
| 322 | 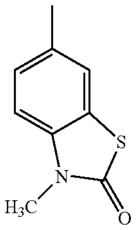 | $CH_3$ | (3aα,4β,7β,7aα)-2-(2,3-Dihydro-3-methyl-2-oxo-6-benzothiazolyl) hexahydro-4,7-dimethyl-4,7-epoxy-1H-isoindole-1,3(2H)-dione. | 2.34 LC | 20 |
| 323 | 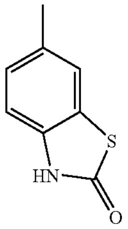 | $CH_3$ | (3aα,4β,7β,7aα)-2-(2,3-Dihydro-2-oxo-6-benzothiazolyl) hexahydro-4,7-dimethyl-4,7-epoxy-1H-isoindole-1,3(2H)-dione. | 2.16 LC | 20 |
| 324 | 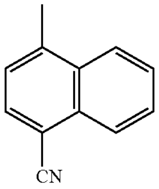 | 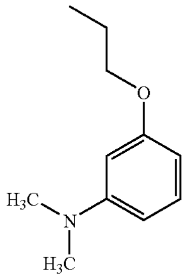 | (3aα,4β,7β,7aα)-4-[4-[2-[3-(Dimethylamino) phenoxy]ethyl] octahydro-7-methyl-1,3-dioxo-4,7-epoxy-2H-isoindol-2-yl]-1-naphthalenecarbonitrile. | 2.63 & 2.79 rotational isomers LC | 223, 35 |
| 325 | 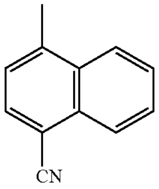 | 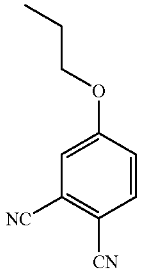 | (3aα,4β,7β,7aα)-4-[2-[4-Cyano-3-(trifluoromethyl) phenyl]octahydro-7-methyl-1,3-dioxo-4,7-epoxy-4H-isoindol-4-yl]ethoxy]-1,2-benzenedicarbonitrile. | 3.42 LC | 223, 35 |
| 326 | 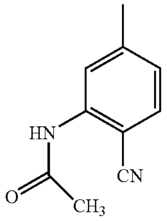 | $CH_3$ | (3aα,4β,7β,7aα)-N-[2-Cyano-5-(octahydro-4,7-dimethyl-1,3-dioxo-4,7-epoxy-2H-isoindol-2-yl) phenyl]acetamide. | 1.94 LC | 20 |
| 327 | 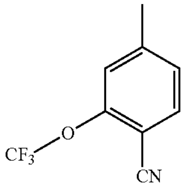 | $CH_3$ | (3aα,4β,7β,7aα)-4-(Octahydro-4,7-dimethyl-1,3-dioxo-4,7-epoxy-2H-isoindol-2-yl)-2-(trifluoromethoxy) benzonitrile. | 3.52 LC | 20 |

TABLE 5-continued

| Ex. No | G | $R^7$ | Compound Name | Retention Time Min./ Molecular Mass | Procedure of Ex. |
|---|---|---|---|---|---|
| 328 | 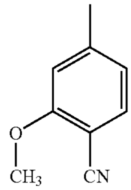 | $CH_3$ | (3aα,4β,7β,7aα)-2-Methoxy-4-(octahydro-4,7-dimethyl-1,3-dioxo-4,7-epoxy-2H-isoindol-2-yl)benzonitrile. | 2.47 LC | 20 |
| 329 | 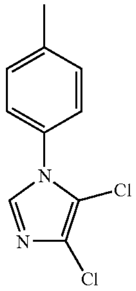 | $CH_3$ | (3aα,4β,7β,7aα)-2-[4-(4,5-Dichloro-1H-imidazol-1-yl) phenyl]hexahydro-4,7-dimethyl-4,7-epoxy-1H-isoindole-1,3(2H)-dione. | 3.09 LC | 20 |
| 330 | 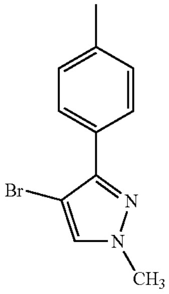 | $CH_3$ | (3aα,4β,7β,7aα)-2-[4-(4-Bromo-1-methyl-1H-pyrazol-3-yl)phenyl]hexahydro-4,7-dimethyl-4,7-epoxy-1H-isoindole-1,3(2H)-dione. | 3.04 LC | 20 |
| 331 | 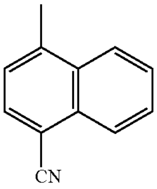 | 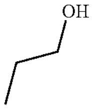 | (3aα,4β,7β,7aα)-4-[Octahydro-4-(2-hydroxyethyl)-7-methyl-1,3-dioxo-4,7-epoxy-2H-isoindol-2-yl]-1-naphthalenecarbonitrile. | 2.44 & 2.60 rotational isomers LC | 223 |
| 332 | 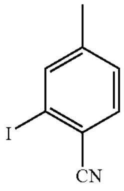 | $CH_3$ | (3aα,4β,7β,7aα)-2-Iodo-4-(Octahydro-4,7-dimethyl-1,3-dioxo-4,7-epoxy-2H-isoindol-2-yl)benzonitrile. | 2.78 LC | 20 |
| 333 | 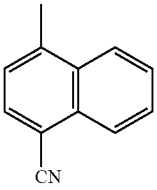 | 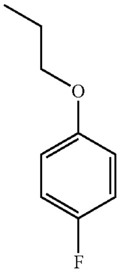 | (3aα,4β,7β,7aα)-4-[4-[2-(4-Fluorophenoxy) ethyl]octahydro-7-methyl-1,3-dioxo-4,7-epoxy-2H-isoindol-2-yl]-1-naphthalenecarbonitrile. | 3.39 & 3.53 rotational isomers LC | 223, 35 |

TABLE 5-continued

| Ex. No | G | $R^7$ | Compound Name | Retention Time Min./ Molecular Mass | Procedure of Ex. |
|---|---|---|---|---|---|
| 334 | 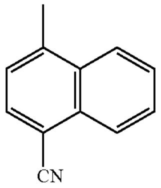 | 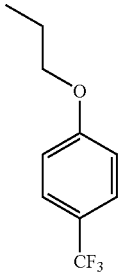 | (3aα,4β,7β,7aα)-4-[Octahydro-4-methyl-1,3-dioxo-7-[2-[4-(trifluoromethyl) phenoxy]ethyl]-4,7-epoxy-2H-isoindol-2-yl]-1-naphthalenecarbonitrile. | 3.66 & 3.78 rotational isomers LC | 223, 35 |
| 335 | 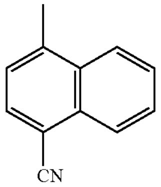 | 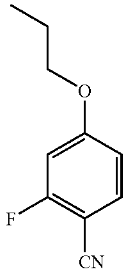 | (3aα,4β,7β,7aα)-4-[4-[2-(4-Cyano-3-fluorophenoxy) ethyl]octahydro-7-methyl-1,3-dioxo-4,7-epoxy-2H-isoindol-2-yl]-1-naphthalenecarbonitrile. | 3.26 & 3.41 rotational isomers LC | 223, 35 |
| 336 | 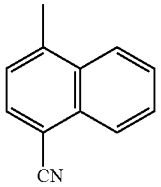 | 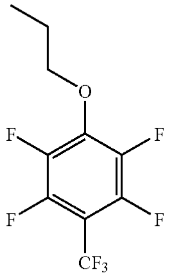 | (3aα,4β,7β,7aα)-4-[Octahydro-4-methyl-1,3-dioxo-7-[2-[2,3,5,6-tetrafluoro-4-(trifluoromethyl) phenoxy]ethyl]-4,7-epoxy-2H-isoindol-2-yl]-1-naphthalenecarbonitrile. | 3.94 & 4.01 rotational isomers LC | 223, 35 |
| 337 | 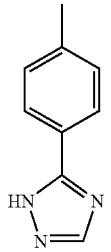 | $CH_3$ | (3aα,4β,7β,7aα)-Hexahydro-4,7-dimethyl-2-[4-(1H-1,2,4-triazol-3-yl)phenyl]-4,7-epoxy-1H-isoindole-1,3(2H)-dione. | 2.06 LC | 20 |
| 338 | 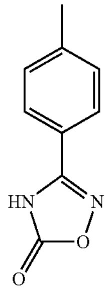 | $CH_3$ | (3aα,4β,7β,7aα)-2-[4-(4,5-Dihydro-5-oxo-1,2,4-oxadiazol-3-yl)phenyl]hexahydro-4,7-dimethyl-4,7-epoxy-1H-isoindole 1,3(2H)-dione. | 2.42 LC | 20 |

TABLE 5-continued

| Ex. No | G | $R^7$ | Compound Name | Retention Time Min./ Molecular Mass | Procedure of Ex. |
|---|---|---|---|---|---|
| 339 | 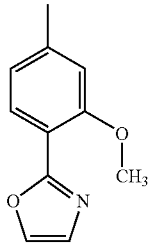 | $CH_3$ | (3aα,4β,7β,7aα)-Hexahydro-2-[3-methoxy-4-(2-oxazolyl)phenyl]-4,7-dimethyl-4,7-epoxy-1H-isoindole-1,3(2H)-dione. | 2.51 LC | 20 |
| 340 | 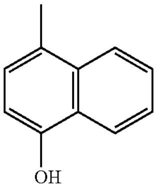 | $CH_3$ | (3aα,4β,7β,7aα)-Hexahydro-2-(4-hydroxy-1-naphthalenyl)-4,7-dimethyl-4,7-epoxy-1H-isoindole-1,3(2H)-dione. | 2.30 LC | 20 |
| 341 | 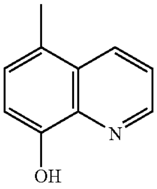 | $CH_3$ | (3aα,4β,7β,7aα)-Hexahydro-2-(8-hydroxy-5-quinolinyl)-4,7-dimethyl-4,7-epoxy-1H-isoindole-1,3(2H)-dione, trifluoroacetate(1:1). | 1.49 LC | 20 |
| 342 | 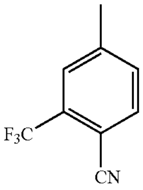 | 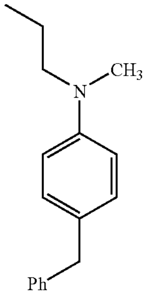 | (3aα,4β,7β,7aα)-4-[Octahydro-4-methyl-1,3-dioxo-7-[2-[methyl(phenylmethyl)amino]ethyl]-4,7-epoxy-2H-isoindol-2-yl]-2-(trifluoromethyl)benzonitrile. | 2.42 LC | 204, 35 |
| 343 | 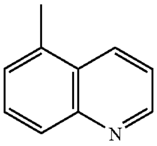 | $CH_3$ | (3aα,4β,7β,7aα)-Hexahydro-4,7-dimethyl-2-(5-quinolinyl)-4,7-epoxy-1H-isoindole-1,3(2H)-dione. | 1.69 LC | 20 |
| 344 | 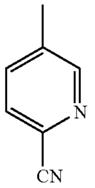 | $CH_3$ | (3aα,4β,7β,7aα)-5-(Octahydro-4,7-dimethyl-1,3-dioxo-4,7-epoxy-2H-isoindol-2-yl)-2-pyridinecarbonitrile. | 2.18 LC | 20 |
| 345 | 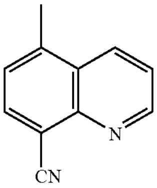 | $CH_3$ | (3aα,4β,7β,7aα)-5-(Octahydro-4,7-dimethyl-1,3-dioxo-4,7-epoxy-2H-isoindol-2-yl)-8-quinolinecarbonitrile. | 2.31 LC | 20 |

TABLE 5-continued

| Ex. No | G | $R^7$ | Compound Name | Retention Time Min./ Molecular Mass | Procedure of Ex. |
|---|---|---|---|---|---|
| 346 | 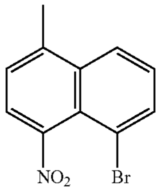 | $CH_3$ | (3aα,4β,7β,7aα)-2-(5-Bromo-4-nitro-1-naphthalenyl) hexahydro-4,7-dimethyl-4,7-epoxy-1H-isoindole-1,3(2H)-dione. | 3.10 & 3.29 rotational isomers LC | 20 |
| 347 | 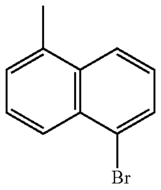 | $CH_3$ | (3aα,4β,7β,7aα)-2-(5-Bromo-1-naphthalenyl) hexahydro-4,7-dimethyl-4,7-epoxy-1H-isoindole-1,3(2H)-dione. | 3.28 & 3.40 rotational isomers LC | 20 |
| 348 | 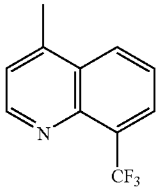 | $CH_3$ | (3aα,4β,7β,7aα)-Hexahydro-4,7-dimethyl-2-[8-(trifluoromethyl)-4-quinolinyl]-4,7-epoxy-1H-isoindole-1,3(2H)-dione. | 3.08 LC | 20 |
| 349 | 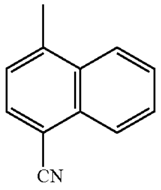 | 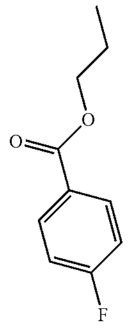 | 4-Fluorobenzoic acid, 2-[(3aα,4β,7β,7aα)-2-(4-cyano-1-naphthalenyl) octahydro-7-methyl-1,3-dioxo-4,7-epoxy-4H-isoindol-4-y]ethyl ester. | 3.64 & 3.77 rotational isomers LC | 223 |
| 350 | 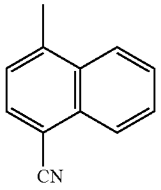 | 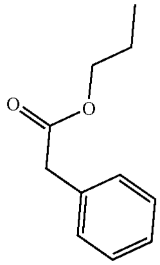 | Benzeneacetic acid, 2-[(3aα,4β,7β,7aα)-2-(4-cyano-1-naphthalenyl) octahydro-7-methyl-1,3-dioxo-4,7-epoxy-4H-isoindol-4-y]ethyl ester. | 3.53 & 3.67 rotational isomers LC | 223 |
| 351 | 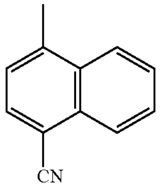 | 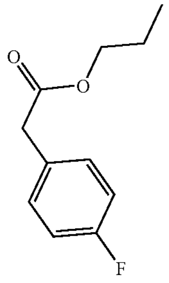 | 4-Fluorobenzeneacetic acid, 2-[(3aα,4β,7β,7aα)-2-(4-cyano-1-naphthalenyl) octahydro-7-methyl-1,3-dioxo-4,7-epoxy-4H-isoindol-4-y]ethyl ester. | 3.53 & 3.66 rotational isomers LC | 223 |

TABLE 5-continued

| Ex. No | G | $R^7$ | Compound Name | Retention Time Min./ Molecular Mass | Procedure of Ex. |
|---|---|---|---|---|---|
| 352 | 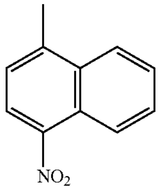 | 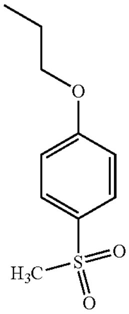 | (3aα,4β,7β,7aα)-Hexahydro-4-methyl-7-[2-[4-(methylsulfonyl)phenoxy]ethyl]-2-(4-nitro-1-naphthalenyl)-4,7-epoxy-1H-isoindole-1,3(2H)-dione. | 3.31 LC | 204, 35 |
| 353 | 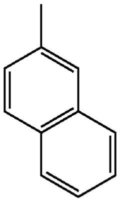 | $CH_3$ | (3aα,4β,7β,7aα)-Hexahydro-2-(2-naphthalenyl)-4,7-dimethyl-4,7-epoxy-1H-isoindole-1,3(2H)-dione. | 2.94 LC | 20 |
| 354 | 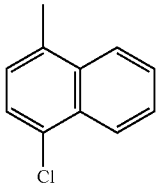 | $CH_3$ | (3aα,4β,7β,7aα)-2-(4-Chloro-1-naphthalenyl)hexahydro-4,7-dimethyl-4,7-epoxy-1H-isoindole-1,3(2H)-dione. | 3.22 & 3.34 rotational isomers LC | 20 |
| 355 | 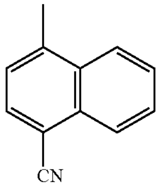 | 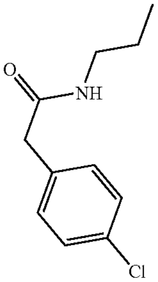 | (3aα,4β,7β,7aα)-N-[(4-Chlorophenyl)methyl]-2-(4-cyano-1-naphthalenyl)octahydro-7-methyl-1,3-dioxo-4,7-epoxy-4H-isoindole-4-acetamide. | 3.52 LC | 237 |
| 356 | 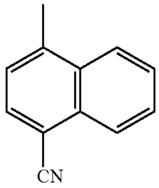 | 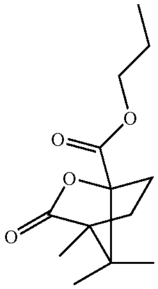 | 4,7,7-Trimethyl-3-oxo-2-oxabicyclo[2.2.1]heptane-1-carboxylic acid, 2-[(3aα,4β,7β,7aα)-2-(4-cyano-1-naphthalenyl)octahydro-7-methyl-1,3-dioxo-4,7-epoxy-4H-isoindol-4-y]ethyl ester. | 3.45 LC | 223 |

TABLE 5-continued

| Ex. No | G | R7 | Compound Name | Retention Time Min./ Molecular Mass | Procedure of Ex. |
|---|---|---|---|---|---|
| 357 | 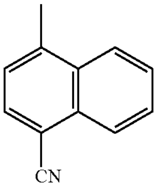 | 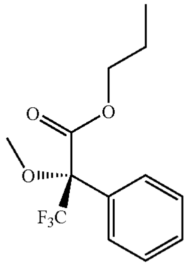 | (αS)-α-Methoxy-α-(trifluoromethyl) benzeneacetic acid, 2-[(3aα,4β,7β,7aα)-2-(4-cyano-1-naphthalenyl) octahydro-7-methyl-1,3-dioxo-4,7-epoxy-4H-isoindol-4-y] ethyl ester. | 3.91 LC | 223 |
| 358 | 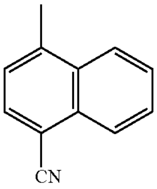 | 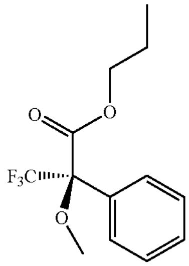 | (αR)-α-Methoxy-α-(trifluoromethyl) benzeneacetic acid, 2-[(3aα,4β,7β,7aα)-2-(4-cyano-1-naphthalenyl) octahydro-7-methyl-1,3-dioxo-4,7-epoxy-4H-isoindol-4-y] ethyl ester. | 2.00 LC | 223 |
| 359 | 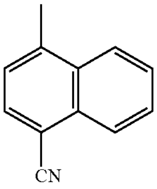 | 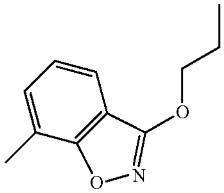 | (3aα,4β,7β,7aα)-4-[Octahydro-4-methyl-7-[2-[(7-methyl-1,2-benzisoxazol-3-yl)oxy]ethyl]-1,3-dioxo-4,7-epoxy-2H-isoindol-2-yl]-1-naphthalenecarbonitrile. | 3.79 & 3.92 LC Rotationale isomers | 250 |
| 360 | 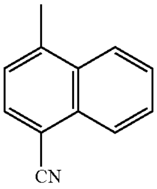 | 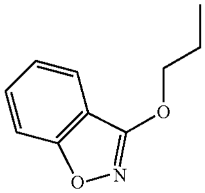 | (3aα,4β,7β,7aα)-4-[4-[2-(1,2-Benzisoxazol-3-yloxy)ethyl] octahydro-7-methyl-1,3-dioxo-4,7-epoxy-2H-isoindol-2-yl]-1-naphthalenecarbonitrile. | 3.55 & 3.70 LC Rotationale Isomers | 250 |
| 361 | 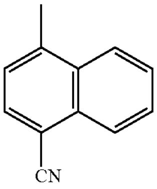 | 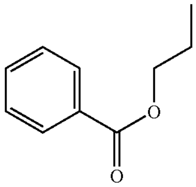 | (3aα,4β,7β,7aα)-4-[2-(Benzoyloxy) ethyl]-2-(4-cyano-1-naphthalenyl) hexahydro-7-methyl-4,7-epoxy-1H-isoindole 1,3(2H)-dione. | 3.51 & 3.66 LC Rotationale isomers | 223 |
| 362 | 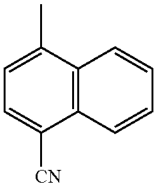 | 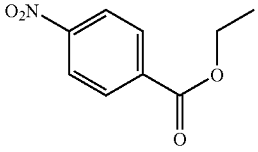 | (3aα,4β,7β,7aα)-2-(4-Cyano-1-naphthalenyl)-4-[2-[(4-nitrobenzoyl) oxy]ethyl] hexahydro-7-methyl-4,7-epoxy-1H-isoindole-1,3(2H)-dione. | 3.52 & 3.67 LC Rotationale Isomers | 223 |
| 363 | 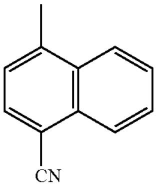 | 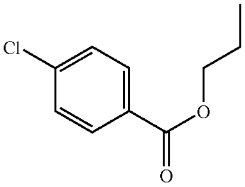 | 4-Chlorobenzoic acid, 2-[(3aα,4β,7β,7aα)-2-(4-cyano-1-naphthalenyl) octahydro-7-methyl-1,3-dioxo-4,7-epoxy-4H-isoindol-4-y]ethyl ester. | 3.79 LC | 223 |

TABLE 5-continued

| Ex. No | G | $R^7$ | Compound Name | Retention Time Min./ Molecular Mass | Procedure of Ex. |
|---|---|---|---|---|---|
| 364 | 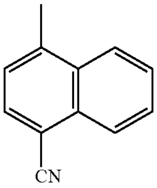 | 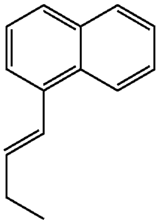 | [3aα,4β,7β,7aα(E)]-4-[Octahydro-4-methyl-7-[3-(1-naphthalenyl)-2-propenyl]-1,3-dioxo-4,7-epoxy-2H-isoindol-2-yl]-1-naphthalenecarbonitrile. | 4.14 LC 499.13 $[M + H]^+$ | 248 |
| 365 | 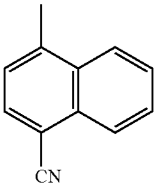 | 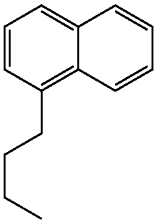 | (3aα,4β,7β,7aα)-4-[Octahydro-4-methyl-7-[3-(1-naphthalenyl)propyl]-1,3-dioxo-4,7-epoxy-2H-isoindol-2-yl]-1-naphthalenecarbonitrile. | 4.14 LC 501.14 $[M + H]^+$ | 248, 249 |
| 366 | 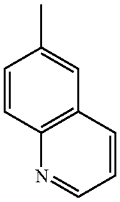 | $CH_3$ | (3aα,4β,7β,7aα)-Hexahydro-4,7-dimethyl-2-(2-methyl-6-quinolinyl)-4,7-epoxy-1H-isoindole-1,3(2H)-dione. | 1.25 LC 337.0 $[M + H]^+$ | 20 |
| 367 | 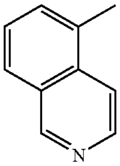 | $CH_3$ | (3aα,4β,7β,7aα)-Hexahydro-2-(5-isoquinolinyl)-4,7-dimethyl-4,7-epoxy-1H-isoindole-1,3(2H)-dione. | 1.06 & 1.29 LC Rotationale Isomers 323.0 $[M + H]^+$ | 20 |
| 368 | 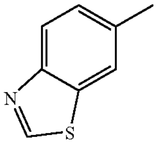 | $CH_3$ | (3aα,4β,7β,7aα)-2-(6-Benzothiazolyl) hexahydro-4,7-dimethyl-4,7-epoxy-1H-isoindole-1,3(2H)-dione. | 2.15 LC 329.0 $[M + H]^+$ | 20 |
| 369 | 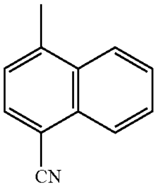 | 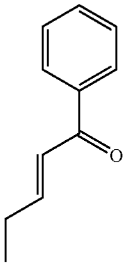 | [3aα,4β,7β,7aα(E)]-4-[Octahydro-4-methyl-1,3-dioxo-7-(4-oxo-4-phenyl-2-butenyl)-4,7-epoxy-2H-isoindol-2-yl]-1-naphthalenecarbonitrile. | 3.50 LC 477.1 $[M + H]^+$ | 265 |
| 370 | 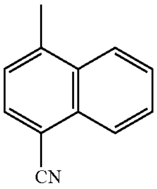 | 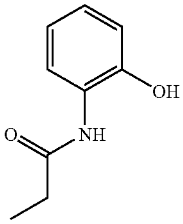 | (3aα,4β,7β,7aα)-2-(4-Cyano-1-naphthalenyl) octahydro-N-(2-hydroxyphenyl)-7-methyl-1,3-dioxo-4,7-epoxy-4H-isoindole-4-acetamide. | 3.07 LC 482.14 $[M + H]^+$ | 236 |

TABLE 5-continued

| Ex. No | G | $R^7$ | Compound Name | Retention Time Min./ Molecular Mass | Procedure of Ex. |
|---|---|---|---|---|---|
| 371 | 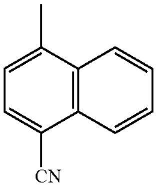 | 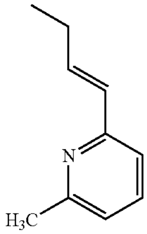 | [3aα,4β(E),7β,7aα]-[Octahydro-4-methyl-7-[3-(6-methyl-2-pyridinyl)-2-propenyl]-1,3-dioxo-4,7-epoxy-2H-isoindol-2-yl]-1-naphthalenecarbonitrile. | 2.28 LC 464.19 $[M + H]^+$ | 248 |
| 372 | 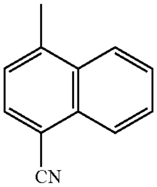 | 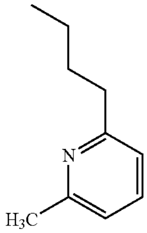 | (3aα,4β,7β,7aα)-4-[Octahydro-4-methyl-7-[3-(6-methyl-2-pyridinyl)propyl]-1,3-dioxo-4,7-epoxy-2H-isoindol-2-yl]-1-naphthalenecarbonitrile. | 2.19 LC 466.32 $[M + H]^+$ | 248, 249 |
| 373 | 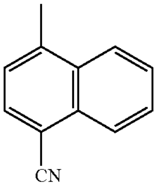 | 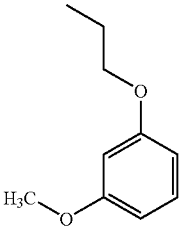 | [3aR-(3aα,4β,7β,7aα)]-4-[Octahydro-4-[2-(3-methoxyphenoxy)ethyl]-7-methyl-1,3-dioxo-4,7-epoxy-2H-isoindol-2-yl]-1-naphthalenecarbonitrile. | 3.73 LC 483.65 $[M + H]^+$ | 238i, 239i |
| 374 | 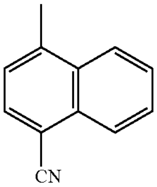 | 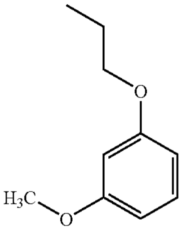 | [3aS-(3aα,4β,7β,7aα)]-4-[Octahydro-4-[2-(3-methoxyphenoxy)ethyl]-7-methyl-1,3-dioxo-4,7-epoxy-2H-isoindol-2-yl]-1-naphthalenecarbonitrile. | 3.73 LC | 238ii, 239ii |
| 375 | 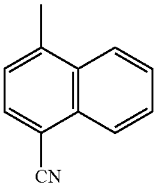 | 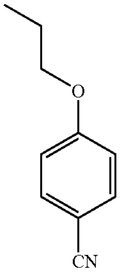 | [3aR-(3aα,4β,7β,7aα)]-4-[4-[2-(4-Cyanophenoxy)ethyl]octahydro-7-methyl-1,3-dioxo-4,7-epoxy-2H-isoindol-2-yl]-1-naphthalenecarbonitrile. | 3.33 & 3.49 LC Rotationale Isomers | 238i, 239i |
| 376 | 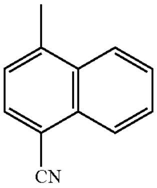 | 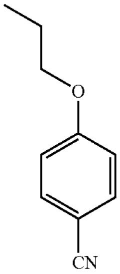 | [3aS-(3aα,4β,7β,7aα)]-4-[4-[2-(4-Cyanophenoxy)ethyl]octahydro-7-methyl-1,3-dioxo-4,7-epoxy-2H-isoindol-2-yl]-1-naphthalenecarbonitrile. | 3.73 LC 483.65 $[M + H]^+$ | 238ii, 239ii |

TABLE 5-continued

| Ex. No | G | $R^7$ | Compound Name | Retention Time Min./ Molecular Mass | Procedure of Ex. |
|---|---|---|---|---|---|
| 377 | 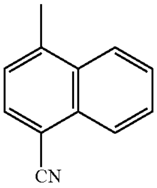 | 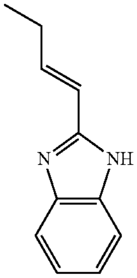 | [3aα,4β(E),7β,7aα]-4-[4-[3-(1H-Benzimidazol-2-yl)-2-propenyl]octahydro-7-methyl-1,3-dioxo-4,7-epoxy-2H-isoindol-2-yl]-1-naphthalenecarbonitrile | 2.48 LC 489.26 $[M + H]^+$ | 248 |
| 378 | 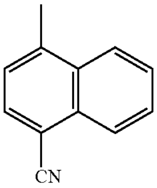 | 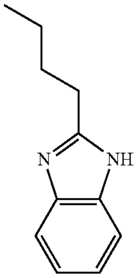 | (3aα,4β,7β,7aα)-4-[4-[3-(1H-Benzimidazol-2-yl)propyl]octahydro-7-methyl-1,3-dioxo-4,7-epoxy-2H-isoindol-2-yl]-1-naphthalenecarbonitrile | 2.37 LC 491.26 $[M + H]^+$ | 249 |

EXAMPLES 379 TO 381

Additional compounds of the present invention were prepared by procedures analogous to those described above. The compounds of Examples 379 to 381 have the following structure (L is a bond):

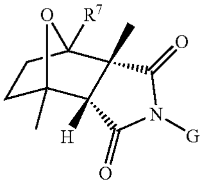

where G, $R^7$, the compound name, retention time, molecular mass, and the procedure employed, are set forth in Table 6. The chromatography techniques used to determine the compound retention times of Table 6 are as follows: LCMS=YMC S5 ODS column, 4.6×50 mm eluting with 10-90% MeOH/$H_2O$ over 4 minutes containing 0.1% TFA; 4 mL/min, monitoring at 220 nm. LCMS*=YMC S5 ODS column, 4.6×50 mm eluting with 10-90% MeOH/$H_2O$ over 2 minutes containing 0.1% TFA; 4 mL/min, monitoring at 220 nm. LC=YMC S5 ODS column 4.6×50 mm eluting with 10-90% MeOH/$H_2O$ over 4 minutes containing 0.2% phosphoric acid, 4 mL/min, monitoring at 220 nm.

The molecular mass of the compounds listed in Table 6 were determined by MS (ES) by the formula m/z.

TABLE 6

| Ex. No | G | $R^7$ | Compound Name | Retention Time Min./ Molecular Mass | Procedure of Ex. |
|---|---|---|---|---|---|
| 379 | 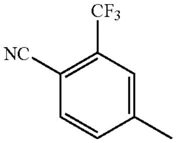 | 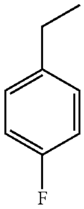 | (3aα,4α,7α,7aα)-4-[4-[(4-Fluorophenyl)methyl]octahydro-7-methyl-1,3-dioxo-4,7-epoxy-2H-isoindol-2-yl]-2-(trifluoromethyl)benzonitrile. | 3.75 LC | 205 |

TABLE 6-continued

| Ex. No | G | $R^7$ | Compound Name | Retention Time Min./ Molecular Mass | Procedure of Ex. |
|---|---|---|---|---|---|
| 380 | 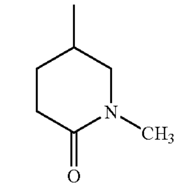 | $CH_3$ | (3aα,4α,7α,7aα)-Hexahydro-4,7-dimethyl-2-(1-methyl-6-oxo-3-piperidinyl)-4,7-epoxy-1H-isoindole-1,3(2H)-dione. | 1.88 LC | 27 |
| 381 | 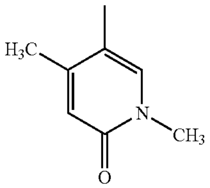 | $CH_3$ | (3aα,4α,7α,7aα)-2-(1,6-Dihydro-1,4-dimethyl-6-oxo-3-pyridinyl)hexahydro-4,7-dimethyl-4,7-epoxy-1H-isoindole-1,3(2H)-dione. | 1.91 LC | 27 |

EXAMPLES 382 TO 383

Additional compounds of the present invention were prepared by procedures analogous to those described above. The compounds of Examples 382 to 383 have the structure, compound name, retention time, molecular mass, and were prepared by the procedure employed, set forth in the following Table 7. The chromatography techniques used to determine the compound retention times of Table 7 are as follows: LCMS=YMC S5 ODS column, 4.6×50 mm eluting with 10-90% MeOH/$H_2O$ over 4 minutes containing 0.1% TFA; 4 mL/min, monitoring at 220 nm. LCMS*=YMC S5 ODS column, 4.6×50 mm eluting with 10-90% MeOH/$H_2O$ over 2 minutes containing 0.1% TFA; 4 mL/min, monitoring at 220 nm. LC=YMC S5 ODS column 4.6×50 mm eluting with 10-90% MeOH/$H_2O$ over 4 minutes containing 0.2% phosphoric acid, 4 mL/min, monitoring at 220 nm. The molecular mass of the compounds listed in Table 7 were determined by MS (ES) by the formula m/z.

TABLE 7

| Ex. No. | Structure | Compound Name | Retention Time Min. | Procedure of Example |
|---|---|---|---|---|
| 382 | 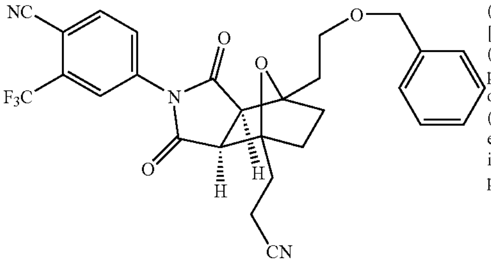 | (3aα,4β,7β,7aα)-2-[4-Cyano-3-(trifluoromethyl)phenyl]octahydro-1,3-dioxo-7-[2-(phenylmethoxy)ethyl]-4,7-epoxy-4H-isoindole-4-propanenitrile. | 3.63 LC | 255 |
| 383 | 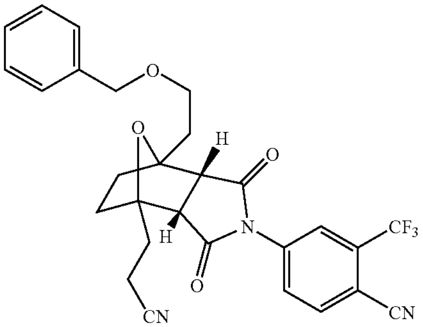 | (3aα,4β,7β,7aα)-2-[4-Cyano-3-(trifluoromethyl)phenyl]octahydro-1,3-dioxo-7-[2-(phenylmethoxy)ethyl]-4,7-epoxy-4H-isoindole-4-propanenitrile | 3.64 LC | 255 |

EXAMPLES 384 TO 418

Additional compounds of the present invention were prepared by procedures analogous to those described above. The compounds of Examples 384 to 418 have the following structure (L is a bond):

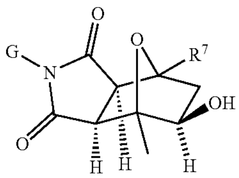

where G, $R^7$, the compound name, retention time, molecular mass, and the procedure employed, are set forth in Table 8. The absolute configuration for the following compounds was not determined. For simplicity in nomenclature, compound 243Di is designated herein as having an "S" configuration and compound 243Dii as having an "R" configuration. Enantiomerically pure products derived from compound 243Di are designated herein as having an "S" configuration and enantiomerically pure products derived from compound 243Dii are designated herein as having an "R" configuration.

The chromatography techniques used to determine the compound retention times of Table 8 are as follows: LCMS=YMC S5 ODS column, 4.6×50 mm eluting with 10-90% MeOH/$H_2O$ over 4 minutes containing 0.1% TFA; 4 mL/min, monitoring at 220 nm. LCMS*=YMC S5 ODS column, 4.6×50 mm eluting with 10-90% MeOH/$H_2O$ over 2 minutes containing 0.1% TFA; 4 mL/min, monitoring at 220 nm. LC=YMC S5 ODS column 4.6×50 mm eluting with 10-90% MeOH/$H_2O$ over 4 minutes containing 0.2% phosphoric acid, 4 mL/min, monitoring at 220 nm. The molecular mass of the compounds listed in Table 8 were determined by MS (ES) by the formula m/z.

TABLE 8

| Ex. No | G | $R^7$ | Compound Name | Retention Time Min./ Molecular Mass | Procedure of Ex. |
|---|---|---|---|---|---|
| 384 | 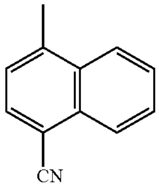 | 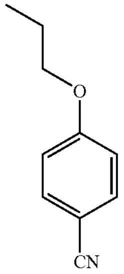 | (3aα,4β,7β,7aα)-4-[7-[2-(4-Cyanophenoxy)ethyl]octahydro-5-hydroxy-4-methyl-1,3-dioxo-4,7-epoxy-2H-isoindol-2-yl]-1-naphthalenecarbonitrile. | 3.18 LC 494.40 $[M + H]^+$ | 227, 228, 229 |
| 385 | 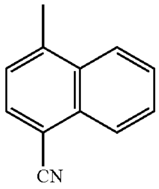 | 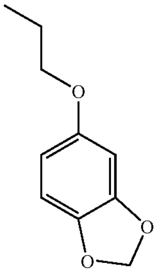 | [3aS-(3aα,4β,7β,7aα)]-4-[7-[2-(1,3-Benzodioxol-5-yloxy)ethyl]octahydro-5-hydroxy-4-methyl-1,3-dioxo-4,7-epoxy-2H-isoindol-2-yl]-1-naphthalenecarbonitrile. | 3.19 LC 571.3 $[M - H + OAc]^-$ | 243Di, 244i |
| 386 | 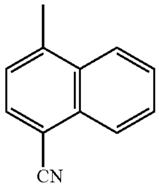 | 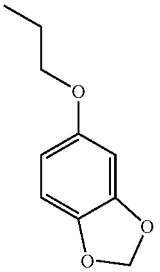 | [3aR-(3aα,4β,7β,7aα)]-4-[7-[2-(1,3-Benzodioxol-5-yloxy)ethyl]octahydro-5-hydroxy-4-methyl-1,3-dioxo-4,7-epoxy-2H-isoindol-2-yl]-1-naphthalenecarbonitrile. | 3.22 LC 571.2 $[M - H + OAc]^-$ | 234Dii, 244ii |

TABLE 8-continued

| Ex. No | G | $R^7$ | Compound Name | Retention Time Min./ Molecular Mass | Procedure of Ex. |
|---|---|---|---|---|---|
| 387 | 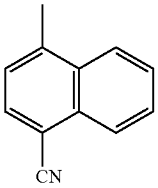 | 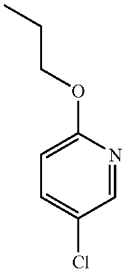 | [3aS-(3aα,4β,7β,7aα)]-4-[7-[2-[(5-Chloro-2-pyridinyl)oxy]ethyl]octahydro-5-hydroxy-4-methyl-1,3-dioxo-4,7-epoxy-2H-isoindol-2-yl]-1-naphthalenecarbonitrile. | 3.37 LC 562.2 $[MH + OAc]^-$ | 243Di, 244i |
| 388 | 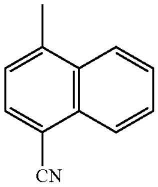 | 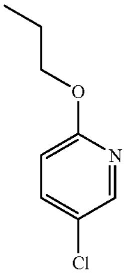 | [3aR-(3aα,4β,7β,7aα)]-4-[7-[2-[(5-Chloro-2-pyridinyl)oxy]ethyl]octahydro-5-hydroxy-4-methyl-1,3-dioxo-4,7-epoxy-2H-isoindol-2-yl]-1-naphthalenecarbonitrile. | 3.37 LC 504.0 $[M + H]^+$ | 243Dii, 244ii |
| 389 | 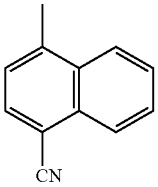 | 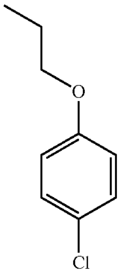 | [3aS-(3aα,4β,7β,7aα)]-4-[7-[2-(4-Chlorophenoxy)ethyl]octahydro-5-hydroxy-4-methyl-1,3-dioxo-4,7-epoxy-2H-isoindol-2-yl]-1-naphthalenecarbonitrile. | 3.51 LC 503.08 $[M + H]^+$ | 243Di, 244i |
| 390 | 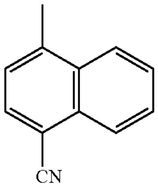 | 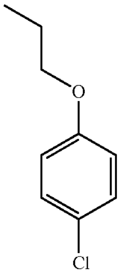 | [3aR-(3aα,4β,7β,7aα)]-4-[7-[2-(4-Chlorophenoxy)ethyl]octahydro-5-hydroxy-4-methyl-1,3-dioxo-4,7-epoxy-2H-isoindol-2-yl]-1-naphthalenecarbonitrile. | 3.51 LC 503.08 $[M + H]^+$ | 243Dii, 244ii |
| 391 | 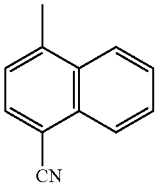 | 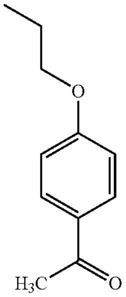 | [3aS-(3aα,4β,7β,7aα)]-4-[7-[2-(4-Acetylphenoxy)ethyl]octahydro-5-hydroxy-4-methyl-1,3-dioxo-4,7-epoxy-2H-isoindol-2-yl]-1-naphthalenecarbonitrile. | 3.05 LC 511.13 $[M + H]^+$ | 243Di, 244i |

TABLE 8-continued

| Ex. No | G | R7 | Compound Name | Retention Time Min./ Molecular Mass | Procedure of Ex. |
|---|---|---|---|---|---|
| 392 | 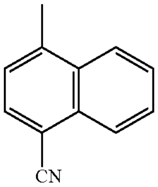 | 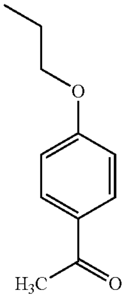 | [3aR-(3aα,4β,7β,7aα)]-4-[7-[2-(4-Acetylphenoxy)ethyl]octahydro-5-hydroxy-4-methyl-1,3-dioxo-4,7-epoxy-2H-isoindol-2-yl]-1-naphthalenecarbonitrile. | 3.05 LC 503.13 $[M + H]^+$ | 243Dii, 244ii |
| 393 | 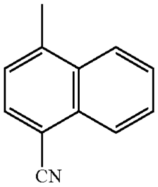 | 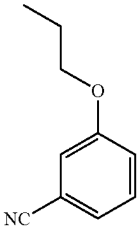 | [3aS-(3aα,4β,7β,7aα)]-4-[7-[2-(3-Cyanophenoxy)ethyl]octahydro-5-hydroxy-4-methyl-1,3-dioxo-4,7-epoxy-2H-isoindol-2-yl]-1-naphthalenecarbonitrile. | 3.09 LC 494.13 $[M + H]^+$ | 243Di, 244i |
| 394 | 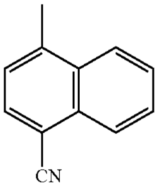 | 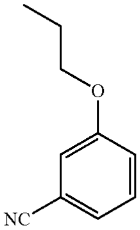 | [3aR-(3aα,4β,7β,7aα)]-4-[7-[2-(3-Cyanophenoxy)ethyl]octahydro-5-hydroxy-4-methyl-1,3-dioxo-4,7-epoxy-2H-isoindol-2-yl]-1-naphthalenecarbonitrile. | 3.09 LC 494.13 $[M + H]^+$ | 243Dii, 244ii |
| 395 | 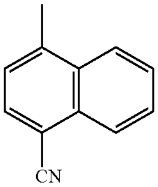 | 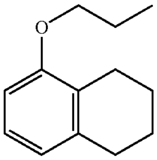 | [3aS-(3aα,4β,7β,7aα)]-4-[Octahydro-5-hydroxy-4-methyl-1,3-dioxo-7-[2-[(5,6,7,8-tetrahydro-1-naphthalenyl)oxy]ethyl]-4,7-epoxy-2H-isoindol-2-yl]-1-naphthalenecarbonitrile. | 3.85 LC 523.17 $[M + H]^+$ | 243Di, 244i |
| 396 | 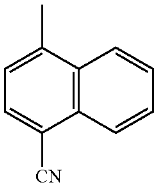 | 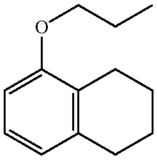 | [3aR-(3aα,4β,7β,7aα)]-4-[Octahydro-5-hydroxy-4-methyl-1,3-dioxo-7-[2-[(5,6,7,8-tetrahydro-1-naphthalenyl)oxy]ethyl]-4,7-epoxy-2H-isoindol-2-yl]-1-naphthalenecarbonitrile. | 3.85 LC 523.17 $[M + H]^+$ | 243Dii, 244ii |
| 397 | 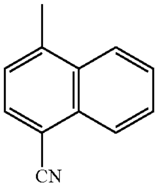 | 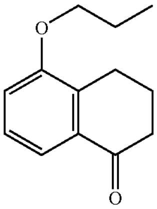 | [3aS-(3aα,4β,7β,7aα)]-4-[Octahydro-5-hydroxy-4-methyl-1,3-dioxo-7-[2-[(5,6,7,8-tetrahydro-5-oxo-1-naphthalenyl)oxy]ethyl]-4,7-epoxy-2H-isoindol-2-yl]-1-naphthalenecarbonitrile. | 3.29 LC 537.13 $[M + H]^+$ | 243Di, 244i |

TABLE 8-continued

| Ex. No | G | $R^7$ | Compound Name | Retention Time Min./ Molecular Mass | Procedure of Ex. |
|---|---|---|---|---|---|
| 398 | 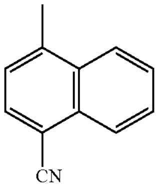 | 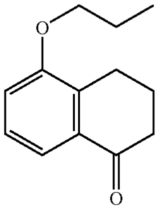 | [3aR-(3aα,4β,7β,7aα)]-4-[Octahydro-5-hydroxy-4-methyl-1,3-dioxo-7-[2-[(5,6,7,8-tetrahydro-5-oxo-1-naphthalenyl)oxy]ethyl]-4,7-epoxy-2H-isoindol-2-yl]-1-naphthalenecarbonitrile. | 3.29 LC 537.13 $[M + H]^+$ | 243Dii, 244ii |
| 399 | 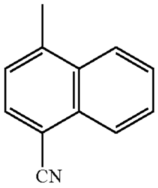 | 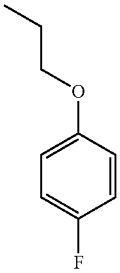 | [3aS-(3aα,4β,7β,7aα)]-4-[7-[2-(4-Fluorophenoxy)ethyl]octahydro-5-hydroxy-4-methyl-1,3-dioxo-4,7-epoxy-2H-isoindol-2-yl]-1-naphthalenecarbonitrile. | 3.28 LC 487.11 $[M + H]^+$ | 243Di, 244i |
| 400 | 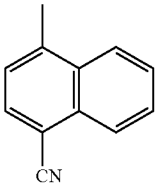 | 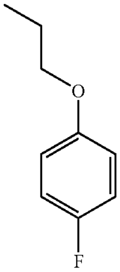 | [3aR-(3aα,4β,7β,7aα)]-4-[7-[2-(4-Fluorophenoxy)ethyl]octahydro-5-hydroxy-4-methyl-1,3-dioxo-4,7-epoxy-2H-isoindol-2-yl]-1-naphthalenecarbonitrile. | 3.27 LC 487.11 $[M + H]^+$ | 243Dii, 244ii |
| 401 | 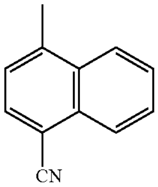 | 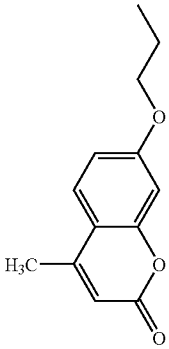 | [3aS-(3aα,4β,7β,7aα)]-4-[Octahydro-5-hydroxy-4-methyl-7-[2-[(4-methyl-2-oxo-2H-1-benzopyran-7-yl)oxy]ethyl]-1,3-dioxo-4,7-epoxy-2H-isoindol-2-yl]-1-naphthalenecarbonitrile. | 3.15 LC 551.15 $[M + H]^+$ | 243Di, 244i |
| 402 | 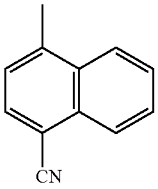 | 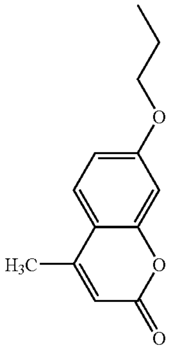 | [3aR-(3aα,4β,7β,7aα)]-4-[Octahydro-5-hydroxy-4-methyl-7-[2-[(4-methyl-2-oxo-2H-1-benzopyran-7-yl)oxy]ethyl]-1,3-dioxo-4,7-epoxy-2H-isoindol-2-yl]-1-naphthalenecarbonitrile. | 3.16 LC 551.10 $[M + H]^+$ | 243Dii, 244ii |

TABLE 8-continued

| Ex. No | G | $R^7$ | Compound Name | Retention Time Min./ Molecular Mass | Procedure of Ex. |
|---|---|---|---|---|---|
| 403 | 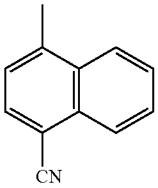 | 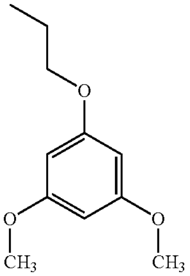 | [3aS-(3aα,4β,7β,7aα)]-4-[7-[2-(3,5-Dimethoxyphenoxy) ethyl]octahydro-5-hydroxy-4-methyl-1,3-dioxo-4,7-epoxy-2H-isoindol-2-yl]-1-naphthalenecarbonitrile. | 3.28 LC 529.19 $[M + H]^+$ | 243Di, 244i |
| 404 | 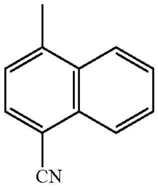 | 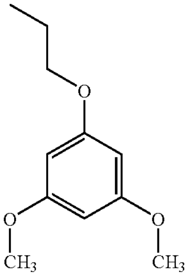 | [3aR-(3aα,4β,7β,7aα)]-4-[7-[2-(3,5-Dimethoxyphenoxy) ethyl]octahydro-5-hydroxy-4-methyl-1,3-dioxo-4,7-epoxy-2H-isoindol-2-yl]-1-naphthalenecarbonitrile. | 3.26 LC 529.12 $[M + H]^+$ | 243Dii, 244ii |
| 405 | 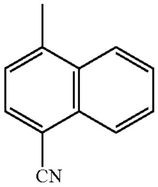 | 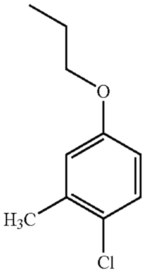 | [3aR-(3aα,4β,7β,7aα)]-]-4-[7-[2-(4-Chloro-3-methylphenoxy) ethyl]octahydro-5-hydroxy-4-methyl-1,3-dioxo-4,7-epoxy-2H-isoindol-2-yl]-1-naphthalenecarbonitrile. | 3.68 LC 517.33 $[M + H]^+$ | 243Dii, 244ii |
| 406 | 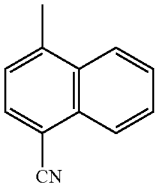 | 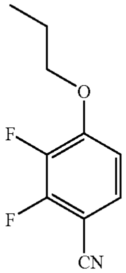 | [3aR-(3aα,4β,7β,7aα)]-4-[7-[2-(4-Cyano-2,3-difluorophenoxy) ethyl]octahydro-5-hydroxy-4-methyl-1,3-dioxo-4,7-epoxy-2H-isoindol-2-yl]-1-naphthalenecarbonitrile. | 3.23 LC 530.13 $[M + H]^+$ | 243Dii, 244ii |
| 407 | 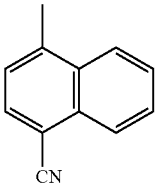 | 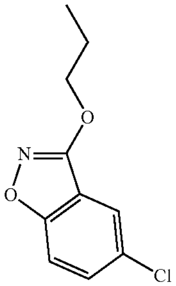 | [3aS-(3aα,4β,7β,7aα)]-4-[7-[2-[(5-Chloro-1,2-benzisoxazol-3-yl)oxy]ethyl]octahydro-5-hydroxy-4-methyl-1,3-dioxo-4,7-epoxy-2H-isoindol-2-yl]-1-naphthalenecarbonitrile. | 3.59 LC 602.1 $[M - H + OAc]^-$ | 243Di, 252 |

TABLE 8-continued

| Ex. No | G | $R^7$ | Compound Name | Retention Time Min./ Molecular Mass | Procedure of Ex. |
|---|---|---|---|---|---|
| 408 | 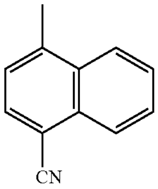 | 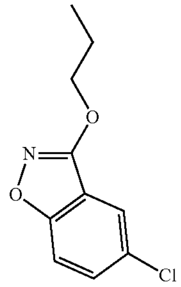 | [3aR-(3aα,4β,7β,7aα)]-4-[7-[2-[(5-Chloro-1,2-benzisoxazol-3-yl)oxy]ethyl]octahydro-5-hydroxy-4-methyl-1,3-dioxo-4,7-epoxy-2H-isoindol-2-yl]-1-naphthalenecarbonitrile. | 3.57 LC 602.0 $[M - H + OAc]^-$ | 243Dii, 253 |
| 409 | 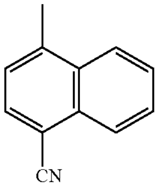 | 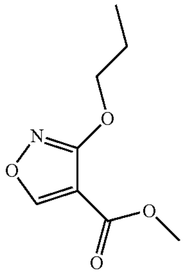 | [3aR-(3aα,4β,7β,7aα)]-3-[2-[2-(4-Cyano-1-naphthalenyl)octahydro-6-hydroxy-7-methyl-1,3-dioxo-4,7-epoxy-4H-isoindol-4-yl]ethoxy]-5-isoxazolecarboxylic acid, methyl ester. | 2.90 LC 518.27 $[M + H]^+$ | 243Dii, 253 |
| 410 | 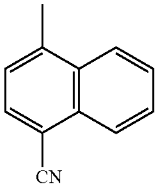 | 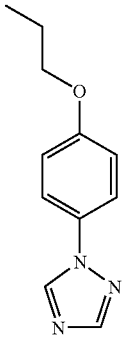 | [3aR-(3aα,4β,7β,7aα)]-4-[Octahydro-5-hydroxy-4-methyl-1,3-dioxo-7-[2-[4-(1H-1,2,4-triazol-1-yl)phenoxy]ethyl]-4,7-epoxy-2H-isoindol-2-yl]-1-naphthalenecarbonitrile. | 2.93 LC 536.30 $[M + H]^+$ | 243Dii, 244ii |
| 411 | 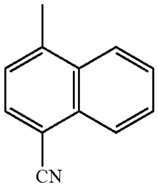 | 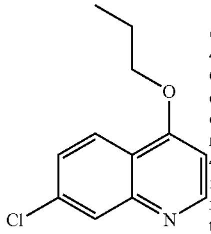 | [3aS-(3aα,4β,7β,7aα)]-4-[7-[2-[(7-Chloro-4-quinolinyl)oxy]ethyl]octahydro-5-hydroxy-4-methyl-1,3-dioxo-4,7-epoxy-2H-isoindol-2-yl]-1-naphthalenecarbonitrile, trifluoroacetate (1:1). | 2.52 LC 554.13 $[M + H]^+$ | 243Di, 244i |
| 412 | 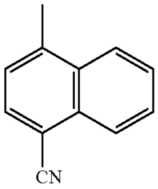 | 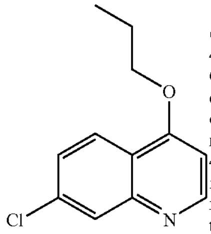 | [3aR-(3aα,4β,7β,7aα)]-4-[7-[2-[(7-Chloro-4-quinolinyl)oxy]ethyl]octahydro-5-hydroxy-4-methyl-1,3-dioxo-4,7-epoxy-2H-isoindol-2-yl]-1-naphthalenecarbonitrile, trifluoroacetate (1:1). | 2.53 LC 554.27 $[M + H]^+$ | 243Dii, 244ii |

TABLE 8-continued

| Ex. No | G | $R^7$ | Compound Name | Retention Time Min./ Molecular Mass | Procedure of Ex. |
|---|---|---|---|---|---|
| 413 | 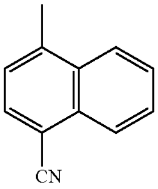 | 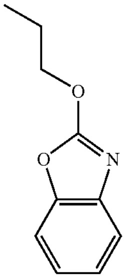 | [3aR-(3α,4β,5β,7β,7aα)]-4-[7-[2-(2-Benzoxazolyloxy)ethyl]octahydro-5-hydroxy-4-methyl-1,3-dioxo-4,7-epoxy-2H-isoindol-2-yl]-1-naphthalenecarbonitrile | 3.13 LC 568.1 $[MH + OAc]^-$ | 243Dii, 244ii |
| 414 | 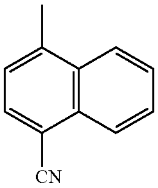 | 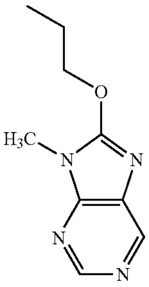 | [3aR-(3α,4β,5β,7β,7aα)]-4-[Octahydro-5-hydroxy-4-methyl-7-[2-[(9-methyl-9H-purin-8-yl)oxy]ethyl]-1,3-dioxo-4,7-epoxy-2H-isoindol-2-yl]-1-naphthalenecarbonitrile | 2.34 LC 525.2 $[M + H]^+$ | 243Dii, 244ii |
| 415 | 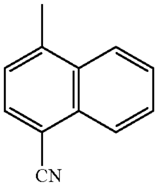 | 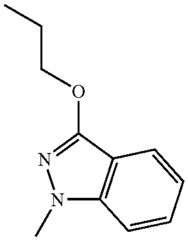 | [3aR-(3α,4β,5β,7β,7aα)]-4-[Octahydro-5-hydroxy-4-methyl-7-[2-[(1-methyl-1H-indazol-3-yl)oxy]ethyl]-1,3-dioxo-4,7-epoxy-2H-isoindol-2-yl]-1-naphthalenecarbonitrile | 3.33 LC | 251, 253 |
| 416 | 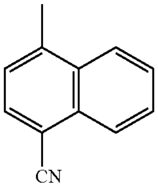 | 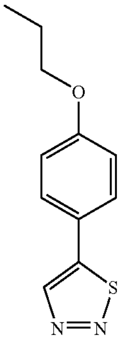 | [3aS-(3α,4β,5β,7β,7aα)]-4-[Octahydro-5-hydroxy-4-methyl-7-[2-[4-(1,2,3-thiadiazol-5-yl)phenoxy]ethyl]-1,3-dioxo-4,7-epoxy-2H-isoindol-2-yl]-1-naphthalenecarbonitrile | 3.17 LC 553.10 $[M + H]^+$ | 243Dii, 244ii |
| 417 | 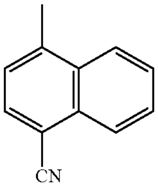 | 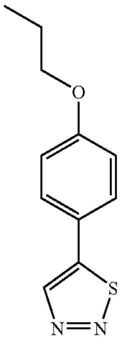 | [3aR-(3α,4β,5β,7β,7aα)]-4-[Octahydro-5-hydroxy-4-methyl-7-[2-[4-(1,2,3-thiadiazol-5-yl)phenoxy]ethyl]-1,3-dioxo-4,7-epoxy-2H-isoindol-2-yl]-1-naphthalenecarbonitrile | 3.20 LC 553.25 $[M + H]^+$ | 243Dii, 244ii |

TABLE 8-continued

| Ex. No | G | $R^7$ | Compound Name | Retention Time Min./ Molecular Mass | Procedure of Ex. |
|---|---|---|---|---|---|
| 418 | 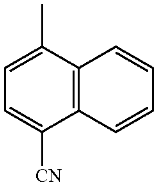 | 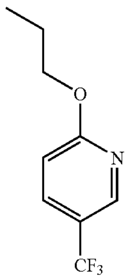 | [3aS-(3α,4β,5β,7β,7aα)]-4-[Octahydro-5-hydroxy-4-methyl-1,3-dioxo-7-[2-[[5-(trifluoromethyl)-2-pyridinyl]oxy]ethyl]-4,7-epoxy-2H-isoindol-2-yl]-1-naphthalenecarbonitrile | 3.45 LC 538.23 $[M + H]^+$ | 243Dii, 244ii |
| 419 | 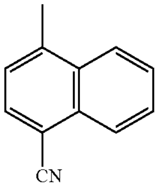 | 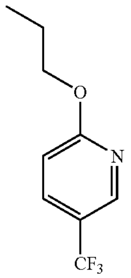 | [3aR-(3α,4β,5β,7β,7aα)]-4-[Octahydro-5-hydroxy-4-methyl-1,3-dioxo-7-[2-[[5-(trifluoromethyl)-2-pyridinyl]oxy]ethyl]-4,7-epoxy-2H-isoindol-2-yl]-1-naphthalenecarbonitrile | 3.45 LC 538.23 $[M + H]^+$ | 243Dii, 244ii |
| 420 | 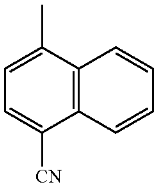 | 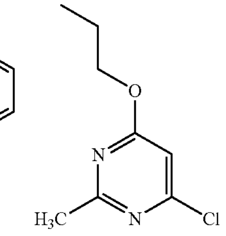 | [3aS-(3α,4β,5β,7β,7aα)]-4-[7-[2-[(6-Chloro-2-methyl-4-pyrimidinyl)oxy] ethyl]octahydro-5-hydroxy-4-methyl-1,3-dioxo-4,7-epoxy-2H-isoindol-2-yl]-1-naphthalenecarbonitrile | 3.02 LC | 243Dii, 244ii |
| 421 | 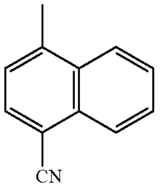 | 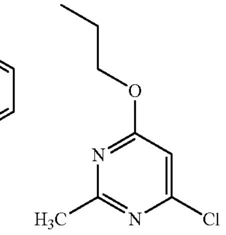 | [3aR-(3α,4β,5β,7β,7aα)]-4-[7-[2-[(6-Chloro-2-methyl-4-pyrimidinyl)oxy] ethyl]octahydro-5-hydroxy-4-methyl-1,3-dioxo-4,7-epoxy-2H-isoindol-2-yl]-1-naphthalenecarbonitrile | 3.02 LC | 243Dii, 244ii |

EXAMPLE 422

(3aα,4β,7β,7aα)-2-(7-Bromo-2,1,3-benzoxadiazol-4-yl)hexahydro-4,7-dimethyl-4,7-epoxy-1H-isoindole-1,3(2H)-dione (422C)

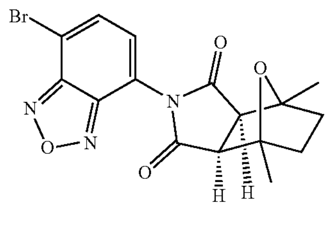

A. 4-Bromo-7-nitrobenzofurazan (422A)

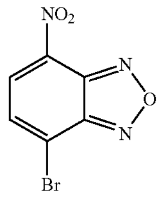

To a solution of 2,6-dibromoaniline (1.0 g, 4.0 mmol) in $CHCl_3$ (8 mL) was added a suspension of mCPBA (70% by HPLC, 1.4 g, 8.0 mmol) in $CHCl_3$ (8 mL) and the resulting mixture was stirred for 24 h at rt. The reaction mixture was diluted with $CHCl_3$ and washed successively with 2% $Na_2S_2O_3$ solution, 5% $Na_2CO_3$ solution and brine. The organic layer was dried over $Na_2SO_4$ and concentrated under reduced pressure to leave a solid, which was suspended, into DMSO (15 mL). To this suspension was added a solution of $NaN_3$ (272 mg, 4.19 mmol) in DMSO (15 mL) at rt. The resulting mixture was stirred at rt until most of the nitrogen had evolved and was then quickly heated to 120° C. for 3 min. The reaction mixture was cooled and poured onto crushed ice (100 g). After standing for 1 h the precipitates were filtered off, dried in vacuo and redissolved in conc. $H_2SO_4$ (5 mL). To this solution was added a solution of $NaNO_3$ (400 mg, 4.7 mmol) in 50% $H_2SO_4$ (1.6 mL) and the temperature was maintained at 60° C. After the addition was complete, the mixture was heated at 85° C. for 30 min, cooled to rt and poured onto crushed ice (40 g). EtOAc was added, the layers were separated and the aqueous layer was extracted with EtOAc. The combined organic layers were dried over $Na_2SO_4$ and concentrated under reduced pressure to leave a solid which was purified by flash chromatography (silica gel, EtOAc (20%) in hexanes) affording compound 422A (785 mg, 81%) as a tan solid.

B. 4-Bromo-7-aminobenzofurazan (422B)

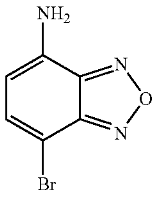

A solution of compound 422A (563 mg, 2.31 mmol) in AcOH (5 mL) was heated to 70° C. and $Fe^0$ powder (258 mg, 4.62 mmol) was added in one portion. The resulting dark reaction mixture was stirred for 15 min, cooled to rt and concentrated under reduced pressure. The residue was taken up in EtOAc and the resulting solution was washed with sat. $Na_2CO_3$ solution. The organic layer was dried over $Na_2SO_4$, concentrated in vacuo and purified by flash chromatography on silica gel eluting with 10-60% EtOAc in hexanes to give 470 mg (95%) of compound 422B as a red solid.

C. (3aα,4β,7β,7aα)-2-(7-Bromo-2,1,3-benzoxadiazol-4-yl)hexahydro-4,7-dimethyl-4,7-epoxy-1H-isoindole-1,3(2H)-dione (422C)

A mixture of compound 422B (43 mg, 0.20 mmol), compound 20A (45 mg, 0.23 mmol), $MgSO_4$ (60 mg, 0.50 mmol), $Et_3N$ (139 μL, 1.0 mmol) and 1,2-dimethoxyethane (300 μL) were placed in a sealed tube and heated at 135° C. for 14 h. After cooling to rt the mixture was filtered through Celite eluting with MeOH to yield a dark solid which was purified by flash chromatography on silica gel eluting with 5-40% EtOAc in hexanes to give 42 mg (54%) of compound 422C as a yellow solid. HPLC: 99% at 2.96 min (retention time) (YMC S5 ODS column 4.6×50 mm Ballistic, 10-90% aqueous methanol over 4 minutes containing 0.2% $H_3PO_4$, 4 mL/min, monitoring at 220 nm). $^1H$ NMR (acetone-$d_6$, 400 MHz): δ=8.00 (d, J=7.5 Hz, 1H), 7.45 (d, J=7.5 Hz, 1H), 3.31 (s, 2H), 1.98-1.93 (m, 2H), 1.74-1.69 (m, 2H), 1.57 (s, 6H).

EXAMPLE 423

(3aα,4β,7β,7aα)-7-[Octahydro-4,7-dimethyl-1,3-dioxo-4,7-epoxy-2H-isoindol-2-yl]-2,1,3-benzoxadiazole-4-carbonitrile (423)

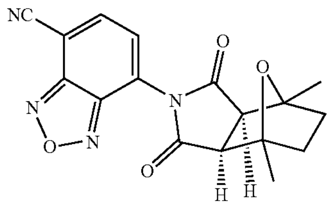

To a solution of compound 422C (42 mg, 0.11 mmol) in DMA (1 mL) was added CuCN (20 mg, 0.22 mmol) and the resulting mixture was heated at 150° C. for 5 h. The mixture was allowed to cool to rt and partitioned between EtOAc and aqueous NaCN solution (5 g/50 mL). The layers were separated and the aqueous layer was extracted once with EtOAc. The combined organic phases were dried over $Na_2SO_4$, concentrated in vacuo and purified by flash chromatography on silica gel eluting with 20-70% EtOAc in hexanes to give 13 mg (35%) of compound 423 as a yellow. oil. HPLC: 99% at 2.66 min (retention time) (YMC S5 ODS column 4.6×50 mm Ballistic, 10-90% aqueous methanol over 4 minutes containing 0.2% $H_3PO_4$, 4 mL/min, monitoring at 220 nm). MS (ES): m/z 396.9 $[M-H+OAc]^-$.

EXAMPLE 424

(3aα,4β,7β,7aα)-7-[Octahydro-4,7-dimethyl-1,3-dioxo-4,7-epoxy-2H-isoindol-2-yl]-2,1,3-benzothiadiazole-4-carbonitrile (424B)

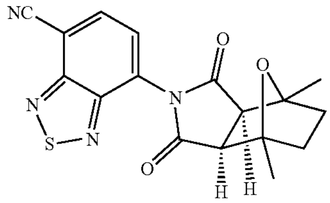

A. 4-Cyano-7-amino-benzothiadiazole (424A)

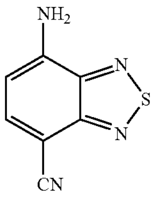

A solution of 2-cyano-5-nitrophenylenediamine (78 mg, 0.44 mmol, prepared as described in WO 0076501) in $SOCl_2$ (2 mL) was heated to reflux for 3 h. The resulting mixture was allowed to cool to rt and was then poured into ice/water. $CH_2Cl_2$ was added, the layers were separated and the aqueous layer was extracted twice with $CH_2Cl_2$. The combined organic phases were dried over $MgSO_4$, concentrated in vacuo and purified by flash chromatography on silica gel eluting with 50% EtOAc in hexanes to give 4-cyano-7-nitrobenzothiadiazole. This material was dissolved in AcOH (2 mL) containing EtOAc (1 mL) and $H_2O$ (0.2 mL) and heated to 70° C. At this temperature $Fe^0$ powder (78 mg, 1.41 mmol) was added in one solid portion and the dark mixture was stirred for 20 min and then cooled to rt. The reaction mixture was filtered through Celite eluting with EtOAc, washed with sat. $Na_2CO_3$ solution, dried over $MgSO_4$ and concentrated in vacuo. Purification by flash chromatography on silica gel eluting with 20-70% EtOAc in hexanes to yield 47 mg (67%) of compound 424A as a brown solid.

B. (3aα,4β,7β,7aα)-7-[Octahydro-4,7-dimethyl-1,3-dioxo-4,7-epoxy-2H-isoindol-2-yl]-2,1,3-benzothiadiazole-4-carbonitrile (424B)

A mixture of compound 424A (35 mg, 0.20 mmol), compound 20A (45 mg, 0.23 mmol), $MgSO_4$ (60 mg, 0.50 mmol), $Et_3N$ (139 μL, 1.0 mmol) and DME (200 μL) was placed in a sealed tube and heated at 135° C. for 14 h. After cooling to rt the mixture was filtered through Celite eluting with MeOH to yield a dark solid which was purified by a combination of flash chromatography on silica gel eluting with 10-50% EtOAc in hexanes reverse phase preparative HPLC (YMC S5 ODS 20×100 mm eluting with 27-100% aqueous methanol over 10 mincontaining 0.1% TFA, 20 mL/min) to give 36 mg (51%) of compound 424B as a yellow solid. HPLC: 98% at 2.45 min (retention time) (YMC S5 ODS column 4.6×50 mm Ballistic, 10-90% aqueous methanol over 4 minutes containing 0.2% $H_3PO_4$, 4 mL/min, monitoring at 220 nm). MS (DCI): m/z 355.0 $[M+H]^+$.

EXAMPLE 425

(3aα,4β,7β,7aα)-N-[2-[2-(4-Cyano-1-naphthalenyl)octahydro-7-methyl-1,3-dioxo-4,7-epoxy-4H-isoindol-4-yl]ethyl]-4-fluoro-N-methylbenzamide (425B)

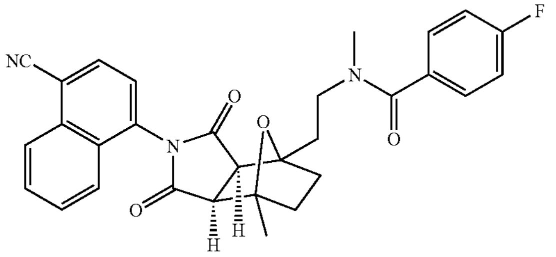

A. 4-Fluoro-N-methyl-N-[2-(5-methyl-furan-2-yl)-ethyl]-benzamide (425A)

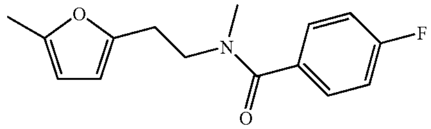

NaH (60% dispersion in oil, 65 mg, 1.63 mmol) was added portionwise to a solution of 4-fluoro-N-[2-(5-methyl-2-furanyl)ethyl]benzamide (269 mg, 1.09 mmol, 237A) in THF (5 mL). After gas evolution ceased, iodomethane (0.14 mL, 2.18 mmol) was added drop-wise. Once HPLC analysis showed the reaction to be 50% complete, the mixture was concentrated under reduced pressure and resubjected to the above conditions. After all the starting material was consumed, $H_2O$ was added and the resulting mixture was extracted with EtOAc (2×5 mL). The combined organic layers were dried over $Na_2SO_4$ and concentrated under reduced pressure. Purification by flash chromatography on silica gel eluting with 20% acetone/$CHCl_3$ gave 238 mg (84%) of compound 425A. HPLC: 98% at 2.94 min (retention time) (Phenomenex-prime S5-C18 column 4.6×50 mm eluting with 10-90% aqueous methanol over 4 minutes containing 0.2% phosphoric acid, 4 mL/min, monitoring at 220 nm). MS (ES): m/z [M+H]=262.38.

B. (3aα,4β,7β,7aα)-N-[2-[2-(4-Cyano-1-naphthalenyl)octahydro-7-25 methyl-1,3-dioxo-4,7-epoxy-4H-isoindol-4-yl]ethyl]-4-fluoro-N-methylbenzamide (425B)

A solution of compound 425A (183 mg, 0.75 mmol) and 4-(2,5-dihydro-2,5-dioxo-1H-1-yl)-1-naphthalenecarbonitrile (174 mg, 0.75 mmol) in benzene (1 mL) was heated at 60° C. for 15 hr. The reaction mixture was concentrated under reduced pressure to give 357 mg crude intermediate. The crude intermediate (156 mg) was dissolved in EtOAc (6 mL) and 10% Pd/C (16 mg) was added and the mixture was stirred under a hydrogen balloon overnight. The reaction mixture was filtered through a pad of Celite and concentrated under reduced pressure. Purification by reverse phase preparative HPLC (YMC S5 ODS 20×100 mm, 20-100% aqueous methanol over 15 minutes containing 0.1% TFA, 20 mL/min, monitoring at 220 nm) gave 160.3 mg (72%) of compound 425B as an off-white solid. HPLC: 99% at 3.23 min (retention time) (Phenomenex-prime S5-C18 column 4.6×50 mm eluting with 10-90% aqueous methanol over 4 minutes containing 0.2% phosphoric acid, 4 mL/min, monitoring at 220 nm). MS (ES): m/z [M+H]=512.19.

EXAMPLE 426

(3aα,4β,7β,7aα)-Hexahydro-4,7-dimethyl-2-[4-(2,2,2-trifluoro-1-hydroxyethyl)phenyl]-4,7-epoxy-1H-isoindole-1,3(2H)-dione (426B)

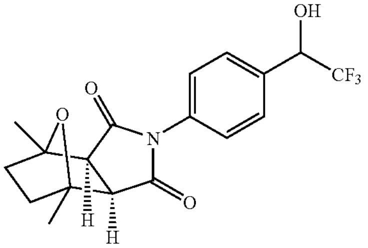

A. 1-(4-Amino-phenyl)-2,2,2-trifluoro-ethanol (426A)

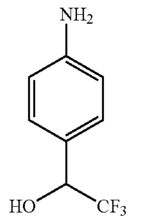

Compound 426A was made according to the procedure described in Stewart, R. et al. *Can. J. Chem.* 58, 2491-2496 (1980). $NaBH_4$ (47 mg, 1.235 mmol) was added to a solution of p-aminotrifluoroacetophenone (155.7 mg, 0.823 mmol, synthesized as described by Klabunde, K. J. et al. *J. Org. Chem.* 35, 1711-1712 (1970)) in isopropanol (3 mL) at rt. After 30 min the reaction was quenched with phosphate buffer (pH 7.2), diluted with $H_2O$ and extracted with EtOAc (2×10 mL). The combined organic layers were dried over $Na_2SO_4$ and concentrated under reduced pressure to give 154 mg (98%) of compound 426A as a tan solid. The material was used directly in the next step without purification. HPLC: 99% at 0.42 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z [M+H]=192.13.

B. (3aα,4β,7β,7aα)-Hexahydro-4,7-dimethyl-2-[4-(2,2,2-trifluoro-1-hydroxyethyl)phenyl]-4,7-epoxy-1H-isoindole-1,3(2H)-dione (426B)

A mixture of compound 426A (75.3 mg, 0.394), compound 20A (51.5 mg, 0.262 mmol), triethylamine (0.15 mL) and $MgSO_4$ (50 mg) in toluene (1 mL) was heated in a sealed tube to 135° C. for 15 hr. The mixture was filtered and concentrated under reduced pressure. Purification by reverse phase preparative HPLC (YMC S5 ODS 20×100 mm, 20-100% aqueous methanol over 15 minutes containing 0.1% TFA, 20 mL/min, monitoring at 220 nm) gave 63.1 mg (65%) of compound 426B as a white solid. HPLC: 98% at 2.49 min (retention time) (Phenomenex-prime S5-C18 column 4.6×50 mm eluting with 10-90% aqueous methanol over 4 minutes containing 0.2% phosphoric acid, 4 mL/min, monitoring at 220 nm). MS (ES): m/z [M+H]=370.16.

EXAMPLE 427

(3aα,4β,7β,7aα)-4-[4-[2-[[(1,1-Dimethylethyl)dimethylsilyl]oxy]ethyl]-1,3,3a,4,7,7a-hexahydro-7-methyl-1,3-dioxo-4,7-epoxy-2H-isoindol-2-yl]-2-(trifluoromethyl)benzonitrile & (3aα,4α,7α,7aα)-4-[4-[2-[[(1,1-Dimethylethyl)dimethylsilyl]oxy]ethyl]-1,3,3a,4,7,7a-hexahydro-7-methyl-1,3-dioxo-4,7-epoxy-2H-isoindol-2-yl]-2-(trifluoromethyl)benzonitrile (427i & 427ii)

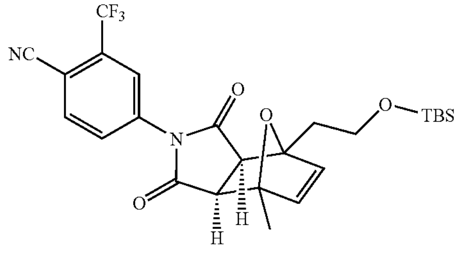

-continued

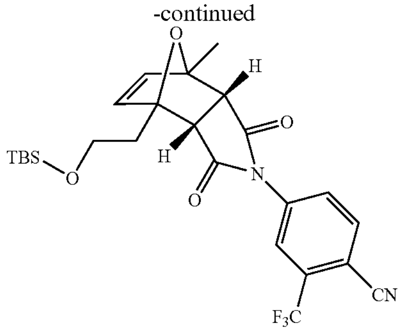

Compound 204A (2.00 g, 8.50 mmol) and 4-(2,5-dihydro-2,5-dioxo-1H-pyrrol-1-yl)-2-trifluoromethylbenzonitrile (1.50 g, 5.60 mmol) were mixed in benzene (5.0 mL) and heated at 60° C. for 14 h, then cooled to 25° C. The solvent was removed at 40° C. under vacuum for 1 h to give the crude material which was purified by flash chromatography on $SiO_2$ eluting with 0.5% $EtOAc/CH_2Cl_2$ to give 2.0 g of compound 427i and 1.3 g of compound 427ii, both as light brown solids. Compound 427i: HPLC: 95% at 4.200 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 507.1 $[M+H]^+$. Compound 427ii: HPLC: 95% at 4.20 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 507.1 $[M+H]^+$.

EXAMPLE 428

[3aR-(3aα,4β,5β,7β,7aα)]-4-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-2-(trifluoromethyl)benzonitrile & [3aS-(3aα,4β,5β,7β,7aα)]-4-[7-[2-[[(1,1-Dimethylethlyl)dimethylsilyl]oxy]ethyl]octahydro-5-hydroxy-4-methyl-1,3-dioxo-4,7-epoxy-2H-isoindol-2-yl]-2-(trifluoromethyl)benzonitrile (428i & 428ii)

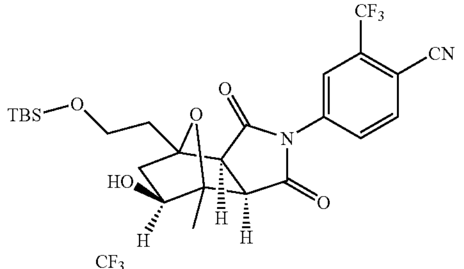

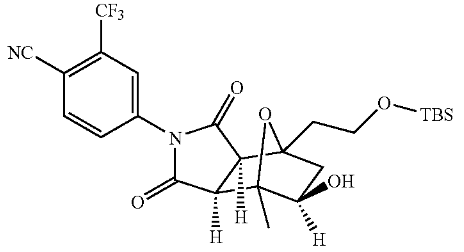

Compound 427i (1.40 g, 2.77 mmol) and $RhCl(PPh_3)_3$ (0.128 g, 0.14 mmol) were mixed in a flask. The flask was then evacuated and filled with argon three times, followed by the syringe addition of THF (3.0 mL). Once all particulates were dissolved, catecholborane (0.59 mL, 5.54 mmol) was added dropwise. The reaction mixture was stirred at 25° C. under argon for 30 min, then cooled to 0° C. Phosphate buffer (pH 7, 20 mL) was added, followed by EtOH (10 mL), 30% $H_2O_2/H_2O$ (2 mL). The reaction mixture was stirred at 0° C. for 3 h, then extracted with dichloromethane (3×25 mL). The combined organic layers were washed with 1 N NaOH (25 mL), 10% $Na_2SO_3$ (25 mL) and brine (25 mL). The crude material was then concentrated in vacuo and purified by flash chromatography on $SiO_2$ eluting with 2% EtOAc/$CH_2Cl_2$ to 10% EtOAc/$CH_2Cl_2$ to give 0.63 g of a racemic mixture of compounds 428i & 428ii as a light yellow solid. HPLC: 99% at 3.867 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 525.1 [M+H]

The racemic mixture of compounds 428i & 428ii was separated by normal phase preparative chiral HPLC using a Chiracel OD column (5 cm×50 cm), eluting with 13% solvent B (EtOH) in solvent A (hexanes), flow rate: 50 mL/min. Compound 428i eluted from 34 min to 38 min and compound 428ii eluted from 44 min to 49 min. Enantiomeric excess was determined by chiral HPLC. Compound 428i: >99% ee (12.576 min (retention time) (Chiralcel OJ column 4.6×250 mm eluting with isocratic 85% heptane/15% MeOH/ethanol (1:1), 1 mL/min, monitoring at 220 nm, 40° C.). Compound 428ii: 99% ee (18.133 min (retention time) (Chiralcel OJ column 4.6×250 mm eluting with isocratic 85% heptane/15% MeOH/ethanol (1:1), 1 mL/min, monitoring at 220 nm, 40° C.).

The absolute configurations for compounds 428i & 428ii were not established. For simplicity in nomenclature, compound 428i is designated herein as having an "R" configuration and compound 428ii as having an "S" configuration. Enantiomerically pure products derived from compound 428i are designated herein as having a "R" configuration and enantiomerically pure products derived from compound 428ii are designated herein as having an "S" configuration.

EXAMPLE 429

[3aR-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-2-(trifluoromethyl)benzonitrile & [3aS-(3aα,4β,5β,7β,7aα)]-4-[Octahydro-5-hydroxy-7-(2-hydroxyethyl)-4-methyl-1,3-dioxo-4,7-epoxy-2H-isoindol-2-yl]-2-(trifluoromethyl)benzonitrile (429i & 429ii)

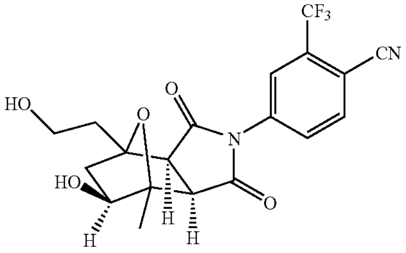

-continued

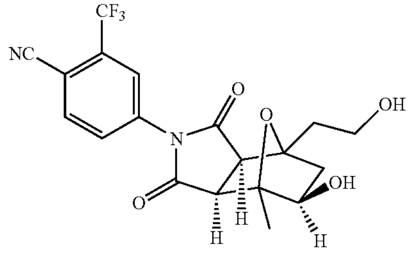

Compound 428i (180 mg, 0.34 mmol) was dissolved in 2% HCl/EtOH (5.0 mL). After 30 min, saturated $NaHCO_3$ was added and the aqueous layer was extracted with dichloromethane (20 mL×3), washed with brine and dried over $Na_2SO_4$ to give 135 mg of compound 429i as a white solid. HPLC: 99% at 2.257 min (retention time) (YMC S5 ODS column 4.6×50 mm eluting with 10-90% aqueous methanol over 4 minutes containing 0.2% phosphoric acid, 4 mL/min, monitoring at 220 nm). MS (ES): m/z 411.1 $[M+H]^+$.

The above procedure was repeated with compound 428ii to yield the desired diol compound 429ii in similar yield.

EXAMPLE 430

[3aR-(3aα,4β,5β,7β,7aα)]-4-[7-[2-[(5-Chloro-2-pyridinyl)oxy]ethyl]octahydro-5-hydroxy-4-methyl-1,3-dioxo-4,7-epoxy-2H-isoindol-2-yl]-2-(trifluoromethyl)benzonitrile (430)

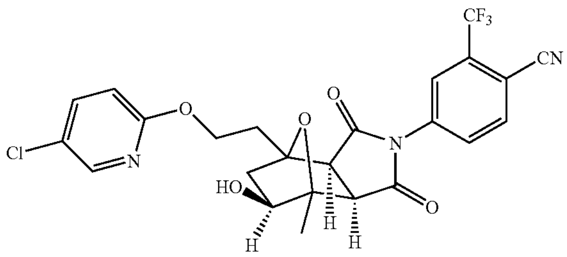

Triphenylphosphine (0.026 g, 0.098 mmol) and DBAD (0.023 g, 0.098 mmol) were mixed in THF (0.5 mL). After allowing the previous mixture to react for 15 min, 2-hydroxy-6-chloropyridine (0.016 g, 0.100 mmol) was added, the mixture was allowed to stir for 10 min and compound 429i (0.020 g, 0.049 mmol) was added. The reaction mixture was stirred at 25° C. for 2 h and then the crude material was purified by preparative TLC, eluting with 10% acetone/$CHCl_3$, to give 0.014 g of compound 430 as a light brown solid. HPLC: 100% at 3.370 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 522.08 $[M+H]^+$.

EXAMPLE 431

[3aS-(3aα,4β,5β,7β,7aα)]-4-[7-[2-[(5-Chloro-2-pyridinyl)oxy]ethyl]octahydro-5-hydroxy-4-methyl-1,3-dioxo-4,7-epoxy-2H-isoindol-2-yl]-2-(trifluoromethyl)benzonitrile (431)

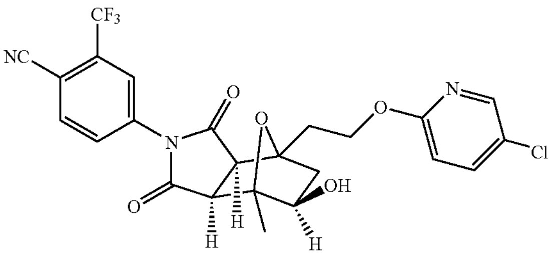

Triphenylphosphine (0.026 g, 0.098 mmol) and DBAD (0.023 g, 0.098 mmol) were mixed in THF (0.5 mL). After allowing the previous mixture to react for 15 min, 2-hydroxy-6-chloropyridine (0.016 g, 0.100 mmol) was added, the mixture was allowed to stir for 10 min and compound 429ii (0.020 g, 0.049 mmol) was added. The reaction mixture was stirred at 25° C. for 2 h and then the crude material was purified by preparative TLC, eluting with 10% acetone/$CHCl_3$, to give 0.015 g of compound 431 as a light brown solid. HPLC: 100% at 3.370 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 522.08 $[M+H]^+$.

EXAMPLE 432

(3aα,4β,7β,7aα)-2-(4-Cyano-1-naphthalenyl)octahydro-N-(2-hydroxyphenyl)-7-methyl-1,3-dioxo-4,7-epoxy-4H-isoindole-4-butanamide (432)

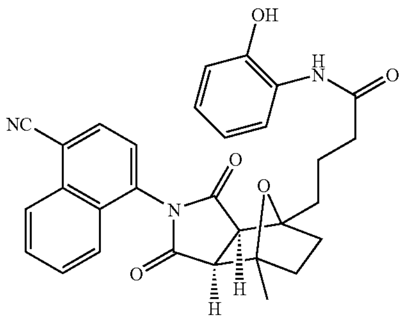

Compound 262 (0.100 g, 0.239 mmol) was dissolved in DMF (anhydrous, 1.5 mL), BOP (0.211 g, 0.478 mmol) was added followed by 2-aminophenol (0.052 g, 0.478 mmol) and N-methyl morpholine (0.052 mL, 0.478 mmol). The reaction mixture was stirred at 25° C. under argon for 3 h, then the crude material was purified by reverse phase preparative HPLC (YMC S5 ODS 20×100 mm, 20-100% aqueous methanol over 15 minutes containing 0.1% TFA, 20 mL/min, monitoring at 220 nm) to give 0.060 g of compound 432 as a light brown solid. HPLC: 100% at 3.037 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 510.34 $[M+H]^+$.

EXAMPLE 433

(3aα,4β,7β,7aα)-4-[4-[3-(2-Benzoxazolyl)propyl]octahydro-7-methyl-1,3-dioxo-4,7-epoxy-2H-isoindol-2-yl]-1-naphthalenecarbonitrile (433)

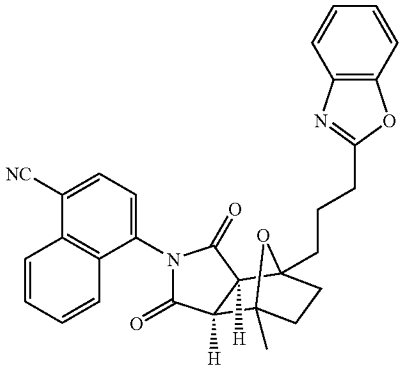

Triphenylphosphine (0.031 g, 0.118 mmol) and DBAD (0.027 g, 0.118 mmol) were mixed in THF (0.5 mL). After allowing the previous mixture to react for 15 min, compound 432 (0.030 g, 0.059 mmol) was added. The reaction mixture was stirred at 25° C. for 2 h and then the crude material was purified by reverse phase preparative HPLC (YMC S5 ODS 20×100 mm, 20-100% aqueous methanol over 15 minutes containing 0.1% TFA, 20 mL/min, monitoring at 220 nm) to give 0.018 g of compound 433 as a light brown solid. HPLC: 100% at 3.357 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 492.37 $[M+H]^+$.

EXAMPLE 434

(3aα,4β,5β,7β,7aα)-4-[4-Ethyloctahydro-5-hydroxy-7-(2-hydroxyethyl)-1,3-dioxo-4,7-epoxy-2H-isoindol-2-yl]-1-naphthalenecarbonitrile (434C)

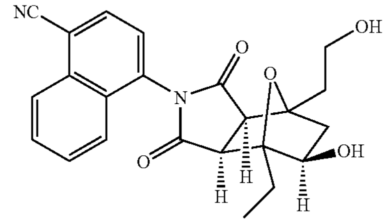

A. tert-Butyl-[2-(5-ethyl-furan-2-yl)-ethoxy]-dimethyl-silane (434A)

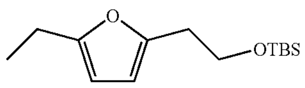

Imidazole (255 mg, 3.75 mmol) and TBSCl (414 mg, 2.75 mmol) were added to the solution of 245A (350 mg, 2.5 mmol) in DMF (4 mL). The mixture was stirred at rt for 15 hr and then 100 mg (0.66 mmol) of additional TBSCl was added to drive the reaction to completion. After stirring for an additional hour, the reaction mixture was diluted with diethylether (100 mL) and washed with water (20 mL), 1 N HCl (20 mL), water (20 mL) and brine (20 mL). The organic layer was dried over $Na_2SO_4$ and concentrated under reduced pressure to give 509 mg of compound 434A (80.3%) as a yellow oil.

B. (3aα,4β,7β,7aα)-4-[4-[2-[[(1,1-Dimethylethyl)-dimethylsilyl]oxy]ethyl]-4-ethyl-1,3,3a,4,7,7a-hexahydro-1,3-dioxo-4,7-epoxy-2H-isoindol-2-yl]-1-naphthalenecarbonitrile (434B)

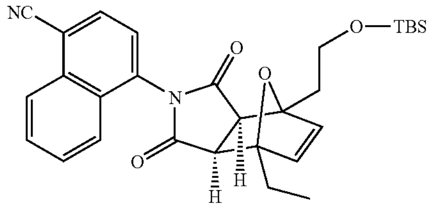

A solution of compound 434A (509 mg, 2.00 mmol) and 4-(2,5-dihydro-2,5-dioxo-1H-1-yl)-1-naphthalenecarbonitrile (498 mg, 2.00 mmol) in benzene (2 mL) was heated at 60° C. for 18 h. The reaction mixture was concentrated under reduced pressure to give 992 mg (99%) of crude compound 434B, which was used directly in the next step without further purification.

C. (3aα,4β,5β,7β,7aα)-4-[7-[2-[[(1,1-Dimethylethyl)-dimethylsilyl]oxy]ethyl]-4-ethyloctahydro-5-hydroxy-1,3-dioxo-4,7-epoxy-2H-isoindol-2-yl]-1-naphthalenecarbonitrile (434C)

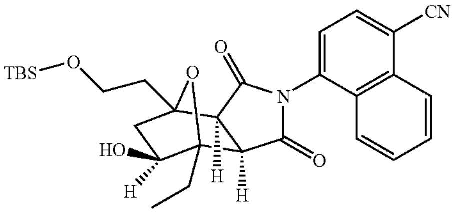

A mixture of compound 434B (992 mg, 1.98 mmol) and $RhCl_2(PPh_3)_3$ (183 mg, 0.198 mmol) was evacuated and filled with argon (3×). THF (20 mL) was added and once all particulates had dissolved, catecholborane (0.42 mL, 3.96 mmol) was slowly added dropwise. When the formation of product ceased, as was determined by HPLC, the reaction mixture was cooled to 0° C. and quenched with phosphate buffer (34 mL, pH 7.2) followed by the addition of EtOH (19 mL) and 30% $H_2O_2$ (2.9 mL). After 2 h, additional phosphate buffer (6.8 mL, pH 7.2), EtOH (3.8 mL) and $H_2O_2$ (0.6 mL) were added. The reaction mixture was stirred at rt for 3 h. Once the boronate intermediate was consumed, the mixture was extracted with $CH_2Cl_2$ (300 mL) and the combined organic layers were washed with 1 N NaOH, 10% aq. $NaHSO_3$ and brine and then dried over $Na_2SO_4$. Purification by flash chromatography on silica gel eluting with 10% MeOH/$CH_2Cl_2$ gave 75 mg (9.3%) of compound 434C as a gray solid. HPLC conditions: 97% at 2.43 min (retention time) (Phenomenex-prime S5-C18 column 4.6×50 mm, 10%-90% aqueous methanol over 4 minute gradient with 0.2% $H_3PO_4$, detecting at 220 nm). MS (ES): m/z 407.18 $[M+H]^+$.

D. (3aα,4β,5β,7β,7aα)-4-[4-Ethyloctahydro-5-hydroxy-7-(2-hydroxyethyl)-1,3-dioxo-4,7-epoxy-2H-isoindol-2-yl]-1-naphthalenecarbonitrile (434D)

Compound 434C (24 mg, 0.046 mmol) was dissolved in 2% conc. HCl/EtOH (0.8 mL) and the mixture was stirred at rt for 20 min. Cold sat. $NaHCO_3$ was added to the mixture until the solution was basic (pH 8). The reaction was extracted with EtOAc (3×2 mL) and the combined organic layers were washed with brine (2×5 mL) and dried over anhydrous sodium sulfate. Concentration in vacuo gave 14 mg (75%) of compound 434D as a white solid. HPLC: 95% at 2.40 min (retention time) (YMC S5 ODS 4.6×50 mm, 10%-90% aqueous methanol over 4 minute gradient with 0.2% $H_8PO_4$, monitoring at 220 nm).

EXAMPLE 435

(3aα,4β,5β,7β,7aα)-4-[7-[2-(4-Cyanophenoxy)ethyl]-4-ethyloctahydro-5-hydroxy-1,3-dioxo-4,7-epoxy-2H-isoindol-2-yl]-1-naphthalenecarbonitrile (435)

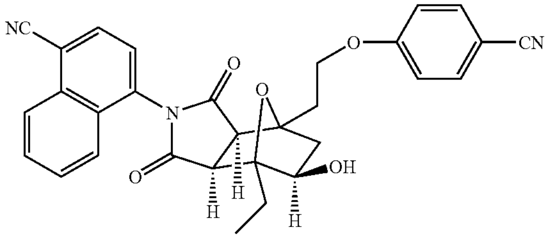

DBAD (39.6 mg, 0.172 mmol) was added to a solution of $PPh_3$ (45.1 mg, 0.172 mmol) in THF (0.8 mL). After stirring for 10 min, 4-cyanophenol (20.5 mg, 0.172 mmol) was added and the reaction mixture was stirred for an additional 5 min. Compound 434C (25.0 mg, 0.062 mmol) was added and the mixture was stirred at rt for 2 h. The reaction was concentrated under reduced pressure. Purification by Prep TLC eluting with 10% acetone/$CHCl_3$ gave 18.1 mg (0.036 mmol, 57.6%) of compound 435. HPLC conditions: 96% at 3.15 min (retention time) (YMC S5 ODS 4.6×50 mm, 10%-90% aqueous methanol over 4 minute gradient with 0.2% $H_3PO_4$, detecting at 220 nm). MS (ES): m/z 508.14 $[M+H]^+$.

EXAMPLE 436

(3aα,4β,7β,7aα)-2-(4-Cyano-1-naphthyalenyl)octahydro-N-(2-hydroxyphenyl)-7-methyl-1,3-dioxo-4,7-expoxy-4H-isoindole-4-ethanamide (436)

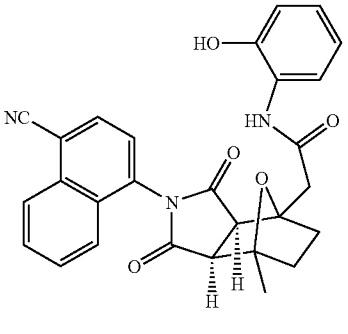

Compound 234B (0.100 g, 0.256 mmol) was dissolved in DMF (anhydrous, 1.5 mL), BOP (0.225 g, 0.51 mmol) was added followed by 2-aminophenol (0.056 g, 0.51 mmol) and N-methyl morpholine (0.056 mL, 0.51 mmol). The reaction mixture was stirred at 25° C. under argon for 3 h, then the crude material was purified by reverse phase preparative HPLC (YMC S5 ODS 20×100 mm, 20-100% aqueous methanol over 15 minutes containing 0.1% TFA, 20 mL/min, monitoring at 220 nm) to give 0.078 g of compound 436 as a light brown solid. HPLC: 100% at 3.037 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 482.34 $[M+H]^+$.

EXAMPLE 437

(3aα,4β,7β,7aα)-4-[4-(2-Benzoxazolylmethyl)octahydro-7-methyl-1,3-dioxo-4,7-epoxy-2H-isoindol-2-yl]-1-naphthalenecarbonitrile (437)

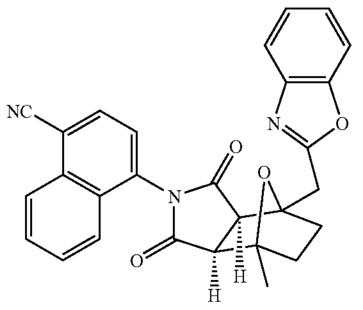

Triphenylphosphine (0.082 g, 0.312 mmol) and DBAD (0.072 g, 0.312 mmol) were mixed in THF (0.5 mL). After allowing the previous mixture to react for 15 min, compound 436 (0.075 g, 0.156 mmol) was added. The reaction mixture was stirred at 25° C. for 2 h and then the crude material was purified by reverse phase preparative HPLC (YMC S5 ODS 20×100 mm, 20-100% aqueous methanol over 15 minutes containing 0.1% TFA, 20 mL/min, monitoring at 220 nm) to give 0.052 g of compound 437 as a light brown solid. HPLC: 100% at 3.443 min (retention time) (YMC S5 ODS column 4.6×50 mm eluting with 10-90% aqueous methanol over 4 minutes containing 0.1% TFA, 4 mL/min, monitoring at 220 nm). MS (ES): m/z 464.18 $[M+H]^+$.

EXAMPLE 438

(3aα,4β,7β,7aα)-Hexahydro-4,7-dimethyl-2-[4-[2,2,2-trifluoro-1-hydroxy-1-(trifluoromethyl)ethyl]phenyl]-4,7-epoxy-1H-isoindole-1,3(2H)-dione (438)

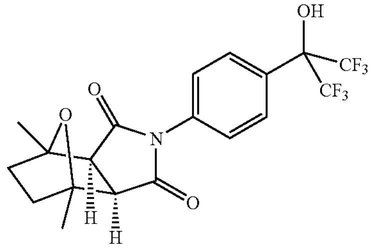

A mixture of 2-(4'-aminophenyl)-1,1,1,3,3,3-hexafluoro-2-propanol (95.7 mg, 0.369), compound 20A (48.3 mg, 0.246 mmol), triethylamine (0.15 mL) and $MgSO_4$ (50 mg) in toluene (1 mL) was heated in a sealed tube to 135° C. overnight. The mixture was filtered and concentrated under reduced pressure. Purification by reverse phase preparative HPLC (YMC S5 ODS 20×100 mm, 20-100% aqueous methanol over 15 minutes containing 0.1% TFA, 20 mL/min, monitoring at 220 nm) gave 44.0 mg (41%) of compound 438 as a white solid. HPLC: 99% at 3.10 min (retention time) (Phenomenex-prime S5-C18 column 4.6×50 mm eluting with 10-90% aqueous methanol over 4 minutes containing 0.2% phosphoric acid, 4 mL/min, monitoring at 220 nm). MS (ES): m/z [M+H]=438.14.

EXAMPLES 439 TO 454

Additional compounds of the present invention were prepared by procedures analogous to those described above. The compounds of Examples 439 to 454 have the following structure (L is a bond):

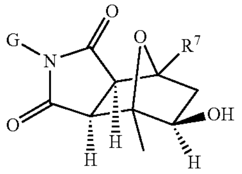

where G, $R^7$, the compound name, retention time, molecular mass, and the procedure employed, are set forth in Table 9. The absolute configuration for the following compounds was not determined. For simplicity in nomenclature, compound 243Di is designated herein as having an "S" configuration and compound 243Dii as having an "R" configuration. Enantiomerically pure products derived from compound 243Di are designated herein as having an "S" configuration and enantiomerically pure products derived from compound 243Dii are designated herein as having an "R" configuration. Similarly, compound 428i is designated herein as having an "S" configuration and compound 428ii as having an "R" configuration. Enantiomerically pure products derived from compound 428i are designated herein as having an "S" configuration and enantiomerically pure products derived from compound 428ii are designated herein as having an "R" configuration.

The chromatography techniques used to determine the compound retention times of Table 9 are as follows: LCMS=YMC S5 ODS column, 4.6×50 mm eluting with 10-90% $MeOH/H_2O$ over 4 minutes containing 0.1% TFA; 4 mL/min, monitoring at 220 nm. LCMS*=YMC S5 ODS column, 4.6×50 mm eluting with 10-90% $MeOH/H_2O$ over 2 minutes containing 0.1% TFA; 4 mL/min, monitoring at 220 nm. LC=YMC S5 ODS column 4.6×50 mm eluting with 10-90% $MeOH/H_2O$ over 4 minutes containing 0.2% phosphoric acid, 4 mL/min, monitoring at 220 nm. The molecular mass of the compounds listed in Table 9 were determined by MS (ES) by the formula m/z.

TABLE 9

| Ex. No | G | $R^7$ | Compound Name | Retention Time Min./ Molecular Mass | Procedure of Ex. |
|---|---|---|---|---|---|
| 439 | 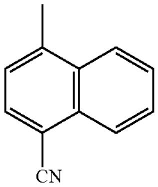 | 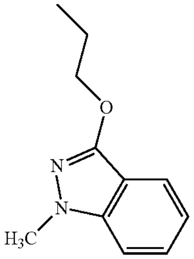 | [3aR-(3aα,4β,5β,7β,7aα)]-4-[Octahydro-5-hydroxy-4-methyl-7-[2-[(1-methyl-1H-indazol-3-yl)oxy]ethyl]-1,3-dioxo-4,7-epoxy-2H-isoindol-2-yl]-1-naphthalenecarbonitrile | 3.33 LC 523.3 $[M + H]^+$ | 251, 253 |
| 440 | 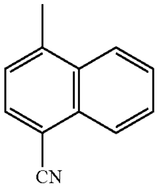 | 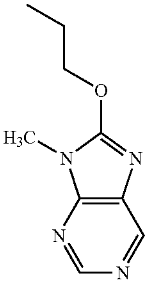 | [3aR-(3aα,4β,5β,7β,7aα)]-4-[Octahydro-5-hydroxy-4-methyl-7-[2-[(9-methyl-9H-purin-8-yl)oxy]ethyl]-1,3-dioxo-4,7-epoxy-2H-isoindol-2-yl]-1-naphthalenecarbonitrile | 2.34 LC 525.2 $[M + H]^+$ | 251, 253 |
| 441 | 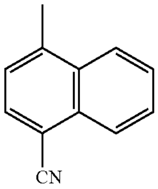 | 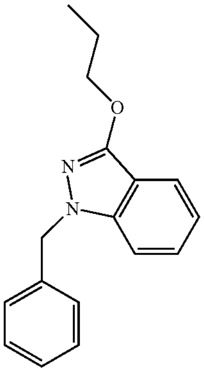 | [3aR-(3aα,4β,5β,7β,7aα)]-4-[Octahydro-5-hydroxy-4-methyl-1,3-dioxo-7-[2-[[1-(phenylmethyl)-1H-indazol-3-yl]oxy]ethyl]-4,7-epoxy-2H-isoindol-2-yl]-1-naphthalenecarbonitrile | 3.73 LC | 251, 253 |
| 442 | 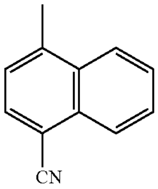 | 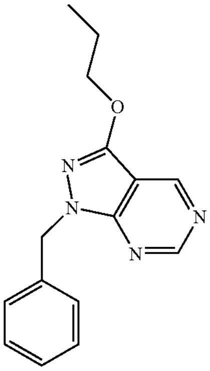 | [3aR-(3aα,4β,5β,7β,7aα)]-4-[Octahydro-5-hydroxy-4-methyl-1,3-dioxo-7-[2-[[1-(phenylmethyl)-1H-pyrazolo[3,4-d]pyrimidin-3-yl]oxy]ethyl]-4,7-epoxy-2H-isoindol-2-yl]-1-naphthalenecarbonitrile | 3.37 LC | 251, 253 |

TABLE 9-continued

| Ex. No | G | $R^7$ | Compound Name | Retention Time Min./ Molecular Mass | Procedure of Ex. |
|---|---|---|---|---|---|
| 443 | 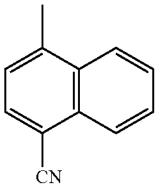 | 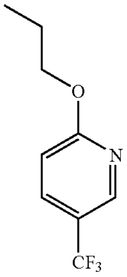 | [3aS-(3aα,4β,5β,7β,7aα)]-4-[Octahydro-5-hydroxy-4-methyl-1,3-dioxo-7-[2-[[5-(trifluoromethyl)-2-pyridinyl]oxy]ethyl]-4,7-epoxy-2H-isoindol-2-yl]-1-naphthalenecarbonitrile | 3.45 LC 538.23 $[M + H]^+$ | 243Di, 244i |
| 444 | 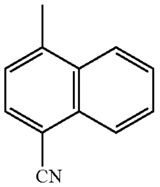 | 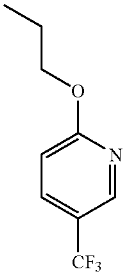 | [3aR-(3aα,4β,5β,7β,7aα)]-4-[Octahydro-5-hydroxy-4-methyl-1,3-dioxo-7-[2-[[5-(trifluoromethyl)-2-pyridinyl]oxy]ethyl]-4,7-epoxy-2H-isoindol-2-yl]-1-naphthalenecarbonitrile | 3.46 LC 538.24 $[M + H]^+$ | 243Dii, 244ii |
| 445 | 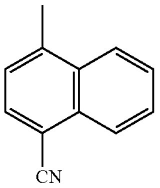 | 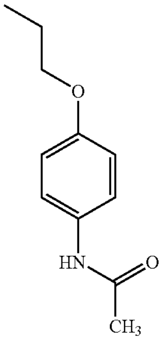 | [3aR-(3aα,4β,5β,7β,7aα)]-N-[4-[2-[2-(4-Cyano-1-naphthalenyl)octahydro-5-hydroxy-4-methyl-1,3-dioxo-4,7-epoxy-7H-isoindol-7-yl]ethoxy]phenyl]acetamide | 2.747 LC 526.28 $[M + H]^+$ | 243Dii, 244ii |
| 446 | 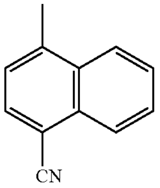 | 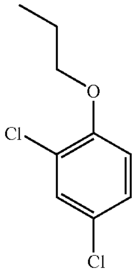 | [3aR-(3aα,4β,5β,7β,7aα)]-4-[7-[2-(2,4-Dichlorophenoxy)ethyl]octahydro-5-hydroxy-4-methyl-1,3-dioxo-4,7-epoxy-2H-isoindol-2-yl]-1-naphthalenecarbonitrile | 3.71 LC 537.17 $[M + H]^+$ | 243Dii, 244ii |
| 447 | 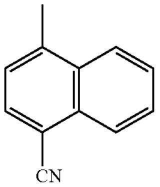 | 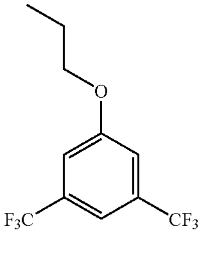 | [3aR-(3aα,4β,5β,7β,7aα)]-4-[7-[2-[3,5-Bis(trifluoromethyl)phenoxy]ethyl]octahydro-5-hydroxy-4-methyl-1,3-dioxo-4,7-epoxy-2H-isoindol-2-yl]-1-naphthalenecarbonitrile | 3.89 LC 605.25 $[M + H]^+$ | 243Dii, 244ii |

TABLE 9-continued

| Ex. No | G | R^7 | Compound Name | Retention Time Min./ Molecular Mass | Procedure of Ex. |
|---|---|---|---|---|---|
| 448 | 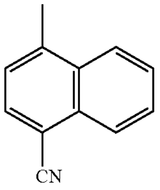 | 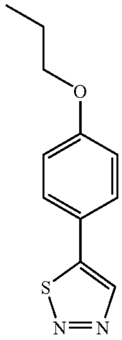 | [3aS-(3aα,4β,5β,7β,7aα)]-4-[Octahydro-5-hydroxy-4-methyl-1,3-dioxo-7-[2-[4-(1,2,3-thiadiazol-5-yl)phenoxy]ethyl]-4,7-epoxy-2H-isoindol-2-yl]-1-naphthalenecarbonitrile | 3.14 LC 553.1 $[M + H]^+$ | 243Di, 244i |
| 449 | 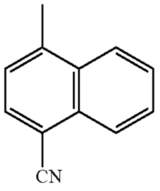 | 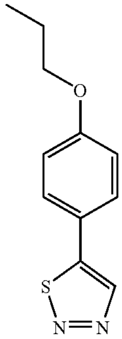 | [3aR-(3aα,4β,5β,7β,7aα)]-4-[Octahydro-5-hydroxy-4-methyl-1,3-dioxo-7-[2-[4-(1,2,3-thiadiazol-5-yl)phenoxy]ethyl]-4,7-epoxy-2H-isoindol-2-yl]-1-naphthalenecarbonitrile | 3.15 LC 553.23 $[M + H]^+$ | 243Dii, 244ii |
| 450 | 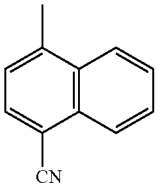 | 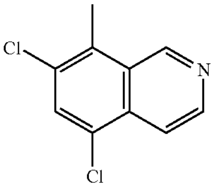 | [3aR-(3aα,4β,5β,7β,7aα)]-4-[7-[2-[(5,7-Dichloro-8-quinolinyl)oxy]ethyl]octahydro-5-hydroxy-4-methyl-1,3-dioxo-4,7-epoxy-2H-isoindol-2-yl]-1-naphthalenecarbonitrile, trifluoroacetate(1:1) | 3.70 LC 588.26 $[M + H]^+$ | 243Dii, 244ii |
| 451 | 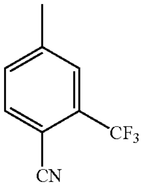 | 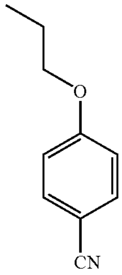 | [3aS-(3aα,4β,5β,7β,7aα)]-4-[7-[2-(4-Cyanophenoxy)ethyl]octahydro-5-hydroxy-4-methyl-1,3-dioxo-4,7-epoxy-2H-isoindol-2-yl]-2-(trifluoromethyl)benzonitrile | 3.087 LC 512.13 $[M + H]^+$ | 431 |
| 452 | 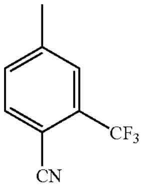 | 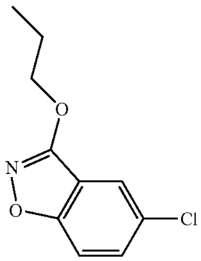 | [3aS-(3aα,4β,5β,7β,7aα)]-4-[7-[2-[(5-Chloro-1,2-benzisoxazol-3-yl)oxy]ethyl]octahydro-5-hydroxy-4-methyl-1,3-dioxo-4,7-epoxy-2H-isoindol-2-yl]-2-(trifluoromethyl)benzonitrile | 3.563 LC 562.08 $[M + H]^+$ | 431 |

TABLE 9-continued

| Ex. No | G | $R^7$ | Compound Name | Retention Time Min./ Molecular Mass | Procedure of Ex. |
|---|---|---|---|---|---|
| 453 | 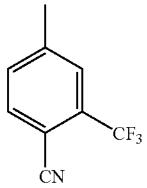 | 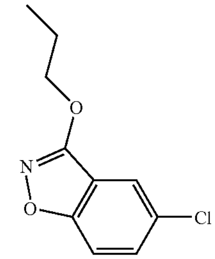 | [3aR-(3aα,4β,5β,7β,7aα)]-4-[7-[2-[(5-Chloro-1,2-benzisoxazol-3-yl)oxy]ethyl]octahydro-5-hydroxy-4-methyl-1,3-dioxo-4,7-epoxy-2H-isoindol-2-yl]-2-(trifluoromethyl) benzonitrile | 3.57 LC 562.08 $[M + H]^+$ | 430 |
| 454 | 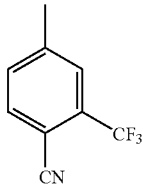 | 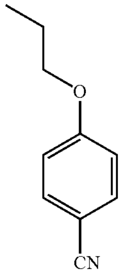 | [3aR-(3aα,4β,5β,7β,7aα)]-4-[7-[2-(4-Cyanophenoxy) ethyl]octahydro-5-hydroxy-4-methyl-1,3-dioxo-4,7-epoxy-2H-isoindol-2-yl]-2-(trifluoromethyl) benzonitrile | 3.087 LC 512.08 $[M + H]^+$ | 430 |

EXAMPLES 455 TO 457

Additional compounds of the present invention were prepared by procedures analogous to those described above. The compounds of Examples 455 to 457 have the following structure (L is a bond):

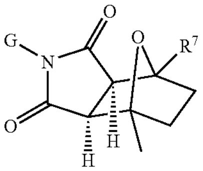

where G, $R^7$, the compound name, retention time, molecular mass, and the procedure employed, are set forth in Table 10. The absolute configuration for the following compounds was not determined. For simplicity in nomenclature, compound 238i is designated herein as having an "R" configuration and compound 238ii as having an "S" configuration. Enantiomerically pure products derived from compound 238i are designated herein as having an "R" configuration and enantiomerically pure products derived from compound 238ii are designated herein as having an "S" configuration.

The chromatography techniques used to determine the compound retention times of Table 10 are as follows: LCMS=YMC S5 ODS column, 4.6×50 mm eluting with 10-90% MeOH/$H_2O$ over 4 minutes containing 0.1% TFA; 4 mL/min, monitoring at 220 nm. LCMS*=YMC S5 ODS column, 4.6×50 mm eluting with 10-90% MeOH/$H_2O$ over 2 minutes containing 0.1% TFA; 4 mL/min, monitoring at 220 nm. LC=YMC S5 ODS column 4.6×50 mm eluting with 10-90% MeOH/$H_2O$ over 4 minutes containing 0.2% phosphoric acid, 4 mL/min, monitoring at 220 nm. The molecular mass of the compounds listed in Table 10 were determined by MS (ES) by the formula m/z.

TABLE 10

| Ex. No | G | $R^7$ | Compound Name | Retention Time Min./ Molecular Mass | Procedure of Ex. |
|---|---|---|---|---|---|
| 455 | 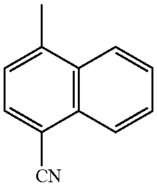 | 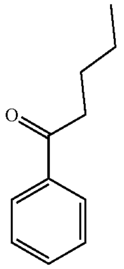 | (3aα,4β,5β,7β,7aα)-4-[Octahydro-4-methyl-1,3-dioxo-7-(4-oxo-4-phenylbutyl)-4,7-epoxy-2H-isoindol-2-yl]-1-naphthalenecarbonitrile | 3.53 LC 479.35 $[M + H]^+$ | 265, 266 |

TABLE 10-continued

| Ex. No | G | $R^7$ | Compound Name | Retention Time Min./ Molecular Mass | Procedure of Ex. |
|---|---|---|---|---|---|
| 456 | 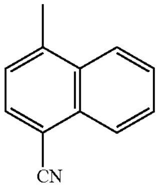 | 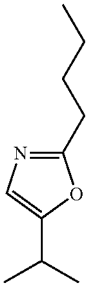 | (3aα,4β,5β,7β,7aα)-4-[Octahydro-4-methyl-7-[3-[5-(1-methylethyl)-2-oxazolyl]propyl]-1,3-dioxo-4,7-epoxy-2H-isoindol-2-yl]-1-naphthalenecarbonitrile | 3.547 LC 484.28 $[m + H]^+$ | 248, 249 |
| 457 | 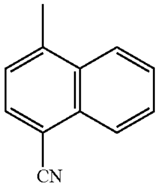 | 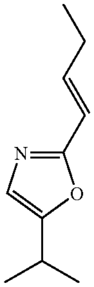 | [3aα,4β,5β,7β,7aα(E)]-4-[Octahydro-4-methyl-7-[3-[5-(1-methylethyl)-2-oxazolyl]-2-propenyl]-1,3-dioxo-4,7-epoxy-2H-isoindol-2-yl]-1-naphthalenecarbonitrile | 3.66 LC 482.28 $[M + H]^+$ | 248, 249 |

EXAMPLE 458

(3aα,4β,5β,7β,7aα)-4-(Octahydro-5-hydroxy-4,7-dimethyl-1,3-dioxo-4,7-epoxy-2H-isoindol-2-yl)-2-(trifluoromethyl)benzonitrile & (3aα,4β,5α,7β,7aα)-4-(Octahydro-5-hydroxy-4,7-dimethyl-1,3-dioxo-4,7-epoxy-2H-isoindol-2-yl)-2-(trifluoromethyl) benzonitrile (221B & 222D)

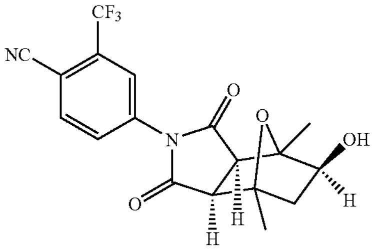

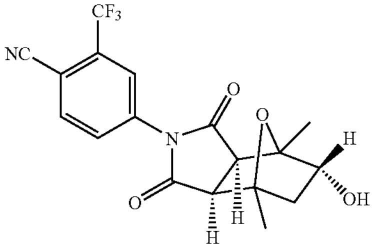

Compound 20B was converted to compounds 221B and 222D (also synthesized as compounds 221B and 222D) by biotransformation.

Compound 20B was hydroxylated by *Amycolatopsis orientalis* (ATCC 43491). A 1 mL culture from a frozen vial was used to inoculate 100 mL medium in a 500 mL portion Erlenmeyer flask and the flask was incubated at 28° C., at 200 rpm for 3 days. A 10 mL portion of this culture was used to inoculate 100 mL medium in a 500 mL Erlenmeyer flask and the flask was incubated at 28° C., at 200 rpm for 1 day. 10 mL portions of the 1-day culture were distributed to each of three 50 mL flasks. Compound 20B (3 mg in 0.1 mL methanol) was added to each culture and the incubations were continued for 3 days. The culture broth in each flask was extracted with 20 mL ethyl acetate, and the pooled ethyl acetate extracts were evaporated to dryness at 40° C. under a nitrogen stream. The residue was dissolved in 1.2 mL methanol and analyzed by HPLC, LC/MS and LC/NMR. The solution contained 2.5 mg of remaining Compound 20B, 1.6 mg of compound 221B, and 1.3 mg of compound 222D. MS and NMR analyses were in agreement with the structures shown above.

Medium: 0.5% toasted nutrisoy, 2% glucose, 0.5% yeast extract, 0.5% $K_2HPO_4$, 0.5% NaCl, adjusted to pH 7 with HCl (R. V. Smith and J. P. Rosazza, Arch. Biochem. Biophys., 161, 551-558 (1974)

HPLC Analysis

Column: Phenomenex Luna C18, 150×2 mm, 5μ mobile phase: solvent A: 95% 20 mM ammonium acetate pH 5.1, 5% acetonitrile solvent B: 95% acetonitrile, 5% 20 mM ammonium acetate pH 5.1 linear gradient going from 100% solvent A to 5% solvent A in 25 minutes followed by equilibration at 100% solvent A for 8 minutes.

temperature: 40° C.

detection: 250 nm injection volume: 1 μL retention times: compound 20B, 20.8 min; compound 221B, 16.5 min; compound 222D, 17.8 min HPLC Conditions Chiral HPLC conditions were employed for the separation of enantiomers and achiral HPLC conditions were employed for the separation of diastereomers of the hydroxylated analogs of compound 20B (i.e., compounds 221B and 222D and compounds 254i and 254ii)

Two methods were used under chiral HPLC conditions, reverse phase (RP) for chiral analysis of biotransformation products in biological samples and normal phase (NP) for non-biological samples.

Chiral RP-HPLC Condition

| | |
|---|---|
| Column: | CHIRALPAK AD-R 4.6 × 250 mm, 10μ |
| Temperature: | 40° C. |
| Injection Volume: | 5 or 20 μL |
| Mobile Phase: | A: MeCN<br>B: $H_2O$<br>Isocratic, 30% of A, 18 min. |
| Flow Rate: | 1 mL/min. |
| UV Detection: | 242 nm |

Chiral NP—HPLC Condition

| | |
|---|---|
| Column: | CHIRALPAK AD 4.6 × 250 mm, 10μ |
| Temperature: | 25° C. |
| Injection Volume: | 5 or 20 μL |
| Mobile Phase: | A: Heptane<br>B: MeOH/Ethanol (1:1)<br>Isocratic, 80% of A, 20 min. |
| Flow Rate: | 1 mL/min. |
| UV Detection: | 242 nm |

Under these conditions compounds 254i and 254ii had retention times of 8.5 minutes and 9.85 minutes, respectively.

Reverse phase HPLC was employed for the separation of the diastereomeric compounds 221B and 222D:

Mobile Phase:

Solvent A: 95% 20 mM ammonium acetate pH 5.1, 5% acetonitrile

Solvent B: 95% acetonitrile, 5% 20 mM ammonium acetate pH 5.1

Gradient:

Linear gradient going from 100% solvent A to 5% solvent A in 25 minutes followed by equilibration at 100% solvent A for 8 minutes. Total run time of 36 minutes.

Flow Rate:

0.2 mL/min

Column:

Phenomenex Luna 5 micron $C_{18}$ 150×2.0 mm id

Detection:

UV detection at 242 nm

Under these conditions, compounds 221B and 222D had retention times of 18.983 min and 20.362 min, respectively.

EXAMPLE 459

(3aα,4β,5β,7β,7aα)-4-[Octahydro-5-hydroxy-7-(2-hydroxyethyl)-4-methyl-1,3-dioxo-4,7-epoxy-2H-isoindol-2-yl]-1-naphthalenecarbonitrile (459)

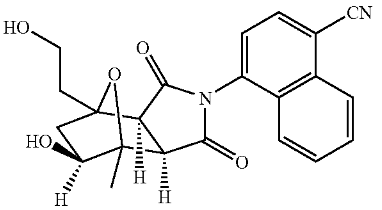

Compounds 223A and 331 were converted to compound 459 by biotransformation.

Microbial hydroxylation of compound 223A

1. Reaction

To a 500 mL flask containing 100 mL of the transformation medium was added one frozen vial (approximately 2 mL) of *Streptomyces griseus* ATCC 10137. The transformation medium was prepared as follows: to a 2 L plastic beaker was added 20 g of dextrose, 5.0 g of yeast extract, 5.0 g of soybean meal, 5.0 g of sodium chloride, 5.0 g of potassium phosphate (diabasic) and 1 L of deionized water, and the mixture was stirred at room temperature for 3 to 30 min. The pH of the mixture was then adjusted to 7.0 with 1 N HCl or 1 N NaOH. The resulting mixture was dispensed into 500 mL flasks (100 mL per flask). The flasks were covered with Bio/Wrap and autoclaved at 121° C. for 15 min. and cooled down to room temperature before use.

The culture was incubated at 28° C. and at 250 rpm for 24 hours. Ten mL of the resulting culture was transferred to a 50 mL flask, to which 1 mg of compound 223A in 0.2 mL ethanol was added. The flask was incubated at 28° C. and 250 rpm for 24 hours, and the reaction culture was extracted with EtOAc (10 mL). The EtOAc extract was dried under $N_2$ and the residue was dissolved in 1 mL of MeOH (reaction extract).

2. Product Analysis

HPLC:

10 μL of the reaction extract was injected into HPLC column (YMC ODS-AQ C-18 column, 150×6.0 mm i.d.). The column was eluted with 1 mM HCl in water/$CH_3CN$ at 1.2 mL/min flow rate: 30 to 60% $CH_3CN$ over 8 min, 60 to 85% $CH_3CN$ over 0.5 min, 85% $CH_3CN$ for 1 min, 85 to 30% $CH_3CN$ over 0.5 min. The eluents were monitored at 300 nm. Two major peaks with about a 1 to 1 area ratio were observed, which had the same UV spectra as those of compounds 459 and 331, and had retention times of 4.55 min and 7.23 min, respectively, matching the retention times of authentic samples of compound 459 (4.53 min) and compound 331 (7.2 min).

LC/MS

The reaction extract: two major UV peaks.

Peak 1, Tr 4.68 min: 391 $[M+H]^+$, 343, 319, 303, 289

Peak 2, Tr 5.35 min: 375 $[M+H]^+$, 345

Authentic samples

Compound 459, Tr 4.82 min: 391 $[M+H]^+$, 343, 319, 289

Compound 331, Tr 5.48 min: 375 $[M+H]^+$, 345

Microbial Hydroxylation of Compound 331

To a 500 mL flask containing 100 mL of the transformation medium was added one frozen vial (approximately 2 mL) of *Streptomyces griseus* ATCC 10137. The transformation medium was prepared as follows: to a 2 L plastic beaker was added 20 g of dextrose, 5.0 g of yeast extract, 5.0 g of soybean meal, 5.0 g of sodium chloride, 5.0 g of potassium phosphate (dibasic) and one L of deionized water, and the mixture was stirred at room temperature for 3 to 30 min. The pH of the mixture was then adjusted to 7.0 with 1 N HCl or 1 N NaOH. The resulting mixture was dispensed into 500 mL flasks (100 mL per flask). The flasks were covered with Bio/Wrap and autoclaved at 121° C. for 15 min. and cooled down to room temperature before use.

The culture was incubated at 28° C. and 250 rpm for 3 days. One mL of the resulting culture was added to a 500 mL flask containing 100 mL of the transformation medium and the flask was incubated at 28° C. and 250 rpm for 24 hours. Ten mL of the resulting culture was transferred to a 50 mL flask, to which 1 mg of compound 331 in 0.2 mL ethanol was added. The flask was incubated at 28° C. and 250 rpm for 23 hours. HPLC analysis showed that the peak area ratio of compound 459 to compound 331 in the reaction culture was about 1.1/1.

EXAMPLE 460

(1aα,2β,2aα,5aα,6βb,6aα)-4-[2-[2-[[(1,1-Dimethylethyl)dimethylsilyl]oxy]ethyl]octahydro-6-methyl-3,5-dioxo-2,6-epoxy-4H-oxireno[f]isoindol-4-yl]-1-naphthalenecarbonitrile (460)

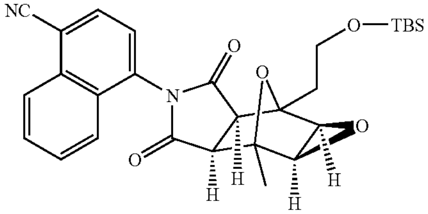

Compound 231A (2.00 g, 4.10 mmol) was dissolved in dicholomethane (40 mL) and cooled to 0° C. mCPBA (2.36 g, 8.20 mmol) was added. The reaction mixture was then warmed up to room temperature and stirred under argon for 18 hours, followed by the addition of 10% $Na_2SO_3$ (25 mL) and saturated $NaHCO_3$ (25 mL). After stirring for 20 minutes, the organic layer was separated and the aqueous layer was extracted with dicholomethane (3×50 mL). The combined organic layers were washed with brine, dried over $Na_2SO_4$ and concentrated under reduced pressure to give 2.0 g compound 460 as light yellow solid. HPLC: 99% at 4.00 min (retention time) (Phenomenex-prime S5-C18 column 4.6×50 mm eluting with 10-90% aqueous methanol over 4 minutes containing 0.2% phosphoric acid, 4 mL/min, monitoring at 220 nm). MS (ES): m/z [M+H]=505.19

EXAMPLE 461

[3aR-(3aα,4β,7β,7aα)]-4-[4-Ethyloctahydro-7-(2-hydroxyethyl)-1,3-dioxo-4,7-epoxy-2H-isoindol-2-yl]-1-naphthalenecarbonitrile & [3aS-(3aα,4β,7β,7aα)]-4-[4-Ethyloctahydro-7-(2-hydroxyethyl)-1,3-dioxo-4,7-epoxy-2H-isoindol-2-yl]-1-naphthalenecarbonitrile (461i & 461ii)

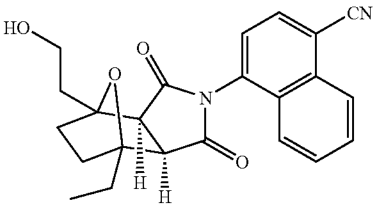

-continued

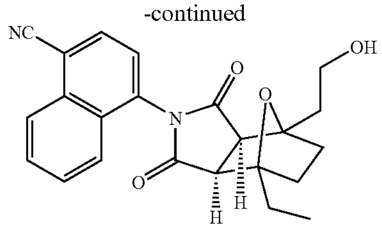

The racemic mixture of compounds 245C was separated by normal phase preparative chiral HPLC using a Chiracel AD column (5 cm×50 cm), eluting with 20% solvent B (50% MeOH/EtOH) in solvent A (Heptane), flow rate: 50 mL/min. Compound 461i eluted from 80 min to 100 min and compound 461ii eluted from 125 min to 150 min.

The absolute conformation for compounds 461i and 461ii was not determined. For simplicity in nomenclature, compound 461i is designated herein as having an "R" configuration and compound 461ii as having an "S" configuration. Enantiomerically pure products derived from compound 461i are designated herein as having an "R" configuration and enantiomerically pure products derived from compound 461ii are designated herein as having an "S" configuration.

EXAMPLE 462

[3aR-(3aα,4β,7β,7aα)]-4-[4-[2-(4-Cyanophenoxy)ethyl]-7-ethyloctahydro-1,3-dioxo-4,7-epoxy-2H-isoindol-2-yl]-1-naphthalenecarbonitrile (462)

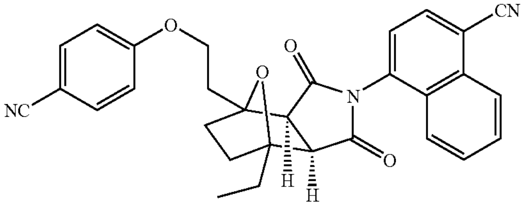

DBAD (29.5 mg, 0.128 mmol) was added to a solution of $PPh_3$ (33.6 mg, 0.128 mmol) in THF (0.5 mL). After stirring for 10 min, 4-cyanophenol (15.2 mg, 0.128 mmol) was added and the reaction mixture was stirred for an additional 5 min. Compound 461i (18.3 mg, 0.047 mmol) was added and the mixture was stirred at rt for 2 h. The reaction was concentrated under reduced pressure. Purification by flash chromatography on silica gel eluting with 40% EtOAc/hexane gave 16.9 mg (0.034 mmol, 73.2%) of compound 462. HPLC conditions: 98% at 3.64 min (retention time) (YMC S5 ODS 4.6×50 mm, 10%-90% aqueous methanol over 4 minute gradient with 0.2% $H_3PO_4$, detecting at 220 nm). MS (ES): m/z 492.23 $[M+H]^+$.

EXAMPLE 463

[3aS-(3aα,4β,7β,7aα)]-4-[4-[2-(4-Cyanophenoxy)ethyl]-7-ethyloctahydro-1,3-dioxo-4,7-epoxy-2H-isoindol-2-yl]-1-naphthalenecarbonitrile (463)

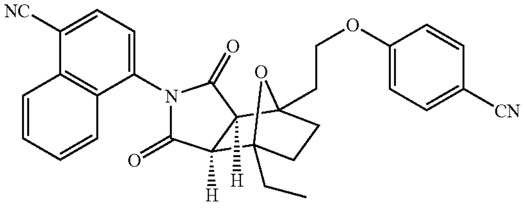

DBAD (29.5 mg, 0.128 mmol) was added to a solution of $PPh_3$ (33.6 mg, 0.128 mmol) in THF (0.5 mL). After stirring for 10 min, 4-cyanophenol (15.2 mg, 0.128 mmol) was added and the reaction mixture was stirred for an additional 5 min. Compound 461ii (18.3 mg, 0.047 mmol) was added and the mixture was stirred at rt for 2 h. The reaction was concentrated under reduced pressure. Purification by flash chromatography on silica gel eluting with 40% EtOAc/hexane gave 18.1 mg (0.037 mmol, 78.4%) of compound 463. HPLC conditions: 97% at 3.63 min (retention time) (YMC S5 ODS 4.6×50 mm, 10%-90% aqueous methanol over 4 minute gradient with 0.2% $H_8PO_4$, detecting at 220 nm). MS (ES): m/z 492.17 $[M+H]^+$.

EXAMPLE 464

(1aα,2β,2aα,5aα,6β,6aα)-5-[2-[2-[(5-Chloro-2-pyridinyl)oxy]ethyl]octahydro-6-methyl-3,5-dioxo-2,6-epoxy-4H-oxireno[f]isoindol-4-yl]-8-quinolinecarbonitrile (464H)

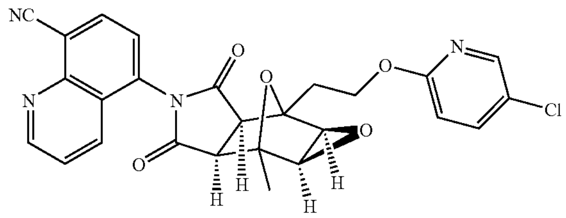

A. 8-Bromo-5-nitro-quinoline (464A)

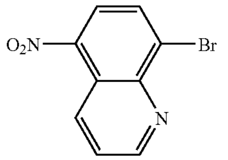

8-Bromoquinoline (25.00 g, 120.2 mmol) was dissolved in sulfuric acid (82.5 mL) at rt and then cooled to 0° C. $HNO_3$ (fuming, 32.5 mL) was then slowly added over a 10 minute period. The reaction was then warmed to rt and then to 65° C. After 48 h at 65° C., the reaction was cooled to rt and poured onto 500 g of ice. This solution was extracted with methylene chloride (5×200 mL). The organic layers were washed once with brine and dried over anhydrous sodium sulfate. Concentration gave the crude compound 464A as a light yellow solid (28.6 g, 94%). HPLC: 98% at 2.717 min (retention time) (YMC S5 ODS column, 4.6×50 mm, eluting with 10-90% aqueous methanol over 4 mincontaining 0.2% phosphoric acid, 4 mL/min, monitoring at 220 nm).

B. 5-Nitro-quinoline-8-carbonitrile (464B)

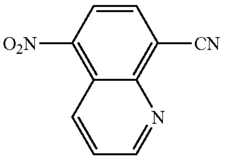

Compound 464A (15.0 g, 59.3 mmol) was dissolved in DMF (120 mL) and zinc cyanide (4.20 g, 35.9 mmol) was added. Bis(diphenylphosphino)ferrocene (3.00 g, 5.40 mmol) and tris(benzylidineacetone)dipalladium (3.00 g, 3.30 mmol) were then added and the reaction was heated to 100° C. for 1.5 h. The reaction was cooled to 22° C. and then poured into concentrated ammonium hydroxide (900 mL) resulting in an orange precipitate which was filtered and rinsed with cold water (1 L). The resulting precipitate was dissolved in methylene chloride, washed with brine (1×300 mL) and then dried over anhydrous sodium sulfate. Concentration in vacuo gave the crude material as an orange solid which was purified by flash chromatography on silica gel eluting with methylene chloride to give 6.01 g (51%) of compound 464B as a yellow solid. HPLC: 99% at 1.900 min (retention time) (YMC S5 ODS column, 4.6×50 mm, eluting with 10-90% aqueous methanol over 4 mincontaining 0.2% phosphoric acid, 4 mL/min, monitoring at 220 nm).

C. 5-Amino-quinoline-8-carbonitrile (464C)

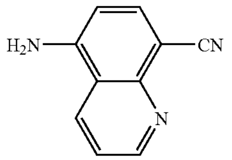

Compound 464B (6.00 g, 30.1 mmol) was dissolved in THF (150 mL) at reflux with mechanical stirring. EtOH (150 mL) was then added followed by aqueous ammonium chloride (2.4 g/225 mL water). The mixture was heated at 70° C. and then iron powder (325 mesh, 6.75 g, 120 mmol) was added with vigorous mechanical stirring. After 1 h, the reaction was cooled to 22° C. and filtered through Celite rinsing with methylene chloride. The filtrate was then concentrated to ~250 mL and the pH was adjusted to 10 by addition of 1N NaOH. The solution was then extracted with ethyl acetate (5×150 mL). The combined organic layers were washed once with brine (250 mL) and then dried over anhydrous magnesium sulfate. Concentration in vacuo gave 5.09 g (100%) of compound 464C as a yellow solid. HPLC: 99% at 1.143 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 170.16 $[M+H]^+$.

D. 5-(2,5-Dioxo-2,5-dihydro-pyrrol-1-yl)-quinoline-8-carbonitrile (464D)

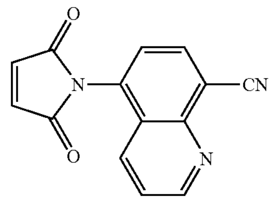

Compound 464C (7.00 g, 41.4 mmol) and maleic anhydride (6.00 g, 62.1 mmol) were combined in a sealed tube and THF (10 mL) was added. The reaction mixture was heated to 115° C. for 15 min then cooled to room temperature, resulting in the precipitation of the intermediate acid amide. The solid was filtered and rinsed with cold THF to give 11.0 g of the acid as a yellow solid. To the above acid amide was added $Ac_2O$ (25 mL) in a sealed tube and the mixture was heated at 100° C. for 15 min then cooled to room temperature. The resulting solid was filtered and rinsed with cold diethyl ether to give 8.30 g (80%) of compound 464D as a yellow solid. HPLC: 97% at 1.783 min (retention time) (YMC S5 ODS column, 4.6×50 mm, eluting with 10-90% aqueous methanol over 4 mincontaining 0.2% phosphoric acid, 4 mL/min, monitoring at 220 nm).

E. (3aα,4β,7β,7aα)-5-[4-[2-[[(1,1-Dimethylethyl) dimethylsilyl]oxy]ethyl]-1,3,3a,4,7,7a-hexahydro-7-methyl-1,3-dioxo-4,7-epoxy-2H-isoindol-2-yl]-8-quinolinecarbonitrile (464E)

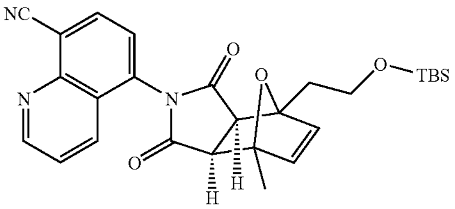

Compound 464D (6.00 g, 24.1 mmol) was dissolved in a mixture of benzene (80 mL) and acetone (20 mL) followed by addition of compound 204A (14.46 g, 60.15 mmol). The mixture was heated at 80° C. for 14 h and then cooled to 22° C. Concentration in vacuo at 40° C. followed by addition of acetone (40 mL) and concentration again at 40° C. The resulting yellow oil was purified by flash column chromatography on silica gel eluting with 0-10% acetone in chloroform to give 9.98 g (85%) of compound 464E as a yellow oil. Compound 464E was shown to be a single isomer by NMR spectroscopy. HPLC: 97% at 3.853 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 490.35 $[M+H]^+$.

F. (1aα,2β,2aα,5aα,6β,6aα)-5-[2-[2-[[(1,1-Dimethylethyl)dimethylsilyl]oxy]ethyl]octahydro-6-methyl-3,5-dioxo-2,6-epoxy-4H-oxireno[f] isoindol-4-yl]-8-quinolinecarbonitrile (464F)

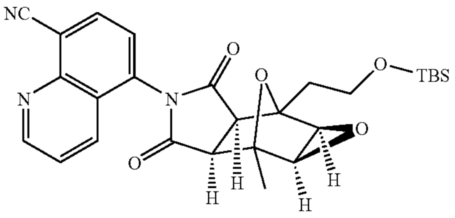

To a solution of compound 464E (0.050 g, 0.10 mmol) in dichloromethane (2 mL) was added mCPBA (60% mixture, 0.063 g, 0.22 mmol). The reaction mixture was stirred at room temperature for 16 h and then additional dichloromethane (20 mL), saturated $NaHCO_3$ (10 mL) and 10% $Na_2SO_3$ (10 mL) were added. The mixture was stirred vigorously for 40 min, the organic layer was then separated, washed once with brine, and dried over $Na_2SO_4$. Concentration in vacuo gave 48 mg (96%) of compound 464F as a light yellow solid. HPLC: 98% at 3.783 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 506.25 $[M+H]^+$.

G. (1aα,2β,2aα,5aα,6β,6aα)-5-[Octahydro-2-(2-hydroxyethyl)-6-methyl-3,5-dioxo-2,6-epoxy-4H-oxireno[f]isoindol-4-yl]-8-quinolinecarbonitrile (464G)

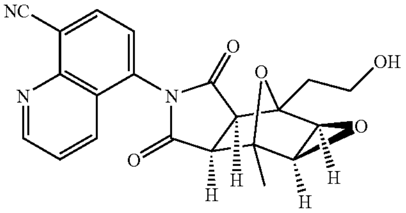

Compound 464F (1.30 g, 2.57 mmol) was dissolved in 2% conc. HCl/EtOH (50 mL). The reaction mixture was stirred at room temperature for 1 h and then saturated $NaHCO_3$ (50 mL) and dichloromethane (100 mL) were added. The organic layer was separated, washed once with brine and dried over $Na_2SO_4$. Concentration in vacuo gave 930 mg (93%) of compound 464G as a yellow solid. HPLC: 98% at 1.863 (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 392.20 $[M+H]^+$.

H. (1aα,2β,2aα,5aα,6β,6aα)-5-[2-[2-[(5-Chloro-2-pyridinyl)oxy]ethyl]octahydro-6-methyl-3,5-dioxo-2,6-dioxo-2,6-epoxy-4H-oxireno[f]isoindol-4-yl]-8-quinolinecarbonitrile (464H)

Triphenylphosphine (25 mg, 0.096 mmol) and DBAD (22 mg, 0.096 mmol) were mixed in THF (0.5 mL) under argon. After 5 min, 5-chloro-2-pyridinol (13 mg, 0.096 mmol) was added. The reaction mixture was stirred at 22° C. for another 10 min, then compound 464G (25 mg, 0.064 mmol) was added. The reaction mixture was stirred at 22° C. under argon for 3 h, and then concentrated in vacuo. The crude material was purified by preparative TLC on silica gel eluting with 10% acetone in chloroform to give 11 mg (23%) of compound 464H as a white solid. HPLC: 100% at 3.177 (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 503.14 $[M+H]^+$.

EXAMPLE 465

(3aα,4β,7β,7aα)-5-[4-[2-[[(1,1-Dimethylethyl)dimethylsilyl]oxy]ethyl]octahydro-7-methyl-1,3-dioxo-4,7-epoxy-2H-isoindol-2-yl]-8-quinolinecarbonitrile (465)

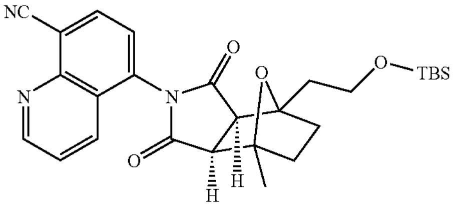

Compound 464E (2.40 g, 4.91 mmol) was dissolved in ethyl acetate and Pd/C (10% Pd, 0.50 g) was added. Hydrogen was then introduced via a balloon. After 3 h, the reaction was purged with nitrogen and filtered through Celite, rinsing with ethyl acetate. Concentration in vacuo gave 2.39 g (99%) of compound 465 as a yellow oil. HPLC: 95% at 4.013 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 492.22 $[M+H]^+$.

EXAMPLE 466

(3aα,4β,7β,7aα)-5-[Octahydro-4-(2-hydroxyethyl)-7-methyl-1,3-dioxo-4,7-epoxy-2H-isoindol-2-yl]-8-quinolinecarbonitrile (466)

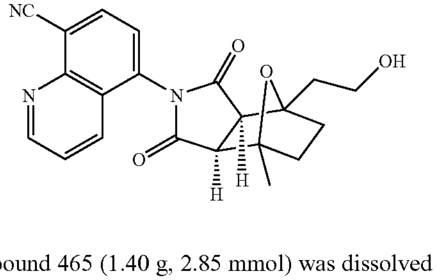

Compound 465 (1.40 g, 2.85 mmol) was dissolved in 2% conc. HCl/MeOH (20 mL) and stirred at 22° C. for 3 h. The reaction was then concentrated to ~5 mL volume and quenched with a minimum amount of sat. aq. sodium bicarbonate. This solution was then extracted with methylene chloride (3×30 mL) and the combined organic layers were dried over anhydrous sodium sulfate. Concentration in vacuo gave 0.893 g (93%) of compound 466 as a yellow solid. This material was taken on without further purification. HPLC: 98% at 2.140 min (retention time) (YMC S5 ODS column, 4.6×50 mm, eluting with 10-90% aqueous methanol over 4 min containing 0.2% phosphoric acid, 4 mL/min, monitoring at 220 nm). MS (ES): m/z 378.25 $[M+H]^+$.

EXAMPLE 467

[3aR-(3aα,4β,7β,7aα)]-5-[Octahydro-4-(2-hydroxyethyl)-7-methyl-1,3-dioxo-4,7-epoxy-2H-isoindol-2-yl]-8-quinolinecarbonitrile (467Bi) & [3aS-(3aα,4β,7β,7aα)]-5-[Octahydro-4-(2-hydroxyethyl)-7-methyl-1,3-dioxo-4,7-epoxy-2H-isoindol-2-yl]-8-quinolinecarbonitrile (467Bii)

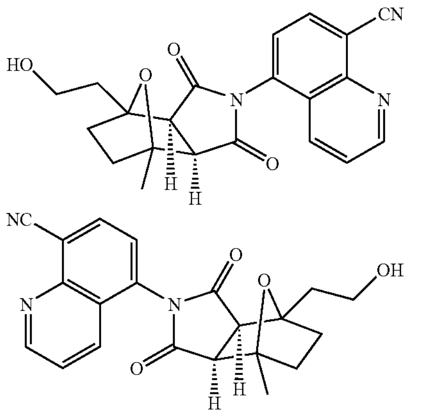

A. [3aR-(3aα,4β,7β,7aα)]-5-[4-[2-[[(1,1-Dimethylethyl)dimethylsilyl]oxy]ethyl]octahydro-7-methyl-1,3-dioxo-4,7-epoxy-2H-isoindol-2-yl]-8-quinolinecarbonitrile (467Ai) & [3aS-(3aα,4β,7β,7aα)]-5-[4-[2-[[(1,1-Dimethylethyl)dimethylsilyl]oxy]ethyl]octahydro-7-methyl-1,3-dioxo-4,7-epoxy-2H-isoindol-2-yl]-8-quinolinecarbonitrile (467Aii)

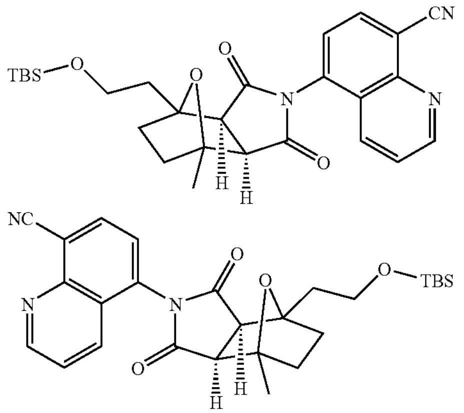

Compounds 465 was separated into its individual antipodes by normal phase preparative chiral HPLC. A Chiralcel OD column (50×500 mm) was used with a flow rate of 50 mL/min (16% EtOH/hexanes) monitoring at 220 nm. The faster eluting antipode compound 467Ai had a retention time of 40.85 min (>99% ee) and the slower antipode compound 467Aii had a retention time of 62.81 min (>99% ee). Both antipodes were isolated as white solids after separation. The absolute conformation for compounds 467Ai & 467Aii was not established. For simplicity in nomenclature, compound 467Ai is designated herein as having an “R” configuration and compound 467Aii as having an “S” configuration. Enantiomerically pure products derived from compound 467Ai are designated herein as having a “R” configuration and enantiomerically pure products derived from compound 467Aii are designated herein as having an “S” configuration.

B. [3aR-(3aα,4β,7β,7aα)]-5-[Octahydro-4-(2-hydroxyethyl)-7-methyl-1,3-dioxo-4,7-epoxy-2H-isoindol-2-yl]-8-quinolinecarbonitrile (467Bi) & [3aS-(3aα,4β,7β,7aα)]-5-[Octahydro-4-(2-hydroxyethyl)-7-methyl-1,3-dioxo-4,7-epoxy-2H-isoindol-2-yl]-8-quinolinecarbonitrile (467Bii)

Both antipodes were deprotected as described in example 464G to give the corresponding alcohols, compounds 467Bi and 467Bii as white solids:

Compound 467Bi: HPLC: 98% at 2.110 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 378.21 $[M+H]^+$.

Compound 467Bii: HPLC: 98% at 2.117 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 378.20 $[M+H]^+$.

EXAMPLE 468

(3aα,4β,7β,7aα)-8-[Octahydro-4,7-dimethyl-1,3-dioxo-4,7-epoxy-2H-isoindol-2-yl]-5-quinoxalinecarbonitrile (468C)

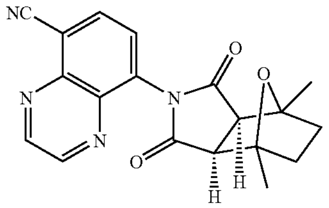

A. 8-Nitro-quinoxaline-5-carbonitrile (468A)

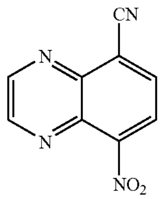

2,3-Diamino-4-nitro-benzonitrile (0.050 g, 0.28 mmol, as prepared in WO-98/32439) was added to solution of glyoxal (40% in water, 0.032 mL, 0.28 mmol) in acetic acid (0.75 mL) and stirred at 22° C. for 3 h. The reaction was cooled to 0° C. and water (2.0 mL) was added and the pH was adjusted to 9.0 by addition of ammonium hydroxide which caused the product to precipitate. The mixture was then filtered and rinsed with cold water. Drying in vacuo gave 0.039 g (70%) of compound 468A as an orange solid. HPLC: 100% at 2.037 min (retention time) (YMC S5 ODS column, 4.6×50 mm, eluting with 10-90% aqueous methanol over 4 mincontaining 0.2% phosphoric acid, 4 mL/min, monitoring at 220 nm).

B. 8-Amino-quinoxaline-5-carbonitrile (468B)

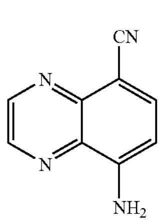

Compound 468A (0.200 g, 1.00 mmol) was suspended in acetic acid (5.0 mL) and iron powder (325 mesh, 0.112 g, 2.00 mmol) was added. The reaction was then heated at 70° C. for 20 min and then cooled to 22° C. The reaction was filtered through Celite, rinsing with ethyl acetate. The ethyl acetate rinse was collected and washed with sat. aq. $K_2CO_3$. The aqueous layer was extracted with ethyl acetate (3×20 mL) and the combined organic layers were dried over anhydrous magnesium sulfate. Concentration in vacuo gave 0.170 g (100%) of compound 468B as a yellow solid. HPLC: 88% at 1.677 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 171.29 $[M+H]^+$.

C. (3aα,4β,7β,7aα)-8-[Octahydro-4,7-dimethyl-1,3-dioxo-4,7-epoxy-2H-isoindol-2-yl]-5-quinoxalinecarbonitrile (468C)

Compound 468B (0.060 g, 0.35 mmol) was suspended in toluene (1.0 mL) with magnesium sulfate (0.060 g) and compound 20A (0.104 g, 0.529 mmol). TEA (0.2 mL) was then added and the mixture was heated to 145° C. in a sealed tube. After 16 h the reaction was cooled to 22° C. and filtered through Celite, rinsing with acetone. The mixture was concentrated in vacuo and then purified by preparative TLC on silica gel eluting with 7% ethyl acetate/methylene chloride. This gave 0.018 g (15%) of compound 468C as a yellow solid. HPLC: 100% at 2.040 and 2.133 min (atropisomers, retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 349.33 $[M+H]^+$.

EXAMPLE 469

(3aαc,4β,7β,7aα)-1,2,3,4-Tetrahydro-8-(octahydro-4,7-dimethyl-1,3-dioxo-4,7-epoxy-2H-isoindol-2-yl)-5-quinoxalinecarbonitrile (469B)

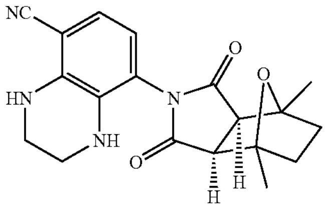

A. 8-Amino-1,2,3,4-tetrahydro-quinoxaline-5-carbonitrile (469A)

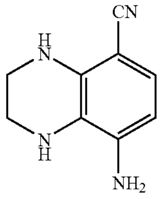

Compound 468A (0.037 g, 0.18 mmol) was dissolved in a mixture of ethyl acetate (1.0 mL)/ethanol (1.0 mL) and 10% Pd/C (0.050 g) was added. Hydrogen was then introduced via a balloon. After 2 h, the reaction was purged with nitrogen and filtered through Celite, rinsing with ethyl acetate. Concentration in vacuo gave 0.029 g (90%) of compound 469A as a red oil, which was taken on without further purification. HPLC: 97% at 3.217 min (retention time) (YMC S5 ODS column, 4.6×50 mm, eluting with 10-90% aqueous methanol over 4 mincontaining 0.2% phosphoric acid, 4 mL/min, monitoring at 220 nm).

B. (3aα,4β,7β,7aα)-1,2,3,4-Tetrahydro-8-(octahydro-4,7-dimethyl-1,3-dioxo-4,7-epoxy-2H-isoindol-2-yl)-5-quinoxalinecarbonitrile (469B)

Compound 469A (0.029 g, 0.17 mmol) was suspended in toluene (1.0 mL) with magnesium sulfate (0.030 g) and compound 20A (0.050 g, 0.256 mmol). TEA (0.2 mL) was then added and the mixture was heated at 145° C. in a sealed tube. After 48 h the reaction was cooled to 22° C. and filtered through Celite, rinsing with acetone. The mixture was concentrated in vacuo and then purified by preparative TLC eluting with 20% acetone in chloroform. This gave 0.014 g (24%) of compound 469B as a yellow solid. HPLC: 85% at 2.267 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 353.19 $[M+H]^+$.

EXAMPLE 470

(3aα,4β,7β,7aα)-4-(Octahydro-4,7-dimethyl-1,3-dioxo-4,7-epoxy-2H-isoindol-2-yl)-1-isoquinolinecarbonitrile (470E)

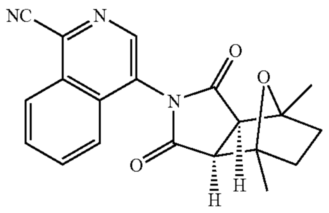

A. 4-Bromo-isoquinoline 2-oxide (470A)

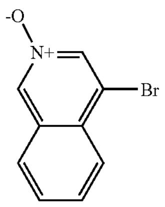

A solution of 4-bromoisoquinoline (4.16 g, 18.6 mmol) in 100 mL of chloroform was added dropwise over 1 h to a solution of 70% mCPBA (12.4 g, 50.3 mmol) in 100 mL of chloroform at room temperature. After stirring 18 h, the reaction mixture was washed with 1N NaOH (2×150 mL), dried over magnesium sulfate and concentrated in vacuo to afford 4.23 g (94%) of compound 470A as an off-white solid. $^1H$ NMR-400 MHz ($CDCl_3$): δ 8.71 (s, 1H), 8.43 (s, 1H), 8.09 (d, 1H, J=8 Hz), 7.70 (m, 3H).

B. 4-Bromo-isoquinoline-1-carbonitrile (470B)

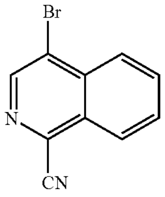

1,8-Diazabicyclo[5.4.0]undec-7-ene (1.67 mL, 11.2 mmol) was added to a mixture of compound 470A (1.12 g, 5.00 mmol) and cyanotrimethylsilane (0.75 mL, 5.5 mmol) in 35 mL of THF. The resulting homogeneous mixture was refluxed for 20 min. After concentrating in vacuo, the residue was purified by flash chromatography on a 5×15 cm silica gel column, eluting with 3:1 hexane:ethyl acetate to give 0.95 g (82%) of compound 470B as a white powder. $^1H$ NMR (400 MHz, $CDCl_3$): δ 8.85 (s, 1H), 8.36 (d, 1H, J=8.5 Hz), 8.28 (d, 1H, J=8.5 Hz), 7.96 (t, 1H, J=8.5 Hz), 7.89 (t, 1H, J=8.5 Hz).

C. 4-(2,4-Dimethoxy-benzylamino)-isoquinoline-1-carbonitrile (470C)

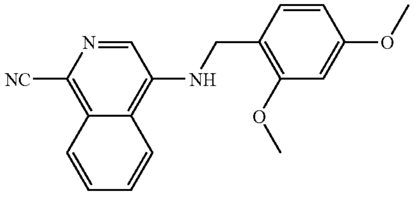

A mixture of compound 470B (699 mg, 3.00 mmol) and 2,4-dimethoxybenzylamine (4.8 mL, 30 mmol) in 15 mL of acetonitrile was refluxed for 16 h. After concentration in vacuo, the residue was purified on a 5×15 cm silica gel column, eluting with 3:2 hexane:ethyl acetate to afford 290 mg (30%) of 470C as a light yellow solid. HPLC: 1.76 min (retention time) (Phenomenex C-18, 5 micron column, 4.6×30 mm, eluting with 10-90% aqueous methanol over 2 mincontaining 0.1% TFA, 4 mL/min, monitoring at 254 nm).

D. 4-Amino-isoquinoline-1-carbonitrile (470D)

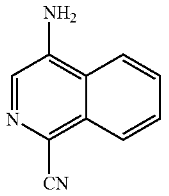

Compound 470C (50 mg, 0.16 mmol) was treated with trifluoroacetic acid (0.5 mL) for 1 h. The highly colored mixture was partitioned between ethyl acetate (30 mL) and 1N NaOH (30 mL). After washing with brine (15 mL), the organic layer was dried over magnesium sulfate and concentrated in vacuo to afford 24 mg (92%) of compound 470D as a yellow solid. HPLC: 99% at 1.09 min (retention time) (Phenomenex C-18, 5 micron column, 4.6×30 mm, eluting with 10-90% aqueous methanol over 2 mincontaining 0.1% TFA, 4 mL/min, monitoring at 254 nm). MS ($ES^+$): m/z 170.2 $[M+H]^+$.

An alternative route to the synthesis of compound 470D is as follows. A mixture of compound 470B (1.17 g, 5.02 mmol), benzophenone imine (1.05 mL, 6.26 mmol), palladium acetate (25 mg, 0.11 mmol), rac-2,2'-bis(diphenylphosphino)-1,1' binaphthyl (100 mg, 0.161 mmol) and cesium carbonate (2.30 g, 7.06 mmol) in 20 mL of toluene was heated at 100° C. for 20 h. The reaction mixture was diluted with ethyl ether (200 mL) and filtered through Celite. After concentrating the filtrate, the residue was dissolved in 120 mL of THF and treated with 40 mL of 1N HCl. After standing for 2 h at room temperature, the mixture was partitioned between ethyl acetate (150 mL) and 0.25 N NaOH (160 mL). After washing with brine (100 mL), the organic layer was dried over magnesium sulfate. The organic layer was filtered and ~50 g of celite was added to the filtrate. After concentration in vacuo, the powdery residue was purified by flash chromatography on a 5×15 cm silica gel column eluting with 1 L each of 1:1 ethyl acetate:hexane, 6:4 ethyl acetate:hexane and 8:2 ethyl acetate:hexane to give 450 mg (53%) of 470D as a yellow powder.

E. (3aα,4β,7β,7aα)-4-(Octahydro-4,7-dimethyl-1,3-dioxo-4,7-epoxy-2H-isoindol-2-yl)-1-isoquinolinecarbonitrile (470E)

A mixture of compound 470D (24 mg, 0.14 mmol), compound 20A (55 mg, 0.28 mmol), triethylamine (0.1 mL), magnesium sulfate (100 mg), 2-methoxyethylether (0.5 mL) and DMF (0.1 mL) was heated in a sealed vessel to 250° C. for a total of 2.5 h using a microwave heating device. After partitioning the reaction mixture between ethyl acetate (25 mL) and water (25 mL), the organic layer was dried over magnesium sulfate and concentrated in vacuo. Approximately half of the residue was purified by reverse phase preparative HPLC (YMC S5 ODS 20×50 mm, eluting with 10-100% aqueous methanol over 10 mincontaining 0.1% TFA, 20 mL/min). Concentration of the pure fraction afforded 6 mg (12%) of compound 470E as a white powder. HPLC: 99% at 1.42 min (retention time) (Phenomenex C-18, 5 micron column, 4.6×30 mm, eluting with 10-90% aqueous methanol over 2 min containing 0.1% TFA, 4 mL/min, monitoring at 254 nm). MS ($ES^+$): m/z 348.23 $[M]^+$.

EXAMPLE 471

[3aR-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (471Di) & [3aS-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (471Dii)

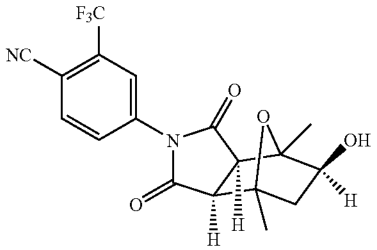

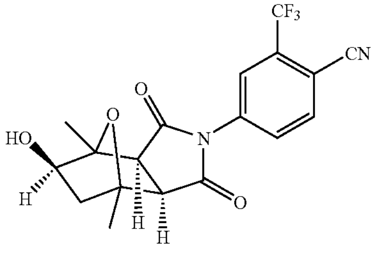

A. 4-(2,5-Dioxo-2,5-dihydro-pyrrol-1-yl)-2-trifluoromethylbenzonitrile (471A)

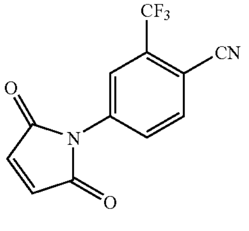

A mixture of 3-trifluoromethyl-4-cyano-aniline (24.0 g, 129 mmol) and maleic anhydride (14.0 g, 143 mmol) in 50 mL of acetic acid was heated at 115° C. overnight. A precipitate was obtained during the heating period. The reaction was allowed to stand at rt for an additional overnight period. The solid was removed by filtration, the filter cake was washed with diethyl ether and dried to give 21 g (79 mmol, 61%) of compound 471A as an off white solid. HPLC: 100% at 2.11 min (retention time) (YMC S5 ODS column, 4.6×50 mm, eluting with 10-90% aqueous methanol over 4 mincontaining 0.2% phosphoric acid, 4 mL/min, monitoring at 220 nm).

B. (3aα,4β,7β,7aα)-4-(1,3,3a,4,7,7a-Hexahydro-4,7-dimethyl-1,3-dioxo-4,7-epoxy-2H-isoindol-2-yl)-2-(trifluoromethyl)benzonitrile (471B)

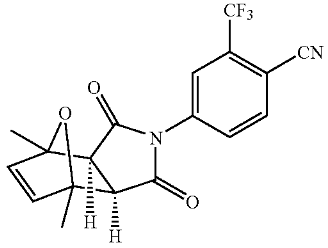

A suspension of compound 471A (13.0 g, 48.8 mmol) and 2,5-dimethylfuran (10.5 mL, 98.6 mmol) in 50 mL of toluene was heated at 60° C., under argon. A solution was obtained on initial heating and a precipitate was observed after approximately 1 h. Heating was continued overnight. After cooling to rt, the suspension was allowed to stand at 4° C. overnight. The resulting solid was filtered and the filter cake was washed with cold toluene followed by air drying to give 13.2 g of pure compound 471B as a white solid. The filtrate volume was reduced in vacuo by one half and the resulting solution was treated as above to yield an additional 2.8 g of pure compound 471B (total 16.0 g, 90%). HPLC: 90% at 3.65 min (retention time) (YMC S5 ODS column, 4.6×50 mm, eluting with 10-90% aqueous methanol over 4 mincontaining 0.2% phosphoric acid, 4 mL/min, monitoring at 220 nm).

C. (3aα,4β,5β,7β,7aα)-4-(Octahydro-5-hydroxy-4,7-dimethyl-1,3-dioxo-4,7-epoxy-2H-isoindol-2-yl)-2-(trifluoromethyl)benzonitrile (471C)

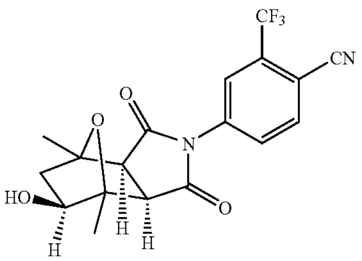

A solution of compound 471B (25 g, 69 mmol) in 125 mL of THF, in a dry flask under nitrogen, was cooled to 10° C. with an ice bath. To this solution was added neat borane-dimethylsulfide complex (13.0 mL, 138 mmol) dropwise over 10 min, while maintaining a reaction temperature of <15° C. The reaction mixture was stirred for 30 min at rt and then in an ice bath cooled to 101C. To the cool solution was slowly added 480 mL of pH 7 phosphate buffer, which resulted in a strong exothermic reaction and vigorous gas evolution. The solution was maintained at <21° C. throughout the addition by means of an ice bath. To the resulting solution was added 240 mL of ethanol and the resulting mixture was cooled to 5° C. with an ice bath. To the cooled solution was added 50 mL of 30% hydrogen peroxide and the resulting mixture was stirred at 10-20° C. for 1.5 h. The mixture was extracted with ethyl acetate (2×1 L) and the combined organic layers were washed with 10% sodium sulfite (1×500 mL) and brine (2×300 mL) and dried over $MgSO_4$. Concentration in vacuo afforded 29 g of crude product as a white solid. This material was subjected to flash chromatography on a 1.2 L column of silica gel equilibrated with 100% $CH_2Cl_2$. The material was applied to the column as a solution consisting of 100 mL EtOAc (warn) and 400 mL $CH_2Cl_2$. Initial elution with $CH_2Cl_2$ (3 L), followed by 25% EtOAc/75% $CH_2Cl_2$ (3 L) and finally 50% EtOAc/50% $CH_2Cl_2$ (6 L) gave 11.8 g (45%) of compound 471C which is a racemic mixture.

Alternatively compound 471C can be made by the following approach: A dry flask containing compound 471B (8.90 g, 24.6 mmol) and Wilkinson's catalyst (0.57 mg, 0.62 mmol) was degassed 4× with vacuum/argon. THF (40 mL) was added to the flask and the mixture was stirred until a clear brown solution was obtained. Catecholborane (49 mL, 49 mmol, 1 M in THF) was then added dropwise over 20 min and a slight exotherm was observed. Stirring was continued for 45 min followed by cooling of the reaction mixture with an ice bath. pH 7 phosphate buffer (175 mL) was slowly added, followed by the consecutive addition of ethanol (87 mL) and 30% hydrogen peroxide (18 mL). Stirring was continued with cooling and the reaction progress was monitored by HPLC for 4 h. The reaction was extracted with $CH_2Cl_2$ (3×250 mL). The combined extracts were washed with 1:1 1N NaOH:15% sodium sulfite (300 mL) and brine, dried over $MgSO_4$, and the solvent was removed in vacuo to afford 8.5 g of a tan solid. The crude product was subjected to flash chromatography on a 500 $cm^3$ silica gel column eluting with a gradient of 25-50% EtOAc/$CH_2Cl_2$ to give 6.00 g compound 471C (15.8 mmol, 64%) as a white solid. HPLC: 90% at 2.45 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 381.11 $[M+H]^+$.

D. [3aR-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (471Di) & [3aS-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (471Dii)

The individual antipodes of compound 471C were separated by normal phase preparative chiral HPLC (CHIRALPAK AD, 5×50 cm column). A 2.5 g portion of 471C was dissolved into 25 mL of warm acetone and diluted to 50-75 mL with hexane for injection. Isocratic elution with 20% MeOH/EtOH (1:1) in heptane at 50 mL/min gave the faster eluting compound 471Di (Chiral HPLC: 10.02 min; CHIRALPAK AD 4.6×250 mm column; isocratic elution with 20% MeOH/EtOH (1:1) in heptane at 1 mL/min) and the slower eluting compound 471Dii (Chiral HPLC: 14.74 min; CHIRALPAK AD 4.6×250 mm column; isocratic elution with 20% MeOH/EtOH (1:1) in heptane at 1 mL/min). Compounds 471Di & 471Dii: HPLC: 90% at 2.45 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 381.11 $[M+H]^+$. The absolute stereochemistry of compounds 471Di & 471Dii was determined by single crystal X-ray diffraction studies and is as described by the designated nomenclature.

The resulting HPLC purified fractions of compounds 471Di & 471Dii were further purified by crystallization using any one of the procedures described below.

1) From Ethyl Acetate

A 700 mg portion of compound 471Di, obtained after chiral chromatography as described above, was dissolved in ethyl acetate (10 mL) at rt. The solution was diluted with small portions of hexane (20 mL) until cloudiness was observed. The solution was allowed to stand overnight at rt. The resulting white solid was filtered and air dried to afford 430 mg of compound 471Di as a white powder. This sample was further dried at 60° C. (3 h, 0.5 Torr), then at 70° C., (12 h, 0.5 Torr).

2) From Acetone

A 500 mg portion of compound 471Di, obtained after chiral chromatography as described above, was dissolved in a minimal amount of acetone (3 mL) and slowly diluted with hexane (1 mL). The clear colorless solution was allowed to stand overnight at rt. The resulting white solid was filtered and air dried to afford 440 mg of compound 471Di as a white powder. This sample was further dried at 60° C., (3 h, 0.5 Torr) then at 70° C., (12 h, 0.5 Torr).

3) From Methanol

A 500 mg portion of compound 471Di, obtained after chiral chromatography as described above, was dissolved in 5 mL of hot (steam bath) methanol. The clear colorless solution was allowed to stand at rt for 2 h, then at 4° C. overnight. The resulting solid was filtered, washed with minimal cold methanol and air dried for to afford 360 mg of compound 471Di as a white powder. This sample was further dried at 70° C., (12 h, 0.5 Torr).

4) From $CH_2Cl_2$

A 7.00 g portion of compound 471Di, obtained after chiral chromatography as described above, was dissolved in 75 mL of $CH_2Cl_2$ at rt. The clear and colorless solution was slowly diluted with hexane (48 mL) until crystallization was observed. The solution was allowed to stand at rt for 1 h, then at 4° C. overnight. The resulting crystalline material was filtered and then washed with a minimal amount of cold 2:1 $CH_2Cl_2$:hexane. The large crystals were ground to a fine powder and dried at 50° C. (12 h, 0.5 Torr) to yield 5.96 g of compound 471Di as a white powder

EXAMPLE 472

(3aα,4β,7β,7aα)-4-(Octahydro-4,7-dimethyl-1,3-dioxo-4,7-epoxy-2H-isoindol-2-yl)-2-(trifluoromethyl)benzonitrile (472)

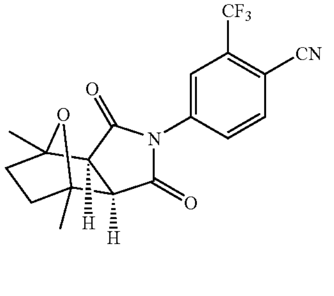

A solution of compound 471B (500 mg, 1.38 mmol) in ethyl acetate (10 mL), containing 10% Pd/C (25 mg, cat.) was stirred at rt under an atmosphere of hydrogen introduced via a balloon. After 2 h the reaction was filtered through Celite and the filter cake was washed with EtOAc. The clear, colorless filtrate was concentrated in vacuo to yield 501 mg (1.38 mmol, 100%) of compound 472 as a white solid. No further purification was required. HPLC: 99% at 3.04 min (retention time) (YMC S5 ODS column, 4.6×50 mm, 10-90% aqueous methanol over 4 mincontaining 0.2% phosphoric acid, 4 mL/min, monitoring at 220 nm). MS (ESI): m/z 382.2 $[M+NH_4]^+$.

EXAMPLE 473

(3aα,4β,5β,7β,7aα)-4-[5-(Acetyloxy)octahydro-4,7-dimethyl-1,3-dioxo-4,7-epoxy-2H-isoindol-2-yl]-2-(trifluoromethyl)benzonitrile (473)

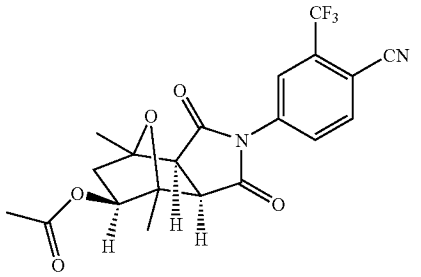

To a solution of compound 471C (1.50 g, 3.95 mmol) in 10 mL of pyridine, cooled to 0° C. under argon, was added acetic anhydride (0.42 mL, 4.4 mmol) dropwise, followed by DMAP (5 mg, 0.04 mmol). Stirring was continued at rt for 4 h. The solution was concentrated in vacuo and the resulting residue was diluted with ethyl acetate, and washed consecutively with 1N HCl (2×), brine (2×), sat. $NaHCO_3$, and brine (2×). The organic layer was dried over $MgSO_4$ and concentrated in vacuo. The resulting solid was dried at 60° C. (20 h, 0.5 Torr) to yield 1.55 g (3.67 mmol, 93%) of compound 473 as a white crystalline solid. HPLC: 99% at 2.10 min (retention time) (Phenomenex Luna C18 column, 2×30 mm, 0-100% aqueous acetonitrile over 3 mincontaining 10 mM $NH_4OAc$ at 1 mL/min, monitoring at 220 nm). MS (ESI): m/z 421.4 $[M-H]^-$.

EXAMPLE 474

(3aα,4β,7β,7aα)-Hexahydro-4,7-dimethyl-2-(2-methyl-4-benzoxazolyl)-4,7-epoxy-1H-isoindole-1,3(2H)-dione (474F)

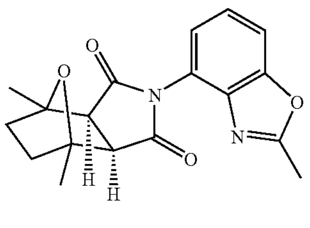

A. 2-Methyl-4-nitrobenzoxazole (474A)

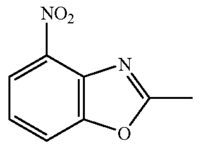

To 2-amino-3-nitrophenol (6.17 g, 40.0 mmol) was added triethylorthoacetate (25.96 g, 160.0 mmol) and the mixture was heated at 100° C. for 12 h to give a dark red solution. Cooling to room temperature produced a crystalline mass which was filtered and washed with hexane to give compound 474A (6.78 g, 95%) as light maroon needles. HPLC: 98.1% at 1.86 min (retention time) (YMC S5 ODS column, 4.6×50 mm, eluting with 10-90% aqueous methanol over 4 mincontaining 0.2% phosphoric acid, 4 mL/min, monitoring at 220 μm). MS (ES): m/z 179.08 $[M+H]^+$.

B. 4-Amino-2-methylbenzoxazole (474B)

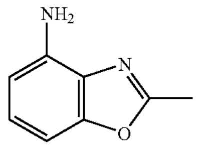

Compound 474A (6.78 g, 38.1 mmol) was dissolved in a 1:1 mixture of 10% acetic acid/ethyl acetate (100 mL total volume) and heated to 65° C. Iron powder (10.63 g, 190.2 mmol) was added portionwise. After stirring for 3 h, TLC indicated complete consumption of starting material. The cooled reaction mixture was filtered through a pad of Celite and the pad was washed with 50 mL of ethyl acetate. The organic layer was separated, washed with water (2×25 mL), brine (1×25 mL), dried over $MgSO_4$, filtered and concentrated in vacuo. The crude material was purified by flash chromatography on silica gel eluting with 25% ether/$CH_2Cl_2$ to give 3.90 g (69%) of compound 474B as a light brown solid. HPLC: 95.8% at 2.43 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 149.11 $[M+H]^+$.

C. 4-Amino-7-bromo-2-methylbenzoxazole (474C)

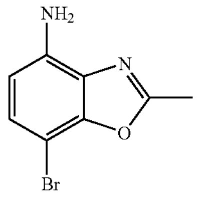

Compound 474B (3.90 g, 26.3 mmol) was dissolved in DMF (45 mL) and cooled to −5° C. and N-bromosuccinimide (4.68 g, 26.3 mmol) was added in small portions and the reaction stirred for 5 h. The mixture was poured into 150 mL of ice water to give a cream colored solid which was filtered, washed with water, dissolved in $CH_2Cl_2$, dried over $MgSO_4$, filtered and concentrated in vacuo. Purification of the crude material by flash chromatography on silica gel eluting with 20% ether/$CH_2Cl_2$ gave compound 474C (3.36 g, 56%) as a beige solid. HPLC: 95.4% at 2.583 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 228.03 $[M+H]^+$.

D. 1-(7-Bromo-2-methyl-benzoxazol-4-yl)-pyrrole-2,5-dione (474D)

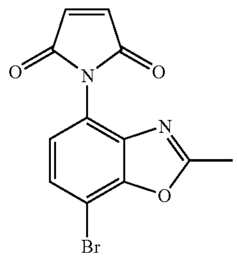

Compound 474C (1.40 g, 6.17 mmol) was dissolved in 20 mL of acetic acid, maleic anhydride (0.635 g, 6.47 mmol) was added and the reaction was heated at reflux under nitrogen for 5 h. The solvent was removed in vacuo and the crude product was purified by flash chromatography on silica gel eluting with 10% ether/$CH_2Cl_2$ to give compound 474D (1.73 g, 91%) as a pale yellow solid. HPLC: 93.6% at 1.36 min. (Phenomenex column, 30×4.6 mm, 10-90% aqueous methanol over 2 mincontaining 0.1% TFA, 5 mL/min, monitoring at 220 nm. MS (ES): m/z 308.02 $[M+H]^+$.

E. (3aα,4β,7β,7aα)-2-(7-Bromo-2-methyl-4-benzoxazolyl)-3a,4,7,7a-tetrahydro-4,7-dimethyl-4,7-epoxy-1H-isoindole-1,3(2H)-dione (474E)

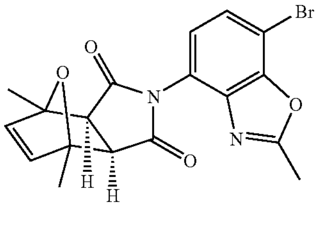

Compound 474D (0.307 g, 1.00 mmol) was dissolved in benzene (2 mL) and 2,5-dimethylfuran (0.154 g, 1.60 mmol) was added via syringe. The reaction mixture was heated to 60° C. for 12 h. The cooled reaction mixture was concentrated in vacuo at 40° C. to give compound 474E as an off-white foam which was used directly in the next reaction without purification.

F. (3aα,4β,7β,7aα)-Hexahydro-4,7-dimethyl-2-(2-methyl-4-benzoxazolyl)-4,7-epoxy-1H-isoindole-1,3(2H)-dione (474F)

Compound 474E (0.403 g, 1.00 mmol) was dissolved in EtOH/EtOAc (4 mL/4 mL) and 10% Pd/C (100 mg) was added. The reaction mixture was stirred at room temperature for 6 h under an atmosphere of $H_2$ supplied by a balloon and then filtered through Celite. Concentration of the filtrate in vacuo gave a brown solid. Purification by flash chromatography on silica gel eluting with 10% acetone/$CHCl_3$ (250 mL), 15% acetone/$CHCl_3$ (250 mL), and 20% acetone/$CHCl_3$ (250 mL) gave compound 474F (0.089 g, 27%) as a white foam. HPLC: 91% at 2.28 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 328.34 $[M+H]^+$.

EXAMPLE 475

(3aα,4β,7β,7aα)-2-(7-Bromo-2-methyl-4-benzoxazolyl)hexahydro-4,7-dimethyl-4,7-epoxy-1H-isoindole-1,3(2H)-dione (475)

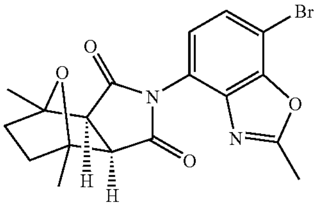

Compound 474E (0.202 g, 0.501 mmol) was dissolved in 1/1 EtOAc/EtOH (10 mL) and 10% Pt/C (100 mg) was added. The reaction mixture was stirred at room temperature under an $H_2$ balloon for 6 h. The reaction was filtered through Celite and concentrated in vacuo. Purification by flash chromatography on silica gel eluting with 10% ether/$CH_2Cl_2$ gave 0.063 g (31%) of compound 475 as a colorless oil which solidified upon standing to give a white solid. HPLC: 92.5% at 2.83 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 406.21 $[M+H]^+$.

EXAMPLE 476

(3aαc,4β,7β,7aα)-Hexahydro-4,7-dimethyl-2-[2-(trifluoromethyl)-4-benzoxazolyl]-4,7-epoxy-1H-isoindole-1,3(2H)-dione (476D)

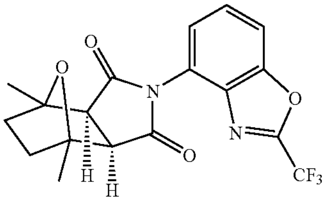

A. 4-Nitro-2-trifluoromethylbenzoxazole (476A)

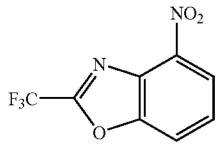

2-Amino-3-nitrophenol (10.00 g, 64.88 mmol) was added to 100 mL of vigorously stirring trifluoroacetic anhydride and the resulting mixture was stirred at room temperature for 12 h. The solvent was removed in vacuo to give a dark blue solid which was dissolved in 200 mL of $CH_2Cl_2$ and washed sequentially with 10% NaOH (2×100 mL), water (100 mL), brine (100 mL), and dried over $MgSO_4$. Filtration and concentration in vacuo gave compound 476A (10.78 g, 72%) as a brown solid. No further purification was required. HPLC: 92.9% at 2.43 min (retention time) (YMC S5 ODS column, 4.6×50 mm, eluting with 10-90% aqueous methanol over 4 mincontaining 0.2% phosphoric acid, 4 mL/min, monitoring at 220 nm).

B. 4-Amino-2-trifluoromethylbenzoxazole (476B)

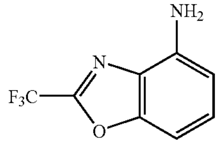

Compound 476A (10.75 g, 46.30 mmol) was dissolved in 1:1 EtOAc/10% HOAc (250 mL) and heated to 65° C. Iron powder (12.93 g, 231.5 mmol) was added portionwise and the reaction was stirred for 6 h at 65° C. After cooling, the mixture was filtered through Celite rinsing with EtOAc. The organic layer was separated, washed with $H_2O$ (3×100 mL), brine (100 mL), dried over $MgSO_4$, and concentrated in vacuo to give a brown oil. The crude material was purified by flash chromatography on silica gel eluting with 70/30 $CH_2Cl_2$/hexanes to give compound 476B (7.02 g, 75%) as a yellow crystalline solid. HPLC: 96.7% at 2.68 min (retention time) (YMC S5 ODS column, 4.6×50 mm, eluting with 10-90% aqueous methanol over 4 mincontaining 0.2% phosphoric acid, 4 mL/min, monitoring at 220 nm).

C. 1-(2-Trifluoromethyl-benzoxazol-4-yl)-pyrrole-2,5-dione (476C)

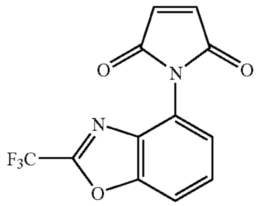

Compound 476B (0.500 g, 2.48 mmol) was dissolved in acetic acid (10 mL) and maleic anhydride (0.267 g, 2.72 mmol) was added. The mixture was heated at reflux for 3 h, cooled and the solvent removed in vacuo to give a tan solid. The crude product was purified by flash chromatography on silica gel eluting with 2% MeOH/$CH_2Cl_2$ to give compound 476C (0.40 g, 57%) as an off-white solid. HPLC: 89.7% at 2.38 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 283.21 $[M+H]^+$.

D. (3aα,4β,7β,7aα)-Hexahydro-4,7-dimethyl-2-[2-(trifluoromethyl)-4-benzoxazolyl]-4,7-epoxy-1H-isoindole-1,3(2H)-dione (476D)

Compound 476C (0.24 g, 0.85 mmol) and 2,5-dimethylfuran (0.132 g, 1.37 mmol) were combined in 3 mL of benzene in a sealed tube and heated at 60° C. for 12 h. The mixture was cooled and concentrated in vacuo to give a yellow oil which was dissolved in 1/1 EtOAc/EtOH (6 mL). 10% Pd/C (100 mg) was added and the mixture was stirred under an $H_2$ balloon for 3.5 h. The reaction was filtered through Celite and the solvent removed in vacuo to give the crude product as a pale yellow oil. Purification by flash chromatography on silica gel eluting with 2% $Et_2O$/$CH_2Cl_2$ gave 0.107 g (33%) of compound 476D as a white foam. HPLC: 96.5% at 2.80 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 381.17 $[M+H]^+$.

EXAMPLE 477

(3aα,4β,7β,7aα)-2-Methyl-4-(octahydro-4,7-dimethyl-1,3-dioxo-4,7-epoxy-2H-isoindol-2-yl)-7-benzoxazolecarbonitrile (477E)

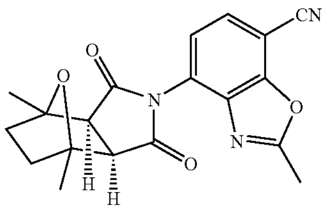

A. 2-Cyano-5-nitrophenol (477A)

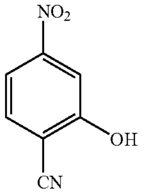

3,4-Methylenedioxynitrobenzene (1.67 g, 10.0 mmol) was dissolved in 20 mL of HMPA and sodium cyanide (0.49 g, 10.0 mmol) was added. The reaction was heated to 150° C. under nitrogen and three portions of sodium cyanide (0.245 g, 5.00 mmol, total) were added over 15 min. The reaction was maintained at 150° C. for 45 min, cooled, and poured into 50 mL of $H_2O$ followed by the addition of 50 mL of 5% NaOH. The aqueous layer was extracted with ether (2×25 mL) and the organic layer was discarded. The basic aqueous layer was carefully acidified to pH 4 by addition of 10% HCl and extracted with ether (3×25 mL). The combined organic layers were washed with brine (25 mL), dried over sodium sulfate and concentrated in vacuo. Purification by flash chromatography on silica gel eluting with 5% $MeOH/CH_2Cl_2$ gave 1.05 g (64%) of compound 477A as a yellow-brown solid. HPLC: 91.6% at 1.03 min (retention time) (Phenomenex column, 30×4.6 mm, 10-90% aqueous methanol over 2 mincontaining 0.1% TFA, 5 mL/min, monitoring at 220 nm. MS (ES): m/z 165.23 $[M+H]^+$.

B. 2-Amino-4-cyano-3-hydroxynitrobenzene (477B)

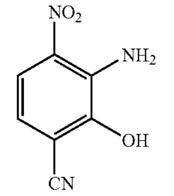

Compound 477A (0.438 g, 2.67 mmol) was dissolved in 25 mL of DMSO and trimethylhydrazinium iodide (0.534 g, 2.67 mmol) was added. Sodium pentoxide (0.880 g, 8.01 mmol) was added under $N_2$ to give a deep red solution and stirring was continued overnight at rt. The reaction mixture was poured into 50 mL of 10% HCl and extracted with EtOAc (2×25 mL). The combined organic layers were washed with water (25 mL), brine (25 mL), dried over sodium sulfate and concentrated in vacuo to give compound 477B as an oily red solid which was used directly in the next reaction without further purification.

C. 7-Cyano-2-methyl-4-nitrobenzoxazole (477C)

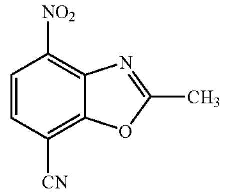

Compound 477B (0.360 g, 2.01 mmol) and triethyl orthoacetate (1.30 g, 8.04 mmol) were combined and heated at reflux under nitrogen for 1 h. The solvent was removed in vacuo and the resulting residue purified by flash chromatography eluting with 5% ether/$CH_2Cl_2$ to give 0.255 g (63%) of compound 477C as a brown solid. HPLC: 98.4% at 1.80 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 204.28 $[M+H]^+$.

D. 4-Amino-7-cyano-2-methylbenzoxazole (477D)

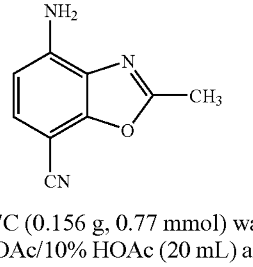

Compound 477C (0.156 g, 0.77 mmol) was dissolved in a 1:1 mixture of EtOAc/10% HOAc (20 mL) and heated to 65° C. Iron powder (325 mesh, 0.214 g, 3.83 mmol) was added and the reaction was stirred for 4 h. The cooled mixture was filtered through Celite and the resulting filtrate was washed with water (25 mL), brine (25 mL), dried over $MgSO_4$, and concentrated to give compound 477D (0.118 g, 89%) as an orange solid. HPLC: 87% at 2.03 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 174.05 $[M+H]^+$.

E. (3aα,4β,7β,7aα)-2-Methyl-4-(octahydro-4,7-dimethyl-1,3-dioxo-4,7-epoxy-2H-isoindol-2-yl)-7-benzoxazolecarbonitrile (477E)

Compound 477D (0.060 g, 0.35 mmol) and compound 20A (0.071 g, 0.37 mmol) were combined in a sealed tube with toluene (2 mL), triethylamine (0.24 mL, 1.7 mmol), and $MgSO_4$ (0.104 g, 0.866 mmol). The sealed tube was heated at 135° C. for two days. The cooled reaction mixture was diluted with EtOAc, filtered, and concentrated in vacuo to give crude product as a brown oil. Purification by flash chromatography on silica gel eluting with 1/1 EtOAc/hexanes gave 0.014 g (12%) of compound 477E as an off-white solid. HPLC: 96.5% at 2.27 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 352.23 $[M+H]^+$.

EXAMPLE 478

(3aα,4β,5β,7β,7aα)-4-[7-[2-(4-Cyanophenoxy)ethyl]octahydro-5-methoxy-4-methyl-1,3-dioxo-4,7-epoxy-2H-isoindol-2-yl]-1-naphthalenecarbonitrile, slow eluting enantiomer (478)

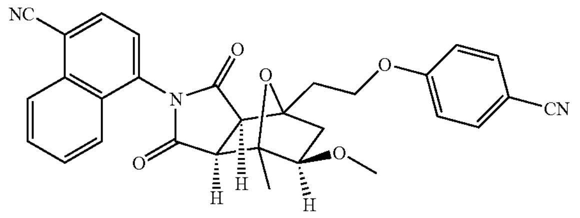

n-BuLi (0.050 mL, 1.6 M, 0.075 mmol) was added to a solution of compound 244ii (33.7 mg, 0.0683 mmol) in THF (1.0 mL) at −78° C. under argon. The reaction mixture was warmed to room temperature and methyl fluorosulfonate (0.010 mL, 0.12 mmol) was added dropwise. Once starting material was consumed, as was evident by HPLC, the reaction was quenched with $H_2O$ and the resulting aqueous mixture was extracted with $CH_2Cl_2$ (3×5 mL). The combined organic layers were dried over $MgSO_4$ and concentrated under reduced pressure. Purification by reverse phase preparative HPLC [22.09 min (YMC S5 ODS column, 20×100 mm, 0-100% aqueous methanol over 25 mincontaining 0.1% TFA, 20 mL/min, monitoring at 220 nm)] gave 13.0 mg (38%) of compound 478 as a white solid. HPLC: 93% at 3.35 min (YMC S5 ODS column, 4.6×50 mm, 10-90% aqueous methanol over 4 min containing 0.2% phosphoric acid, 4 mL/min, monitoring at 220 nm). MS (ES): m/z 508.17 $[M+H]^+$.

EXAMPLE 479

(3aα,4β,7β,7aα)-Hexahydro-4,7-dimethyl-2-(2-methyl-6-benzoxazolyl)-4,7-epoxy-1H-isoindole-1,3 (2H)-dione (479B)

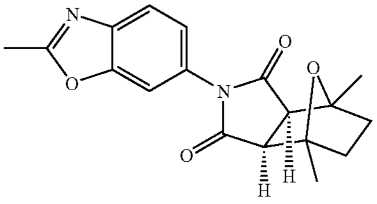

A. 2-Methyl-6-aminobenzoxazole (479A)

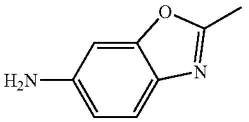

To a solution of 2-methyl-6-nitrobenzoxazole (100 mg, 0.560 mmol) in AcOH (2 mL) was added iron powder (325 mesh, 63.0 mg, 1.12 mmol) at 70° C. in a single portion. After 15 min at 70° C. additional iron powder (325 mesh, 63.0 mg, 1.12 mmol) was added and stirring was continued for 15 min. The mixture was cooled and concentrated under reduced pressure. The resulting residue was taken up into EtOAc and washed with sat. $Na_2CO_3$ followed by $H_2O$. The organic layer was dried over $MgSO_4$, concentrated under reduced pressure and purified by flash chromatography on silica gel eluting with a gradient of 0 to 25% EtOAc in $CH_2Cl_2$ to yield 69 mg (83%) of compound 479A as a solid. HPLC: 97% at 0.24 min (retention time) (YMC S5 ODS column, 4.6×50 mm Ballistic, 10-90% aqueous methanol over 4 min containing 0.2% $H_3PO_4$, 4 mL/min, monitoring at 220 nm). MS (ES): m/z 149.2 $[M+H]^+$.

B. (3aα,4β,7β,7aα)-Hexahydro-4,7-dimethyl-2-(2-methyl-6-benzoxazolyl)-4,7-epoxy-1H-isoindole-1,3 (2H)-dione (479B)

Compound 479A (30 mg, 0.20 mmol), $MgSO_4$ (60 mg, 0.50 mmol), triethylamine (140 µL, 1.00 mmol) and compound 20A (45 mg, 0.23 mmol) were taken up in 0.25 mL of toluene and placed in a sealed tube. The sealed tube was heated at 135° C. for 14 h and the reaction was allowed to cool to rt. The mixture was filtered through a short pad of Celite, eluting with MeOH and the solvent was removed in vacuo. The residue was purified by flash chromatography on silica gel eluting with a gradient of 0 to 50% EtOAc in $CH_2Cl_2$ to give 49 mg (65%) of compound 479B as a tan solid. HPLC: 98% at 2.30 min (retention time) (YMC S5 ODS column, 4.6×50 mm, eluting with 10-90% aqueous methanol over 4 min containing 0.2% phosphoric acid, 4 mL/min, monitoring at 220 nm). MS (ES): m/z 326.9 $[M+H]^+$.

EXAMPLE 480

(3aα,4β,7β,7aα)-2-(2,1,3-Benzoxadiazol-5-yl) hexahydro-4,7-dimethyl-4,7-epoxy-1H-isoindole-1,3 (2H)-dione (480B)

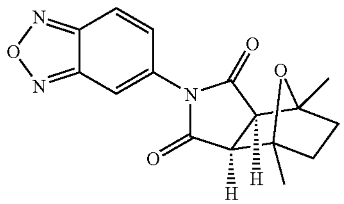

A. 5-Amino-2,1,3-benzoxadiazole (480A)

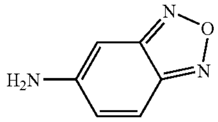

To a solution of 2,1,3-benzoxadiazole-5-carboxylic acid (102 mg, 0.621 mmol) in THF (3 mL) was added triethylamine (103 µL, 0.739 mmol) followed by DPPA (160 µL, 0.739 mmol) at room temperature. The mixture was stirred for 4 h, diluted with $CH_2Cl_2$ and washed with water. The organic layer was dried over $MgSO_4$, concentrated and purified by flash chromatography on silica gel with 0 to 50% EtOAc in $CH_2Cl_2$. The resulting material was dissolved in AcOH (2 mL) and water (0.7 mL) was added dropwise yielding a slightly cloudy solution which was heated at 105° C. for 30 min. The mixture was cooled, made basic with sat. $Na_2CO_3$ solution and extracted several times with THF. The combined organic layers were dried over $MgSO_4$, concentrated and purified by flash chromatography on silica gel eluting with 0 to 15% MeOH in $CH_2Cl_2$ to give 34 mg (41%) of compound 480A as a yellow solid. HPLC: 100% at 1.27 min (retention time) (YMC S5 ODS column, 4.6×50 mm Ballistic, 10-90% aqueous methanol over 4 mincontaining 0.2% $H_3PO_4$, 4 mL/min, monitoring at 220 nm). MS (ES): m/z 136.0 $[M+H]^+$.

B. (3aα,4β,7β,7aα)-2-(2,1,3-Benzoxadiazol-5-yl) hexahydro-4,7-dimethyl-4,7-epoxy-1H-isoindole-1,3 (2H)-dione (480B)

Compound 480A (34 mg, 0.25 mmol), $MgSO_4$ (76 mg, 0.63 mmol), triethylamine (180 µL, 1.26 mmol) and compound 20A (74 mg, 0.38 mmol) were dissolved in 0.25 mL of toluene and placed in a sealed tube. The sealed tube was heated at 135° C. for 14 h. The cooled reaction mixture was filtered through a short pad of Celite, eluting with acetone and the solvent was removed in vacuo. The residue was purified by reverse phase preparative HPLC (YMC S5 ODS 20×100 mm, eluting with 30-100% aqueous methanol over 10 mincontaining 0.1% TFA, 20 mL/min). Concentration of the desired fractions afforded a residue which was partitioned between $CH_2Cl_2$ and sat. $NaHCO_3$ solution. The aqueous layer was extracted once with $CH_2Cl_2$ and the combined organic phases were dried over $Na_2SO_4$. Concentration under reduced pressure gave 42 mg (53%) of compound 480B as a yellow solid. HPLC: 100% at 2.62 min (retention time) (YMC S5 ODS column, 4.6×50 mm, eluting with 10-90% aqueous methanol over 4 mincontaining 0.2% phosphoric acid, 4 mL/min, monitoring at 220 nm). $^1$H NMR (400 MHz, $CDCl_3$) δ=7.91 (d, 1H), 7.90 (dd, 1H), 7.37 (dd, 1H), 3.09 (s, 2H), 1.85 (s, 4H), 1.67 (s, 6H).

EXAMPLE 481

[3aR-(3aα,4β,5β,7β,7aα)]-2-(6-Benzothiazolyl)-7-[2-[(5-chloro-2-pyridinyl)oxy]ethyl]hexahydro-5-hydroxy-4-methyl-4,7-epoxy-1H-isoindole-1,3(2H)-dione (481D) & [3aS-(3aα,4β,5β,7β,7aα)]-2-(6-Benzothiazolyl)-7-[2-[(5-chloro-2-pyridinyl)oxy]ethyl]hexahydro-5-hydroxy-4-methyl-4,7-epoxy-1H-isoindole-1,3(2H)-dione (481E)

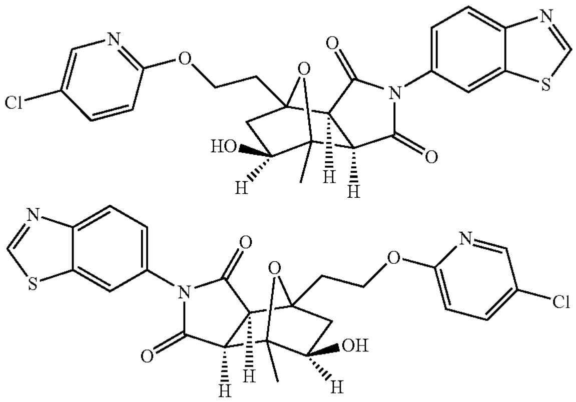

A. 1-Benzothiazol-6-yl-pyrrole-2,5-dione (481A)

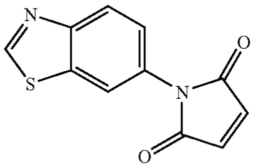

A mixture of 5-aminobenzothiazole (2.00 g, 13.3 mmol) and maleic anhydride (1.96 g, 20.0 mmol) in AcOH (27 mL) was heated at 115° C. for 20 h. The mixture was cooled and concentrated under reduced pressure. The residue was taken up in THF and washed with saturated $Na_2CO_3$. The aqueous layer was extracted several times with THF and the combined organic layers were dried over $MgSO_4$. Purification by flash chromatography on silica gel eluting with 0 to 50% EtOAc in $CH_2Cl_2$ gave 1.37 g (45%) of compound 481A as a pale yellow solid. HPLC: 100% at 2.62 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 231.0 $[M+H]^+$.

B. (3aα,4β,7β,7aα)-2-(6-Benzothiazolyl)-4-[2-[[(1,1-dimethylethyl)dimethylsilyl]oxy]ethyl]-3a,4,7,7a-tetrahydro-7-methyl-4,7-epoxy-1H-isoindole-1,3(2H)-dione (481B)

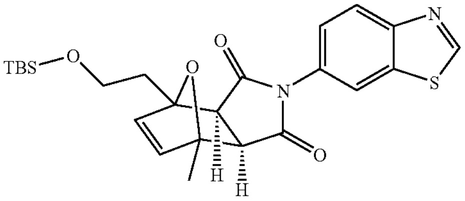

A suspension of compound 481A (445 mg, 1.93 mmol) and compound 204A (929 mg, 3.87 mmol) in benzene (2 mL) was heated to 60° C. and acetone was added until a clear solution was obtained. The resulting mixture was stirred at 60° C. for 24 h and was then slowly concentrated in vacuo. The resulting residue was dissolved in acetone and slowly concentrated in vacuo. This process was repeated a total of three times. Purification by flash chromatography on silica gel eluting with 0 to 30% acetone in hexanes gave 820 mg (90%) of compound 481B as a white solid. HPLC: 100% at 2.62 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 471.3 $[M+H]^+$.

C. [3aR-(3aαc,4β,5β,7β,7aα)]-2-(6-Benzothiazolyl)-7-[2-[[(1,1-dimethylethyl)dimethylsilyl]oxy]ethyl]hexahydro-5-hydroxy-4-methyl-4,7-epoxy-1H-isoindole-1,3(2H)-dione (481Ci) & [3aS-(3aα,4β,5β,7β,7aα)]-2-(6-Benzothiazolyl)-7-[2-[[(1,1-dimethylethyl)dimethylsilyl]oxy]ethyl]hexahydro-5-hydroxy-4-methyl-4,7-epoxy-1H-isoindole-1,3(2H)-dione (481Cii)

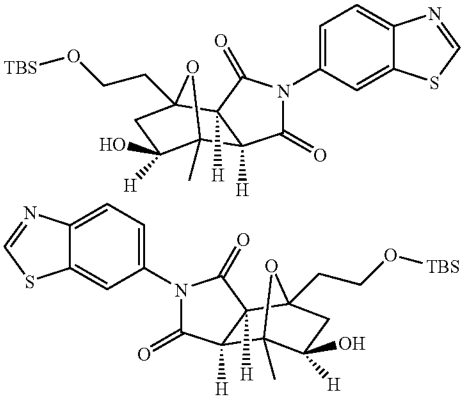

To a solution of compound 481B (75 mg, 0.16 mmol) in THF (1 mL) was added Wilkinson's catalyst (32 mg, 0.030 mmol) and catecholborane (1.0 M in THF, 1.6 mL, 1.6 mmol) at room temperature under nitrogen. The resulting mixture was stirred for 2.5 h before it was cooled to 0° C. EtOH (5 mL), 3 N NaOH (2 mL) and $H_2O_2$ (30%, 1 mL) were added sequentially, and the mixture was stirred for 2 h at 0° C. The reaction was quenched by the addition of cold 10% $Na_2SO_3$ solution (excess) followed by water. The aqueous layer was extracted several times with $CH_2Cl_2$ and the combined organic layerss were dried over $Na_2SO_4$. Concentration under reduced pressure followed by purification by flash chromatography on silica gel eluting with 0 to 100% EtOAc in hexanes gave 13 mg (17%) of a racemic mixture of compounds 481Ci & 481Cii as a tan solid. HPLC: 96% at 3.58 min (retention time) (YMC S5 ODS column, 4.6×50 mm Ballistic, 10-90% aqueous methanol over 4 min containing 0.2% $H_3PO_4$, 4 mL/min, monitoring at 220 nm). MS (ES): m/z 489.3 $[M+H]^+$. The racemic mixture was separated into its individual enantiomers by normal phase preparative chiral HPLC (CHIRALPAK AD 5×50 cm column; eluting with 20% MeOH/EtOH (1:1) in heptane (isocratic) at 50 mL/min) to give the faster eluting enantiomer, compound 481Ci: (Chiral HPLC: 9.40 min; CHRALPAK AD 4.6×250 mm column; eluting with 20% MeOH/EtOH (1:1) in heptane at 1 mL/min) and the slower eluting enantiomer, compound 481Cii: (Chiral HPLC: 10.47 min; CHIRALPAK AD 4.6×250 mm column; eluting with 20% MeOH/EtOH (1:1) in heptane at 1 mL/min). The absolute conformation for compounds 481Ci & 481Cii was not established. For simplicity in nomenclature, compound 481Ci is designated herein as having an "R" configuration and compound 481Cii as having an "S" configuration. Enantiomerically pure products derived from compound 481Ci are designated herein as having a "R" configuration and enantiomerically pure products derived from compound 481Cii are designated herein as having an "S" configuration.

D. [3aR-(3aα,4β,5β,7β,7aα)]-2-(6-Benzothiazolyl)-7-[2-[(5-chloro-2-pyridinyl)oxy]ethyl]hexahydro-5-hydroxy-4-methyl-4,7-epoxy-1H-isoindole-1,3(2H)-dione (481D)

Compound 481Ci (84 mg, 0.17 mmol) was suspended into EtOH (2 mL) and conc. HCl (40 μL) was added at room temperature. The mixture was stirred for 15 min before several drops of sat. $NaHCO_3$ solution were added. Concentration under reduced pressure yielded a residue which was partitioned between $CH_2Cl_2$ and sat. $NaHCO_3$ solution. The aqueous layer was extracted several times with $CH_2Cl_2$ and finally with EtOAc. The combined organic phases were dried over $Na_2SO_4$, concentrated and purified by preparative TLC eluting with 50% acetone in $CHCl_3$. This procedure served to remove the TBS group from compound 481Ci, yielding the free primary alcohol. A 12 mg (0.03 mmol) portion of the free alcohol of compound 481Ci was reacted with 5-chloro-2-pyridinol (8 mg, 0.06 mmol), $PPh_3$ (17 mg, 0.060 mmol) and di-tert-butylazodicarboxylate (15 mg, 0.060 mmol) in THF (0.5 mL) according to the general procedure described in Example 244. The mixture was stirred for 24 h at room temperature, diluted with 1N NaOH and the aqueous layer was extracted several times with $CH_2Cl_2$. The combined organic layers were dried over $Na_2SO_4$, concentrated and purified by preparative TLC, eluting with 25% acetone in $CHCl_3$ to give 9 mg (58%) compound 481D as a white solid. HPLC: 98% at 2.94 min (retention time) (YMC S5 ODS column, 4.6×50 mm Ballistic, 10-90% aqueous methanol over 4 mincontaining 0.2% $H_3PO_4$, 4 mL/min, monitoring at 220 rm). MS (ES): m/z 486.2 $[M+H]^+$.

E. [3aS-(3aα,4β,5β,7β,7aα)]-2-(6-Benzothiazolyl)-7-[2-[(5-chloro-2-pyridinyl)oxy]ethyl]hexahydro-5-hydroxy-4-methyl-4,7-epoxy-1H-isoindole-1,3(2H)-dione (481E)

As described in Example 481D, compound 481Cii (58 mg, 0.12 mmol) was treated with EtOH (2 mL) containing 12 N HCl (40 μL) to yield the free primary alcohol product of compound 481Cii. A 15 mg (0.040 mmol) of the free alcohol of compound 481Cii was reacted with 5-chloro-2-pyridinol (10 mg, 0.080 mmol), $PPh_3$ (21 mg, 0.080 mmol) and di-tert-butylazodicarboxylate (18 mg, 0.080 mmol) in THF (0.5 mL) in the manner described above and the resulting product was purified as described above to yield 8 mg (41%) of compound 481E as a white solid. HPLC: 99% at 2.93 min (retention time) (YMC S5 ODS column, 4.6×50 mm Ballistic, 10-90% aqueous methanol over 4 mincontaining 0.2% $H_3PO_4$, 4 mL/min, monitoring at 220 nm). MS (ES): m/z 486.2 $[M+H]^+$.

EXAMPLE 482

[3aR-(3aα,4β,5β,7β,7aα)]-7-[7-[2-[(5-Chloro-2-pyridinyl)oxy]ethyl]octahydro-5-hydroxy-4-methyl-1,3-dioxo-4,7-epoxy-2H-isoindol-2-yl]-2,1,3-benzothiadiazole-4-carbonitrile (482F) & [3aS-(3aα,4β,5β,7β,7aα)]-7-[7-[2-[(5-Chloro-2-Pyridinyl)oxy]ethyl]octahydro-5-hydroxy-4-methyl-1,3-dioxo-4,7-epoxy-2H-isoindol-2-yl]-2,1,3-benzothiadiazole-4-carbonitrile (482G)

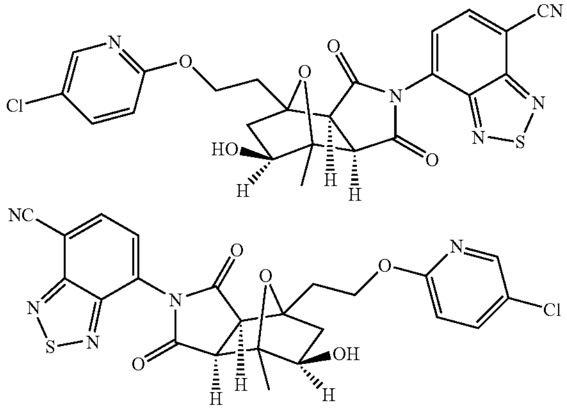

A. 7-(2,5-Dioxo-2,5-dihydro-pyrrol-1-yl)-benzo[1,2,5]thiadiazole-4-carbonitrile (482A)

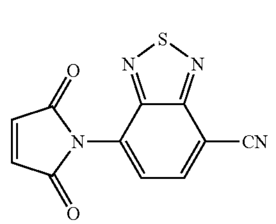

Maleic anhydride (667 mg, 6.80 mmol) was added to a solution of compound 424A (600 mg, 3.41 mmol) in THF (9 mL). The mixture was heated at 110° C. for 10 h. The reaction was concentrated under reduced pressure and acetic anhydride (1 mL) was added to the residue. The reaction mixture was heated at 75° C. for 30 min and then cooled to rt. Purification by flash chromatography on silica gel eluting with 3% acetone/$CHCl_3$ gave 758 mg (2.96 mmol, 67%) of compound 482A. HPLC: 97% at 1.98 min (retention time) (YMC S5 ODS 4.6×50 mm, 10%-90% aqueous methanol over 4 min gradient with 0.2% $H_3PO_4$, monitoring at 220 nm). MS (ES): m/z 257.01 $[M+H]^+$.

B. (3aα,4β,7β,7aα)-7-[4-[2-[[(1,1-Dimethylethyl) dimethylsilyl]oxy]ethyl]-1,3,3a,4,7,7a-hexahydro-7-methyl-1,3-dioxo-4,7-epoxy-2H-isoindol-2-yl]-2,1,3-benzothiadiazole-4-carbonitrile (482B)

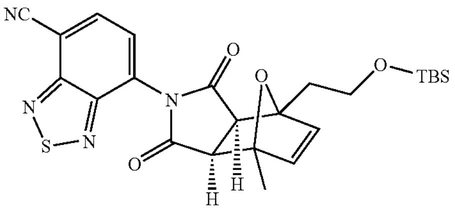

A solution of compound 482A (758 mg, 2.96 mmol) and compound 204A (711 mg, 2.96 mmol) in benzene (2 mL) and acetone (2 mL) was heated at 60° C. for 6 h. The reaction mixture was concentrated in vacuo at 42° C. for 40 min to give 1.5 g of crude compound 482B, which was used directly in the next step without further purification.

C. (3aα,4β,5β,7β,7aα)-7-[7-[2-[[(1,1-Dimethylethyl) dimethylsilyl]oxy]ethyl]octahydro-5-hydroxy-4-methyl-1,3-dioxo-4,7-epoxy-2H-isoindol-2-yl]-2,1,3-benzothiadiazole-4-carbonitrile (482C)

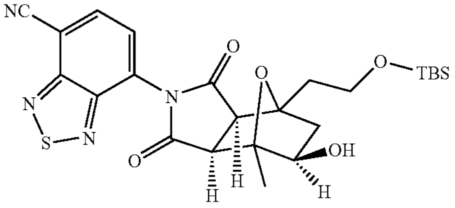

Borane-dimethylsulfide complex (0.66 mL, 6.96 mmol) was added to a solution of compound 482B (1.15 g, 2.32 mmol) in THF (6 mL) at 0° C. After stirring at 0° C. for 2 h, the reaction mixture was quenched with phosphate buffer (60 mL, pH 7.2) and then EtOH (35 mL), $H_2O_2$ (8 mL, 30% aq.) and THF (4 mL) were added. The reaction mixture was stirred at 0° C. for 1 h and was then extracted with $CH_2Cl_2$ (4×100 mL). The combined organic layers were washed with 10% aq. $Na_2SO_3$ (1×160 mL) followed by brine (1×160 mL) and dried over $Na_2SO_4$. Purification by flash chromatography on silica gel eluting with 10% acetone/$CHCl_3$ gave 250 mg (0.486 mmol, 21%) of compound 482C as an orange solid. HPLC: 85% at 3.70 min (retention time) (YMC S5 ODS 4.6×50 mm, 10%-90% aqueous methanol over 4 min gradient with 0.2% $H_3PO_4$, monitoring at 220 nm). MS (ES): m/z 515.27 $[M+H]^+$.

D. [3aR-(3aα,4β,5β,7β,7aα)]-7-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-2,1,3-benzothiadiazole-4-carbonitrile & [3aS-(3aα4β,5β,7β,7aα)]-7-[7-[2-[[(1,1-Dimethylethyl) dimethylsilyl]oxy]ethyl]octahydro-5-hydroxy-4-methyl-1,3-dioxo-4,7-epoxy-2H-isoindol-2-yl]-2,1,3-benzothiadiazole-4-carbonitrile (482Di & 482Dii)

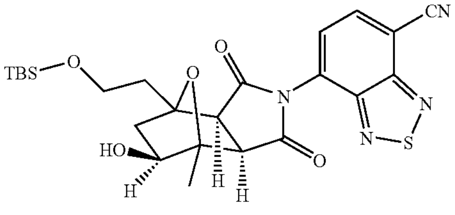

-continued

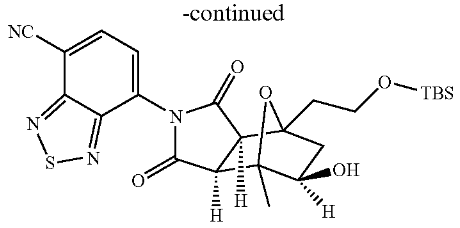

The racemic compounds 482C was separated by normal phase preparative chiral HPLC using a Chiracel OD column (5 cm×50 cm), eluting with 10% EtOH in hexane at 50 mL/min to give the faster eluting compound 482Di (Chiral HPLC: 11.89 min; CHIRALCEL OD 4.6×250 mm column; isocratic elution with 12% EtOH in hexane at 2 mL/min) and the slower eluting compound 482Dii (Chiral HPLC: 16.10 min; CHIRALCEL OD 4.6×250 mm column; isocratic elution with 12% EtOH in hexane at 2 mL/min). The absolute conformation for compounds 482Di & 482Dii was not established. For simplicity in nomenclature, compound 482Di is designated herein as having an "R" configuration and compound 482Dii as having an "S" configuration. Enantiomerically pure products derived from compound 482Di are designated herein as having a "R" configuration and enantiomerically pure products derived from compound 482Dii are designated herein as having an "S" configuration.

E. [3aR-(3aα,4β,5β,7β,7aα)]-7-[Octahydro-5-hydroxy-7-(2-hydroxyethyl)-4-methyl-1,3-dioxo-4,7-epoxy-2H-isoindol-2-yl]-2,1,3-benzothiadiazole-4-carbonitrile (482Ei) & [3aR-(3aα,4β,5β,7β,7aα)]-7-[Octahydro-5-hydroxy-7-(2-hydroxyethyl)-4-methyl-1,3-dioxo-4,7-epoxy-2H-isoindol-2-yl]-2,1,3-benzothiadiazole-4-carbonitrile (482Eii)

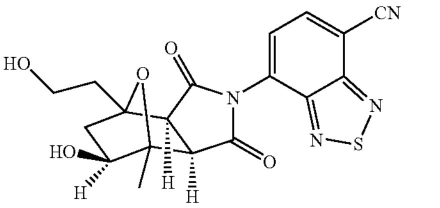

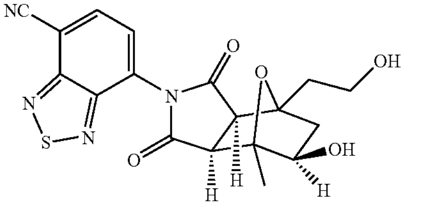

Compound 482Di (91 mg, 0.18 mmol) was dissolved in 2% 12 N HCl/EtOH (3.0 mL) and the mixture was stirred at rt for 20 min. Cold sat. $NaHCO_3$ was added to the mixture until it was basic (pH 8). The reaction was extracted with EtOAc. The organic layers were then washed with brine and dried over anhydrous sodium sulfate. Concentration in vacuo gave 73 mg (0.18 mmol, 100%) compound 482Ei as a yellow solid which was not purified further. HPLC: 95% at 1.73 min (retention time) (YMC S5 ODS 4.6×50 mm, 10%-90% aqueous methanol over 4 min gradient with 0.2% $H_3PO_4$, monitoring at 220 nm). MS (ES): m/z 401.13 $[M+H]^+$.

Compound 482Dii (90 mg, 0.17 mmol) was dissolved in 2% 12 N HCl/EtOH (3.0 mL) and the mixture was stirred at rt for 20 min. Cold sat. $NaHCO_3$ was added to the mixture until it was basic (pH 8). The reaction was extracted with EtOAc. The organic layers were then washed with brine and dried over anhydrous sodium sulfate. Concentration in vacuo gave 70 mg (0.17 mmol, 100%) compound 482Eii as an orange solid which was not purified further. HPLC: 90% at 1.74 min (retention time) (YMC S5 ODS 4.6×50 mm, 10%-90% aqueous methanol over 4 min gradient with 0.2% $H_3PO_4$, monitoring at 220 nm). MS (ES): m/z 401.14 $[M+H]^+$.

F. [3aR-(3aα,4β,5β,7β,7aα)]-7-[7-[2-[(5-Chloro-2-pyridinyl)oxy]ethyl]octahydro-5-hydroxy-4-methyl-1,3-dioxo-4,7-epoxy-2H-isoindol-2-yl]-2,1,3-benzothiadiazole-4-carbonitrile (482F)

DBAD (21 mg, 0.090 mmol) was added to a solution of $PPh_3$ (24 mg, 0.090 mmol) in THF (0.4 mL). After stirring for 10 min, 5-chloro-2-pyridinol (12 mg, 0.090 mmol) was added and the reaction mixture was stirred for an additional 5 min. Compound 482Ei (18 mg, 0.045 mmol) was added and the mixture was stirred at rt for 1 h. The reaction was then concentrated under reduced pressure. Purification by preparative TLC eluting with 20% acetone/$CHCl_3$ gave 12 mg (0.023 mmol, 52%) of compound 482F. HPLC: 98% at 3.15 min (retention time) (YMC S5 ODS 4.6×50 mm, 10%-90% aqueous methanol over 4 min gradient with 0.2% $H_3PO_4$, monitoring at 220 nm). MS (ES): m/z 512.11 $[M+H]^+$.

G. [3aS-(3aα,4β,5β,7β,7aα)]-7-[7-[2-[(5-Chloro-2-pyridinyl)oxy]ethyl]octahydro-5-hydroxy-4-methyl-1,3-dioxo-4,7-epoxy-2H-isoindol-2-yl]-2,1,3-benzothiadiazole-4-carbonitrile (482G)

DBAD (21 mg, 0.090 mmol) was added to a solution of $PPh_3$ (24 mg, 0.090 mmol) in THF (0.4 mL). After stirring for 10 min, 5-chloro-2-pyridinol (12 mg, 0.090 mmol) was added and the reaction mixture was stirred for an additional 5 min. Compound 482Eii (18 mg, 0.045 mmol) was added and the mixture was stirred at rt for 1 h. The reaction was then concentrated under reduced pressure. Purification by preparative TLC eluting with 20% acetone/$CHCl_3$ gave 11 mg (0.021 mmol, 47.0%) of compound 482G. HPLC: 98% at 3.15 min (retention time) (YMC S5 ODS 4.6×50 mm, 10%-90% aqueous methanol over 4 min gradient with 0.2% $H_3PO_4$, monitoring at 220 nm). MS (ES): m/z 512.15 $[M+H]^+$.

EXAMPLE 483

(1S,4R)-4,7,7-Trimethyl-3-oxo-2-oxabicyclo[2,2,1]heptane-1-carboxylic acid, [3aS-(3aα,4β,5β,7β,7aα)]-2-[4-cyano-3-(trifluoromethyl)phenyl]octahydro-4,7-dimethyl-1,3-dioxo-4,7-epoxy-1H-isoindol-5-yl ester (483)

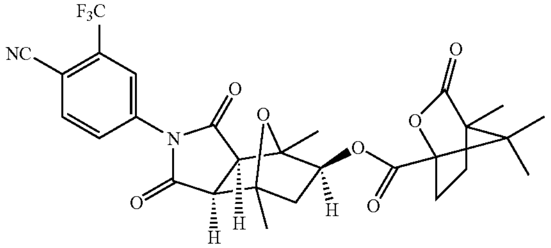

To a solution of compound 471Di (25 mg, 0.066 mmol) in 0.25 mL of $CH_2Cl_2$ at rt and under argon, was added a solution of (1S)-(-)-camphanic acid (20 mg, 0.10 mmol) in 0.2 mL of $CH_2Cl_2$. A solution of DCC (20 mg, 0.10 mmol) in 0.25 mL of $CH_2Cl_2$ was then added followed by DMAP (4.0 mg, 0.034 mmol). A white precipitate was obtained immediately and stirring was continued overnight. The precipitate was removed by filtration and the filtrate was diluted with EtOAc. The resulting solution was washed with 1N HCl, brine, sat. $NaHCO_3$, and brine then dried over $MgSO_4$. Concentration in vacuo afforded a viscous oily residue. The crude material was subjected to flash chromatography on a 20 $cm^3$ column of silica gel eluting with 50% EtOAc in hexanes to 32 mg of a white solid. Recrystallization from $CH_2Cl_2$/hexane yielded 20 mg (86%) of compound 483 as large crystals. This material was subjected to X-ray crystal diffraction studies to elucidate the exact stereochemistry of compound 471Di as referenced to the known fixed stereochemistry of the (1S)-(-)-camphanic acid appendage. LCMS: 100% at 1.9 min (retention time) (Phenomenex Luna C18 column, 2×30 mm, 0-100% aqueous acetonitrile over 3 min containing 10 mM $NH_4OAc$ at 1 mL/min, monitoring at 220 nm). MS (ESI): m/z 559.3 $[M-H]^-$.

EXAMPLE 484

(3a α,4β,5β,7β,7aα)-5-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-8-quinolinecarbonitrile (484)

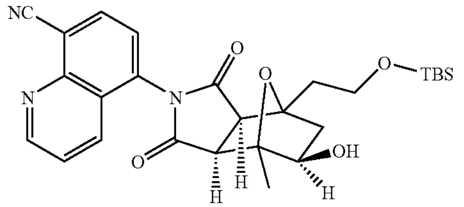

To a dry, 3-necked, 25 mL round-bottom was added $TiCl_2Cp_2$ (0.500 g, 2.01 mmol) and THF (4 mL) to give a deep red solution. Activated zinc dust (0.392 g, 6 mmol, prepared as described in Fieser and Fieser, Volume 1, p. 1276) was added and the suspension was stirred for 30 min during which time the color changed from brick-red to emerald-green. The unreacted zinc dust was allowed to settle. In a separate 3-necked, 25 mL round-bottom flask was added compound 464F (0.202 g, 0.399 mmol), THF (1 mL) and 1,4-cyclohexadiene (0.380 mL, 4.02 mmol). The Ti(III) reagent (0.90 mL, 0.45 mmol) was added via an addition funnel with a cotton plug at the bottom rinsing with THF (1 mL). After 1 h, HPLC showed ~50% conversion and an additional 0.9 mL (0.45 mmol) of the titanium reagent was added. After 1 h, HPLC showed complete consumption of starting material. Saturated ammonium chloride (5 mL) was added, followed by 10 mL of EtOAc. The organic layer was separated, washed with brine (5 mL), dried over $Na_2SO_4$, and concentrated in vacuo to give the crude product as an orange semi-solid. The crude material was purified by flash chromatography on silica gel eluting with 50% $CH_2C12$/48% EtOAc/2% MeOH to give 0.10 g (59%) of compound 484 as a light yellow foam. HPLC: 91% at 3.65 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 508.27 $[M+H]^+$.

EXAMPLE 485

[3aR-(3aα,4β,5β,7β,7aα)]-5-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-8-quinolinecarbonitrile (485i) & [3aS-(3aα,4β,5β,7β,7aα)]-5-[7-[2-[[(1,1-Dimethylethyl)dimethylsilyl]oxy]ethyl]octahydro-5-hydroxy-4-methyl-1,3-dioxo-4,7-epoxy-2H-isoindol-2-yl]-8-quinolinecarbonitrile (485ii)

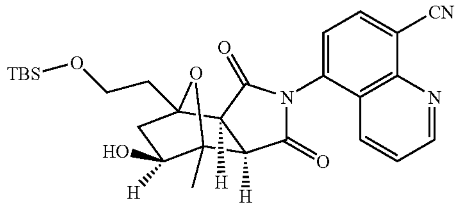

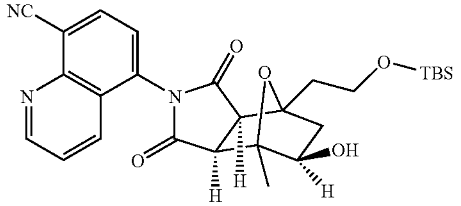

The racemic compound 484, was separated into its individual antipodes by normal phase preparative chiral HPLC. A Chiralcel OD column (50×500 mm) was used with a flow rate of 50 mL/min (20% EtOH/hexanes) monitoring at 220 nm. The faster eluting antipode, compound 485i had a retention time of 35.8 min and the slower antipode, compound 485ii had a retention time of 49.7 min. Both antipodes were isolated as white solids after separation. Compound 485i: HPLC: 100% at 4.980 min (retention time) (Chiracel OD column (5×50 mm), 2.0 mL/min, 20% EtOH/hexanes, monitoring at 220 nm), >99% ee. MS (ES): m/z 508.23 $[M+H]^+$. Compound 485ii: HPLC: 98.6% at 7.357 min (retention time) (Chiracel OD column (5×50 mm), 2.0 mL/min, 20% EtOH/hexanes, monitoring at 220 nm), 97.2% ee. MS (ES): m/z 508.21 $[M+H]^+$. The absolute conformation for compounds 485i & 485ii was not established. For simplicity in nomenclature, compound 485i is designated herein as having an "R" configuration and compound 485ii as having an "S" configuration. Enantiomerically pure products derived from compound 485i are designated herein as having a "R" configuration and enantiomerically pure products derived from compound 485ii are designated herein as having an "S" configuration.

EXAMPLE 486

[3aR-(3aα,4β,5β,7β,7aα)]-5-[Octahydro-5-hydroxy-7-(2-hydroxyethyl)-4-methyl-1,3-dioxo-4,7-epoxy-2H-isoindol-2-yl]-8-quinolinecarbonitrile (486i) & [3aS-(3aα,4β,5β,7β,7aα)]-5-[Octahydro-5-hydroxy-7-(2-hydroxyethyl)-4-methyl-1,3-dioxo-4,7-epoxy-2H-isoindol-2-yl]-8-quinolinecarbonitrile (486ii)

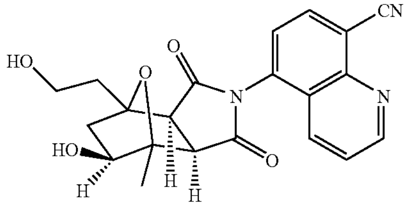

-continued

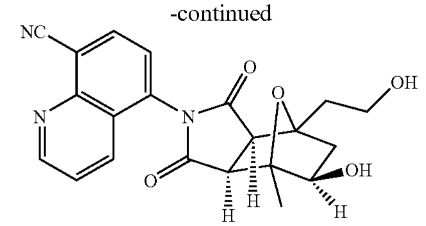

Compounds 485i & 485ii were converted to the free primary alcohol products as described in example 466 to give compounds 486i and 486ii as white solids.

Compound 486i: HPLC: 98% at 1.650 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 394.21 $[M+H]^+$.

Compound 486ii: HPLC: 98% at 1.663 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 394.20 $[M+H]^+$.

EXAMPLE 487

[3aR-(3aα,4β,7β,7aα)]-5-[7-[2-[(5-Chloro-2-Pyridinyl)oxy]ethyl]octahydro-5-hydroxy-4-methyl-1,3-dioxo-4,7-epoxy-2H-isoindol-2-yl]-8-quinolinecarbonitrile (487)

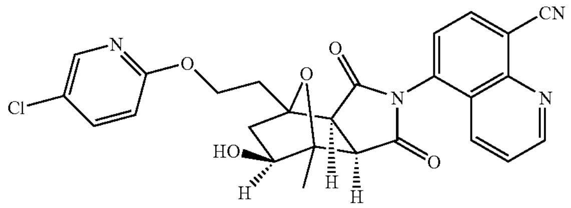

DBAD (0.088 g, 0.38 mmol) was added to a solution of triphenylphosphine (0.100 g, 0.382 mmol) in THF (1.0 mL) at 22° C. and stirred for 10 min. 5-Chloro-2-pyridinol (0.049 g, 0.38 mmol) was added as a solid and stirring was continued for 10 min. The reaction mixture was added to compound 486i (0.100 g, 0.250 mmol) in THF (1.0 mL). After stirring for 3 h, the reaction was concentrated in vacuo and purified by flash chromatography on silica gel eluting with 20-50% acetone/chloroform to give 0.080 g (63%) of compound 487 as a white solid. HPLC: 100% at 3.023 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 505.16 $[M+H]^+$.

EXAMPLE 488

[3 aS-(3aα,4β,7β,7aα)]-5-[7-[2-[(5-Chloro-2-pyridinyl)oxy]ethyl]octahydro-5-hydroxy-4-methyl-1,3-dioxo-4,7-epoxy-2H-isoindol-2-yl]-8-quinolinecarbonitrile (488)

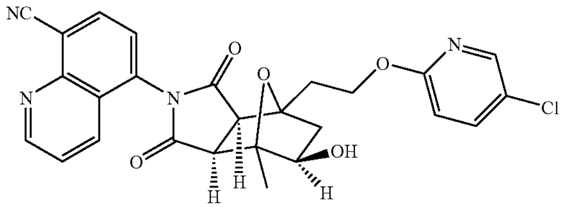

DBAD (0.088 g, 0.38 mmol) was added to a solution of triphenylphosphine (0.100 g, 0.382 mol) in THF (1.0 mL) at 22° C. and stirred for 10 min. 5-Chloro-2-pyridinol (0.049 g, 0.38 mmol) was added as a solid and stirring was continued for 10 min. The reaction mixture was added to compound 486ii (0.100 g, 0.250 mmol) in THF (1.0 mL). After stirring for 3 h, the reaction was concentrated in vacuo and purified by flash chromatography on silica gel eluting with 10-50% acetone/chloroform to give 0.080 g (63%) of compound 488 as a white solid. HPLC: 95% at 3.030 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 505.12 $[M+H]^+$.

EXAMPLE 489

[3aR-(3aα,4β,5β,7β,7aα)]-4-(Octahydro-5-hydroxy-4,7-dimethyl-1,3-dioxo-4,7-epoxy-2H-isoindol-2-yl)-2-iodobenzonitrile (489Gi) & [3aS-(3aα,4β,5β,7β,7aα)]-4-(Octahydro-5-hydroxy-4,7-dimethyl-1,3-dioxo-4,7-epoxy-2H-isoindol-2-yl)-2-iodobenzonitrile (489Gii)

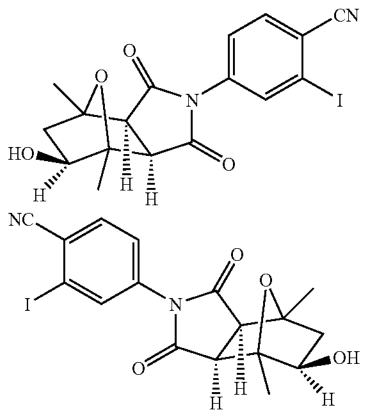

A. 2-Iodo-4-nitro-phenylamine (489A)

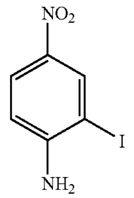

To a mixture of iodine (46.0 g, 0.180 mol) and silver sulfate (56.3 g, 0.180 mol) in anhydrous ethanol (500 mL) was added 4-nitroaniline (25.0 g, 0.180 mol) and the reaction mixture was stirred for 5 h at rt. The resulting yellow solution was filtered and concentrated in vacuo. The resulting residue was dissolved into 400 mL ethyl acetate, washed with 1N sodium hydroxide solution (2×250 mL), dried over sodium sulfate, filtered, and concentrated in vacuo to yield 45.5 (95%) of compound 489A, as a yellow solid. HPLC: 98% at 2.837 min (retention time) (Shimadzu VP-ODS column, 4.6×50 mm, eluting with 10-90% aqueous methanol over 4 min containing 0.1% trifluoracetic acid, 4 mL/min, monitoring at 220 nm). MS (ES): m/z 265.08 $[M+H]^+$.

B. 2-Iodo-4-nitro-benzonitrile (489B)

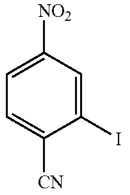

Compound 489A (10.0 g, 37.9 mmol) was dissolved in a mixture of 20 mL 12 N HCl/40 mL water and then cooled to 0° C. To this mixture was slowly added a solution of sodium nitrite (5.23 g, 75.8 mmol) in 10 mL water while maintaining the reaction temperature at 0° C. The reaction was stirred for 1 h at 0° C. and then slowly added to a mechanically stirred solution of freshly prepared cuprous cyanide (3.0 g, 33 mmol, prepared as described in Vogel's Textbook of Practical Organic Chemistry, $5^{th}$ edition, pg. 429) and potassium cyanide (6.30 g, 96.7 mmol) in water (50 mL) at 50° C. The reaction was stirred for 1 h at 50° C., cooled to 25° C. and extracted with methylene chloride (2×200 mL). The organic portion was dried over sodium sulfate, filtered and concentrated in vacuo. The resulting residue was purified by chromatography on silica gel eluting with 4:1 hexane:ethyl acetate to yield 4.6 g (44%) of compound 489B as an orange solid. HPLC: 98% at 2.647 min (retention time) (YMC S5 ODS column, 4.6×50 mm, eluting with 10-90% aqueous methanol over 4 mincontaining 0.2% phosphoric acid, 4 mL/min, monitoring at 220 nm).

C. 4-Amino-2-iodo-benzonitrile (489C)

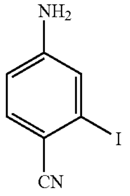

A mixture of compound 489B (4.60 g, 16.8 mmol), tetrahydrofuran (75 mL), ethanol (100 mL), ammonium chloride solution (1.51 g, 28.3 mmol, dissolved in 100 mL of water), and iron (325 mesh, 4.21 g, 75.4 mmol) was mechanically stirred. The reaction mixture was heated to reflux for 3 h or until all starting material was consumed. The reaction mixture was cooled, filtered through Celite and concentrated in vacuo. The resulting residue was dissolved in ethyl acetate (200 mL) and washed with 1N sodium hydroxide (2×150 mL), dried over sodium sulfate, filtered and concentrated in vacuo to yield 3.97 g (97%) of compound 489C as a dark solid. HPLC: 95% at 1.877 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 245.13 $[M+H]^+$.

D. 4-(2,5-Dioxo-2,5-dihydro-pyrrol-1-yl)-2-iodo-benzonitrile (489D)

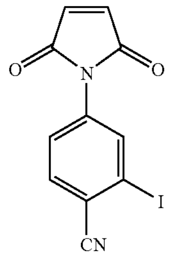

Compound 489C (3.97 g, 16.3 mmol) and maleic anhydride (2.41 g, 24.4 mmol) were refluxed in glacial acetic acid (15 mL) for 5 h. The reaction was cooled to 25° C. and then poured onto ice (100 mL). The resulting precipitate was isolated by filtration and washed with water (2×25 mL) and dried under vacuum to yield 4.78 g (90%) of compound 489D as a tan solid. HPLC: 82% at 2.68 min (retention time) C Shimadzu VP-ODS column, 4.6×50 mm, eluting with 10-90% aqueous methanol over 4 mincontaining 0.1% trifluoroacetic acid, 4 mL/min, monitoring at 220 nm). MS (ES): m/z 325.04 $[M+H]^+$.

E. (3aα,4β,7β,7aα)-4-(1,3,3a,4,7,7a-Hexahydro-4,7-dimethyl-1,3-dioxo-4,7-epoxy-2H-isoindol-2-yl)-2-iodobenzonitrile (489E)

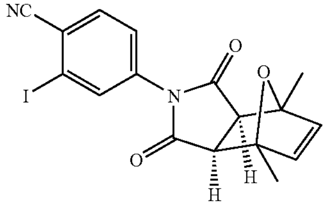

A solution of compound 489D (0.40 g, 1.2 mmol) in 2,5-dimethylfuran (2.0 g) was stirred at 75° C. for 2 h. The reaction was decanted from any insoluble materials and the particulates were washed with diethyl ether. The combined decant and ether washes were combined and concentrated in vacuo while maintaining a temperature of <50° C. The resulting residue was triturated with hexanes to yield 0.56 g (94% based on purity) of compound 489E as a tan solid. Due to the propensity of the product to undergo a retro-Diels-Alder reaction, no further purification was attempted. HPLC: 85% at 3.01 min (retention time) (Shimadzu VP-ODS column, 4.6×50 mm, eluting with 10-90% aqueous methanol over 4 mincontaining 0.1% trifluoroacetic acid acid, 4 mL/min, monitoring at 254 nm). MS (ES): m/z 421.05$[M+H]^+$.

F. (3aα,4β,5β,7β,7aα)-4-(Octahydro-5-hydroxy-4,7-dimethyl-1,3-dioxo-4,7-epoxy-2H-isoindol-2-yl)-2-iodobenzonitrile (489F)

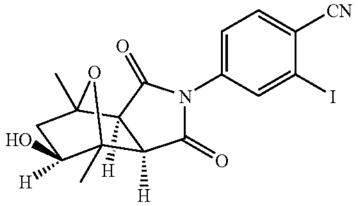

To a solution of compound 489E (0.40 g, 0.95 mmol) in dry THF (5 mL) cooled to 0° C. was added borane-dimethylsulfide complex (0.2 mL, 1.9 mmol, 10 M) and the reaction solution was allowed to warm to 25° C. After stirring for 30 min, the reaction was cooled to 0° C. and pH 7 phosphate buffer (6.6 mL) was slowly added, followed by the addition of 30% hydrogen peroxide (0.7 mL). The reaction was stirred at 25° C. for 1 h and then partitioned between ethyl acetate (100 mL) and water (100 mL). The organic portion was isolated, dried over sodium sulfate, filtered and concentrated in vacuo. The resulting residue was purified by silica gel eluting with 3:1 methylene chloride:ethyl acetate to yield 0.11 g (25%) of compound 489F as a white solid. HPLC: 99% at 2.527 min (retention time) (Shimadzu VP-ODS column, 4.6×50 mm, eluting with 10-90% aqueous methanol over 4 mincontaining 0.1% trifluoroacetic acid, 4 mL/min, monitoring at 220 nm). MS (ES): m/z 439.09 $[M+H]^+$.

G. [3aR-(3aα,4β,5β,7β,7aα)]-4-(Octahydro-5-hydroxy-4,7-dimethyl-1,3-dioxo-4,7-epoxy-2H-isoindol-2-yl)-2-iodobenzonitrile (489Gi) & [3aS-(3aα,4β,5β,7β,7aα)]-4-(Octahydro-5-hydroxy-4,7-dimethyl-1,3-dioxo-4,7-epoxy-2H-isoindol-2-yl)-2-iodobenzonitrile (489Gii)

The racemic compounds 489F, was separated into its individual antipodes by normal phase preparative chiral HPLC. A Chiralcel AD column (50×500 mm) was used with a flow rate of 50 mL/min (70% Isopropanol/hexanes) monitoring at 220 nm. The faster eluting antipode, compound 489Gi had a retention time of 4.587 min and the slower eluting antipode, compound 489Gii had a retention time of 6.496 min. Both antipodes were isolated as white solids after separation. The absolute conformation for compounds 489Gi & 489Gii was not established. For simplicity in nomenclature, compound 489Gi is designated herein as having an "R" configuration and compound 489Gii as having an "S" configuration.

EXAMPLE 490

(3aα,4β,5β,7β,7aα)-4-[7-[2-[(5-Chloro-2-pyridinyl)oxy]ethyl]octahydro-5-methoxy-4-methyl-1,3-dioxo-4,7-epoxy-2H-isoindol-2-yl]-1-naphthalenecarbonitrile (490B)

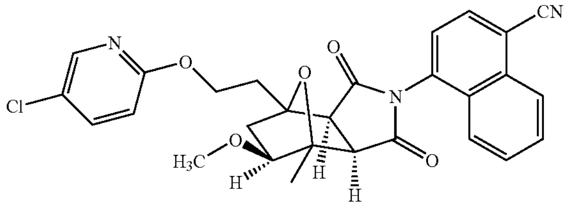

A. (3aα,4β,7β,7aα)-4-[7-[2-[(5-Chloro-2-pyridinyl)oxy]ethyl]octahydro-5-hydroxy-4-methyl-1,3-dioxo-4,7-epoxy-2H-isoindol-2-yl]-1-naphthalenecarbonitrile (490A)

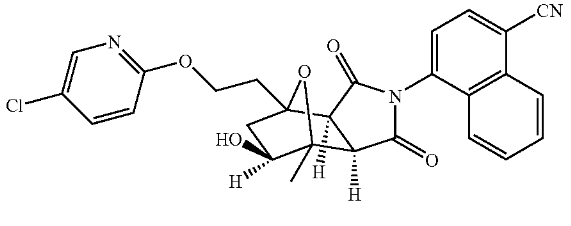

A mixture of triphenylphosphine (166 mg, 0.633 mmol) and DBAD (146 mg, 0.633 mmol) was dissolved in THF (4 mL) under nitrogen and the yellow solution was stirred for 10 min. 5-Chloro-pyridin-2-ol (82 mg, 0.63 mmol) was added and the mixture was stirred for 5 min after which compound 242B (165 mg, 0.327 mmol) was added. The mixture was stirred for 12 h and the solvent was removed under a stream of nitrogen. The resulting oil was adsorb onto silica gel (1 g) and purified by flash chromatography on a Jones Chromatography silica cartridge (5 g/25 mL) eluting with a gradient of 0-50% acetone in chloroform to give 79.4 mg (47%) of compound 490A as a white foam. HPLC: 99% at 3.48 min (retention time) (Phenomenex ODS column, 4.6×50 mm, eluting with 10-90% aqueous methanol over 4 mincontaining 0.1% TFA, 4 mL/min, monitoring at 220 nm). MS (ES): m/z 504.17 $[M+H]^+$.

B. (3aα,4β,5β,7β,7aα)-4-[7-[2-[(5-Chloro-2-pyridinyl)oxy]ethyl]octahydro-5-methoxy-4-methyl-1,3-dioxo-4,7-epoxy-2H-isoindol-2-yl]-1-naphthalenecarbonitrile (490B)

Compound 490A (24 mg, 0.048 mmol) was dried into a 1 dram vial with a magnetic stir bar. Silver oxide (57 mg, 0.24 mmol), $CH_3CN$ (500 μL) and iodomethane (20 μL, 0.32 mmol) were added under nitrogen and the mixture was put in a heated block (82° C.) and stirred for 14 h. The mixture turned brown after 20 min then green. The mixture was filtered through Celite and Florisil and was purified by reverse phase preparative HPLC (Shimadzu Shimpac VP ODS column, 20×50 mm, 0-100% aqueous methanol over 6 mincontaining 0.1% TFA, monitoring at 220 nm) to give 6.9 mg (28%) of compound 490B as a white foam. HPLC: 99% at 3.64 min, 3.76 min (atropisomers, retention time) (Phenomenex ODS column, 4.6×50 mm, eluting with 10-90% aqueous methanol over 4 mincontaining 0.1% TFA, 4 mL/min, monitoring at 220 nm). MS (ES): m/z 518.19 $[M+H]^+$.

EXAMPLE 491

[3aR-(3aα,4β,5β,7β,7aα)]-4-[7-[2-[(5-Chloro-2-pyridinyl)oxy]ethyl]octahydro-5-methoxy-4-methyl-1,3-dioxo-4,7-epoxy-2H-isoindol-2-yl]-1-naphthalenecarbonitrile, (491Ci) & [3aR-(3aα,4β,5β,7β,7aα)]-4-[7-[2-(5-Chloro-2-oxo-1(2H)-pyridinyl)ethyl]octahydro-5-methoxy-4-methyl-1,3-dioxo-4,7-epoxy-2H-isoindol-2-yl]-1-naphthalenecarbonitrile (491Cii)

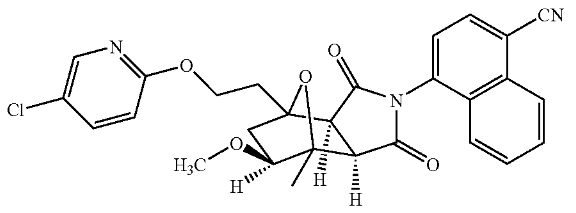

-continued

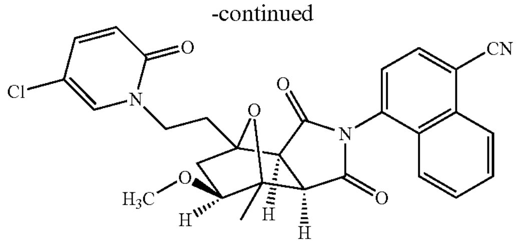

A. (3aα,4β,5β,7β,7aα)-4-[7-[2-[[(1,1-Dimethylethyl)dimethylsilyl]oxy]ethyl]octahydro-5-methoxy-4-methyl-1,3-dioxo-4,7-epoxy-2H-isoindol-2-yl]-1-naphthalenecarbonitrile (491A)

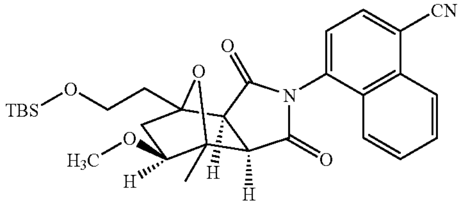

Compound 243Cii (142 mg, 0.280 mmol) was dried into a 1 dram vial equipped with a magnetic stir-bar and a Teflon lined cap. Silver oxide (324 mg, 1.40 mmol), $CH_3CN$ (3 mL) and iodomethane (90 μL, 1.4 mmol) were added under nitrogen and the mixture was put in a heated block (82° C.). The reaction was stirred overnight, then filtered through Celite and concentrated in vacuo. The resulting residue was purified by flash chromatography on silica gel eluting with a gradient of 0-50% acetone in chloroform to yield 62.2 mg (43%) of compound 491A. HPLC: 99% at 3.87 & 3.95 min (atropisomers, retention time) (Phenomenex ODS column, 4.6×50 mm, eluting with 10-90% aqueous methanol over 4 mincontaining 0.1% TFA, 4 mL/min, monitoring at 220 nm). MS (ES): m/z 521.37 $[M+H]^+$.

B. 3aα,4β,5β,7β,7aα)-4-[Octahydro-7-(2-hydroxyethyl)-5-methoxy-4-methyl-1,3-dioxo-4,7-epoxy-2H-isoindol-2-yl]-1-naphthalenecarbonitrile (491B)

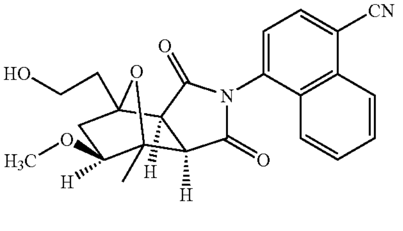

Compound 491A (62.2 mg, 0.119 mmol) was dissolved in ethanol (2 mL) and 12 N hydrochloric acid (50 μL) was added and the mixture was stirred for 10 min. The solvent was removed in vacuo and the product was purified by flash chromatography on silica gel eluting with a gradient of 0-20% acetone in chloroform to yield 40.3 mg (83%) of compound 491B as a white solid. HPLC: 96% at 2.30 & 2.45 min (atropisomers, retention time) (Phenomenex ODS column, 4.6×50 mm, eluting with 10-90% aqueous methanol over 4 mincontaining 0.1% TFA, 4 mL/min, monitoring at 220 nm). MS (ES): m/z 407.22 [M+H]$^+$.

C. [3aR-(3aα,4β,5β,7β,7aα)]-4-[7-[2-[(5-Chloro-2-pyridinyl)oxy]ethyl]octahydro-5-methoxy-4-methyl-1,3-dioxo-4,7-epoxy-2H-isoindol-2-yl]-1-naphthalenecarbonitrile, slow eluting enantiomer (491Ci) & [3aR-(3aα,4β,5β,7β,7aα)]-4-[7-[2-(5-Chloro-2-oxo-1(2H)-pyridinyl)ethyl]octahydro-5-methoxy-4-methyl-1,3-dioxo-4,7-epoxy-2H-isoindol-2-yl]-1-naphthalenecarbonitrile (491Cii)

Triphenylphosphine (40 mg, 0.15 mmol) and DBAD (35 mg, 0.15 mmol) were dissolved in THF under nitrogen and stirred 10 min. 5-Chloropyridin-2-ol (20 mg, 0.15 mmol) was added and the mixture was stirred for 5 min. Compound 491B (40.3 mg, 0.0991 mmol) was added and the resulting mixture was stirred for 2.5 h. The solvent was concentrated in vacuo and the resulting residue was purified by chromatography over Florisil (1.3 g) eluting with a gradient of 0-40% acetone in chloroform to give 140 mg of a mixture of 491Ci, 491Cii and DBAD. The oil was suspended in dichloromethane (3 mL) and trifluoroacetic acid (2 mL) was added. After 45 min, the solvent was removed in vacuo and the resulting oil was partitioned between saturated sodium bicarbonate (20 mL) and EtOAc (20 mL). The aqueous layer was extracted with EtOAc (2×20 mL) and the combined organic layers were dried over magnesium sulfate. Purification by reverse phase preparative HPLC (Shimadzu Shimpac VP ODS column, 20×50 mm, 0-100% aqueous methanol over 6 mincontaining 0.1% TFA, monitoring at 220 nm) gave 22 mg (44%) of compound 491Ci and 4.6 mg (9% yield) of compound 491Cii. Compound 491Ci: HPLC: 95% at 3.50 min (retention time) (Phenomenex ODS column, 4.6×50 mm, eluting with 10-90% aqueous methanol over 4 mincontaining 0.1% TFA, 4 mL/min, monitoring at 220 nm). MS (ES): m/z 518.28 [M+H]$^+$. Compound 491Cii: HPLC: 85% at 2.94 & 3.07 min (atropisomers, retention time) (Phenomenex ODS column, 4.6×50 mm, eluting with 10-90% aqueous methanol over 4 mincontaining 0.1% TFA, 4 mL/min, monitoring at 220 nm). MS (ES): m/z 518.27 [M+H]$^+$.

EXAMPLE 492

[3aR-(3aα,4β,5β,7β,7aα)]-4-[5-(Acetyloxy)-7-[2-[(5-chloro-2-pyridinyl)oxy]ethyl]octahydro-4-methyl-1,3-dioxo-4,7-epoxy-2H-isoindol-2-yl]-1-naphthalenecarbonitrile, slow eluting enantiomer (492)

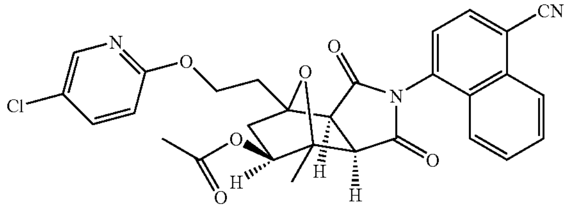

Acetyl chloride (25 μL, 0.35 mmol) was added to a solution of compound 490A (30 mg, 0.060 mmol) in pyridine (600 μL). The mixture was stirred overnight, diluted with hydrochloric acid (0.5 N, 10 mL), extracted with chloroform (3×7 mL). The organic layers were combined, washed with water (3×4 mL) and brine (4 mL), dried over magnesium sulfate and concentrated in vacuo. Purification by flash chromatography on silica gel eluting with a gradient of 0-50% acetone in chloroform gave 17 mg (53%) of compound 492. HPLC: 99% at 3.48 & 3.63 min (atropisomers, retention time) (Phenomenex ODS column, 4.6×50 mm, eluting with 10-90% aqueous methanol over 4 mincontaining 0.1% TFA, 4 mL/min, monitoring at 220 nm). MS (ES): m/z 546.15 [M+H]$^+$.

EXAMPLE 493

Dimethylcarbamic acid, [3aR-(3aα,4β,5β,7β,7aα)]-7-[2-[(5-chloro-2-Pyridinyl)oxy]ethyl]-2-(4-cyano-1-naphthalenyl)octahydro-4-methyl-1,3-dioxo-4,7-epoxy-1H-isoindol-5-yl ester, slow eluting enantiomer (493)

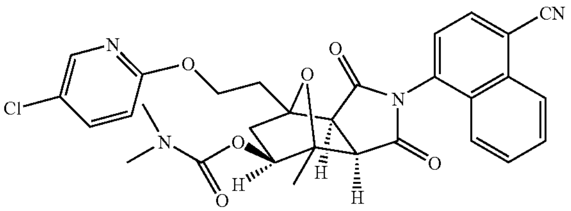

To a solution of compound 490A (30 mg, 0.060 mmol) in pyridine (300 μl) was added dimethylcarbamyl chloride (28 μl, 0.30 mmol) and the mixture was stirred at 25° C. for 12 h. An additional portion of dimethylcarbamyl chloride (28 μL, 0.30 mmol) was added and the reaction was heated at 70° C. for 12 h. A third portion of dimethylcarbamoyl chloride (28 μl, 0.30 mmol) as well as pyridine (300 μl) were added and the mixture was stirred at 100° C. for 24 h. The solution was diluted with 0.5 N HCl (10 mL) and extracted with chloroform (3×7 mL). The organic layers were combined and washed with water (3×4 mL) and brine (4 mL), dried over magnesium sulfate and concentrated in vacuo. Purification by reverse phase preparative HPLC (Shimadzu Shimpac VP ODS column, 20×50 mm, 0-100% aqueous methanol over 6 mincontaining 0.1% TFA, monitoring at 220 nm) gave 15.7 mg (46%) of compound 493 as a white solid. HPLC: 99% at 3.52 min & 3.69 min (atropisomers, retention time) (Phenomenex ODS column, 4.6×50 mm, eluting with 10-90% aqueous methanol over 4 mincontaining 0.1% TFA, 4 mL/min, monitoring at 220 nm). MS (ES): m/z 575.10 [M+H]$^+$.

EXAMPLE 494

[3aR-(3aα,4β,5β,7β,7aα)]-4-[7-[2-[(5-Chloro-2-pyridinyl)oxy]ethyl]octahydro-4-methyl-5-[[(methylamino)carbonyl]oxy]-1,3-dioxo-4,7-epoxy-2H-isoindol-2-yl]-1-naphthalenecarbonitrile, slow eluting enantiomer (494)

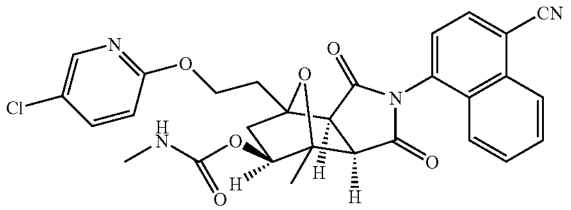

Methyl isocyanate (36 μL, 0.60 mmol) was added to a solution of compound 490A (30 mg, 0.060 mmol) in dioxane (600 μL) and was heated at 80° C. overnight. An additional portion of methyl isocyanate (36 μL, 0.60 mmol) was added and the mixture was heated at 100° C. for 24 h. A third portion of methyl isocyanate (36 μL, 0.60 mmol) was added and the mixture was stirred at 100° C. for 24 h. The solvent was removed in vacuo and the oil was purified by reverse phase preparative HPLC (Shimadzu Shimpac VP ODS column, 20×50 mm, 0-100% aqueous methanol over 6 mincontaining 0.1% TFA, monitoring at 220 nm) to give 20 mg (59%) of compound 494 as a clear glass. HPLC: 99% at 3.33 min & 3.42 min (atropisomers, retention time) (Phenomenex ODS column, 4.6×50 mm, eluting with 10-90% aqueous methanol over 4 mincontaining 0.1% TFA, 4 mL/min, monitoring at 220 nm). MS (ES): m/z 561.08 $[M+H]^+$.

EXAMPLE 495

[3aR(3aα,4β,5β,7β,7aα)]-4-[Octahydro-4-(2-hydroxyethyl)-7-methyl-1,3-dioxo-4,7-epoxy-2H-isoindol-2-yl]-1-naphthalenecarbonitrile (495Ai) & [3aS (3aα,4β,5β,7β,7aα)]-4-[Octahydro-4-(2-hydroxyethyl)-7-methyl-1,3-dioxo-4,7-epoxy-2H-isoindol-2-yl]-1-naphthalenecarbonitrile (495B)

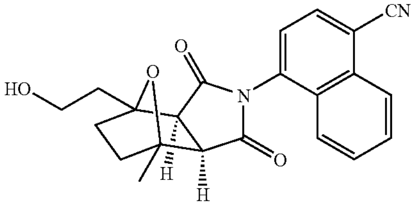

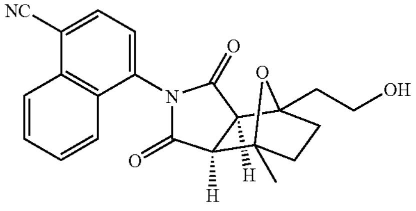

A. [3aS-(3aα,4β,5β,7β,7aα)]-4-[Octahydro-4-(2-hydroxyethyl)-7-methyl-1,3-dioxo-4,7-epoxy-2H-isoindol-2-yl]-1-naphthalenecarbonitrile (495Ai) & (3aα,4β,5β,7β,7aα)-4-[2-(Acetyloxy)ethyl]-2-(4-cyano-1-naphthalenyl)hexahydro-7-methyl-4,7-epoxy-1H-isoindole-1,3(2H)-dione (495Aii)

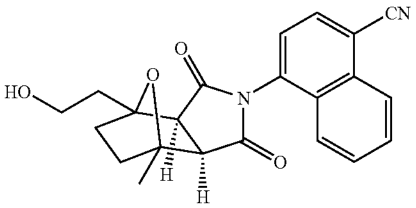

-continued

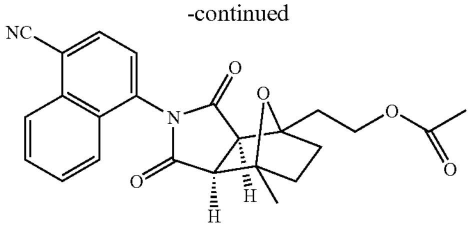

Racemic compound 223B (10.26 g, 27.26 mmol) was dissolved in anhydrous THF (500 mL) in a 10 L bottle. tert-Butyl methyl ether (4.86 L), vinyl acetate (216 mL) and Lipase (108 g, [Sigma, Lipase type II, crude from Porcine pancreas, product No. L3126, Lot No. 021K1445]) were added. The reaction mixture was agitated for 24 h at rt and the reaction was monitored by HPLC using the following conditions: A 200 μL sample of the reaction mixture was filtered, dried under a stream of nitrogen and subjected to HPLC analysis (YMC ODS column, 4.6×50 mm, eluting with 10-90% aqueous methanol over 4 mincontaining 0.1% TFA, 4 mL/min, monitoring at 220 nm). The reaction was stopped after 60% of the starting material was consumed. The enzyme was removed by filtration and the filtrate was concentrated in vacuo. The resulting residue was dissolved in $CHCl_3$ and absorbed onto silica gel. Purification by flash chromatography on silica gel eluting with a gradient of 1-5% MeOH in $CHCl_3$ gave 3.78 g (37%) of compound 495Ai and 6.84 g (60%) of compound 495Aii, both as white solids. Compound 495Ai: HPLC: 99% at 3.47 min (retention time) (YMC S5 ODS column, 4.6×50 mm, eluting with 10-90% aqueous methanol over 4 min containing 0.1% TFA, 4 mL/min, monitoring at 220 nm). MS (ES): m/z 377.09 $[M+H]^+$. Normal phase preparative chiral HPLC: 37.8 min (retention time) (chiralpak AD column, 4.6×250 mm, 10 micron, 40° C., isocratic elution with 8% EtOH/MeOH (1:1) in heptane, monitoring at 220 nm), 99% ee. Compound 495Aii: HPLC: 99% at 2.92 min (retention time) (YMC S5 ODS column, 4.6×50 mm, eluting with 10-90% aqueous methanol over 4 mincontaining 0.1% TFA, 4 mL/min, monitoring at 220 nm).

B. [3aR-(3aα,4β,5β,7β,7aα)]-4-[Octahydro-4-(2-hydroxyethyl)-7-methyl-1,3-dioxo-4,7-epoxy-2H-isoindol-2-yl]-1-naphthalenecarbonitrile (495B)

Lipase (134 g, [Sigma, Lipase type II, crude from Porcine pancreas, product No. L3126, Lot No. 021K1445]) was added to 3.5 L of deionized water. The mixture was centrifuged to remove most of the suspended material. The pH of the supernatant was adjusted to 7.06 with 1N sodium hydroxide and a solution of compound 495Aii (8.04 g, 19.2 mmol) in TBME (1.5 L) was added. The pH was increased to 7.16 by addition of 1N sodium hydroxide. The reaction mixture was agitated at rt and was monitored by analytical HPLC as described in Example 495A. After 30 min, the reaction was filtered through Celite and the filtrate was extracted with ethyl acetate (4×1 L) until HPLC showed that all the alcohol has been removed. The organic fractions were combined, dried over magnesium sulfate, filtered and concentrated in vacuo. Purification by flash chromatography on silica gel (Jones, 50 g column) using a gradient of 0-70% acetone in chloroform followed by 5% MeOH in chloroform gave 2.44 g (33%) of compound 495B as a white solid. HPLC: 99% at 2.89 min (retention time) (YMC S5 ODS column, 4.6×50 mm, eluting with 10-90% aqueous methanol over 4 mincontaining 0.1% TFA, 4 mL/min, monitoring at 220 nm). MS (ES): m/z 377.09

$[M+H]^+$. Normal phase preparative chiral HPLC: 11.1 min (retention time) (chiralpak AD column, 4.6×250 mm, 10 micron, 40° C., isocratic elution with 8% EtOH/MeOH (1:1) in heptane, monitoring at 220 nm), 95% ee.

EXAMPLE 496

[3aR-(3aα,4β,7β,7aα)]-4-[4-[2-[(5-Chloro-2-pyridinyl)oxy]ethyl]octahydro-7-methyl-1,3-dioxo-4,7-epoxy-2H-isoindol-2-yl]-1-naphthalenecarbonitrile (496Bi) & [3aR-(3aα,4β,7β,7aα)]-4-[4-[2-(5-Chloro-2-oxo-1(2H)-pyridinyl)ethyl]octahydro-7-methyl-1,3-dioxo-4,7-epoxy-2H-isoindol-2-yl]-1-naphthalenecarbonitrile (496Bii)

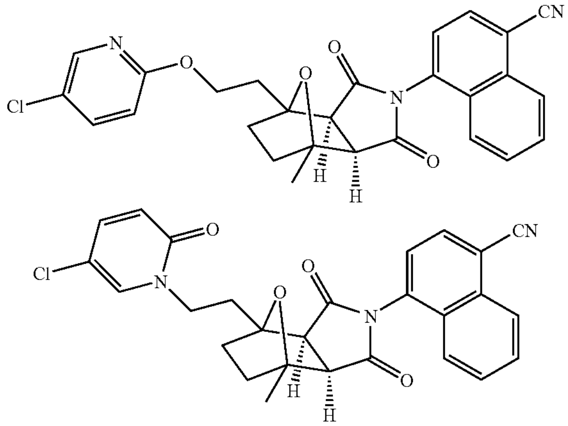

A. Preparation of Solid Support (496A)

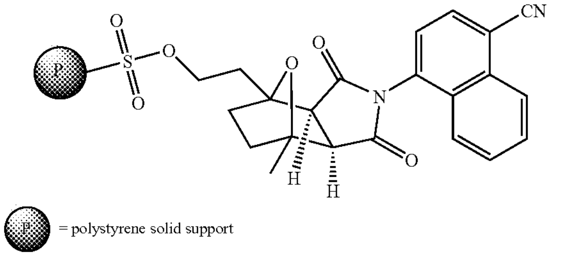

A mixture of anhydrous $CH_2Cl_2$ (10 mL) and pyridine (10 mL) was added under nitrogen to chlorosulfonylpolystyrene (Argonaut, 1.70 mmol/g, 3.0 g, 5.1 mmol) and compound 495Ai (3.78 g, 10.0 mmol) in a polymer synthesis tube. The mixture turned into a yellow gel and was vigorously shaken (wrist action shaker for 4 h.). All the solvents were absorbed by the resin and it looked dry. The resin was washed in portions with $CH_2Cl_2$ (200 mL) and the washes were combined and extracted with 200 mL 1N HCl. The HCl fraction was re-extracted with ethyl acetate (200 mL). The organic fractions were combined and extracted with water (50 mL), brine (50 mL) and the organic fractions were dried over sodium sulfate, filtered and concentrated to give 2.1 g of resin bound compound 496A (89% loaded based on recovered unbound compound 495Ai). The resin was washed consecutively with DMF (5×), DMF:water (3:1, 5×), THF (3×) and $CH_2Cl_2$ (3×) (~30 mL each wash). The resin was dried in vacuo for 1 h to yield 5.35 g of resin. The resin was still wet and was re-treated with the alcohol. The above described loading process was repeated using the recovered un-reacted compound 495Ai from the above procedure. Recovered compound 495Ai (2.1 g, 5.6 mmol) and anhydrous dichloromethane (15 mL) and pyridine (15 mL) and the resin were combined and subjected to the reaction conditions described above. The resulting resin was washed as described previously and dried in vacuo overnight to yield 4.49 g of resin (87% loaded based on recovered unbound compound 495Ai). The starting alcohol was recovered from the dichloromethane:pyridine mixture as described previously (2.04 g of white solid, which would suggest a 92% loading based on recovered alcohol). The resin weigh increase is usually more accurate for loading assessment. The resin loading was calculated to be 0.87 (determined by resin weight increase)×1.08 mmol/g (calculated 100% loading)=0.94 mmol/g. The resin was used as is for the next step.

B. [3aR-(3aα,4β,7β,7aα)]-4-[4-[2-[(5-Chloro-2-pyridinyl)oxy]ethyl]octahydro-7-methyl-1,3-dioxo-4,7-epoxy-2H-isoindol-2-yl]-1-naphthalenecarbonitrile (496Bi) & [3aR-(3aα,4β,7β,7aα)]-4-[4-[2-(5-Chloro-2-oxo-1(2H)-pyridinyl)ethyl]octahydro-7-methyl-1,3-dioxo-4,7-epoxy-2H-isoindol-2-yl]-1-naphthalenecarbonitrile (496Bii)

The following procedure describes a general process by which arrays of compounds of Formula I can be made using automated approaches. Additional information on such automated synthetic approaches can be found in Example 8. Compounds 496Bi & 496Bii are an example of compounds made by such a procedure. For compounds 496Bi & 496Bii, 4-chloropyridinol represents the nuceophile reagent. A broader definition of the term nucleophile is contained in the body of this document and is well understood by one skilled in the art. A Bohdan MiniReactor equipped with a heating/cooling block was used with 0.5 Dram vials stacked over one another to achieve the same level as the reactor tubes. Resin (compound 496A) was measured into the individual vials by using each Bohdan resin Transfer module plate "10 mg" and "20 mg" once. The weights of resin delivered ranged from 17-23 mg (0.016-0.022 mmol). Cesium carbonate was added using the Bohdan "20 mg" plate which delivered ~57-60 mg (0.17-0.18 mmol). The nucleophiles were weighted into 1 Dram vials and were diluted in THF to 0.06 M using a Tecan eight channel liquid handler. The resulting solutions (250 μL, 0.015 mmol) were added manually via a micro-pipette to each of the reaction vials containing resin and the resulting array of reaction vials were placed in a Bohdan reactor. When the nucleophiles are amines, 13 μL of diisopropylethylamine was added to the THF solution of the amine. The vials were capped (Teflon-lined) and the reactions were heated with orbital shaking (short stroke 500 rpm) at 70° C. for 24 h. The reactions were cooled to 25° C. and 1 mL of a mixture of heptane and ethyl acetate (1:1) was added followed by 0.5 mL of water. The organic layer was extracted manually and individually transferred to a synthesis block tube containing magnesium sulfate (~150 mg). The array of synthesis block tubes were simultaneously filtered and the filtrates were individually collected into microtubes (96 well block). The aqueous layer was re-extracted with 1 mL of a mixture of heptane and ethyl acetate (1:1), the organic layer was filtered as described above and the filtrate was individually collected as described above into the existing microtubes.

Analysis of the array of compounds prepared by the above procedure was performed using the following automated approach. A 120 μl portion of each of the above reaction (filtrates) was aliquoted into two 96 deep well blocks for analysis. The solvent was concentrated in vacuo and the plates were re-diluted with methanol (500 μL). One plate was analyzed by LCMS (Phenomenex ODS column, 4.6×50 mm, 4 mL/min, gradient 0% A to 100% B (A: 90% water, 10% MeOH, 0.1% TFA; B: A: 90% MeOH, 10% water, 0.1% TFA) and the other by flow-NMR (Varian Inova-500 MHz, MeOH, WET solvent suppression pulse sequence, 128 scans, 60 μl flow cell probe). The criteria for submission was: correct molecular ion present and HPLC/NMR purity >70%. Compounds which did not meet the desired criteria were purified by reverse phase preparative HPLC (Shimadzu UP-ODS column, 20×50 mm, 20 mL/min, gradient 40% B to 100% B in 6 min with 2 min hold (A: 90% water, 10% MeOH, 0.1% TFA; B: A: 90% MeOH, 10% water, 0.1% TFA). HPLC purification yielded 3.4 mg (21%) of compound 496Bi as a glassy solid and 6.8 mg (41%) of compound 496Bii as a glassy solid. Compound 496Bi: HPLC: 96% at 3.47 min & 3.62 min (atropisomers, retention time) (Phenominex ODS column, 4.6×50 mm, 4 mL/min, gradient 0% A to 100% B (A: 90% water, 10% MeOH, 0.1% TFA; B: A: 90% MeOH, 10% water, 0.1% TFA), monitoring at 220 nm). MS (ES): m/z 487.94 $[M+H]^+$. Compound 496Bii: HPLC: 96% at 3.00 min & 3.12 min (atropisomers, retention time) (Phenominex ODS column, 4.6×50 mm, 4 mL/min, gradient 0% A to 100% B (A: 90% water, 10% MeOH, 0.1% TFA; B: A: 90% MeOH, 10% water, 0.1% TFA), monitoring at 220 nm). MS (ES): m/z 488.12 $[M+H]^+$. Additional compounds made by this procedure are set forth in Table 17.

EXAMPLE 497

(3aα,4β,5β,7β,7aα)-Hexahydro-4,7-dimethyl-2-(7-methyl-6-benzothiazolyl)-4,7-epoxy-1H-isoindole-1,3(2H)-dione (497B)

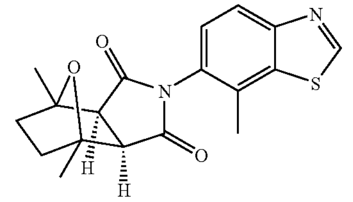

A. 6-Amino-7-methylbenzothiazole (497A)

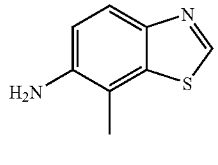

7-Methyl-6-nitrosobenzothiazole was prepared from 6-nitrobenzothiazole according to the general procedure described by Bartoli et al. *Synlett* 270 (1976). To a solution of 7-methyl-6-nitrosobenzothiazole (889 mg, 5.00 mmol) in AcOH (40 mL) at 70° C. was added iron powder (325 mesh, 559 mg, 10.0 mmol) in a single portion. The resulting dark reaction mixture was stirred for 15 min before it was cooled and concentrated in vacuo to leave a residue which was partitioned between 1N HCl (50 mL) and $CH_2Cl_2$ (50 mL). The layers were separated and the organic layer was washed once with 1N HCl (25 mL). The combined aqueous layers were made basic by the addition of solid $NaHCO_3$ and were extracted twice with EtOAc. The organic phases were combined, dried over $MgSO_4$ and concentrated in vacuo to give 534 mg (65%) of compound 497A as a light brown solid. HPLC: 96% at 0.55 min (retention time) (YMC S5 ODS column, 4.6×50 mm Ballistic, 10-90% aqueous methanol over 4 mincontaining 0.2% $H_3PO_4$, 4 mL/min, monitoring at 220 nm). MS (ES): m/z 165.0 $[M+H]^+$.

B. (3aα,4β,5β,7β,7aα)-Hexahydro-4,7-dimethyl-2-(7-methyl-6-benzothiazolyl)-4,7-epoxy-1H-isoindole-1,3(2H)-dione (497B)

6-Amino-7-methylbenzothiazole (29 mg, 0.18 mmol), $MgSO_4$ (54 mg, 0.45 mmol), triethylamine (125 μL, 0.897 mmol) and compound 20A (52 mg, 0.26 mmol) were taken up in 0.18 mL of DME and placed in a sealed tube. The sealed tube was heated at 135° C. for 14 h. The cooled reaction mixture was filtered through a short pad of Celite eluting with EtOAc and the solvent was removed in vacuo. The residue was purified by reverse phase preparative HPLC (YMC S5 ODS column, 20×100 mm, eluting with 30-100% aqueous methanol over 10 mincontaining 0.1% TFA, 20 mL/min, monitoring at 220 nm). Concentration of the desired fractions afforded a residue which was partitioned between $CH_2Cl_2$ (10 mL) and sat. $NaHCO_3$ solution (10 mL). The aqueous layer was extracted once with $CH_2Cl_2$ and the combined organic phases were dried over $Na_2SO_4$ and concentrated in vacuo to give 42 mg (68%) of compound 497B as a tan solid. HPLC: 2.36 min & 2.55 min (atropisomers, retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 343.3 $[M+H]^+$.

EXAMPLE 498

(3aα,4β,5β,7β,7aα)-5-[Octahydro-5-hydroxy-7-(2-hydroxyethyl)-4-methyl-1,3-dioxo-4,7-epoxy-2H-isoindol-2-yl]-8-quinolinecarbonitrile (498i) & (3aα,4β,5β,7β,7aα)-5-[Octahydro-5-hydroxy-4-(2-hydroxyethyl)-7-methyl-1,3-dioxo-4,7-epoxy-2H-isoindol-2-yl]-8-quinolinecarbonitrile (498ii)

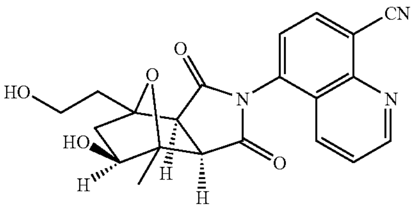

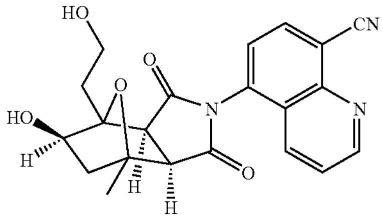

Compound 464E (0.500 g, 1.02 mmol) was dissolved in THF (5.00 mL) and cooled to 0° C. $BH_3$.DMS (0.193 mL, 2.04 mmol) was then added slowly followed by warming to 25° C. After 1 h, the reaction was cooled to 0° C. and pH 7 phosphate buffer (15.0 mL) was added resulting in the evolution of gas. EtOH (7.0 mL) and hydrogen peroxide (30%, 1.5 mL) were then added and the reaction was warmed to 25° C. over 2 h. After 3 h, the mixture was extracted with methylene chloride (3×50 mL). The combined organic layers were washed once with brine and dried over anhydrous sodium sulfate. The product was complexed to boron after workup. All attempts to break up this complex failed to give the free product. The crude material was taken on to the next step without further purification.

The crude reaction mixture was dissolved in 2% conc. HCl/MeOH (5.0 mL) at rt. After 1 h, the volatiles were removed in vacuo and the resulting residue was dissolved in methylene chloride and washed once with sat. aq. sodium bicarbonate and dried over anhydrous sodium sulfate. Solvent removal in vacuo gave the crude mixture of compounds 498i and 498ii as a yellow solid. The mixture of compounds was separated by reverse phase preparative HPLC: Compound 498i: 17.994 min (retention time) & compound 498ii: 19.767 min (retention time) (YMC S5 ODS column, 30×250 mm, 25 mL/min, 10-90% aqueous methanol over 35 mincontaining 0.1% TFA, monitoring at 220 nm). Solvent removal in vacuo gave 0.012 g (3%) of compound 498i as a white solid and 0.009 g (2%) of compound 498ii as a white solid. Compound 498i: HPLC: 85% at 1.843 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 394.21 $[M+H]^+$. Compound 498ii: HPLC: 98% at 1.650 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 394.21 $[M+H]^+$.

EXAMPLE 499

[3aR-(3aα,4β,5β,7β,7aα)]-4-[7-[2-[[(1,1-Dimethylethyl)dimethylsilyl]oxy]ethyl]-4-ethyloctahydro-5-hydroxy-1,3-dioxo-4,7-epoxy-2H-isoindol-2-yl]-1-naphthalenecarbonitrile (499i) & [3aS-(3aα,4β,5β,7β,7aα)]-4-[7-[2-[[1(1,1-Dimethylethyl) dimethylsilyl]oxy]ethyl]-4-ethyloctahydro-5-hydroxy-1,3-dioxo-4,7-epoxy-2H-isoindol-2-yl]-1-naphthalenecarbonitrile (499ii)

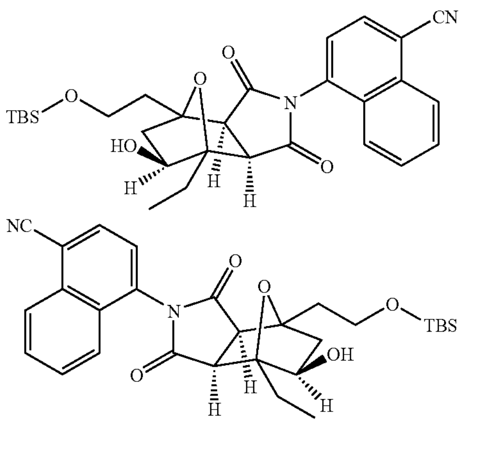

The racemic compound 434C was separated into its individual antipodes by normal phase preparative chiral HPLC using a Chiracel AD column (5 cm×50 cm), eluting with 8% EtOH in hexane at 50 mL/min to give the faster eluting compound 499i (Chiral HPLC: 6.74 min; CHIRALCEL AD 4.6×250 mm column; isocratic elution with 10% EtOH in hexane at 2 mL/min) and the slower eluting compound 499ii (Chiral HPLC: 9.99 min; CHIRALCEL AD 4.6×250 mm column; isocratic elution with 10% EtOH in hexane at 2 mL/min). For either compound 499i or 499ii: HPLC: 100% at 3.96 min (retention time) (YMC CombiSreen ODS column, 4.6×50 mm, eluting with 10-90% aqueous methanol containing 0.2% phosphoric acid over 4 min, 4 mL/min, monitoring at 220 nm). MS (ES): m/z 521.25 $[M+H]^+$. The absolute stereochemistry for compounds 499i & 499ii was not established. For simplicity in nomenclature, compound 499i is designated herein as having an "R" configuration and compound 499ii as having an "S" configuration. Enantiomerically pure products derived from compound 499i are designated herein as having a "R" configuration and enantiomerically pure products derived from compound 499ii are designated herein as having an "S" configuration.

EXAMPLE 500

[3aR-(3aα,4β,5β,7β,7aα)]-4-[4-Ethyloctahydro-5-hydroxy-7-(2-hydroxyethyl)-1,3-dioxo-4,7-epoxy-2H-isoindol-2-yl]-1-naphthalenecarbonitrile (500i) & [3aS-(3aα,4β,5β,7β,7aα)]-4-[4-Ethyloctahydro-5-hydroxy-7-(2-hydroxyethyl)-1,3-dioxo-4,7-epoxy-2H-isoindol-2-yl]-1-naphthalenecarbonitrile (500ii)

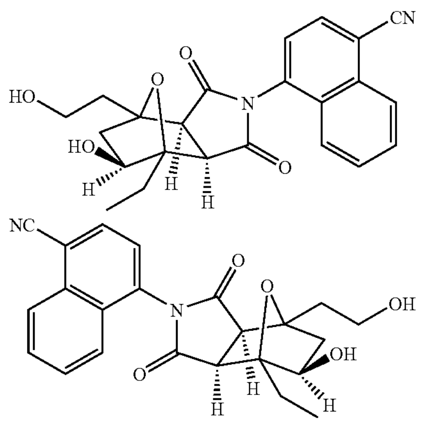

Compound 499i (24.0 mg, 0.0461 mmol) was dissolved in 2% conc. HCl/EtOH (0.8 mL) and the mixture was stirred at rt for 20 min. Cold sat. $NaHCO_3$ was added to the mixture until the solution reached pH 8, then extracted with EtOAc. The organic layers were combined, washed with brine and dried over anhydrous sodium sulfate. Concentration in vacuo gave 14.7 mg (78%) of compound 500i as a white solid which did not require further purification. HPLC: 95% at 2.40 min (retention time) (YMC S5 ODS 4.6×50 mm, 10%-90% aqueous methanol over 4 min gradient with 0.2% $H_3PO_4$, monitoring at 220 nm).

Compound 499ii (18.0 mg, 0.0346 mmol) was dissolved in 2% conc. HCl/EtOH (0.6 mL) and the mixture was stirred at rt for 20 min. Cold sat. $NaHCO_3$ was added to the mixture until the solution reached pH 8, then extracted with EtOAc. The organic layers were combined, washed with brine and dried over anhydrous sodium sulfate. Concentration in vacuo gave 14.1 mg (99%) of compound 500ii as a white solid which did not require further purification. HPLC: 95% at 2.40 min (retention time) (YMC S5 ODS 4.6×50 mm, 10%-90% aqueous methanol over 4 min gradient with 0.2% $H_3PO_4$, monitoring at 220 nm).

EXAMPLE 501

[3aR-(3aα,4β,7β,7aα)]-4-[4-[2-[(5-Chloro-2-pyridinyl)oxy]ethyl]octahydro-1,3-dioxo-7-propyl-4,7-epoxy-2H-isoindol-2-yl]-1-naphthalenecarbonitrile (501D)

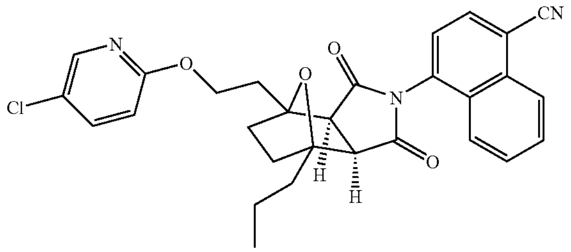

A. 2-(5-Propyl-furan-2-yl)-ethanol (501A)

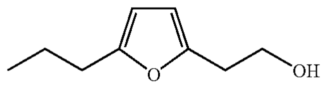

To a solution of 2-propylfuran (3.00 g, 31.2 mmol) in THF (31 mL) at −78° C. was added n-BuLi (15.0 mL, 2.5 M, 37.4 mmol) dropwise over 10 min. The reaction was warmed to rt and stirred for 3.5 h. After cooling to 0° C., ethylene oxide (2.33 mL, 46.8 mmol) was added, the reaction was warmed to rt and stirring was continued for 19 h. The reaction was then cooled to 0° C. and quenched with sat. $NH_4Cl$ (20 mL), followed by extraction with $Et_2O$ (2×50 mL). The combined organic layers were washed with brine, dried over $Na_2SO_4$, filtered, and concentrated to give 4.38 g (91%) of compound 501A as a bright orange oil. This material was used without further purification. HPLC: 94% at 2.91 min (retention time) (YMC Combiscreen ODS-A column, 4.6×50 mm, eluting with 10-90% aqueous methanol containing 0.2% phosphoric acid over 4 min, 4 mL/min, monitoring at 220 nm). MS (ES): m/z 137.13 $[M-H_2O+H]^+$.

B. (3aα,4β,7β,7aα)-4-[1,3,3a,4,7,7a-Hexahydro-4-(2-hydroxyethyl)-1,3-dioxo-7-propyl-4,7-epoxy-2H-isoindol-2-yl]-1-naphthalenecarbonitrile (501B)

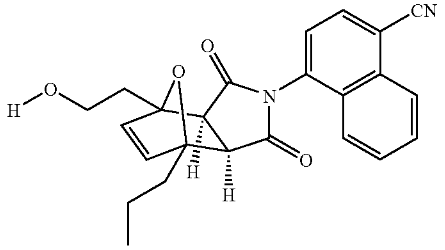

A suspension of 2-(5-propyl-furan-2-yl)-ethanol (2.50 g, 16.2 mmol) and 4-(2,5-dihydro-2,5-dioxo-1H-1-yl)-1-naphthalenecarbonitrile (4.02 g, 16.2 mmol) in benzene (16 mL) was warmed to 60° C. After 3 h, the reaction was concentrated in vacuo to give a brown foam. Methanol (17 mL) was added and the mixture was sonicated to give a fine beige solid with a brown supernatant. Filtration gave 1.75 g (27%) of compound 501B as an off-white solid. This material was used without further purification. HPLC: 85% at 3.02 min & 3.14 min (atropisomers, retention time) (YMC Combiscreen ODS-A column, 4.6×50 mm, eluting with 10-90% aqueous methanol containing 0.2% phosphoric acid over 4 min, 4 mL/min, monitoring at 220 nm). MS (ES): m/z 403.31 $[M+H]^+$.

C. [3aR-(3aα,4β,7β,7aα)]-4-[Octahydro-4-(2-hydroxyethyl)-1,3-dioxo-7-propyl-4,7-epoxy-2H-isoindol-2-yl]-1-naphthalenecarbonitrile (501Ci) & [3aS-(3aα,4β,7β,7aα)]-4-[Octahydro-4-(2-hydroxyethyl)-1,3-dioxo-7-propyl-4,7-epoxy-2H-isoindol-2-yl]-1-naphthalenecarbonitrile (50Cii)

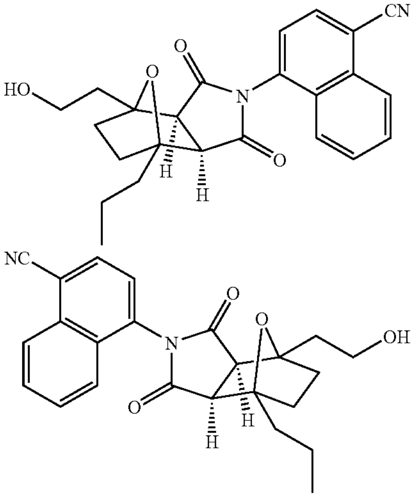

To a suspension of compound 501B (1.60 g, 3.97 mmol) in ethyl acetate (79.5 mL) was added 10% Pd/C (0.422 g, 0.397 mmol). Hydrogen gas was bubbled through the reaction for several minutes and the reaction was allowed to stir under a hydrogen atmosphere for 3 h. The reaction was filtered through Celite and the filtrate was concentrated in vacuo to give a white solid (1.74 g). The crude material was dissolved in minimum amount of methylene chloride and loaded on a 120 g silica gel ISCO cartridge. Elution with a step gradient of 0 to 100% ethyl acetate/hexane gave 1.06 g (66%) of the racemic mixture of compounds 501Ci & 501Cii as a white foam. A 500 mg portion of the racemic mixture was separated by normal phase preparative chiral HPLC (Chiralpak AD; 5×50 cm column; isocratic elution with 13% MeOH/EtOH (1:1) in heptane at 50 mL/min, monitoring at 220 nm) to give 245 mg of the faster eluting enantiomer, compound 501Ci and 245 mg of the slower eluting enantiomer, compound 501Cii, both as a white foams. Compound 501Ci: Normal phase preparative chiral HPLC: 28.0 min (retention time), >95% ee (Chiralpak AD 4.6×250 mm column, eluting with 12% MeOH/EtOH (1:1) in heptane at 1.0 mL/min). HPLC: 99% at 3.04 & 3.17 min (atropisomers, retention time) (YMC Combiscreen ODS-A column, 4.6×50 mm, eluting with 10-90% aqueous methanol over 4 mincontaining 0.2% phosphoric acid, 4 mL/min, monitoring at 220 nm). HRMS m/z Calc'd for $C_{24}H_{23}N_2O_4$ $[M-H]^-$: 403.1658. Found 403.1644. Compound 501Cii: Chiral HPLC: 65.7 min (retention time), >95% ee (Chiral HPLC: 65.7 min; >95% ee; Chiralpak AD 4.6×250 mm column; eluting with 12% MeOH/EtOH (1:1) in heptane at 1.0 mL/min). HPLC: 98% at 3.02 & 3.15 min (atropisomers, retention time) (YMC Combiscreen ODS-A column, 4.6×50 mm, eluting with 10-90% aqueous methanol over 4 mincontaining 0.2% phosphoric acid, 4 mL/min, monitoring at 220 nm). The absolute stereochemistry for compounds 501Ci & 501Cii was not established. For simplicity in nomenclature, compound 500Ci is designated herein as having an "R" configuration and compound 501Cii as having an "S" configuration. Enantiomerically pure products derived from compound 501Clare designated herein as having a "R" configuration and enantiomerically pure products derived from compound 500Cii are designated herein as having an "S" configuration.

D. [3aR-(3aα4β,7β,7aα)]-4-[4-[2-[(5-Chloro-2-pyridinyl)oxy]ethyl]octahydro-1,3-dioxo-7-propyl-4,7-epoxy-2H-isoindol-2-yl]-1-naphthalenecarbonitrile (501D)

To a solution of DBAD (17.1 mg, 0.0741 mmol) in THF (0.5 mL) was added $PPh_3$ (19.4 mg, 0.0741 mmol). After 10 min, 5-chloro-2-pyridinol (9.6 mg, 0.074 mmol) was added. After 5 min, compound 501Ci (20.0 mg, 0.0494 mmol) was added. After 1 h, DBAD (17.1 mg, 0.0741 mmol), $PPh_3$ (19.4 mg, 0.0741 mmol), and 5-chloro-2-pyridinol (9.6 mg, 0.074 mmol) were added. After 3 h, the solvent was removed in vacuo to give a yellow residue. Preparative reverse phase HPLC (YMC ODS column, 20×100 mm, eluting with 40-100% aqueous methanol containing 0.1% TFA over 30 min, 25 mL/min, monitoring 220 nm) gave 9.5 mg (37%) of the trifluoracetic acid salt of compound 501D as a clear, colorless residue. HPLC: 99% at 7.88 min & 8.11 min (atropisomers, retention time) (Zorbax SB C18 4.6×75 mm, eluting with 10-90% aqueous methanol over containing 0.2% phosphoric acid over 8 min, 2.5 mL/min, monitoring at 220 nm). HRMS m/z Calc'd for $C_{29}H_{27}N_3O_4Cl$ $[M+H]^+$: 516.1690. Found 516.1676.

EXAMPLE 502

[3aR-(3aα,4β,7β,7aα)]-4-[4-Butyl-7-[2-[(5-chloro-2-pyridinyl)oxy]ethyl]octahydro-1,3-dioxo-4,7-epoxy-2H-isoindol-2-yl]-1-naphthalene-carbonitrile (502D)

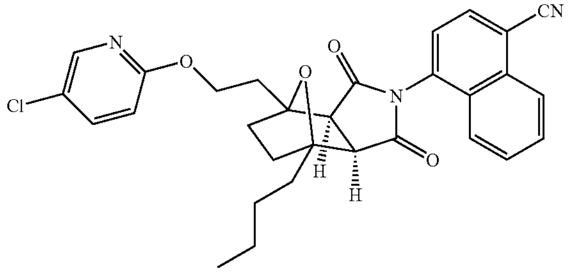

A. 2-(5-Butyl-furan-2-yl)-ethanol (502A)

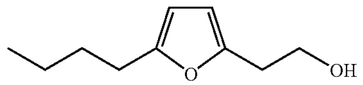

To a solution of 2-butylfuran (3.00 g, 24.2 mmol) in THF (24 mL) at −78° C. was added n-BuLi (11.6 mL, 2.5 M, 29.0 mmol) dropwise over 10 min. The reaction was warmed to rt and stirred for 3.5 h. After cooling to 0° C., ethylene oxide (1.81 mL, 36.2 mmol) was added, the reaction was warmed to rt and stirring was continued for 19 h. The reaction was then cooled to 0° C. and quenched with sat. $NH_4Cl$ (20 mL), followed by extraction with diethyl ether (2×50 mL). The combined organic layers were washed with brine, dried over $Na_2SO_4$, filtered, and concentrated in vacuo to give 4.07 g (100%) compound 502A as a bright orange oil. This material was used without further purification. HPLC: 96% at 3.23 min (retention time) (YMC Combiscreen ODS-A column, 4.6×50 mm, eluting with 10-90% aqueous methanol containing 0.2% phosphoric acid over 4 min, 4 mL/min, monitoring at 220 mm). MS (ES): m/z 169.22 $[M+H]^+$.

B. (3aα,4β,7β,7aα)-4-[4-Butyl-1,3,3a,4,7,7a-hexahydro-7-(2-hydroxyethyl)-1,3-dioxo-4,7-epoxy-2H-isoindol-2-yl]-1-naphthalenecarbonitrile (502B)

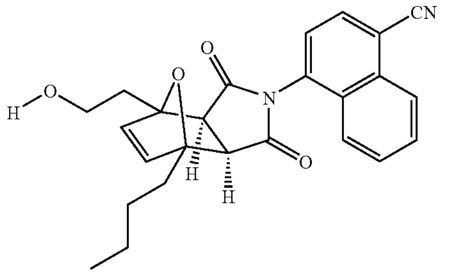

A suspension of compound 502A (2.50 g, 14.9 mmol) and 4-(2,5-dihydro-2,5-dioxo-1H-1-yl)-1-naphthalenecarbonitrile (3.70 g, 14.9 mmol) in benzene (15 mL) was warmed to 60° C. After 3 h, the reaction was concentrated in vacuo to give a brown foam. Methanol (17 mL) was added and the mixture was sonicated to give a fine beige solid with an orange-brown supernatant. Filtration of the precipitate gave 2.64 g (44%) of compound 502B as an off-white solid. This material was used without further purification. HPLC: 95% at 3.25 min & 3.35 min (atropisomers, retention time) (YMC Combiscreen ODS-A column, 4.6×50 mm, eluting with 10-90% aqueous methanol containing 0.2% phosphoric acid over 4 min, 4 mL/min, monitoring at 220 nm). MS (ES): m/z 417.29 $[M+H]^+$.

C. [3aR-(3aα,4β,7β,7aα)]-4-[4-Butyloctahydro-7-(2-hydroxyethyl)-1,3-dioxo-4,7-epoxy-2H-isoindol-2-yl]-1-naphthalenecarbonitrile (502Ci) & [3aS-(3aα,4β,7β,7aα)]-4-[4-Butyloctahydro-7-(2-hydroxyethyl)-1,3-dioxo-4,7-epoxy-2H-isoindol-2-yl]-1-naphthalenecarbonitrile (502Cii)

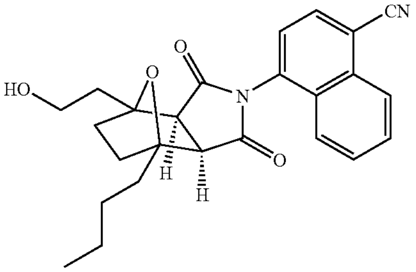

-continued

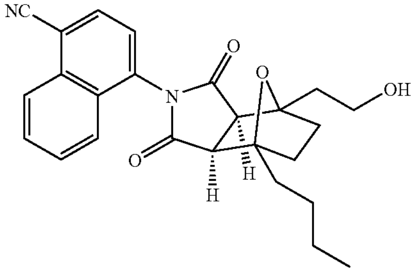

To a suspension of compound 502C (1.47 g, 3.52 mmol) in ethyl acetate (70 mL) was added 10% Pd/C (0.375 g, 0.352 mmol). Hydrogen was bubbled through the reaction for several minutes and the reaction was allowed to stir under a hydrogen atmosphere for 3 h. The reaction was filtered through Celite®, rinsing with ethyl acetate (2×70 mL). The filtrate was concentrated in vacuo to give a white foam (1.50 g). The crude material was dissolved in a minimum amount of methylene chloride and loaded on a 120 g silica gel ISCO cartridge. Elution with a step gradient of 0 to 100% ethyl acetate/hexane gave 1.05 g (74%) a racemic mixture of compounds 502Ci & 502Cii as a white foam. A 438 mg portion of racemic mixture of compounds 502Ci & 502ii was separated by normal phase preparative chiral HPLC (Chirapak AD column, 5×50 cm, isocratic elution with 12% MeOH/EtOH (1:1) in heptane at 50 mL/min, monitoring at 220 nm) to yield 178 mg of the faster eluting enantiomer, compound 502Ci as a white foam and 132 mg of the slower eluting enantiomer, compound 502Cii, as a clear, viscous oil. Compound 502Ci: Chiral HPLC: 25.5 min (retention time), >95% ee (Chiral HPLC: Chiralpak AD 4.6×250 mm column, eluting with 12% MeOH/EtOH (1:1) in heptane at 1.0 mL/min) and HPLC: 99% at 6.50 min & 6.71 min (atropisomers, retention time) (YMC Combiscreen ODS-A column, 4.6×50 mm, eluting with 10-90% aqueous methanol containing 0.2% phosphoric acid over 4 min, 4 mL/min, monitoring at 220 nm) HRMS m/z Calc'd for $C_{25}H_{25}N_2O_4$ $[M-H]^-$: 417.1814. Found 417.1800. Compound 502Cii: HPLC: 55.6 min (retention time), >95% ee (Chiral HPLC: Chiralpak AD 4.6×250 mm column; eluting with 12% MeOH/EtOH (1:1) in heptane at 1.0 mL/min). HPLC: 99% at 3.26 min & 3.38 min (atropisomers, retention time) (YMC Combiscreen ODS-A column, 4.6×50 mm, eluting with 10-90% aqueous methanol containing 0.2% phosphoric acid over 4 min, 4 mL/min, monitoring at 220 nm). The absolute stereochemistry for compounds 502Ci & 502Cii was not established. For simplicity in nomenclature, compound 502Ci is designated herein as having an "R" configuration and compound 502Cii as having an "S" configuration. Enantiomerically pure products derived from compound 502Clare designated herein as having a "R" configuration and enantiomerically pure products derived from compound 502Cii are designated herein as having an "S" configuration.

D. [3aR-(3aα,4β,7β,7aα)]-4-[4-Butyl-7-[2-[(5-chloro-2-pyridinyl)oxy]ethyl]octahydro-1,3-dioxo-4,7-epoxy-2H-isoindol-2-yl]-1-naphthalene-carbonitrile (502D)

To a solution of compound 502Ci (20.0 mg, 0.0478 mmol), $PPh_3$ (37.6 mg, 0.143 mmol) and 5-chloro-2-pyridinol (18.6 mg, 0.143 mmol) in THF (0.5 mL) was added DBAD (33.0 mg, 0.143 mmol). The resulting solution was stirred at rt for 15.5 h. The solvent was removed in vacuo to give a yellow residue. Preparative HPLC (Shimadzu VP ODS column, 20×250 mm, eluting with 40-100% aqueous methanol containing 0.1% TFA over 30 min and 100% for 25 min, 25 mL/min, monitoring at 220 nm) gave 9.4 mg (37%) of the trifluoracetic acid salt of compound 502D as a clear, colorless residue. HPLC: 99% at 8.14 min & 8.36 min (atropisomers, retention time) (Zorbax SB C18 column, 4.6×75 mm, eluting with 10-90% aqueous methanol containing 0.2% phosphoric acid over 8 min, 2.5 mL/min, monitoring at 220 nm). HRMS m/z Calc'd for $C_{30}H_{29}N_3O_4Cl$ $[M+H]^+$: 530.1847. Found 530.1855.

EXAMPLE 503

(3aα,4β,7β,7aα)-Hexahydro-4,7-dimethyl-2-[4-(5-oxazolyl)-1-naphthalenyl]-4,7 epoxy-1H-isoindole-1,3(2H)-dione (503E)

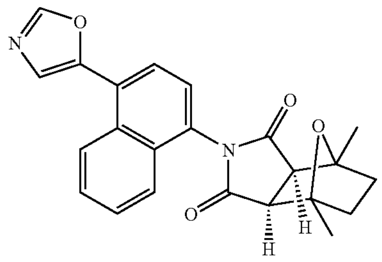

A. (4-Cyano-naphthalen-1-yl)-carbamic acid tert-butyl ester (503A)

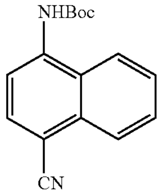

To a solution of 4-amino-1-naphthalenecarbonitrile (9.67 g, 57.5 mmol) in THF (100 mL) at rt was added, over 10 min, sodium hexamethyldisilazane (1.0 M in THF, 133 mL, 133 mmol). After stirring for 15 min, a solution of di-t-butyldicarbonate (15.1 g, 69.0 mmol) in THF (20 mL) was added. After stirring for 18 h at rt, the reaction mixture was partitioned between $Et_2O$ (400 mL) and saturated potassium bisulfate solution (200 mL). The organic layer was washed with saturated potassium bisulfate solution (200 mL), saturated sodium bicarbonate solution (200 mL) and brine (100 mL). Drying over anhydrous magnesium sulfate, treatment with decolorizing carbon and concentration in vacuo, afforded a residue that was partially purified by flash chromatography on silica gel eluting with 20% ethyl acetate in hexane. The partially purified material was crystallized from ethyl acetate/hexane to give 5.26 g of compound 503A as a colorless crystals. The mother liquor was concentrated and crystallized from ethyl acetate/hexane to give an additional 2.8 g of compound 503A to yield a total of 8.06 g (52%) of compound 503A. $^1$HNMR (400 MHz, DMSO-$d^6$): δ 9.81 (s, 1H), 8.36 (d, 1H, J=8.5 Hz), 8.11 (m, 2H), 7.92 (d, 1H, J=8 Hz), 7.78 (m, 1H), 7.67 (m, 1H), 1.53 (s, 9H).

B. (4-Formyl-naphthalen-1-yl)-carbamic acid tert-butyl ester (503B)

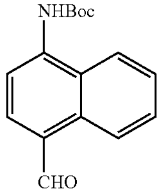

A mixture of compound 503A (4.02 g, 15.0 mmol), Raney nickel (1.5 g), sodium hypophosphite (9.00 g, 86.5 mmol), pyridine (50 mL), water (25 mL) and acetic acid (25 mL) was stirred at 45° C. for 5 h. The mixture was filtered through celite and the filter cake was rinsed with warm ethanol (100 mL). After adding water (600 mL) to the filtrate and allowing it to stand for 1 h, the resulting precipitate was filtered and rinsed with water. Drying in vacuo afforded 3.38 g of a white solid which was a 3:1 mixture of compounds 503B & 503A. The material was used in the next step without further purification. $^1$HNMR (400 MHz, DMSO-$d^6$): δ 10.28 (s, 1H), 9.77 (s, 1H), 9.27 (d, 1H, J=8.5 Hz), 8.31 (m, 1H), 8.13 (m, 1H), 8.00 (d, 1H, J=8 Hz), 7.80 (m, 1H), 7.70 (m, 1H), 1.54 (s, 9H).

C. (4-Oxazol-5-yl-naphthalen-1-yl)-carbamic acid tert-butyl ester (503C)

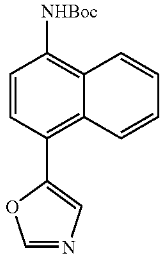

The above mixture of compounds 503A & 503B (3.37 g, 10.0 mmol; corrected for presence of compound 503A), toluene-sulfonylisocyanide (2.15 g, 11.0 mmol) and potassium carbonate (1.66 g, 12.0 mmol) in 50 mL of methanol was refluxed for 4 h. The reaction mixture was partitioned between water (200 mL) and chloroform (200 mL). After extracting the aqueous layer with chloroform (100 mL), the combined organic layers were dried over magnesium sulfate and concentrated in vacuo. The crude residue was purified by flash chromatography on silica gel eluting with a gradient of 10-40% ethyl acetate in hexane to give 1.35 g (44%) of compound 503C as a white solid. $^1$HNMR (400 MHz, DMSO-$d^6$): δ 9.45 (s, 1H), 8.57 (s, 1H), 8.20 (m, 2H), 7.76 (m, 2H), 7.64 (s, 1H), 7.62 (m, 2H), 1.51 (s, 9H).

D. 4-Oxazol-5-yl-naphthalen-1-ylamine (503D)

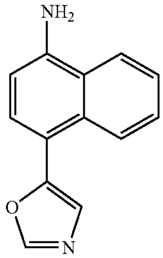

Compound 503C (1.34 g, 4.3 mmol) was dissolved in trifluoroacetic acid (10 mL) and the resulting mixture was allowed to stand for 1 h at room temperature. After removing the volatiles in vacuo, the residue was co-evaporated from ethyl acetate/heptane (2×50 mL) to remove traces of trifluoroacetic acid. After partitioning the residue between ethyl acetate (100 mL) and 1N NaOH (75 mL), the organic layer was washed with brine (50 mL), dried over magnesium sulfate and concentrated in vacuo to afford 900 mg (99%) of compound 503D as a yellow crystalline solid. HPLC conditions: 95% at 0.92 min (retention time) (Phenomenex 5 micron ODScolumn, 4.6×30 mm, 10%-90% aqueous methanol over 2 min gradient with 0.1% TFA, monitoring at 254 nm.). MS (ES): m/z 211.22 [M+H]$^+$.

E. (3aα,4β,7β,7aα)-Hexahydro-4,7-dimethyl-2-[4-(5-oxazolyl)-1-naphthalenyl]-4,7-epoxy-1H-isoindole-1,3(2H)-dione (503E)

A mixture of compound 503D (42 mg, 0.020 mmol) and 20A (78 mg, 0.40 mmol) in acetic acid (1.0 mL) was refluxed for 18 h. The reaction mixture was cooled to rt, concentrated in vacuo and the residue was partitioned between ethyl acetate (30 mL) and saturated sodium bicarbonate solution (30 mL). The organic layer was isolated, dried over magnesium sulfate and concentrated in vacuo. Purification by flash chromatography on a 2.5×15 cm silica gel column, using a gradient of 40-60% ethyl acetate in hexane gave 28 mg (37%) of compound 503E as a white powder. HPLC: 99% at 1.46 min & 1.36 min (atropisomers, retention time) (Phenomenex 5 micron ODS 4.6×30 mm, 10%-90% aqueous methanol over 2 min gradient with 0.1% TFA, monitoring at 254 nm.). MS (ES): m/z 389.10 [M+H]$^+$.

EXAMPLE 504

[3aS-(3aα,4β,5β,7β,7aα)]-4-[7-[2-(4-Cyanophenoxy)ethyl]-4-ethyloctahydro-5-methoxy-1,3-dioxo-4,7-epoxy-2H-isoindol-2-yl]-1-naphthalenecarbonitrile (504C)

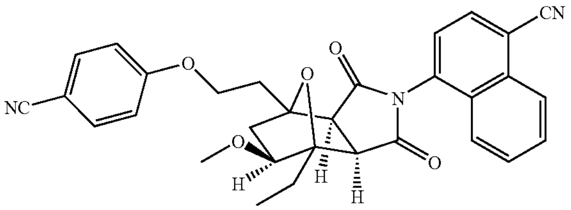

A. [3aS-(3aα,4β,5β,7β,7aα)]-4-[7-[2-[[(1,1-Dimethylethyl)dimethylsilyl]oxy]ethyl]-4-ethyloctahydro-5-methoxy-1,3-dioxo-4,7-epoxy-2H-isoindol-2-yl]-1-naphthalenecarbonitrile (504A)

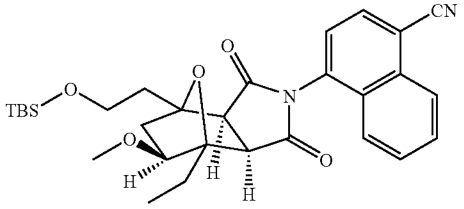

To a solution of compound 499ii (0.235 g, 0.451 mmol) in $CH_3CN$ (6 mL) was added silver oxide (0.523 g, 2.26 mmol) and iodomethane (0.56 mL, 9.0 mmol, stirred over $K_2CO_3$ before addition). The resulting suspension was placed in a preheated oil bath (80° C.). After 24 h, the reaction was cooled to rt, diluted with $CH_3CN$ (20 mL), filtered through a plug of Celite, and concentrated in vacuo to give a brown gum. Purification by flash chromatography on silica gel eluting with 30% ethyl acetate/hexanes gave 0.156 g (65%) of compound 504A as a white solid. HPLC: 95% at 4.17 min & 4.25 min (atropisomers, retention time) (YMC CombiSreen ODS column, 4.6×50 mm, eluting with 10-90% aqueous methanol containing 0.2% phosphoric acid over 4 min, 4 mL/min, monitoring at 220 nm). MS (ES): m/z 521.25 $[M+H]^+$.

B. (3aα,4β,5β,7β,7aα)-4-[4-Ethyloctahydro-7-(2-hydroxyethyl)-5-methoxy-1,3-dioxo-4,7-epoxy-2H-isoindol-2-yl]-1-naphthalenecarbonitrile (504B)

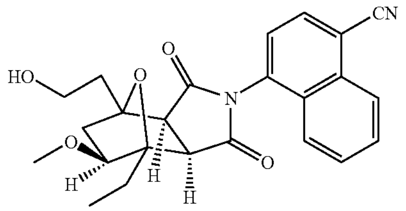

To a solution of compound 504A (0.156 g, 0.292 mmol) in ethanol (6 mL) was added 1N HCl (0.44 mL, 0.44 mmol). After 20 min, the reaction was cooled to 0° C. and quenched with sat. aq. $NaHCO_3$ (2 mL) to give a white suspension. Added $H_2O$ until the solid dissolved. The mixture was extracted with ethyl acetate (3×30 mL). The combined organic layers were washed with brine (20 mL), dried over $Na_2SO_4$, filtered, and concentrated in vacuo to give a white solid. Purification by flash chromatography on silica gel eluting with 5% $MeOH/CH_2Cl_2$ gave 120 mg (99%) of compound 504A as a white solid. HPLC: 98% at 5.17 and 5.44 min (atropisomers, retention time) (YMC CombiSreen ODS column, 4.6×50 mm, eluting with 10-90% aqueous methanol containing 0.2% phosphoric acid over 8 min, 2.5 mL/min, monitoring at 220 nm). HRMS m/z Calc'd for $C_{24}H_{24}N_2O_5$ $[M-H]^+$: 419.1607. Found 419.1611.

C. [3aS-(3aα,4β,5β,7β,7aα)]-4-[7-[2-(4-Cyanophenoxy)ethyl]-4-ethyloctahydro-5-methoxy-1,3-dioxo-4,7-epoxy-2H-isoindol-2-yl]-1-naphthalenecarbonitrile (504C)

To a solution of compound 504B (20 mg, 0.048 mmol) in anhydrous THF (0.5 mL) was added $PPh_3$ (37.0 mg, 0.143 mmol), para-cyanophenol (17.0 mg, 0.143 mmol) and DBAD (32.0 mg, 0.143 mmol). After 30 min, the solution was concentrated to give a brown gum. Purification by reverse phase preparative HPLC (YMC S5 ODS column, 20×250 mm, eluting with 10-90% aqueous methanol containing 0.2% phosphoric acid over 35 min, 20 mL/min, monitoring at 220 nm) gave 16 mg (64%) of compound 504C as a clear, colorless oil. HPLC 98% at 6.84 and 7.10 min (atropisomers, retention time) (Zorbax SB C18 column, 4.6×75 mm, eluting with 10-90% aqueous methanol containing 0.2% phosphoric acid over 8 min, 2.5 mL/min, monitoring at 220 nm). HRMS m/z Calc'd for $C_{31}H_{27}N_3O_5$ $[M+NH_4]^+$: 539.2295. Found 539.2302.

EXAMPLE 505

(3aα,4β,5β,7β,7aα)-4-[7-[2-[[(1,1-Dimethylethyl)dimethylsilyl]oxy]ethyl]-4-ethyloctahydro-5-hydroxy-1,3-dioxo-4,7-epoxy-2H-isoindol-2-yl]-1-naphthalenecarbonitrile (505Bi) & (3aα,4β,5β,7β,7aα)-4-[4-[2-[[(1,1-Dimethylethyl)dimethylsilyl]oxy]ethyl]-7-ethyloctahydro-5-hydroxy-1,3-dioxo-4,7-epoxy-2H-isoindol-2-yl]-1-naphthalenecarbonitrile (505Bii)

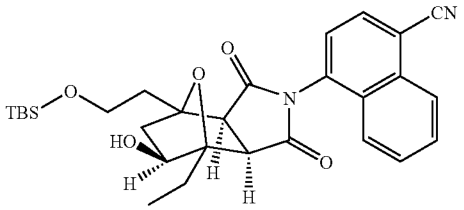

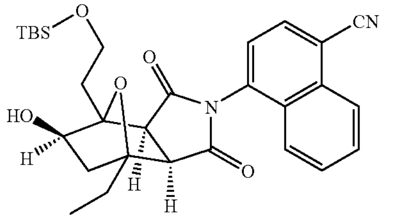

A. (1aα,2β,2aα,5aα,6β,7aα)-4-[2-[2-[[(1,1-Dimethylethyl)dimethylsilyl]oxy]ethyl]-6-ethyloctahydro-3,5-dioxo-2,6-epoxy-4H-oxireno[f]isoindol-4-yl]-1-naphthalenecarbonitrile (505A)

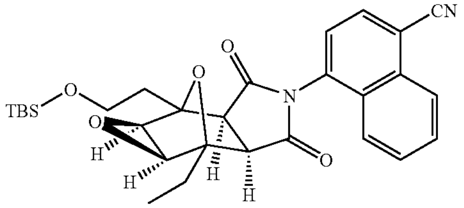

To a solution of compound 434B (1.01 g, 2.01 mmol) in methylene chloride (20 mL) was added 60% m-CPBA (0.863 g, 3.00 mmol). After 48 h, the reaction was diluted with methylene chloride (50 mL) and washed with sat. $Na_2SO_3$ (20 mL) and sat. $NaHCO_3$ (20 mL). The combined aqueous layers were extracted with $CH_2Cl_2$ (20 mL). The combined organic layers were washed with brine (30 mL), dried over $Na_2SO_4$, filtered, and concentrated in vacuo to give 1.01 g (97%) of compound 505A as a yellow solid. This material used without further purification. HPLC: 95% at 4.22 min (retention time) (Phenominex Luna C18 column, 4.6×50 mm, eluting with 10-90% aqueous methanol containing 0.2% phosphoric acid over 4 min, 4 mL/min, monitoring at 220 nm). HRMS m/z Calc'd for $C_{29}H_{34}N_2O_5Si$ [M−H]$^+$: 517.2159. Found 517.2163.

B. (3aα,4β,5β,7β,7aα)-4-[7-[2-[[(1,1-Dimethylethyl) dimethylsilyl]oxy]ethyl]-4-ethyloctahydro-5-hydroxy-1,3-dioxo-4,7-epoxy-2H-isoindol-2-yl]-1-naphthalenecarbonitrile (505Bi) & (3aα,4β,5β,7β,7aα)-4-[4-[2-[[(1,1-Dimethylethyl)dimethylsilyl] oxy]ethyl]-7-ethyloctahydro-5-hydroxy-1,3-dioxo-4,7-epoxy-2H-isoindol-2-yl]-1-naphthalenecarbonitrile (505Bii)

To a red solution of titanocene dichloride (0.500 g, 2.00 mmol) in anhydrous THF (4.0 mL) was added zinc dust (0.392 g, 6.00 mmol). The resulting suspension was vigorously stirred for 1 h under an argon atmosphere to give a green suspension. Excess zinc was removed by filtration through a 0.45 μm microfilter to give a green solution of dicyclopentadienyl titanium (III) chloride. To a solution of compound 505A (0.207 g, 0.399 mmol) and 1,4-cyclohexadiene (0.380 mL, 4.02 mmol) in anhydrous THF (1 mL) was added dropwise a 0.5 M solution of the above described dicyclopentadienyl titanium (III) chloride (0.9 mL, 0.45 mmol). After 1 h, an additional aliquot of the 0.5 M solution of dicyclopentadienyl titanium (III) chloride (0.9 mL, 0.45 mmol) was added and stirring was continued for 1 h. The reaction was then quenched with water (2 mL) and diluted with ethyl acetate (10 mL). The layers were separated and the organic layer was washed with brine (5 mL), dried over $Na_2SO_4$, filtered, and concentrated in vacuo to give a yellow gum. The crude material was dissolved in a minimum amount of methylene chloride and loaded on a 35 g silica gel ISCO column. Gradient elution with 0-80% ethyl acetate in hexane gave 0.043 g (21%) of compound 505Bi as a white solid and 0.023 g (11%) of compound 505Bii as a white solid. Compound 505Bi: HPLC: 3.92 min (retention time) (YMC CombiSreen ODS-A column, 4.6×50 mm, eluting with 10-90% aqueous methanol containing 0.2% phosphoric acid over 4 min, 4 mL/min, monitoring at 220 nm). MS (ES): m/z 521.36 [M+H]$^+$. Compound 505Bii: HPLC: 91% at 3.97 min (retention time) (YMC CombiScreen ODS-A column, 4.6×50 mm, eluting with 10-90% aqueous methanol containing 0.2% phosphoric acid over 4 min, 4 mL/min, monitoring at 220 nm). MS (ES): m/z 521.34 [M+H]$^+$.

EXAMPLE 506

4-[[3aS-(3aα,4β,5β,7β,7aα)]-5-(α-D-Glucopyranosyloxy)octahydro-4,7-dimethyl-1,3-dioxo-4,7-epoxy-2H-isoindol-2-yl]-2-(trifluoromethyl)benzonitrile (506B)

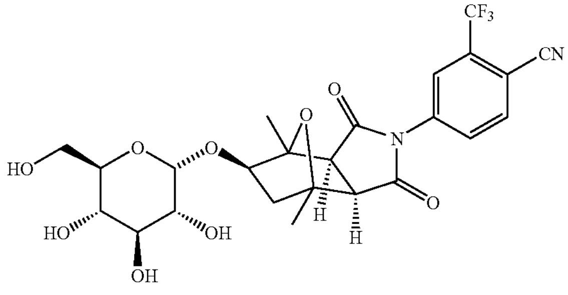

A. [3aS-(3aα,4β,5β,7β,7aα)]-4-[Octahydro-4,7-dimethyl-1,3-dioxo-5-[[2,3,4,6-tetrakis-O-(phenylmethyl)-α-D-glucopyranosyl]oxy]-4,7-epoxy-2H-isoindol-2-yl]-2-(trifluoromethyl)benzonitrile (506A)

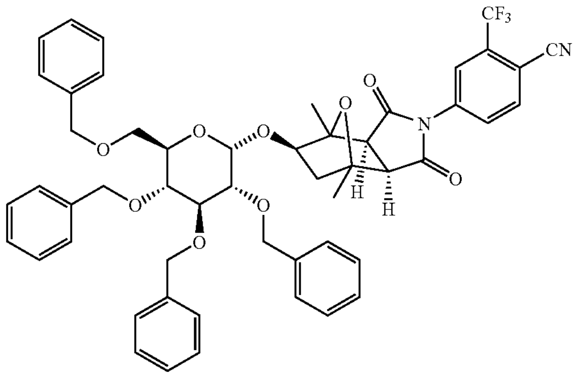

2,3,4,6-Tetra-O-benzyl-α-D-glucopyranosyl bromide was made according to the procedure by Spohr et al. *Can. J. Chem.* 71, 1928-42 (1993). Oxalyl bromide (0.48 mL, 0.95 mmol, 2 M in $CH_2Cl_2$) was added dropwise to a solution of 2,3,4,6-tetra-O-benzyl-D-glucopyranose (412 mg, 0.763 mmol) in $CH_2Cl_2$ (5 mL) and DMF (0.28 mL) at rt under Ar. The reaction mixture was stirred for 20 min, poured onto a mixture of ice and $H_2O$ (1:1, 30 mL) and diluted with $CH_2Cl_2$ (30 mL). The layers were separated and the organic layer was washed with cold $H_2O$ (2×30 mL) and brine (1×30 mL) and dried over $MgSO_4$. Concentration in vacuo gave the desired bromide as a brown oil. This oil was taken up in $CH_2Cl_2$ (2 mL) and DMF (1 mL). Compound 471Dii (100 mg, 0.763 mmol), tetrabutylammonium bromide (111 mg, 0.526 mmol) and 4 Å sieves (600 mg) were added to this solution and the reaction was stirred under Ar for 4 d. The reaction was quenched with MeOH (2 mL), stirred for 0.5 h, diluted with $CH_2Cl_2$ (10 mL) and then filtered through a medium porosity fritted funnel, rinsing with $CH_2Cl_2$ (5 mL). The solvent was removed in vacuo and the resulting residue was dissolved in $CH_2Cl_2$ (25 mL). The organic solution was washed with sat. aq. $NaHCO_3$ (1×20 mL) and $H_2O$ (1×20 mL) and dried over $MgSO_4$. Purification by flash chromatography on $SiO_2$ eluting with 50% EtOAc/hexanes gave 79 mg (33%) of 506A as a white solid. HPLC: 99% at 4.56 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 902 [M+H]$^+$.

B. 4-[[3aS-(3aα,4β,5β,7β,7aα)]-5-(α-D-Glucopyranosyloxy)octahydro-4,7-dimethyl-1,3-dioxo-4,7-epoxy-2H-isoindol-2-yl]-2-(trifluoromethyl)benzonitrile (506B)

Palladium hydroxide (62 mg, 20 wt. % Pd (dry basis) on carbon, wet) was added to a solution of 506A (65 mg, 0.07 mmol) in EtOAc (2 mL) and the mixture was stirred under a hydrogen atmosphere introduced via a balloon. After 5 h, the reaction was complete as was evident by HPLC, so the mixture was filtered through a medium porosity fritted funnel rinsing with MeOH (2 mL) and concentrated in vacuo. The resulting residue was dissolved in MeOH (2 mL) and filtered through a Gelman Acrodisc CR 13 mm syringe filter with a 0.45 μM PTFE membrane. Concentration yielded 38 mg of 506B as a white solid. HPLC: 90% at 2.16 min (retention time) (YMC S5 ODS column, 4.6×50 mm, eluting with 10-90% aqueous methanol over 4 mincontaining 0.2% phosphoric acid, 4 mL/min, monitoring at 220 mm). MS (ES): m/z 543.20 $[M+H]^+$. A 10 mg portion was recrystallized from MeOH:$H_2O$ to give crystals suitable for X-ray crystal diffraction studies to elucidate the exact stereochemistry of compound 506B as referenced to the known fixed stereochemistry of the D-glucoside appendage.

EXAMPLE 507

(3aα,4β,7β,7aα)-4-(1,3,3a,4,7,7a-Hexahydro-4,7-dimethyl-1,3-dioxo-4,7-epoxy-2H-isoindol-2-yl)-2-(trifluoromethyl)benzonitrile (507)

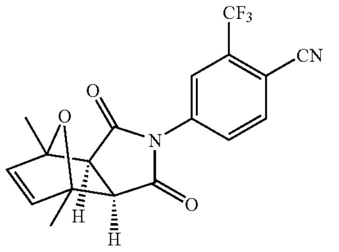

To 25 g (94.2 mmol) of compound 471A was added neat 2,5-dimethylfuran (30 mL, 280 mmol), and the resulting slurry was heated to 60° C. for 1 to 3 h with mechanical agitation. The resulting slurry was cooled to 0-5° C., and diluted with cold toluene (25 mL, 0-10° C.). The cold slurry was filtered under vacuum. The flask and filter cake were washed with cold toluene (2×25 mL), and the cake was deliquored with house vacuum. The precipitate was dried in vacuo to yield 31.3 g (91.6%) of a compound 507 as a tan solid. HPLC: 99.6%, 19.43 min (retention time) (Column: Zorbax™ SB-C18, 4.6×15 cm; Mobile Phase: 40% $CH_3CN$/60% $H_2O$ w/0.1% v/v TFA, isocratic; Flow Rate: 1 mL/min; Detection: $\lambda_{max}$ 210 nm; Temperature: 30° C.; Injection Volume: 5 μL).

EXAMPLE 508

(3aα,4β,5β,7β,7aα)-4-(Octahydro-5-hydroxy-4,7-dimethyl-1,3-dioxo-4,7-epoxy-2H-isoindol-2-yl)-2-(trifluoromethyl)benzonitrile (508)

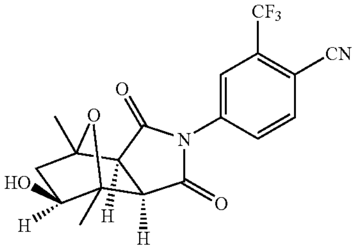

To THF (275 mL) that had been cooled to −3° C. was added compound 507 (55.0 g, 152 mmol), which resulted in a slurry. To the slurry was added borane methylsulfide (14.4 mL, 152 mmol), at a rate such that the temperature did not exceed 0° C. The reaction mixture was slowly warmed to 20° C. over 2.5 h. The temperature of the reaction mixture was then returned to 0° C., where upon phosphate buffer (1056 mL, pH 7) was carefully added at a rate to control the hydrogen gas evolution and maintain a temperature ≦20° C. The resulting suspension was dissolved by adding ethanol (528 mL, 190 proof). At 15° C., hydrogen peroxide (55 mL, 30 wt %) was added at a rate to maintain the temperature <20° C. The homogeneous solution was left stirring for 12 h at 20° C. and pH 7.8, whereby crystallization occurred. The resulting slurry was collected by filtration and washed with water (4×100 mL) and methyl-tert-butyl ether (2×100 mL). Drying in vacuo afforded 37.3 g (64.6%) of compound 508. The aqueous mother liquor was extracted with ethyl acetate (3×500 mL). The combined rich organics were washed with 10 wt % aqueous sodium sulfite (1×100 mL), and 25 wt % aqueous sodium chloride (1×100 mL). The organics were dried over sodium sulfate, filtered, and concentrated to recover 8.9 g (15.4%) of compound 508, and a third 11.5 g (20%) fraction of compound 508 was recovered from the methyl-tert-butyl ether cake wash. The above three solid samples of crude material were separately recrystallized from 190 proof ethanol (1 g/10 mL) to afford a total of 35.6 g (61.7%) of compound 508 having a purity level of 98.7% as determined by HPLC analysis (conditions as below). A second crop of compound 508 was isolated from the mother liquor to afford 9.3 g (16.1%) of solid having a purity level of 98.4% as determined by HPLC analysis. The remaining mother liquor was purified by silica gel chromatography using 200 g of $SiO_2$ and eluting with 4 L of 50V % ethyl acetate and 50 V % heptane to yield 5.6 g (9.7%) of compound 508, having a purity level of 94.0% as determined by HPLC analysis. HPLC conditions: 9.74 minute retention time on a YMC S5 ODS-AQ column (4.6×150 mm) using a gradient elution from 100% solvent A to 100% solvent B over 15 minutes at 1.0 mL/min. Solvent A=95 V % water (0.01 M $NH_4OAc$); 5 V % acetonitrile. Solvent B=5 V % water (0.01 M $NH_4OAc$); 95 V % acetonitrile. Duel wavelength detector set at 210 and 245 nm. MS (ES): m/z 381.11 $[M+H]^+$.

EXAMPLE 509

(3aα,4β,5β,7β,7aα)-4-(Octahydro-5-hydroxy-4,7-dimethyl-1,3-dioxo-4,7-epoxy-2H-isoindol-2-yl)-2-(trifluoromethyl)benzonitrile (509)

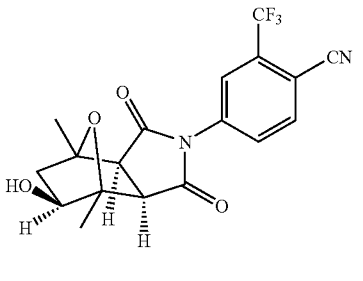

Compound 471A (0.37 g, 1.4 mmol) and 2,5-dimethylfuran (0.73 mL, 6.9 mmol) were combined to form a slurry which was heated to 60° C. for 1 h. The reaction mixture was cooled to −10° C. and THF (1.0 mL) was added followed by the addition of borane tetrahydrofuran (2.1 mL, 1 M). The reaction mixture was stirred for 30 minutes at 0° C. and 30 minutes at +10° C. To the reaction mixture was added acetone (3.0 mL), and the resulting mixture was warmed to 20° C. and maintained at 20° C. for 1 h. To this solution was added sodium bicarbonate (1.5 mL, pH 9, 8 wt %) and the mixture was then cooled to 5° C. before adding hydrogen peroxide (0.3 mL, 30 wt %). Addition of hydrogen peroxide was exothermic bringing the temperature to 20° C. A solution of sodium sulfite (4.0 mL, 10 wt %) was added at 20° C. resulting in an exotherm to 30° C. The biphasic mixture was allowed to stand at 25° C. for 12 h. After the phases were separated, the aqueous waste was back extracted twice with ethyl acetate (5 mL) and the combined organic layers were washed with water (2 mL) followed by sodium chloride (2 mL, 25 wt %). The organic layers were concentrated in vacuo to yield a yellow oil which rapidly crystallized. To the crude product was added 190 proof ethanol (5.0 mL) and the mixture was heated to 60° C. to afford complete dissolution. Cooling to 20° C. for 17 h resulted in crystallization. The crystal slurry was collected by filtration, washed with heptane (5 mL), and dried at 60° C. under vacuum (30 in/Hg) to afford 0.23 g (44%) of compound 509 having 93.1 HPLC Area %. HPLC conditions: 9.74 minute retention time on a YMC S5 ODS-AQ column (4.6×150 mm) using a gradient elution from 100% solvent A to 100% solvent B over 15 minutes at 1.0 mL/min. Solvent A=95 V % water (0.01 M $NH_4OAc$); 5 V % acetonitrile. Solvent B=5 V % water (0.01 M $NH_4OAc$); 95 V % acetonitrile. Detector set at 245 nm. MS (ES): m/z 381.11 $[M+H]^+$.

EXAMPLE 510

[3aR-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (510i) & [3aS-(3aα,4β,5β,7β,7aα)-4-[5-(Acetyloxy)octahydro-4,7-dimethyl-1,3-dioxo-4,7-epoxy-2H-isoindol-2-yl]-2-(trifluoromethyl)benzonitrile (510ii)

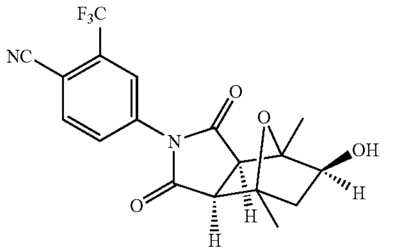

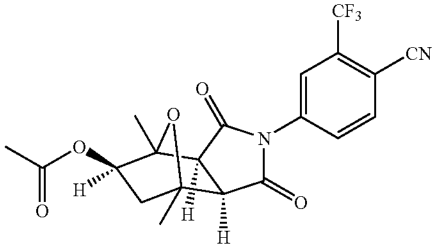

Compound 509 (4 mg), vinyl acetate (0.1 mL) and toluene (2 mL) were combined and 20 mg of each of the enzymes shown in Table 12 were added. The mixture was stirred with a magnetic stirring bar at rt in a 16×100 mm capped tube for the time period listed in Table 12. The enantioselective acetylation of the racemic mixture resulted in the formation of compound 510i and the acetylated compound 510ii. The enantiomeric purity of compound 510i was determined by chiral HPLC (method below) and the results for each enzyme are as shown in Table 12. The resulting information was used to prepare a large scale batch of compounds 510i & 510ii as described below.

TABLE 12

| Enzyme | Supplier | Source | Time H | Comp. 510i mg/mL | Comp. 510i % yield | Comp. 510i % ee | Comp. 510ii mg/mL |
|---|---|---|---|---|---|---|---|
| AK-20 | Amano | *Pseudomonas fluorescens* | 15 | 0.74 | 39 | 100 | 1.02 |
| AP-12 | Amano | *Aspergillus niger* | 144 | 1.10 | 58 | 55.4 | 0.74 |
| PS-30 | Amano | *Pseudomonas cepacia* | 15 | 0.46 | 24 | 100 | 1.24 |
| Acylase 30000 | Amano | *Aspergillus* | 15 | 0.51 | 27 | 12.2 | 1.26 |
| Chirazyme L3 | Boehringer | *Candida rugosa* | 144 | 0.81 | 42 | 87.2 | 1.04 |
| Lipase type VII | Sigma | *Candida rugosa* | 144 | 0.74 | 39 | 100 | 1.06 |

To a 500 mL jacketed flask were added Amano lipase AK20 from *Pseudomonas fluorescens* (25 g), compound 509 (25 g), methyl-isobutyl-ketone (475 mL) and vinyl acetate (25 mL). The flask was maintained at 25° C. with a circulating water bath and stirred with a magnetic stir bar. The incubation was continued for 42 h, at which point the enantiomeric excess of compound 510i reached 100%. The solution was filtered through Whatman 4 filter paper to remove enzyme and the filter cake was washed with 50 mL methyl isobutyl ketone. The filtrate was concentrated in vacuo and the resulting residue was dissolved in EtOAc (50 mL) followed by the addition of heptane (50 mL). This solution was loaded onto a Phenomenex cartridge column (silica 800 g) in a Biotage 75L system and the column was eluted with 75% EtOAc/heptane at flow rate 110 mL/min. Fractions were collected (500 mL) which contained compound 510ii and then the eluting solvent was changed to 100% EtOAc to elute off compound 510i. The desired fractions were pooled and the solvent was removed in vacuo to yield 11.0 g of compound 510i, (44%, 100% ee) and 12.10 g of compound 510ii (44%). Compound 510i was recrystallized from 95% EtOH (5 mL/g) in two crops to afford 9.61 g (38%) of compound 510i as a white crystalline solid. Compounds 510i: Chiral HPLC: 10.02 min (retention time) (CHIRALPAK AD 4.6×250 mm column; isocratic elution with 20% MeOH/EtOH (1:1) in heptane at 1 mL/min). HPLC: 99% at 2.45 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 381.11 $[M+H]^+$.

EXAMPLE 511

[3aR-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (511i) & Butanedioic acid, mono[3aS-(3aα,4β,5β,7β,7aα)]-[2-[4-cyano-3-(trifluoromethyl)phenyl]octahydro-4,7-dimethyl-1,3-dioxo-4,7-epoxy-1H-isoindol-5-yl] ester-(511ii)

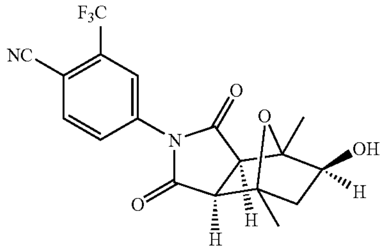

-continued

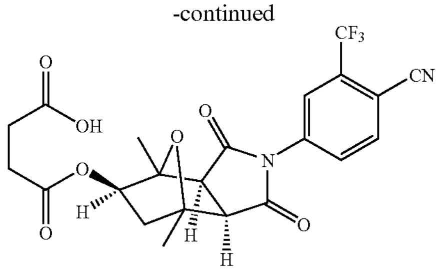

A mixture of the racemic compound 509 (10 mg), succinic anhydride (100 mg) and lipase AK-20 Amano (50 mg) in toluene or MTBE (5 mL) was stirred at rt for 20 hours. After 16 and 20 h, samples (0.1 mL) were taken out from each reaction mixture, evaporated, redissolved in acetonitrile (1 mL) and analyzed by reversed phase HPLC (YMC Pro-pack ODS-A, 3μ, 15×0.6 cm, acetonitrile:water 20:80 to 90:10 in 12 min) to determine the area ratio of products compound 511i (RT=8.8 min) and compound 511ii (RT=9.9 min). A second sample (0.1 mL) of each reaction mixture was removed, evaporated and redissolved in 1 mL isopropyl alcohol-heptane (1:1) and analyzed by Chiral HPLC (Chiralpak AD, 25×0.46 cm, 20° C., heptane:ethanol 85:15, 0.5 mL/min, UV 210 nm) to determine the % ee of compound 511i (RT=32.2 min) and compound 471Dii (RT=34.8 min). After 20 h, the reaction mixtures were filtered off to separate the insoluble components (enzyme, etc.). The filtrates were washed with 5% aqueous $NaHCO_3$ (3×1 volume) and water (3×1 volume), evaporated in vacuo and analyzed by HPLC as described above. The results showed an average yield of 48% (theoretical max yield is 50%) and 100% ee for compound 511i. Complete separation of compound 511ii was achieved via the above described $NaHCO_3$ extraction. Table 13 gives the details of each reaction as determined by the methods described above. Compound 511i: Chiral HPLC: 10.02 min; CHIRALPAK AD 4.6×250 mm column; isocratic elution with 20% MeOH/EtOH (1:1) in heptane at 1 mL/min, 100% ee. HPLC: 99% at 2.45 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 381.11 $[M+H]^+$.

TABLE 13

| Solvent | Solvent Vol., ml | Comp. 509 mg | Lipase AK-20 mg | Succinic Anhydride mg | Time Hr | Comp. 511i 8.8 min Area Ratio | Comp. 511ii 9.9 min Area Ratio | Comp 511i 32.2 min % | Comp 471Dii 34.8 min % | Comp. 511i ee % |
|---|---|---|---|---|---|---|---|---|---|---|
| Toluene | 5 | 10 | 50 | 100 | 16 | 53% | 47% | 93.1% | 6.9% | 86.2% |
| | | | | | 20 | 54% | 46% | 96.0% | 4.0% | 92.0% |
| Toluene Wash NaHCO3 | | | | | | 100% | 0% | 96.1% | 3.9% | 92.2% |
| MTBE | 5 | 10 | 50 | 100 | 16 | 49% | 51% | 100.0% | 0.0% | 100.0% |
| | | | | | 20 | 50% | 50% | 100.0% | 0.0% | 100.0% |

TABLE 13-continued

| Solvent | Solvent Vol., ml | Comp. 509 mg | Lipase AK-20 mg | Succinic Anhydride mg | Time Hr | Comp. 511i 8.8 min Area Ratio | Comp. 511ii 9.9 min Area Ratio | Comp 511i 32.2 min % | Comp 471Dii 34.8 min % | Comp. 511i ee % |
|---|---|---|---|---|---|---|---|---|---|---|
| MTBE Wash NaHCO3 | | | | | | 100% | 0% | 100.0% | 0.0% | 100.0% |

EXAMPLE 512

[3aR-(3aα,4β,5β,7β,7aα)-4-[5-(Acetyloxy)octahydro-4,7-dimethyl-1,3-dioxo-4,7-epoxy-2H-isoindol-2-yl]-2-(trifluoromethyl)benzonitrile (512i) & [3aS-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (512ii)

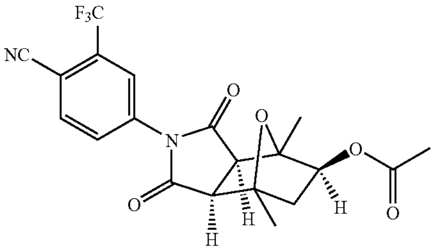

-continued

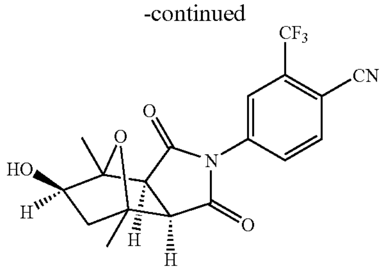

A series of 50 mL flasks were arranged and enzymes (see Table 14 for enzyme type and amounts) were weighed into each followed by the addition of phosphate buffer (BF45, 5 mL, 100 mM, pH 7). A solution of compound 473 (5 mg) in DMSO (50 μL) was added to each flask. The flasks were shaken at 200 rpm at 28° C. for 24 hours. After 24 hours, the reaction mixtures were extracted with EtOAc (10 mL). A portion of the EtOAc extract (1 mL) was evaporated, redissolved in acetonitrile (1 mL) and analyzed by reversed phase HPLC (C-18, acetonitrile:water 20:80 to 90:10 in 12 min) to determine the area ratio of compound 512i (RT=11.0 min) and compound 512ii, (RT=8.9 min). Another portion of EtOAc extract (4 mL) was evaporated, redissolved in 1 mL isopropyl alcohol-heptane (1:1) and analyzed by chiral HPLC (Chiralpak AD, heptane:ethanol 85:15, 0.5 mL/min) to determine the % ee of the compound 512ii (RT=34.8 min) and compound 471Di (RT=32.2 min) in this system. Table 14 gives details for an array of different enzymes examined and the resulting yields and % ee for the desired products.

TABLE 14

| Enzyme | Supplier | Source | Enz Amt mg | Area Ratio by HPLC Comp. 512ii | Comp. 512i | Exo-Alcohol Comp 471Di | Exo-Alcohol Comp. 511ii | % ee of Comp 512ii |
|---|---|---|---|---|---|---|---|---|
| Lipase AP-12 | Amano | *Aspergillus niger* | 5 | 18% | 82% | 18.8% | 81.2% | 62.5% |
| Lipase AP-12 | Amano | *Aspergillus niger* | 25 | 50% | 50% | 41.0% | 59.0% | 17.9% |
| Lipase PS | Amano | *Pseudomonas cepacia* | 5 | 20% | 80% | 31.3% | 68.7% | 37.4% |
| Lipase PS | Amano | *Pseudomonas cepacia* | 25 | 46% | 54% | 40.2% | 59.8% | 19.6% |
| Acylase 150000 | Amano | *Aspergillus* sp | 5 | 30% | 70% | 52.0% | 48.0% | −3.9% |
| Acylase 150001 | Amano | *Aspergillus* sp | 25 | 71% | 29% | 50.4% | 49.6% | −0.8% |
| Newlase F | Amano | *Rhizopus niveus* | 50 | 3% | 97% | 31.3% | 68.7% | 37.5% |
| Newlase F | Amano | *Rhizopus niveus* | 100 | 3% | 97% | 25.7% | 74.3% | 48.5% |
| Acylase I | Sigma | *Apergillus melleus* | 5 | 10% | 90% | 9.7% | 90.3% | 80.6% |
| Acylase I | Sigma | *Apergillus melleus* | 25 | 38% | 62% | 10.9% | 89.1% | 78.3% |
| Esterase | Sigma | Porcine liver | 5 | 76% | 24% | 36.0% | 64.0% | 27.9% |

EXAMPLE 513

[3aR-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (513i) & [3aS-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile & (513ii) & (3aα,4β,5α,7β,7aα)-4-(Octahydro-5-hydroxy-4,7-dimethyl-1,3-dioxo-4,7-epoxy-2H-isoindol-2-yl)-2-(trifluoromethyl)benzonitrile (513iii)

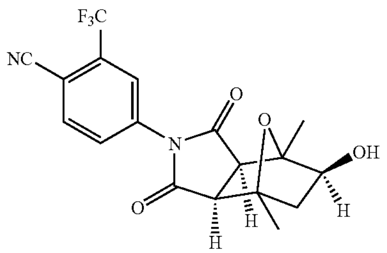

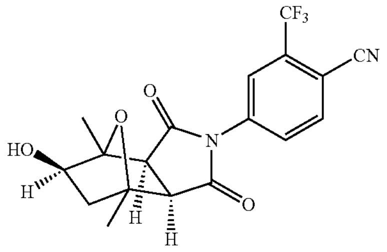

-continued

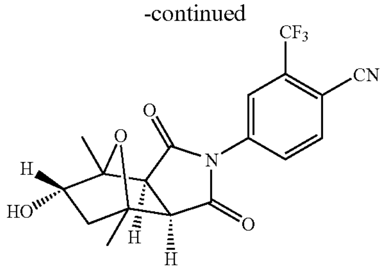

A series of microbial biotransformation reactions were set up to generate compounds 513i, 513ii & 513iii. The details of the reactions for several microorganisms are shown in Table 15 and a general procedure is described below. One thawed vial of the microbe (1 mL culture) was inoculated into sterile soybean-glucose media (10 mL) in a 50 mL flask. The microbes were grown by shaking at 200 rpm at 28° C. for 40 h. A solution of compound 472 (10 mg in 100 μL DMSO) was added to each flask and the flasks were shaken at 200 rpm at 28° C. At 24 and 48 h, 5 mL of the reaction mixtures were extracted by EtOAc (10 mL). A portion of EtOAc extract (1 mL) was evaporated, redissolved in acetonitrile (1 mL) and analyzed by reversed phase HPLC (C-18, acetonitrile:water 20:80 to 90:10 in 12 min) to determine the area ratio of compound 472 (RT=11.2 min) and the product compounds 513i (RT=8.9 min), 513ii (RT=8.9 min) & 513iii (RT=9.6 min). A second portion of the EtOAc extract (4 mL) was evaporated, redissolved in isopropyl alcohol-heptane (1:1, 1 mL) and analyzed by chiral HPLC (Chiralpak AD, Heptane: Ethanol 85:15, 0.5 mL/min) to determine the % ee of compounds 513i (RT=32.2 min) compound 513ii (RT=34.8 min) in this system.

TABLE 15

| | | Time | Analysis by Reversed Phase HPLC (Area Ratio) | | | Analysis for % ee by HPLC | | % ee of |
|---|---|---|---|---|---|---|---|---|
| Microorganism | ID | Hrs | Comp 513i | Comp 513ii | Comp 472 | Comp 513i | Comp 513ii | Comp 513i |
| *Streptomyces* sp | SC1754 | 24 | 7% | 0% | 93% | 96.9% | 3.1% | 93.9% |
| | | 48 | 12% | 0% | 88% | 96.7% | 3.3% | 93.3% |
| *Streptomyces* sp | SC3740 | 24 | 1% | 0% | 99% | 88.0% | 12.0% | 76.0% |
| | | 48 | 2% | 0% | 98% | 85.8% | 14.2% | 71.7% |
| *Nocardia interforma* | ATCC 21072 | 24 | 5% | 0% | 95% | 93.2% | 6.8% | 86.3% |
| | | 48 | 8% | 0% | 92% | 92.6% | 7.4% | 85.1% |
| *Streptomyces antibioticus* | ATCC 14890 | 24 | 11% | 1% | 88% | 95.7% | 4.3% | 91.4% |
| | | 48 | 48% | 13% | 39% | 94.1% | 5.9% | 88.2% |
| *Streptomyces mediocidicus* | ATCC 13278 | 24 | 1% | 0% | 99% | 82.0% | 18.0% | 64.1% |
| | | 48 | 7% | 0% | 93% | 79.4% | 20.6% | 58.8% |
| *Streptomyces griseus* | NRRL B8090 | 24 | 23% | 0% | 77% | 85.0% | 15.0% | 70.0% |
| | | 48 | 28% | 0% | 72% | 85.9% | 14.1% | 71.8% |
| *Amycolatopsis orientalis* | ATCC 43490 | 24 | 12% | 1% | 86% | 81.3% | 18.7% | 62.5% |
| | | 48 | 25% | 4% | 71% | 77.4% | 22.6% | 54.9% |

EXAMPLE 514

[3aR-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (514i) & [3aS-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile & (514ii) & (3aα,4β,5α,7aα)-4-(Octahydro-5-hydroxy-4,7-dimethyl-1,3-dioxo-4,7-epoxy-2H-isoindol-2-yl)-2-(trifluoromethyl)benzonitrile (514iii)

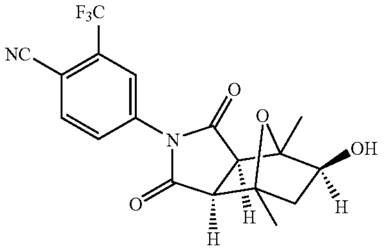

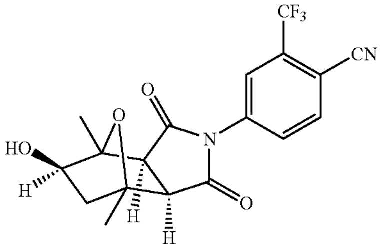

-continued

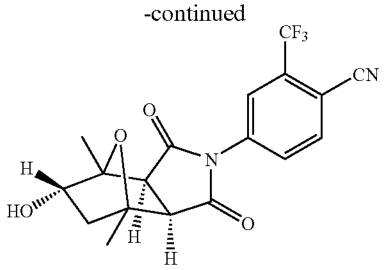

A series of microbial biotransformation reactions were set up to generate compounds 514i, 514ii & 514iii. The details of the reactions for several microorganisms are shown in Table 16 and a general procedure is described below. A 1 mL culture of *Streptomyces griseus* SC13971 from a frozen vial was used to inoculate 100 mL of medium (0.5% toasted nutrisoy, 2% glucose, 0.5% yeast extract, 0.5% $K_2HPO_4$, 0.5% NaCl, adjusted to pH 7 with 1N HCl (R. V. Smith and J. P. Rosazza, Arch. Biochem. Biophys., 161, 551-558 (1974)) in a 500 mL Erlenmeyer flask and the flask was incubated at 28° C. at 200 rpm for 3 days. 10 mL of this culture was used to inoculate 100 mL of medium (as above) in a 500 mL Erlenmeyer flask and the flask was incubated at 28° C. at 200 rpm for 1 day. For the filamentous fungi *Mucor rouxii* and *Cunninghamella echinulata,* 1 mL of spore suspension, prepared by washing a slant with 10 mL water, was used to inoculate 100 mL of medium (as above) in a 500 mL Erlenmeyer flask and the flask was incubated at 28° C. at 200 rpm for 1 day. Compound 472 (30 mg in 1 mL methanol) was added to each culture and the incubations were continued for 6 to 10 days. Samples of 10 mL of the culture broth in each flask were removed and extracted with ethyl acetate (20 mL). Samples of 10 mL of the organic layers were each individually evaporated to dryness at 40° C. under a nitrogen stream. The residues were dissolved in 1.2 mL isopropanol and analyzed by reversed phase HPLC (YMC Pak ODS 150×6 mm, 3μ C-18, acetonitrile: water 20:80 to 90:10 in 12 min, 1 mL/min, 40° C.) to determine the concentration of compound 472 (RT=11.2 min) and product compounds 514i (RT=8.9 min), 514ii (RT=8.9 min) & 514iii (RT=9.6 min). The same samples were analyzed by chiral HPLC (Chiralpak AD, heptane:ethanol 85:15, 0.5 mL/min) to determine the % ee of compounds 514i (RT=32.2 min) compound 514ii (RT=34.8 min) in this system.

TABLE 16

| strain | SC | ATCC | time days | Comp. 472 mg/ml | Comp. 514i mg/ml | Comp 514i ee % | Comp514iii mg/ml |
|---|---|---|---|---|---|---|---|
| 1. *Mucor rouxii* | 13920 | 24905 | 3 | 0.30 | 0.01 | 100.00 | 0.000 |
| | | | 6 | 0.27 | 0.01 | 100.00 | 0.000 |
| 2. *Streptomyces griseus* | 13971 | 13273 | 3 | 0.29 | 0.01 | 100.00 | 0.000 |
| | | | 6 | 0.30 | 0.01 | 100.00 | 0.000 |
| 3. *Cunninghamella echinulata* | 16027 | 9244 | 3 | 0.34 | 0.02 | 100.00 | 0.002 |
| | | | 6 | 0.06 | 0.02 | 100.00 | 0.001 |
| | | | 10 | 0.16 | 0.02 | 100.00 | 0.001 |

EXAMPLE 515

[3aR-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (515)

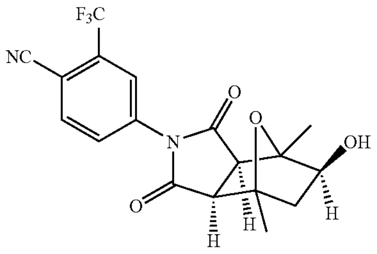

Microbial transformation of compound 472 to compound 515 was conducted on a 3 L scale in a 5 L fermentor, using *Cunninghamella echinulata* SC 16027 (ATCC 9244) and a medium consisting of the following: 0.5% toasted nutrisoy, 2% glucose, 0.5% yeast extract, 0.5% $K_2HPO_4$, 0.5% NaCl, adjusted to pH 7 with 1N HCl (R. V. Smith and J. P. Rosazza, Arch. Biochem. Biophys., 161, 551-558 (1974)). The fermentor was batched with 0.05% SAG antifoam before sterilization. Spore inoculum was prepared by washing the spores from a 10 day slant culture of *Cunninghamella echinulata* SC 16027 (ATCC 9244) with 0.9% saline/0.1% Tween 80. The inoculum stage was prepared by adding 1 mL of spore inoculum into 100 mL medium in a 500 mL flask, then the cultures were grown at 28° C. at 200 rpm for 1 day. 10% inoculum from the flask was blended in a sterile Waring blender and used to inoculate the sterile fermentor, containing 3 L of sterile media. The fermentor was run at 28° C. at 600 rpm and 1 vvm aeration. A sterile solution of three antibiotics was added to the fermentor after inoculation; 12 mg of tetracycline chloride, 12 mg of kanamycin sulfate, and 60 mg of cephalexin hydrate in 10 mL of deionized water. After 22 hours of growth in the fermentor, a sterile substrate solution was added containing 0.75 g of compound 472 dissolved in 30 mL of methanol, this step was repeated two hours later for a total of 0.5 g/L of compound 472 in the bioconversion. The fermentation conditions were maintained at 28° C. at 600 rpm and 1 vvm aeration. pH 6.5 was maintained by the automatic addition of 10% $H_2SO_4$ or 10% NaOH. Periodically, 10 mL aseptic samples were taken and extracted with two 10 mL portions of ethyl acetate. The ethyl acetate layer was isolated, dried under a nitrogen stream at 40° C., and the residue was dissolved in 2.0 mL of isopropyl alcohol. The samples were analyzed by reverse phase HPLC (method below) to determine the ratio of compound 472 and the product compound 515. In addition, each sample was analyzed by chiral HPLC (method below) in order to determine the % ee of compound 515. During the bioconversion process, a sterile solution of 30% cerelose and 1.5% yeast extract was fed into the reaction at ~5 mL/hour. After 114 h from the time of substrate addition, reverse phase HPLC analysis indicated the production of a 78% yield of compound 515. Chiral HPLC analysis measured the % e.e. of compound 515 at 94.9%. The above process was repeated in another 3 L bioconversion, and the reaction was conducted at 28° C. at 600 rpm, 1 vvm aeration, with 0.5 g/L of compound 472 input. After 44 h, this reaction gave a 80% yield of compound 515 with 95% e.e. The broth was flittered through a pad of HyFlo™ to provide a clarified fermentation broth. The broth was flittered through a pad of HyFlo™ to provide a clarified fermentation broth. Compound 515 was completely adsorbed onto 55 g of XAD-16 and extracted back into a 1:1 mixture of EtOAc and acetone (3×100 mL) or methyl-tert-butyl ether (3×100 mL). The solvent was removed in vacuo and the resulting residue was purified by silica pad (5 g), eluting with EtOAc. The desired fractions were collected and treated with activated carbon (0.5 g) to declorize the solution and the solvent was removed in vacuo to yield 1.27 g of compound 515. Re-crystallization of this material from EtOAc/heptane (10 mL/20 mL) resulted 950 mg of crystalline compound 515 having 97% purity by reverse phase HPLC and 95% ee by chiral HPLC. Reverse Phase HPLC: YMC Pak ODS-A C18 column, 4.6×50 mm, eluting with a gradient of: 0 min 20% acetonitrile/80% 0.1% TFA in water, 12 min 90% acetonitrile/10% 0.1% TFA in water, 12.01-15 min 20% acetonitrile/80% 0.1% TFA in water, monitoring at 250 nm, 40° C., 5 μL injection volume). Compound 515: RT=8.86 min. Chiral HPLC: CHIRALPAK OD 25×0.46 cm column; isocratic elution with 15% ethanol/85% heptane at 0.5 mL/min, 18° C., monitoring at 220 nm, injection volume: 20 μL. Compound 515: RT=36.5 min.

In an alternate recovery process, the fermentation broth (1 L) from the above biohydroxylation reaction was filtered and the cake of cells was washed with 100 mL of water. Clear broth was extracted with ethyl acetate (2×600 mL) and the cake of cells was extracted with 400 mL of ethyl acetate. The combined ethyl acetate layers were concentrated and the resulting residue was dissolved in 5 mL of 1:1 heptane/ethyl acetate and loaded on to silica gel pad pad (70 g in 250 mL fritted glass filter). The silica gel pad was eluted with a gradient of 80 to 90% EtOAc/heptane. Fractions were collected and the fractions containing compound 515 were pooled. The solvent was removed in vacuo and resulting product was crystallized from EtOAc/heptane to give a 90% yield of compound 515 with 98% purity by reverse phase HPLC and 95% ee by chiral HPLC. Reverse Phase HPLC: YMC Pak ODS-A C18 column, 4.6×50 mm, eluting with a gradient of: 0 min 20% acetonitrile/80% 0.1% TFA in water, 12 min 90% acetonitrile/10% 0.1% TFA in water, 12.01-15 min 20% acetonitrile/80% 0.1% TFA in water, monitoring at 250 nm, 40° C., 5 μL injection volume). Compound 472: RT=11.12 min. Compound 515: RT=8.86 min. Chiral HPLC: CHIRALPAK OD 25×0.46 cm column; isocratic elution with 15% ethanol/85% heptane at 0.5 mL/min, 18° C., monitoring at 220 nm, injection volume: 20 μL. Compound 472: RT=27.4 min. Compound 515: RT=36.5 min. Compound (514iii) RT=39.1 min.

EXAMPLE 516

4-(2,5-Dioxo-2,5-dihydro-pyrrol-1-yl)-2-trifluoromethylbenzonitrile (516B)

The following Example demonstrates preparation of an intermediate useful for preparing compounds of the formula I of the present invention.

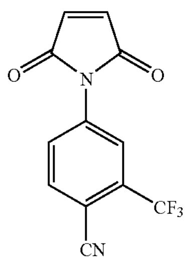

A. 3-(4-Cyano-3-trifluoromethylphenylcarbamoyl) acrylic acid (516A)

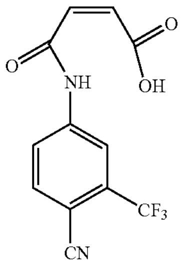

5-amino-2-cyanobenzotrifluoride (210.6 mmoles; 40.00 g) and butyl acetate (80 mL) were added to a 250 mL round bottom flask, followed by the addition of maleic anhydride (231.9 mmoles, 23.20 g). The resulting suspension was heated to 60° C. for 3.5 h. The reaction mixture was cooled to 25° C. and then heptane (160 mL) was added dropwise over a period of 25 minutes. The resulting suspension was filtered and washed with a mixture of 4:1, hepatane:butyl acetate (30 mL) and heptane (45 mL). The cake was dried in vacuo to give 60 g (95% yield) of compound 516A.

B. 4-(2,5-Dioxo-2,5-dihydro-pyrrol-1-yl)-2-trifluoromethylbenzonitrile(516B)

Compound 516A (17.42 mmoles, 5.000 g) was added to the reaction flask followed by the addition of zinc bromide (17.58 mmoles, 3.960 g) and then toluene (50.00 mL, 43.25 g) was added to the mixture. The resulting suspension was stirred for 20 min. Hexamethyldisilazane (26.35 mmoles, 5.560 mL, 4.253 g) was added to this suspension which was then heated to 60° C. for 4.5 h. The reaction mixture was diluted with EtOAc (25 mL) and then poured into a 1N HCl solution (30 mL) at 25° C. The organic phase was collected and the aqueous phase was extracted with EtOAc (15 mL). The organic phase was isolated, combined with the earlier organic phase and washed consecutively with saturated $NaHCO_3$ (15 mL), a mixture of 1:1 water:brine solution (15 mL) and brine (15 mL). The resulting solution was dried over $MgSO_4$, filtered and concentrated in vacuo to a 50 mL suspension. Heptane (125 mL) was added dropwise to this suspension with agitation. The resulting thicker suspension was filtered and washed with a mixture of 2:1 heptane:toluene (15 mL) and then heptane (15 mL) to give 4 g (85% yield) of compound 516B. HPLC: 100% at 2.11 min (retention time) (YMC S5 ODS column, 4.6×50 mm, eluting with 10-90% aqueous methanol over 4 mincontaining 0.2% phosphoric acid, 4 mL/min, monitoring at 220 nm).

EXAMPLES 517 TO 746

Additional compounds of the present invention were prepared by procedures analogous to those described above. The compounds of Examples 517 to 746 have the structures shown in the following Table 17.

Table 17 also provides the compound name, retention time/molecular mass, and the procedure employed for preparation of these compounds. The chromatography techniques used to determine the compound retention times of Table 17 are as follows: LC and LCMS were described in Examples 439 to 454 (Table 9). The molecular mass of the compounds listed in Table 17, where provided, was determined by MS (ES) by the formula m/z.

| Ex. No. | Compound Structure | Compound Name | Retention Time Min./ Molecular Mass | Pro. of Ex. |
|---|---|---|---|---|
| 517 | 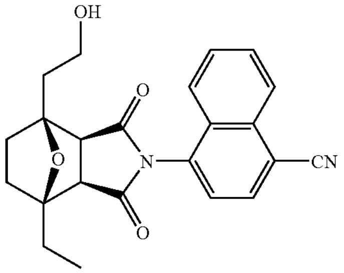 | [3aR-(3aα,4β,7β,7aα)]-4-[4-Ethyloctahydro-7-(2-hydroxyethyl)-1,3-dioxo-4,7-epoxy-2H-isoindol-2-yl]-1-naphthalenecarbonitrile | 2.84 LC $[M+H]^+$ = 391.16 | 245 & 461 |
| 518 | 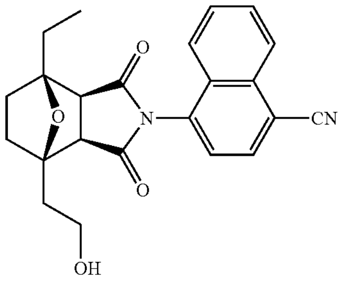 | [3aS-(3aα,4β,7β,7aα)]-4-[4-Ethyloctahydro-7-(2-hydroxyethyl)-1,3-dioxo-4,7-epoxy-2H-isoindol-2-yl]-1-naphthalenecarbonitrile | 2.84 LC $[M+H]^+$ = 391.16 | 245 & 461 |

-continued

| Ex. No. | Compound Structure | Compound Name | Retention Time Min./ Molecular Mass | Pro. of Ex. |
|---|---|---|---|---|
| 519 | 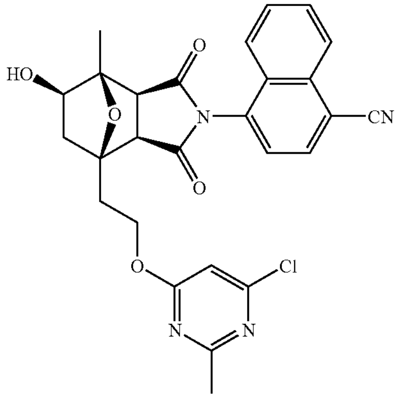 | [3aS-(3aα,4β,5β,7β,7aα)]-4-[7-[2-[(6-Chloro-2-methyl-4-pyrimidinyl)oxy]ethyl] octahydro-5-hydroxy-4-methyl-1,3-dioxo-4,7-epoxy-2H-isoindol-2-yl]-1-naphthalenecarbonitrile | 3.04 LC $[M + H]^+$ = 519.0 | 243 & 244 |
| 520 | 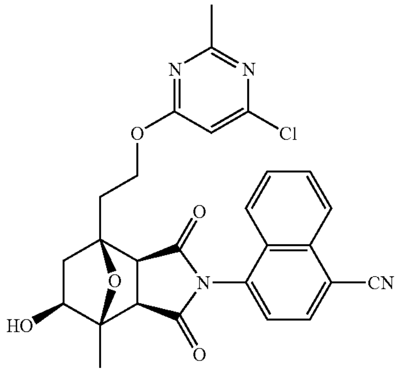 | [3aR-(3aα,4β,5β,7β,7aα)]-4-[7-[2-[(6-Chloro-2-methyl-4-pyrimidinyl)oxy]ethyl] octahydro-5-hydroxy-4-methyl-1,3-dioxo-4,7-epoxy-2H-isoindol-2-yl]-1-naphthalenecarbonitrile | 3.04 LC $[M + H]^+$ = 519.0 | 243 & 244 |
| 521 | 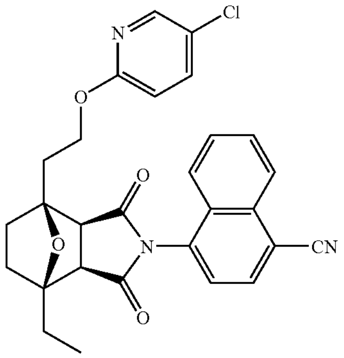 | [3aR-(3aα,4β,7β,7aα)]-4-[4-[2-[(5-Chloro-2-pyridinyl)oxy]ethyl]-7-ethyloctahydro-1,3-dioxo-4,7-epoxy-2H isoindol-2-yl]-1-naphthalenecarbonitrile | 3.90 LC $[M + H]^+$ = 502.28 | 245 & 461 |
| 522 | 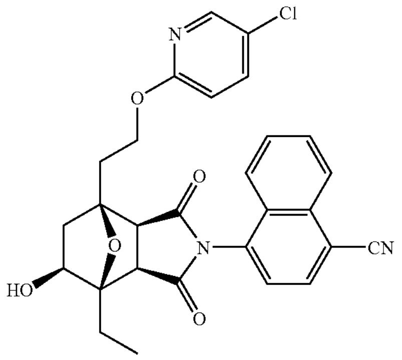 | [3aR-(3aα,4β,5β,7β,7aα)]-4-[7-[2-[(5-Chloro-2-pyridinyl)oxy]ethyl]-4-ethyloctahydro-5-hydroxy-1,3-dioxo-4,7-epoxy-2H-isoindol-2-yl]-1-naphthalenecarbonitrile | 3.37 LC $[M + H]^+$ = 518.28 | 435, 499 & 500 |

-continued

| Ex. No. | Compound Structure | Compound Name | Retention Time Min./ Molecular Mass | Pro. of Ex. |
|---|---|---|---|---|
| 523 | 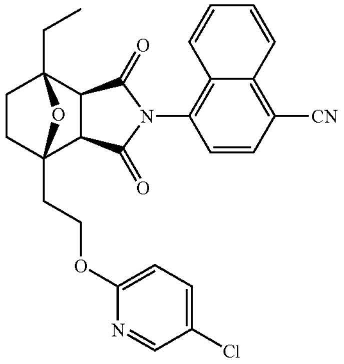 | [3aS-(3aα,4β,7β,7aα)]-4-[4-[2-[(5-Chloro-2-pyridinyl)oxy]ethyl]-7-ethyloctahydro-1,3-dioxo-4,7-epoxy-2H-isoindol-2-yl]-1-naphthalenecarbonitrile | 3.90 LC $[M + H]^+$ = 502.27 | 245 & 461 |
| 524 | 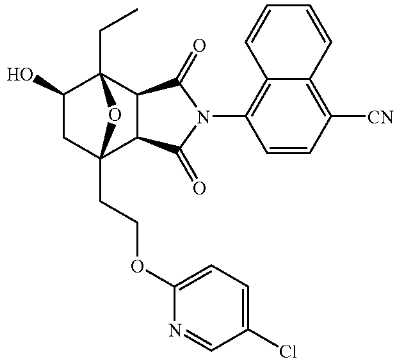 | [3aS-(3aα,4β,5β,7β,7aα)]-4-[7-[2-[(5-Chloro-2-pyridinyl)oxy]ethyl]-4-ethyloctahydro-5-hydroxy-1,3-dioxo-4,7-epoxy-2H-isoindol-2-yl]-1-naphthalenecarbonitrile | 3.40 LC $[M + H]^+$ = 518.27 | 435, 499 & 500 |
| 525 | 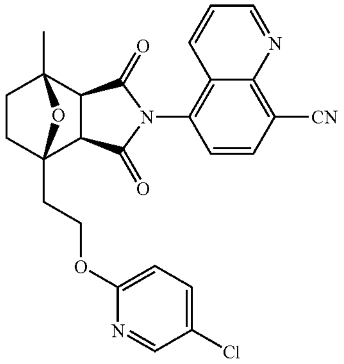 | (3aα,4β,7β,7aα)-5-[4-[2-[(5-Chloro-2-pyridinyl)oxy]ethyl]octahydro-7-methyl-1,3-dioxo-4,7-epoxy-2H-isoindol-2-yl]-8-quinolinecarbonitrile | 3.32 LC $[M + H]^+$ = 489.26 | 467 |
| 526 | 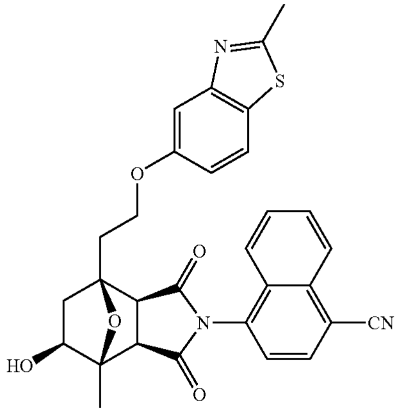 | [3aR-(3aα,4β,5β,7β,7aα)]-4-[Octahydro-5-hydroxy-4-methyl-7-[2-[(2-methyl-5-benzothiazolyl)oxy]ethyl]-1,3-dioxo-4,7-epoxy-2H-isoindol-2-yl]-1-naphthalenecarbonitrile | 3.36 LC $[M + H]^+$ = 540.0 | 243 & 244 |

-continued

| Ex. No. | Compound Structure | Compound Name | Retention Time Min./ Molecular Mass | Pro. of Ex. |
|---|---|---|---|---|
| 527 | 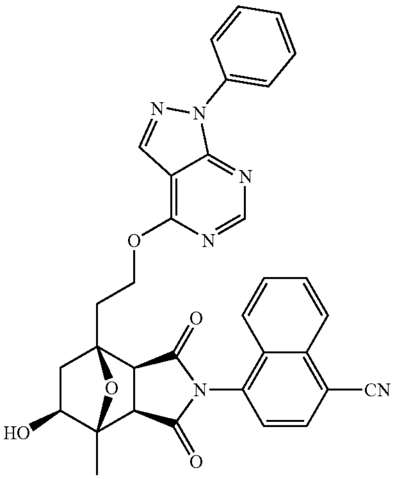 | [3aR-(3aα,4β,5β,7β,7aα)]-4-[Octahydro-5-hydroxy-4-methyl-1,3-dioxo-7-[2-[(1-phenyl-1H-pyrazolo[3,4-d]pyrimidin-4-yl)oxy]ethyl]-4,7-epoxy-2H-isoindol-2-yl]-1-naphthalenecarbonitrile | 3.35 LC $[M + OAc]^-$ = 644.8 | 243 & 244 |
| 528 | 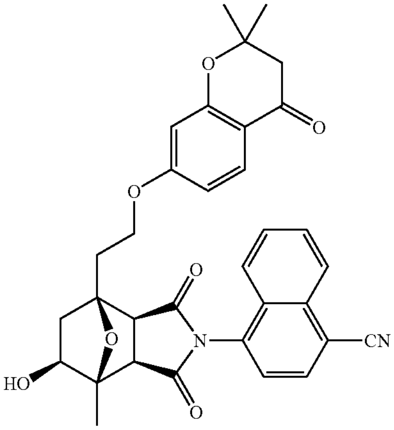 | [3aR-(3aα,4β,5β,7β,7aα)]-4-[7-[2-[(3,4-Dihydro-2,2-dimethyl-4-oxo-2H-1-benzopyran-7-yl)oxy]ethyl]octahydro-5-hydroxy-4-methyl-1,3-dioxo-4,7-epoxy-2H-isoindol-2-yl]-1-naphthalenecarbonitrile | 3.37 LC $[M + OAc]^-$ = 391.16 | 243 & 244 |
| 529 | 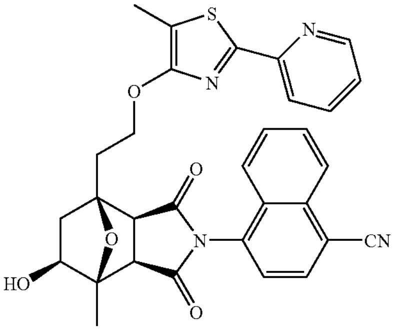 | [3aR-(3aα,4β,5β,7β,7aα)]-4-[Octahydro-5-hydroxy-4-methyl-7-[2-[[5-methyl-2-(2-pyridinyl)-4-thiazolyl]oxy]ethyl]-1,3-dioxo-4,7-epoxy-2H-isoindol-2-yl]-1-naphthalenecarbonitrile | 3.47 LC $[M + H]^+$ = 566.9 | 243 & 244 |

-continued

| Ex. No. | Compound Structure | Compound Name | Retention Time Min./ Molecular Mass | Pro. of Ex. |
|---|---|---|---|---|
| 530 | 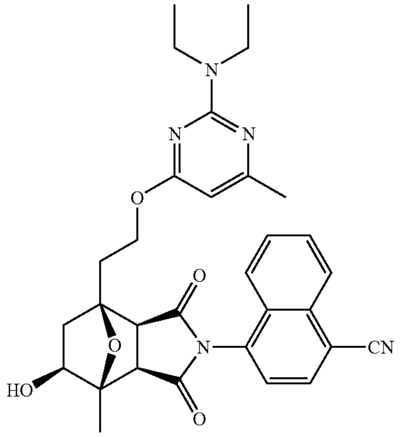 | [3aR-(3aα,4β,5β,7β,7aα)]-4-[7-[2-[[2-(Diethylamino)-6-methyl-4-pyrimidinyl]oxy]ethyl]octahydro-5-hydroxy-4-methyl-1,3-dioxo-4,7-epoxy-2H-isoindol-2-yl]-1-naphthalenecarbonitrile | 3.47 LC $[M + H]^+$ = 556.1 | 243 & 244 |
| 531 | 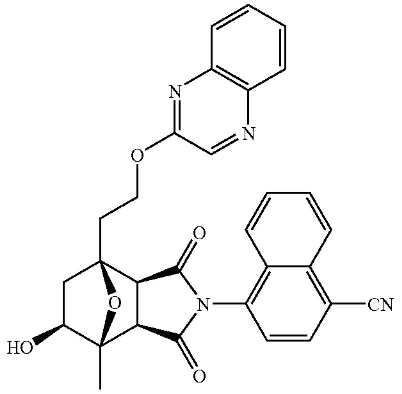 | [3aR-(3aα,4β,5β,7β,7aα)]-4-[Octahydro-5-hydroxy-4-methyl-1,3-dioxo-7-[2-(2-quinoxalinyloxy)ethyl]-4,7-epoxy-2H-isoindol-2-yl]-1-naphthalenecarbonitrile | 3.39 LC $[M + H]^+$ = 520.6 | 243 & 244 |
| 532 | 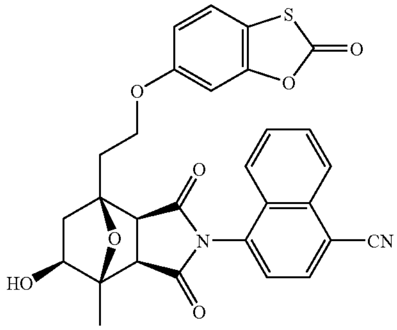 | [3aR-(3aα,4β,5β,7β,7aα)]-4-[Octahydro-5-hydroxy-4-methyl-1,3-dioxo-7-[2-[(2-oxo-1,3-benzoxathiol-5-yl)oxy]ethyl]-4,7-epoxy-2H-isoindol-2-yl]-1-naphthalenecarbonitrile | 3.35 LC $[M + OAc]^-$ = 600.8 | 243 & 244 |
| 533 | 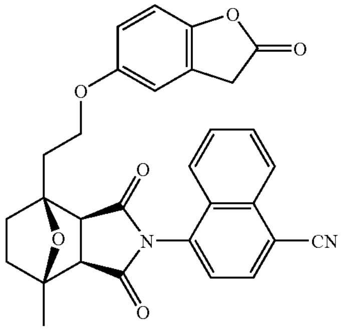 | (3aα,4β,7β,7aα)-4-[4-[2-[(2,3-Dihydro-2-oxo-5-benzofuranyl)oxy]ethyl]octahydro-7-methyl-1,3-dioxo-4,7-epoxy-2H-isoindol-2-yl]-1-naphthalenecarbonitrile | 3.28 LC $[M + OAc]^-$ = 566.6 | 223 & 250 |

-continued

| Ex. No. | Compound Structure | Compound Name | Retention Time Min./ Molecular Mass | Pro. of Ex. |
|---|---|---|---|---|
| 534 | 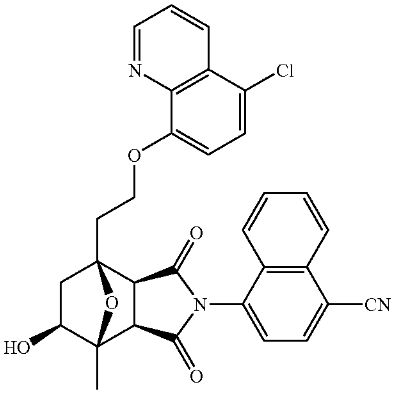 | [3aR-(3aα,4β,5β,7β,7aα)]-4-[7-[2-[(5-Chloro-8-quinolinyl)oxy]ethyl]octahydro-5-hydroxy-4-methyl-1,3-dioxo-4,7-epoxy-2H-isoindol-2-yl]-1-naphthalenecarbonitrile | 3.18 LC $[M + H]^+$ = 553.6 | 243 & 244 |
| 535 | 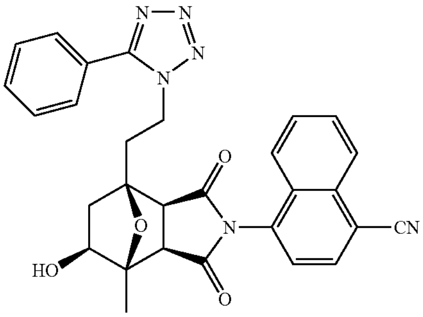 | [3aR-(3aα,4β,5β,7β,7aα)]-4-[Octahydro-5-hydroxy-4-methyl-1,3-dioxo-7-[2-(5-phenyl-1H-tetrazol-1-yl)ethyl]-4,7-epoxy-2H-isoindol-2-yl]-1-naphthalenecarbonitrile | 3.32 LC $[M + H]^+$ = 521.5 | 243 & 244 |
| 536 | 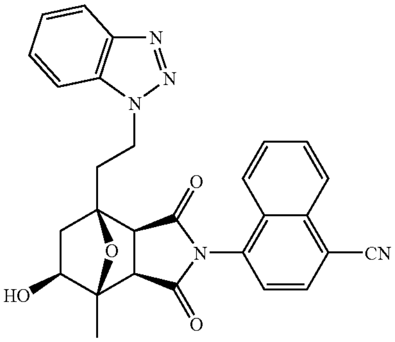 | [3aR-(3aα,4β,5β,7β,7aα)]-4-[7-[2-(1H-1,2,3-Benzotriazol-1-yl)ethyl]octahydro-5-hydroxy-4-methyl-1,3-dioxo-4,7-epoxy-2H-isoindol-2-yl]-1-naphthalenecarbonitrile | 3.15 LC $[M + H]^+$ = 493.8 | 243 & 244 |
| 537 | 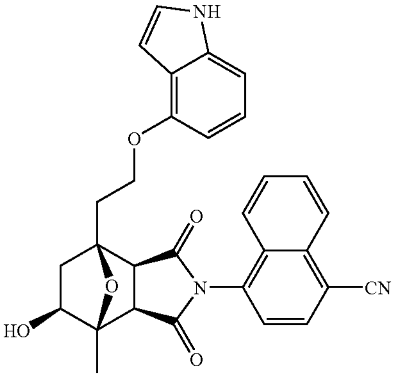 | [3aR-(3aα,4β,5β,7β,7aα)]-4-[Octahydro-5-hydroxy-7-[2-(1H-indol-4-yloxy)ethyl]-4-methyl-1,3-dioxo-4,7-epoxy-2H-isoindol-2-yl]-1-naphthalenecarbonitrile | 3.05 LC $[M]^+$ = 507.6 | 243 & 244 |

-continued

| Ex. No. | Compound Structure | Compound Name | Retention Time Min./ Molecular Mass | Pro. of Ex. |
|---|---|---|---|---|
| 538 | 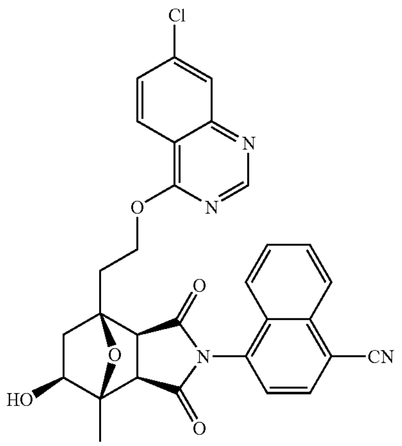 | [3aR-(3aα,4β,5β,7β,7aα)]-4-[7-[2-[(7-Chloro-4-quinazolinyl)oxy]ethyl]octahydro-5-hydroxy-4-methyl-1,3-dioxo-4,7-epoxy-2H-isoindol-2-yl]-1-naphthalenecarbonitrile | 3.33 LC $[M + H]^+$ = 555.2 | 243 & 244 |
| 539 | 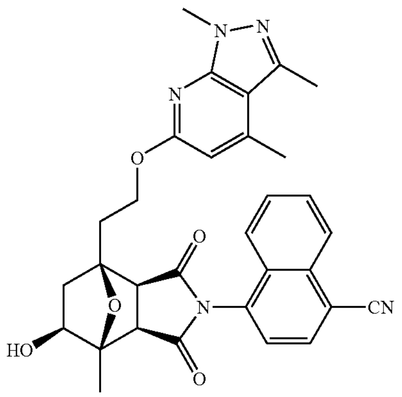 | [3aR-(3aα,4β,5β,7β,7aα)]-4-[Octahydro-5-hydroxy-4-methyl-1,3-dioxo-7-[2-[(1,3,4-trimethyl-1H-pyrazolo[3,4-b]pyridin-6-yl)oxy]ethyl]-4,7-epoxy-2H-isoindol-2-yl]-1-naphthalenecarbonitrile | 3.48 LC $[M + H]^+$ = 552.2 | 243 & 244 |
| 540 | 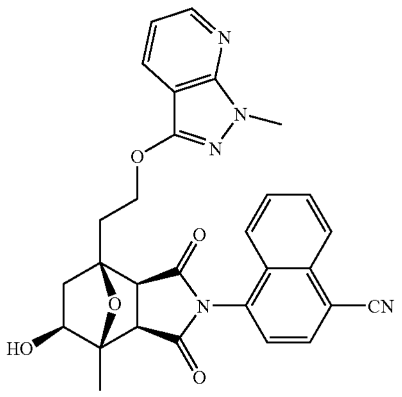 | [3aR-(3aα,4β,5β,7β,7aα)]-4-[Octahydro-5-hydroxy-4-methyl-7-[2-[(1-methyl-1H-pyrazolo[3,4-b]pyridin-3-yl)oxy]ethyl]-1,3-dioxo-4,7-epoxy-2H-isoindol-2-yl]-1-naphthalenecarbonitrile | 3.08 LC $[M + H]^+$ = 524.2 | 243 & 244 |

-continued

| Ex. No. | Compound Structure | Compound Name | Retention Time Min./ Molecular Mass | Pro. of Ex. |
|---|---|---|---|---|
| 541 | 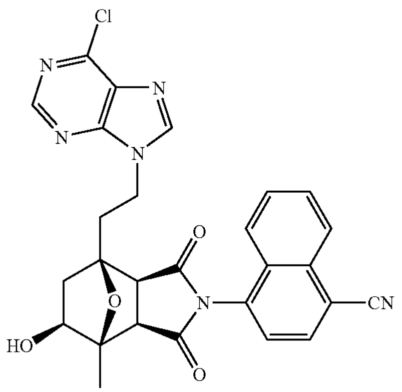 | [3aR-(3aα,4β,5β,7β,7aα)]-4-[7-[2-(6-Chloro-9H-purin-9-yl)ethyl]octahydro-5-hydroxy-4-methyl-1,3-dioxo-4,7-epoxy-2H-isoindol-2-yl]-1-naphthalenecarbonitrile | 2.70 LC $[M + H]^+$ = 529.0 | 243 & 244 |
| 542 | 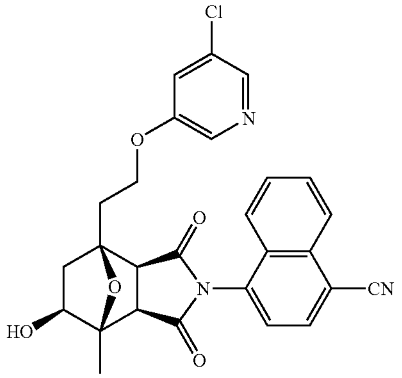 | [3aR-(3aα,4β,5β,7β,7aα)]-4-[7-[2-[(5-Chloro-3-pyridinyl)oxy]ethyl] octahydro-5-hydroxy-4-methyl-1,3-dioxo-4,7-epoxy-2H-isoindol-2-yl]-1-naphthalenecarbonitrile | 3.17 LC $[M + H]^+$ = 504.1 | 243 & 244 |
| 543 | 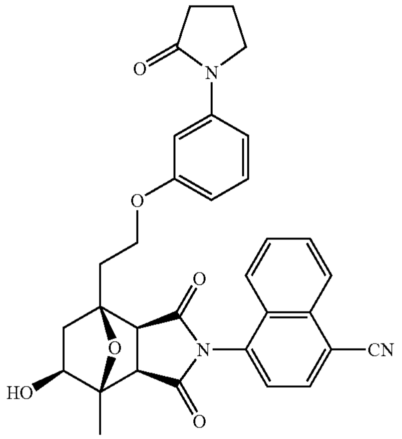 | [3aR-(3aα,4β,5β,7β,7aα)]-4-[Octahydro-5-hydroxy-4-methyl-1,3-dioxo-7-[2-[3-(2-oxo-1-pyrrolidinyl)phenoxy] ethyl]-4,7-epoxy-2H-isoindol-2-yl]-1-naphthalenecarbonitrile | 3.10 LC $[M + H]^+$ = 552.3 | 243 & 244 |

-continued

| Ex. No. | Compound Structure | Compound Name | Retention Time Min./ Molecular Mass | Pro. of Ex. |
|---|---|---|---|---|
| 544 | 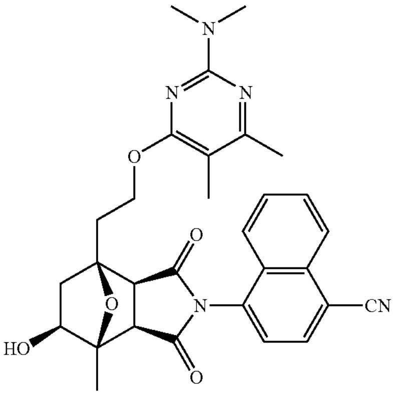 | [3aR-(3aα,4β,5β,7β,7aα)]-4-[7-[2-[[2-(Dimethylamino)-5,6-dimethyl-4-pyrimidinyl]oxy]ethyl] octahydro-5-hydroxy-4-methyl-1,3-dioxo-4,7-epoxy-2H-isoindol-2-yl]-1-naphthalenecarbonitrile | 2.40 LC $[M + H]^+$ = 542.3 | 243 & 244 |
| 545 | 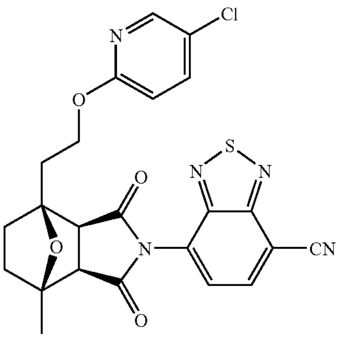 | (3aα,4β,7β,7aα)-7-[4-[2-[(5-Chloro-2-pyridinyl)oxy]ethyl] octahydro-7-methyl-1,3-dioxo-4,7-epoxy-2H-isoindol-2-yl]-2,1,3-benzothiadiazole-4-carbonitrile | 3.52 LC $[M + H]^+$ = 495.6 | 424A, 204, 482F & 482G |
| 546 | 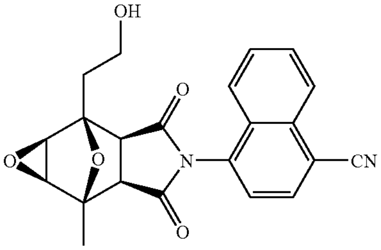 | (1aα,2β,2aα,5aα,6β,6aα)-4-[Octahydro-2-(2-hydroxyethyl)-6-methyl-3,5-dioxo-2,6-epoxy-4H-oxireno[f]isoindol-4-yl]-1-naphthalenecarbonitrile | 2.36 LC $[M + H]^+$ = 391.31 | 460 & 228 |
| 547 | 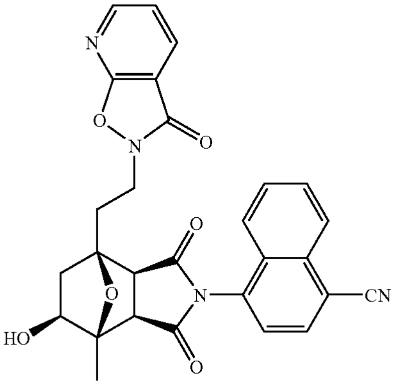 | [3aR-(3aα,4β,5β,7β,7aα)]-4-[Octahydro-5-hydroxy-4-methyl-1,3-dioxo-7-[2-(3-oxoisoxazolo[5,4-b]pyridin-2(3H)-yl)ethyl]-4,7-epoxy-2H-isoindol-2-yl]-1-naphthalenecarbonitrile | 2.92 LC $[M + OAc]^-$ = 568.6 | 243 & 244 |

-continued

| Ex. No. | Compound Structure | Compound Name | Retention Time Min./ Molecular Mass | Pro. of Ex. |
|---|---|---|---|---|
| 548 | 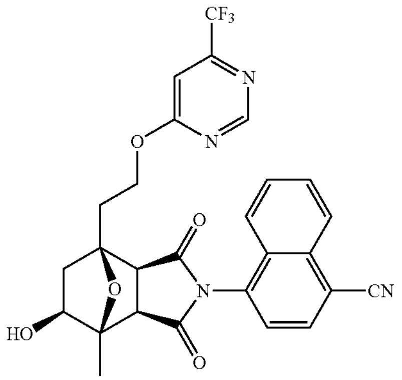 | [3aR-(3aα,4β,5β,7β,7aα)]-4-[Octahydro-5-hydroxy-4-methyl-1,3-dioxo-7-[2-[[6-(trifluoromethyl)-4-pyrimidinyl]oxy]ethyl]-4,7-epoxy-2H-isoindol-2-yl]-1-naphthalenecarbonitrile | 3.18 LC $[M + OAc]^-$ = 596.7 | 243 & 244 |
| 549 | 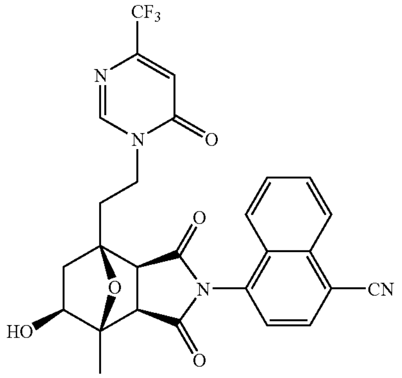 | [3aR-(3aα,4β,5β,7β,7aα)]-4-[Octahydro-5-hydroxy-4-methyl-1,3-dioxo-7-[2-[6-oxo-4-(trifluoromethyl)-1(6H)-pyrimidinyl]ethyl]-4,7-epoxy-2H-isoindol-2-yl]-1-naphthalenecarbonitrile | 2.94 LC $[M + OAc]^-$ = 596.5 | 243 & 244 |
| 550 | 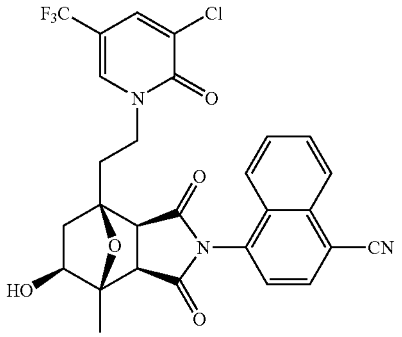 | [3aR-(3aα,4β,5β,7β,7aα)]-4-[7-[2-[3-Chloro-2-oxo-5-(trifluoromethyl)-1(2H)-pyridinyl]ethyl]octahydro-5-hydroxy-4-methyl-1,3-dioxo-4,7-epoxy-2H-isoindol-2-yl]-1-naphthalenecarbonitrile | 3.39 LC $[M + OAc]^-$ = 629.3 | 243 & 244 |
| 551 | 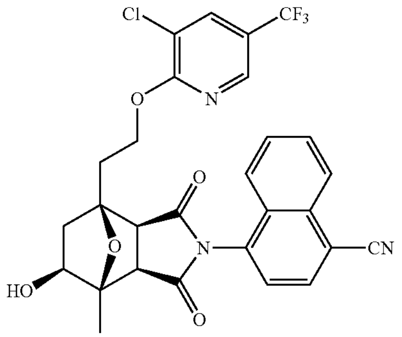 | [3aR-(3aα,4β,5β,7β,7aα)]-4-[7-[2-[[3-Chloro-5-(trifluoromethyl)-2-pyridinyl]oxy]ethyl] octahydro-5-hydroxy-4-methyl-1,3-dioxo-4,7-epoxy-2H-isoindol-2-yl]-1-naphthalenecarbonitrile | 3.76 LC $[M + OAc]^-$ = 629.6 | 243 & 244 |

-continued

| Ex. No. | Compound Structure | Compound Name | Retention Time Min./ Molecular Mass | Pro. of Ex. |
|---|---|---|---|---|
| 552 | 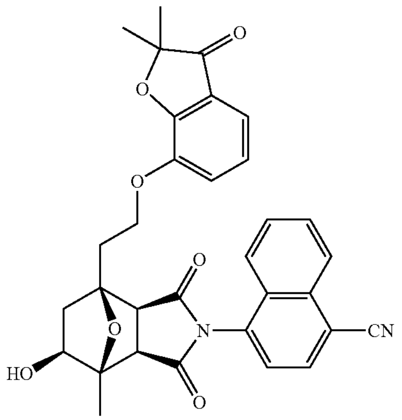 | [3aR-(3aα,4β,5β,7β,7aα)]-4-[7-[2-[(2,3-Dihydro-2,2-dimethyl-3-oxo-7-benzofuranyl)oxy]ethyl] octahydro-5-hydroxy-4-methyl-1,3-dioxo-4,7-epoxy-2H-isoindol-2-yl]-1-naphthalenecarbonitrile | 3.26 LC $[M + OAc]^-$ = 611.5 | 243 & 244 |
| 553 | 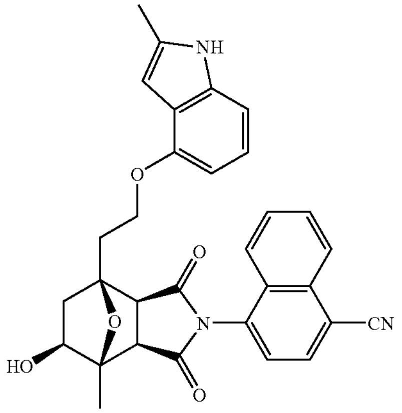 | [3aR-(3aα,4β,5β,7β,7aα)]-4-[Octahydro-5-hydroxy-4-methyl-7-[2-[(2-methyl-1H-indol-4-yl)oxy]ethyl]-1,3-dioxo-4,7-epoxy-2H-isoindol-2-yl]-1-naphthalenecarbonitrile | 3.16 LC $[M + H]^+$ = 522.5 | 243 & 244 |
| 554 | 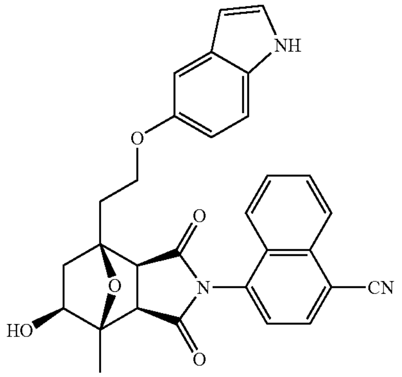 | [3aR-(3aα,4β,5β,7β,7aα)]-4-[Octahydro-5-hydroxy-7-[2-(1H-indol-5-yloxy)ethyl]-4-methyl-1,3-dioxo-4,7-epoxy-2H-isoindol-2-yl]-1-naphthalenecarbonitrile | 3.03 LC $[M + H]^+$ = 506.3 | 243 & 244 |
| 555 | 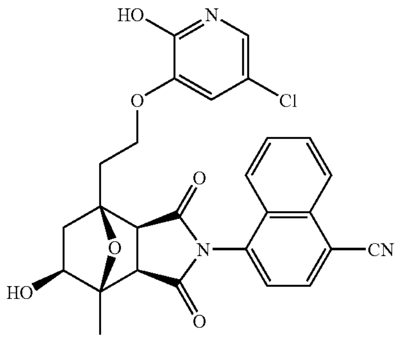 | [3aR-(3aα,4β,5β,7β,7aα)]-4-[7-[2-[(5-Chloro-1,2-dihydro-2-oxo-3-pyridinyl)oxy]ethyl] octahydro-5-hydroxy-4-methyl-1,3-dioxo-4,7-epoxy-2H-isoindol-2-yl]-1-naphthalenecarbonitrile | 2.85 LC $[M + H]^+$ = 520.5 | 243 & 244 |

-continued

| Ex. No. | Compound Structure | Compound Name | Retention Time Min./ Molecular Mass | Pro. of Ex. |
|---|---|---|---|---|
| 556 | 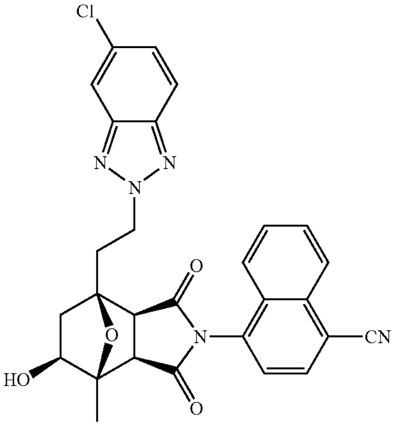 | [3aR-(3aα,4β,5β,7β,7aα)]-4-[7-[2-(5-Chloro-2H-1,2,3-benzotriazol-2-yl)ethyl]octahydro-5-hydroxy-4-methyl-1,3-dioxo-4,7-epoxy-2H-isoindol-2-yl]-1-naphthalenecarbonitrile | 3.53 LC [M + OAc]$^-$ = 586.3 | 243 & 244 |
| 557 | 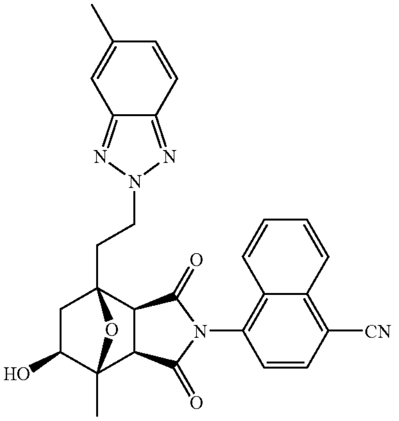 | [3aR-(3aα,4β,5β,7β,7aα)]-4-[Octahydro-5-hydroxy-4-methyl-7-[2-(5-methyl-2H-1,2,3-benzotriazol-2-yl)ethyl]-1,3-dioxo-4,7-epoxy-2H-isoindol-2-yl]-1-naphthalenecarbonitrile | 3.35 LC [M + H]$^+$ = 508.5 | 243 & 244 |
| 558 | 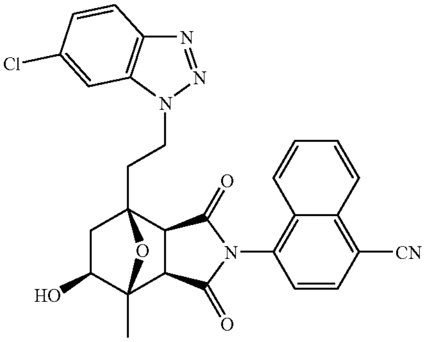 | [3aR-(3aα,4β,5β,7β,7aα)]-4-[7-[2-(6-Chloro-1H-1,2,3-benzotriazol-1-yl)ethyl]octahydro-5-hydroxy-4-methyl-1,3-dioxo-4,7-epoxy-2H-isoindol-2-yl]-1-naphthalenecarbonitrile | 3.32 LC [M + H]$^+$ = 528.3 | 243 & 244 |
| 559 | 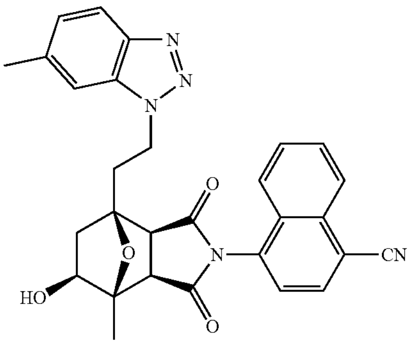 | [3aR-(3aα,4β,5β,7β,7aα)]-4-[Octahydro-5-hydroxy-4-methyl-7-[2-(6-methyl-1H-1,2,3-benzotriazol-1-yl)ethyl]-1,3-dioxo-4,7-epoxy-2H-isoindol-2-yl]-1-naphthalenecarbonitrile | 2.97 LC [M + H]$^+$ = 508.4 | 243 & 244 |

-continued

| Ex. No. | Compound Structure | Compound Name | Retention Time Min./ Molecular Mass | Pro. of Ex. |
|---|---|---|---|---|
| 560 | 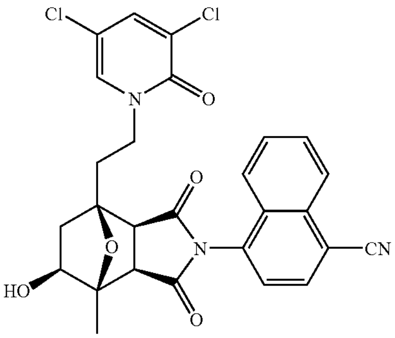 | [3aR-(3aα,4β,5β,7β,7aα)]-4-[7-[2-(3,5-Dichloro-2-oxo-1(2H)-pyridinyl)ethyl]octahydro-5-hydroxy-4-methyl-1,3-dioxo-4,7-epoxy-2H-isoindol-2-yl]-1-naphthalenecarbonitrile | 3.22 LC $[M + H]^+$ = 538.3 | 243 & 244 |
| 561 | 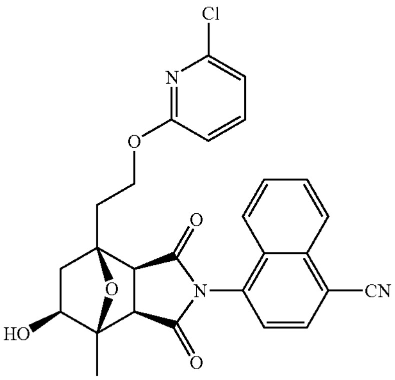 | [3aR-(3aα,4β,5β,7β,7aα)]-4-[7-[2-[(6-Chloro-2-pyridinyl)oxy]ethyl] octahydro-5-hydroxy-4-methyl-1,3-dioxo-4,7-epoxy-2H-isoindol-2-yl]-1-naphthalenecarbonitrile | 3.30 LC $[M + H]^+$ = 504.3 | 243 & 244 |
| 562 | 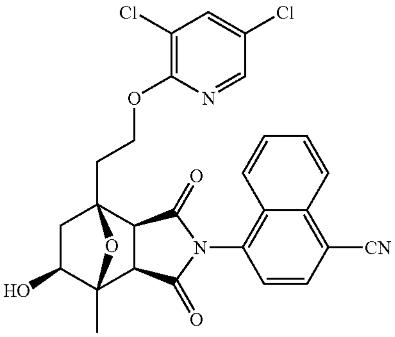 | [3aR-(3aα,4β,5β,7β,7aα)]-4-[7-[2-[(3,5-Dichloro-2-pyridinyl)oxy]ethyl] octahydro-5-hydroxy-4-methyl-1,3-dioxo-4,7-epoxy-2H-isoindol-2-yl]-1-naphthalenecarbonitrile | 3.67 LC $[M + H]^+$ = 596.3 | 243 & 244 |
| 563 | 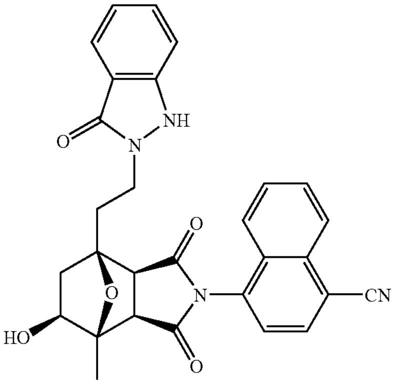 | [3aR-(3aα,4β,5β,7β,7aα)]-4-[7-[2-(1,3-Dihydro-3-oxo-2H-indazol-2-yl)ethyl]octahydro-5-hydroxy-4-methyl-1,3-dioxo-4,7-epoxy-2H-isoindol-2-yl]-1-naphthalenecarbonitrile | 2.82 LC $[M + H]^+$ = 509.1 | 243 & 244 |

-continued

| Ex. No. | Compound Structure | Compound Name | Retention Time Min./ Molecular Mass | Pro. of Ex. |
|---|---|---|---|---|
| 564 | 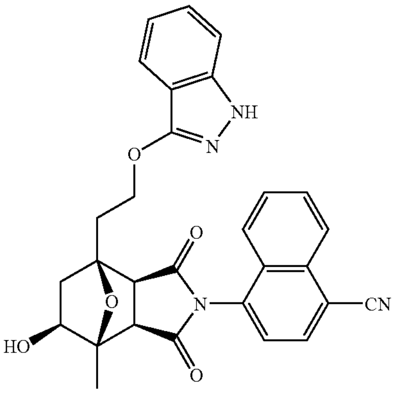 | [3aR-(3aα,4β,5β,7β,7aα)]-4-[Octahydro-5-hydroxy-7-[2-(1H-indazol-3-yloxy)ethyl]-4-methyl-1,3-dioxo-4,7-epoxy-2H-isoindol-2-yl]-1-naphthalenecarbonitrile | 3.19 LC $[M + H]^+$ = 509.2 | 243 & 244 |
| 565 | 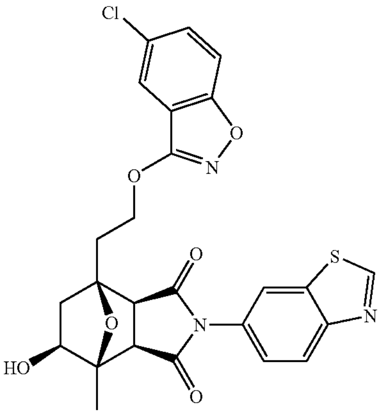 | [3aR-(3aα,4β,5β,7β,7aα)]-2-(6-Benzothiazolyl)-7-[2-[(5-chloro-1,2-benzisoxazol-3-yl)oxy]ethyl]hexahydro-5-hydroxy-4-methyl-4,7-epoxy-1H-isoindole-1,3(2H)-dione | 3.21 LC $[M + H]^+$ = 526.2 | 481 |
| 566 | 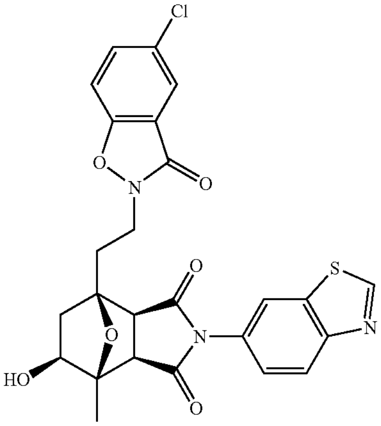 | [3aR-(3aα,4β,5β,7β,7aα)]-2-(6-Benzothiazolyl)-7-[2-(5-chloro-3-oxo-1,2-benzisoxazol-2(3H)-yl)ethyl]hexahydro-5-hydroxy-4-methyl-4,7-epoxy-1H-isoindole-1,3(2H)-dione | 2.81 LC $[M + H]^+$ = 526.2 | 481 |

-continued

| Ex. No. | Compound Structure | Compound Name | Retention Time Min./ Molecular Mass | Pro. of Ex. |
|---|---|---|---|---|
| 567 | 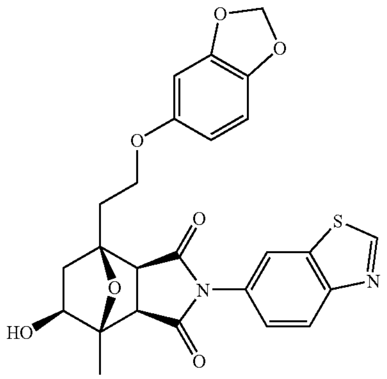 | [3aR-(3aα,4β,5β,7β,7aα)]-7-[2-(1,3-Benzodioxol-5-yloxy)ethyl]-2-(6-benzothiazolyl) hexahydro-5-hydroxy-4-methyl-4,7-epoxy-1H-isoindole-1,3(2H)-dione | 2.80 LC $[M + H]^+$ = 495.2 | 481 |
| 568 | 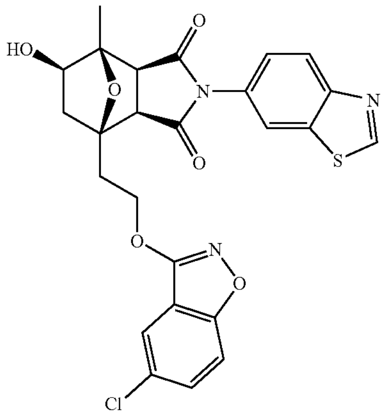 | [3aS-(3aα,4β,5β,7β,7aα)]-2-(6-Benzothiazolyl)-7-[2-[(5-chloro-1,2-benzisoxazol-3-yl)oxy]ethyl]hexahydro-5-hydroxy-4-methyl-4,7-epoxy-1H-isoindole-1,3(2H)-dione | 3.21 LC $[M + H]^+$ = 526.1 | 481 |
| 569 | 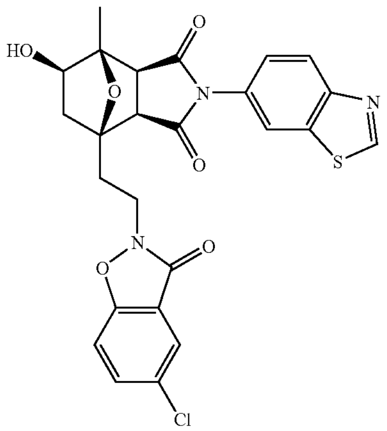 | [3aS-(3aα,4β,5β,7β,7aα)]-2-(6-Benzothiazolyl)-7-[2-(5-chloro-3-oxo-1,2-benzisoxazol-2(3H)-yl)ethyl]hexahydro-5-hydroxy-4-methyl-4,7-epoxy-1H-isoindole-1,3(2H)-dione | 2.84 LC $[M + H]^+$ = 391.16 | 481 |

-continued

| Ex. No. | Compound Structure | Compound Name | Retention Time Min./ Molecular Mass | Pro. of Ex. |
|---|---|---|---|---|
| 570 | 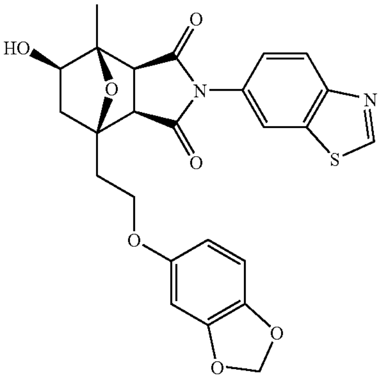 | [3aS-(3aα,4β,5β,7β,7aα)]-7-[2-(1,3-Benzodioxol-5-yloxy)ethyl]-2-(6-benzothiazolyl) hexahydro-5-hydroxy-4-methyl-4,7-epoxy-1H-isoindole-1,3(2H)-dione | 2.82 LC $[M + H]^+$ = 495.2 | 481 |
| 571 | 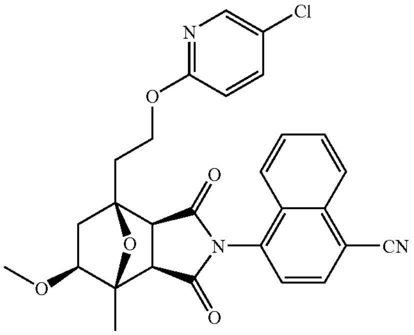 | (3aα,4β,5β,7β,7aα)-4-[7-[2-[(5-Chloro-2-pyridinyl)oxy]ethyl] octahydro-5-methoxy-4-methyl-1,3-dioxo-4,7-epoxy-2H-isoindol-2-yl]-1-naphthalenecarbonitrile | 3.64 & 3.76 atropisomers LCMS $[M + H]^+$ = 518.19 | 491 |
| 572 | 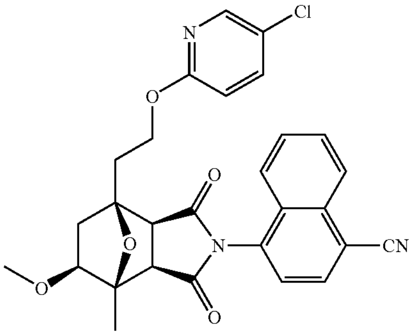 | [3aR-(3aα,4β,5β,7β,7aα)]-4-[7-[2-[(5-Chloro-2-pyridinyl)oxy]ethyl] octahydro-5-methoxy-4-methyl-1,3-dioxo-4,7-epoxy-2H-isoindol-2-yl]-1-naphthalenecarbonitrile | 3.50 LC $[M + H]^+$ = 518.28 | 491 |
| 573 | 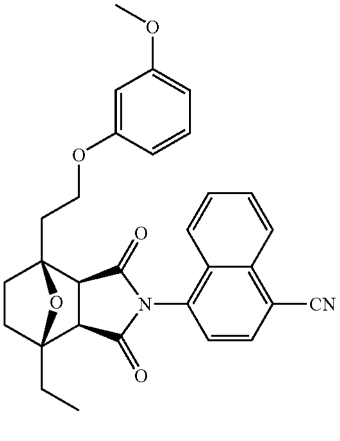 | [3aR-(3aα,4β,7β,7aα)]-4-[4-Ethyloctahydro-7-[2-(3-methoxyphenoxy)ethyl]-1,3-dioxo-4,7-epoxy-2H-isoindol-2-yl]-1-naphthalenecarbonitrile | 7.49 & 7.75 atropisomers LC HRMS $[M + CH_3—CO_2]^-$ = 555.2144 | 245C, 461 & 462 |

-continued

| Ex. No. | Compound Structure | Compound Name | Retention Time Min./ Molecular Mass | Pro. of Ex. |
|---|---|---|---|---|
| 574 | 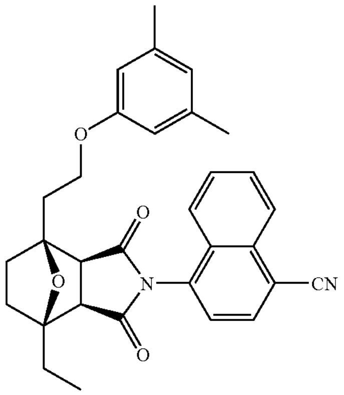 | [3aR-(3aα,4β,7β,7aα)]-4-[4-[2-(3,5-Dimethylphenoxy)ethyl]-7-ethyloctahydro-1,3-dioxo-4,7-epoxy-2H-isoindol-2-yl]-1-naphthalenecarbonitrile | 8.10 & 8.31 atropisomers HRMS $[M + CH_3CO_2]^-$ = 553.2363 | 245C, 461 & 462 |
| 575 | 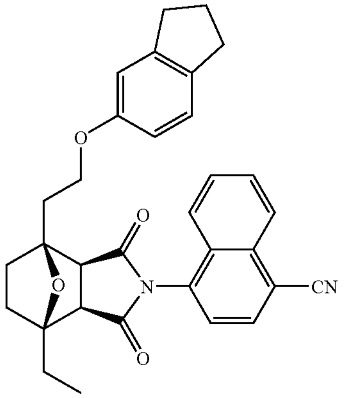 | [3aR-(3aα,4β,7β,7aα)]-4-[4-[2-[(2,3-Dihydro-1H-inden-5-yl)oxy]ethyl]-7-ethyloctahydro-1,3-dioxo-4,7-epoxy-2H-isoindol-2-yl]-1-naphthalenecarbonitrile | 8.17 & 8.37 atropisomers HRMS $[M + CH_3CO_2]^-$ = 565.2326 | 245C, 461 & 462 |
| 576 | 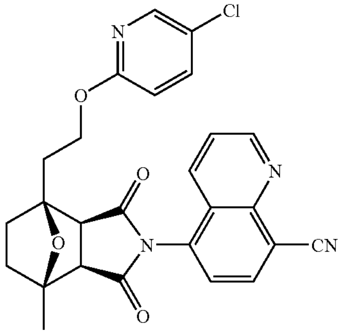 | [3aR-(3aα,4β,7β,7aα)]-5-[4-[2-[(5-Chloro-2-pyridinyl)oxy]ethyl] octahydro-7-methyl-1,3-dioxo-4,7-epoxy-2H-isoindol-2-yl]-8-quinolinecarbonitrile | 3.45 LC $[M + H]^+$ = 489.0 | 467 & 487 |
| 577 | 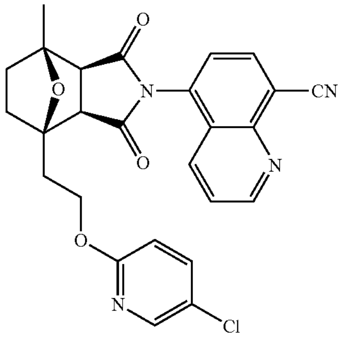 | [3aS-(3aα,4β,7β,7aα)]-5-[4-[2-[(5-Chloro-2-pyridinyl)oxy]ethyl] octahydro-7-methyl-1,3-dioxo-4,7-epoxy-2H-isoindol-2-yl]-8-quinolinecarbonitrile | 3.45 LC $[M + H]^+$ = 488.99 | 467 & 487 |

-continued

| Ex. No. | Compound Structure | Compound Name | Retention Time Min./ Molecular Mass | Pro. of Ex. |
|---|---|---|---|---|
| 578 | 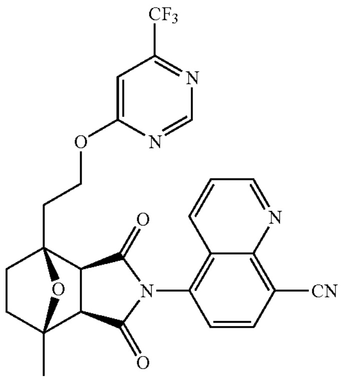 | [3aR-(3aα,4β,7β,7aα)]-5-[Octahydro-4-methyl-1,3-dioxo-7-[2-[[6-(trifluoromethyl)-4-pyrimidinyl]oxy]ethyl]-4,7-epoxy-2H-isoindol-2-yl]-8-quinolinecarbonitrile | 3.25 LC $[M + H]^+$ = 524.0 | 467 & 487 |
| 579 | 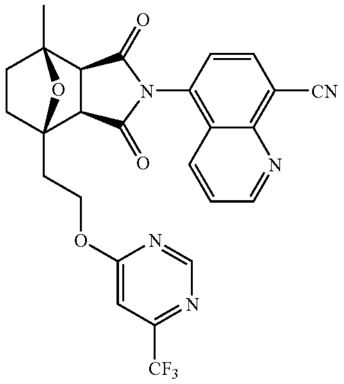 | [3aS-(3aα,4β,7β,7aα)]-5-[Octahydro-4-methyl-1,3-dioxo-7-[2-[[6-(trifluoromethyl)-4-pyrimidinyl]oxy]ethyl]-4,7-epoxy-2H-isoindol-2-yl]-8-quinolinecarbonitrile | 3.45 LC $[M + H]^+$ = 523.98 | 467 & 487 |
| 580 | 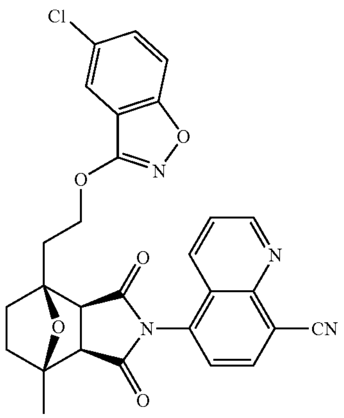 | [3aR-(3aα,4β,7β,7aα)]-5-[4-[2-[(5-Chloro-1,2-benzisoxazol-3-yl)oxy]ethyl]octahydro-7-methyl-1,3-dioxo-4,7-epoxy-2H-isoindol-2-yl]-8-quinolinecarbonitrile | 3.66 LC $[M + H]^+$ = 529.16 | 467 & 487 |

-continued

| Ex. No. | Compound Structure | Compound Name | Retention Time Min./ Molecular Mass | Pro. of Ex. |
|---|---|---|---|---|
| 581 | 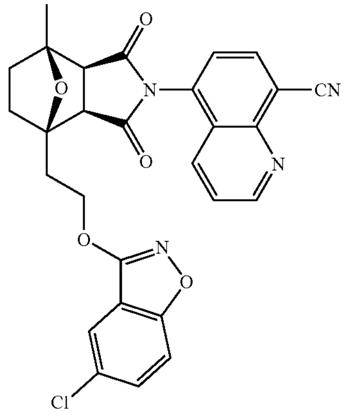 | [3aS-(3aα,4β,7β,7aα)]-5-[4-[2-[(5-Chloro-1,2-benzisoxazol-3-yl)oxy]ethyl]octahydro-7-methyl-1,3-dioxo-4,7-epoxy-2H-isoindol-2-yl]-8-quinolinecarbonitrile | 3.66 LC $[M + H]^+$ = 529.16 | 467 & 487 |
| 582 | 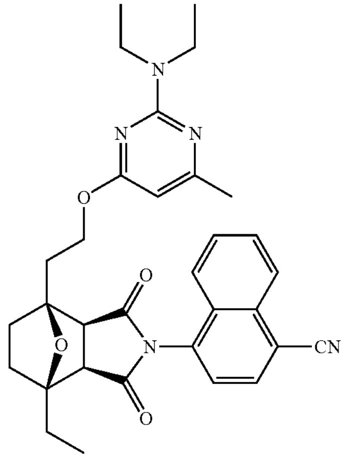 | [3aR-(3aα,4β,7β,7aα)]-4-[4-[2-[[2-(Diethylamino)-6-methyl-4-pyrimidinyl]oxy]ethyl]-7-ethyloctahydro-1,3-dioxo-4,7-epoxy-2H-isoindol-2-yl]-1-naphthalenecarbonitrile | 5.85 & 6.06 atropisomers LC $[M + H]^+$ = 554.26 | 245C, 461 & 462 |
| 583 | 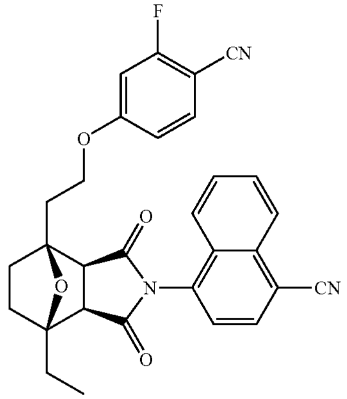 | [3aR-(3aα,4β,7β,7aα)]-4-[4-[2-(4-Cyano-3-fluorophenoxy)ethyl]-7-ethyloctahydro-1,3-dioxo-4,7-epoxy-2H-isoindol-2-yl]-1-naphthalenecarbonitrile | 7.23 & 7.50 atropisomers HRMS $[M - H]^-$ = 508.1682 | 245C, 461 & 462 |

-continued

| Ex. No. | Compound Structure | Compound Name | Retention Time Min./ Molecular Mass | Pro. of Ex. |
|---|---|---|---|---|
| 584 | 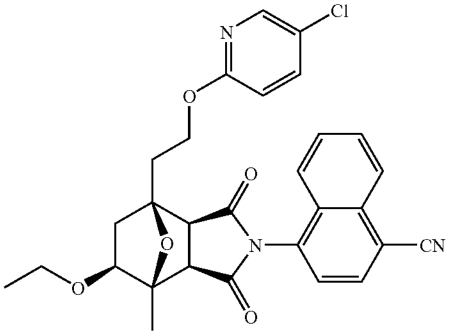 | [3aR-(3aα,4β,5β,7β,7aα)]-4-[7-[2-[(5-Chloro-2-pyridinyl)oxy]ethyl]-5-ethoxyoctahydro-4-methyl-1,3-dioxo-4,7-epoxy-2H-isoindol-2-yl]-1-naphthalenecarbonitrile | 3.60 LC $[M + H]^+$ = 532.23 | 223, 495 & 496 |
| 585 | 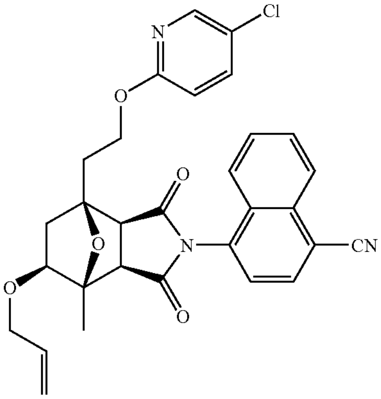 | [3aR-(3aα,4β,5β,7β,7aα)]-4-[7-[2-[(5-Chloro-2-pyridinyl)oxy]ethyl] octahydro-4-methyl-1,3-dioxo-5-(2-propenyloxy)-4,7-epoxy-2H-isoindol-2-yl]-1-naphthalenecarbonitrile | 3.68 LC $[M + H]^+$ = 544.23 | 491 |
| 586 | 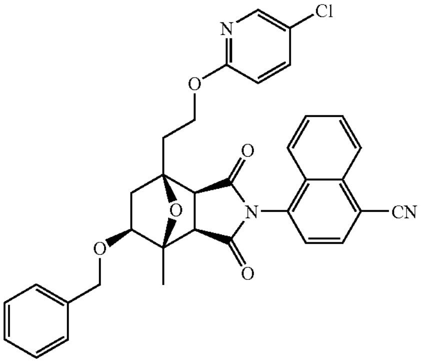 | [3aR-(3aα,4β,5β,7β,7aα)]-4-[7-[2-[(5-Chloro-2-pyridinyl)oxy]ethyl] octahydro-4-methyl-1,3-dioxo-5-(phenylmethoxy)-4,7-epoxy-2H-isoindol-2-yl]-1-naphthalenecarbonitrile | 3.63 LC $[M + H]^+$ = 594.26 | 491 |
| 587 | 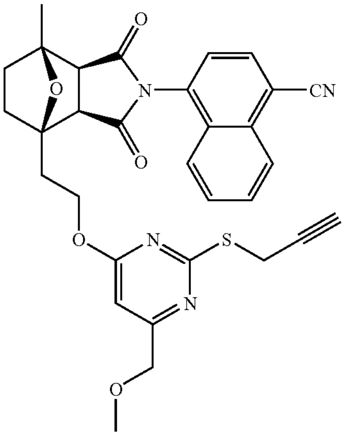 | [3aS-(3aα,4β,7β,7aα)]-4-[Octahydro-4-[2-[[6-(methoxymethyl)-2-(2-propynylthio)-4-pyrimidinyl]oxy]ethyl]-7-methyl-1,3-dioxo-4,7-epoxy-2H-isoindol-2-yl]-1-naphthalenecarbonitrile | 4.02 LC $[M + H]^+$ = 567.31 | 491 |

-continued

| Ex. No. | Compound Structure | Compound Name | Retention Time Min./ Molecular Mass | Pro. of Ex. |
|---|---|---|---|---|
| 588 | 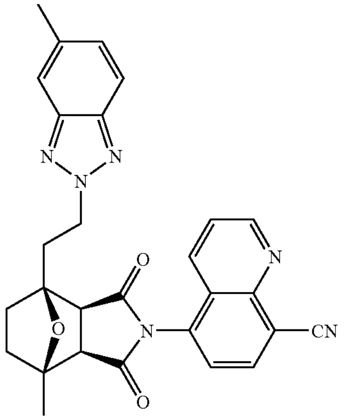 | [3aR-(3aα,4β,7β,7aα)]-5-[Octahydro-4-methyl-7-[2-(5-methyl-2H-1,2,3-benzotriazol-2-yl)ethyl]-1,3-dioxo-4,7-epoxy-2H-isoindol-2-yl]-8-quinolinecarbonitrile | 3.37 LC $[M + H]^+$ = 493.24 | 467 & 487 |
| 589 | 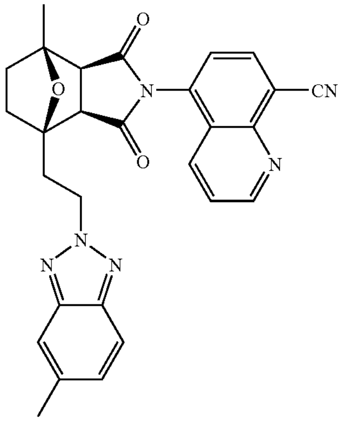 | [3aS-(3aα,4β,7β,7aα)]-5-[Octahydro-4-methyl-7-[2-(5-methyl-2H-1,2,3-benzotriazol-2-yl)ethyl]-1,3-dioxo-4,7-epoxy-2H-isoindol-2-yl]-8-quinolinecarbonitrile | 3.37 LC $[M + H]^+$ = 493.24 | 467 & 487 |
| 590 | 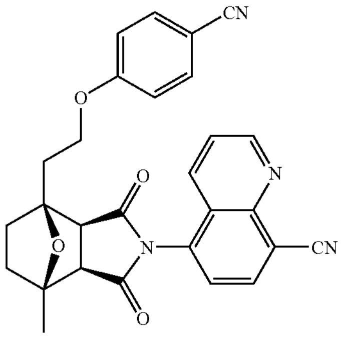 | [3aR-(3aα,4β,7β,7aα)]-5-[4-[2-(4-Cyanophenoxy)ethyl] octahydro-7-methyl-1,3-dioxo-4,7-epoxy-2H-isoindol-2-yl]-8-quinolinecarbonitrile | 3.14 LC $[M + H]^+$ = 479.22 | 467 & 487 |
| 591 | 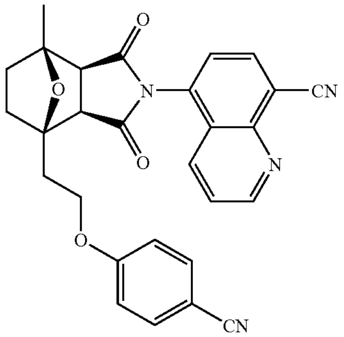 | [3aS-(3aα,4β,7β,7aα)]-5-[4-[2-(4-Cyanophenoxy)ethyl] octahydro-7-methyl-1,3-dioxo-4,7-epoxy-2H-isoindol-2-yl]-8-quinolinecarbonitrile | 3.14 LC $[M + H]^+$ = 479.22 | 467 & 487 |

-continued

| Ex. No. | Compound Structure | Compound Name | Retention Time Min./ Molecular Mass | Pro. of Ex. |
|---|---|---|---|---|
| 592 | 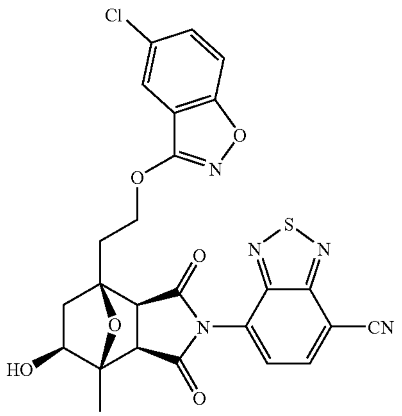 | [3aR-(3aα,4β,5β,7β,7aα)]-7-[7-[2-[(5-Chloro-1,2-benzisoxazol-3-yl)oxy]ethyl]octahydro-5-hydroxy-4-methyl-1,3-dioxo-4,7-epoxy-2H-isoindol-2-yl]-2,1,3-benzothiadiazole-4-carbonitrile | 3.38 LC $[M + H]^+$ = 5552.12 | 482 |
| 593 | 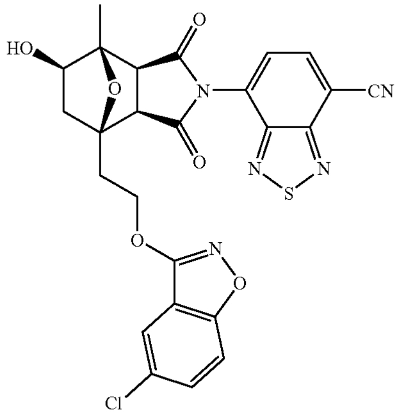 | [3aS-(3aα,4β,5β,7β,7aα)]-7-[7-[2-[(5-Chloro-1,2-benzisoxazol-3-yl)oxy]ethyl]octahydro-5-hydroxy-4-methyl-1,3-dioxo-4,7-epoxy-2H-isoindol-2-yl]-2,1,3-benzothiadiazole-4-carbonitrile | 3.39 LC $[M + H]^+$ = 552.10 | 482 |
| 594 | 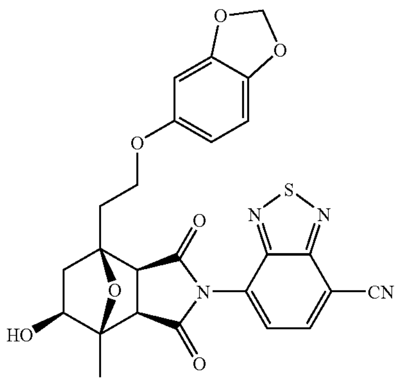 | [3aR-(3aα,4β,5β,7β,7aα)]-7-[7-[2-(1,3-Benzodioxol-5-yloxy)ethyl]octahydro-5-hydroxy-4-methyl-1,3-dioxo-4,7-epoxy-2H-isoindol-2-yl]-2,1,3-benzothiadiazole-4-carbonitrile | 3.00 LC $[M + H]^+$ = 521.15 | 482 |

-continued

| Ex. No. | Compound Structure | Compound Name | Retention Time Min./ Molecular Mass | Pro. of Ex. |
|---|---|---|---|---|
| 595 | 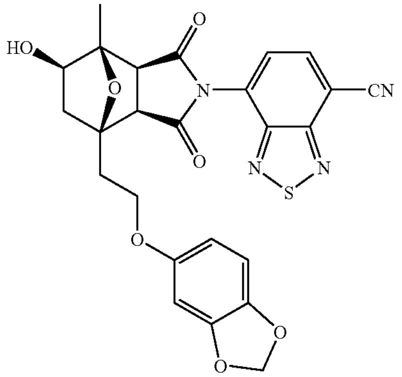 | [3aS-(3aα,4β,5β,7β,7aα)]-7-[7-[2-(1,3-Benzodioxol-5-yloxy)ethyl]octahydro-5-hydroxy-4-methyl-1,3-dioxo-4,7-epoxy-2H-isoindol-2-yl]-2,1,3-benzothiadiazole-4-carbonitrile | 2.99 LC $[M + H]^+$ = 521.14 | 482 |
| 596 | 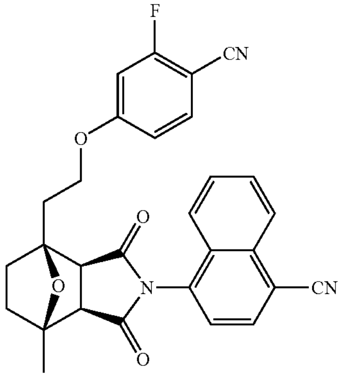 | [3aR-(3aα,4β,7β,7aα)]-4-[4-[2-(4-Cyano-3-fluorophenoxy)ethyl] octahydro-7-methyl-1,3-dioxo-4,7-epoxy-2H-isoindol-2-yl]-1-naphthalenecarbonitrile | 3.76 LCMS $[M + H]^+$ = 496.2 | 496 |
| 597 | 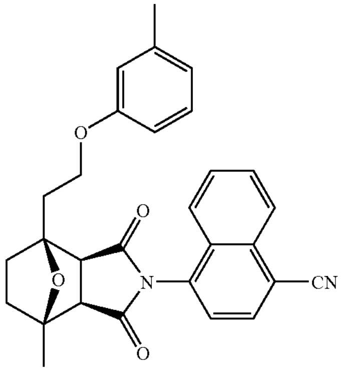 | [3aR-(3aα,4β,7β,7aα)]-4-[Octahydro-4-methyl-7-[2-(3-methylphenoxy)ethyl]-1,3-dioxo-4,7-epoxy-2H-isoindol-2-yl]-1-naphthalenecarbonitrile | 1.79 LCMS $[M + H]^+$ = 467.2 | 496 |
| 598 | 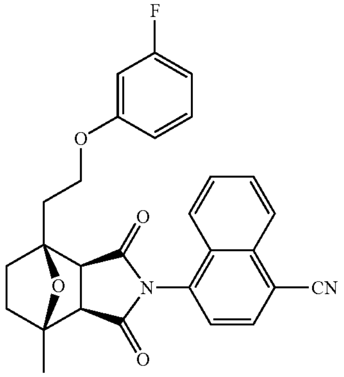 | [3aR-(3aα,4β,7β,7aα)]-4-[4-[2-(3-Fluorophenoxy)ethyl] octahydro-7-methyl-1,3-dioxo-4,7-epoxy-2H-isoindol-2-yl]-1-naphthalenecarbonitrile | 2.01 LCMS $[M + H]^+$ = 471.2 | 496 |

-continued

| Ex. No. | Compound Structure | Compound Name | Retention Time Min./ Molecular Mass | Pro. of Ex. |
|---|---|---|---|---|
| 599 | 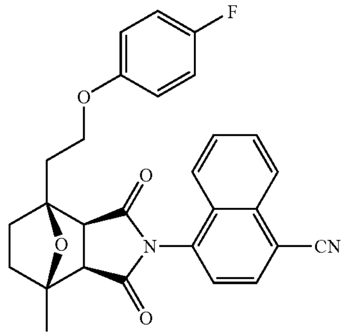 | [3aR-(3aα,4β,7β,7aα)]-4-[4-[2-(4-Fluorophenoxy)ethyl] octahydro-7-methyl-1,3-dioxo-4,7-epoxy-2H-isoindol-2-yl]-1-naphthalenecarbonitrile | 1.98 LCMS $[M + H]^+$ = 471.2 | 496 |
| 600 | 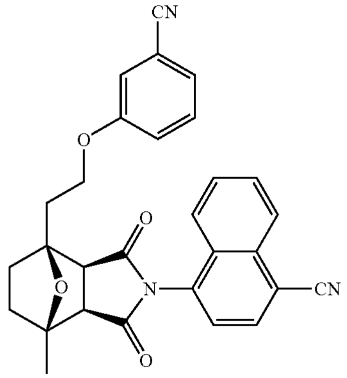 | [3aR-(3aα,4β,7β,7aα)]-4-[4-[2-(3-Cyanophenoxy)ethyl] octahydro-7-methyl-1,3-dioxo-4,7-epoxy-2H-isoindol-2-yl]-1-naphthalenecarbonitrile | 1.88 LCMS $[M + H]^+$ = 478.2 | 496 |
| 601 | 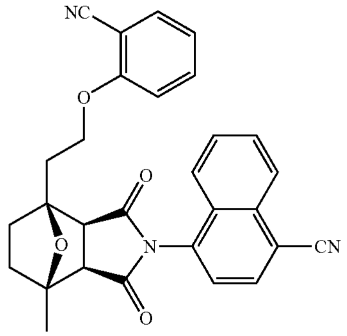 | [3aR-(3aα,4β,7β,7aα)]-4-[4-[2-(2-Cyanophenoxy)ethyl] octahydro-7-methyl-1,3-dioxo-4,7-epoxy-2H-isoindol-2-yl]-1-naphthalenecarbonitrile | 3.42 LCMS $[M + H]^+$ = 478.2 | 496 |
| 602 | 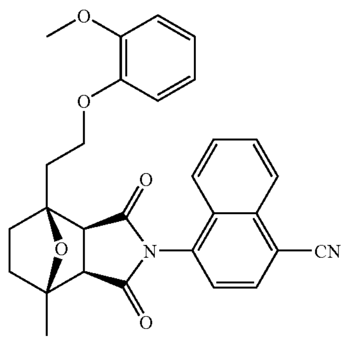 | [3aR-(3aα,4β,7β,7aα)]-4-[Octahydro-4-[2-(2-methoxyphenoxy)ethyl]-7-methyl-1,3-dioxo-4,7-epoxy-2H-isoindol-2-yl]-1-naphthalenecarbonitrile | 1.83 LCMS $[M + H]^+$ = 483.2 | 496 |

-continued

| Ex. No. | Compound Structure | Compound Name | Retention Time Min./ Molecular Mass | Pro. of Ex. |
|---|---|---|---|---|
| 603 | 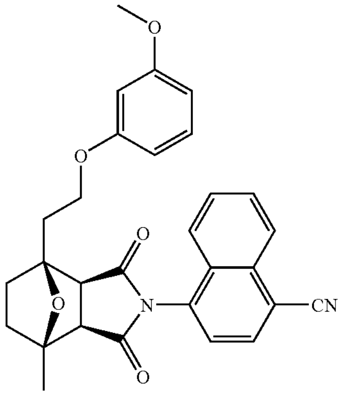 | [3aR-(3aα,4β,7β,7aα)]-4-[Octahydro-4-[2-(3-methoxyphenoxy)ethyl]-7-methyl-1,3-dioxo-4,7-epoxy-2H-isoindol-2-yl]-1-naphthalenecarbonitrile | 2.14 LCMS $[M + H]^+$ = 483.2 | 496 |
| 604 | 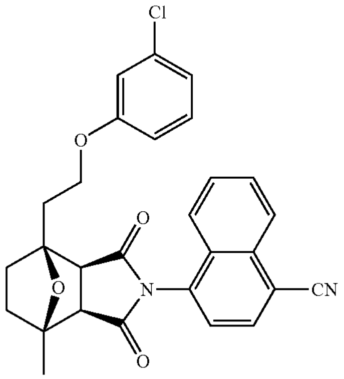 | [3aR-(3aα,4β,7β,7aα)]-4-[4-[2-(3-Chlorophenoxy)ethyl] octahydro-7-methyl-1,3-dioxo-4,7-epoxy-2H-isoindol-2-yl]-1-naphthalenecarbonitrile | 2.09 LCMS $[M + H]^+$ = 487.2 | 496 |
| 605 | 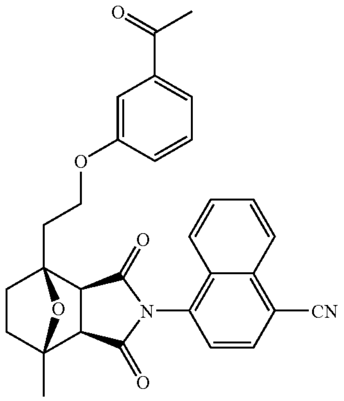 | [3aR-(3aα,4β,7β,7aα)]-4-[4-[2-(3-Acetylphenoxy)ethyl] octahydro-7-methyl-1,3-dioxo-4,7-epoxy-2H-isoindol-2-yl]-1-naphthalenecarbonitrile | 2.20 LCMS $[M + H]^+$ = 495.2 | 496 |

-continued

| Ex. No. | Compound Structure | Compound Name | Retention Time Min./ Molecular Mass | Pro. of Ex. |
|---|---|---|---|---|
| 606 | 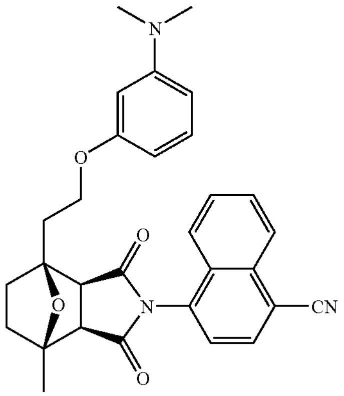 | [3aR-(3aα,4β,7β,7aα)]-4-[4-[2-[3-(Dimethylamino) phenoxy]ethyl] octahydro-7-methyl-1,3-dioxo-4,7-epoxy-2H-isoindol-2-yl]-1-naphthalenecarbonitrile | 1.94 LCMS $[M + H]^+$ = 496.2 | 496 |
| 607 | 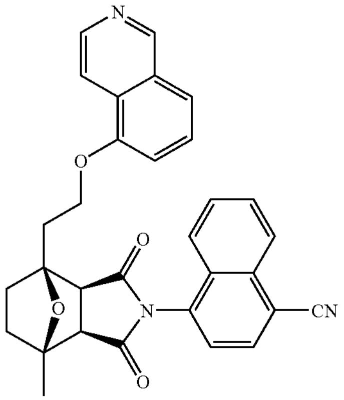 | [3aR-(3aα,4β,7β,7aα)]-4-[Octahydro-4-[2-(5-isoquinolinyloxy)ethyl]-7-methyl-1,3-dioxo-4,7-epoxy-2H-isoindol-2-yl]-1-naphthalenecarbonitrile | 1.89 LCMS $[M + H]^+$ = 504.2 | 496 |
| 608 | 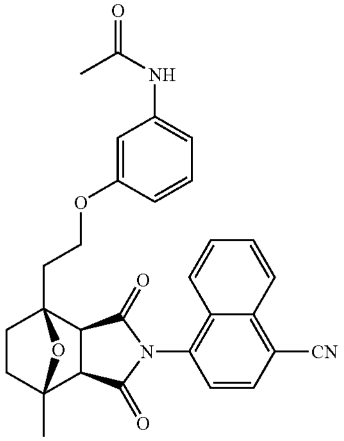 | N-[3-[2-[3aR-(3aα,4β,7β,7aα)]-2-(4-Cyano-1-naphthalenyl)octahydro-7-methyl-1,3-dioxo-4,7-epoxy-4H-isoindol-4-yl]ethoxy] phenylacetamide | 1.97 LCMS $[M + H]^+$ = 510.6 | 496 |

-continued

| Ex. No. | Compound Structure | Compound Name | Retention Time Min./ Molecular Mass | Pro. of Ex. |
|---|---|---|---|---|
| 609 | 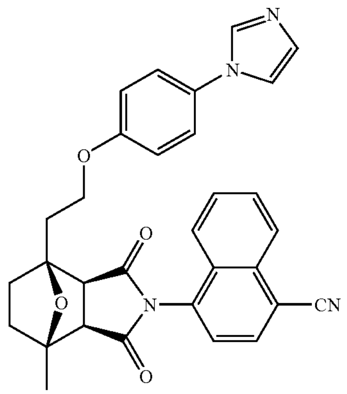 | [3aR-(3aα,4β,7β,7aα)]-4-[Octahydro-4-[2-[4-(1H-imidazol-1-yl)phenoxy]ethyl]-7-methyl-1,3-dioxo-4,7-epoxy-2H-isoindol-2-yl]-1-naphthalenecarbonitrile | 3.81 LCMS $[M+H]^+$ = 519.6 | 496 |
| 610 | 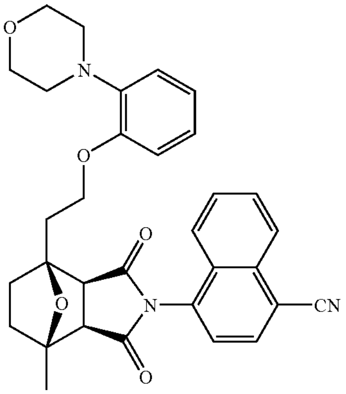 | [3aR-(3aα,4β,7β,7aα)]-4-[Octahydro-4-methyl-7-[2-[2-(4-morpholinyl)phenoxy]ethyl]-1,3-dioxo-4,7-epoxy-2H-isoindol-2-yl]-1-naphthalenecarbonitrile | 2.16 LCMS $[M+H]^+$ = 538.2 | 496 |
| 611 | 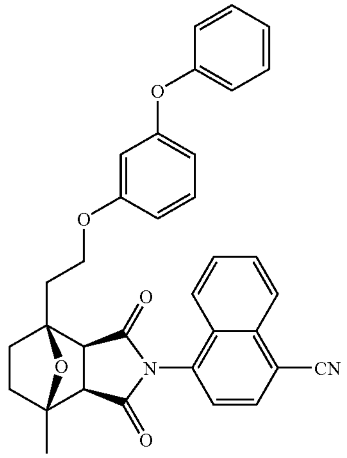 | [3aR-(3aα,4β,7β,7aα)]-4-[Octahydro-4-methyl-1,3-dioxo-7-[2-(3-phenoxyphenoxy)ethyl]-4,7-epoxy-2H-isoindol-2-yl]-1-naphthalenecarbonitrile | 1.89 LCMS $[M+H]^+$ = 545.2 | 496 |

-continued

| Ex. No. | Compound Structure | Compound Name | Retention Time Min./ Molecular Mass | Pro. of Ex. |
|---|---|---|---|---|
| 612 | 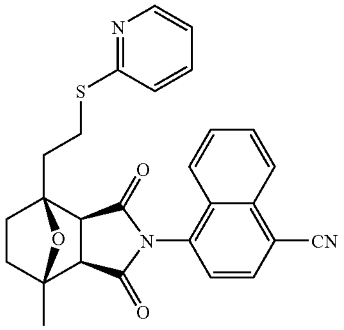 | [3aR-(3aα,4β,7β,7aα)]-4-[Octahydro-4-methyl-1,3-dioxo-7-[2-(2-pyridinylthio)ethyl]-4,7-epoxy-2H-isoindol-2-yl]-1-naphthalenecarbonitrile | 1.91 LCMS $[M + H]^+$ = 469.6 | 496 |
| 613 | 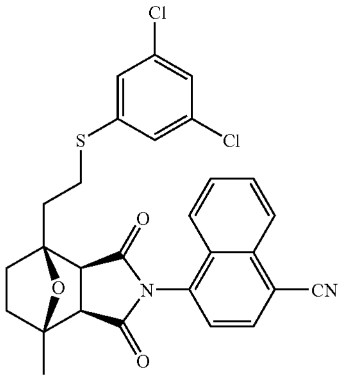 | [3aR-(3aα,4β,7β,7aα)]-4-[4-[2-[(3,5-Dichlorophenyl)thio]ethyl]octahydro-7-methyl-1,3-dioxo-4,7-epoxy-2H-isoindol-2-yl]-1-naphthalenecarbonitrile | 1.53 LCMS $[M + H]^+$ = 537.1 | 496 |
| 614 | 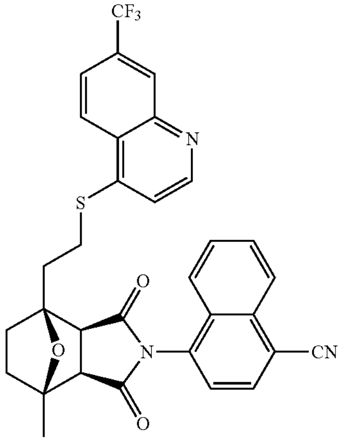 | [3aR-(3aα,4β,7β,7aα)]-4-[Octahydro-4-methyl-1,3-dioxo-7-[2-[[7-(trifluoromethyl)-4-quinolinyl]thio]ethyl]-4,7-epoxy-2H-isoindol-2-yl]-1-naphthalenecarbonitrile | 1.49 LCMS $[M + H]^+$ = 588.2 | 496 |
| 615 | 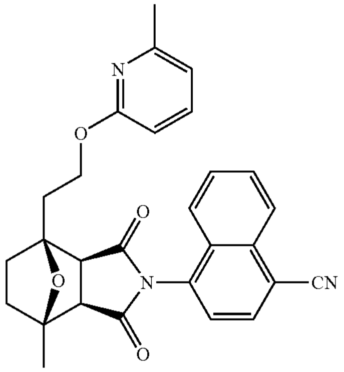 | [3aR-(3aα,4β,7β,7aα)]-4-[Octahydro-4-methyl-7-[2-[(6-methyl-2-pyridinyl)oxy]ethyl]-1,3-dioxo-4,7-epoxy-2H-isoindol-2-yl]-1-naphthalenecarbonitrile | 1.79 LCMS $[M + H]^+$ = 467.5 | 496 |

-continued

| Ex. No. | Compound Structure | Compound Name | Retention Time Min./ Molecular Mass | Pro. of Ex. |
|---|---|---|---|---|
| 616 | 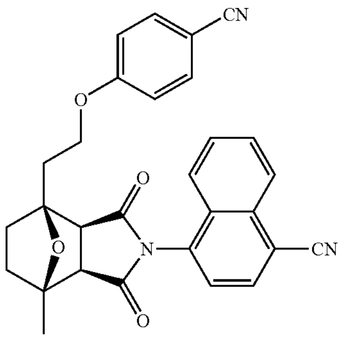 | [3aR-(3aα,4β,7β,7aα)]-4-[4-[2-(4-Cyanophenoxy)ethyl] octahydro-7-methyl-1,3-dioxo-4,7-epoxy-2H-isoindol-2-yl]-1-naphthalenecarbonitrile | 1.98 LCMS $[M + H]^+$ = 478.2 | 496 |
| 617 | 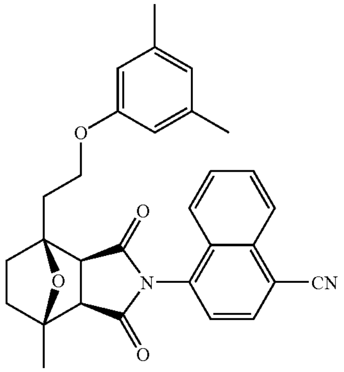 | [3aR-(3aα,4β,7β,7aα)]-4-[4-[2-(3,5-Dimethylphenoxy)ethyl] octahydro-7-methyl-1,3-dioxo-4,7-epoxy-2H-isoindol-2-yl]-1-napthalenecarbonitrile | 1.80 LCMS $[M + H]^+$ = 481.2 | 496 |
| 618 | 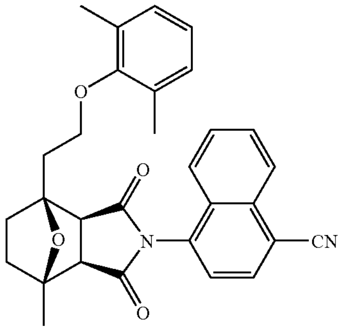 | [3aR-(3aα,4β,7β,7aα)]-4-[4-[2-(2,6-Dimethylphenoxy)ethyl] octahydro-7-methyl-1,3-dioxo-4,7-epoxy-2H-isoindol-2-yl]-1-naphthalenecarbonitrile | 1.88 LCMS $[M + H]^+$ = 481.2 | 496 |
| 619 | 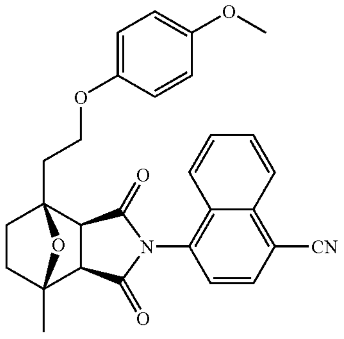 | [3aR-(3aα,4β,7β,7aα)]-4-[Octahydro-4-[2-(4-methoxyphenoxy)ethyl]-7-methyl-1,3-dioxo-4,7-epoxy-2H-isoindol-2-yl]-1-naphthalenecarbonitrile | 1.50 LCMS $[M + H]^+$ = 483.2 | 496 |

-continued

| Ex. No. | Compound Structure | Compound Name | Retention Time Min./ Molecular Mass | Pro. of Ex. |
|---|---|---|---|---|
| 620 | 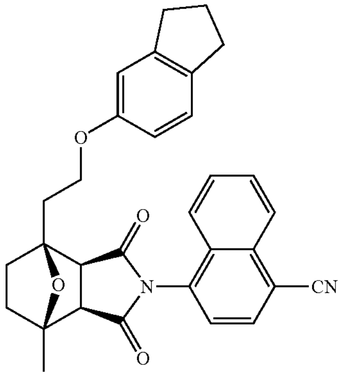 | [3aR-(3aα,4β,7β,7aα)]-4-[4-[2-[(2,3-Dihydro-1H-inden-5-yl)oxy]ethyl]octahydro-7-methyl-1,3-dioxo-4,7-epoxy-2H-isoindol-2-yl]-1-naphthalenecarbonitrile | 2.14 LCMS $[M + H]^+$ = 493.3 | 496 |
| 621 | 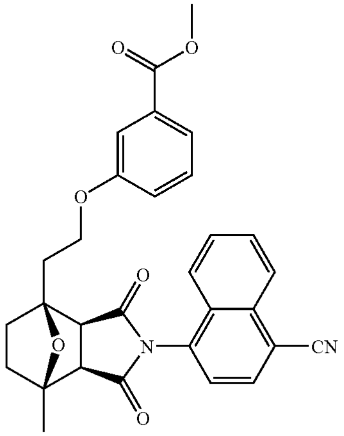 | 3-[2-[[3aR-(3aα,4β,7β,7aα)]-2-(4-Cyano-1-naphthalenyl)octahydro-7-methyl-1,3-dioxo-4,7-epoxy-4H-isoindol-4-yl]ethoxy]benzoic acid, methyl ester | 3.99 LCMS $[M + H]^+$ = 511.2 | 496 |
| 622 | 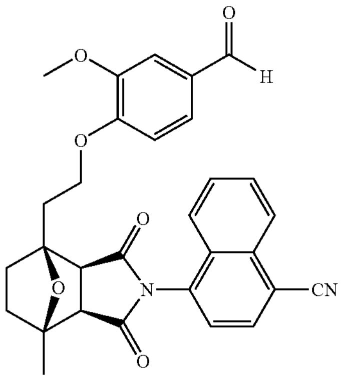 | [3aR-(3aα,4β,7β,7aα)]-4-[4-[2-(4-Formyl-2-methoxyphenoxy)ethyl] octahydro-7-methyl-1,3-dioxo-4,7-epoxy-2H-isoindol-2-yl]-1-naphthalenecarbonitrile | 2.01 LCMS $[M + H]^+$ = 511.2 | 496 |
| 623 | 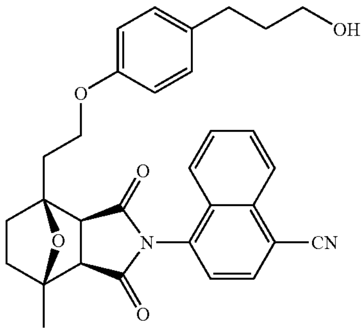 | [3aR-(3aα,4β,7β,7aα)]-4-[Octahydro-4-[2-[4-(3-hydroxypropyl)phenoxy] ethyl]-7-methyl-1,3-dioxo-4,7-epoxy-2H-isoindol-2-yl]-1-naphthalenecarbonitrile | 1.93 LCMS $[M + H]^+$ = 511.3 | 496 |

-continued

| Ex. No. | Compound Structure | Compound Name | Retention Time Min./ Molecular Mass | Pro. of Ex. |
|---|---|---|---|---|
| 624 | 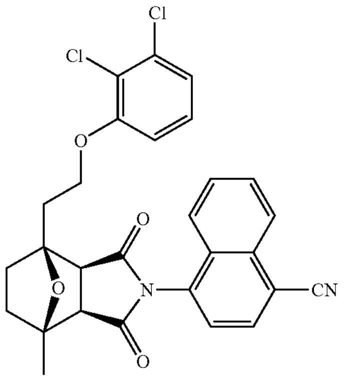 | [3aR-(3aα,4β,7β,7aα)]-4-[4-[2-(2,3-Dichlorophenoxy)ethyl] octahydro-7-methyl-1,3-dioxo-4,7-epoxy-2H-isoindol-2-yl]-1-naphthalenecarbonitrile | 1.79 LCMS $[M + H]^+$ = 521.1 | 496 |
| 625 | 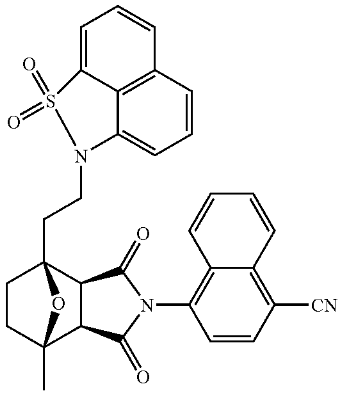 | [3aR-(3aα,4β,7β,7aα)]-4-[4-[2-(1,1-Dioxido-2H-naphtho[1,8-cd]isothiazol-2-yl)ethyl]octahydro-7-methyl-1,3-dioxo-4,7-epoxy-2H-isoindol-2-yl]-1-naphthalenecarbonitrile | 1.69 LCMS $[M + H]^+$ = 564.2 | 496 |
| 626 | 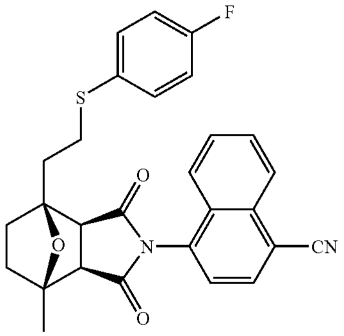 | [3aR-(3aα,4β,7β,7aα)]-4-[4-[2-[(4-Fluorophenyl)thio]ethyl] octahydro-7-methyl-1,3-dioxo-4,7-epoxy-2H-isoindol-2-yl]-1-naphthalenecarbonitrile | 2.03 LCMS $[M + H]^+$ = 487.2 | 496 |
| 627 | 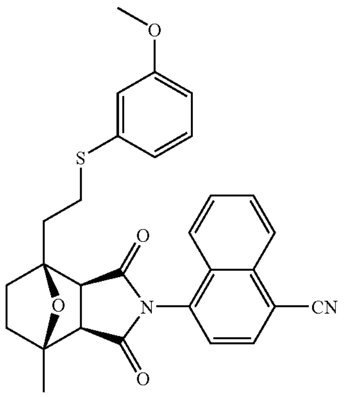 | [3aR-(3aα,4β,7β,7aα)]-4-[Octahydro-4-[2-[(3-methoxyphenyl)thio] ethyl]-7-methyl-1,3-dioxo-4,7-epoxy-2H-isoindol-2-yl]-1-naphthalenecarbonitrile | 2.02 LCMS $[M + H]^+$ = 499.2 | 496 |

-continued

| Ex. No. | Compound Structure | Compound Name | Retention Time Min./ Molecular Mass | Pro. of Ex. |
|---|---|---|---|---|
| 628 | 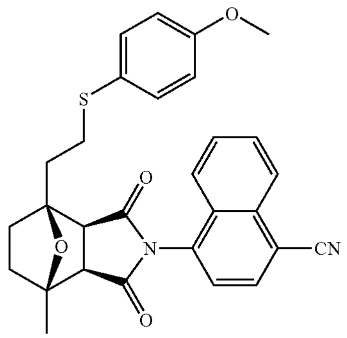 | [3aR-(3aα,4β,7β,7aα)]-4-[Octahydro-4-[2-[(4-methoxyphenyl)thio]ethyl]-7-methyl-1,3-dioxo-4,7-epoxy-2H-isoindol-2-yl]-1-naphthalenecarbonitrile | 1.99 LCMS $[M + H]^+$ = 499.2 | 496 |
| 629 | 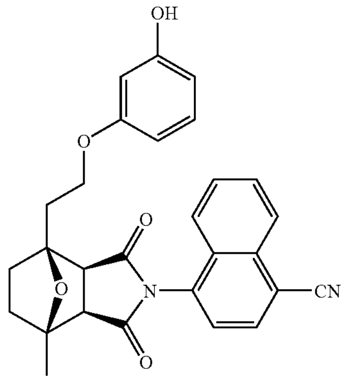 | [3aR-(3aα,4β,7β,7aα)]-4-[Octahydro-4-[2-(3-hydroxyphenoxy)ethyl]-7-methyl-1,3-dioxo-4,7-epoxy-2H-isoindol-2-yl]-1-naphthalenecarbonitrile | 2.27 LCMS $[M + H]^+$ = 469.2 | 496 |
| 630 | 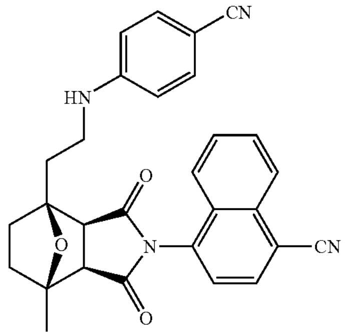 | [3aR-(3aα,4β,7β,7aα)]-4-[4-[2-[(4-Cyanophenyl)amino]ethyl]octahydro-7-methyl-1,3-dioxo-4,7-epoxy-2H-isoindol-2-yl]-1-naphthalenecarbonitrile | 3.56 LCMS $[M + H]^+$ = 477.2 | 496 |
| 631 | 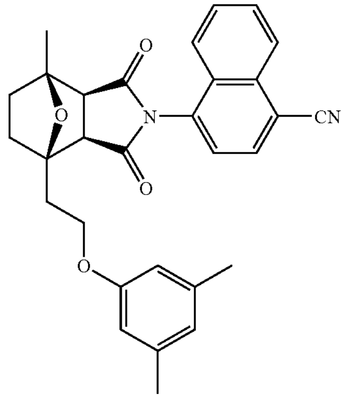 | [3aS-(3aα,4β,7β,7aα)]-4-[4-[2-(3,5-Dimethylphenoxy)ethyl]octahydro-7-methyl-1,3-dioxo-4,7-epoxy-2H-isoindol-2-yl]-1-naphthalenecarbonitrile | 4.10 LCMS $[M + H]^+$ = 481.2 | 496 |

-continued

| Ex. No. | Compound Structure | Compound Name | Retention Time Min./ Molecular Mass | Pro. of Ex. |
|---|---|---|---|---|
| 632 | 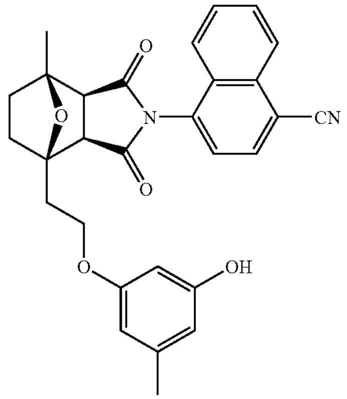 | [3aS-(3aα,4β,7β,7aα)]-4-[Octahydro-4-[2-(3-hydroxy-5-methylphenoxy)ethyl]-7-methyl-1,3-dioxo-4,7-epoxy-2H-isoindol-2-yl]-1-naphthalenecarbonitrile | 3.56 LCMS $[M + H]^+$ = 483.2 | 496 |
| 633 | 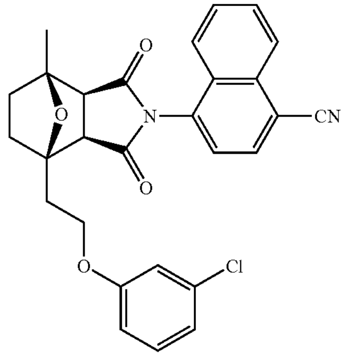 | [3aS-(3aα,4β,7β,7aα)]-4-[4-[2-(3-Chlorophenoxy)ethyl] octahydro-7-methyl-1,3-dioxo-4,7-epoxy-2H-isoindol-2-yl]-1-naphthalenecarbonitrile | 4.03 LCMS $[M + H]^+$ = 487.1 | 496 |
| 634 | 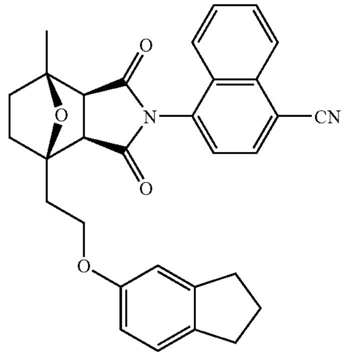 | [3aS-(3aα,4β,7β,7aα)]-4-[4-[2-[(2,3-Dihydro-1H-inden-5-yl)oxy] ethyl]octahydro-7-methyl-1,3-dioxo-4,7-epoxy-2H-isoindol-2-yl]-1-naphthalenecarbonitrile | 4.15 LCMS $[M + H]^+$ = 493.2 | 496 |
| 635 | 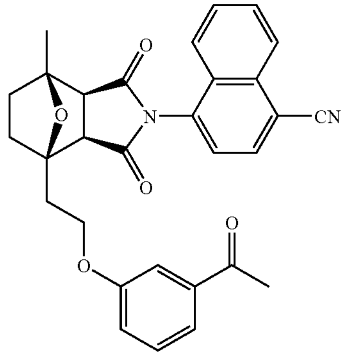 | [3aS-(3aα,4β,7β,7aα)]-4-[4-[2-(3-Acetylphenoxy)ethyl] octahydro-7-methyl-1,3-dioxo-4,7-epoxy-2H-isoindol-2-yl]-1-naphthalenecarbonitrile | 3.65 LCMS $[M + H]^+$ = 495.2 | 496 |

-continued

| Ex. No. | Compound Structure | Compound Name | Retention Time Min./ Molecular Mass | Pro. of Ex. |
|---|---|---|---|---|
| 636 | 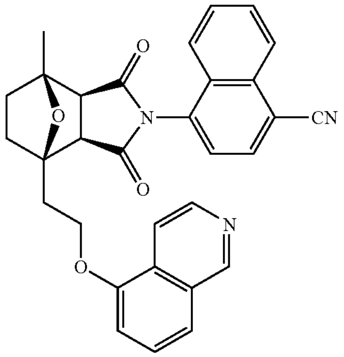 | [3aS-(3aα,4β,7β,7aα)]-4-[Octahydro-4-[2-(5-isoquinolinyloxy)ethyl]-7-methyl-1,3-dioxo-4,7-epoxy-2H-isoindol-2-yl]-1-naphthalenecarbonitrile, trifluoroacetate (1:1) | 3.67 LCMS $[M + H]^+$ = 504.2 | 496 |
| 637 | 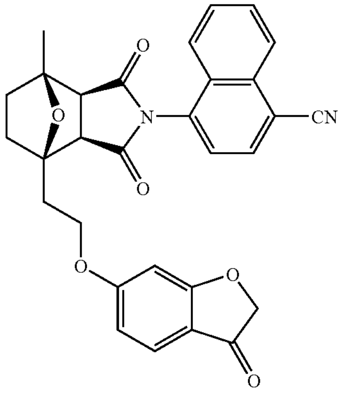 | [3aS-(3aα,4β,7β,7aα)]-4-[4-[2-[(2,3-Dihydro-3-oxo-6-benzofuranyl)oxy]ethyl] octahydro-7-methyl-1,3-dioxo-4,7-epoxy-2H-isoindol-2-yl]-1-naphthalenecarbonitrile | 2.90 LCMS $[M + H]^+$ = 509.2 | 496 |
| 638 | 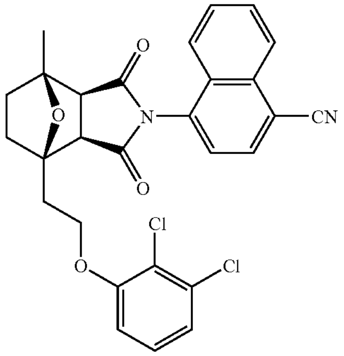 | [3aS-(3aα,4β,7β,7aα)]-4-[4-[2-(2,3-Dichlorophenoxy)ethyl] octahydro-7-methyl-1,3-dioxo-4,7-epoxy-2H-isoindol-2-yl]-1-naphthalenecarbonitrile | 2.80 LCMS $[M + H]^+$ = 521.1 | 496 |
| 639 | 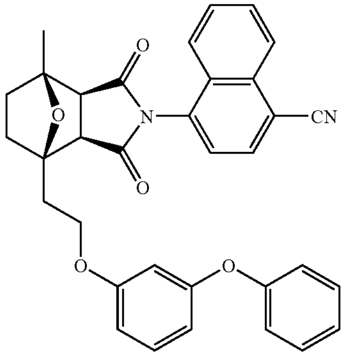 | [3aS-(3aα,4β,7β,7aα)]-4-[Octahydro-4-methyl-1,3-dioxo-7-[2-(3-phenoxyphenoxy)ethyl]-4,7-epoxy-2H-isoindol-2-yl]-1-naphthalenecarbonitrile | 3.54 LCMS $[M + H]^+$ = 545.2 | 496 |

-continued

| Ex. No. | Compound Structure | Compound Name | Retention Time Min./ Molecular Mass | Pro. of Ex. |
|---|---|---|---|---|
| 640 | 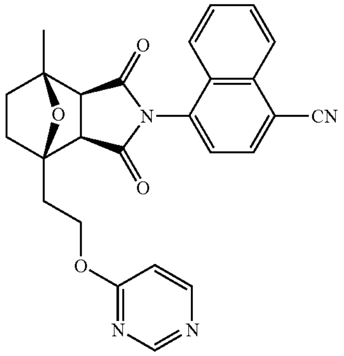 | [3aS-(3aα,4β,7β,7aα)]-4-[Octahydro-4-methyl-1,3-dioxo-7-[2-(4-pyrimidinyloxy)ethyl]-4,7-epoxy-2H-isoindol-2-yl]-1-naphthalenecarbonitrile | 4.13 LCMS $[M + H]^+$ = 455.2 | 496 |
| 641 | 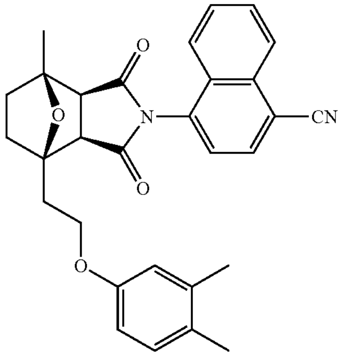 | [3aS-(3aα,4β,7β,7aα)]-4-[4-[2-(3,4-Dimethylphenoxy)ethyl]octahydro-7-methyl-1,3-dioxo-4,7-epoxy-2H-isoindol-2-yl]-1-naphthalenecarbonitrile | 4.19 LCMS $[M + H]^+$ = 481.2 | 496 |
| 642 | 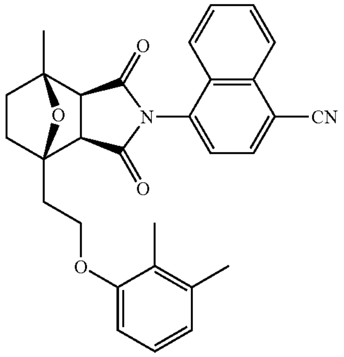 | [3aS-(3aα,4β,7β,7aα)]-4-[4-[2-(2,3-Dimethylphenoxy)ethyl]octahydro-7-methyl-1,3-dioxo-4,7-epoxy-2H-isoindol-2-yl]-1-naphthalenecarbonitrile | 2.80 LCMS $[M + H]^+$ = 481.2 | 496 |
| 643 | 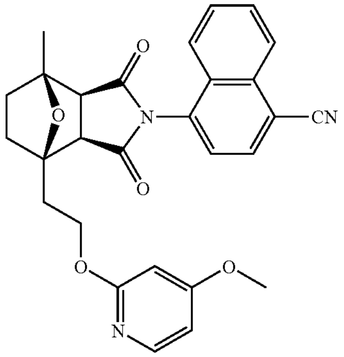 | [3aS-(3aα,4β,7β,7aα)]-4-[Octahydro-4-[2-[(4-methoxy-2-pyridinyl)oxy]ethyl]-7-methyl-1,3-dioxo-4,7-epoxy-2H-isoindol-2-yl]-1-naphthalenecarbonitrile | 2.72 LCMS $[M + H]^+$ = 484.2 | 496 |

-continued

| Ex. No. | Compound Structure | Compound Name | Retention Time Min./ Molecular Mass | Pro. of Ex. |
|---|---|---|---|---|
| 644 | 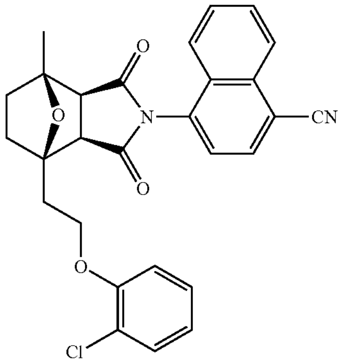 | [3aS-(3aα,4β,7β,7aα)]-4-[4-[2-(2-Chlorophenoxy)ethyl]octahydro-7-methyl-1,3-dioxo-4,7-epoxy-2H-isoindol-2-yl]-1-naphthalenecarbonitrile | 2.63 LCMS $[M + H]^+$ = 487.1 | 496 |
| 645 | 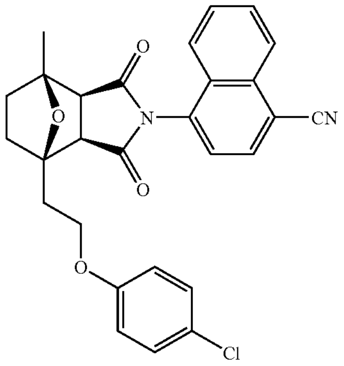 | [3aS-(3aα,4β,7β,7aα)]-4-[4-[2-(4-Chlorophenoxy)ethyl]octahydro-7-methyl-1,3-dioxo-4,7-epoxy-2H-isoindol-2-yl]-1-naphthalenecarbonitrile | 4.07 LCMS $[M + H]^+$ = 487.1 | 496 |
| 646 | 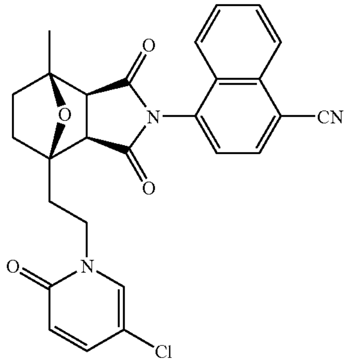 | [3aS-(3aα,4β,7β,7aα)]-4-[4-[2-(5-Chloro-2-oxo-1(2H)-pyridinyl)ethyl]octahydro-7-methyl-1,3-dioxo-4,7-epoxy-2H-isoindol-2-yl]-1-naphthalenecarbonitrile | 4.13 LCMS $[M + H]^+$ = 488.1 | 496 |
| 647 | 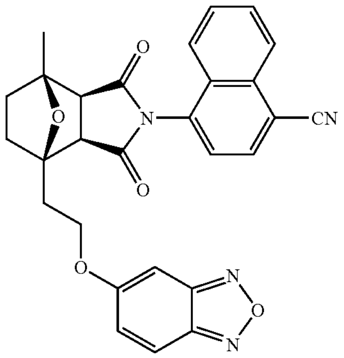 | [3aS-(3aα,4β,7β,7aα)]-4-[4-[2-(2,1,3-Benzoxadiazol-5-yloxy)ethyl]octahydro-7-methyl-1,3-dioxo-4,7-epoxy-2H-isoindol-2-yl]-1-naphthalenecarbonitrile | 3.15 LCMS $[M + H]^+$ = 495.2 | 496 |

-continued

| Ex. No. | Compound Structure | Compound Name | Retention Time Min./ Molecular Mass | Pro. of Ex. |
|---|---|---|---|---|
| 648 | 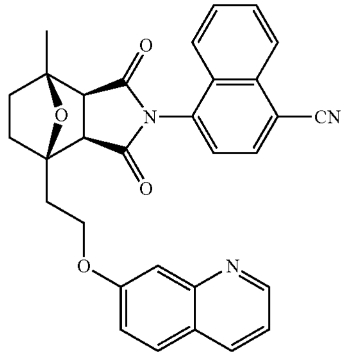 | [3aS-(3aα,4β,7β,7aα)]-4-[Octahydro-4-methyl-1,3-dioxo-7-[2-(7-quinolinyloxy)ethyl]-4,7-epoxy-2H-isoindol-2-yl]-1-naphthalenecarbonitrile, trifluoroacetate (1:1) | 3.93 LCMS $[M + H]^+$ = 504.2 | 496 |
| 649 | 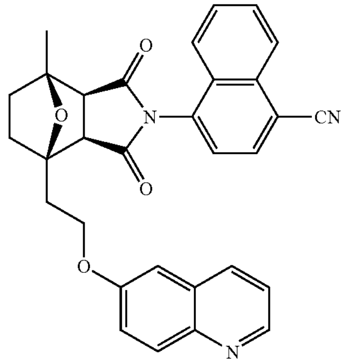 | [3aS-(3aα,4β,7β,7aα)]-4-[Octahydro-4-methyl-1,3-dioxo-7-[2-(6-quinolinyloxy)ethyl]-4,7-epoxy-2H-isoindol-2-yl]-1-naphthalenecarbonitrile, trifluoroacetate (1:1) | 4.01 LCMS $[M + H]^+$ = 504.2 | 496 |
| 650 | 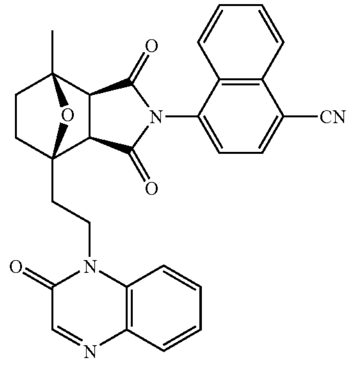 | [3aS-(3aα,4β,7β,7aα)]-4-[Octahydro-4-methyl-1,3-dioxo-7-[2-(2-oxo-1(2H)-quinoxalinyl)ethyl]-4,7-epoxy-2H-isoindol-2-yl]-1-naphthalenecarbonitrile, trifluoroacetate (1:1) | 3.33 LCMS $[M + H]^+$ = 505.2 | 496 |
| 651 | 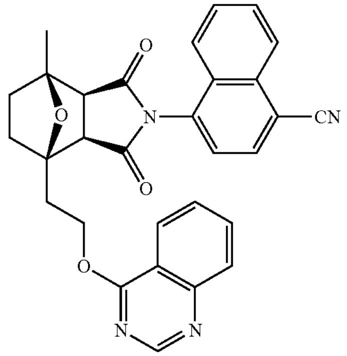 | [3aS-(3aα,4β,7β,7aα)]-4-[Octahydro-4-methyl-1,3-dioxo-7-[2-(4-quinazolinyloxy)ethyl]-4,7-epoxy-2H-isoindol-2-yl]-1-naphthalenecarbonitrile, trifluoroacetate (1:1) | 3.39 LCMS $[M + H]^+$ = 505.2 | 496 |

-continued

| Ex. No. | Compound Structure | Compound Name | Retention Time Min./ Molecular Mass | Pro. of Ex. |
|---|---|---|---|---|
| 652 | 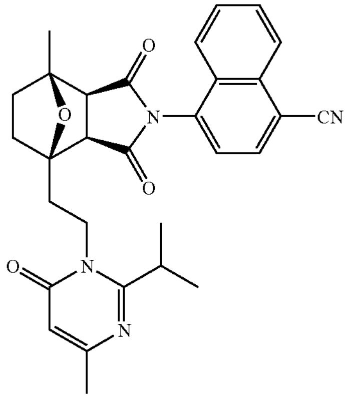 | [3aS-(3aα,4β,7β,7aα)]-4-[Octahydro-4-methyl-7-[2-[4-methyl-2-(1-methylethyl)-6-oxo-1(6H)-pyrimidinyl]ethyl]-1,3-dioxo-4,7-epoxy-2H-isoindol-2-yl]-1-naphthalenecarbonitrile | 3.72 LCMS $[M + H]^+$ = 511.3 | 496 |
| 653 | 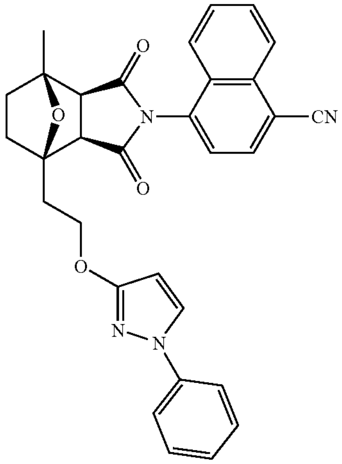 | [3aS-(3aα,4β,7β,7aα)]-4-[Octahydro-4-methyl-1,3-dioxo-7-[2-[(1-phenyl-1H-pyrazol-3-yl)oxy]ethyl]-4,7-epoxy-2H-isoindol-2-yl]-1-naphthalenecarbonitrile, trifluoroacetate (1:1) | 3.48 LCMS $[M + H]^+$ = 519.2 | 496 |
| 654 | 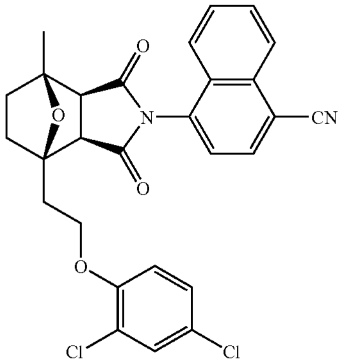 | [3a-(3aα,4β,7β,7aα)]-4-[4-[2-(2,4-Dichlorophenoxy)ethyl]octahydro-7-methyl-1,3-dioxo-4,7-epoxy-2H-isoindol-2-yl]-1-naphthalenecarbonitrile | 2.85 LCMS $[M + H]^+$ = 521.1 | 496 |

-continued

| Ex. No. | Compound Structure | Compound Name | Retention Time Min./ Molecular Mass | Pro. of Ex. |
|---|---|---|---|---|
| 655 | 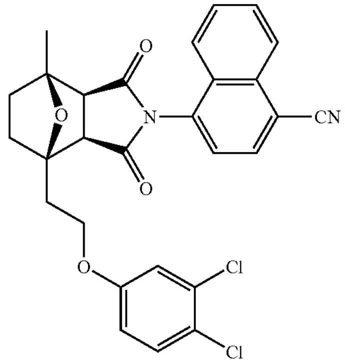 | [3aS-(3aα,4β,7β,7aα)]-4-[4-[2-(3,4-Dichlorophenoxy)ethyl]octahydro-7-methyl-1,3-dioxo-4,7-epoxy-2H-isoindol-2-yl]-1-naphthalenecarbonitrile | 2.86 LCMS $[M + H]^+$ = 521.1 | 496 |
| 656 | 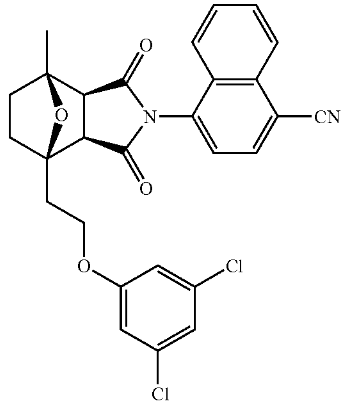 | [3aS-(3aα,4β,7β,7aα)]-4-[4-[2-(3,5-Dichlorophenoxy)ethyl]octahydro-7-methyl-1,3-dioxo-4,7-epoxy-2H-isoindol-2-yl]-1-naphthalenecarbonitrile | 3.47 LCMS $[M + H]^+$ = 521.1 | 496 |
| 657 | 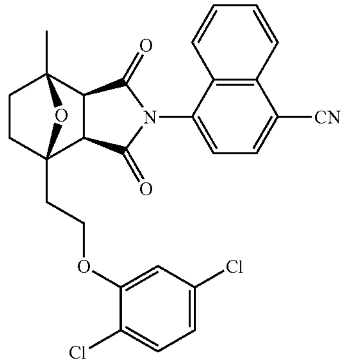 | [3aS-(3aα,4β,7β,7aα)]-4-[4-[2-(2,5-Dichlorophenoxy)ethyl]octahydro-7-methyl-1,3-dioxo-4,7-epoxy-2H-isoindol-2-yl]-1-naphthalenecarbonitrile | 3.33 LCMS $[M + H]^+$ = 521.1 | 496 |
| 658 | 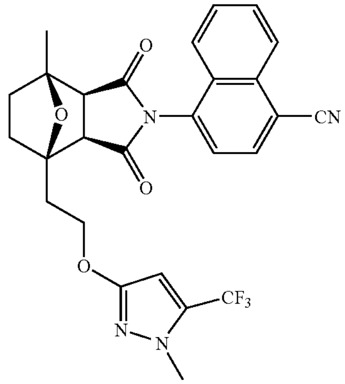 | [3aS-(3aα,4β,7β,7aα)]-4-[Octahydro-4-methyl-7-[2-[[1-methyl-5-(trifluoromethyl)-1H-pyrazol-3-yl]oxy]ethyl]-1,3-dioxo-4,7-epoxy-2H-isoindol-2-yl]-1-naphthalenecarbonitrile, trifluoroacetate (1:1) | 3.87 LCMS $[M + H]^+$ = 525.2 | 496 |

-continued

| Ex. No. | Compound Structure | Compound Name | Retention Time Min./ Molecular Mass | Pro. of Ex. |
|---|---|---|---|---|
| 659 | 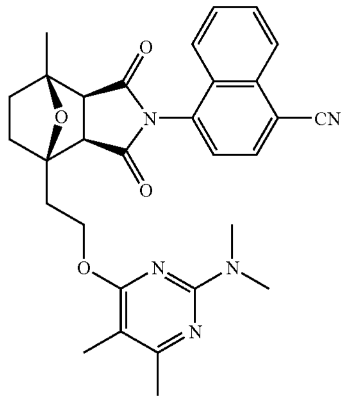 | [3aS-(3aα,4β,7β,7aα)]-4-[4-[2-[[2-(Dimethylamino)-5,6-dimethyl-4-pyrimidinyl]oxy]ethyl]octahydro-7-methyl-1,3-dioxo-4,7-epoxy-2H-isoindol-2-yl]-1-naphthalenecarbonitrile, trifluoroacetate (1:1) | 2.71 LCMS $[M + H]^+$ = 526.2 | 496 |
| 660 | 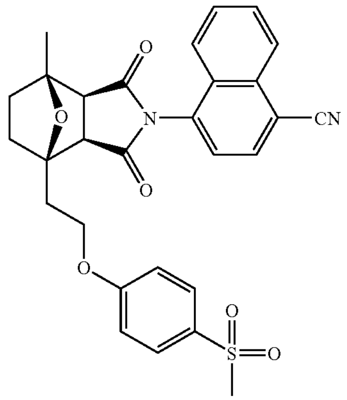 | [3aS-(3aα,4β,7β,7aα)]-4-[Octahydro-4-methyl-7-[2-[4-(methylsulfonyl)phenoxy]ethyl]-1,3-dioxo-4,7-epoxy-2H-isoindol-2-yl]-1-naphthalenecarbonitrile | 2.91 LCMS $[M + H]^+$ = 531.2 | 496 |
| 661 | 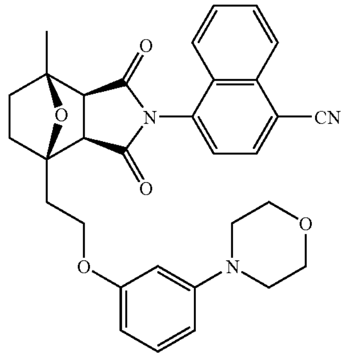 | [3aS-(3aα,4β,7β,7aα)]-4-[Octahydro-4-methyl-7-[2-[3-(4-morpholinyl)phenoxy]ethyl]-1,3-dioxo-4,7-epoxy-2H-isoindol-2-yl]-1-naphthalenecarbonitrile, trifluoroacetate (1:1) | 3.78 LCMS $[M + H]^+$ = 538.2 | 496 |

-continued

| Ex. No. | Compound Structure | Compound Name | Retention Time Min./ Molecular Mass | Pro. of Ex. |
|---|---|---|---|---|
| 662 | 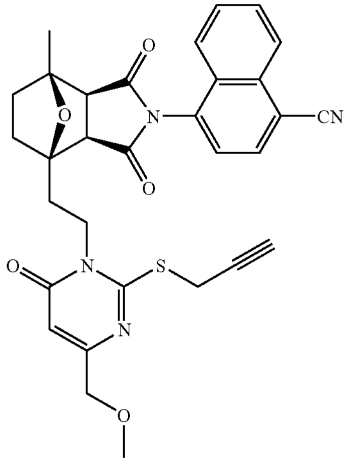 | [3aS-(3aα,4β,7β,7aα)]-4-[Octahydro-4-[2-[4-(methoxymethyl)-6-oxo-2-(2-propynylthio)-1(6H)-pyrimidinyl]ethyl]-7-methyl-1,3-dioxo-4,7-epoxy-2H-isoindol-2-yl]-1-naphthalenecarbonitrile, trifluoroacetate (1:1) | 4.18 LCMS $[M + H]^+$ = 569.2 | 496 |
| 663 | 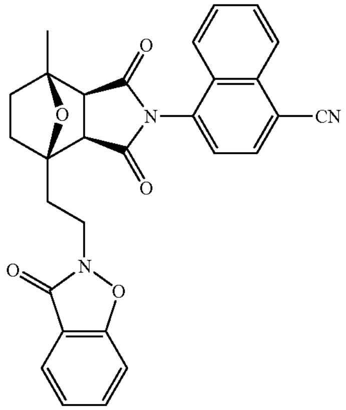 | [3aS-(3aα,4β,7β,7aα)]-4-[Octahydro-4-methyl-1,3-dioxo-7-[2-(3-oxo-1,2-benzisoxazol-2(3H)-yl)ethyl]-4,7-epoxy-2H-isoindol-2-yl]-1-naphthalenecarbonitrile | 4.18 LCMS $[M + H]^+$ = 494.2 | 496 |
| 664 | 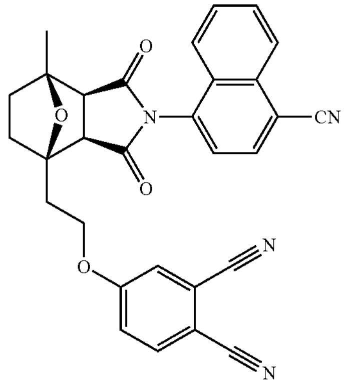 | [3aS-(3aα,4β,7β,7aα)]-4-[2-[2-(4-Cyano-1-naphthalenyl)octahydro-7-methyl-1,3-dioxo-4,7-epoxy-4H-isoindol-4-yl]ethoxy]-1,2-benzenedicarbonitrile | 4.30 LCMS $[M + H]^+$ = 503.1 | 496 |

-continued

| Ex. No. | Compound Structure | Compound Name | Retention Time Min./ Molecular Mass | Pro. of Ex. |
|---|---|---|---|---|
| 665 | 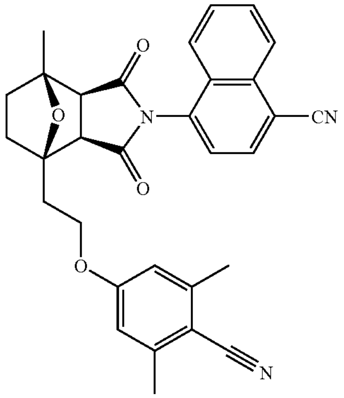 | [3aS-(3aα,4β,7β,7aα)]-4-[4-[2-(4-Cyano-3,5-dimethylphenoxy)ethyl]octahydro-7-methyl-1,3-dioxo-4,7-epoxy-2H-isoindol-2-yl]-1-naphthalenecarbonitrile | 4.13 LCMS $[M + H]^+$ = 506.2 | 496 |
| 666 | 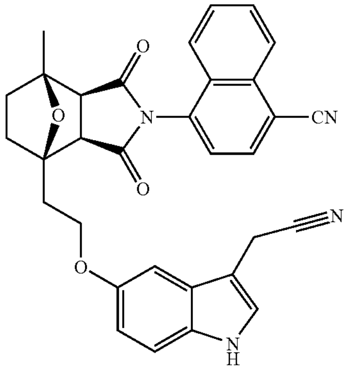 | [3aS-(3aα,4β,7β,7aα)]-5-[2-[2-(4-Cyano-1-naphthalenyl)octahydro-7-methyl-1,3-dioxo-4,7-epoxy-4H-isoindol-4-yl]ethoxy]-1H-indole-3-acetonitrile, trifluoroacetate (1:1) | 3.36 LCMS $[M + H]^+$ = 531.2 | 496 |
| 667 | 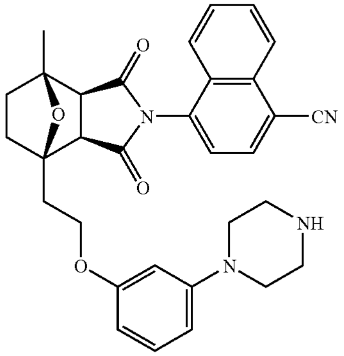 | [3aS-(3aα,4β,7β,7aα)]-4-[Octahydro-4-methyl-1,3-dioxo-7-[2-[3-(1-piperazinyl)phenoxy]ethyl]-4,7-epoxy-2H-isoindol-2-yl]-1-naphthalenecarbonitrile, trifluoroacetate (1:1) | 3.81 LCMS $[M + H]^+$ = 537.2 | 496 |
| 668 | 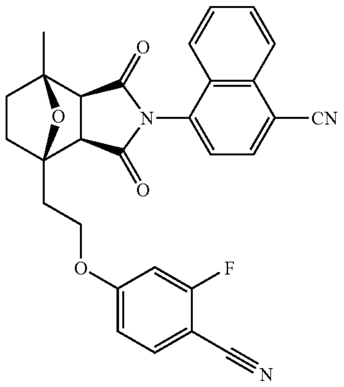 | [3aS-(3aα,4β,7β,7aα)]-4-[4-[2-(4-Cyano-3-fluorophenoxy)ethyl]octahydro-7-methyl-1,3-dioxo-4,7-epoxy-2H-isoindol-2-yl]-1-naphthalenecarbonitrile | 2.89 LCMS $[M + H]^+$ = 496.2 | 496 |

-continued

| Ex. No. | Compound Structure | Compound Name | Retention Time Min./ Molecular Mass | Pro. of Ex. |
|---|---|---|---|---|
| 669 | 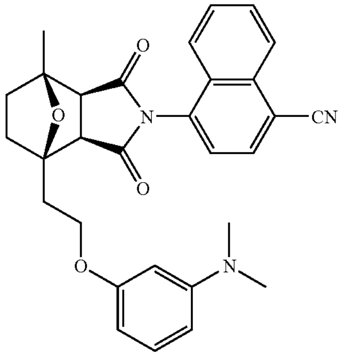 | [3aS-(3aα,4β,7β,7aα)]-4-[4-[2-[3-(Dimethylamino)phenoxy]ethyl]octahydro-7-methyl-1,3-dioxo-4,7-epoxy-2H-isoindol-2-yl]-1-naphthalenecarbonitrile, trifluoroacetate (1:1) | 3.37 LCMS $[M + H]^+$ = 496.2 | 496 |
| 670 | 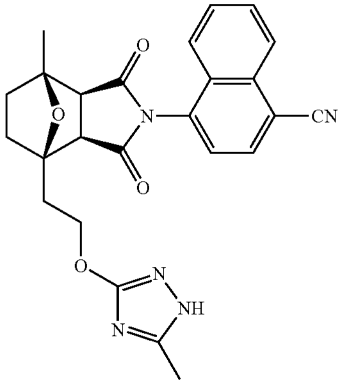 | [3aS-(3aα,4β,7β,7aα)]-4-[Octahydro-4-methyl-7-[2-[(5-methyl-1H-1,2,4-triazol-3-yl)oxy]ethyl]-1,3-dioxo-4,7-epoxy-2H-isoindol-2-yl]-1-naphthalenecarbonitrile, trifluoroacetate (1:1) | 3.26 LCMS $[M + H]^+$ = 458.2 | 496 |
| 671 | 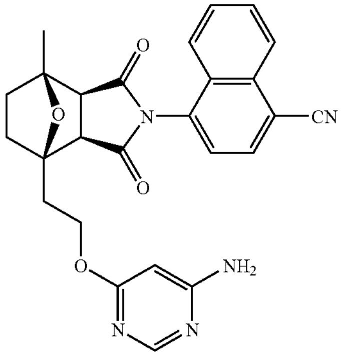 | [3aS-(3aα,4β,7β,7aα)]-4-[4-[2-[(6-Amino-4-pyrimidinyl)oxy]ethyl]octahydro-7-methyl-1,3-dioxo-4,7-epoxy-2H-isoindol-2-yl]-1-naphthalenecarbonitrile, trifluoroacetate (1:1) | 2.97 LCMS $[M + H]^+$ = 470.2 | 496 |
| 672 | 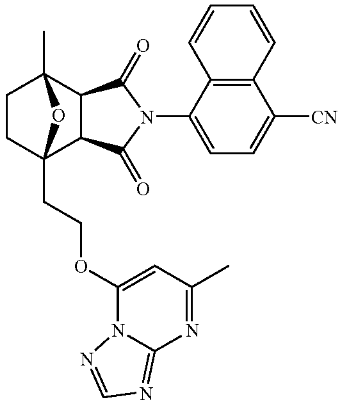 | [3aS-(3aα,4β,7β,7aα)]-4-[Octahydro-4-methyl-7-[2-[(5-methyl[1,2,4]triazolo[1,5-a]pyrimidin-7-yl)oxy]ethyl]-1,3-dioxo-4,7-epoxy-2H-isoindol-2-yl]-1-naphthalenecarbonitrile, trifluoroacetate (1:1) | 3.45 LCMS $[M + H]^+$ = 509.2 | 496 |

-continued

| Ex. No. | Compound Structure | Compound Name | Retention Time Min./ Molecular Mass | Pro. of Ex. |
|---|---|---|---|---|
| 673 | 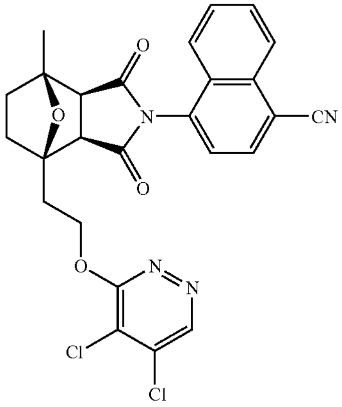 | [3aS-(3aα,4β,7β,7aα)]-4-[4-[2-[(4,5-Dichloro-3-pyridazinyl)oxy]ethyl]octahydro-7-methyl-1,3-dioxo-4,7-epoxy-2H-isoindol-2-yl]-1-naphthalenecarbonitrile | 3.79 LCMS $[M + H]^+$ = 523.1 | 496 |
| 674 | 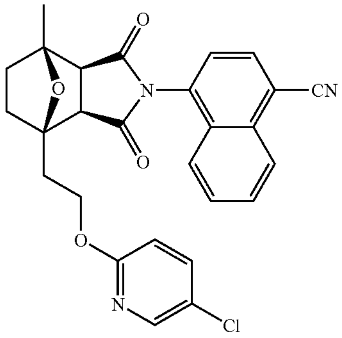 | [3aS-(3aα,4β,7β,7aα)]-4-[4-[2-[(5-Chloro-2-pyridinyl)oxy]ethyl]octahydro-7-methyl-1,3-dioxo-4,7-epoxy-2H-isoindol-2-yl]-naphthalenecarbonitrile | 3.86 LCMS $[M + H]^+$ = 488.4 | 496 |
| 675 | 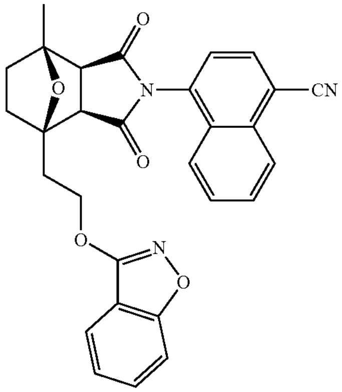 | [3aS-(3aα,4β,7β,7aα)]-4-[4-[2-(1,2-Benzisoxazol-3-yloxy)ethyl]octahydro-7-methyl-1,3-dioxo-4,7-epoxy-2H-isoindol-2-yl]-1-naphthalenecarbonitrile | 3.78 LCMS $[M + H]^+$ = 494.41 | 496 |
| 676 | 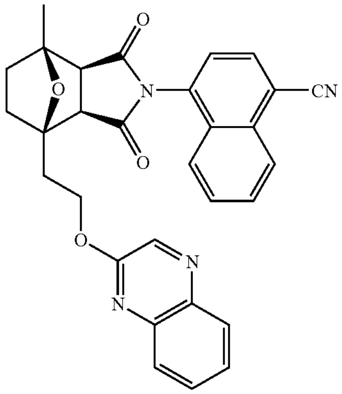 | [3aS-(3aα,4β,7β,7aα)]-4-[Octahydro-4-methyl-1,3-dioxo-7-[2-(2-quinoxalinyloxy)ethyl]-4,7-epoxy-2H-isoindol-2-yl]-1-napthalenecarbonitrile | 3.83 LCMS $[M + H]^+$ = 505.43 | 496 |

-continued

| Ex. No. | Compound Structure | Compound Name | Retention Time Min./ Molecular Mass | Pro. of Ex. |
|---|---|---|---|---|
| 677 | 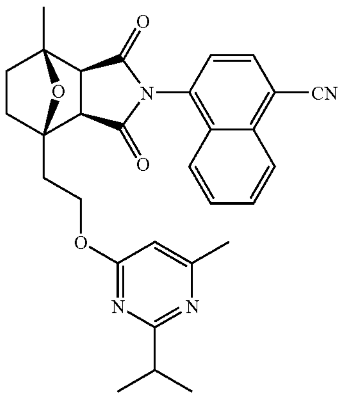 | [3aS-(3aα,4β,7β,7aα)]-4-[Octahydro-4-methyl-7-[2-[[6-methyl-2-(1-methylethyl)-4-pyrimidinyl]oxy]ethyl]-1,3-dioxo-4,7-epoxy-2H-isoindol-2-yl]-1-naphthalenecarbonitrile | 3.52 LCMS $[M + H]^+$ = 511.49 | 496 |
| 678 | 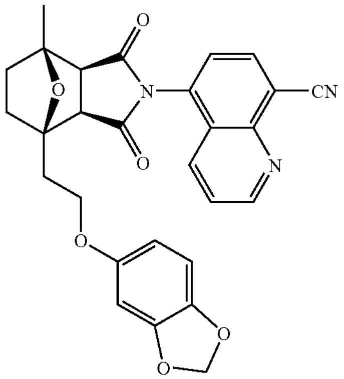 | [3aS-(3aα,4β,7β,7aα)]-5-[4-[2-(1,3-Benzodioxol-5-yloxy)ethyl]octahydro-7-methyl-1,3 -dioxo-4,7-epoxy-2H-isoindol-2-yl]-8-quinolinecarbonitrile | 3.327 LC $[M + H]^+$ = 498.24 | 467 & 487 |
| 679 | 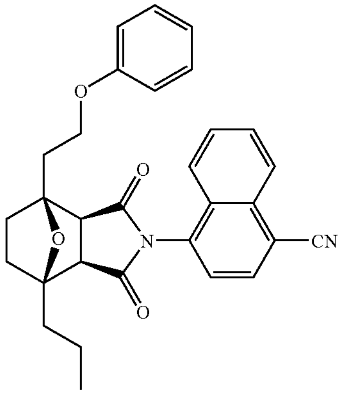 | [3aR-(3aα,4β,7β,7aα)]-4-[Octahydro-1,3-dioxo-4-(2-phenoxyethyl)-7-propyl-4,7-epoxy-2H-isoindol-2-yl]-1-naphthalenecarbonitrile | 7.77 & 8.01 atropisomers LC $[M + H]^+$ = 481.4 | 501 |

-continued

| Ex. No. | Compound Structure | Compound Name | Retention Time Min./ Molecular Mass | Pro. of Ex. |
|---|---|---|---|---|
| 680 | 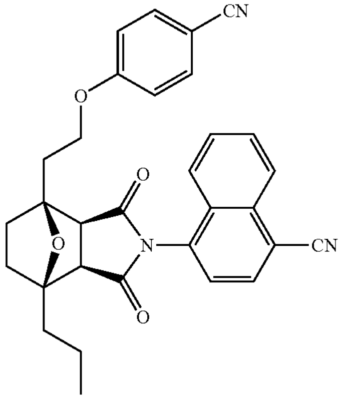 | [3aR-(3aα,4β,7β,7aα)]-4-[4-[2-(4-Cyanophenoxy)ethyl] octahydro-1,3-dioxo-7-propyl-4,7-epoxy-2H-isoindol-2-yl]-1-naphthalenecarbonitrile | 7.42 & 7.68 atropisomers LC $[M + H]^+$ = 506.38 | 501 |
| 681 | 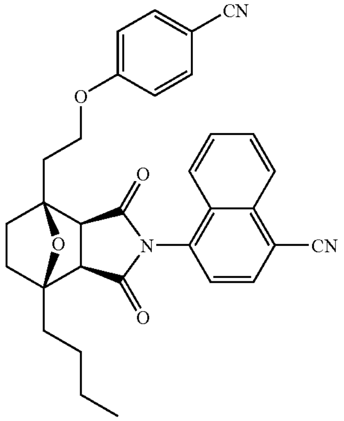 | [3(3aα,4β,7β,7aα)]-4-[4-Butyl-7-[2-(4-cyanophenoxy)ethyl] octahydro-1,3-dioxo-4,7-epoxy-2H-isoindol-2-yl]-1-naphthalenecarbonitrile | 7.69 & 7.92 atropisomers LC $[M + H]^+$ = 520.38 | 502 |
| 682 | 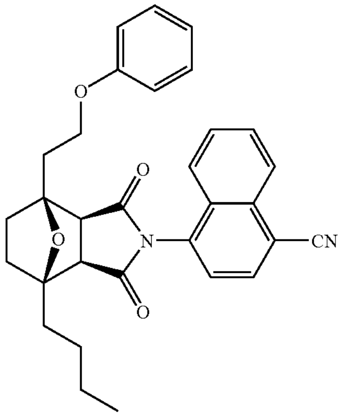 | [3aR-(3aα,4β,7β,7aα)]-4-[4-Butyloctahydro-1,3-dioxo-7-(2-phenoxyethyl)-4,7-epoxy-2H-isoindol-2-yl]-1-naphthalenecarbonitrile | 8.02 & 8.23 atropisomers LC $[M + H]^+$ = 495.33 | 502 |

-continued

| Ex. No. | Compound Structure | Compound Name | Retention Time Min./ Molecular Mass | Pro. of Ex. |
|---|---|---|---|---|
| 683 | 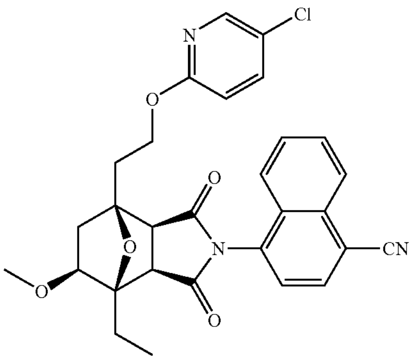 | [3aR-(3aα,4β,5β,7β,7aα)]-4-[7-[2-[(5-Chloro-2-pyridinyl)oxy]ethyl]-4-ethyloctahydro-5-methoxy-1,3-dioxo-4,7-epoxy-2H-isoindol-2-yl]-1-naphthalenecarbonitrile, trifluoroacetate (1:1) | 7.31 & 7.55 atropisomers LC $[M + H]^+$ = 532.3 | 504 |
| 684 | 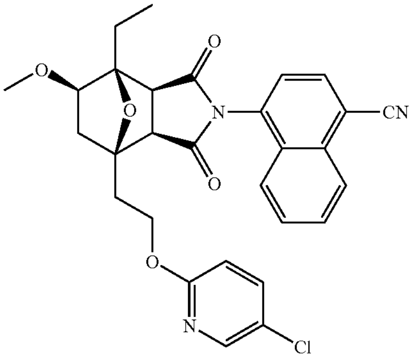 | [3aS-(3aα,4β,5β,7β,7aα)]-4-[7-[2-[(5-Chloro-2-pyridinyl)oxy]ethyl]-4-ethyloctahydro-5-methoxy-1,3-dioxo-4,7-epoxy-2H-isoindol-2-yl]-1-naphthalenecarbonitrile, trifluoroacetate (1:1) | 7.31 & 7.55 atropisomers LC $[M + H]^+$ = 532.3 | 504 |
| 685 | 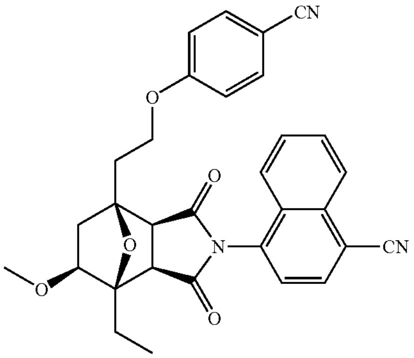 | [3aR-(3aα,4β,5β,7β,7aα)]-4-[7-[2-(4-Cyanophenoxy)ethyl]-4-ethyloctahydro-5-methoxy-1,3-dioxo-4,7-epoxy-2H-isoindol-2-yl]-1-naphthalenecarbonitrile | 6.84 & 7.10 atropisomers LC $[M + H]^+$ = 522.33 | 504 |
| 686 | 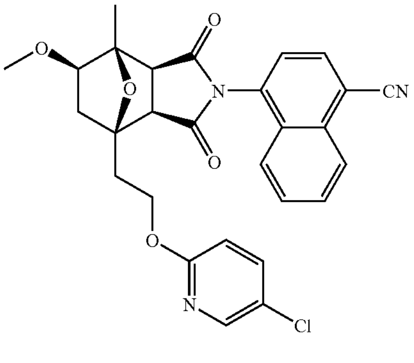 | [3aS-(3aα,4β,5β,7β,7aα)]-4-[7-[2-[(5-Chloro-2-pyridinyl)oxy]ethyl] octahydro-5-methoxy-4-methyl-1,3-dioxo-4,7-epoxy-2H-isoindol-2-yl]-1-naphthalenecarbonitrile | 3.37 & 3.52 atropisomers LC $[M + H]^+$ = 518.16 | 491 |

-continued

| Ex. No. | Compound Structure | Compound Name | Retention Time Min./ Molecular Mass | Pro. of Ex. |
|---|---|---|---|---|
| 687 | 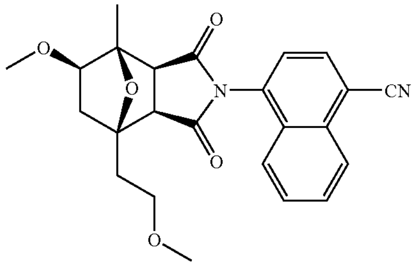 | [3aS-(3aα,4β,5β,7β,7aα)]-4-[Octahydro-5-methoxy-7-(2-methoxyethyl)-4-methyl-1,3-dioxo-4,7-epoxy-2H-isoindol-2-yl]-1-naphthalenecarbonitrile | 2.57 & 2.75 atropisomers LC $[M + H]^+$ = 421.18 | 491 |
| 688 | 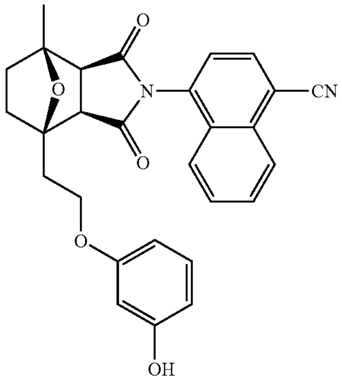 | [3aS-(3aα,4β,7β,7aα)]-4-[Octahydro-4-[2-(3-hydroxyphenoxy)ethyl]-7-methyl-1,3-dioxo-4,7-epoxy-2H-isoindol-2-yl]-1-naphthalenecarbonitrile | 3.38 LCMS $[M + H]^+$ = 469.38 | 496 |
| 689 | 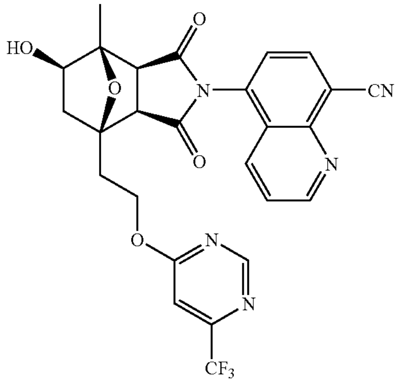 | [3aS-(3aα,4β,5β,7β,7aα)]-5-[Octahydro-5-hydroxy-4-methyl-1,3-dioxo-7-[2-[[6-(trifluoromethyl)-4-pyrimidinyl]oxy]ethyl]-4,7-epoxy-2H-isoindol-2-yl]-8-quinolinecarbonitrile | 2.833 LC $[M + H]^+$ = 540.17 | 485, 486, 487 & 488 |
| 690 | 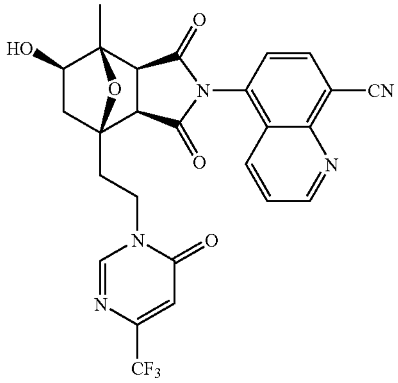 | [3aS-(3aα,4β,5β,7β,7aα)]-5-[Octahydro-5-hydroxy-4-methyl-1,3-dioxo-7-[2-[6-oxo-4-(trifluoromethyl)-1(6H)-pyrimidinyl]ethyl]-4,7-epoxy-2H-isoindol-2-yl]-8-quinolinecarbonitrile | 2.59 LC $[M + H]^+$ = 540.16 | 485, 486, 487 & 488 |

-continued

| Ex. No. | Compound Structure | Compound Name | Retention Time Min./ Molecular Mass | Pro. of Ex. |
|---|---|---|---|---|
| 691 | 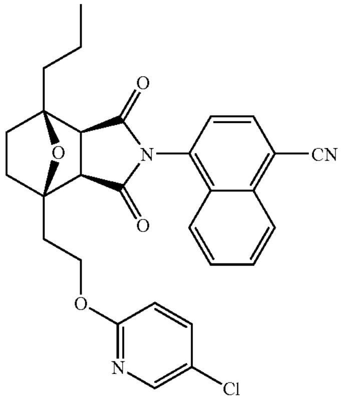 | [3aS-(3aα,4β,7β,7aα)]-4-[4-[2-[(5-Chloro-2-pyridinyl)oxy]ethyl] octahydro-1,3-dioxo-7-propyl-4,7-epoxy-2H-isoindol-2-yl]-1-naphthalenecarbonitrile | 7.91 & 8.15 atropisomers LC $[M + H]^+$ = 516.25 | 501 |
| 692 | 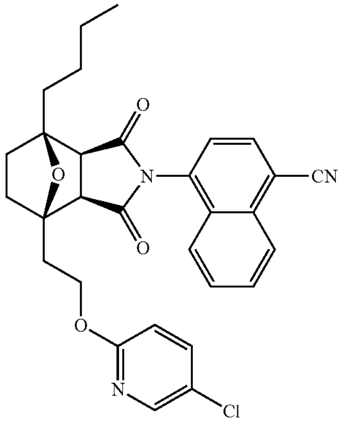 | [3aS-(3aα,4β,7β,7aα)]-4-[4-Butyl-7-[2-[(5-chloro-2-pyridinyl)oxy]ethyl] octahydro-1,3-dioxo-4,7-epoxy-2H-isoindol-2-yl]-1-naphthalenecarbonitrile | 8.18 & 8.39 atropisomers LC $[M + H]^+$ = 530.28 | 502 |
| 693 | 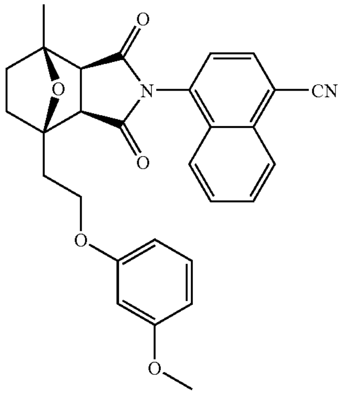 | [3aS-(3aα,4β,7β,7aα)]-4-[Octahydro-4-[2-(3-methoxyphenoxy)ethyl]-7-methyl-1,3-dioxo-4,7-epoxy-2H-isoindol-2-yl]-1-naphthalenecarbonitrile | 3.97 LCMS $[M + H]^+$ = 483.1 | 496 |

-continued

| Ex. No. | Compound Structure | Compound Name | Retention Time Min./ Molecular Mass | Pro. of Ex. |
|---|---|---|---|---|
| 694 | 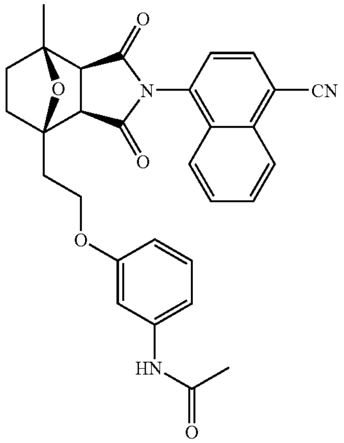 | N-[3-[2-[3aS-(3aα,4β,7β,7aα)]-2-(4-Cyano-1-naphthalenyl)octahydro-7-methyl-1,3-dioxo-4,7-epoxy-4H-isoindol-4-yl]ethoxy]phenylacetamide | 3.42 LCMS $[M + H]^+$ = 510.1 | 496 |
| 695 | 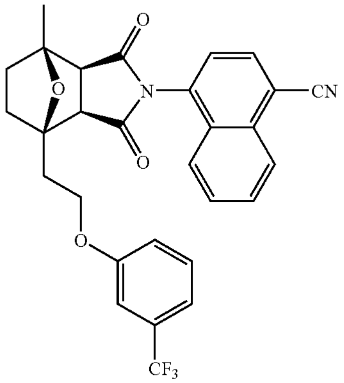 | [3aS-(3aα,4β,7β,7aα)]-4-[Octahydro-4-methyl-1,3-dioxo-7-[2-[3-(trifluoromethyl)phenoxy]ethyl]-4,7-epoxy-2H-isoindol-2-yl]-1-naphthalenecarbonitrile | 3.83 LCMS $[M + H]^+$ = 521.1 | 496 |
| 696 | 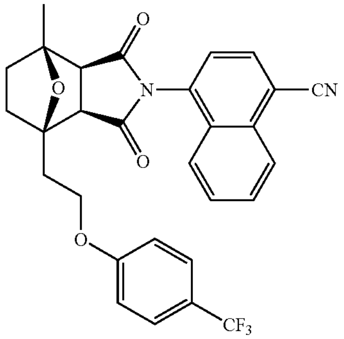 | [3aS-(3aα,4β,7β,7aα)]-4-[Octahydro-4-methyl-1,3-dioxo-7-[2-[4-(trifluoromethyl)phenoxy]ethyl]-4,7-epoxy-2H-isoindol-2-yl]-1-naphthalenecarbonitrile | 3.86 LCMS $[M + H]^+$ = 521.2 | 496 |

-continued

| Ex. No. | Compound Structure | Compound Name | Retention Time Min./ Molecular Mass | Pro. of Ex. |
|---|---|---|---|---|
| 697 | 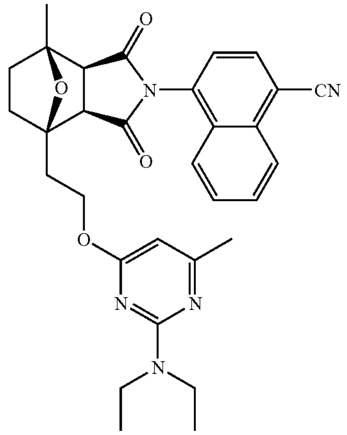 | [3aS-(3aα,4β,7β,7aα)]-4-[4-[2-[[2-(Diethylamino)-6-methyl-4-pyrimidinyl]oxy]ethyl]octahydro-7-methyl-1,3-dioxo-4,7-epoxy-2H-isoindol-2-yl]-1-naphthalenecarbonitrile | 3.63 LCMS $[M + H]^+$ = 540.2 | 496 |
| 698 | 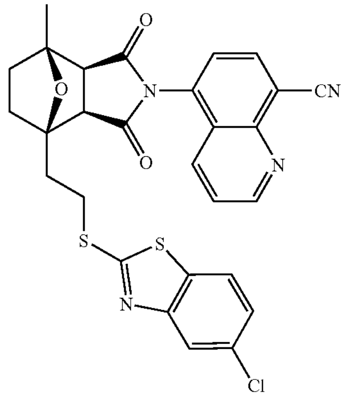 | [3aS-(3aα,4β,7β,7aα)]-4-[4-[2-[(5-Chloro-2-benzothiazolyl)thio]ethyl]octahydro-7-methyl-1,3-dioxo-4,7-epoxy-2H-isoindol-2-yl]-1-naphthalenecarbonitrile | 4.15 LCMS $[M]^+$ = 560.0 | 496 |
| 699 | 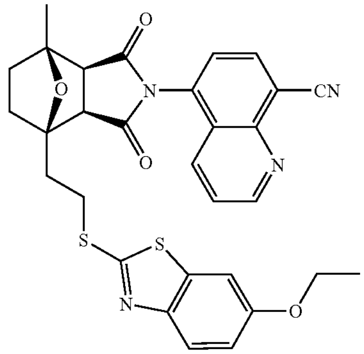 | [3aS-(3aα,4β,7β,7aα)]-4-[4-[2-[(6-Ethoxy-2-benzothiazolyl)thio]ethyl]octahydro-7-methyl-1,3-dioxo-4,7-epoxy-2H-isoindol-2-yl]-1-naphthalenecarbonitrile | 4.15 LCMS $[M + H]^+$ = 570.1 | 496 |
| 700 | 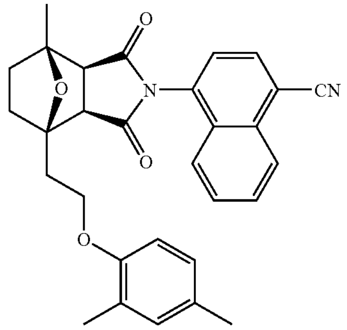 | [3aS-(3aα,4β,7β,7aα)]-4-[4-[2-(2,4-Dimethylphenoxy)ethyl]octahydro-7-methyl-1,3-dioxo-4,7-epoxy-2H-isoindol-2-yl]-1-naphthalenecarbonitrile | 3.71 LCMS $[M + H]^+$ = 481.2 | 496 |

-continued

| Ex. No. | Compound Structure | Compound Name | Retention Time Min./ Molecular Mass | Pro. of Ex. |
|---|---|---|---|---|
| 701 | 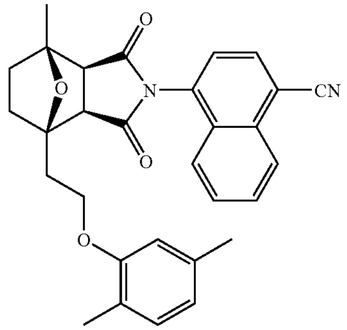 | [3aS-(3aα,4β,7β,7aα)]-4-[4-[2-(2,5-Dimethylphenoxy)ethyl]octahydro-7-methyl-1,3-dioxo-4,7-epoxy-2H-isoindol-2-yl]-1-naphthalenecarbonitrile | 3.79 LCMS $[M + H]^+$ = 481.2 | 496 |
| 702 | 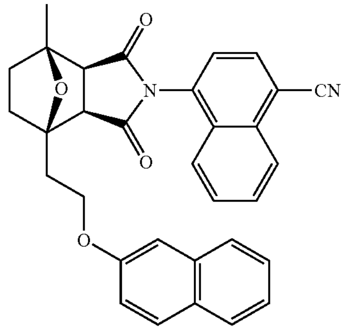 | [3aS-(3aα,4β,7β,7aα)]-4-[Octahydro-4-methyl-7-[2-(2-naphthalenyloxy)ethyl]-1,3-dioxo-4,7-epoxy-2H-isoindol-2-yl]-1-naphthalenecarbonitrile | 2.66 LCMS $[M + H]^+$ = 503.2 | 496 |
| 703 | 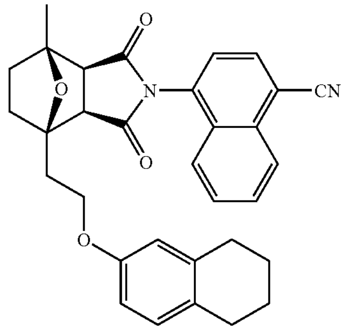 | [3aS-(3aα,4β,7β,7aα)]-4-[Octahydro-4-methyl-1,3-dioxo-7-[2-[(5,6,7,8-tetrahydro-2-naphthalenyl)oxy]ethyl]-4,7-epoxy-2H-isoindol-2-yl]-1-naphthalenecarbonitrile | 2.72 LCMS $[M + H]^+$ = 507.2 | 496 |
| 704 | 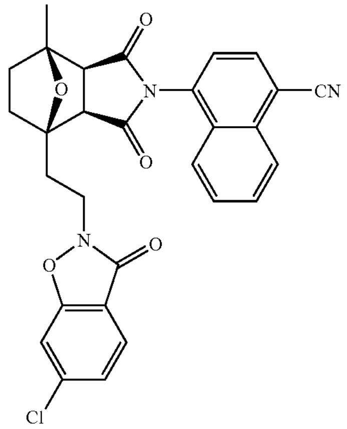 | [3aS-(3aα,4β,7β,7aα)]-4-[4-[2-(6-Chloro-3-oxo-1,2-benzisoxazol-2(3H)-yl)ethyl]octahydro-7-methyl-1,3-dioxo-4,7-epoxy-2H-isoindol-2-yl]-1-naphthalenecarbonitrile | 2.71 LCMS $[M + H]^+$ = 528.1 | 496 |

-continued

| Ex. No. | Compound Structure | Compound Name | Retention Time Min./ Molecular Mass | Pro. of Ex. |
|---|---|---|---|---|
| 705 | 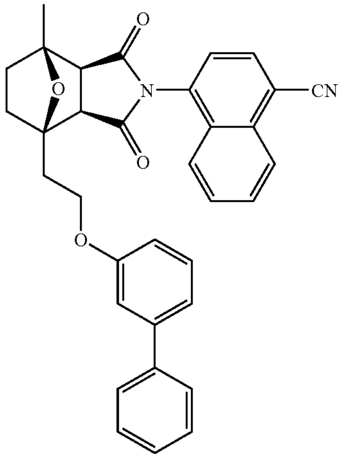 | [3aS-(3aα,4β,7β,7aα)]-4-[4-[2-([1,1'-Biphenyl]-3-yloxy)ethyl]octahydro-7-methyl-1,3-dioxo-4,7-epoxy-2H-isoindol-2-yl]-1-naphthalenecarbonitrile | 3.03 LCMS $[M + H]^+$ = 529.2 | 496 |
| 706 | 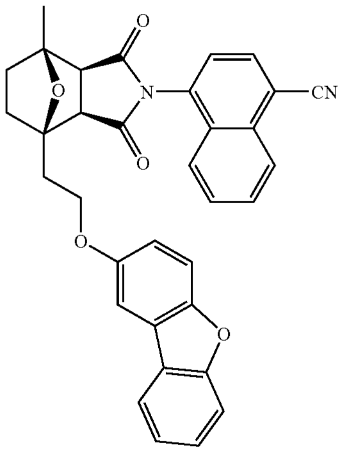 | [3aS-(3aα,4β,7β,7aα)]-4-[4-[2-(2-Dibenzofuranyloxy) ethyl]octahydro-7-methyl-1,3-dioxo-4,7-epoxy-2H-isoindol-2-yl]-1-naphthalenecarbonitrile | 3.51 LCMS $[M + H]^+$ = 543.2 | 496 |
| 707 | 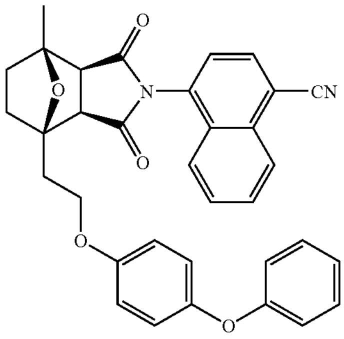 | [3aS-(3aα,4β,7β,7aα)]-4-[Octahydro-4-methyl-1,3-dioxo-7-[2-(4-phenoxyphenoxy)ethyl]-4,7-epoxy-2H-isoindol-2-yl]-1-naphthalenecarbonitrile | 3.73 LCMS $[M + H]^+$ = 545.2 | 496 |

-continued

| Ex. No. | Compound Structure | Compound Name | Retention Time Min./ Molecular Mass | Pro. of Ex. |
|---|---|---|---|---|
| 708 | 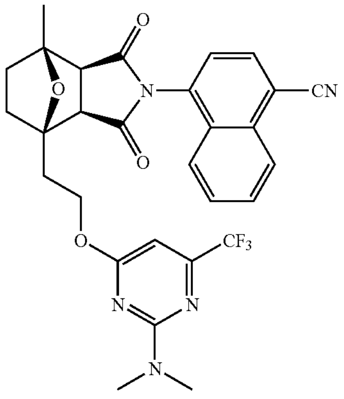 | [3aS-(3aα,4β,7β,7aα)]-4-[4-[2-[[2-(Dimethylamino)-6-(trifluoromethyl)-4-pyrimidinyl]oxy]ethyl]octahydro-7-methyl-1,3-dioxo-4,7-epoxy-2H-isoindol-2-yl]-1-naphthalenecarbonitrile, trifluoroacetate (1:1) | 4.15 LCMS $[M + H]^+$ = 566.2 | 496 |
| 709 | 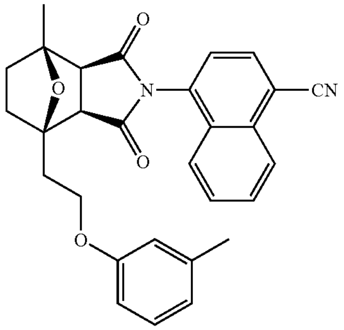 | [3aS-(3aα,4β,7β,7aα)]-4-[Octahydro-4-methyl-7-[2-(3-methylphenoxy)ethyl]-1,3-dioxo-4,7-epoxy-2H-isoindol-2-yl]-1-naphthalenecarbonitrile | 3.17 LCMS $[M + H]^+$ = 466.5 | 496 |
| 710 | 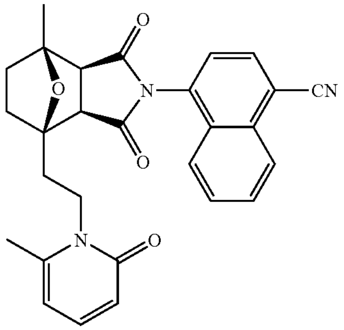 | [3aS-(3aα,4β,7β,7aα)]-4-[Octahydro-4-methyl-7-[2-(6-methyl-2-oxo-1(2H)-pyridinyl)ethyl]-1,3-dioxo-4,7-epoxy-2H-isoindol-2-yl]-1-naphthalenecarbonitrile | 3.41 LCMS $[M + H]^+$ = 468.2 | 496 |
| 711 | 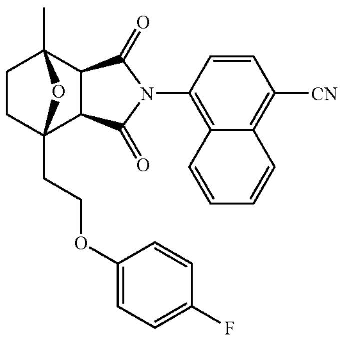 | [3aS-(3aα,4β,7β,7aα)]-4-[4-[2-(4-Fluorophenoxy)ethyl]octahydro-7-methyl-1,3-dioxo-4,7-epoxy-2H-isoindol-2-yl]-1-naphthalenecarbonitrile | 4.10 LCMS $[M + H]^+$ = 471.2 | 496 |

-continued

| Ex. No. | Compound Structure | Compound Name | Retention Time Min./ Molecular Mass | Pro. of Ex. |
|---|---|---|---|---|
| 712 | 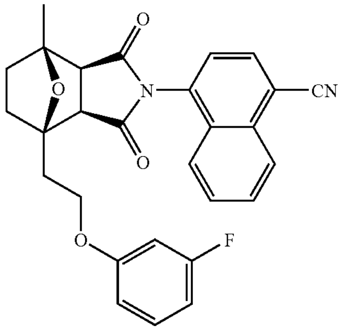 | [3aS-(3aα,4β,7β,7aα)]-4-[4-[2-(3-Fluorophenoxy)ethyl] octahydro-7-methyl-1,3-dioxo-4,7-epoxy-2H-isoindol-2-yl]-1-naphthalenecarbonitrile | 3.56 LCMS $[M + H]^+$ = 471.2 | 496 |
| 713 | 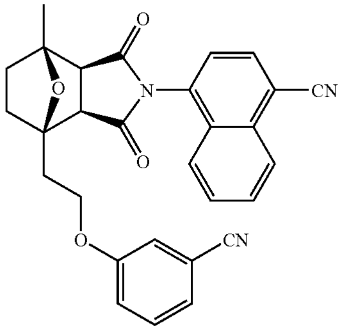 | [3aS-(3aα,4β,7β,7aα)]-4-[4-[2-(3-Cyanophenoxy)ethyl] octahydro-7-methyl-1,3-dioxo-4,7-epoxy-2H-isoindol-2-yl]-1-naphthalenecarbonitrile | 4.28 LCMS $[M + H]^+$ = 478.2 | 496 |
| 714 | 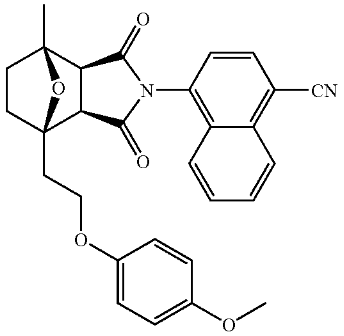 | [3aS-(3aα,4β,7β,7aα)]-4-[Octahydro-4-[2-(4-methoxyphenoxy)ethyl]-7-methyl-1,3-dioxo-4,7-epoxy-2H-isoindol-2-yl]-1-naphthalenecarbonitrile | 3.58 LCMS $[M + H]^+$ = 483.2 | 496 |
| 715 | 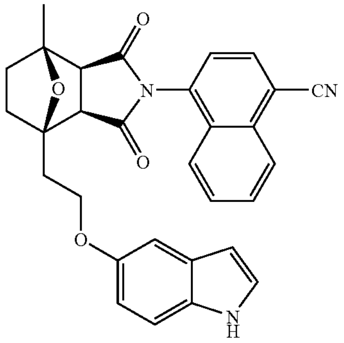 | [3aS-(3aα,4β,7β,7aα)]-4-[Octahydro-4-[2-(1H-indol-5-yloxy)ethyl]-7-methyl-1,3-dioxo-4,7-epoxy-2H-isoindol-2-yl]-1-naphthalenecarbonitrile | 3.40 LCMS $[M + H]^+$ = 492.2 | 496 |

-continued

| Ex. No. | Compound Structure | Compound Name | Retention Time Min./ Molecular Mass | Pro. of Ex. |
|---|---|---|---|---|
| 716 | 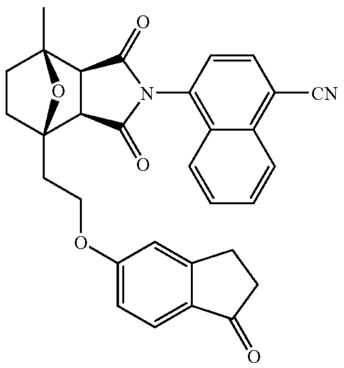 | [3aS-(3aα,4β,7β,7aα)]-4-[4-[2-[(2,3-Dihydro-1-oxo-1H-inden-5-yl)oxy]ethyl]octahydro-7-methyl-1,3-dioxo-4,7-epoxy-2H-isoindol-2-yl]-1-naphthalenecarbonitrile | 3.20 LCMS $[M + H]^+$ = 507.2 | 496 |
| 717 | 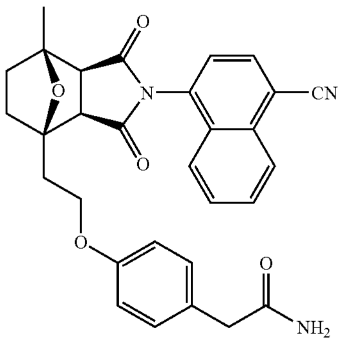 | [3aS-(3aα,4β,7β,7aα)]-4-[2-[2-(4-Cyano-1-naphthalenyl)octahydro-7-methyl-1,3-dioxo-4,7-epoxy-4H-isoindol-4-yl]ethoxy]benzeneacetamide | 3.26 LCMS $[M + H]^+$ = 510.2 | 496 |
| 718 | 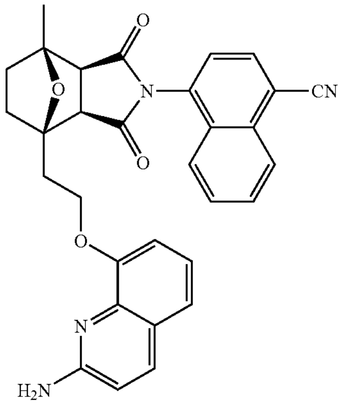 | [3aS-(3aα,4β,7β,7aα)]-4-[4-[2-[(2-Amino-8-quinolinyl)oxy]ethyl] octahydro-7-methyl-1,3-dioxo-4,7-epoxy-2H-isoindol-2-yl]-1-naphthalenecarbonitrile, trifluoroacetate (1:1) | 2.77 LCMS $[M + H]^+$ = 519.2 | 496 |
| 719 | 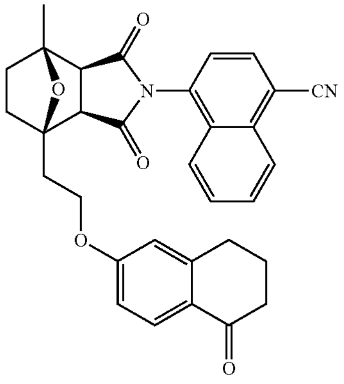 | [3aS-(3aα,4β,7β,7aα)]-4-[Octahydro-4-methyl-1,3-dioxo-7-[2-[(5,6,7,8-tetrahydro-5-oxo-2-naphthalenyl)oxy]ethyl]-4,7-epoxy-2H-isoindol-2-yl]-1-naphthalenecarbonitrile | 2.88 LCMS $[M + H]^+$ = 521.2 | 496 |

-continued

| Ex. No. | Compound Structure | Compound Name | Retention Time Min./ Molecular Mass | Pro. of Ex. |
|---|---|---|---|---|
| 720 | 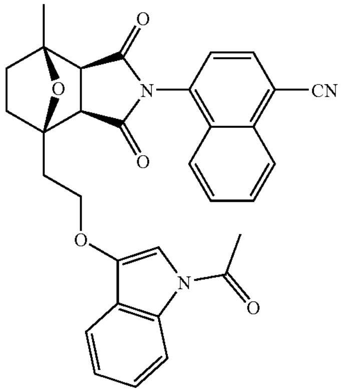 | [3aS-(3aα,4β,7β,7aα)]-1-Acetyl-3-[2-[2-(4-cyano-1-naphthalenyl)octahydro-7-methyl-1,3-dioxo-4,7-epoxy-4H-isoindol-4-yl]ethoxy]-1H-indole | 4.03 LCMS $[M + H]^+$ = 534.2 | 496 |
| 721 | 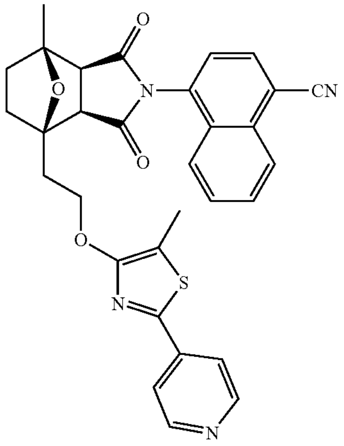 | [3aS-(3aα,4β,7β,7aα)]-4-[Octahydro-4-methyl-7-[2-[[5-methyl-2-(4-pyridinyl)-4-thiazolyl]oxy]ethyl]-1,3-dioxo-4,7-epoxy-2H-isoindol-2-yl]-1-naphthalenecarbonitrile, trifluoroacetate (1:1) | 4.02 LCMS $[M + H]^+$ = 551.2 | 496 |
| 722 | 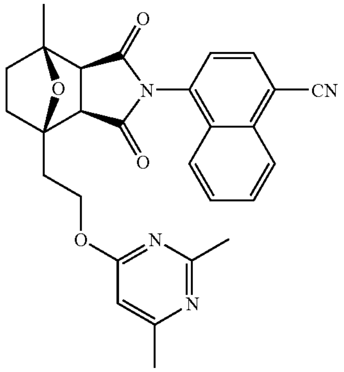 | [3aS-(3aα,4β,7β,7aα)]-4-[4-[2-[(2,6-Dimethyl-4-pyrimidinyl)oxy]ethyl] octahydro-7-methyl-1,3-dioxo-4,7-epoxy-2H-isoindol-2-yl]-1-naphthalenecarbonitrile | 3.74 LCMS $[M + H]^+$ = 483.2 | 496 |

-continued

| Ex. No. | Compound Structure | Compound Name | Retention Time Min./ Molecular Mass | Pro. of Ex. |
|---|---|---|---|---|
| 723 | 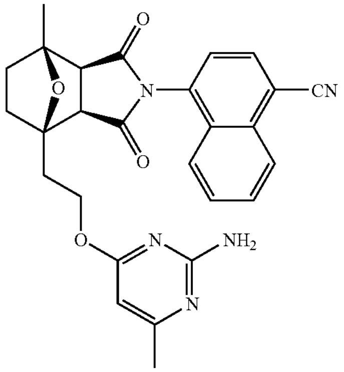 | [3aS-(3aα,4β,7β,7aα)]-4-[4-[2-[(2-Amino-6-methyl-4-pyrimidinyl)oxy]ethyl]octahydro-7-methyl-1,3-dioxo-4,7-epoxy-2H-isoindol-2-yl]-1-naphthalenecarbonitrile | 3.71 LCMS $[M + H]^+$ = 484.2 | 496 |
| 724 | 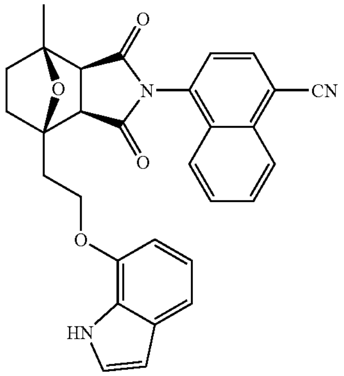 | [3aS-(3aα,4β,7β,7aα)]-4-[Octahydro-4-[2-(1H-indol-7-yloxy)ethyl]-7-methyl-1,3-dioxo-4,7-epoxy-2H-isoindol-2-yl]-1-naphthalenecarbonitrile | 4.23 LCMS $[M + H]^+$ = 492.2 | 496 |
| 725 | 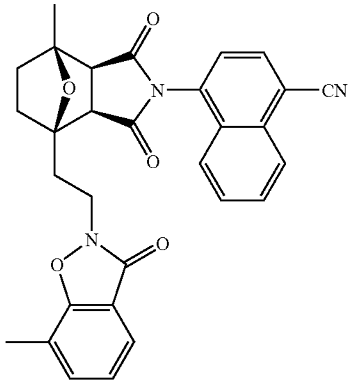 | [3aS-(3aα,4β,7β,7aα)]-4-[Octahydro-4-methyl-7-[2-(7-methyl-3-oxo-1,2-benzisoxazol-2(3H)-yl)ethyl]-1,3-dioxo-4,7-epoxy-2H-isoindol-2-yl]-1-naphthalenecarbonitrile | 3.02 LCMS $[M + H]^+$ = 508.2 | 496 |

-continued

| Ex. No. | Compound Structure | Compound Name | Retention Time Min./ Molecular Mass | Pro. of Ex. |
|---|---|---|---|---|
| 726 | 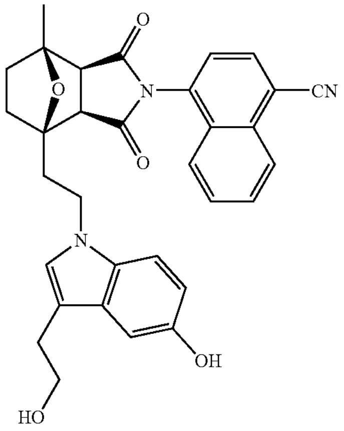 | [3aS-(3aα,4β,7β,7aα)]-4-[Octahydro-4-[2-[5-hydroxy-3-(2-hydroxyethyl)-1H-indol-1-yl]ethyl]-7-methyl-1,3-dioxo-4,7-epoxy-2H-isoindol-2-yl]-1-naphthalenecarbonitrile | 2.94 LCMS $[M + H]^+$ = 536.2 | 496 |
| 727 | 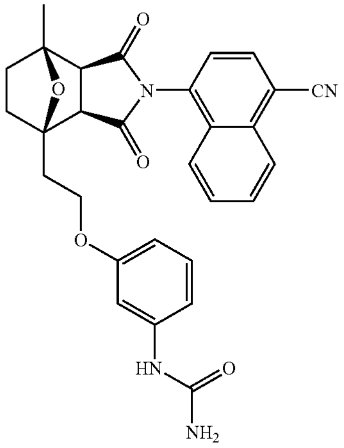 | N-[3-[2-[[3aS-(3aα,4β,7β,7aα)]-2-(4-Cyano-1-naphthalenyl)octahydro-7-methyl-1,3-dioxo-4,7-epoxy-4H-isoindol-4-yl]ethoxy]phenyl]urea | 4.26 LCMS $[M + H]^+$ = 511.2 | 496 |
| 728 | 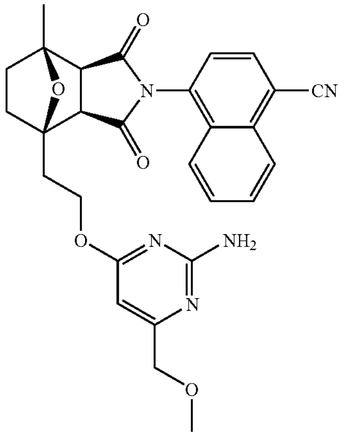 | [3aS-(3aα,4β,7β,7aα)]-4-[4-[2-[[2-Amino-6-(methoxymethyl)-4-pyrimidinyl]oxy]ethyl]octahydro-7-methyl-1,3-dioxo-4,7-epoxy-2H-isoindol-2-yl]-1-naphthalenecarbonitrile | 4.18 LCMS $[M + H]^+$ = 514.2 | 496 |

-continued

| Ex. No. | Compound Structure | Compound Name | Retention Time Min./ Molecular Mass | Pro. of Ex. |
|---|---|---|---|---|
| 729 | 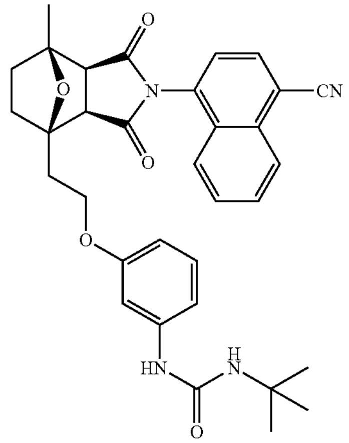 | N-[3-[2-[[3aS-(3aα,4β,7β,7aα)]-2-(4-Cyano-1-naphthalenyl)octahydro-7-methyl-1,3-dioxo-4,7-epoxy-4H-isoindol-4-yl]ethoxy]phenyl]-N'-(1,1-dimethylethyl)urea | 3.13 LCMS $[M + H]^+$ = 567.2 | 496 |
| 730 | 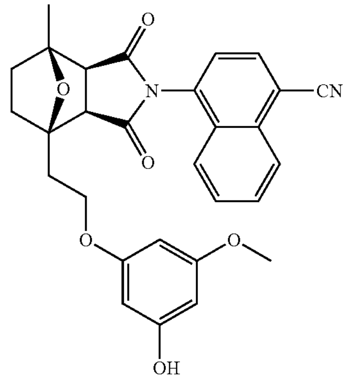 | [3aS-(3aα,4β,7β,7aα)]-4-[Octahydro-4-[2-(3-hydroxy-5-methoxyphenoxy)ethyl]-7-methyl-1,3-dioxo-4,7-epoxy-2H-isoindol-2-yl]-1-naphthalenecarbonitrile | 4.22 LCMS $[M + H]^+$ = 499.2 | 496 |
| 731 | 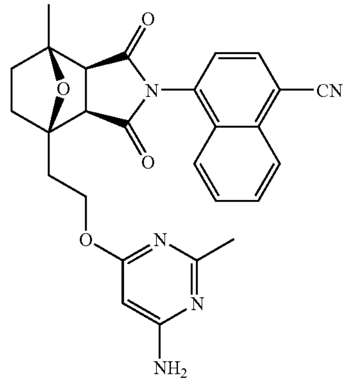 | [3aS-(3aα,4β,7β,7aα)]-4-[4-[2-[(6-Amino-2-methyl-4-pyrimidinyl)oxy]ethyl]octahydro-7-methyl-1,3-dioxo-4,7-epoxy-2H-isoindol-2-yl]-1-naphthalenecarbonitrile | 4.19 LCMS $[M + H]^+$ = 484.2 | 496 |

-continued

| Ex. No. | Compound Structure | Compound Name | Retention Time Min./ Molecular Mass | Pro. of Ex. |
|---|---|---|---|---|
| 732 | 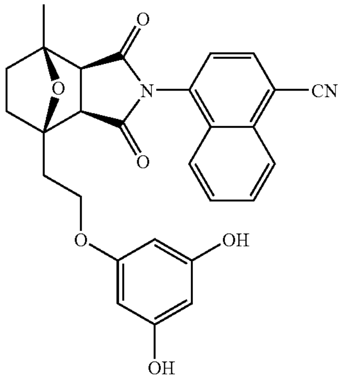 | [3aS-(3aα,4β,7β,7aα)]-4-[4-[2-(3,5-Dihydroxyphenoxy)ethyl]octahydro-7-methyl-1,3-dioxo-4,7-epoxy-2H-isoindol-2-yl]-1-naphthalenecarbonitrile | 3.73 LCMS $[M + H]^+ =$ 485.1 | 496 |
| 733 | 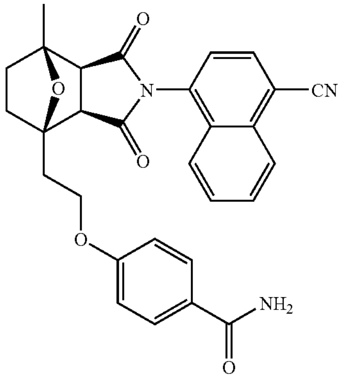 | [3aS-(3aα,4β,7β,7aα)]-4-[2-[2-(4-Cyano-1-naphthalenyl)octahydro-7-methyl-1,3-dioxo-4,7-epoxy-4H-isoindol-4-yl]ethoxy]benzamide | 4.11 LCMS $[M + H]^+ =$ 496.2 | 496 |
| 734 | 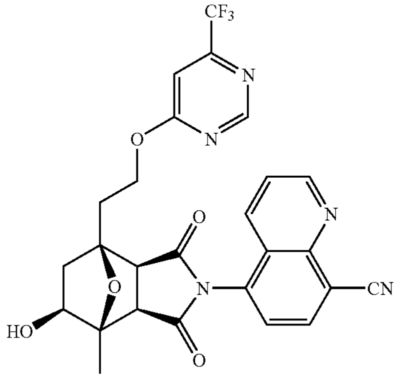 | [3aR-(3aα,4β,5β,7β,7aα)]-5-[Octahydro-5-hydroxy-4-methyl-1,3-dioxo-7-[2-[[6-(trifluoromethyl)-4-pyrimidinyl]oxy]ethyl]-4,7-epoxy-2H-isoindol-2-yl]-8-quinolinecarbonitrile | 2.847 LC $[M + H]^+ =$ 540.14 | 485, 486, 487 & 488 |
| 735 | 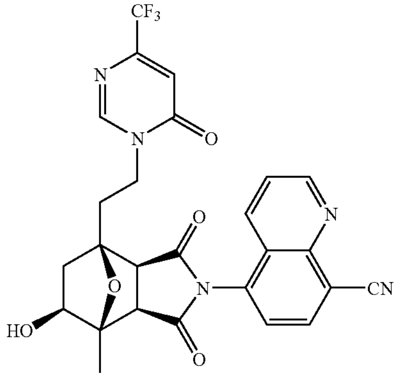 | [3aR-(3aα,4β,5β,7β,7aα)]-5-[Octahydro-5-hydroxy-4-methyl-1,3-dioxo-7-[2-[6-oxo-4-(trifluoromethyl)-1(6H)-pyrimidinyl]ethyl]-4,7-epoxy-2H-isoindol-2-yl]-8-quinolinecarbonitrile | 2.577 LCMS $[M + H]^+ =$ 540.14 | 485, 486, 487 & 488 |

-continued

| Ex. No. | Compound Structure | Compound Name | Retention Time Min./ Molecular Mass | Pro. of Ex. |
|---|---|---|---|---|
| 736 | 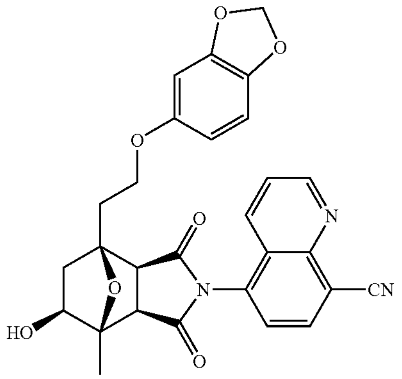 | [3aR-(3aα,4β,5β,7β,7aα)]-5-[7-[2-(1,3-Benzodioxol-5-yloxy)ethyl]octahydro-5-hydroxy-4-methyl-1,3-dioxo-4,7-epoxy-2H-isoindol-2-yl]-8-quinolinecarbonitrile | 2.867 LCMS $[M + H]^+$ = 514.16 | 485, 486, 487 & 488 |
| 737 | 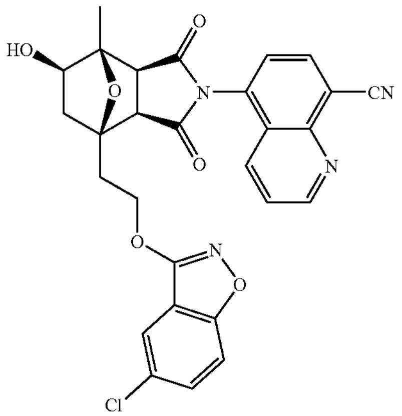 | [3aS-(3aα,4β,5β,7β,7aα)]-5-[7-[2-[(5-Chloro-1,2-benzisoxazol-3-yl)oxy]ethyl]octahydro-5-hydroxy-4-methyl-1,3-dioxo-4,7-epoxy-2H-isoindol-2-yl]-8-quinolinecarbonitrile | 3.24 LCMS $[M + H]^+$ = 545.12 | 485, 486, 487 & 488 |
| 738 | 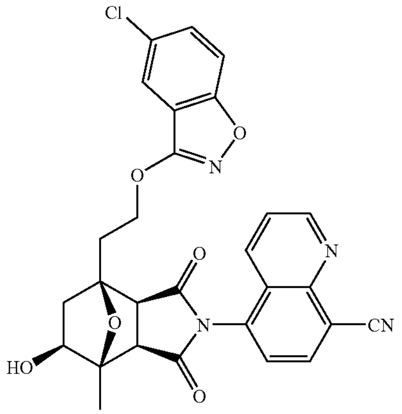 | [3aR-(3aα,4β,5β,7β,7aα)]-5-[7-[2-[(5-Chloro-1,2-benzisoxazol-3-yl)oxy]ethyl]octahydro-5-hydroxy-4-methyl-1,3-dioxo-4,7-epoxy-2H-isoindol-2-yl]-8-quinolinecarbonitrile | 3.25 LCMS $[M + H]^+$ = 545.12 | 485, 486, 487 & 488 |

-continued

| Ex. No. | Compound Structure | Compound Name | Retention Time Min./ Molecular Mass | Pro. of Ex. |
|---|---|---|---|---|
| 739 | 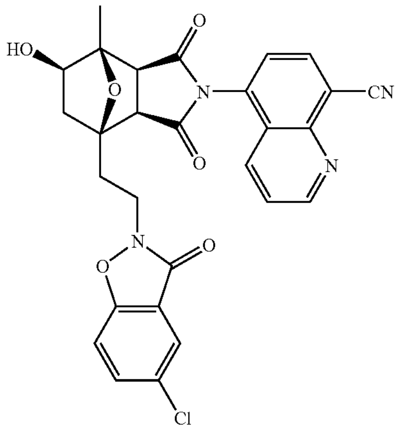 | [3aS-(3aα,4β,5β,7β,7aα)]-5-[7-[2-(5-Chloro-3-oxo-1,2-benzisoxazol-2(3H)-yl)ethyl]octahydro-5-hydroxy-4-methyl-1,3-dioxo-4,7-epoxy-2H-isoindol-2-yl]-8-quinolinecarbonitrile | 2.863 LCMS $[M + H]^+$ = 545.12 | 485, 486, 487 & 488 |
| 740 | 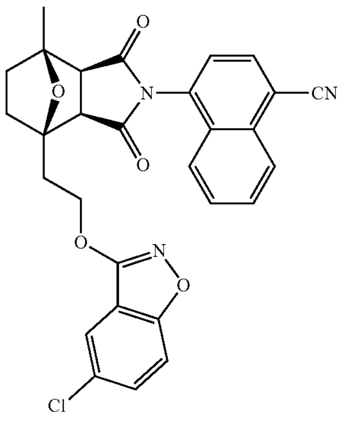 | [3aS-(3aα,4β,7β,7aα)]-4-[4-[2-[(6-Chloro-1,2-benzisoxazol-3-yl)oxy]ethyl]octahydro-7-methyl-1,3-dioxo-4,7-epoxy-2H-isoindol-2-yl]-1-naphthalenecarbonitrile | 4.04 LCMS $[M + H]^+$ = 528.1 | 496 |
| 741 | 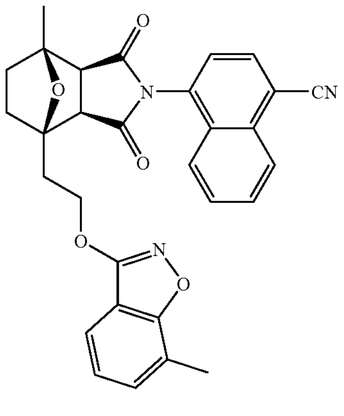 | [3aS-(3aα,4β,7β,7aα)]-4-[Octahydro-4-methyl-7-[2-[(7-methyl-1,2-benzisoxazol-3-yl)oxy]ethyl]-1,3-dioxo-4,7-epoxy-2H-isoindol-2-yl]-1-naphthalenecarbonitrile | 3.94 LCMS $[M + H]^+$ = 508.1 | 496 |

-continued

| Ex. No. | Compound Structure | Compound Name | Retention Time Min./ Molecular Mass | Pro. of Ex. |
|---|---|---|---|---|
| 742 | 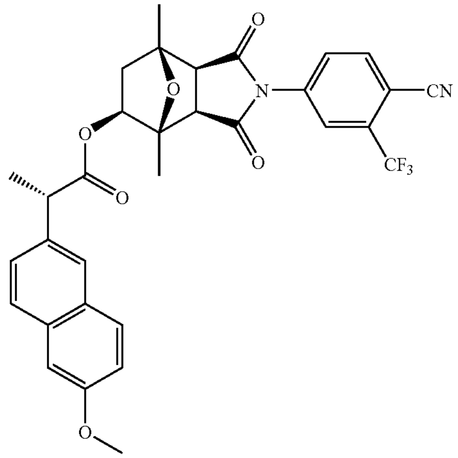 | (αS)-6-Methoxy-α-methyl-2-naphthaleneacetic acid, [3aR-(3aα,4β,5β,7β,7aα)]-2-[4-cyano-3-(trifluoromethyl)phenyl] octahydro-4,7-dimethyl-1,3-dioxo-4,7-epoxy-1H-isoindol-5-yl ester | $[M-H]^- = 591.3$ | 483 |
| 743 | 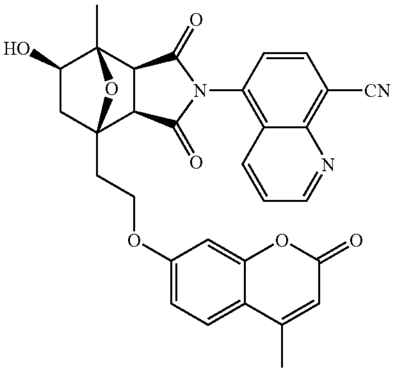 | [3aS-(3aα,4β,5β,7β,7aα)]-5-[Octahydro-5-hydroxy-4-methyl-7-[2-[(4-methyl-2-oxo-2H-1-benzopyran-7-yl)oxy]ethyl]-1,3-dioxo-4,7-epoxy-2H-isoindol-2-yl]-8-quinolinecarbonitrile | 2.89 LCMS $[M+H]^+ =$ 552.19 | 486, 486, 487 & 488 |
| 744 | 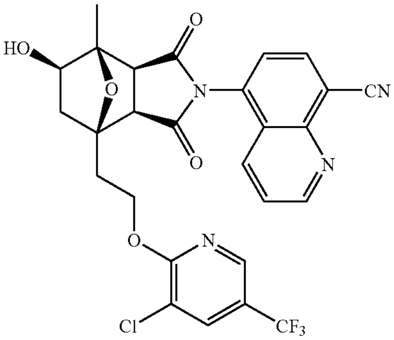 | [3aS-(3aα,4β,5β,7β,7aα)]-5-[7-[2-[[3-Chloro-5-(trifluoromethyl)-2-pyridinyl]oxy]ethyl] octahydro-5-hydroxy-4-methyl-1,3-dioxo-4,7-epoxy-2H-isoindol-2-yl]-8-quinolinecarbonitrile | 3.46 LCMS $[M+H]^+ =$ 573.12 | 485, 486, 487 & 488 |
| 745 | 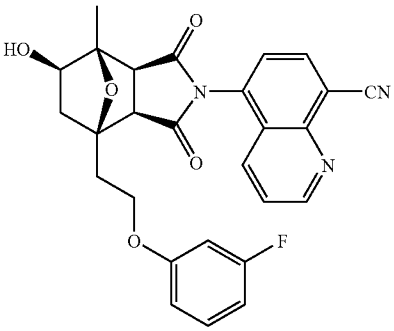 | [3aS-(3aα,4β,5β,7β,7aα)]-5-[7-[2-(3-Fluorophenoxy)ethyl] octahydro-5-hydroxy-4-methyl-1,3-dioxo-4,7-epoxy-2H-isoindol-2-yl]-8-quinolinecarbonitrile | 3.05 LCMS $[M+H]^+ =$ 488.03 | 485, 486, 487 & 488 |

-continued

| Ex. No. | Compound Structure | Compound Name | Retention Time Min./ Molecular Mass | Pro. of Ex. |
|---|---|---|---|---|
| 746 | 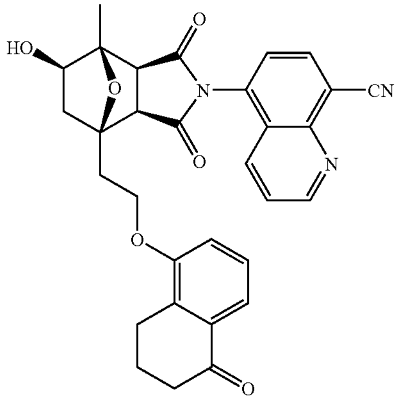 | [3aS-(3aα,4β,5β,7β,7aα)]-5-[Octahydro-5-hydroxy-4-methyl-1,3-dioxo-7-[2-[(5,6,7,8-tetrahydro-5-oxo-1-naphthalenyl)oxy]ethyl]-4,7-epoxy-2H-isoindol-2-yl]-8-quinolinecarbonitrile | 2.98 LCMS $[M + H]^+$ = 538.23 | 485, 486, 487 & 488 |

EXAMPLE 747

[3aR-(3aα,4β,7β,7aα)]-4-[7-[2-[(5-Chloro-2-pyridinyl)oxy]ethyl]octahydro-4-methyl-1,3,5-trioxo-4,7-epoxy-2H-isoindol-2-yl]-1-naphthalenecarbonitrile (747)

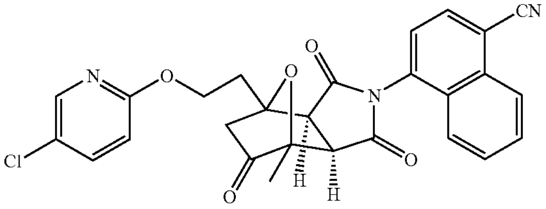

Dess-Martin periodinane (122 mg, 0.29 mmol, prepared as described in Ishiharaa, J., T. Fukuzakia, et al. *Tetrahedron Letters* 40(10), 1907-1910 (1999)) was added to a solution of the compound 490A (120 mg, 0.24 mmol) in dichloromethane (2.5 mL) under nitrogen and the mixture was stirred for 4 h. The reaction was half concentrated under a stream of nitrogen and was applied on a flash cartridge (Jones 2 g) with celite on top and was eluted with chloroform: heptane (9:1) to chloroform:acetone (4:1) to give 148 mg of a still impure white solid. The solid was disolved in dichloromethane (5 mL) and heptane (3 mL) and the precipitate was filtered over 1 g silica and was eluted with dichloromethane to chloroform:acetone (4:1). Fractions 3-9 (58.8 mg white solid) was almost pure and fractions 10-13 (68 mg white foam) were still impure. Fractions 3-9 were purified over silica (1 g) using heptane to heptane:ethyl acetate (1:1) as eluant to give 35.8 mg (30% yield) compound 747 as a white solid. Fractions 10-13 were purified by adding ~400 mg of silica to an excess solution of crude compound 747 in ethyl acetate and heptane and concentrating it. The silica was then put on top of a preconditioned (heptane) silica column (1 g) and was eluted with a gradient from heptane to heptane ethyl acetate (1:1) to give an additional 36.7 mg (31% yield) of compound 747 as a white solid. HPLC: 94% at 3.46 & 3.59 min (atropisomers, retention time) (YMC S5 ODS 4.6×50 mm, 4 mL min, 4 min gradient 100% A to 100% B (A: 10% methanol, 89.1% water, 0.1% TFA; B: 10% water, 89.1% methanol, 0.1% TFA, 4 mL/min, monitoring at 220 nm). MS (ES): m/z 502.11 $[M+H]^+$.

EXAMPLE 748

(3aα,5β,7β,7aα)-4-[Octahydro-5-hydroxy-4,7-dimethy-1,3-dioxo-4,7-epoxy-2H-isoindol-2-yl]-1-isoquinolinecarbonitrile (748D)

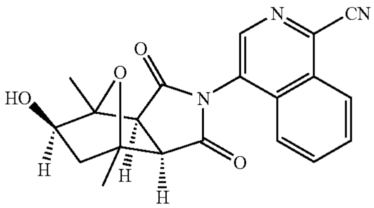

A. 4-(2,5-Dioxo-2,5-dihydro-pyrrol-1-yl)-isoquinoline-1-carbonitrile (748A)

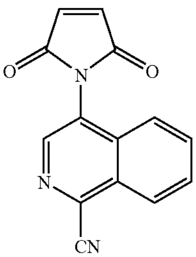

A mixture of compound 470D (200 mg, 1.18 mmol) and maleic anhydride (470 mg, 4.7 mmol) in glacial acetic acid (5 μL) was heated to reflux for 4 hours. After removing the volatiles in vacuo, the residue was partitioned between ethyl acetate (50 mL) and water (50 mL). The organic layer was washed with saturated sodium bicarbonate solution (2×50 mL) and brine (50 mL). After drying over magnesium sulfate, the organic layer was filtered through a 1×5 cm plug of silica gel. The filtrate was concentrated to afford 263 mg (90%) of 748a as an off-white solid. HPLC: 99% at 1.12 min (Phenomenex 5 micron ODS 4.6×30 mm, 10%-90% aqueous methanol over 2 minute gradient with 0.1% TFA, detecting at 254 nm). MS (ES): m/z 250.2 $[M+H]^+$.

B. (3aα,4β,7β,7aα)-4-(1,3,3a,4,7,7a-Hexahydro-4,7-dimethyl-1,3-dioxo-4,7-epoxy-2H-isoindol-2-yl)-1-isoquinolinecarbonitrile (748B)

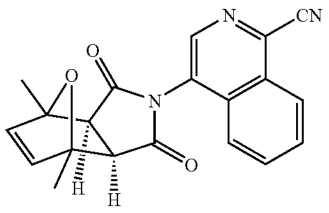

A mixture of compound 748A (250 mg, 1 mmol) and 2,5-dimethylfuran (4 mL) was heated to 60° C. for 2 h. At 15 min, the reaction mixture became homogeneous. A precipitate formed at 45 minutes. After cooling to 25° C., the reaction mixture was diluted with hexane and the filter cake was washed with ethyl ether:hexane, 1:1. Drying under high vacuum afforded 270 mg (78%) of compound 748B as a light yellow solid. $^1$HNMR-400 MHz ($CDCl_3$): δ 8.55 (s, 1H), 8.54 (m, 1H), 7.86 (m, 3H), 6.45 (s, 2H), 3.18 (s, 2H), 1.81 (s, 6H).

C. (1aα,2β,2aα,5aα,6β,6aα)-4-[Octahydro-2,6-dimethyl-3,5-dioxo-2,6-epoxy-4H-oxireno[f]isoindol-4-yl]-1-isoquinolinecarbonitrile (748C)

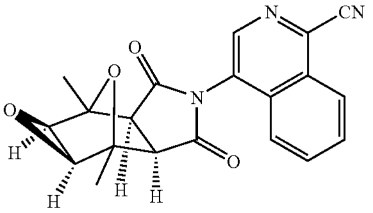

m-CPBA, (70%, 110 mg, 0.45 mmol) was added to a solution of compound 748B (100 mg, 0.29 mmol) in 3 mL of dichloromethane at 25° C. After 1 h, additional m-CPBA, (70%, 110 mg, 0.45 mmol) was added and the reaction mixture was stirred an additional 18 h. After partitioning the reaction mixture between ethyl acetate (30 mL) and water (30 mL), the organic layer was washed with saturated sodium bisulfite solution (30 mL), saturated sodium bicarbonate solution (2×30 mL) and brine (30 mL). The sample was dried over magnesium sulfate and concentration to yield 103 mg (98%) of compound 748C as an off-white solid. HPLC: 99% at 1.09 & 1.22 min (atropisomers, retention time) (Phenomenex 5 micron ODS 4.6×30 mm, 10%-90% aqueous methanol over a 2 min gradient with 0.1% TFA, detecting at 254 nm). MS (ES): m/z 362.07 $[M+H]^+$.

D. (3aα,4β,5β,7β,7aα)-4-[Octahydro-5-hydroxy-4,7-dimethyl-1,3-dioxo-4,7-epoxy-2H-isoindol-2-yl]-1-isoquinolinecarbonitrile (748D)

A 0.5 M solution of bis(cyclopentadienyl)titanium chloride in THF (1.2 mL, 0.6 mmol) was added dropwise over 20 min to a well stirred suspension of compound 748C (103 mg, 0.29 mmol) in THF (2.5 mL) and 1,4-cyclohexadiene (1.2 mL) at 60° C. After stirring 1 h at 60° C., the reaction mixture was partitioned between 1N HCl (40 mL) and ethyl acetate (50 mL). The pH of the aqueous layer was adjusted to 7 with solid sodium bicarbonate. After extracting the aqueous with ethyl acetate, the combined organic layers were dried over sodium sulfate. Decolorizing carbon (~1 g) was added and the mixture was allowed to stand for 18 h. Filtration and concentration of the filtrate in vacuo afforded a yellow oil that was chromatographed on a 2.5×15 cm silica gel column, using dichloro-methane:acetone, 6:4 as the mobile phase. Concentration of the product containing fractions in vacuo gave a partially purified residue that was subjected to preparative thin layer silica gel chromatography, using dichloromethane: acetone, 6:4 as the mobile phase. Extraction of the desired band with $CH_2Cl_2$, filtration and concentration of the filtrate in vacuo yielded 3 mg (31%) of compound 748D as an off-white solid. HPLC conditions: 95% at 1.46 min (Phenomenex 5 micron ODS 4.6×30 mm, 10%-90% aqueous methanol over 2 minute gradient with 0.1% TFA, detecting at 254 nm). MS (ES): m/z 364.19 $[M+H]^+$.

EXAMPLE 749

(3aα,4β,7β,7aα)-4-[Octahydro-4,7-dimethyl-1,3-dioxo-4,7-epoxy-2H-isoindol-2-yl]-2-thiophenecarbonitrile (749C)

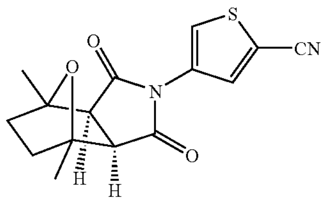

A. 2-Cyano-4-nitrothiophene (749Ai) & 2-Cyano-5-nitrothiophene (749Aii)

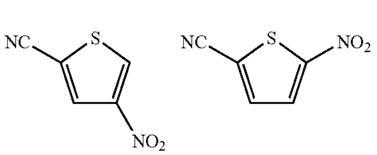

Fuming nitric acid (21 mL) was slowly added to glacial acetic acid (105 mL) and the mixture was then cooled in an ice-bath. 2-Cyanothiophene (7.98 g, 73.1 mmol) was dissolved in 20 mL of acetic anhydride and added dropwise to the above acid mixture such that the temperature did not exceed 25° C. Upon completion of the addition, the reaction mixture was warmed to 22° C. and stirred for 48 h. The reaction was poured over 400 mL of ice and extracted with 200 mL of diethylether. The ether layer was isolated, washed with water, followed by brine and dried over $MgSO_4$. Filtration and concentration in vacuo gave a sticky, orange residue which was purified by column chromatography using 1:1 hexanes/methylene chloride as the eluent to give 1.69 g (15%) of compound 749Ai as a white solid and 1.71 g (15%) of compound 749Aii as a yellow crystalline substance. Compound 749Ai: HPLC: 0.73 minutes (retention time) (Phenomenex column 30×4.6 mm eluting with 10-90% aqueous methanol over 2 minutes containing 0.1% TFA, 5 mL/min, monitoring at 220 nm). Compound 749Aii: HPLC: 99% at 0.89 minutes (retention time) (Phenomenex column 30×4.6 mm eluting with 10-90% aqueous methanol over 2 minutes containing 0.1% TFA, 5 mL/min, monitoring at 220 nm).

B. 4-Amino-2-cyanothiophene (749B)

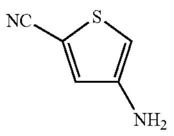

To a 100 mL 3-necked flask was added compound 749Ai (1.42 g, 9.21 mmol) dissolved in ethyl acetate (20 mL) followed by a 10% acetic acid solution (20 mL). The biphasic mixture was heated to 65° C. and then iron powder (2.95 g, 52.9 mmol) was added portion-wise over 5 minutes. After stirring for 1.5 h at 65° C., the reaction was filtered through a bed of Celite and the pad was washed with ethyl acetate. The organic layer was separated, washed with water (3×20 mL), brine and dried over $MgSO_4$. Filtration and concentration in vacuo gave a dark amber residue which was purified by column chromatography using 30% diethyl ether/methylene chloride as the eluent to give 84 mg (73%) of compound 749B as a brown solid. HPLC: 93.4% at 0.26 minutes (retention time) (YMC S5 ODS column 4.6×50 mm eluting with 10-90% aqueous methanol over 4 minutes containing 0.2% phosphoric acid, 4 mL/min, monitoring at 220 nm).

C. (3aα,4β,7β,7aα)-4-[Octahydro-4,7-dimethyl-1,3-dioxo-4,7-epoxy-2H-isoindol-2-yl]-2-thiophenecarbonitrile (749C)

To a Pyrex tube was added compound 749B (0.06 g, 0.5 mmol), toluene (1 mL), triethylamine (0.25 g, 0.35 mL, 2.5 mmol), $MgSO_4$ (0.15 g, 1.3 mmol), and compound 20A. The tube was sealed with a teflon cap and heated overnight at 145° C. The reaction was cooled, diluted with methylene chloride and filtered through Celite. The filtrate was concentrated in vacuo and the residue was purified by column chromatography using 10% ether/methylene chloride as the eluent to give 14 mg (95%) of compound 749C as a light yellow crystalline solid. HPLC: 94.6% at 2.6 minutes (retention time) (YMC S5 ODS column 4.6×50 mm eluting with 10-90% aqueous methanol over 4 minutes containing 0.2% phosphoric acid, 4 mL/min, monitoring at 220 nm. MS (ES): m/z 303.05 $[M+H]^+$.

EXAMPLE 750

(3aα,4β,7β,7aα)-5-[Octahydro-4,7-dimethyl-1,3-dioxo-4,7-epoxy-2H-isoindol-2-yl]-2-thiophenecarbonitrile (750B)

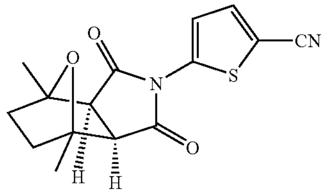

A. 5-Amino-2-cyanothiophene (750A)

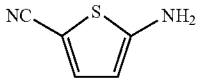

To a 100 mL 3-necked flask was added compound 749Aii (1.63 g, 10.1 mmol) dissolved in ethyl acetate (20 mL) followed by a 10% solution of acetic acid (20 mL). The biphasic mixture was heated to 65° C. and then iron powder (2.95 g, 52.9 mmol) was added portion-wise over 5 minutes. After stirring for 1.5 h at 65° C., the reaction was filtered through a bed of Celite and the pad was washed with ethyl acetate. The organic layer was separated, washed with water (3×20 mL), brine and dried over $MgSO_4$. Filtration and concentration in vacuo gave a dark amber residue which was purified by column chromatography using 10% diethyl ether/methylene chloride as the eluent to give 87 mg (66%) of compound 750A as a brown solid. HPLC: 94.2% at 1.05 minutes (retention time) (YMC S5 ODS column 4.6×50 mm eluting with 10-90% aqueous methanol over 4 minutes containing 0.2% phosphoric acid, 4 mL/min, monitoring at 220 nm).

B. (3aα,4β,7β,7aα)-5-[Octahydro-4,7-dimethyl-1,3-dioxo-4,7-epoxy-2H-isoindol-2-yl]-2-thiophenecarbonitrile (750B)

To a Pyrex tube was added compound 750A (0.06 g, 0.5 mmol), toluene (1 mL), triethylamine (0.25 g, 0.35 mL, 2.5 mmol), $MgSO_4$ (0.15 g, 1.3 mmol), and compound 20B. The tube was sealed with a teflon cap and heated overnight at 145° C. The reaction was cooled, diluted with methylene chloride and filtered through Celite. The filtrate was concentrated in vacuo and the residue was purified by column chromatography using 10% ether/methylene chloride as the eluent to yield 143 mg (96%) of compound 750B as a light yellow crystalline solid. HPLC: 92.7% at 2.93 minutes (retention time) (YMC S5 ODS column 4.6×50 mm eluting with 10-90% aqueous methanol over 4 minutes containing 0.2% phosphoric acid, 4 mL/min, monitoring at 220 nm. MS (ES): m/z 303.21 $[M+H]^+$.

EXAMPLE 751

[3aS-(3aα,4β,7β,7aα)]-Hexahydro-5-hydroxy-4,7-dimethyl-4,7-epoxyisobenzofuran-1,3-dione (751)

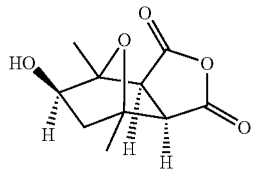

To a solution of compound 471Dii (2.36 g, 6.21 mmol) in tetrahydrofuran (THF, 20 mL) cooled in an ice-bath (~5° C.) was added, in one portion, aq 1M NaOH solution (10 mL, 10 mmol). The resulting light yellow reaction mixture was stirred for 30 min then acidified by addition of aq 1M HCl solution (12 mL, 12 mmol) and partitioned between water (100 mL) and EtOAc (40 mL). The aqueous layer was separated and extracted with EtOAc (25 mL). The organic phases were combined, dried rapidly over sodium sulfate and filtered, rinsing with hot THF to dissolve some precipitated solid product. The filtrate was concentrated in vacuo to give the crude ring opened amido-acid intermediate as a white solid. A slurry of the crude material suspended in 60 mL of dry THF and 25 mL of glacial HOAc and was heated with stirring to 60° C. during which time the mixture became homogeneous. After 9 h, the reaction mixture was cooled and concentrated in vacuo to give a pale yellow solid. The solid was triturated with 30 mL of toluene, warmed (~50° C.), then allowed to cool to rt. The insoluble product was collected on a Buchner funnel, washed with toluene and dried under vacuum to afford compound 751 (75%) as a white solid. 400 MHz $^{1}$H NMR (DMSO-$d_6$) δ 1.34 (s, 3H), 1.34 (m, 1H), 1.45 (s, 3H), 2.32 (dd, J=7.3, 13.1, 1H), 3.20 (d, J=7.3, 1H), 3.28 (d, J=7.2, 1H), 3.79 (m, 1H), 5.11 (d, J=6.1, 1H); 100 MHz $^{13}$C NMR (DMSO-$d_6$) δ 169.6, 86.7, 82.3, 72.8, 52.9, 50.3, 46.5, 16.0, 11.2. The absolute stereochemistry of compound 751 is established by the known stereochemistry of the intermediate compound 471Dii and the retention of configuration therein. The absolute stereochemistry is as drawn in the above FIGURE.

EXAMPLE 752

[3aR-(3aα,4β,7β,7aα)]-Hexahydro-5-hydroxy-4,7-dimethyl-4,7-epoxyisobenzofuran-1,3-dione (752)

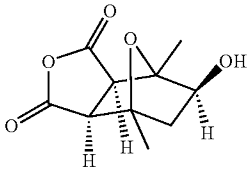

Compound 752 was synthesized as described in example 751 with the exception that the starting compound 471Di was utilized as the starting material rather than compound 471Dii. 400 MHz $^{1}$H NMR (DMSO-$d_6$) δ 1.34 (s, 3H), 1.34 (m, 1H), 1.45 (s, 3H), 2.32 (dd, J=7.3, 13.1, 1H), 3.20 (d, J=7.3, 1H), 3.28 (d, J=7.2, 1H), 3.79 (m, 1H), 5.11 (d, J=6.1, 1H); 100 MHz $^{13}$C NMR (DMSO-$d_6$) δ 169.6, 86.7, 82.3, 72.8, 52.9, 50.3, 46.5, 16.0, 11.2. The absolute stereochemistry of compound 752 is established by the known stereochemistry of the intermediate compound 471Di and the retention of configuration therein. The absolute stereochemistry is as drawn in the above FIGURE.

EXAMPLE 753

[3aR-(3aα,4β,5β,7β,7aα)]-4-(Octahydro-5-hydroxy-4,7-dimethyl-1,3-dioxo-4,7-epoxy-2H-isoindol-2-yl)-2-iodobenzonitrile (753G)

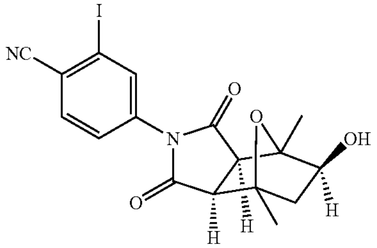

A. 4-(2,5-Dioxo-2,5-dihydro-pyrrol-1-yl)-2-trifluoromethylbenzonitrile (453A)

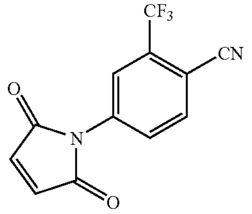

A mixture of 3-trifluoromethyl-4-cyano-aniline (24.0 g, 129 mmol) and maleic anhydride (14.0 g, 143 mmol) in 50 mL of acetic acid was heated at 115° C. overnight. A precipitate was obtained during the heating period. The reaction was allowed to stand at rt for an additional overnight period. The solid was removed by filtration, the filter cake was washed with diethyl ether and dried to give 21 g (79 mmol, 61%) of compound 753A as an off white solid. HPLC: 100% at 2.11 min (retention time) (YMC S5 ODS column, 4.6×50 mm, eluting with 10-90% aqueous methanol over 4 mincontaining 0.2% phosphoric acid, 4 mL/min, monitoring at 220 nm).

B. (3aα,4β,7β,7aα)-4-(1,3,3a,4,7,7a-Hexahydro-4,7-dimethyl-1,3-dioxo-4,7-epoxy-2H-isoindol-2-yl)-2-(trifluoromethyl)benzonitrile (753B)

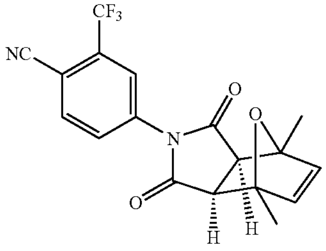

A slurry of 4-(2,5-dihydro-2,5-2,5-dioxo-1H-pyrrol-1-yl)-2-trifluoromethylbenzonitrile (15.0 g, 56.35 mmol) and 2,5-dimethylfuran (32.5 g, 338 mmol) was stirred at 60° C. for 3 h, followed by continued stirring for another 14 h at 23° C. The mixture was diluted with cold (~5° C.) toluene (15 mL) and the resulting off white solid was collected by filtration while cold. The filter cake was washed with cold toluene (20 mL) and dried at 23° C. in vacuum oven for 24 h to provide compound 753B (18:6 g, 91% yield) with a purity of 98.7% as judged by HPLC.

C. [3aR-(3aα,4β,5β,7β,7aα)]-4-(Octahydro-5-hydroxy-4,7-dimethyl-1,3-dioxo-4,7-epoxy-2H-isoindol-2-yl)-2-(trifluoromethyl)benzonitrile (753C)

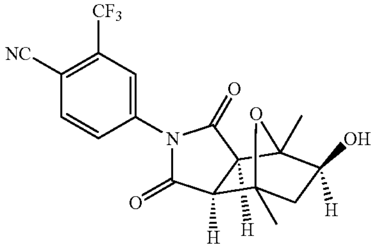

A slurry of compound 753B (5.0 g, 13.81 mmol), allylpalladium chloride dimer (10 mg, 0.027 mmol) and (R)-2-methoxy-2'-diphenylphosphino-1,1'-binaphthyl (R-MOP, 26 mg, 0.055 mmol) in THF (14 mL) was purged with nitrogen and cooled to 10° C. To the above mixture, was added trichlorosilane (3.7 g, 27.62 mmol) slowly over a period of 10 min and the resulting heterogeneous mixture was stirred for 24 h at 10° C. The mixture was diluted with THF (85 mL) and further cooled to −20° C. To the above mixture, a solution of triethylamine (9.76 g, 96.67 mmol) in ethanol (6.35 g, 138.1 mmol) was added slowly keeping the temperature <25° C. and stirred for another 2 h at rt. The white solid was filtered and the filter cake was washed with THF (50 mL) and the filtrate was evaporated under the reduced pressure. The oily residue was dissolved in ethyl acetate (100 mL) and stirred at 23° C. in the presence of trithiocyanuric acid (TMT, 500 mg) and charcoal (500 mg) for 5 h. The slurry was filtered through a pad of celite and silica gel and the filtrate was evaporated under the reduced pressure. The residue was dissolved in a mixture of THF (175 mL) and methanol (125 mL), and to this mixture was added anhydrous potassium fluoride (2.0 g, 34.5 mmol), potassium hydrogencarbonate (6.9 g, 69 mmol), followed by ureahydrogen peroxide adduct (6.5 g, 69 mmol). This suspension was stirred at rt for 14 h and an additional amount of potassium fluoride (800 mg, 13.81 mmol), potassium hydrogencarbonate (1.38 g, 13.81 mmol) and urea-hydrogen peroxide adduct (2.59 g, 27.62 mmol) was added. Stirring continued for another 12 h and the slurry was filtered and the filter cake was washed with ethyl acetate (100 mL). The filtrate was washed consecutively with 10% aqueous sodium hydrogensulfite (50 mL×2), water (50 mL) and brine (50 mL). The solvent was evaporated under the reduced pressure to provide a light brown foam. Column chromatography of this foam using silica gel and EtOAc-heptane (2:3) afforded compound 753C (4.72 g, 90%, >99% pure by HPLC) as an off white solid. This material has an enantiomeric purity of >96% ee by chiral HPLC and LC-MS: m/z 379 (M+H-). The absolute stereochemistry of compound 753C was established by comparison to existing material of known stereochemistry as described in Example 483.

D. [1S-(1β,2α,3α,4β,6β)]-3-[[(4-Cyano-3-(trifluoromethyl)phenyl)amino]carbonyl]-6-hydroxy-1,4-dimethyl-7-oxa-bicyclo[2.2.1]heptane-2-carboxylic acid & [1R-(1β,2α,3α,4β,5β)]-3-[[(4-Cyano-3-(trifluoromethyl)phenyl)amino]carbonyl]-5-hydroxy-1,4-dimethyl-7-oxa-bicyclo[2.2.1]heptane-2-carboxylic acid (753Di &753Dii)

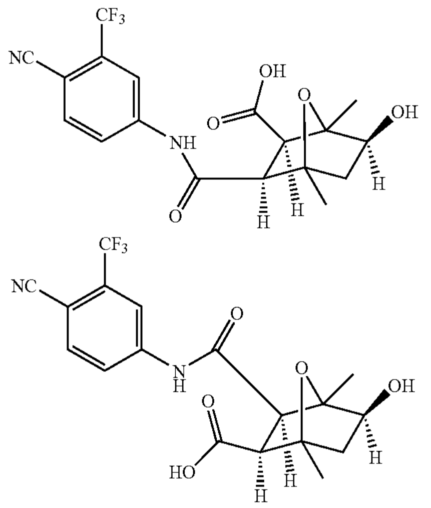

Compound 753C (25.0 g, 65.7 mmol) was dissolved in THF (100 mL) at 22° C. and 1 N NaOH (100 mL) was added. After 1 h, THF (100 mL), 1 N HCl (110 mL) and brine (100 mL) were added. The mixture was then extracted once with EtOAc (200 mL) and twice with 1:1 THF/EtOAc (200 mL). The combined organics were dried over anhydrous $MgSO_4$, filtered and concentrated in vacuo to give compounds 753Di and 753Dii (1:1 by HPLC) as a white solid. No purification was necessary. HPLC: 100% at 2.217 and 2.413 min (retention time) (YMC S5 ODS-A column 4.6×50 mm eluting with 10-90% aqueous methanol over 4 mincontaining 0.2% phosphoric acid, 4 mL/min, monitoring at 220 nm).

E. [3aR-(3aα,4β,7β,7aα)]-Hexahydro-5-hydroxy-4,7-dimethyl-4,7-epoxyisobenzofuran-1,3-dione (753E)

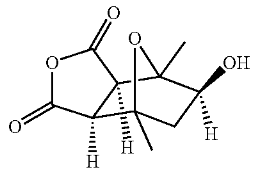

Compounds 753Di and 753Dii were suspended in a mixture of THF (500 mL) and AcOH (200 mL) and heated to 60° C. for 16 h. The reaction became homogenous after 4 h. The reaction was cooled to 22° C. and concentrated in vacuo. Toluene (200 mL) was then added and the mixture was heated to 90° C. for 4 h until all product was dissolved. The mixture was then cooled to 22° C. and left standing for 20 h. Compound 753E precipitates from solution over the 20 h period. The resulting solid was filtered and rinsed with toluene followed by drying in vacuo. A yield of 11.93 g of crude compound 753E was obtained as an off-white solid. Crude compound 753E (10 g) was dissolved in 350 ml of warm EtOAc (the solution was turbid), and then 5 g of decolorizing carbon was added and the mixture was stirred at rt for 40 mins. After filtering through celite, the filter cake was washed with hot EtOAc (2×50 ml). Concentration of the filtrate afforded an off-white solid that was dissolved in 40 ml of hot acetonitrile. After carefully adding 200 ml of ethyl ether, 300 ml of hexane was added and the flask was allowed to stand 18 hrs at rt. Filtration and drying afforded 8.32 g of compound 753E as a colorless crystalline solid. $^1H$ NMR (DMSO-$d^6$): δ=5.11 (d, 1H, J=6.0 Hz), 3.78 (dd, 1H, J=7.2, 30.6 Hz), 3.27 (d, 1H, J=7.2 Hz), 3.20 (d, 1H, J=7.3 Hz), 2.27 (dd, 1H, J=7.3, 13.1 Hz), 1.44 (s, 3H), 1.33 (s, 3H) and 1.32 ppm (m, 1H).

F. 4-Amino-2-iodo-benzonitrile (753F)

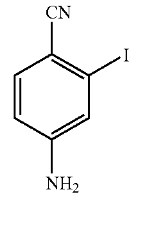

2-Iodo-4-nitro-benzonitrile (1.00 g, 3.65 mmol, was prepared by the method given in *J. Med. Chem.* 2000, 43, 3344-47) was dissolved in THF (20 mL) at 60° C. with mechanical stirring. EtOH (25 mL) was then added followed by aq $NH_4Cl$ (0.293 g, 5.48 mmol in 20 mL $H_2O$). Iron powder (325 mesh, 0.815 g, 14.6 mmol) was then added with vigorous stirring. After 2 h, reaction was complete. Cooled to 22° C. and filtered through celite rinsing with EtOAc. The mixture was then concentrated to ~20 mL and then diluted with EtOAc (200 mL) and washed once with 1 N NaOH (50 mL), once with brine (50 mL) and dried over anhydrous $MgSO_4$, to give, compound 753F (0.710 g) as a light yellow solid. No additional purification was needed. HPLC: 99% at 2.147 min (retention time) (YMC S5 ODS column, 4.6×50 mm, eluting with 10-90% aqueous methanol over 4 mincontaining 0.2% phosphoric acid, 4 mL/min, monitoring at 220 nm).

G. [3aR-(3aα,4β,5β,7β,7aα)]-4-(Octahydro-5-hydroxy-4,7-dimethyl-1,3-dioxo-4,7-epoxy-2H-isoindol-2-yl)-2-iodobenzonitrile (753G)

A mixture of compound 753E (1.60 g, 7.57 mmol), compound 753F (1.32 g, 5.41 mmol), 4 Å molecular sieves (2.0 g) in dimethylacetamide (8 mL) was stirred in a 175° C. oil bath for 4 h. The resulting dark mixture was cooled, diluted with EtOAc (50 mL) then filtered to remove sieves and rinsed with EtOAc. The filtrate was partitioned between EtOAc (50 mL) and water (75 mL). The organic phase was separated, washed with water (2×75 mL), brine (50 mL), then diluted with tetrahydrofuran (20 mL), dried over sodium sulfate and concentrated in vacuo to give a solid foam. The crude material was triturated with diethyl ether (100 mL) then stirred for 1.5 h. The solid precipitate was collected on a Buchner funnel then suspended in diethyl ether (50 mL) and stirred for 16 h. The resulting solid was collected on a Buchner funnel, rinsed with diethyl ether and dried under vacuum (90° C.) to afford compound 753G (67%) as an off-white solid. HPLC: 96% at 3.00 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 438.90 $[M+H]^+$. The absolute stereochemistry of compound 753G is established by the known stereochemistry of the intermediate compound 753C and the retention of configuration therein. The absolute stereochemistry is as drawn in the above FIGURE and rendered by the nomenclature.

EXAMPLE 754

[3aS-(3aα,4β,5β,7β,7aα)]-4-(Octahydro-5-hydroxy-4,7-dimethyl-1,3-dioxo-4,7-epoxy-2H-isoindol-2-yl)-2-iodobenzonitrile (754)

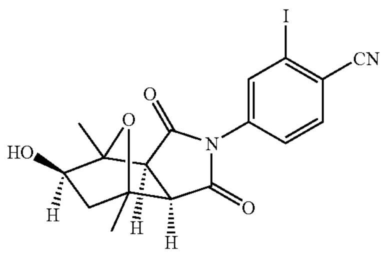

A mixture of compound 751 (850 mg, 4.01 mmol), 4-cyano-3-iodo-aniline (975 mg, 4.01 mmol), 4 Å molecular sieves (1.2 g) in dimethylacetamide (4.5 mL) was stirred in a 175° C. oil bath for 4 h. The resulting dark mixture was cooled, filtered to remove sieves and rinsed with EtOAc. The filtrate was partitioned between EtOAc (50 mL) and water (50 mL). The organic phase was separated, washed with water (2×50 mL), brine (25 mL), dried over sodium sulfate and concentrated in vacuo. The crude material was dissolved in tetrahydrofuran and purified by silica gel flash chromatography, eluting with 1:4 acetone/methylene chloride to give an impure white solid. The impure material was suspended in diethyl ether (75 mL), stirred for 18 h then collected on a Buchner funnel to afford 650 mg (37%) of compound 754 as a white solid. HPLC: 100% at 2.90 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 438.95 $[M+H]^+$. The absolute stereochemistry of compound 754 is established by the known stereochemistry of the intermediate compound 751 and the retention of configuration therein. The absolute stereochemistry is as drawn in the above FIGURE and rendered by the nomenclature.

EXAMPLE 755

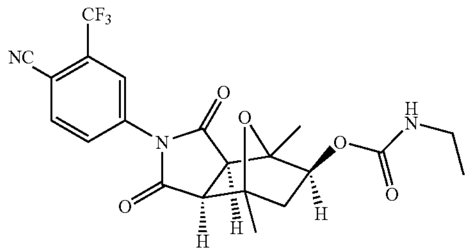

A solution of compound 471Di (80 mg, 0.21 mmol), ethyl isocyanate (30 mg, 0.43 mmol) and 4-dimethyaminopyridine (5 mg, 0.04 mmol) in dry tetrahydrofuran (1 mL) was heated to 55° C. for 2 h, then additional ethyl isocyanate (30 mg) was added and heated for another 2 h. A final portion of EIC (30 mg) was added, then after 16 h the reaction mixture was cooled, concentrated in vacuo and purified by silica gel flash chromatography on $SiO_2$ eluting with 2:1 EtOAc/heptane to give 80 mg (86%) of compound 755 as a white solid. HPLC: 94% at 3.51 min (retention time) (YMC S5 ODS column, 4.6×50 mm, eluting with 10-90% aqueous methanol over 4 min containing 0.2% phosphoric acid, 4 mL/min, monitoring at 220 nm). MS (ES): m/z 452.29 $[M+H]^+$. The absolute stereochemistry of compound 755 is established by the known stereochemistry of the intermediate compound 471Di and the retention of configuration therein. The absolute stereochemistry is as drawn in the above FIGURE and rendered by the nomenclature.

EXAMPLE 756

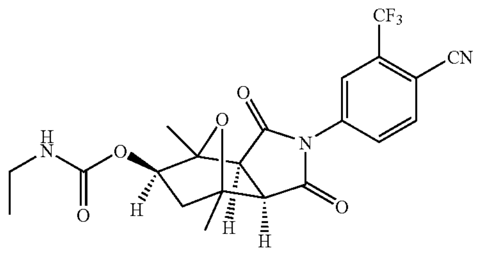

A solution of compound 471Dii (80 mg, 0.21 mmol), ethyl isocyanate (100 mg, 1.4 mmol) and 4-dimethyaminopyridine (8 mg, 0.07 mmol) in dry tetrahydrofuran (2 mL) was heated to 60° C. for 16 h, then cooled, MeOH was added and the solution was concentrated in vacuo. The reaction mixture was purified by silica gel flash chromatography, eluting with 2:1 EtOAc/heptane to give 84 mg (90%) of compound 756 as a white solid foam. HPLC: 94% at 3.54 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 452.34 $[M+H]^+$. The absolute stereochemistry of compound 756 is established by the known stereochemistry of the intermediate compound 471Dii and the retention of configuration therein. The absolute stereochemistry is as drawn in the above FIGURE and rendered by the nomenclature.

EXAMPLE 757

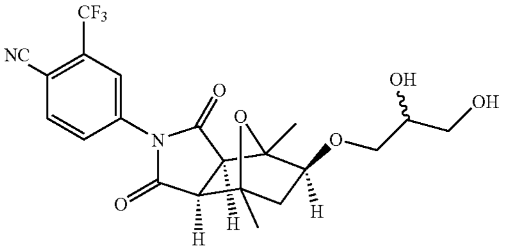

A. (757A)

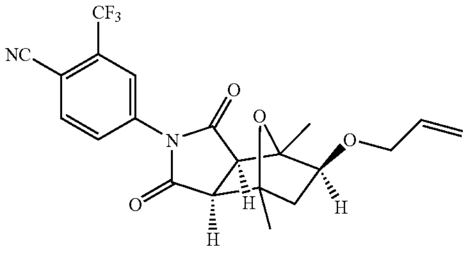

A mixture of compound 471Di (620 mg, 1.63 mmol), silver(I) oxide (3.78 g, 16.3 mmol), allyl iodide (2.74 g, 16.3 mmol) and dry MeCN (15 mL) was stirred rapidly at 75-80° C. for 7.5 h. The resulting mixture was cooled and filtered though a pad of Celite rinsing with EtOAc. The filtrate was concentrated in vacuo and the crude material purified by silica gel flash chromatography on $SiO_2$ eluting with 1:1 EtOAc/heptane to give 570 mg (83%) of compound 757A as a glass. HPLC: 96% at 3.72 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 421.27 $[M+H]^+$.

B. (757B)

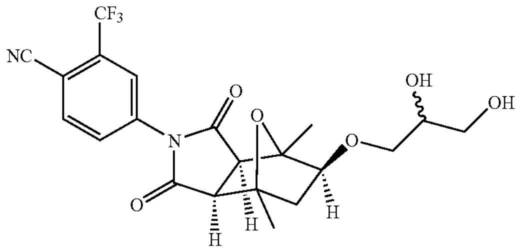

To a mixture of compound 757A (85 mg, 0.20 mmol), 4-methylmorpholine-N-oxide (26 mg, 0.22 mmol) and acetone (1.6 mL) at rt was added water (0.4 mL) and then 2.5% osmium tetroxide solution in t-butanol (17 mg, 0.002 mmol). The reaction mixture was stirred for 5 h, then filtered through a pad of Florosil. The filtrate was concentrated in vacuo and the residue partitioned between EtOAc and 1M aq HCl solution. The organic phase was separated, dried over sodium sulfate, concentrated in vacuo and the crude material purified by silica gel flash chromatography on $SiO_2$ eluting with 2:1 acetone/heptane to give compound 757B (52 mg, 55%) as a white solid. HPLC: 100% at 3.11 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 455 $[M+H]^+$. The absolute stereochemistry of compound 757B is established by the known stereochemistry of the intermediate compound 471Di and the retention of configuration there in. The absolute stereochemistry is as drawn in the above FIGURE and rendered by the nomenclature.

EXAMPLE 758

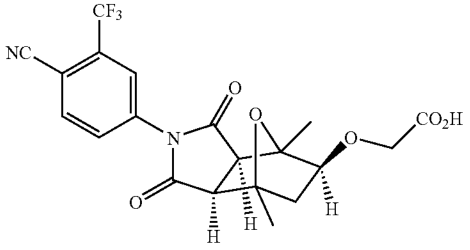

To a solution of compound 757A (45 mg, 0.11 mmol), carbon tetrachloride (0.50 mL), acetonitrile (0.5 mL) and water (0.75 mL) at rt was added sodium periodate (94 mg, 0.44 mmol) then after several minutes, ruthenium(III) chloride hydrate (50 mg, 0.24 mmol). After 30 min the dark mixture was partitioned between methylene chloride (20 mL) and water (20 mL). The mixture was filtered to remove solids, then the organic phase was separated, dried over sodium sulfate and concentrated in vacuo. The crude material purified by silica gel flash chromatography on $SiO_2$ eluting with 1:20 MeOH/EtOAc then 1:5:100 HOAc/MeOH/EtOAc to give compound 758 (19 mg, 36%) as a white solid foam. HPLC: 99% at 3.31 min (retention time) (YMC S5 ODS column, 4.6×50 mm, eluting with 10-90% aqueous methanol over 4 mincontaining 0.2% phosphoric acid, 4 mL/min, monitoring at 220 rm). MS (ES): m/z 437.23 $[M-H]^-$. The absolute stereochemistry of compound 758 is established by the known stereochemistry of the intermediate compound 471Di and the retention of configuration therein. The absolute stereochemistry is as drawn in the above FIGURE and rendered by the nomenclature.

EXAMPLE 759

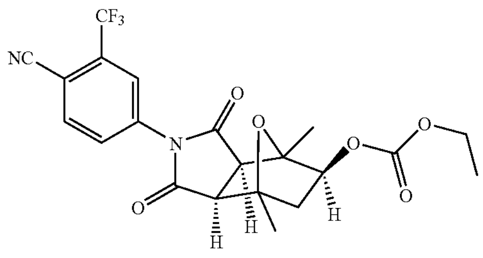

To a solution of compound 471Di (100 mg, 0.26 mmol) and triethylamine (50 mg, 0.50 mmol) in dry methylene chloride (3 mL) cooled in an ice-bath was added ethyl chloroformate (40 μL, 0.40 mmol). The reaction was warmed to rt for 2 h and an additional portion of ethyl chloroformate (40 μL), triethylamine (50 mg), 4-dimethylaminopyridine (10 mg, 0.08 mmol) was added. The reaction mixture was stirred for 18 h at rt, then partitioned between 25 mL of EtOAc and 25 mL of 1M aq HCl solution. The organic phase was separated, washed with 1M aq HCl (2×25 mL), brine (1×25 mL), dried (sodium sulfate) and concentrated in vacuo. Purification by silica gel flash chromatography eluting with 1:1 EtOAc/heptane followed by recrystallization (EtOAc/heptane) afforded 76 mg (65%) of compound 759 as a white solid. HPLC: 100% at 3.85 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 453.01 $[M+H]^+$. The absolute stereochemistry of compound 759 is established by the known stereochemistry of the intermediate compound 471Di and the retention of configuration therein. The absolute stereochemistry is as drawn in the above FIGURE and rendered by the nomenclature.

EXAMPLE 760

[3aS-(3aα,4β,5β,7β,7aα)]-2-(4-Chloro-2-methyl-3-(trifluoromethyl)phenyl)hexahydro-5-hydroxy-4,7-dimethyl-4,7-epoxy-1H-isoindole-1.3(2H)-dione (760D)

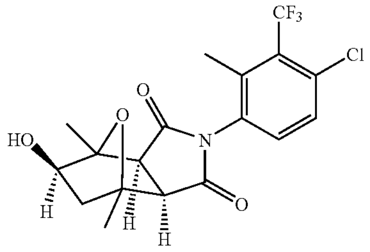

A. N-(4-Chloro-3-trifluoromethylphenyl)-2,2-dimethylpropionamide (760A)

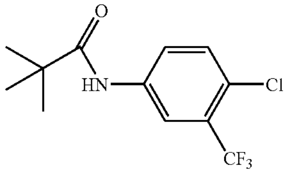

To a solution of commercially available 4-chloro-3-(trifluoromethyl)aniline (15.0 g, 76.7 mmol) in anhydrous THF (200 mL) cooled to 0-5° C. was added triethylamine (11.7 mL, 84.4 mmol) followed by pivaloyl chloride (10.4 mL, 84.4 mmol) over 30 min. The ice bath was removed and the mixture stirred at rt for 1 h. The mixture was diluted with ether and filtered. The filtrate was washed with water (2×) and brine, dried over $MgSO_4$, filtered and concentrated. The residue was triturated with hexanes and the solid was filtered and dried in vacuo to afford compound 760A (20.4 g, 95%); MS (ES): m/z=280 $[M+1]^+$.

B. N-(4-Chloro-2-methyl-3-trifluoromethylphenyl)-2,2-dimethylpropionamide (760B)

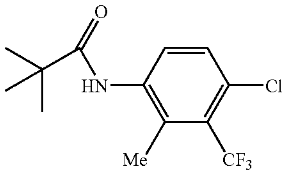

To a solution of N-(4-chloro-3-trifluoromethylphenyl)-2,2-dimethylpropionamide (2.29 g, 8.19 mmol) in anhydrous THF (25 mL) cooled to 0-5° C. was added a solution of 1.6M n-butyllithium in hexanes (12.3 mL, 19.7 mmol) slowly so that the reaction temperature was maintained below 5° C. The solution was stirred at 0-5° C. for 1.5 h. A solution of iodomethane (0.56 mL, 9.01 mmol) in petroleum ether (2 mL) was added over 20 min while maintaining the temperature below 5° C. The suspension was stirred at 0-5° C. for 1 h and diluted with water and ether. The aqueous layer was extracted with ether and the combined organic layers washed with brine, dried over $MgSO_4$, filtered and concentrated. The residue was chromatographed (silica gel) eluting with $CH_2Cl_2$ to afford compound 760B (1.60 g, 67%). MS (ES): m/z=294 $[M+1]^+$.

C. 4-Chloro-2-methyl-3-trifluoromethyl-aniline (760C)

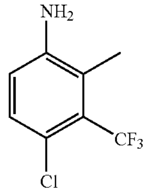

N-(4-Chloro-2-methyl-3-trifluoromethylphenyl)-2,2-dimethyl-propionamide 1.0 g, 3.4 mmol) was added to a 1:1 mixture (15 mL) of concentrated HCl and ethanol and heated at reflux for overnight. The reaction was cooled and concentrated in vacuo to give a tan solid which was then partitioned between EtOAc and saturated $NaHCO_3$. The organic layer was separated, washed with water, brine, dried ($Na_2SO_4$), filtered and concentrated to give compound 760C (0.54 g, 76%) as a brown oily solid.

D. [3aS-(3aα,4β,5β,7β,7aα)]-2-(4-Chloro-2-methyl-3-(trifluoromethyl)phenyl)hexahydro-5-hydroxy-4,7-dimethyl-4,7-epoxy-1H-isoindole-1,3(2H)-dione (760D)

To a Pyrex sealable tube was added 4-chloro-2-methyl-3-trifluoromethylaniline (0.1 g, 0.48 mmol), compound 751 (0.15 g, 0.72 mmol), TEA (0.24 g, 0.33 mL, 2.4 mmol), $MgSO_4$ (0.14 g, 1.2 mmol), and toluene (0.5 mL). The reaction was heated in the sealed tube at 150° C. for 18 h. The cooled reaction was diluted with EtOAc, filtered, concentrated and purified by Prep-TLC using $CH_2Cl_2$ as eluent to give compound 760D (0.078 g, 40%) as an off-white solid. HPLC: 90% at 3.26 min(YMC S5 ODS column) eluting with 10-90% aqueous methanol containing 0.2% phosphoric acid over a 4 min gradient monitoring at 220 nm. MS (ES): m/z 404.01 $[M+H]^+$. The absolute stereochemistry of compound 760D is established by the known stereochemistry of the intermediate compound 751 and the retention of configuration therein. The absolute stereochemistry is as drawn in the above FIGURE and rendered by the nomenclature.

EXAMPLE 761

[3aR-(3aα,4β,5β,7β,7aα)]-2-(4-Chloro-2-methyl-3-(trifluoromethyl)phenyl)hexahydro-5-hydroxy-4,7-dimethyl-4,7-epoxy-1H-isoindole-1,3(2H)-dione (761)

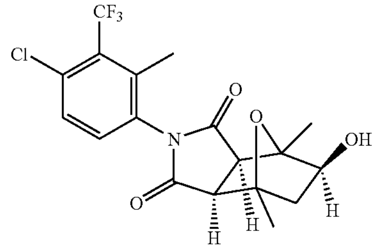

To a Pyrex sealable tube was added compound 760C (0.1 g, 0.48 mmol), compound 752 (0.15 g, 0.72 mmol), TEA (0.24 g, 0.33 mL, 2.4 mmol), $MgSO_4$ (0.14 g, 1.2 mmol), and toluene (0.5 mL). The reaction was heated in the sealed tube at 150° C. for 18 h. The cooled reaction was diluted with EtOAc, filtered, concentrated and purified by $SiO_2$ Prep-TLC using $CH_2Cl_2$ as eluent to give compound 761 (0.056 g, 29%) as an off-white solid. HPLC: 90% at 3.27 min(YMC S5 ODS column) eluting with 10-90% aqueous methanol containing 0.2% phosphoric acid over a 4 min gradient monitoring at 220 nm. MS (ES): m/z 403.91 $[M+H]^+$. The absolute stereochemistry of compound 761 is established by the known stereochemistry of the intermediate compound 752 and the retention of configuration therein. The absolute stereochemistry is as drawn in the above FIGURE and rendered by the nomenclature.

EXAMPLE 762

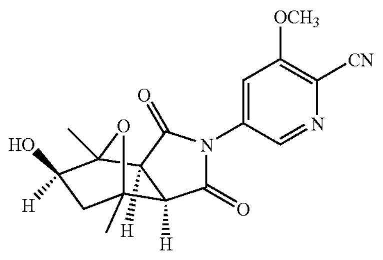

A. 3-Methoxypyridine-1-oxide (762A)

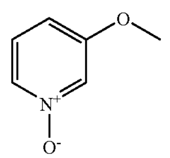

3-Methoxypyridine (20.08 g, 209 mmol) was dissolved in 100 mL of acetic acid. 30% $H_2O_2$ (28.3 mL, 275 mmol) was added and the reaction mixture was heated at 70° C. for six h. The cooled reaction mixture was concentrated and the residue dissolved in $CH_2Cl_2$ and stirred overnight with 20 g of solid potassium carbonate. The mixture was filtered and concentrated to give compound 762A (25.2 g, 100%) as a light yellow solid which was characterized by $^1H$ NMR and carried on to the next step.

B. 2-Cyano-3-methoxypyridine (762B)

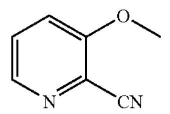

3-Methoxypyridine-1-oxide (25.2 g, 209 mmol) was dissolved in acetonitrile (260 mL). Trimethylsilycyanide (66.35 g, 669 mmol) and triethylamine (45.13 g, 446 mmol) were added and the reaction mixture heated at reflux for overnight. The cooled solution was concentrated in vacuo to give a brown solid which was partitioned between $CH_2Cl_2$ and 3M $Na_2CO_3$. The organic layer was separated, washed with brine, dried ($MgSO_4$), filtered and concentrated in vacuo. The residue was purified by silica gel chromatography using 1:1 EtOAc/hexanes as eluent. Compound 762B was isolated (17.63 g, 63%) as a light yellow solid. HPLC: 96.2% at 1.37 min(YMC S5 ODS column) eluting with 10-90% aqueous methanol containing 0.2% phosphoric acid over a 4 min gradient monitoring at 220 nm. MS (ES): m/z 134.88 $[M+H]^+$.

C. 2-Cyano-3-methoxy-5-nitropyridine (762C)

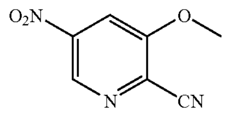

2-Cyano-3-methoxypyridine (17.63 g, 131.4 mmol) was dissolved in $CH_2Cl_2$ (400 mL) and cooled in an ice bath. Tetrabutylammonium nitrate (52.02 g, 170.8 mmol) and trifluoroacetic anhydride (35.88 g, 170.8 mmol) were dissolved in 200 mL of $CH_2Cl_2$ and added in a thin stream via addition funnel. The mixture was warmed to 23° C. and stirred for 60 h. The reaction mixture was stirred for one h with saturated sodium bicarbonate. The organic layer was separated, washed with brine, dried ($MgSO_4$), filtered, concentrated in vacuo, and purified by silica gel column chromatography using $CH_2Cl_2$ as eluent to give compound 762C (18.07 g, 79%) as a light yellow crystalline solid. HPLC: 100% at 1.67 min (YMC S5 ODS column) eluting with 10-90% aqueous methanol containing 0.2% phosphoric acid over a 4 min gradient monitoring at 220 nm. MS (ES): m/z 179.93 $[M+H]^+$.

D. 5-Amino-2-cyano-3-methoxypyridine (762D)

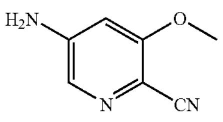

2-Cyano-3-methoxy-5-nitropyridine (1.0 g, 5.6 mmol) was dissolved in 1:1 EtOAc/AcOH (10 mL) and heated to 65° C. Iron powder (1.61 g, 28 mmol, 325 mesh) was added and the mixture stirred for two h. The mixture was filtered though Celite and the filtrate concentrated in vacuo. The residue was partitioned between EtOAc and saturated aqueous sodium bicarbonate. The organic layer was separated, washed with brine, dried ($MgSO_4$), filtered and concentrated. The residue was purified by $SiO_2$ Prep-TLC using $CH_2Cl_2$ as the eluent to give the compound 762D (0.805 g, 97%) as an off-white solid. HPLC: 100% at 1.31 min(YMC S5 ODS column) eluting with 10-90% aqueous methanol containing 0.2% phosphoric acid over a 4 min gradient monitoring at 220 nm. MS (ES): m/z 149.90 $[M+H]^+$.

E. (762E)

5-Amino-2-cyano-3-methoxypyridine (0.1 g, 0.67 mmol), 4 Å molecular sieves (0.4 g), compound 751 (0.142 g, 0.67 mmol), and N,N-dimethylacetamide (0.67 mL) were combined in a sealable Pyrex tube and heated at 170° C. for 1 h. The cooled reaction mixture was diluted with EtOAc and filtered. The filtrate was washed 3× with 1:1 saturated $NH_4Cl$/water and then brine. The filtrate was dried over $Na_2SO_4$, filtered, concentrated and purified by Prep-TLC using 4:1 chloroform/acetone as the eluent to give the compound 762E (0.062 g, 27%) as a white solid. HPLC: 94% at 1.85 min (YMC S5 ODS column) eluting with 10-90% aqueous methanol containing 0.2% phosphoric acid over a 4 min gradient monitoring at 220 nm. MS (ES): m/z 344.02 $[M+H]^+$. The absolute stereochemistry of compound 762E is established by the known stereochemistry of the intermediate compound 751 and the retention of configuration therein. The absolute stereochemistry is as drawn in the above FIGURE and rendered by the nomenclature.

EXAMPLE 763

[3aR-(3aα,4β,5β,7β,7aα)]-5-(Octahydro-5-hydroxy-4,7-dimethyl-1,3-dioxo-4,7-epoxy-2H-isoindol-2-yl)-3-(trifluoromethyl)-2-pyridinecarbonitrile (763F)

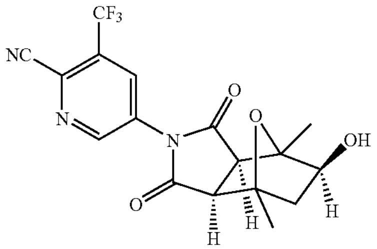

A. 3-Bromopyridine-1-oxide (763A)

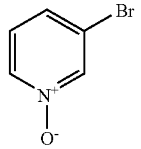

3-Bromopyridine (11.06 g, 70 mmol), 30% $H_2O_2$ (14 mL, 140 mmol), and methyltrioxorhenium (0.035 g, 0.14 mmol) were added to 28 mL of $CH_2Cl_2$ and stirred at rt overnight. A 25 mg portion of manganese dioxide was added and the reaction was stirred until the evolution of oxygen was complete (~1 h). The organic layer was separated, washed with brine, dried over $MgSO_4$, filtered, and concentrated in vacuo to give compound 673A (9.84 g (81%) as a yellow oil.

B. 3-Bromo-2-cyanopyridine (763B)

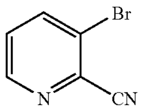

3-Bromopyridine-1-oxide was converted to compound 763B as described in example 762B. The crude product was purified by silica gel chromatography using $CH_2Cl_2$ as eluent to give compound 763B (6.64 g, 65%) as an off-white solid. The product was characterized by $^1H$ NMR.

C. 3-Bromo-2-cyano-5-nitropyridine (763C)

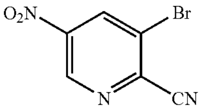

3-Bromo-2-cyanopyridine was converted to compound 763C as described in example 762C. The crude product was purified by silica gel chromatography using 20% hexanes/$CH_2Cl_2$ as eluent to give compound 763C (1.27 g, 16%) as an off-white solid. The product was characterized by $^1H$ NMR.

D. 2-Cyano-5-nitro-3-trifluoromethylpyridine (763D)

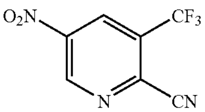

3-Bromo-2-cyano-5-nitropyridine (0.23 g, 1 mmol) was dissolved in DMF (3 mL). copper iodide (0.023 g, 0.12 mmol) and methyl 2,2-difluoro-2-(fluorosulfonyl)acetate (0.1 g, 0.5 mmol) were added and the reaction mixture heated at 80° C. for 7 h. Additional methyl 2,2-difluoro-2-(fluorosulfonyl)acetate (0.05 g, 0.25 mmol) was added and heating at 80° C. was continued for an additional 8 h. The cooled reaction mixture was poured into water to give a dark oil. Water was decanted and the oil was dissolved in EtOAc and washed with water and brine. The organic layer was dried over $MgSO_4$, filtered, and concentrated in vacuo. The residue was purified by silica gel chromatography using $CH_2Cl_2$ as eluent to compound 763D (0.065 g, 43%) as a yellow oil. HPLC: 90% at 2.09 min(YMC S5 ODS column) eluting with 10-90% aqueous methanol containing 0.2% phosphoric acid over a 4 min gradient monitoring at 220 nm.

E. 5-Amino-2-cyano-3-trifluoromethylpyridine (763E)

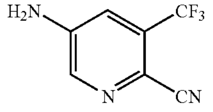

2-Cyano-5-nitro-3-trifluoromethylpyridine (0.065 g, 0.3 mmol) was reacted in the same manner as described in example 762D to give the desired compound 763E (0.046 g, 82%) as a gold colored solid after trituration with ether. HPLC: 100% at 2.07 min(YMC S5 ODS column) eluting with 10-90% aqueous methanol containing 0.2% phosphoric acid over a 4 min gradient monitoring at 220 nm. MS (ES): m/z 187.82 $[M+H]^+$.

F. [3aR-(3aα,4β,5β,7β,7aα)]-5-(Octahydro-5-hydroxy-4,7-dimethyl-1,3-dioxo-4,7-epoxy-2H-isoindol-2-yl)-3-(trifluoromethyl)-2-pyridinecarbonitrile (763F)

5-Amino-2-cyano-3-trifluoromethylpyridine (0.044 g, 0.24 mmol) was reacted with compound 752 (0.087 g, 0.41 mmol) according to the procedure described for the synthesis of compound 762. The crude product was purified by $SiO_2$ Prep-TLC using 15% acetone/$CHCl_3$ as eluent to give compound 763F (0.058 g, 65%) as an off-white solid. HPLC: 92% at 2.58 min(YMC S5 ODS column) eluting with 10-90% aqueous methanol containing 0.2% phosphoric acid over a 4 min gradient monitoring at 220 nm. MS (ES): m/z 382.33 $[M+H]^+$. The absolute stereochemistry of compound 763F is established by the known stereochemistry of the intermediate compound 752 and the retention of configuration there in. The absolute stereochemistry is as drawn in the above FIGURE and rendered by the nomenclature.

EXAMPLE 764

[3aS-(3aα,4β,5β,7β,7aα)]-5-(Octahydro-5-hydroxy-4,7-dimethyl-1,3-dioxo-4,7-epoxy-2H-isoindol-2-yl)-3-(trifluoromethyl)-2-pyridinecarbonitrile (764)

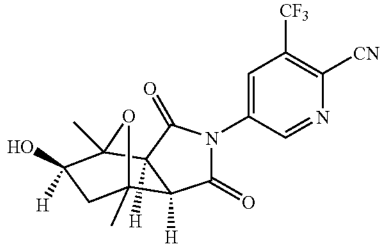

5-Amino-2-cyano-3-trifluoromethylpyridine (0.2 g, 1.07 mmol) was reacted with compound 751 (0.386 g, 1.82 mmol) according to the procedure described in example 763F. The crude product was purified by $SiO_2$ Prep-TLC using 15% acetone/$CHCl_3$ as the eluent to give compound 764 (0.293 g, 72%) as an off-white solid. HPLC: 92% at 2.58 min(YMC S5 ODS column) eluting with 10-90% aqueous methanol containing 0.2% phosphoric acid over a 4 min gradient monitoring at 220 nm. MS (ES): m/z 382.23 $[M+H]^+$. The absolute stereochemistry of compound 764 is established by the known stereochemistry of the intermediate compound 751 and the retention of configuration therein. The absolute stereochemistry is as drawn in the above FIGURE and rendered by the nomenclature.

EXAMPLE 765

765D

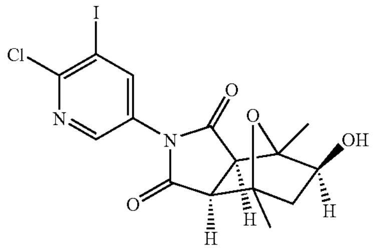

A. 2-Hydroxy-3-iodo-5-nitropyridine (765A)

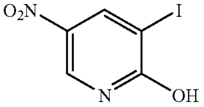

2-Hydroxy-5-nitropyridine (7.0 g, 50 mmol) was suspended in 100 mL of 20% sulfuric acid and then treated with potassium iodate (4.2 g, 19.6 mmol) dissolved in 10 mL of water. The mixture was heated to 100° C. and potassium iodide (8.0 g, 48.2 mmol) dissolved in 20 mL of water was added dropwise over one h. The reaction mixture turns a purplish-red and a precipitate forms. After 0.5 h, the reaction mixture is cooled and filtered. The solid is stirred for 15 min with 10% sodium meta-bisulfite solution, filtered, washed with water and dried at 80° C. overnight on a vacuum pump to give the desired compound 765A (12.32 g, 92%) as a yellow solid. The product was characterized by $^1H$ NMR.

B. 2-Chloro-3-iodo-5-nitropyridine (765B)

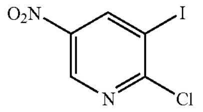

2-Hydroxy-3-iodo-5-nitropyridine (2.55 g, 9.5 mmol), phosphorous pentachloride (2.60 g, 12 mmol) and phosphorous oxychloride (2 mL) were combined in a flask under nitrogen and heated to 140° C. for 45 mins. The cooled reaction mixture was poured over ice to give a solid which was partitioned between $CH_2Cl_2$ and water. The organic layer was separated, washed with brine, dried ($MgSO_4$), filtered, and the solvent was removed in vacuo to give compound 765B (2.25 g, 83%) as a yellow solid. HPLC: 98.5% at 2.75 min(YMC S5 ODS column) eluting with 10-90% aqueous methanol containing 0.2% phosphoric acid over a 4 min gradient monitoring at 220 nm.

C. 5-Amino-2-chloro-3-iodopyridine (765C)

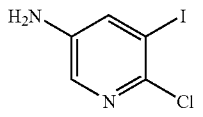

2-Chloro-3-iodo-5-nitropyridine (0.25 g, 0.88 mmol) was reacted with iron powder (0.25 g, 4.4 mmol) in the manner described in example 762D. Removal of the solvent in vacuo gave compound 765C (0.172 g, 77%). as a golden yellow solid. HPLC: 100% at 2.32 min(YMC S5 ODS column) eluting with 10-90% aqueous methanol containing 0.2% phosphoric acid over a 4 min gradient monitoring at 220 nm. MS (ES): m/z 255.03 $[M+H]^+$.

D. (765D)

5-Amino-2-chloro-3-iodopyridine (0.06 g, 0.24 mmol) and compound 752 (0.085 g, 0.4 mmol) was reacted as previously described in example 762E. The crude product obtained after workup was purified by $SiO_2$ Prep-TLC using 10% acetone/$CHCl_3$ as eluent to give compound 765D (0.067 g, 62%) as an off-white foam. HPLC: 95% at 2.65 min(YMC S5 ODS column) eluting with 10-90% aqueous methanol containing 0.2% phosphoric acid over a 4 min gradient monitoring at 220 nm. MS (ES): m/z 448.96 $[M+H]^+$. The absolute stereochemistry of compound 765D is established by the known stereochemistry of the intermediate compound 752 and the retention of configuration therein. The absolute stereochemistry is as drawn in the above FIGURE and rendered by the nomenclature.

EXAMPLE 766

[3aR-(3aα,4β,5β,7β,7aα)]-2-(4-Chloro-3-(trifluoromethyl)pyridinyl)hexahydro-5-hydroxy-4,7-dimethyl-4,7-epoxy-1H-isoindole-1,3(2H)-dione (766C)

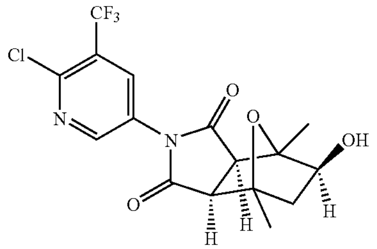

A. 2-Chloro-5-nitro-3-trifluoromethylpyridine (766A)

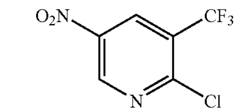

2-Chloro-3-iodo-5-nitropyridine (1.0 g, 3.5 mmol), methyl 2,2-difluoro-2-(fluorosulfonyl)acetate (0.35 g, 1.82 mmol), and copper iodide (0.083 g, 0.44 mmol) were reacted in DMF (10 mL) according to the method described in example 763D. The crude product was purified by silica gel chromatography using 30% $CH_2Cl_2$/hexane as the eluent to give compound 766A (0.278 g, 35%) as a colorless oil. The product was characterized by $^1H$ NMR and $^{19}F$ NMR.

B. 5-Amino-2-chloro-3-trifluoromethylpyridine (766B)

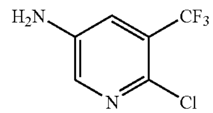

2-Chloro-5-nitro-3-trifluoromethylpyridine (0.16 g, 0.68 mmol) and iron powder (0.2 g, 3.42 mmol, 325 Mesh) were reacted as described in example 762D. Purification of the crude product by Prep-TLC using 10% ether/$CH_2Cl_2$ as eluent gave compound 766B (0.098 g, 73%) as a yellow solid. HPLC: 89% at 2.52 min(YMC S5 ODS column) eluting with 10-90% aqueous methanol containing 0.2% phosphoric acid over a 4 min gradient monitoring at 220 nm. MS (ES): m/z 197.01 $[M+H]^+$.

C. [3aR-(3aα,4β,5β,7β,7aα)]-2-(4-Chloro-3-(trifluoromethyl)pyridinyl)hexahydro-5-hydroxy-4,7-dimethyl-4,7-epoxy-1H-isoindole-1,3(2H)-dione (766C)

5-Amino-2-chloro-3-trifluoromethylpyridine (0.045 g, 0.23 mmol) and compound 751 (0.085 g, 0.4 mmol) were reacted as described in example 762E. After workup, the crude product was purified by Prep-TLC using 10% acetone/$CHCl_3$ as the eluent to give compound 766C (0.038 g, 42%) as an off-white solid. HPLC: 100% at 2.92 min(YMC S5 ODS column) eluting with 10-90% aqueous methanol containing 0.2% phosphoric acid over a 4 min gradient monitoring at 220 nm. MS (ES): m/z 391.06 $[M+H]^+$. The absolute stereochemistry of compound 766C is established by the known stereochemistry of the intermediate compound 751 and the retention of configuration therein. The absolute stereochemistry is as drawn in the above FIGURE and rendered by the nomenclature.

EXAMPLE 767

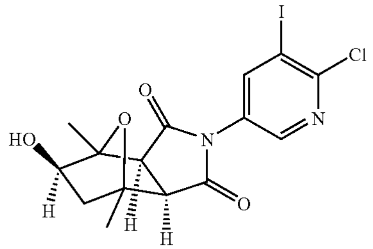

5-Amino-2-chloro-3-iodopyridine (0.06 g, 0.24 mmol) and compound 752 (0.085 g, 0.4 mmol) were reacted as described in example 762E. The crude reaction product was purified by Prep-TLC using 20% acetone/$CHCl_3$ as the eluent to give compound 767 (0.061 g, 58%) as a yellow solid. HPLC: 100% at 2.64 min(YMC S5 ODS column) eluting with 10-90% aqueous methanol containing 0.2% phosphoric acid over a 4 min gradient monitoring at 220 nm. MS (ES): m/z 449.02 $[M+H]^+$. The absolute stereochemistry of compound 767 is established by the known stereochemistry of the intermediate compound 752 and the retention of configuration therein. The absolute stereochemistry is as drawn in the above FIGURE and rendered by the nomenclature.

EXAMPLE 768

[3aS-(3aα,4β,5β,7β,7aα)]-2-(4-Chloro-3-(trifluoromethyl)pyridinyl)hexahydro-5-hydroxy-4,7-dimethyl-4,7-epoxy-1H-isoindole-1,3(2H)-dione (768)

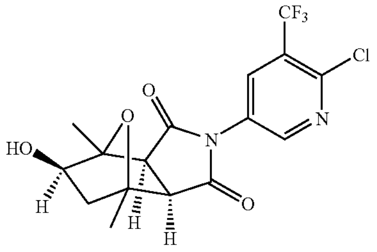

6-Chloro-5-trifluoromethyl-pyridin-3-ylamine (0.045 g, 0.23 mmol) and compound 752 (0.085 g, 0.4 mmol) were reacted as described in example 762E. The crude product was purified by $SiO_2$ Prep-TLC using 10% acetone/$CHCl_3$ as the eluent to give compound 768 (0.048 g, 54%) as a white solid. HPLC: 100% at 2.91 min(YMC S5 ODS column) eluting with 10-90% aqueous methanol containing 0.2% phosphoric acid over a 4 min gradient monitoring at 220 nm. MS (ES): m/z 391.21 $[M+H]^+$. The absolute stereochemistry of compound 768 is established by the known stereochemistry of the intermediate compound 752 and the retention of configuration therein. The absolute stereochemistry is as drawn in the above FIGURE and rendered by the nomenclature.

EXAMPLE 769

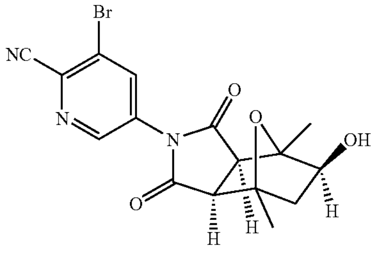

A. 5-Amino-3-bromo-2-cyanopyridine (769A)

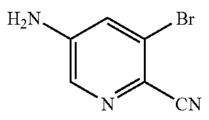

3-Bromo-2-cyano-5-nitropyridine (0.4 g, 1.75 mmol) and iron powder (0.51 g, 8.8 mmol, 325 Mesh) were reacted as described in example 762D. The crude solid obtained by trituration with ether was purified by $SiO_2$ Prep-TLC using 4:1 $CH_2Cl_2$/ether as eluent to give compound 769A (0.16 g, (65%) as an off-white solid. HPLC: 100% at 1.77 min(YMC S5 ODS column) eluting with 10-90% aqueous methanol containing 0.2% phosphoric acid over a 4 min gradient monitoring at 220 nm. MS (ES): m/z 197.93 $[M+H]^+$.

B. (769B)

5-Amino-3-bromo-2-cyanopyridine (0.06 g, 0.3 mmol) and compound 752 (0.096 g, 0.45 mmol) were reacted as previously in example 762E. The crude product was purified by $SiO_2$ Prep-TLC using 20% acetone/$CHCl_3$ as the eluent to give compound 769B (0.036 g, 30%) as an off-white solid. HPLC: 100% at 2.29 min(YMC S5 ODS column) eluting with 10-90% aqueous methanol containing 0.2% phosphoric acid over a 4 min gradient monitoring at 220 nm. MS (ES): m/z 393.33 $[M+H]^+$. The absolute stereochemistry of compound 769B is established by the known stereochemistry of the intermediate compound 752 and the retention of configuration therein. The absolute stereochemistry is as drawn in the above FIGURE and rendered by the nomenclature.

EXAMPLE 770

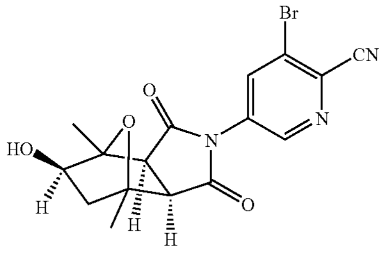

5-Amino-3-bromo-2-cyanopyridine (0.06 g, 0.3 mmol) and compound 751 (0.096 g, 0.45 mmol) were reacted as previously in example 762E. The crude product was purified by $SiO_2$ Prep-TLC using 20% acetone/$CHCl_3$ to give compound 770 (0.038 g (31%) as an off-white solid. HPLC: 99.2% at 2.28 min(YMC S5 ODS column) eluting with 10-90% aqueous methanol containing 0.2% phosphoric acid over a 4 min gradient monitoring at 220 nm. MS (ES): fn/z 392.27 $[M]^+$. The absolute stereochemistry of compound 770 is established by the known stereochemistry of the intermediate compound 751 and the retention of configuration therein. The absolute stereochemistry is as drawn in the above FIGURE and rendered by the nomenclature.

EXAMPLE 771

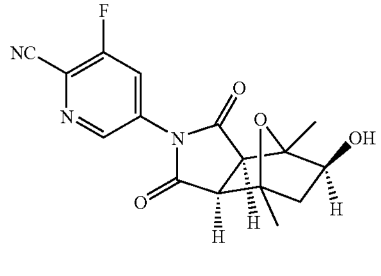

A. 3-Fluoropyridine-1-oxide (771A)

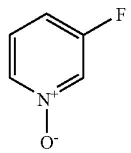

3-Fluoropyridine (9.71 g, 100 mmol), 30% $H_2O_2$ (20 mL, 200 mmol), and methyltrioxorhenium (0.13 g, 0.5 mmol) were reacted in 40 mL of $CH_2Cl_2$ according to the same procedure described in example 760C. Filtration and concentration of the solvent in vacuo gave compound 771A (8.79 g, 78%) as a yellow solid.

B. 2-Cyano-3-fluoropyridine (771B)

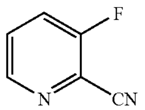

3-Fluoropyridine-1-oxide (10.0 g, 88.4 mmol), trimethylsilylcyanide (26.32 g, 265.3 mmol), and triethylamine (17.89 g, 177 mmol) were reacted in 90 mL of acetonitrile utilizing the procedure described in example 762B. Purification of the crude by silica gel chromatography using $CH_2Cl_2$ as eluent gives compound 771B (7.5 g, 70%) as a light yellow solid.

C. 2-Cyano-3-fluoro-5-nitropyridine (771C)

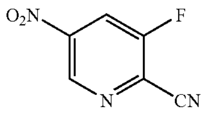

2-Cyano-3-fluoropyridine (6.5 g, 53.2 mmol), tetrabutylammonium nitrate (21.07 g, 69.2 mmol), and trifluoroacetic anhydride (14.53 g, 69.2 mmol) were reacted in 245 mL of $CH_2Cl_2$ utilizing the procedure described in example 762C. Purification of the crude by silica gel chromatography using 20% hexanes/$CH_2Cl_2$ gave compound 771C (0.12 g, 1.3%) as a yellow oil.

D. 5-Amino-2-cyano-3-fluoropyridine (771D)

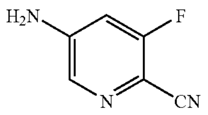

2-Cyano-3-fluoro-5-nitropyridine (0.12 g, 0.72 mmol) and iron powder (0.21 g, 3.6 mmol, 325 Mesh) were reacted in 1:1 EtOAc/AcOH (10 mL) utilizing the procedure described in example 762D. Trituration of the crude product with ether gave compound 771D (0.093 g, 94%) as a pale yellow solid. HPLC: 99% at 1.27 min(YMC S5 ODS column) eluting with 10-90% aqueous methanol containing 0.2% phosphoric acid over a 4 min gradient monitoring at 220 nm. MS (ES): m/z 138.02 $[M+H]^+$.

E. (771E)

5-Amino-2-cyano-3-fluoropyridine (0.45 g, 0.33 mmol) and compound 752 (0.104 g, 0.49 mmol) were reacted in 0.33 mL of dimethylacetamide utilizing the procedure described in example 762E. The crude residue was purified by Prep-TLC using 20% acetone/$CHCl_3$ as the eluent, yielding compound 771E (0.026 g, 23%) as a pale peach-colored solid. HPLC: 90.2% at 1.97 min(YMC S5 ODS column) eluting with 10-90% aqueous methanol containing 0.2% phosphoric acid over a 4 min gradient monitoring at 220 nm. MS (ES): m/z 332.2 $[M+H]^+$. The absolute stereochemistry of compound 771E is established by the known stereochemistry of the intermediate compound 752 and the retention of configuration therein. The absolute stereochemistry is as drawn in the above FIGURE and rendered by the nomenclature.

EXAMPLE 772

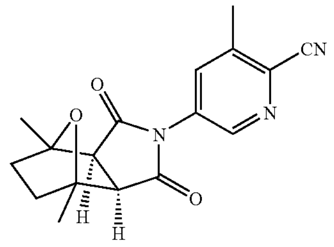

A. 2-Cyano-3-methyl-5-nitropyridine (772A)

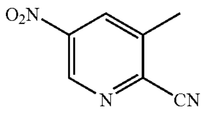

Commercially available 2-cyano-3-methylpyridine (2.36 g, 20 mmol), tetrabutylammonium nitrate (6.7 g, 22 mmol) and trifluoroacetic anhydride (4.20 g, 20 mmol) were reacted in 65 mL of $CH_2Cl_2$ utilizing the procedure described in example 762B. Purification of the crude by silica gel chromatography using 20% hexanes/$CH_2Cl_2$ as the eluent gives compound 772A (1.05 g (32%) as a light yellow solid.

B. 5-Amino-2-cyano-3-methylpyridine (772B)

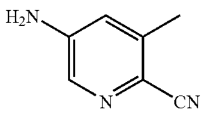

2-Cyano-3-methyl-5-nitropyridine (0.2 g, 1.23 mmol) was dissolved in 6 mL of 90% ethanol and calcium chloride (0.07 g, 0.64 mmol) was added followed by iron powder (0.62 g, 11.1 mmol, 325 Mesh). The heterogeneous mixture was stirred for one h. The mixture was filtered though Celite and concentrated to give compound 772B (0.13 g, 81%) as a light-brown solid.

C. (772C)

5-Amino-2-cyano-3-methylpyridine (0.067 g, 0.5 mmol), compound 20A (0.103 g, 0.53 mmol), $MgSO_4$ (0.15 g, 1.25 mmol), triethylamine (0.25 g, 2.5 mmol) and 1 mL of toluene were combined in a sealed tube and heated at 145° C. for 16 h. The cooled mixture was diluted with $CH_2Cl_2$, filtered, and purified by silica gel chromatography using 5% ether/$CH_2Cl_2$ as the eluent to give compound 772C (0.055 g, 35%) as an off-white solid. HPLC: 100% at 2.49 min(YMC S5 ODS column) eluting with 10-90% aqueous methanol containing 0.2% phosphoric acid over a 4 min gradient monitoring at 220 nm. MS (ES): m/z 312.2 $[M+H]^+$.

EXAMPLE 773

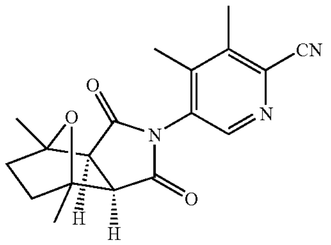

A. 2-Cyano-3,4-dimethyl-5-nitropyridine (773A)

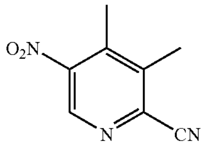

2-Cyano-3-methyl-5-nitropyridine (0.33 g, 2 mmol) was dissolved in 10 mL of THF and cooled in a dry ice/acetone bath under nitrogen. Methylmagnesium bromide (1.33 mL, 4 mmol) was added via syringe over five mins. The reaction was stirred for 2 h at −70° C. DDQ (0.068 g, 3 mmol) in 7 mL of THF was added and the mixture warmed to 25° C. The solvent was removed in vacuo and the residue was purified by silica gel chromatography using $CH_2Cl_2$ as the eluent to give compound 773A (0.15 g, 42%) as a red oil.

B. 5-Amino-2-cyano-3,4-dimethylpyridine (773B)

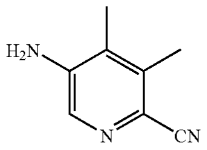

2-Cyano-3,4-dimethyl-5-nitropyridine (0.15 g, 0.85 mmol), calcium chloride (0.05 g, 0.42 mmol), and iron powder (0.44 g, 7.8 mmol, 325 Mesh) were reacted as described in example 772B. Purification of the crude product by silica gel chromatography using 1:1 ether/$CH_2Cl_2$ as the eluent gave compound 773B (0.054 g, 50%) as a yellow solid.

C. (773C)

5-Amino-2-cyano-3,4-dimethylpyridine (0.05 g, 0.34 mmol) and compound 20A (0.1 g, 0.5 mmol) were reacted as described in example 772C. The crude product obtained after filtration though Celite was purified by silica gel chromatography using 10% ether/$CH_2Cl_2$ as the eluent to give compound 773C (0.33 g, 30%). as a yellow solid. HPLC: 90% at 2.58 min(YMC S5 ODS column) eluting with 10-90% aqueous methanol containing 0.2% phosphoric acid over a 4 min gradient monitoring at 220 nm. MS (ES): m/z 326.22 $[M+H]^+$.

EXAMPLE 774

[3aR-(3aα,4β,5α,7β,7aα)]-4-(Octahydro-5-hydroxy-4,7-dimethyl-1,3-dioxo-4,7-epoxy-2H-isoindol-2-yl)-2-(trifluoromethyl)benzonitrile & [3aS(3aα,4β,5α,7β,7aα)]-4-(Octahydro-5-hydroxy-4,7-dimethyl-1,3-dioxo-4,7-epoxy-2H-isoindol-2-yl)-2-(trifluoromethyl)benzonitrile (774Bi and 774Bii)

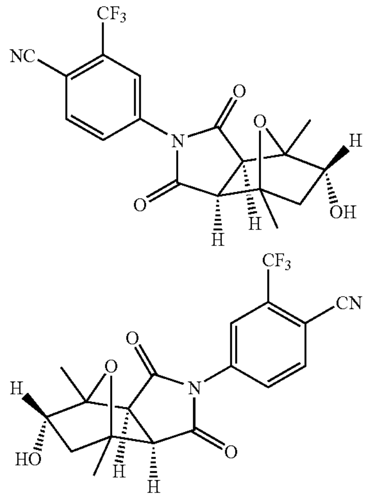

A. [3aR-(3aα,4β,5α,7β,7aα)]-4-[5-[[(1,1-Dimethylethyl)dimethylsilyl]oxy]octahydro-4,7-dimethyl-1,3-dioxo-4,7-epoxy-2H-isoindol-2-yl]-2-(trifluoromethyl)benzonitrile & [3aS(3aα,4β,5α,7β,7aα)]-4-[5-[[(1,1-Dimethylethyl)dimethylsilyl]oxy]octahydro-4,7-dimethyl-1,3-dioxo-4,7-epoxy-2H-isoindol-2-yl]-2-(trifluoromethyl)benzonitrile (774Ai & 774Aii)

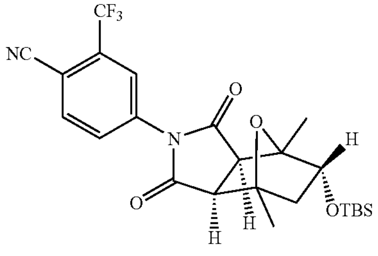

-continued

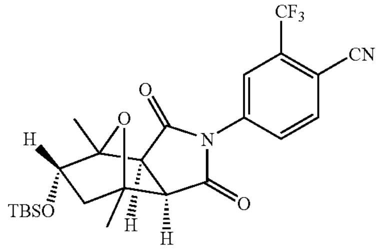

Racemic compound 222C was separated into its enantiomers by normal phase preparative chiral HPLC (CHIRALPAK AD 5×50 cm column; eluting with 7% EtOH in hexanes (isocratic) at 50 mL/min) to give the faster eluting compound 774Ai (18 mins) and the slower eluting compound 774Aii.

B. [3aR-(3aα,4β,5α,7β,7aα)]-4-(Octahydro-5-hydroxy-4,7-dimethyl-1,3-dioxo-4,7-epoxy-2H-isoindol-2-yl)-2-(trifluoromethyl)benzonitrile & [3aS-(3aα,4β,5α,7β,7aα)]-4-(Octahydro-5-hydroxy-4,7-dimethyl-1,3-dioxo-4,7-epoxy-2H-isoindol-2-yl)-2-(trifluoromethyl)benzonitrile (774Bi & 774Bii)

774Ai and 774Aii (0.12 g, 0.25 mmol) were each dissolved in 2 mL of THF and 2 mL of 10% HCl/MeOH was added and the reactions stirred overnight at rt. Saturated sodium bicarbonate and EtOAc were added and the organic layer was separated, washed with brine, dried ($Na_2SO_4$), filtered, and concentrated in vacuo to give compound 774Bi (0.084 mg, 88%) and compound 774Bii (0.076 g, 82%). as white solids. Compound 774Bi: HPLC: 100% at 2.89 min(YMC S5 ODS column) eluting with 10-90% aqueous methanol containing 0.2% phosphoric acid over a 4 min gradient monitoring at 220 nm. MS (ES): m/z 381.19 [M+H]. Compound 774Bii: HPLC: 100% at 2.89 min(YMC S5 ODS column) eluting with 10-90% aqueous methanol containing 0.2% phosphoric acid over a 4 min gradient monitoring at 220 nm. MS (ES): m/z 381.16 $[M+H]^+$. The absolute stereochemistry of compounds 774Bi & 774Bii has not been established. Although each compound represents a single antipode, the nomenclature and structure shown does not reflect the absolute stereochemistry of the compound.

EXAMPLE 775

775F

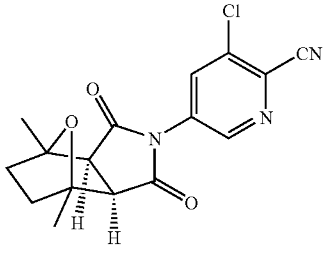

A. 3-Chloropyridine-1-oxide (775A)

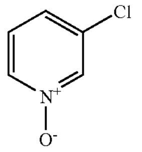

Commercially available 3-chloropyridine (11.36 g, 100 mmol) was dissolved in 60 mL of acetic acid and 30% hydrogen peroxide (15 mL) was added. The reaction mixture was heated to 70° C. for 16 h. The cooled reaction mixture was diluted with chloroform and stirred with solid potassium carbonate. The mixture was filtered and solvent removed in vacuo to give compound 775A (10.21 g, 79%) as a yellow-green oil.

B. 3-Chloro-2-cyanopyridine (775B)

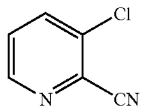

3-Chloropyridine-1-oxide (2.59 g, 20 mmol), trimethylsilyl cyanide (5.95 g, 60 mmol), and triethylamine (4.05 g, 40 mmol) were combined in 40 mL of acetonitrile and reacted as described in example 763A. The solvent was removed in vacuo and the residue partitioned between $CH_2Cl_2$ and 3M potassium carbonate. The organic layer was separated, washed with brine, dried ($MgSO_4$), and concentrated in vacuo. Purification of the crude product by silica gel chromatography using 5% ether/$CH_2Cl_2$ as the eluent gave compound 775B (1.84 g, 67%) as a white crystalline solid. HPLC: 100% at 1.64 min(YMC S5 ODS column) eluting with 10-90% aqueous methanol containing 0.2% phosphoric acid over a 4 min gradient monitoring at 220 nm. MS (ES): m/z 139.0 $[M+H]^+$.

C. 3-Chloro-2-cyano-5-nitropyridine (775C)

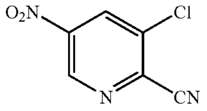

3-Chloro-2-cyanopyridine (1.75 g, 12.7 mmol), tetrabutylammonium nitrate (5.02 g, 16.5 mmol), and trifluoroacetic anhydride (3.15 g, 15 mmol) were combined in 65 mL of $CH_2Cl_2$ and reacted as described in example 762C. The crude product was purified by silica gel chromatography using $CH_2Cl_2$ as the eluent to give compound 775C (0.43 g, 16%) as a pale yellow solid.

D. 5-Amino-3-chloro-2-cyanopyridine (775D)

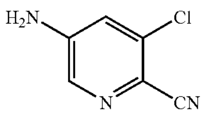

3-Chloro-2-cyano-5-nitropyridine (0.35 g, 1.9 mmol), iron powder (0.56 g, 10 mmol, 325 Mesh) and calcium chloride (0.06 g, 0.55 mmol) were combined in 10 mL of 90% ethanol and as described in example 772B. Purification of the crude product via silica gel chromatography using 10% ether/$CH_2Cl_2$ as the eluent gives compound 775D (0.14 g, 43%) as a light brown solid. HPLC: 95.5% at 1.69 min(YMC S5 ODS column) eluting with 10-90% aqueous methanol containing 0.2% phosphoric acid over a 4 min gradient monitoring at 220 nm. MS (ES): m/z 154.03 $[M+H]^+$.

E. (775E)

5-Amino-3-chloro-2-cyanopyridine (0.05 g, 0.33 mmol) and compound 20A (0.07 g, 0.36 mmol) were reacted as described in example 772C. The crude product obtained after workup was purified by silica gel chromatography using 5% ether/$CH_2Cl_2$ to give compound 775E (0.054 g, 50%) as an off-white solid. HPLC: 97.6% at 2.86 min(YMC S5 ODS column) eluting with 10-90% aqueous methanol containing 0.2% phosphoric acid over a 4 min gradient monitoring at 220 nm. MS (ES): m/z 332.16 $[M+H]^+$.

EXAMPLE 776

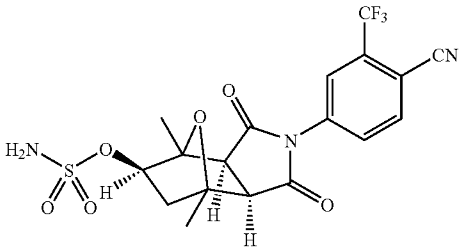

To a clear solution of compound 741Di (190 mg, 0.5 mmol) in anhydrous dioxane (3.5 mL) was added Burgess Reagent (143 mg, 0.6 mmol) at rt under Argon. After the mixture was stirred at rt for 70 min, bis(cyclopentadienyl) titanium dichloride (137 mg, 0.55 mmol) was added. The mixture was stirred at 100° C. for 1 day, then cooled to rt. $H_2O$ and a saturated aqueous solution of $KHSO_4$ were added. The mixture was extracted with EtOAc (3×). The combined extracts were dried over $Na_2SO_4$ and concentrated under reduced pressure. Purification by silica gel flash chromatography eluting with EtOAc/heptane (gradient from 1:4 to 1:0 ratio) gave compound 776 (170 mg, 74%) as a yellow glassy solid. HPLC: 99% at 3.27 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 458 $[M-H]^-$. The absolute stereochemistry of compound 776 is established by the known stereochemistry of the intermediate compound 741Di and the retention of configuration therein. The absolute stereochemistry is as drawn in the above FIGURE and rendered by the nomenclature.

EXAMPLE 777

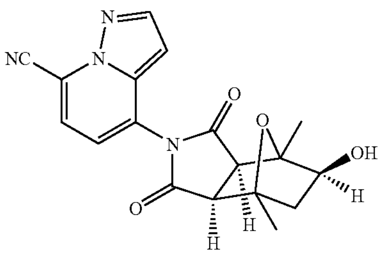

A. Pyrazolo[1,5-a]pyridine-4-carboxylic acid ethyl ester (777A)

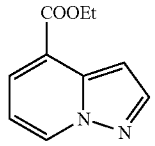

To a clear solution of 2-methyl-nicotinic acid ethyl ester (50.6 g, 306 mmol) in anhydrous methylene chloride (200 mL) was added Omesitylenesulfonylhydroxylamine (73 g, 337 mmol; prepared according to a literature procedure described in Krause; J. G., Synthesis 1972, 140); in portions at 0° C. The solution obtained was stirred at 0° C. for 15 min, and then at rt for 1 h. Concentration under reduced pressure gave a yellow solid. After the solid was dissolved in anhydrous DMF (300 mL), N,N-dimethylformamide dimethyl acetal (122 mL, 918 mmol) was added at 0° C. The mixture was stirred at 0° C. for 15 min, and then at 90° C. for 3 h. The reaction mixture was concentrated under reduced pressure, mixed with $H_2O$ (200 mL), and extracted with $Et_2O$ (3×180 mL). The combined organic solutions were washed sequentially with brine (50 mL), 1N aqueous HCl (50 mL), and brine (50 mL), and dried over $Na_2SO_4$. Filtration through a $SiO_2$ column, which was then eluted with 30% EtOAc in heptane, gave compound 777A (43.3 g, 74%) as a yellow solid. HPLC: 80% at 3.20 min (retention time) plus 20% corresponding methyl ester at 2.83 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 191 $[M+H]^+$.

B. Pyrazolo[1,5-a]pyridine-4-carboxylic acid (777B)

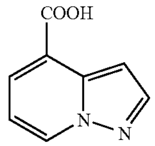

To a stirred mixture of pyrazolo[1,5-a]pyridine-4-carboxylic acid ester (35.1 g, 185 mmol), KOH (85%, 25 g, 379 mmol), and MeOH (200 mL), cooled to rt in a water bath, was added $H_2O$ slowly. The reaction mixture obtained was stirred at rt for 1.5 h and then concentrated under reduced pressure to remove MeOH. A minimal amount of $H_2O$ was added to the residue to make a clear solution that was then acidified to pH=1 at 0° C. with aqueous HCl (concentrated HCl, 11 mL; 5N HCl, 10 mL, Then 2N and 1N HCl). After heating on a steam bath, the mixture was cooled. The solid was filtered, washed with $H_2O$, and dried under vacuum to give compound 777B (29 g, 97%) as a yellow solid. HPLC: 100% at 2.14 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 163 $[M+H]^+$.

C. 7-Iodo-pyrazolo[1,5-a]pyridine-4-carboxylic acid (777C)

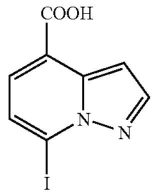

To a stirred suspension of pyrazolo[1,5-a]pyridine-4-carboxylic acid (29 g, 179 mmol) in anhydrous THF (1000 mL)

cooled at 0° C. was added lithium hexamethyldisilazide solution (1M in THF, 200 mL, 200 mmol). After the mixture was stirred at 0° C. for 30 min, additional LHMDS solution (1M in THF, 320 mL, 320 mmol) was added at −4° C. After the mixture was stirred for 10 min, iodine (55 g, 215 mmol) was added in portions. The reaction mixture was stirred at −4° C. for 1.5 h, at rt for 1 h, and then cooled to 0° C. Aqueous HCl (5N, 40 mL) and $NaS_2O_3$ solution (10 g in 40 mL of $H_2O$) were added. The mixture was stirred at 0° C. for 30 min, and then concentrated under reduced pressure. The residual mixture was mixed with sat. $NaHCO_3$ solution (100 mL), ethyl ether (150 mL), and $H_2O$ (130 mL). The ether solution was separated and extracted with $H_2O$ (50 mL). The combined aqueous solutions were washed with ethyl ether (150 mL), acidified to pH=1 with saturated aqueous solution of $KHSO_4$, heated in a steam bath, and then cooled. The solid was filtered, washed with $H_2O$, and then dried to give compound 777C (50 g, 97%) as a yellow solid. HPLC: 100% at 2.88 min (retention time) (YMC S5 ODS-A column 4.6x50 mm eluting with 10-90% aqueous methanol over 4 mincontaining 0.2% phosphoric acid, 4 mL/min, monitoring at 220 nm). MS (ES): m/z 289 $[M+H]^+$.

D. (7-Iodo-pyrazolo[1,5-a]pyridin-4-yl)-carbamic acid tert-butyl ester (777D)

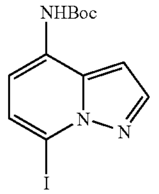

To a clear solution of 7-iodo-pyrazolo[1,5-a]pyridine-4-carboxylic acid (23.4 g, 81.2 mmol) and diisopropylethylamine (65 mL) in tert-butanol (250 mL) and anhydrous toluene (200 mL) was added diphenyl phosphoryl azide (25 mL, 114 mmol) under argon. After the mixture was stirred at rt for 30 min, the temperature was raised slowly to 90° C. The mixture was stirred at 90° C. overnight and concentrated under reduced pressure to remove the solvents. The residue was partitioned between EtOAc (200 mL) and aqueous NaOH solution (2N, 75 mL). The aqueous solution was separated and extracted with EtOAc (100 mL). The combined organic solutions were washed with aqueous NaOH solution (1N, 75 mL), dried over $Na_2SO_4$, and concentrated under reduced pressure. Purification by silica gel flash chromatography eluting with EtOAc/heptane (gradient from 0:1 to 1:1 ratio) gave a brownish solid. Recrystallization in heptane with some EtOAc gave compound 777D (19.6 g, 67%) as a yellow solid. HPLC: 95% at 3.83 min (retention time) (YMC S5 ODS-A column 4.6x50 mm eluting with 10-90% aqueous methanol over 4 mincontaining 0.2% phosphoric acid, 4 mL/min, monitoring at 220 nm). MS (ES): m/z 360 $[M+H]^+$.

E. (7-Cyano-pyrazolo[1,5-a]pyridin-4-yl)-carbamic acid tert-butyl ester (777E)

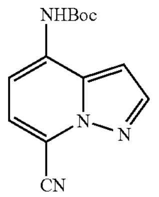

A mixture of (7-iodo-pyrazolo[1,5-a]pyridin-4-yl)-carbamic acid tert-butyl ester (36 mg, 0.1 mmol), zinc cyanide (24 mg, 0.2 mmol), tetrakis(triphenylphosphine) palladium (0) (23 mg, 0.02 mmol), and anhydrous DMF (1 mL) was degassed with argon. Then, the mixture was stirred at 80° C. for 4.5 h, cooled to rt, mixed with EtOAc (6 mL), and filtered. The filtrate was concentrated under reduced pressure. Purification by silica gel flash chromatography eluting with EtOAc/heptane (gradient from 1:4 to 1:2 ratio) gave compound 777E (24 mg, 93%) as a white solid. HPLC: 93% at 3.64 min (retention time) (YMC S5 ODS-A column 4.6x50 mm eluting with 10-90% aqueous methanol over 4 mincontaining 0.2% phosphoric acid, 4 mL/min, monitoring at 220 nm). MS (ES): m/z 259 $[M+H]^+$.

F. 4-Amino-pyrazolo[1,5-a]pyridine-7-carbonitrile (777F)

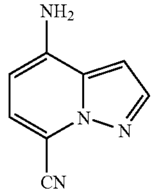

To a clear solution of (7-cyano-pyrazolo[1,5-a]pyridin-4-yl)-carbamic acid tert-butyl ester (3 g, 11.6 mmol) in methylene chloride (40 mL) was added TFA (8 mL). The mixture was stirred at rt for 3 h, and then concentrated under reduced pressure. The residue was partitioned between EtOAc (100 mL) and sat. $NaHCO_3$ solution (50 mL). The aqueous solution was separated and extracted with EtOAc (2x50 mL). The combined organic solutions were dried over $Na_2SO_4$, filtered though $SiO_2$ pad, and concentrated under reduced pressure. Crystallization in EtOAc and 95% EtOH gave compound 777F (1.07 g, 58%) as a dark yellow solid. HPLC: 97% at 1.96 min (retention time) (YMC S5 ODS-A column 4.6x50 mm eluting with 10-90% aqueous methanol over 4 mincontaining 0.2% phosphoric acid, 4 mL/min, monitoring at 220 nm). MS (ES): m/z 159 $[M+H]^+$.

G. (777G)

A mixture of 4-amino-pyrazolo[1,5-a]pyridine-7-carbonitrile (135 mg, 0.85 mmol), compound 752 (225 mg, 1.06 mmol), 4 Å molecular sieve powder (850 mg), and DMA (0.85 mL) was stirred under argon at rt for 10 min, at 170° C. for 3 h, and then cooled to rt. The molecular sieve powder was filtered off, and the filtrate was concentrated under reduced pressure. Purification by silica gel flash chromatography eluting with EtOAc (gradient with MeOH from 0% to 5%) gave compound 777G (98 mg, 33%) as a yellowish solid. HPLC: 99% at 2.28 min (retention time) (YMC S5 ODS-A column 4.6x50 mm eluting with 10-90% aqueous methanol over 4 mincontaining 0.2% phosphoric acid, 4 mL/min, monitoring at 220 nm). MS (ES): m/z 353 $[M+H]^+$. The absolute stereochemistry of compound 777G is established by the known stereochemistry of the intermediate compound 752 and the retention of configuration therein. The absolute stereochemistry is as drawn in the above FIGURE and rendered by the nomenclature.

EXAMPLE 778

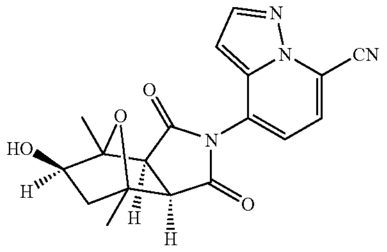

A mixture of 4-amino-pyrazolo[1,5-a]pyridine-7-carbonitrile (60 mg, 0.38 mmol), compound 751 (110 mg, 0.52 mmol), $MgSO_4$ (360 mg, 3 mmol), diisopropylethylamine (0.35 mL, 2 mmol), and anhydrous toluene (0.6 mL) was stirred at 135° C. under argon for 20 h. Purification by silica gel flash chromatography eluting with EtOAc (gradient with MeOH from 0% to 5%) gave compound 778 (115 mg, 86%) as a greyish solid. HPLC: 98% at 2.28 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 353 $[M+H]^+$. The absolute stereochemistry of compound 778 is established by the known stereochemistry of the intermediate compound 751 and the retention of configuration therein. The absolute stereochemistry is as drawn in the above FIGURE and rendered by the nomenclature.

EXAMPLE 779

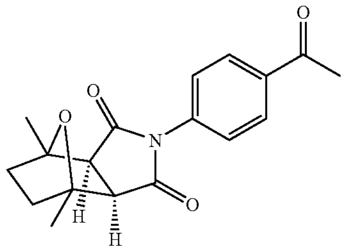

A clear solution of compound 20A (50 mg, 0.25 mmol), p-aminoacetophenone (68 mg, 0.5 mmol), and N,N-dimethylformamide dimethyl acetal (0.065 mL, 0.49 mmol) in anhydrous N,N-dimethylformamide (0.2 mL) was stirred at 10° C. under argon for 18 h, and then concentrated. Purification by silica gel flash chromatography on $SiO_2$ eluting with EtOAc/heptane (gradient from 1:4 to 1:0 ratio) gave a solid that was crystallized in a mixture of EtOAc and heptane to give compound 779 (11 mg, 14%) as a white solid. HPLC: 98% at 2.89 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 314 $[M+H]^+$.

EXAMPLE 780

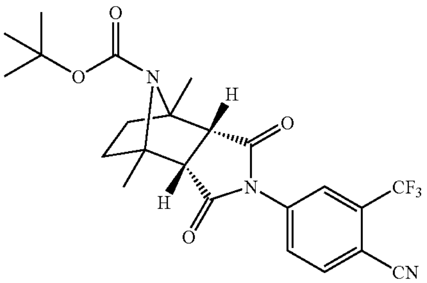

A. 1,4-Dimethyl-7-aza-bicyclo[2.2.1]hepta-2,5-diene-2,3,7-tricarboxylic acid 7-tert-butyl ester 2,3-dimethyl ester (780A)

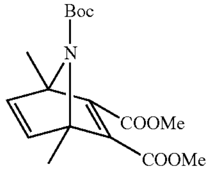

A mixture of crude 2,5-dimethyl-pyrrole-1-carboxylic acid tert-butyl ester (prepared according to a literature (Haiser, H.-P.; et al. *J. Org. Chem.* 1984 49(22) 4203-4209); 500 mg) and dimethyl acetylenedicarboxylate (0.5 mL, ca 4 eq) was stirred at 120° C. under argon for 2 h. Purification by silica gel flash chromatography on $SiO_2$ eluting with EtOAc/heptane (gradient from 1:20 to 1:2 ratio) gave compound 780A (166 mg, 50% yield) as a colorless liquid. HPLC: 90% at 3.67 min (retention time) (YMC S5 ODS-A column 4.6×50 mm eluting with 10-90% aqueous methanol over 4 mincontaining 0.2% phosphoric acid, 4 mL/min, monitoring at 220 nm).

B. (780B)

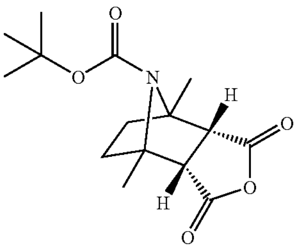

To a clear solution of 1,4-dimethyl-7-aza-bicyclo[2.2.1]hepta-2,5-diene-2,3,7-tricarboxylic acid 7-tert-butyl ester 2,3-dimethyl ester (1.5 g, 4.4 mmol) in MeOH (10 mL) and $H_2O$ (5 mL) cooled in ice water was added KOH (2.9 g, 44 mmol) in portions. More $H_2O$ (5 mL) was then added. After the reaction mixture was stirred at rt for 1 h, hydrazine (1.4 mL, 44 mmol), HCl (2N aqueous solution, 17 mL, 34 mmol), and hydrogen peroxide (50% aqueous solution, 1.27 mL, 22 mmol) were added sequentially at 0° C. The reaction mixture was stirred at rt for 3 h, and then concentrated under reduced pressure to remove MeOH. The aqueous solution obtained was acidified to pH=1 with saturated aqueous solution of $KHSO_4$ and extracted with EtOAc (3×). The combined extracts were dried over $Na_2SO_4$, and concentrated under reduced pressure to give a yellow solid. The yellow solid above was dissolved in acetic anhydride (15 mL). The solution was stirred at 100° C. for 1 h. Concentration under reduced pressure gave 1.3 g (100%) of compound 780B as an orange solid.

C. (780C)

A mixture of compound 780B (0.8 g, 2.7 mmol), 4-amino-2-trifluoromethylbenzonitrile (0.5 g, 2.7 mmol), $MgSO_4$ (2.6 g, 22 mmol), diisopropylethylamine (2.35 mL, 13.5 mmol), and anhydrous toluene (2.9 mL) was stirred at 135° C. under argon for 15 h. The solid was filtered and washed with EtOAc. The filtrate was concentrated under reduced pressure. Purification by silica gel flash chromatography eluting with EtOAc/heptane (gradient from 1:4 to 1:2 ratio) gave compound 780C (1.03 g, 82%) as a glassy solid. HPLC: 100% at 4.26 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 462.34 $[M-H]^-$.

EXAMPLE 781

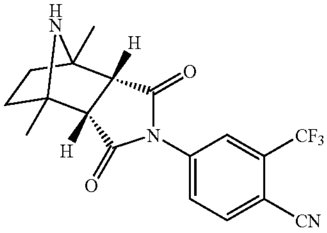

To a solution of compound 780C (770 mg, 1.66 mmol) in methylene chloride (10 mL) was added trifloroacetic acid (5 mL). The reaction mixture was stirred at rt for 40 min. The mixture was then concentrated under reduced pressure, basified with sat. $NaHCO_3$ solution, and extracted with EtOAc (3×). The combined extracts were dried over $Na_2SO_4$ and concentrated under reduced pressure to give compound 781 (600 mg, 99%) as an orange solid. HPLC: 100% at 2.55 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 364 $[M+H]^+$.

EXAMPLE 782

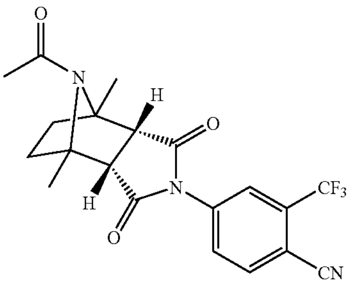

To a clear solution of compound 781 (27 mg, 0.074 mmol) and triethylamine (0.061 mL, 0.44 mmol) in anhydrous methylene chloride (3 mL) was added acetyl chloride (0.016 mL, 0.22 mmol) at 0° C. under argon. After the mixture was stirred at 0° C. for 30 min and at rt for 30 min, sat. $NaHCO_3$ solution was added. After the mixture was stirred for 15 min, the organic solution was separated, dried over $Na_2SO_4$, and filtered though a $SiO_2$ pad that was then rinsed with EtOAc. The filtrate was concentrated under reduced pressure. Crystallization in a mixture of EtOAc and heptane gave compound 782 (19 mg, 63%) as a white solid. HPLC: 99% at 3.56 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 406 $[M+H]^+$.

EXAMPLE 783

(3aα,4β,7β,7aα)-4-(Octahydro-4,7,8-trimethyl-1,3-dioxo-4,7-imino-2H-isoindol-2-yl)-2-(trifluoromethyl)benzonitrile (783)

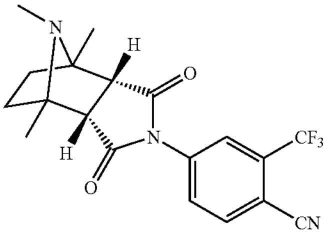

A mixture of compound 781 (180 mg, 0.5 mmol), formaldehyde (37% aqueous solution, 0.11 mL, 1.5 mmol), NaHB$(OAc)_3$ (318 mg, 1.5 mmol), and 1,2-dichloroethane (9 mL) was stirred at rt under argon overnight, and then dried over $Na_2SO_4$. Purification by silica gel flash chromatography eluting with EtOAc (gradient with triethylamine from 2% to 10%) gave compound 783 (160 mg, 84%) as a white solid. HPLC: 100% at 2.46 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 378 $[M+H]^+$.

EXAMPLE 784

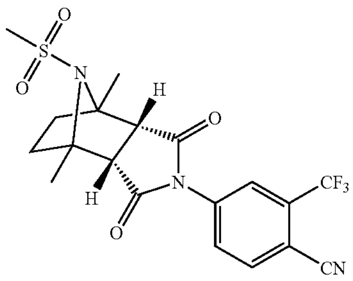

To a clear solution of compound 781 (20 mg, 0.055 mmol) and triethylamine (0.04 mL, 0.24 mmol) in anhydrous methylene chloride (1 mL) cooled at 0° C. was added methanesulfonyl chloride (0.01 mL, 0.13 mmol). After the reaction mixture was stirred at 0° C. for 30 min, sat. $NaHCO_3$ solution (0.1 mL) was added. The mixture was stirred for 10 min, dried over $Na_2CO_3$, and filtered though a $SiO_2$ pad that was then rinsed with EtOAc. The filtrate was concentrated under reduced pressure. Crystallization in a mixture of EtOAc and heptane gave compound 784 (14 mg, 58%) as a white solid. HPLC: 98% at 3.58 min (retention time) (YMC S5 ODSA column 4.6×50 mm eluting with 10-90% aqueous methanol over 4 mincontaining 0.2% phosphoric acid, 4 mL/min, monitoring at 220 nm). MS (ES): m/z 440 $[M-H]^-$.

EXAMPLE 785

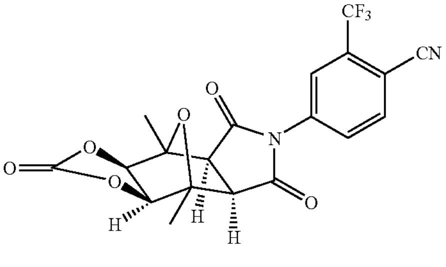

To a stirred solution of compound 230Bi (50 mg, 0.13 mmol) and triethylamine (0.09 mL, 0.65 mmol) in anhydrous methylene chloride (5 mL) was added phosgene (20% in toluene, 0.25 mL, 0.48 mmol) dropwise. After the reaction was completed, sat. $NaHCO_3$ solution was added. The mixture was extracted with EtOAc (3×). The combined extracts were dried over $Na_2SO_4$, filtered though a $SiO_2$ pad, and concentrated under reduced pressure. Crystallization in a mixture of EtOH and $H_2O$ gave compound 785 (40 mg, 73%) as a white solid. HPLC: 100% at 3.55 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 377 $[M—CO_2—H]^-$.

EXAMPLES 786i & 786ii

[3aR-(3aα,4β,5β,6α,7β,7aα)]-4-(Octahydro-5,6-dichloro-4,7-dimethyl-1,3-dioxo-4,7-epoxy-2H-isoindol-2-yl)-2-(trifluoromethyl)benzonitrile & [3aR(3aα,4β,5β,6α,7β,7aα)]-4-(Octahydro-5,6-dichloro-4,7-dimethyl-1,3-dioxo-4,7-epoxy-2H-isoindol-2-yl)-2-(trifluoromethyl)benzonitrile (786i & 7861i)

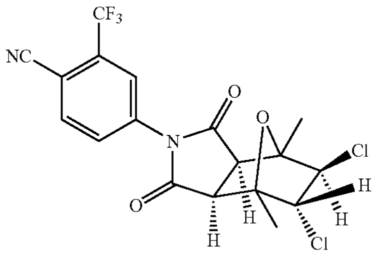

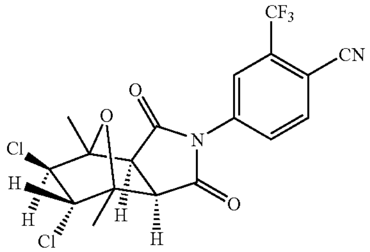

To a stirred mixture of compound 230Bi (544 mg, 1.5 mmol), acetone (10 mL), acetic acid (2 mL), and brine (2 mL) cooled at 0° C. was added bleach (5 mL) dropwise. The clear solution obtained was stirred at rt for 1 h, and then concentrated under reduced pressure. The residual mixture was extracted with EtOAc (3×). The combined extracts were dried over $Na_2SO_4$, and concentrated under reduced pressure. Purification by silica gel flash chromatography on $SiO_2$ eluting with EtOAc/heptane (gradient from 1:9 to 1:2 ratio) gave a white solid that was crystallized in a mixture of EtOAc and heptane to give 301 mg (46%) of racemic mixture of compounds 786i & 786ii as a white solid. HPLC: 100% at 4.11 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 395 $[M-HCl—H]^-$.

Chiral HPLC separation the racemic mixture gave two enantiomers: compound 786i & compound 786ii.

Chiral HPLC conditions employed for the separation:

Chiral HPLC Condition

| | |
|---|---|
| Column: | CHIRALPAK AD 50 × 500 mm, 20μ |
| Temperature: | rt |
| Injection Volume: | 20 mL |
| Mobile Phase: | A: IPA with 0.1% diethylamine B: Heptane with diethylamine Isocratic, 45% of A, 60 min. |
| Flow Rate: | 50 mL/min. |
| UV Detection: | 245 nm |

Chiral HPLC Conditions Employed for the Analysis:

Chiral HPLC Condition

| | |
|---|---|
| Column: | CHIRALPAK AD 4.6 × 250 mm, 10μ |
| Temperature: | 25° C. |
| Injection Volume: | 10 μL |
| Mobile Phase: | A: IPA with 0.1% diethylamine B: Heptane with diethylamine Isocratic, 45% of A, 15 min. |
| Flow Rate: | 1 mL/min. |
| UV Detection: | 245 nm |
| RT: Compound 786i | 10.6 min |
| Compound 786ii | 7.0 min |

The absolute stereochemistry of compounds 785i & 785ii has not been established. Although each compound represents a single antipode, the nomenclature and structure shown does not reflect the absolute stereochemistry of the compound.

EXAMPLES 787i & 787ii

[3aR-(3aα,4β,5β,6β,7β,7aα)]-4-(Octahydro-5-chloro-6-hydroxy-4,7-dimethyl-1,3-dioxo-4,7-epoxy-2H-isoindol-2-yl)-2-(trifluoromethyl)benzonitrile & [3aS-(3aα,4β,5β,6β,7β,7aα)]-4-(Octahydro-5-chloro-6-hydroxy-4,7-dimethyl-1,3-dioxo-4,7-epoxy-2H-isoindol-2-yl)-2-(trifluoromethyl) benzonitrile (787i & 787ii)

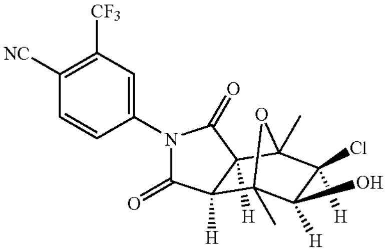

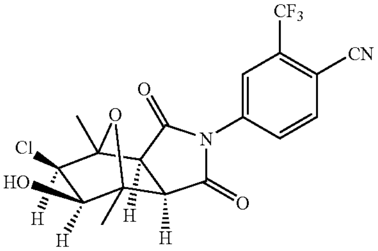

To a stirred solution of compound 230Bi (181 mg, 0.5 mmol) in anhydrous methylene chloride (4 mL) cooled at −78° C. under argon was added chromyl chloride (0.048 mL, 0.6 mmol) dropwise. After the reaction mixture was stirred at −78° C. for 1 h, the reaction temperature was raised slowly to rt. The reaction mixture was stirred at rt for 2 h. Sat. $NaHCO_3$ solution (10 mL) was then added at 0° C. with vigorous stirring. The mixture was extracted with EtOAc (3×). The combined extracts were dried over $Na_2SO_4$, and concentrated under reduced pressure. Purification by silica gel flash chromatography on $SiO_2$ eluting with EtOAc/heptane (gradient from 1:4 to 1:0 ratio) gave 98 mg (47%) of racemic mixture of compounds 787i & 787ii as a white solid. HPLC: 100% at 3.32 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 377 $[M—HCl—H]^-$.

Chiral HPLC separation of the racemate gave two enantiomers: compound 787i & compound 787ii.

Chiral HPLC Conditions Employed for the Separation:

Chiral HPLC Condition

| | |
|---|---|
| Column: | CHIRALCEL OD<br>50 × 500 mm, 20μ |
| Temperature: | rt |
| Injection Volume: | 20 mL |
| Mobile Phase: | A: IPA with 0.1%<br>diethylamine<br>B: Heptane with<br>0.1%<br>diethylamine<br>Isocratic, 35% of A, 90 min. |
| Flow Rate: | 50 mL/min. |
| UV Detection: | 245 nm |
| RT: Compound 787i | 41 min |
| Compound 787ii | 51 min |

The absolute stereochemistry of compounds 787i & 787ii has not been established. Although each compound represents a single antipode, the nomenclature and structure shown does not reflect the absolute stereochemistry of the compound.

EXAMPLE 788

(3aα,4β,5β,6α,7β,7aα)-4-(Octahydro-5,6-dihydroxy-4,7-dimethyl-1,3-dioxo-4,7-epoxy-2H-isoindol-2-yl)-2-(trifluoromethyl)benzonitrile (788B)

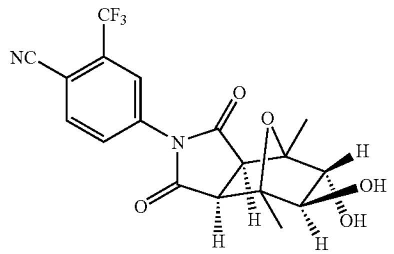

A. (3aα,4β,5α,6β,7β,7aα)-4-(Octahydro-5-[[(1,1-dimethylethyl)dimethylsilyl]oxy]-6-hydroxy-4,7-dimethyl-1,3-dioxo-4,7-epoxy-2H-isoindol-2-yl)-2-(trifluoromethyl)benzonitrile (788A)

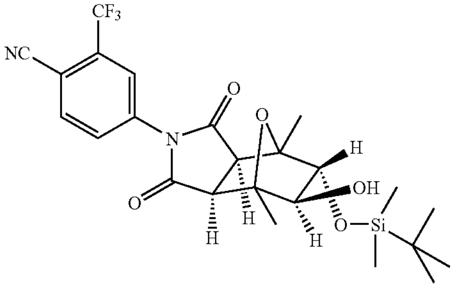

To a stirred solution of compound 222B (1.49 g, 3 mmol) in anhydrous THF (31 mL) was added borane-methyl sufide complex (0.61 mL, 6.1 mmol) dropwise at rt under argon. After the reaction mixture was stirred at rt for 1.5 h, EtOH (20 mL) was added slowly at 0° C., followed by phosphate buffer (pH=7.2, 39 mL), and $H_2O_2$ (30% aqueous, 12 mL). The mixture was vigorously stirred at 0° C. for 30 min, at rt for 21 h, and then concentrated under reduced pressure at rt to remove THF. The residue was partitioned between EtOAc (160 mL) and brine (160 mL). The organic solution was separated, washed with 5% $Na_2SO_3$ solution (120 mL), dried over $Na_2SO_4$, and concentrated under reduced pressure. Purification by silica gel flash chromatography on $SiO_2$ eluting with EtOAc/heptane (gradient from 1:8 to 1:0 ratio) compound 788A (1.15 g, 75%) as a foam solid.

B. [3aS-(3aα,4β,5β,6α,7β,7aα)]-4-(Octahydro-5,6-dihydroxy-4,7-dimethyl-1,3-dioxo-4,7-epoxy-2H-isoindol-2-yl)-2-(trifluoromethyl)benzonitrile (788B)

To a stirred solution of compound 788A (0.67 g, 1.3 mmol) in EtOH (100%, 19 mL) was added concentrated HCl (3.7 mL). The mixture was stirred at rt for 21 h, at 40° C. for 3 h, and then concentrated under reduced pressure. Purification by silica gel flash chromatography eluting with EtOAc/heptane (gradient from 1:1 to 1:0 ratio) gave compound 788B (0.47 mg, 92%) as a glassy solid. HPLC: 98% at 3.07 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 397 $[M+H]^+$. Compound 788B represents a racemic mixture of antipodes. The nomenclature and structure shown does not reflect the absolute stereochemistry of the compound.

EXAMPLE 789

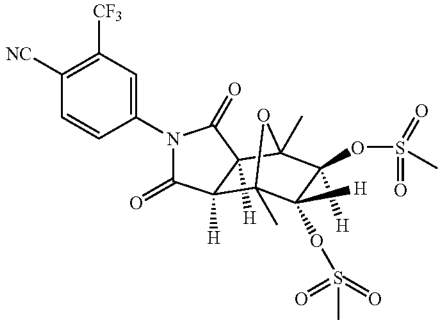

To a stirred solution of compound 788B (40 mg, 0.1 mmol) and triethylamine (0.16 mL, 1.1 mmol) in anhydrous methylene chloride (1 mL) was added methanesulfonyl chloride (0.042 mL, 0.54 mmol) at 0° C. under argon. The reaction mixture was stirred at 0° C. for 10 min, and at rt for 30 min. Purification by silica gel flash chromatography eluting with EtOAc/heptane (gradient from 1:2 to 1:0 ratio) gave compound 789 (50 mg, 90%) as a glassy solid. HPLC: 100% at 3.66 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 575 $[M+Na]^+$. Compound 789 represents a racemic mixture of antipodes. The nomenclature and structure shown does not reflect the absolute stereochemistry of the compound.

EXAMPLE 790

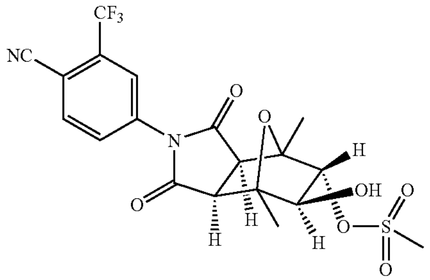

A clear solution of compound 788B (40 mg, 0.1 mmol), pyridine (0.04 mL, 0.49 mmol), and methanesulfonyl chloride (0.032 mL, 0.41 mmol) in anhydrous methylene chloride (1 mL) was stirred at rt for 1 day. Purification by preparative HPLC (YMC S5 ODS column 20×100 mm, 20 mL/min, monitoring at 245 nm, gradient elution with 10-100% solvent B over 10 mins. Solvent A: 10% MeOH-90% $H_2O$-0.1% TFA. Solvent B: 90% MeOH-10% $H_2O$-0.1% TFA.) gave compound 790 (23 mg, 48%) as a glassy solid. HPLC: 98% at 3.46 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 475 $[M+H]^+$. Compound 790 represents a racemic mixture of antipodes. The nomenclature and structure shown does not reflect the absolute stereochemistry of the compound.

EXAMPLE 791

[3aS-(3aα,4β,5β,6α,7β,7aα)]-4-(Octahydro-5,6-dihydroxy-4,7-dimethyl-1,3-dioxo-4,7-epoxy-2H-isoindol-2-yl)-2-(trifluoromethyl)benzonitrile & [3aR(3aα,4β,5β,6α,7β,7aα)]-4-(Octahydro-5,6-dihydroxy-4,7-dimethyl-1,3-dioxo-4,7-epoxy-2H-isoindol-2-yl)-2-(trifluoromethyl)benzonitrile (791i &791ii)

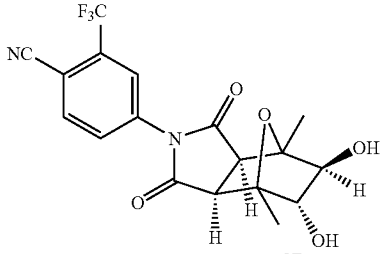

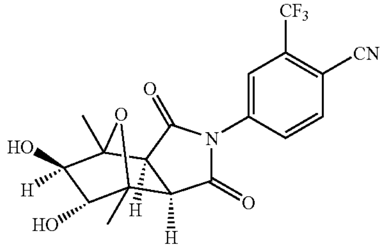

Racemic compound 788B (1 g) was separated into its enantiomers by normal phase preparative chiral HPLC (CHIRALPAK OJ 5×50 cm column; eluting with 20% MeOH/EtOH (1:1) in heptane (isocratic)+0.1% diethylamine at 50 mL/min) to give 296 mg of faster eluting compound 791i (Chiral HPLC: 8.92 min; CHIRALPAK OJ 4.6×250 mm column; eluting with 20% MeOH/EtOH (1:1) in heptane+0.1% diethylamine at 1 mL/min); HPLC: 95% at 1.25 min (retention time) (Phenomenex S5 ODS column 4.6×50 mm eluting with 10-90% aqueous methanol over 2 mincontaining 0.1% TFA, 4 mL/min, monitoring at 254 nm); MS (ES): m/z 397.37 $[M+H]^+$ and 274 mg of the slower eluting 791ii (Chiral HPLC: 11.25 min; CHIRALPAK OJ 4.6×250 mm column; eluting with 20% MeOH/EtOH (1:1) in heptane+0.1% diethylamine at 1 mL/min); HPLC: 95% at 1.25 min (retention time) (Phenomenex S5 ODS column 4.6×50 mm eluting with 10-90% aqueous methanol over 2 mincontaining 0.1% TFA, 4 mL/min, monitoring at 254 nm); MS (ES): m/z 397.43 $[M+H]^+$. The absolute stereochemistry of compounds 791i & 791ii has not been established. Although each compound represents a single antipode, the nomenclature and structure shown does not reflect the absolute stereochemistry of the compound.

EXAMPLE 792

(3aα,4β,5α,7β,7aα)-2-(4-Cyano-3-(trifluoromethyl)phenyl)hexahydro-4,7-dimethyl-1,3-dioxo-4,7-epoxy-1H-isoindole-5-carboxylic acid (792B)

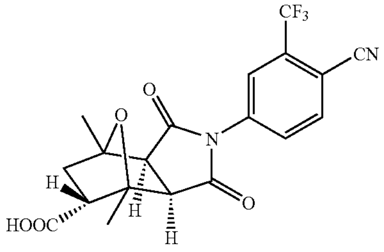

A. (3aα,4β,7β,7aα)-2-(4-Cyano-3-(trifluoromethyl)phenyl)tetrahydro-4,7-dimethyl-1,3-dioxo-4,7-epoxy-1H-isoindole-5-carboxylic acid (792A)

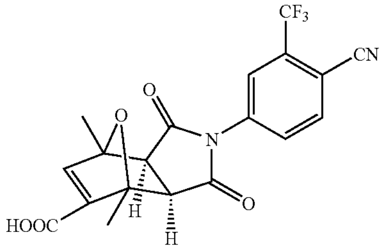

A mixture of 2,5-dimethyl-3-furoic acid (11.2 g; 80 mmol) and 4-(2,5-dihydro-2,5-2,5-dioxo-1H-pyrrol-1-yl)-2-trifluoromethylbenzonitrile (5.32 g; 20 mmol) in 20 mL of THF was heated to 65° C. for 2 h. After cooling to rt, the solid residue was slurried in EtOAc and loaded onto a 5×30 cm silica gel column packed in hexanes. The column was eluted with 2 L of EtOAc, followed by 1.5 L of 1% AcOH/EtOAc. Fractions containing the desired acrylic acid were concentrated and the residue was co-evaporated from EtOAc/Heptane (3×100 mL). After dissolving the solid residue in ~15 mL of EtOAc, heptane (~50 mL) was added and the mixture was concentrated to ~25 mL volume. The suspension was filtered and the filter cake was washed with hexane. Removing the solvent in vacuo afforded compound 792A (1.5 g, 16%) as a white powder.

B. (3aα,4β,5α,7β,7aα)-2-(4-Cyano-3-(trifluoromethyl)phenyl)hexahydro-4,7-dimethyl-1,3-dioxo-4,7-epoxy-1H-isoindole-5-carboxylic acid (792B)

Compound 792A (220 mg; 0.54 mmol) was hydrogenated at 1 atm. in EtOAc (5 mL) over 10% Pd/C (20 mg) for 4 hs. After filtering though Celite, the filtrate was concentrated and the residue was chromatographed on a 2.5×15 cm silica gel column eluting with EtOAc:Heptane, 1:1+0.5% AcOH. Pure fractions were concentrated to afford compound 792B (173 mg, 79%) as a colorless glass. HPLC: 95.7% at 1.64 min (retention time) (Phenomonex S5 ODS column 4.6×50 mm eluting with 10-90% aqueous methanol over 2 mincontaining 0.1% TFA, 4 mL/min, monitoring at 254 nm); MS (ES): m/z 409.23 $[M+H]^+$.

EXAMPLE 793

(3aα,4β,5α,7β,7aα)-2-(4-Cyano-3-(trifluoromethyl)phenyl)hexahydro-4,7-dimethyl-1,3-dioxo-4,7-epoxy-1H-isoindole-5-carboxylic acid, methyl ester (793B)

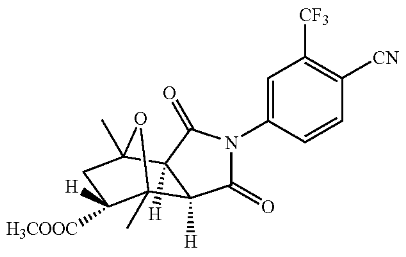

A. (3aα,4β,7β,7aα)-2-(4-Cyano-3-(trifluoromethyl)phenyl)tetrahydro-4,7-dimethyl-1,3-dioxo-4,7-epoxy-1H-isoindole-5-carboxylic acid, methyl ester (793A)

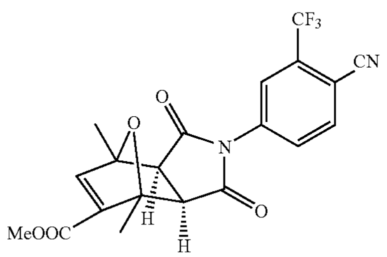

A mixture of methyl-2,5-dimethyl-3-furoate (30 mL; 200 mmol) and 4-(2,5-dihydro-2,5-2,5-dioxo-1H-pyrrol-1-yl)-2-trifluoromethylbenzonitrile (13.3 g; 50 mmol) was heated to 120° C. for 5 h. After cooling slowly to rt over 18 h, ethyl ether (~150 mL) was added and the resulting thick suspension was filtered. Rinsing thoroughly with ethyl ether and drying afforded compound 793A (11.3 g, 54%) as a white powder.

B. (3aα,4β,5α,7β,7aα)-2-(4-Cyano-3-(trifluoromethyl)phenyl)hexahydro-4,7-dimethyl-1,3-dioxo-4,7-epoxy-1H-isoindole-5-carboxylic acid, methyl ester (793B)

Compound 793A (1 g; 2.38 mmol) was hydrogenated at 1 atm. in EtOAc (25 mL) over 10% Pd/C (100 mg) for 2 h. After filtering though Celite, the filtrate was concentrated and the residue was chromatographed on a 2.5×15 cm silica gel column eluting with EtOAc:Hexane, 1:3. Pure fractions were concentrated to afford compound 793B (665 mg, 65%) as a yellow powder. HPLC: 99% at 1.67 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 423.27 $[M+H]^+$. Compound 793B represents a racemic mixture of antipodes. The nomenclature and structure shown does not reflect the absolute stereochemistry of the compound.

EXAMPLE 794B

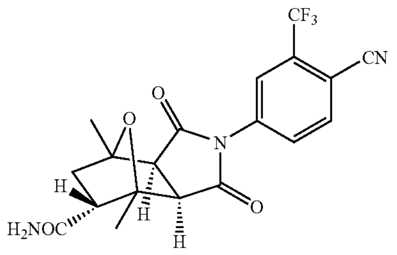

A. (794A)

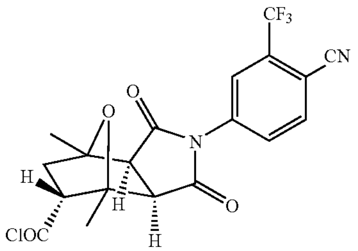

One drop of DMF was added to a solution of compound 792B (160 mg; 0.4 mmol) and oxalyl chloride (0.09 mL; 1 mmol) in methylene chloride (4 mL) at rt. After stirring 1 h at rt, the volatiles were removed in vacuo and the residue was dissolved in 2 mL of THF to afford a 0.2M solution of compound 794A in THF.

C. (794B)

A 0.2M solution of compound 794A in THF (1 mL; 0.2 mmol) was added to a 0.5M solution of ammonia in dioxane (5 mL; 2.5 mmol) at rt. After standing 1 h at rt, the reaction mixture was partitioned between EtOAc (25 mL) and water (25 mL). The organic layer was washed with saturated potassium bisulfate solution (25 mL) and brine (25 mL). Drying over $MgSO_4$ followed by concentration in vacuo gave a solid residue that was triturated with ethyl ether to afford compound 794B (60 mg, 74%) as a white solid. HPLC: 95.6% at 1.41 min (retention time) (Phenominex S5 ODS column 4.6×50 mm eluting with 10-90% aqueous methanol over 2 min-containing 0.1% TFA, 4 mL/min, monitoring at 254 nm); MS (ES): m/z 408.03 $[M+H]^+$. Compound 794B represents a racemic mixture of antipodes. The nomenclature and structure shown does not reflect the absolute stereochemistry of the compound.

EXAMPLE 795

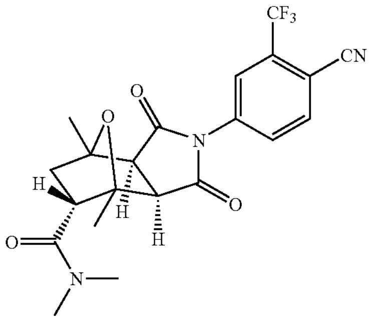

A 0.2M solution of compound 794A in THF (1 mL; 0.2 mmol) was added to a 2.0M solution of dimethylamine in dioxane (2.5 mL; 5 mmol) at rt. After standing 1 h at rt, the reaction mixture was partitioned between EtOAc (25 mL) and water (25 mL). The organic layer was washed with saturated potassium bisulfate solution (25 mL) and brine (25 mL). Drying over $MgSO_4$ followed by concentration in vacuo gave a residue that was purified by preparative TLC (EtOAc:Hexane, 3:2) to afford compound 795 (45 mg, 52%) as a white powder. HPLC: 99% at 1.52 min (retention time) (Phenominex S5 ODS column 4.6×50 mm eluting with 10-90% aqueous methanol over 2 mincontaining 0.1% TFA, 4 mL/min, monitoring at 2541m); MS (ES): m/z 435.10 $[M+H]^+$. Compound 795 represents a racemic mixture of antipodes. The nomenclature and structure shown does not reflect the absolute stereochemistry of the compound.

EXAMPLE 796

[3aR-(3aα,4β,7β,7aα)]-4-(Octahydro-4,7-dimethyl-1,3,5-trioxo-4,7-epoxy-2H-isoindol-2-yl)-2-(trifluoromethyl)benzonitrile (796)

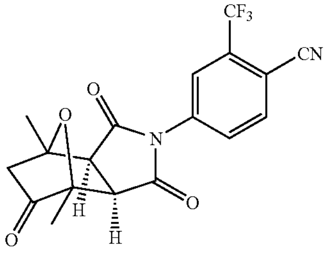

Compound 471Di (0.10 g, 0.263 mmol) was dissolved in a mixture of $CH_2Cl_2$ (1.0 mL) and THF (2.0 mL) at 22° C. Dess-Martin periodinane (0.279 g, 0.658 mmol) was added with stirring. After 3 h, the reaction was quenched with a 1:1 mixture of sat aq $NaHCO_3$ and sat aq $NaHSO_3$ (5 mL). After stirring for 15 min, the mixture was extracted with $CH_2Cl_2$ (3×10 mL) and the combined organics were dried over $Na_2SO_4$. The crude material was purified by silica gel flash chromatography eluting with 5-10-20% acetone in chloroform to give compound 796 (0.090 g) as a white solid. HPLC: 100% at 3.170 min (retention time) (YMC S5 ODS column 4.6×50 mm eluting with 10-90% aqueous methanol over 4 mincontaining 0.2% phosphoric acid, 4 mL/min, monitoring at 220 nm), MS (ES): m/z 379.11 $[M+H]^+$. Chiral analytical HPLC using a Chiracel OD column, 4.6×250 mm, eluting with 20% (1:1) EtOH/MeOH in hexanes at 2.0 mL/min and monitoring at 220 nm gave a retention time of 9.097 mins. The absolute stereochemistry of compound 796 is established by the known stereochemistry of the intermediate compound 741Di and the retention of configuration therein. The absolute stereochemistry is as drawn in the above FIGURE and rendered by the nomenclature.

EXAMPLE 797

[3aS-(3aα,4β,7β,7aα)]-4-(Octahydro-4,7-dimethyl-1,3,5-trioxo-4,7-epoxy-2H-isoindol-2-yl)-2-(trifluoromethyl)benzonitrile (797)

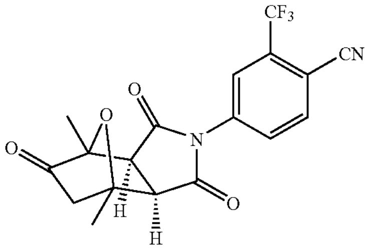

Compound 471Dii (0.10 g, 0.263 mmol) was dissolved in a mixture of $CH_2Cl_2$ (1.0 mL) and THF (2.0 mL) at 22° C. Dess-Martin periodinane (0.279 g, 0.658 mmol) was added with stirring. After 3 h, the reaction was quenched with a 1:1 mixture of sat aq $NaHCO_3$ and sat aq $NaHSO_3$ (5 mL). After stirring for 15 min, the mixture was extracted with $CH_2Cl_2$ (3×10 mL) and the combined organics were dried over $Na_2SO_4$. The crude material was purified by silica gel flash chromatography on $SiO_2$ eluting with 5-10-20% acetone in chloroform to give compound 797 (0.094 g) as a white solid. HPLC: 100% at 3.170 min (retention time) (YMC S5 ODS column 4.6×50 mm eluting with 10-90% aqueous methanol over 4 mincontaining 0.2% phosphoric acid, 4 mL/min, monitoring at 220 nm), MS (ES): m/z 379.11 $[M+H]^+$. Chiral analytical HPLC using a Chiracel OD column, 4.6×250 mm, eluting with 20% (1:1) EtOH/MeOH in hexanes at 2.0 mL/min and monitoring at 220 nm gave a retention time of 5.710 mins. The absolute stereochemistry of compound 797 is established by the known stereochemistry of the intermediate compound 471Dii and the retention of configuration therein. The absolute stereochemistry is as drawn in the above FIGURE and rendered by the nomenclature.

EXAMPLE 798

[3aR-(3aα,4β,7β,7aα)]-4-[5-[[(1,1-Dimethylethyl)dimethylsilyl]oxy]tetrahydro-4,7-dimethyl-1,3-dioxo-4,7-epoxy-2H-isoindol-2-yl]-2-(trifluoromethyl)benzonitrile & [3aR-(3aα,4β,7β,7aα)]-4-[5-[[(1,1-Dimethylethyl)dimethylsilyl]oxy]tetrahydro-4,7-dimethyl-1,3-dioxo-4,7-epoxy-2H-isoindol-2-yl]-2-(trifluoromethyl)benzonitrile (798i and 798ii)

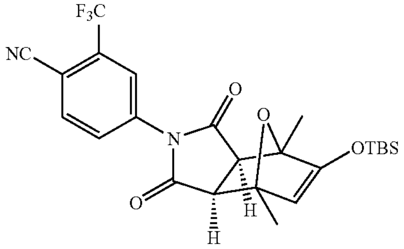

-continued

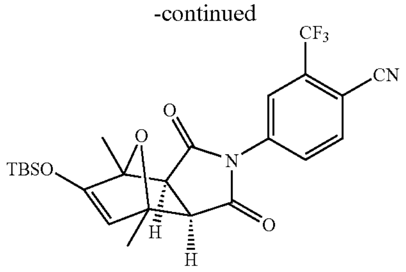

The individual enantiomers of compound 222B were separated by preparativechiral HPLC using a Chiracel OD column, 50×500 mm, eluting with 12% EtOH in hexanes at 50 mL/min and monitoring at 220 nm. Compound 798i has a retention time of 22 min(>99% ee by analytical) and Compound 798ii had a retention time of 40 min(95% ee by analytical). Absolute stereochemistry was confirmed by acid hydrolysis of the silyl enol ether to the corresponding ketone (compounds 796 & 797). Comparison by chiral analytical HPLC clearly demonstrated that the ketone product derived from compound 798i had an identical retention time to that seen for compound 796 and the ketone product derived from compound 798ii had an identical retention time to that seen for compound 797. In this fashion, the absolute configuration of compounds 798i & 798ii can be inferred by the known absolute configuration of compounds 796 & 797. Compound 798i: HPLC: 100% at 4.211 min (retention time) (YMC S5 ODS column 4.6×50 mm eluting with 10-90% aqueous methanol over 4 mincontaining 0.2% phosphoric acid, 4 mL/min, monitoring at 220 nm). Compound 798ii: HPLC: 100% at 4.210 min (retention time) (YMC S5 ODS column 4.6×50 mm eluting with 10-90% aqueous methanol over 4 mincontaining 0.2% phosphoric acid, 4 mL/min, monitoring at 220 nm).

EXAMPLE 799

[3aS-(3aα,4β,6β,7β,7aα)]-4-(Octahydro-6-fluoro-5,5-dihydroxy-4,7-dimethyl-1,3-dioxo-4,7-epoxy-2H-isoindol-2-yl)-2-(trifluoromethyl)benzonitrile (799)

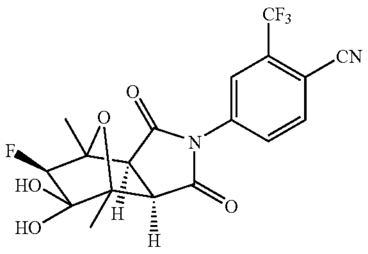

Compound 798i (2.20 g, 4.47 mmol) was dissolved in acetonitrile (45 mL) and cooled to 0° C. 1-Fluoro-4-hydroxy-1,4-diazoniabicyclo[2.2.2]octane bis-(tetrafluoroborate) (50% w/w on alumina, 5.75 g, 8.94 mmol) was then added with vigorous stirring. After 0.5 h, the reaction was quenched with sat aq $NaHCO_3$ (20 mL) and brine (20 mL). The resulting mixture was extracted with EtOAc (3×50 mL). The combined organics were dried over anhydrous $MgSO_4$ and concentrated in vacuo. The crude material was purified by silica gel flash chromatography on $SiO_2$ eluting with 0-35% acetone in chloroform to give a mixture of ketone and hydrate. The mixture was dissolved in $CH_3CN$ (50 mL) and water (5.0 mL) was added. The mixture was stirred for 3 h and then concentrated in vacuo followed by azeotroping with additional $CH_3CN$ three times and then dried in vacuo at 50° C. for 12 h to give compound 799 (1.09 g) as a white solid. Compound 799 was shown to be the hydrate only by $^1H$ and $^{19}F$ NMR spectroscopy. HPLC: 100% at 2.687 min (retention time) (YMC S5 ODS column 4.6×50 mm eluting with 10-90% aqueous methanol over 4 mincontaining 0.2% phosphoric acid, 4 mL/min, monitoring at 220 nm), MS (ES): m/z 413.27 $[M-H]^+$. The absolute stereochemistry of compound 799 is established by the known stereochemistry of the intermediate compound 798i and the retention of configuration therein. The absolute stereochemistry is as drawn in the above FIGURE and rendered by the nomenclature.

EXAMPLE 800

[3aS-(3aα,4β,6β,7β,7aα)]-4-(Octahydro-6-hydroxy-4-methyl-1,3-dioxo-4,7-epoxy-2H-isoindol-2-yl)-2-(trifluoromethyl)benzonitrile & [3aR(3aα,4β,6β,7β,7aα)]-4-(Octahydro-6-hydroxy-4-methyl-1,3-dioxo-4,7-epoxy-2H-isoindol-2-yl)-2-(trifluoromethyl)benzonitrile (799Ci and 799Cii)

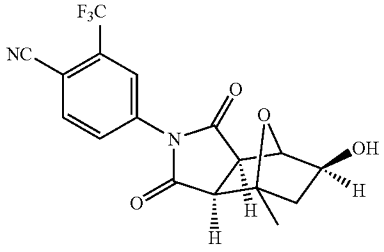

A. (800A)

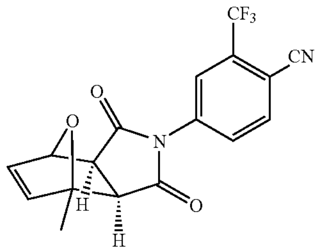

2-Methyl furan (5.33 mL, 59.1 mmol) was added to 4-(2,5-dioxo-2,5-dihydropyrrol-1-yl)-2-trifluoromethylbenzonitrile (1.50 g, 5.91 mmol) and the mixture was heated at 60° C. for 3 h. Upon heating, the reaction became homogenous followed shortly by the product crashing out of solution. The mixture was cooled to 22° C. and diluted with heptane (25 mL) and filtered, rinsing with cold heptane. Concentration in vacuo gave compound 800A (1.76 g) as a white solid. This compound was taken forward without further purification. HPLC: 100% at 2.250 min (retention time) (YMC S5 ODS column 4.6×50 mm eluting with 10-90% aqueous methanol over 4 mincontaining 0.2% phosphoric acid, 4 mL/min, monitoring at 220 nm).

B. (3aα,4β,6β,7β,7aα)]-4-(Octahydro-6-hydroxy-4-methyl-1,3-dioxo-4,7-epoxy-2H-isoindol-2-yl)-2-(trifluoromethyl)benzonitrile (800B)

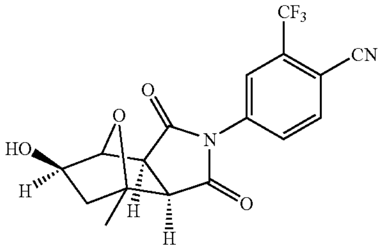

Compound 800A (0.500 g, 1.49 mmol) was dissolved in dry THF (15 mL) and Wilkinson's catalyst (0.028 g, 0.029 mmol) was added. After stirring for 10 min, catecholborane (1.0 M soln in THF, 3.00 mL, 3.00 mmol) was then added over a 5 min period. After 1 h, the reaction was cooled to 0° C. followed by sequential addition of EtOH (7.0 mL), pH 7.4 phosphate buffer (16.0 mL) and 30% aq $H_2O_2$ (1.5 g). The mixture was slowly warmed to 22° C. and after 2 h, extracted with $CH_2Cl_2$ (3×50 mL). The combined organics were washed once with a 1:1 mixture of 1N NaOH/sat aq $NaHSO_3$ (50 mL), once with brine and dried over anhydrous $Na_2SO_3$. The crude material was purified by silica gel flash chromatography on $SiO_2$ eluting with 5-10-20-40% acetone in chloroform to give compound 800B (0.344 g) as a white foam. NMR spectroscopy confirmed assignment and no other isomers were present. HPLC: 94% at 2.460 min (retention time) (YMC S5 ODS column 4.6×50 mm eluting with 10-90% aqueous methanol over 4 mincontaining 0.2% phosphoric acid, 4 mL/min, monitoring at 220 nm), MS (ES): m/z 367.22 $[M+H]^+$.

C. [3aS-(3aα,4β,6β,7β,7aα)]-4-(Octahydro-6-hydroxy-4-methyl-1,3-dioxo-4,7-epoxy-2H-isoindol-2-yl)-2-(trifluoromethyl)benzonitrile & [3aR-(3aα,4β,6β,7β,7aα)]-4-(Octahydro-6-hydroxy-4-methyl-1,3-dioxo-4,7-epoxy-2H-isoindol-2-yl)-2-(trifluoromethyl)benzonitrile (800Ci & 800Cii)

The individual enantiomers of compound 800B were separated by preparative chiral HPLC using a Chiralcel OD column (50×500 mm) eluting with 17% EtOH/hexanes at 50 mL/min monitoring at 220 nm. Compound 800Ci has a retention time of 69.4 min and compound 800Cii has a retention time of 84.1 min. Absolute stereochemistry was not determined. Compound 800Ci: HPLC: 100% at 2.460 min (retention time) (YMC S5 ODS column 4.6×50 mm eluting with 10-90% aqueous methanol over 4 mincontaining 0.2% phosphoric acid, 4 mL/min, monitoring at 220 nm). Compound 800Cii: HPLC: 100% at 2.460 min (retention time) (YMC S5 ODS column 4.6×50 mm eluting with 10-90% aqueous methanol over 4 mincontaining 0.2% phosphoric acid, 4 mL/min, monitoring at 220 nm). The absolute stereochemistry of compounds 800Ci & 800Cii has not been established. Although each compound represents a single antipode, the nomenclature and structure shown does not reflect the absolute stereochemistry of the compound.

EXAMPLE 801

[3aR-(3aα,4β,5β,7β,7aα)]-2-(4-Chloro-3-iodophenyl)hexahydro-5-hydroxy-4,7-dimethyl-4,7-epoxy-1H-isoindole-1,3(2H)-dione (801C)

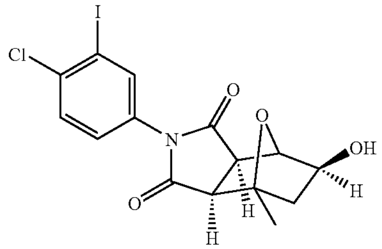

A. 1-Chloro-2-iodo-4-nitro-benzene (801A)

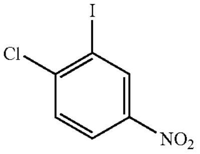

2-amino-5-nitro-iodobenzene (10.00 g, 37.9 mmol) was suspended in 12 N HCl (25 mL) and water (40 mL) and stirred for 30 min at 22° C. The mixture was then cooled to 0° C. and $NaNO_2$ (5.23 g, 75.8 mmol in 18 mL of $H_2O$) was added over a 10 min period. After 1 h, this solution was transferred to a solution of CuCl (3.75 g, 37.9 mmol) in water (50 mL) at 60° C. After 2 h, the mixture was cooled to 22° C. and extracted with EtOAc (3×150 mL) and the organics were dried over anhydrous $MgSO_4$. The crude product was purified by silica gel flash chromatography eluting with 10-20% $CH_2Cl_2$ in hexanes to give compound 801A (4.20 g) as a yellow solid. HPLC: 100% at 3.447 min (retention time) (YMC S5 ODS column 4.6×50 mm eluting with 10-90% aqueous methanol over 4 mincontaining 0.2% phosphoric acid, 4 mL/min, monitoring at 220 nm).

B. 4-Chloro-3-iodo-phenylamine (801B)

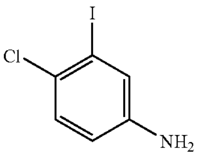

1-Chloro-2-iodo-4-nitro-benzene (2.00 g, 7.09 mmol) was dissolved in THF (30 mL) at 60° C. and EtOH (35 mL) was added followed by $NH_4Cl$ (0.569 g, 10.6 mmol in 30 mL of water) and iron powder (1.58 g, 28.4 mmol). This mixture was stirred vigorously for 3 h and then cooled in 22° C. and filtered though celite rinsing with EtOAc. The solution was then concentrated to 30 mL in vacuo and then poured into a 1:1 solution of 1N NaOH/brine (100 mL). This mixture was then extracted with EtOAc (3×50 mL) and the organics were dried over anhydrous $MgSO_4$. Filtration and concentration gave compound 801B as a yellow solid. No purification was necessary. HPLC: 100% at 2.310 min (retention time) (YMC S5 ODS column 4.6×50 mm eluting with 10-90% aqueous methanol over 4 mincontaining 0.2% phosphoric acid, 4 mL/min, monitoring at 220 nm), MS (ES): m/z 517.6 $[M+Na]^+$.

C. [3aR-(3aα,4β,5β,7β,7aα)]-2-(4-Chloro-3-iodophenyl)hexahydro-5-hydroxy-4,7-dimethyl-4,7-epoxy-1H-isoindole-1,3(2H)-dione (801C)

Compound 801B (0.300 g, 1.19 mmol) and compound 752 (0.229 g, 1.08 mmol) were added to DMA (1.2 mL) in a high pressure reaction vessel. 4A molecular seives (0.300 g) were then added and the vessel sealed and heated to 190° C. After 45 min, the reaction was cooled to rt and poured into EtOAc (50 mL). The solution was then washed once with water (20 mL), three times with sat aq $NH_4Cl$ (20 mL) and dried over anhydrous $MgSO_4$. The crude material was purified by flash chromatography on silica eluting with 10-20-30% acetone in chloroform to give compound 801C (0.217 g) as a tan solid. HPLC: 100% at 3.000 min (retention time) (YMC S5 ODS column 4.6×50 mm eluting with 10-90% aqueous methanol over 4 mincontaining 0.2% phosphoric acid, 4 mL/min, monitoring at 220 nm), MS (ES): m/z 448.18 $[M+H]^+$. The absolute stereochemistry of compound 801C is established by the known stereochemistry of the intermediate compound 752 and the retention of configuration therein. The absolute stereochemistry is as drawn in the above FIGURE and rendered by the nomenclature.

EXAMPLE 802

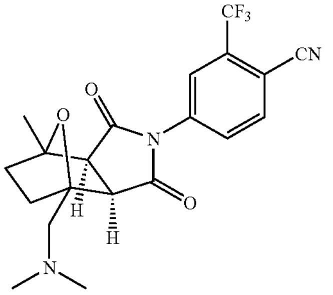

A. (802A)

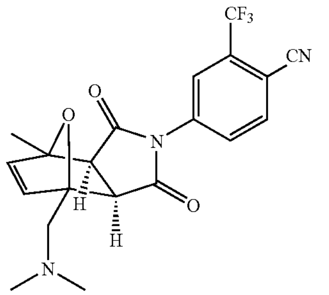

4-(2,5-Dioxo-2,5-dihydro-pyrrol-1-yl)-2-trifluoromethyl-benzonitrile (0.200 g, 0.79 mmol) and 2-(N,N-dimethylaminomethyl)-5-methylfuran (0.548 g, 3.94 mmol) were dissolved in THF (0.5 mL) and heated to 60° C. for 3 h. The mixture was then concentrated in vacuo to give compound 802A as a brown oil. The crude material was used without purification.

B. (802B)

Compound 802A (~0.4 mmol) was dissolved in EtOAc (5.0 mL) and Pd/C (10% Pd, 0.020 g) was added followed by introduction of $H_2$ via a balloon. After 3 h, the reaction was purged with $N_2$ and filtered through celite rinsing with EtOAc. The crude material was purified by silica gel flash chromatography eluting with 10-20-30% acetone in chloroform to give compound 802B (0.080 g) as a tan oil. HPLC: 95% at 2.040 min (retention time) (YMC S5 ODS column 4.6×50 mm eluting with 10-90% aqueous methanol over 4 mincontaining 0.2% phosphoric acid, 4 mL/min, monitoring at 220 nm), MS (ES): m/z 408.31 $[M+H]^+$. Compound 802B represents a racemic mixture of antipodes. The nomenclature and structure shown does not reflect the absolute stereochemistry of the compound.

EXAMPLE 803

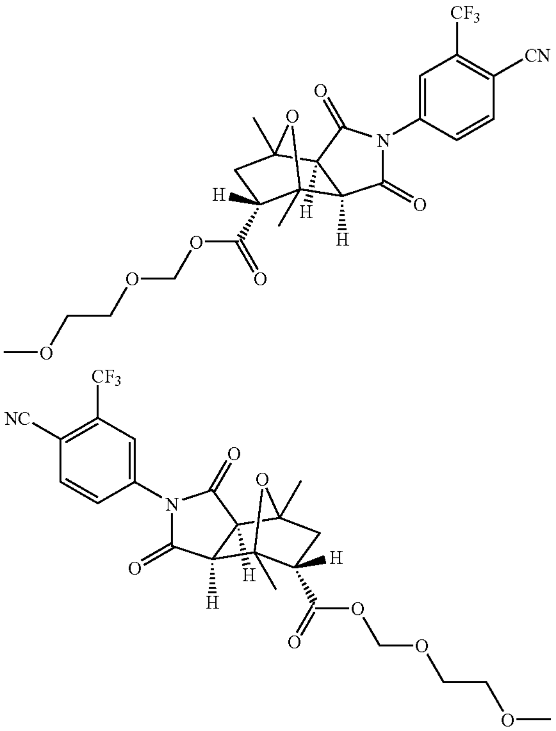

A. 2,5-Dimethylfuran-3-carboxylic Acid 2-Methoxyethoxymethyl Ester (803A)

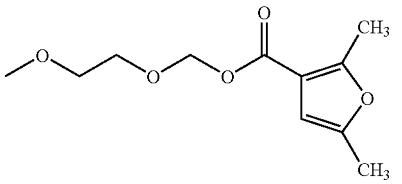

A 2 L round-bottomed flask equipped with a mechanical stirrer was charged with 2,5-dimethyl-3-furoic acid (81.0 g, 0.58 mol) and potassium carbonate (95.9 g, 0.69 mol) in DMF (500 mL). An ice bath was used to cool the reaction as 2-methoxyethoxymethyl chloride (72.2 g, 0.58 mol) was added portionwise. The reaction was stirred for 5 h at rt. The mixture was then diluted with water (1.5 L) and extracted with EtOAc (2×600 mL). The combined organics were washed with water (2×900 mL) and saturated sodium chloride solution (1 L), dried over $MgSO_4$, filtered and concentrated to afford compound 803A (103 g, 82%) as a yellow oil. $^1H$ NMR ($CDCl_3$): δ=6.23 (s, 1H), 5.47 (s, 1H), 3.84 (m, 2H), 3.56 (m, 2H), 3.38 (s, 3H), 2.51 (s, 3H) and 2.20 ppm (s, 3H).

B. (803B)

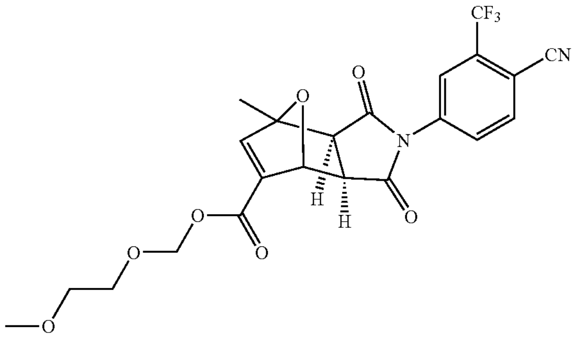

A 250 mL round-bottomed flask was charged with 4-(2,5-dioxo-2,5-dihydropyrrol-1-yl)-2-trifluoromethylbenzonitrile (15.0 g, 0.056 mol) and 2,5-dimethylfuran-3-carboxylic acid 2-methoxyethoxymethyl ester (22.8 g, 0.10 mol). The mixture was heated to 125° C. for 1.5 h then stirred at rt overnight. The crude product was dissolved in EtOAc and adsorbed onto silica gel. Purification by silica gel chromatography, eluting with 30% EtOAc in hexanes, afforded compound 803B (8.21 g, 30%) as a viscous oil. $^1H$ NMR ($CDCl_3$): δ=7.95 (d, J=8.3 Hz, 1H), 7.86 (d, J=1.9 Hz, 1H), 7.75 (m, 1H), 7.13 (s, 1H), 5.44 (m, 2H), 3.83 (m, 2H), 3.57 (m, 2H), 3.39 (s, 3H), 3.19 (d, J=6.5 Hz, 1H), 3.09 (d, J=6.5 Hz, 1H), 2.04 (s, 3H) and 1.91 ppm (s, 3H).

C. (803C)

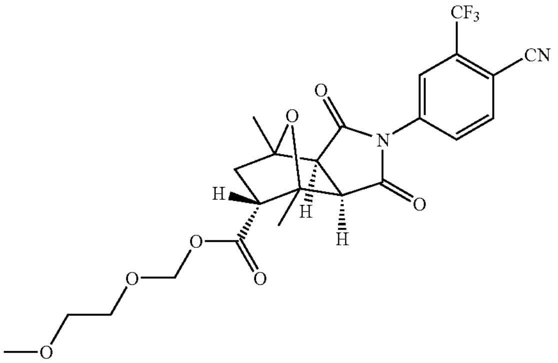

A 250 mL Parr hydrogenation bottle was charged with compound 803B (7.75 g, 0.015 mol), EtOAc (80 mL) and palladium on carbon (0.40 g, 10% Pd, 50% wet). The bottle was placed on a Parr hydrogenation apparatus, pressurized with hydrogen to 5 psi, and shook until the uptake of hydrogen ceased. Filtration of the contents over celite and concentration afforded a yellow oil. Purification by silica gel chromatography, eluting with 30% EtOAc in hexanes, afforded compound 803C (3.92 g, 50%) as a white solid. HPLC: 100% at 14.5 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used). $R_f$=0.61 ($SiO_2$, 60% EtOAc in hexanes). Mpt>300° C. $^1H$ NMR ($CDCl_3$): δ=7.94 (d, J=8.3 Hz, 1H), 7.84 (d, J=1.9 Hz, 1H), 7.74 (m, 1H), 5.46 (d, J=6.1 Hz, 1H), 5.34 (d, J=6.1 Hz, 2H), 3.85 (m, 2H), 3.57 (t, J=4.5 Hz, 2H), 3.38 (s, 3H), 3.33 (d, J=7.2 Hz, 1H), 3.19 (d, J=7.2 Hz, 1H), 3.04 (m, 1H), 2.28 (m, 1H), 2.05 (t, J=12.2 Hz, 1H), 1.78 (s, 3H) and 1.64 ppm (s, 3H). m/z=496 $[M+H]^+$.

D. (803Di and 803Dii)

Racemic compound 803C was separated into its two enantiomers by preparative chiral HPLC using a Chiracel OD column (50×500 mm) eluting with 50% EtOH in Heptane at 100 mL/min and 290 nm detection. Compound 803Di had a retention time of 6.68 min and $[\alpha]_{25}^{D}$=+28.7° (c=1.0, MeOH). Compound 803Dii had a retention time of 13.9 min and $[\alpha]_{25}^{D}$=−29.2° (c=1.0, MeOH). The absolute stereochemistry of compounds 803Di & 803Dii has not been established. Although each compound represents a single antipode, the nomenclature and structure shown does not reflect the absolute stereochemistry of the compound.

EXAMPLE 804

[3aR-(3aα,4β,5α,7β,7aα)]-2-(4-Cyano-3-(trifluoromethyl)phenyl)hexahydro-4,7-dimethyl-1,3-dioxo-4,7-epoxy-1H-isoindole-5-carboxylic acid (804)

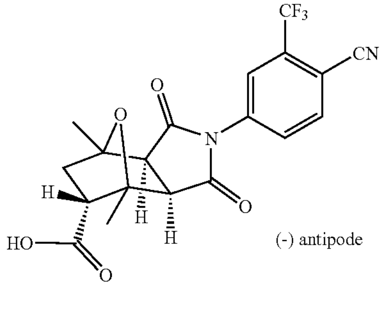

(-) antipode

A 250 mL round-bottomed flask was charged with compound 803Di (9.85 g, 19.8 mmol) and THF (60 mL). A solution of 3N hydrochloric acid (50 mL) was added and the reaction mixture stirred for 16 h at rt. Water (60 mL) was then added and the aqueous layer extracted with EtOAc (3×120 mL). The combined organics were dried over sodium sulfate, filtered and concentrated to afford compound 804 (8.00 g, 98%) which was shown to be identical to compound 791. HPLC: 100% at 13.3 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used), MS (ES): m/Z 409 $[M+H]^+$. $R_f$=0.41 ($SiO_2$, 10% MeOH in $CH_2Cl_2$). Mpt>300° C. $[\alpha]_{25}^{D}$=−28.50

(c=1.0, MeOH). $^{1}H$ NMR ($CD_3OD$): δ=8.12 (d, J=8.3 Hz, 1H), 7.92 (s, 1H), 7.82 (dd, J=8.3 and 2.0 Hz, 1H), 3.39 (t, J=6.7 Hz, 1H), 3.30 (d, J=6.7 Hz, 1H), 3.00 (dd, J=12.0 and 5.2 Hz, 1H), 2.23 (dd, J=12.0 and 5.2 Hz, 1H), 2.01 (t, J=12.0 Hz, 1H), 1.70 (s, 3H) and 1.57 ppm (s, 3H). The absolute stereochemistry of compound 804 has not been established. Although the compound represent a single antipode the nomenclature and structure shown does not reflect the absolute stereochemistry of the compound.

EXAMPLE 805

[3S-(3aα,4β,5α,7β,7aα)]-2-(4-Cyano-3-(trifluoromethyl)phenyl)hexahydro-4,7-dimethyl-1,3-dioxo-4,7-epoxy-1H-isoindole-5-carboxylic acid (805)

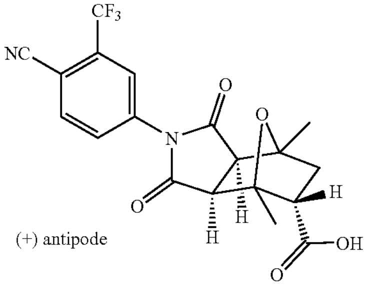

(+) antipode

Compound 805 was prepared in identical fashion as described in example 804 with the exception that compound 803Dii was the starting material in place of compound 803Di. Compound 805 was obtained in 98% yield. $[\alpha]^{25}_{D}$=+28.0° (c=1.0, MeOH). The absolute stereochemistry of compound 805 has not been established. Although the compound represent a single antipode the nomenclature and structure shown does not reflect the absolute stereochemistry of the compound.

EXAMPLE 806

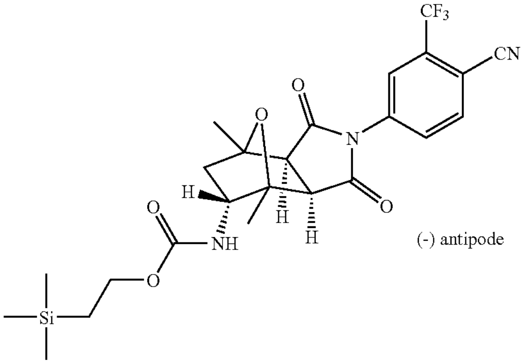

(-) antipode

A 50 mL round-bottomed flask was charged with dioxane (6 mL), compound 804 (400 mg, 0.984 mmol), diphenylphosphoryl azide (334 mg, 1.21 mmol), triethylamine (123 mg, 1.22 mmol) and powdered 4 Å molecular sieves (400 mg). The resulting suspension was heated at 50° C. for 1.5 h, the temperature was then raised to 75° C. and 2-(trimethylsilyl) ethanol (590 mg, 5.02 mmol) was added. Heating was continued for an additional 1.5 h. The reaction mixture was then cooled, filtered though a celite pad and the filtrate concentrated under reduced pressure. Purification of the residue by silica gel chromatography, eluting with 20% then 40% EtOAc in hexanes, afforded compound 806 (400 mg, 78%) as a white solid. HPLC: 100% at 15.3 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used), MS (ES): m/z 524 $[M+H]^{+}$. $R_f$=0.79 ($SiO_2$, 50% EtOAc in hexanes). Mpt>300° C. $[\alpha]_{25}^{D}$=−1.8° (c=1.0, MeOH). $^{1}H$ NMR ($CDCl_3$): δ=7.96 (d, J=8.3 Hz, 1H), 7.83 (s, 1H), 7.73 (dd, J=8.3 and 2.0 Hz, 1H), 4.72 (bs, 1H), 4.19 (t, J=12.0 Hz, 2H), 4.05 (m, 1H), 3.45 (d, J=8.3 Hz, 1H), 3.12 (d, J=8.3 Hz, 1H), 2.36 (t, J=12.0 Hz, 1H), 1.61 (s, 6H), 1.04 (t, J=12.0 Hz, 2H) and 0.05 ppm (s, 6H). The absolute stereochemistry of compound 806 has not been established. Although the compound represents a single antipode, the nomenclature and structure shown does not reflect the absolute stereochemistry of the compound.

EXAMPLE 807

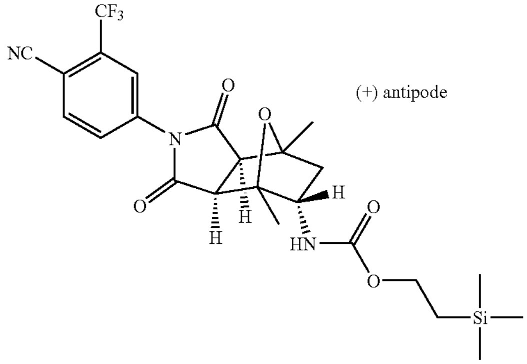

(+) antipode

Compound 807 was prepared in identical fashion as described in example 806 with the exception that compound 805 was the starting material in place of compound 804. Compound 807 was obtained in 80% yield. $[\alpha]^{25}_{D}$=+ 1.10 (c=1.0, MeOH). The absolute stereochemistry of compound 807 has not been established. Although the compound represents a single antipode, the nomenclature and structure shown does not reflect the absolute stereochemistry of the compound.

EXAMPLE 808

[3aR-(3aα,4β,5α,7β,7aα)]-4-(Octahydro-5-amino-4,7-dimethyl-1,3-dioxo-4,7-epoxy-2H-isoindol-2-yl)-2-(trifluoromethyl)benzonitrile (808)

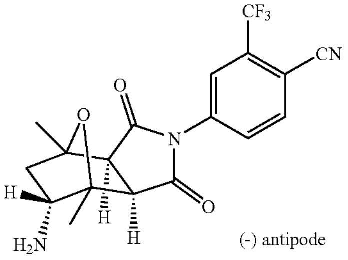

(-) antipode

A solution of compound 806 (400 mg, 0.76 mmol) in methylene chloride (10 mL) was treated with trifluoroacetic acid (2 mL) and the mixture stirred at rt for 2 h. After this time the reaction was rendered basic (pH=9) by the addition of saturated aqueous sodium carbonate solution (20 mL) and solid potassium carbonate. The organic phase was then separated and the aqueous layer extracted with methylene chloride (3×40 mL). The combined organics were dried over sodium sulfate, filtered, and concentrated to afford compound 808

(283 mg, 99%) as a white solid. HPLC: 100% at 10.5 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used), MS (ES): m/z 380 $[M+H]^+$. $R_f$=0.59 ($SiO_2$, 5% MeOH in $CH_2Cl_2$). $[\alpha]_{25}^{D}$=−26.7° (c=1.0, MeOH). Mpt=150-152° C. $^1$H NMR ($CD_3OD$): δ=8.12 (d, J=8.3 Hz, 1H), 7.94 (s, 1H), 7.83 (dd, J=8.3 and 2.0 Hz, 1H), 3.66 (d, J=7.2 Hz, 1H), 3.21 (m, 4H), 2.16 (t, J=12.0 Hz, 1H), 1.51 (s, 3H), 1.49 (s, 3H) and 1.42 ppm (dd, J=12.0 and 5.0 Hz, 1H). The absolute stereochemistry of compound 808 has not been established. Although the compound represents a single antipode, the nomenclature and structure shown does not reflect the absolute stereochemistry of the compound.

EXAMPLE 809

[3aS-(3aα,4β,5α,7β,7aα)]-4-(Octahydro-5-amino-4,7-dimethyl-1,3-dioxo-4,7-epoxy-2H-isoindol-2-yl)-2-(trifluoromethyl)benzonitrile (809)

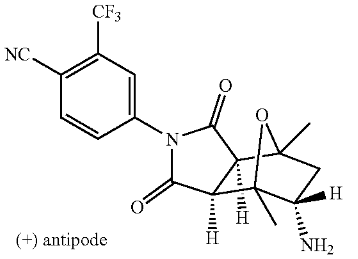

(+) antipode

Compound 809 was prepared in identical fashion as described in example 808 with the exception that compound 807 was the starting material in place of compound 806. Compound 809 was isolated in 94% overall yield. $[\alpha]^{25}_{D}$=+27.3° (c=1.0, MeOH). The absolute stereochemistry of compound 809 has not been established. Although the compound represents a single antipode, the nomenclature and structure shown does not reflect the absolute stereochemistry of the compound.

EXAMPLE 810

(3aα,4β,5α,7β,7aα)-4-(Octahydro-5-ethylsulfonamido-4,7-dimethyl-1,3-dioxo-4,7-epoxy-2H-isoindol-2-yl)-2-(trifluoromethyl)benzonitrile (810)

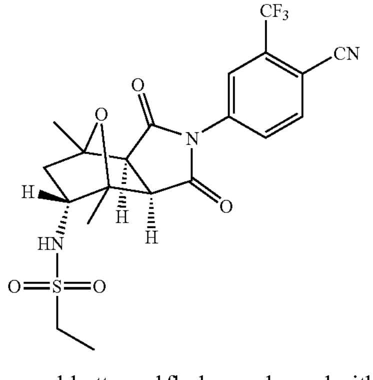

A 25 mL round-bottomed flask was charged with a racemic mixture of compounds 808 & 809 (102 mg, 0.27 mmol) and methylene chloride (10 mL). Ethanesulfonyl chloride (54.3 mg, 0.42 mmol) and triethylamine (43.6 mg, 0.43 mmol) were added and the resulting mixture stirred at rt overnight. Analysis of the reaction mixture by TLC ($SiO_2$, EtOAc) indicated the presence of starting material so an additional equivalent of ethanesulfonyl chloride (54.3 mg, 0.42 mmol) was added and stirring continued at rt for 4 h. The reaction mixture was then diluted with $CH_2Cl_2$ (25 mL) and washed with water (10 mL). Drying over magnesium sulfate, filtration, and concentration afforded a yellow oil. Purification of this oil by silica gel chromatography, eluting with 25% EtOAc in hexanes, then 50% EtOAc in hexanes and finally EtOAc, afforded compound 810 (55.9 mg, 44%). as a white solid. HPLC: 100% at 13.8 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used), MS (ES): m/z 472 $[M+H]^+$. $R_f$=0.72 (EtOAc). Mpt=189-192° C. $^1$H NMR ($CDCl_3$): δ=7.94 (d, J=−8.3 Hz, 1H), 7.85 (s, 1H), 7.74 (dd, J=8.3 and 2.0 Hz, 1H), 5.72 (d, J=8.3 Hz, 1H), 3.71 (m, 1H), 3.51 (d, J=7.2 Hz, 1H), 3.18 (d, J=7.2 Hz, 1H), 3.11 (q, J=7.2 Hz, 2H), 2.37 (t, J=12.0 Hz, 1H), 1.67 (m, 1H), 1.62 (s, 3H), 1.61 (s, 3H) and 1.40 ppm (t, J=7.2 Hz, 3H). The absolute stereochemistry of compound 810 has not been established. Although the compound represents a single antipode, the nomenclature and structure shown does not reflect the absolute stereochemistry of the compound.

EXAMPLE 811

(3aα,4β,5α,7β,7aα)-4-(Octahydro-5-[[r((phenylmethyl)amino)carbonyl]oxy]-4,7-dimethyl-1,3-dioxo-4,7-epoxy-2H-isoindol-2-yl)-2-(trifluoromethyl) benzonitrile (811)

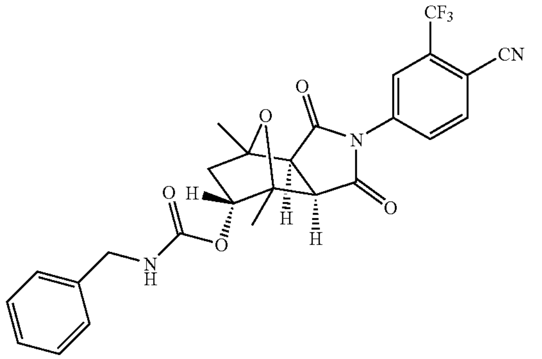

A 25 mL round-bottomed flask was charged with compound 222D (102 mg, 0.27 mmol) and THF (2 mL). Benzyl isocyanate (37.7 mg, 0.28 mmol) was added and the resulting mixture stirred at rt for 1.5 h then heated at 60° C. for an additional 1.5 h. Sodium hydride (50 mg, 60% dispersion in mineral oil) was then added followed by additional benzyl isocyanate (37.7 mg, 0.28 mmol). Heating was continued at 60° C. overnight. Benzyl isocyanate (75.4 mg, 0.56 mmol) and THF (2 mL) were then added and the reaction re-heated to 60° C. for an additional 3 h. The reaction mixture was then cooled to rt and concentrated under reduced pressure to afford an off white solid. Ether (20 mL) was then added and a precipitate formed. The mixture was filtered and the filtrate concentrated to a white solid, which was further purified by preparative HPLC. Fractions containing the desired product were concentrated and a solution of saturated sodium bicarbonate (15 mL) added. The aqueous layer was extracted with methylene chloride (3×25 mL), dried over magnesium sulfate, filtered, and concentrated to afford compound 811 (119 mg, 80%) as a white solid. HPLC: 100% at 15.3 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used), MS (ES): m/z 514 $[M+H]^+$. $R_f$=0.58 ($SiO_2$, 50% EtOAc in hexanes). Mpt>300° C. $^1H$ NMR ($CDCl_3$): δ=7.94 (d, J=8.1 Hz, 1H), 7.85 (s, 1H), 7.74 (m, 1H), 7.36-7.34 (m, 5H), 5.07 (bs, 1H), 4.92 (m, 1H), 4.39 (bs, 2H), 3.59 (m, 1H), 3.11 (m, 1H), 2.35 (t, J=12.0 Hz, 1H) and 1.61 ppm (s, 6H). The absolute stereochemistry of compound 811 has not been established. Although the compound represents a single antipode, the nomenclature and structure shown does not reflect the absolute stereochemistry of the compound.

EXAMPLE 812

[3aR-(3aα,4β,5α,7β,7aα)]-2-(4-Cyano-3-(trifluoromethyl)phenyl)hexahydro-4,7-dimethyl-1,3-dioxo-4,7-epoxy-N-methyl-N-phenyl-1H-isoindole-5-carboxamide (812)

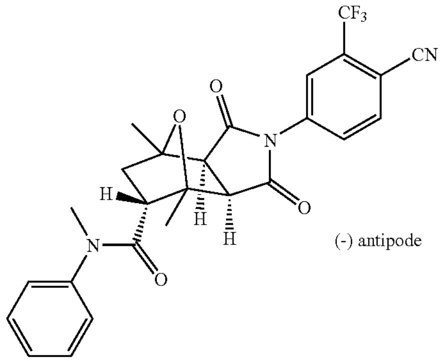

(-) antipode

To a dry, nitrogen purged 100 mL round-bottomed flask was added compound 804 (100 mg, 0.245 mmol) and $CH_2Cl_2$ (10 mL). The solution was stirred at rt and oxalyl chloride (311 mg, 2.45 mmol) and N,N-dimethylformamide (28.0 mg, 0.387 mmol) were added. Gas evolution was observed and the reaction was stirred at rt for 1 h. The resulting solution was then concentrated to dryness under reduced pressure and $CH_2Cl_2$ (10 mL) was added. N-Methylaniline (262 mg, 2.45 mmol) was added and the reaction stirred for 15 h at rt. After concentrating the resulting solution under reduced pressure, the resulting oil was chromatographed on silica gel, using 50% EtOAc in hexanes as the eluant, to give an orange oil that was contaminated with N-methylaniline. The material was re-chromatographed on silica gel, using 40% EtOAc in hexanes as eluant, to afford compound 812 (115 mg, 94%) as a white foam. HPLC: 100% at 18.7 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used), MS (ES): m/z 498 $[M+H]^+$. $R_f$=0.37 ($SiO_2$, 40% EtOAc in hexanes). Mpt>300° C. $[\alpha]^{25}_D$=−30.0° (c=1.0, MeOH). $^1H$ NMR ($CDCl_3$): δ=7.92 (d, J=8.4 Hz, 1H), 7.84 (d, J=1.5 Hz, 1H), 7.73 (dd, J=8.3 and 2.0 Hz, 1H), 7.52-7.35 (m, 3H), 7.17 (d, J=7.1 Hz, 2H), 4.24 (d, J=7.3 Hz, 1H), 3.30 (s, 3H), 3.28 (d, J=7.3 Hz, 1H), 3.09-2.96 (m, 1H), 2.10-1.99 (m, 1H), 1.81 (t, J=12.0 Hz, 1H), 1.56 (s, 3H) and 1.41 ppm (s, 3H). The absolute stereochemistry of compound 812 has not been established. Although the compound represents a single antipode, the nomenclature and structure shown does not reflect the absolute stereochemistry of the compound.

EXAMPLE 813

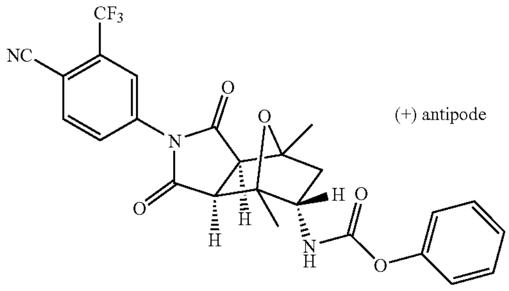

(+) antipode

A 25 mL round-bottomed flask was charged with dioxane (3 mL), compound 805 (76.3 mg, 0.187 mmol), diphenylphosphoryl azide (62.6 mg, 0.227 mmol), triethylamine (23.2 mg, 0.230 mmol) and powdered 4 Å molecular sieves (200 mg) and the resulting suspension heated at 50° C. for 1.5 h. The temperature was then raised to 75° C. and phenol (93.0 mg, 0.988 mmol) added. Heating was continued for an additional 1.5 h. The reaction mixture was then cooled, filtered though a celite pad and the filtrate concentrated under reduced pressure. Purification of the residue by silica gel chromatography, eluting with 10%-50% EtOAc in hexanes, afforded compound 813 (71.5 mg, 77%) as a white solid. HPLC: 100% at 15.9 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used), $R_f$ 0.70 ($SiO_2$, 50% EtOAc in hexanes). $[\alpha]_{25}^D$=+ 13.0° (c=1.0, MeOH). Mpt>300° C. HPLC: $R_t$=15.9 min. $^1H$ NMR ($CD_3OD$): δ=8.14 (d, J=8.3 Hz, 1H), 7.95 (s, 1H), 7.85 (dd, J=8.3 and 2.0 Hz, 1H), 7.41-7.12 (m, 5H), 4.06 (dd, J=12.0 and 5.0 Hz, 1H), 3.55 (d, J=7.2 Hz, 1H), 3.29 (d, J=7.2 Hz, 1H), 2.29 (t, J=12.0 Hz, 1H), 1.71 (dd, J=12.0 and 5.0 Hz, 1H), 1.56 (s, 3H) and 1.54 ppm (s, 3H). The absolute stereochemistry of compound 813 has not been established. Although the compound represents a single antipode, the nomenclature and structure shown does not reflect the absolute stereochemistry of the compound.

EXAMPLE 814

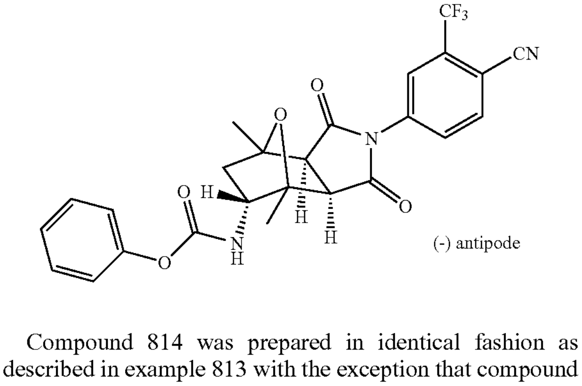

(-) antipode

Compound 814 was prepared in identical fashion as described in example 813 with the exception that compound 804 was the starting material in place of compound 805. Compound 814 was isolated in 62% overall yield. $[\alpha]^{25}_D$=−11.7° (c=1.0, MeOH). The absolute stereochemistry of compound 814 has not been established. Although the compound represents a single antipode, the nomenclature and structure shown does not reflect the absolute stereochemistry of the compound.

EXAMPLE 815

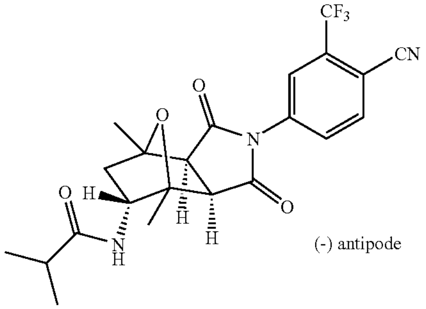

(-) antipode

Compound 807 (0.060 g, 0.15 mmol) was dissolved in 2 mL of $CH_2Cl_2$ and triethylamine (0.020 g, 0.16 mmol) and a catalytic amount of DMAP were added followed by isobutyryl chloride (0.02 g, 0.16 mmol). The reaction was stirred for 1 h at 23° C. when HPLC showed complete consumption of starting material. The reaction was diluted with $CH_2Cl_2$, washed successively with 1N HCl, saturated sodium bicarbonate, brine, dried ($MgSO_4$), filtered and concentrated in vacuo to give compound 815 (0.06 g, 83%), as a white solid. No was purification necessary. HPLC: 100% at 3.12 min (YMC S5 ODS column) eluting with 10-90% aqueous methanol containing 0.2% phosphoric acid over a 4 min gradient monitoring at 220 nm. LC/MS—[M+H]=450.12. The absolute stereochemistry of compound 815 has not been established. Although the compound represents a single antipode, the nomenclature and structure shown does not reflect the absolute stereochemistry of the compound.

EXAMPLE 816

[3aR-(3aα,4β,5α,7β,7aα)]-4-(Octahydro-5-[[[(cyclopropylmethyl)amino]carbonyl]amino]-4,7-dimethyl-1,3-dioxo-4,7-epoxy-2H-isoindol-2-yl)-2-(trifluoromethyl)benzonitrile (816)

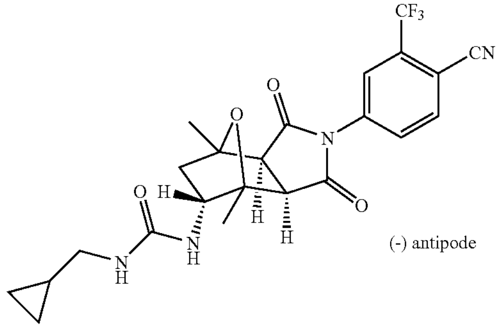

(-) antipode

A 50 mL round-bottomed was charged with compound 815 (0.052 g, 0.10 mmol), methyl sulfoxide (2 mL) and aminomethylcyclopropane (10 μL, 8.2 mg, 0.11 mmol). The reaction was stirred for 4 h after which time the reaction mixture was diluted with water (9 mL) and saturated $NaHCO_3$ solution (1 mL). Extraction with $CH_2Cl_2$ (1×20 mL then 1×10 mL), drying over $MgSO_4$, filtration and concentration afforded the crude product as a yellow oil. Purification by silica gel chromatography, eluting with 20% to 50% EtOAc in hexanes afforded compound 816 (33.6 mg, 67%). HPLC: 100% at 12.9 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used), MS (ES): m/z 477 $[M+H]^+$. $R_f$=0.42 ($SiO_2$, 50% EtOAc in hexanes). Mpt>300° C. $[\alpha]^{25}_D$=−31.5° (c=1.0, MeOH). $^1H$ NMR ($CDCl_3$): δ=8.12 (d, J=8.3 Hz, 1H), 7.94 (s, 1H), 7.84 (d, J=8.3 Hz, 1H) 4.12-4.06 (m, 1H), 3.46 (d, J=8.3 Hz, 1H), 3.34 (bs, 1H), 3.22 (d, J=8.3 Hz, 1H), 1.41 (t, J=12.3 Hz, 1H), 1.54 (s, 3H), 1.50 (s, 3H), 1.01-0.92 (m, 1H), 0.51-0.45 (m, 2H) and 0.21-0.17 ppm (m, 2H). The absolute stereochemistry of compound 816 has not been established. Although the compound represents a single antipode, the nomenclature and structure shown does not reflect the absolute stereochemistry of the compound.

EXAMPLE 817

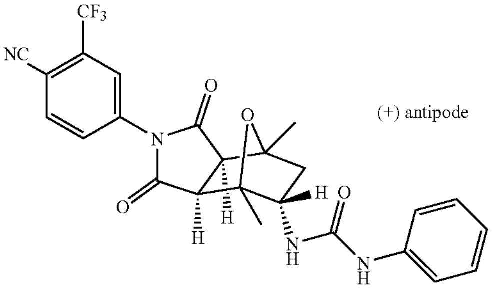

(+) antipode

A 50 mL round-bottomed was charged with compound 809 (0.057 g, 0.15 mmol) and phenyl isocyanate (0.1 mL, 0.9 mmol). After heating for 3 h at 65-70° C., analysis of the reaction by HPLC indicated complete consumption of starting material. Dilution with EtOAc (0.5 mL) and purification by silica gel chromatography, eluting with 60% EtOAc in hexanes afforded compound 817 (39 mg, 52%) as a white solid. HPLC: 100% at 14.2 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used), MS (ES): m/z 499 $[M+H]^+$. $R_f$=0.17 (50% EtOAc in hexanes). Mpt>300° C. $[\alpha]^{25}_D$=+30.7° (c=1.0, MeOH). $^1H$ NMR ($CDCl_3$): δ=8.12 (d, J=8.3 Hz, 1H), 7.94 (s, 1H), 7.84 (d, J=8.3 Hz, 1H), 7.35 (d, J=7.8 Hz, 2H), 7.26 (t, J=7.7 Hz, 2H), 6.99 (t, J=7.1 Hz, 1H), 4.19-4.14 (m, 1H), 3.51 (d, J=7.1 Hz, 1H), 3.27-3.25 (m, 2H), 2.31 (t, J=12.3 Hz, 1H), 1.63-1.61 (m, 1H), 1.56 (s, 3H) and 1.55 ppm (s, 3H). The absolute stereochemistry of compound 817 has not been established. Although the compound represents a single antipode, the nomenclature and structure shown does not reflect the absolute stereochemistry of the compound.

EXAMPLE 818

[3aR-(3aα,4β,5α,7β,7aα)]-4-(Octahydro-5-[[(dimethylamino)sulfonyl]amino]-4,7-dimethyl-1,3-dioxo-4,7-epoxy-2H-isoindol-2-yl)-2-(trifluoromethyl) benzonitrile (817)

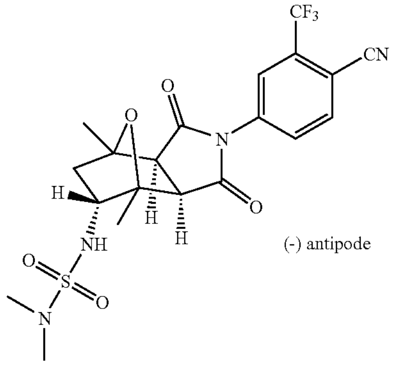

(-) antipode

A 50 mL round-bottomed flask was charged with compound 808 (100 mg, 0.28 mmol), methylene chloride (2 mL), triethylamine (28.3 mg, 0.28 mmol) and dimethylsulfamoyl chloride (40.2 mg, 0.28 mmol). The reaction was then stirred at rt for 3 h, after which time it was quenched with water (10 mL) and extracted with $CH_2Cl_2$ (2×20 mL). The organic layer was washed once more with water (10 mL), dried over $MgSO_4$, filtered and concentrated to a yellow oil. Purification by silica gel chromatography, eluting with 20% EtOAc in hexanes to 100% EtOAc afforded compound 818 (64.2 mg, 47%). HPLC: 100% at 14.2 min (retention time) (Hypersil C18 BDS column, 250×4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used), MS (ES): m/z 487 $[M+H]^+$. $R_f$=0.19 ($SiO_2$, 50% EtOAc in hexanes). $[\alpha]^{25}_D$=−22.8° (c=1.0, MeOH). Mpt=262-269° C. $^1H$ NMR ($CDCl_3$): δ=8.12 (d, J=8.3 Hz, 1H), 7.94 (s, 1H), 7.84 (d, J=8.2 Hz, 1H), 3.61 (m, 1H), 3.54 (d, J=7.2 Hz, 1H), 3.35 (s, 1H), 3.22 (d, J=7.2 Hz, 1H), 2.79 (s, 6H), 2.27 (t, J=12.4 Hz, 1H), 1.68 (m, 1H), 1.54 (s, 3H) and 1.53 ppm (s, 3H). The absolute stereochemistry of compound 818 has not been established. Although the compound represents a single antipode, the nomenclature and structure shown does not reflect the absolute stereochemistry of the compound.

EXAMPLE 819

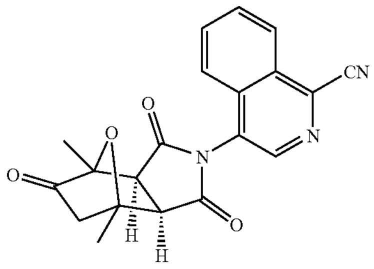

A mixture of 4-(2,5-dioxo-2,5-dihydro-pyrrol-1-yl)-isoquinoline-1-carbonitrile (1 g, 4 mmol), 2,5-dimethyl-2,3-dihydrofuran-3-one (0.45 g, 4 mmol), DMAP (20 mg, 0.16 mmol), anhydrous methylene chloride (10 mL), and THF (20 mL) was stirred at 80° C. overnight, and then concentrated under reduced pressure. Purification by silica gel flash chromatography on $SiO_2$ eluting with EtOAc/heptane (gradient from 1:4 to 1:0 ratio) gave a solid that was crystallized in a mixture of EtOAc and heptane to give 0.4 g (28%) of compound 819 as a yellowish solid. HPLC: 90% at 3.37 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 362 $[M+H]^+$. Compound 819 represents a racemic mixture of antipodes. The nomenclature and structure shown does not reflect the absolute stereochemistry of the compound.

EXAMPLE 820

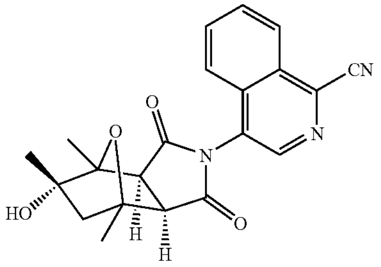

To a stirred solution of compound 819 (36 mg, 0.1 mmol) in anhydrous THF (1 mL) cooled at 0° C. under argon was added MeMgBr (1.4 M THF solution, 0.3 mL, 0.4 mmol) dropwise. After the mixture was stirred at 0° C. for 1 h and at rt for 10 min, saturated aqueous solution of $NH_4Cl$ was added with stirring. The mixture was extracted with EtOAc (3×). The combined extracts were dried over $Na_2SO_4$, and concentrated under reduced pressure. Purification by silica gel flash chromatography eluting with EtOAc/heptane (gradient from 1:2 to 1:0 ratio) gave a solid that was crystallized in a mixture of EtOH and $H_2O$ to give compound 820 (8 mg, 21%) as a white solid. HPLC: 97% at 3.36 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 378 $[M+H]^+$. Compound 820 represents a racemic mixture of antipodes. The nomenclature and structure shown does not reflect the absolute stereochemistry of the compound.

EXAMPLE 821

[3aS-(3aα,4β,5β,7β,7aα)]-5-(Octahydro-5-hydroxy-4,7-dimethyl-1,3-dioxo-4,7-epoxy-2H-isoindol-2-yl)-3-methyl-2-pyridinecarbonitrile (821)

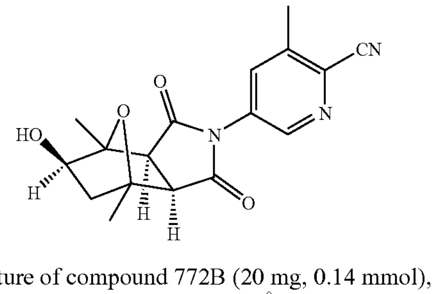

A mixture of compound 772B (20 mg, 0.14 mmol), compound 751 (48 mg, 0.20 mmol) and 4 Å molecular sieves (100 mg) in DMA (0.2 mL) was heated at 70° C. in a sealed tube for 5 h. The reaction mixture was filtered and the residue was washed with EtOAc. The filtrates were combined and washed with $H_2O$ (2×5 mL) and brine (1×5 mL). The combined aqueous layers were extracted with EtOAc (2×5 mL) and the combined organic layers were dried over $Na_2SO_4$ and concentrated under reduced pressure. Purification by silica gel flash chromatography eluting with 30% acetone/$CHCl_3$ gave 55 mg of product contaminated with compound 751. Further purification by silica gel flash chromatography on $SiO_2$ eluting with 90% EtOAc/hexanes gave compound 821 (46 mg, 62%) as a white solid. HPLC: 100% at 2.27 min (retention time) (YMC S5 ODS column 4.6×50 mm eluting with 10-90% aqueous methanol over 4 mincontaining 0.2% phosphoric acid, 4 mL/min, monitoring at 220 nm). MS (ES): m/z 328.2 $[M+H]^+$. The absolute stereochemistry of compound 821 is established by the known stereochemistry of the intermediate compound 751 and the retention of configuration therein. The absolute stereochemistry is as drawn in the above FIGURE and rendered by the nomenclature.

EXAMPLE 822

[3aR-(3a α,4β,4aα,5aα,6β,7aα)]-4-(Octahydro-4a-hydroxy-4,6-dimethyl-1,3-dioxo-4,6-epoxycycloprop[f]isoindol-2(1H)-yl)-2-(trifluoromethyl)benzonitrile (822)

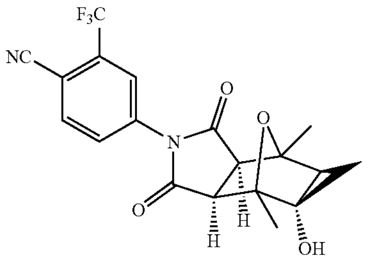

A solution of compound 222B (114 mg, 0.231 mmol) in 1,2-dichloroethane (2.30 mL), in a dry flask under argon, was cooled to 0° C. with an ice bath. To this solution was added $Et_2Zn$ solution (0.460 mL, 0.462 mmol, 1 M in hexanes), followed by dropwise addition of chloroiodomethane (70.0 μL, 0.926 mmol). The reaction mixture was stirred at 0° C. for 1 h then at rt for 18 h. After judging the reaction to be only 50% complete by TLC and HPLC methods, more $Et_2Zn$ (0.469 mL) and chloroiodomethane (70 μL) were added and the mixture was stirred at rt for 2.5 h. The reaction mixture was quenched with saturated $NH_4Cl$, extracted with t-butyl methyl ether (2×10 mL) and the combined organic layers were dried over $MgSO_4$ and in vacuo. The crude material (174 mg) was dissolved in a mixture of EtOH (5 mL) and conc. HCl (2 mL) and stirred at rt for 1 h. The mixture was then diluted with $H_2O$ and extracted with EtOAc (1×25 mL). The organic layer was washed with brine (1×25 mL), dried and concentrated under reduced pressure. Purification by preparative TLC ($SiO_2$) eluting with 30% aetone/$CHCl_3$ gave compound 822 (9.1 mg, 10%) as a tan solid. HPLC: 90% at 3.15 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 393.03 $[M+H]^+$. Compound 822 represents a racemic mixture of antipodes. The nomenclature and structure shown does not reflect the absolute stereochemistry of the compound.

EXAMPLE 823

[3'aR-(3'aα,4'β,7'β,7'aα)]-Tetrahydro-4',7'-dimethyl-2'-[4-cyano-3(trifluoromethyl)phenyl]-spiro[1,3-dioxolane-2,5'-4,7-epoxy(5H)isoindole]-1',3'(2'H,4'H)-dione (823)

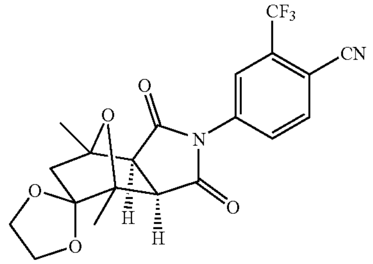

A mixture of compound 796 (44.3 mg, 0.117 mmol), ethylene glycol (0.065 mL, 1.17 mmol) and p-toluenesulphonic acid (2.2 mg, 0.012 mmol) in benzene (3 mL) was refluxed for 18 h. The reaction mixture was then diluted with benzene, washed with 5% $Na_2CO_3$ (1×10 mL), $H_2O$ (1×10 mL), dried ($Na_2SO_4$) and concentrated in vacuo. Purification by silica gel flash chromatography on silica gel eluting with 10% acetone/$CHCl_3$ gave compound 823 (44.5 mg, 90%) as a white solid. HPLC: 99% at 3.11 min (retention time) (YMC S5 ODS column, 4.6×50 mm, 10-90% aqueous methanol over 4 mincontaining 0.2% phosphoric acid, 4 mL/min, monitoring at 220 nm). MS (ESI): m/z 423.01 $[M+H]^+$. Compound 823 represents a racemic mixture of antipodes. The nomenclature and structure shown does not reflect the absolute stereochemistry of the compound.

EXAMPLE 824

[3'aR-(3'aα,4'β,6'β,7'β,7'aα)]-Tetrahydro-6'-hydroxy-4',7'-dimethyl-2'-[4-cyano-3(trifluoromethyl)phenyl]-spiro[1,3-dioxolane-2,5'-4,7-epoxy(5H)isoindole]-1',3'(2'H,4'H)-dione (824B)

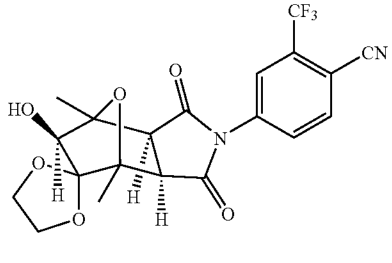

A. (824A)

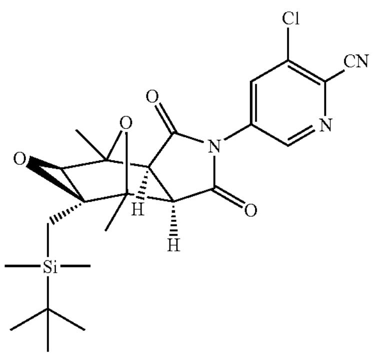

A solution of dimethyldioxirane (32 mL, 1.588 mmol, 0.05 M) was added to a solution of compound 222B (521.6 mg, 1.059 mmol) in acetone (1 mL) at rt. After 2.5 h the reaction was shown to be complete by HPLC and was concentrated under reduced pressure to give 559 mg (quant.) of crude compound 824A as a yellow solid.

B. [3'aR-(3'aα,4'β,6'β,7'β,7'aα)]-Tetrahydro-6'-hydroxy-4',7'-dimethyl-2'-[4-cyano-3(trifluoromethyl) phenyl]-spiro[1,3-dioxolane-2,5'-4,7-epoxy(5H) isoindole]-1',3'(2'H,4'H)-dione (824B)

A mixture of compound 824A (57.5 mg, 0.113 mmol), ethylene glycol (0.100 mL, 1.13 mmol) and p-toluenesulphonic acid (11.0 mg, 0.057 mmol) in benzene (5 mL) was refluxed for 18 h. The reaction mixture was concentrated in vacuo. Purification by silica gel flash chromatography eluting with 30% acetone/$CHCl_3$ gave compound 824B (43 mg, 88%) as a white solid. HPLC: 98% at 2.87 min (retention time) (YMC S5 ODS column, 4.6×50 mm, 10-90% aqueous methanol over 4 min containing 0.2% phosphoric acid, 4 mL/min, monitoring at 220 nm). MS (ESI): m/z 439.07 $[M+H]^+$. Compound 824B represents a racemic mixture of antipodes. The nomenclature and structure shown does not reflect the absolute stereochemistry of the compound.

EXAMPLE 825

[3aR-(3aα,4β,5β,7β,7aα)]-4-[Octahydro-5-hydroxy-4,7-dimethyl-1,3-dioxo-4,7-epoxy-2H-isoindol-2-yl]-3-chloro-2-methylbenzonitrile (825)

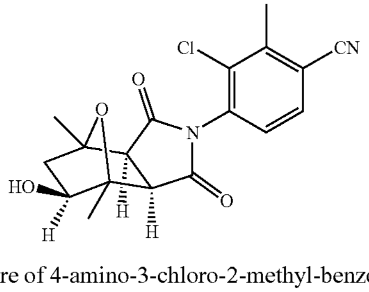

A mixture of 4-amino-3-chloro-2-methyl-benzonitrile (23 mg, 0.14 mmol), compound 752 (44 mg, 0.21 mmol) and 4 Å molecular sieves (100 mg) in DMA (0.2 mL) was heated at 135° C. in a sealed tube for 18 h. Purification by preparative TLC ($SiO_2$) eluting with 30% aetone/$CHCl_3$ gave compound 825 (5.0 mg, 10%) as a yellow film. HPLC: 90% at 2.37 min (retention time) (YMC S5 ODS column 4.6×50 mm eluting with 10-90% aqueous methanol over 4 mincontaining 0.2% phosphoric acid, 4 mL/min, monitoring at 220 nm). MS (ES): m/z 360.97 $[M+H]^+$. The absolute stereochemistry of compound 825 is established by the known stereochemistry of the intermediate compound 752 and the retention of configuration therein. The absolute stereochemistry is as drawn in the above FIGURE and rendered by the nomenclature.

EXAMPLE 826

[3aR-(3aα,4β,5β,7β,7aα)]-4-[Octahydro-5-hydroxy-4,7-dimethyl-1,3-dioxo-4,7-epoxy-2H-isoindol-2-yl]-2-(trifluoromethyl)benzenecarbothioamide (826)

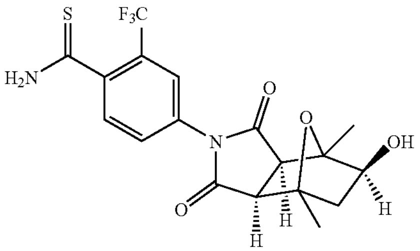

$H_2S$ gas was condensed into a pyrex tube at −78° C. until there was 5 mL of liquid. Compound 471Di (108 mg, 0.284 mmol), $Et_3N$ (50.0 μL, 0.341 mmol) and DMF (1 mL) were added at −78° C. and the tube was sealed. The reaction mixture was allowed to warm to rt with stirring behind a blast shield then heated at 90° C. for 50 mins at which time the color changed to green. The reaction mixture was recooled to −78° C. to check the progress by HPLC. All the starting material was consumed, so the mixture was allowed to warm to rt to remove $H_2S$, diluted with EtOAc and washed with $H_2O$ (4×10 mL). Purification by silica gel flash chromatography eluting with 50% acetone/$CHCl_3$ gave compound 826 (116 mg, 98%) as a white solid. HPLC: 98% at 1.90 min (retention time) (YMC S5 ODS column 4.6×50 mm eluting with 10-90% aqueous methanol over 4 mincontaining 0.2% phosphoric acid, 4 mL/min, monitoring at 220 nm). MS (ES): m/z 415.23 $[M+H]^+$. The absolute stereochemistry of compound 826 is established by the known stereochemistry of the intermediate compound 471Di and the retention of configuration therein. The absolute stereochemistry is as drawn in the above FIGURE and rendered by the nomenclature.

EXAMPLE 827

[3aR-(3aα,4β,5β,7β,7aα)]-2-[3-(trifluoromethyl)-4-(2-thiazolyl)phenyl]-5-(acetoxy)hexahydro-4,7-dimethyl-4,7-epoxy-1H-isoindole-1,3(2H)-dione (827i) & [3aR-(3aα,4β,5β,7β,7aα)]-2-[3-(trifluoromethyl)-4-(2-thiazolyl)phenyl]hexahydro-5-hydroxy-4,7-dimethyl-4,7-epoxy-1H-isoindole-1,3(2H)-dione (827ii)

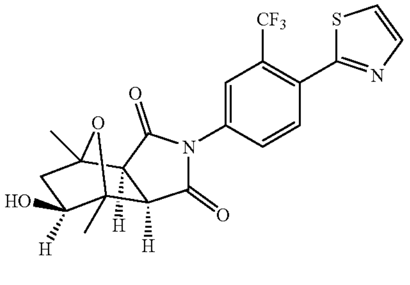

-continued

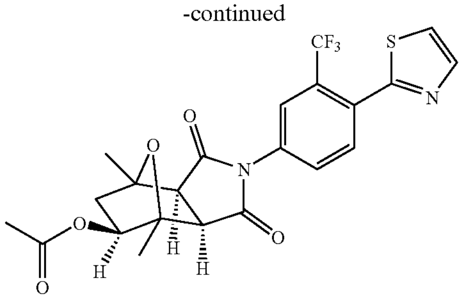

A solution of compound 826 (61.6 mg, 0.149 mmol), bromoacetaldehyde diethyl acetal (30.0 μL, 0.186 mmol) and p-toluene sulphonic acid (1 mg, cat.) in AcOH (1 mL) was heated at 100° C. for 1 h. The reaction mixture was cooled to rt and diluted with $H_2O$. The mixture was extracted with EtOAc (1×10 mL) and the resulting organic layer was washed with $H_2O$ (1×10 mL), saturated $NaHCO_3$ (1×10 mL) and brine (1×10 mL), then dried over $MgSO_4$ and concentrated in vacuo. Purification by preparative TLC ($SiO_2$) eluting with 30% acetone/$CHCl_3$ gave two products both of which were subjected to further purification. The less polar product was purified further by silica gel flash chromatography eluting with 50% EtOAc/hexanes to give compound 827i (30.0 mg, 42%) as a white solid. The more polar product was purified further by silica gel flash chromatography eluting with 10% acetone/$CHCl_3$ to give compound 827ii (4.6 mg, 7%) as a white solid. Compound 827i: HPLC: 99% at 3.12 min (retention time) (YMC S5 ODS column 4.6×50 mm eluting with 10-90% aqueous methanol over 4 mincontaining 0.2% phosphoric acid, 4 mL/min, monitoring at 220 nm). MS (ES): m/z 481.04 $[M+H]^+$. Compound 827ii: HPLC: 99% at 2.62 min (retention time) (YMC S5 ODS column 4.6×50 mm eluting with 10-90% aqueous methanol over 4 mincontaining 0.2% phosphoric acid, 4 mL/min, monitoring at 220 nm). MS (ES): m/z 439.02 $[M+H]^+$. The absolute stereochemistry of compounds 827i & 827ii is established by the known stereochemistry of the intermediate compound 471Di and the retention of configuration there in. The absolute stereochemistry is as drawn in the above FIGURE and rendered by the nomenclature.

EXAMPLE 828

[3aR-(3aα,4β,5β,7β,7aα)]-5-(Octahydro-5-hydroxy-4,7-dimethyl-1,3-dioxo-4,7-epoxy-2H-isoindol-2-yl)-3,4-dimethyl-2-pyridinecarbonitrile (828)

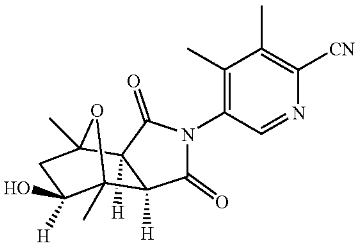

A mixture of 5-amino-3,4-dimethylpyridine-2-carbonitrile (30 mg, 0.20 mmol), compound 752 (65 mg, 0.31 mmol) and 4 Å molecular sieves (200 mg) in DMA (1 mL) was heated at 160° C. in a sealed tube for 18 h. The reaction mixture was filtered, the residue was washed with EtOAc and the combined filtrates were concentrated under reduced pressure. Purification by preparative TLC ($SiO_2$) eluting with 90% EtOAc/hexanes gave compound 828 (42 mg, 40%) as a light pink solid. HPLC: 94% at 1.92 & 2.00 min (retention time-atropisomers) (YMC S5 ODS column 4.6×50 mm eluting with 10-90% aqueous methanol over 4 mincontaining 0.2% phosphoric acid, 4 mL/min, monitoring at 220 nm). MS (ES): m/z 342.21 $[M+H]^+$. The absolute stereochemistry of compound 828 is established by the known stereochemistry of the intermediate compound 752 and the retention of configuration therein. The absolute stereochemistry is as drawn in the above FIGURE and rendered by the nomenclature.

EXAMPLE 829

[3aS-(3aα,4β,5β,7β,7aα)]-5-(Octahydro-5-hydroxy-4,7-dimethyl-1,3-dioxo-4,7-epoxy-2H-isoindol-2-yl)-3,4-dimethyl-2-pyridinecarbonitrile (829)

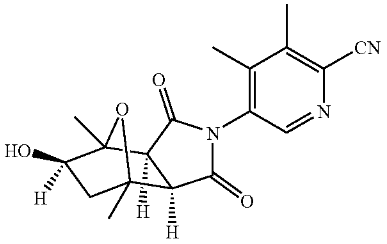

A mixture of 5-amino-3,4-dimethylpyridine-2-carbonitrile (30 mg, 0.20 mmol), compound 751 (65 mg, 0.31 mmol) and 4 Å molecular sieves (200 mg) in DMA (0.25 mL) was heated at 160° C. in a sealed tube for 18 h. The reaction mixture was filtered, the residue was washed with EtOAc and the combined filtrates were washed with $H_2O$ (2×10 mL), brine (1×10 mL), dried ($Na_2SO_4$) and concentrated under reduced pressure. Purification by silica gel flash chromatography on silica gel eluting with 90% EtOAc/hexanes followed by preparative TLC ($SiO_2$) eluting with 90% EtOAc/hexanes gave compound 829 (35 mg, 33%) as a light pink solid. HPLC: 98% at 1.92 & 2.00 min (retention time-atropisomers) (YMC S5 ODS column 4.6×50 mm eluting with 10-90% aqueous methanol over 4 mincontaining 0.2% phosphoric acid, 4 mL/min, monitoring at 220 nm). MS (ES): m/z 342.21 $[M+H]^+$. The absolute stereochemistry of compound 829 is established by the known stereochemistry of the intermediate compound 751 and the retention of configuration therein. The absolute stereochemistry is as drawn in the above FIGURE and rendered by the nomenclature.

EXAMPLE 830

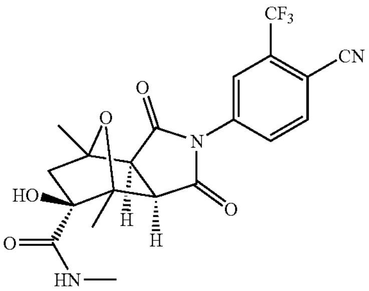

A solution of compound 791B (41 mg; 0.1 mmol), 2.0M methylamine in THF (0.2 mL; 0.4 mmol), 1-hydroxy-7-azabenzotriazole (17 mg; 0.12 mmol), EDCI (40 mg; 0.2 mmol) and diisopropylethylamine (0.075 mL; 0.4 mmol) in 0.5 mL of DMF was heated to 55° C. for 3 hs. After partitioning the reaction mixture between EtOAc (20 mL) and water (20 mL), the organic layer was washed with 1N NaOH (2×20 mL), saturated potassium bisulfate solution (2×20 mL) and brine (20 mL). Drying ($MgSO_4$) and concentration in vacuo gave an residue that was crystallized from ethyl ether to afford compound 830 (30 mg, 71%) as a white solid. HPLC: 97.5% at 1.48 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 422.30 $[M+H]^+$. Compound 830 represents a racemic mixture of antipodes. The nomenclature and structure shown does not reflect the absolute stereochemistry of the compound.

EXAMPLE 831

Name 831

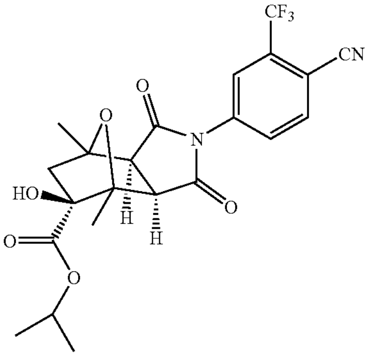

One drop of DMF was added to a solution of compound 792B (60 mg; 0.15 mmol) and oxalyl chloride (0.026 mL; 0.3 mmol) in methylene chloride (1 mL) at rt. After stirring 2 h at rt, the volatiles were removed in vacuo. The residue was dissolved in ~2 mL of isopropanol. After standing 30 min at rt, the volatiles were removed in vacuo and the residue was dissolved in EtOAc:isopropanol, 9:1 (20 mL). The solution was allowed to stand 15 min over decolorizing carbon. Filtration though celite and concentration of the filtrate afforded compound 831 (56 mg, 83%) as a light yellow foam. HPLC: 96.9% at 1.52 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 451.08 $[M+H]^+$. Compound 831 represents a racemic mixture of antipodes. The nomenclature and structure shown does not reflect the absolute stereochemistry of the compound.

EXAMPLE 832

Name 832i & 832ii

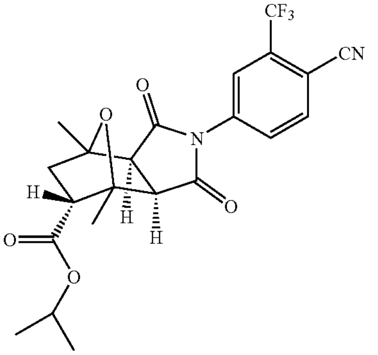

-continued

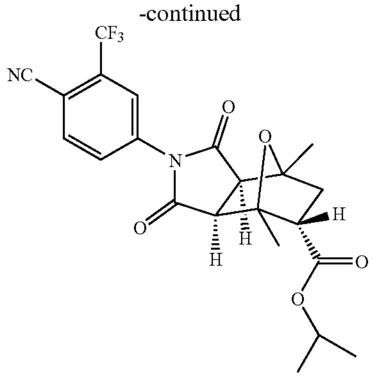

Racemic compound 831 (0.4 g) was separated into its enantiomers by normal phase preparative chiral HPLC (CHIRALPAK OJ 5×50 cm column; eluting with 25% MeOH/EtOH (1:1) in hexane (isocratic) at 50 mL/min) to give 170 mg of faster eluting enantiomer, compound 832i (Chiral HPLC: 8.97 min; CHIRALPAK OJ 4.6×250 mm column; eluting with 20% MeOH/EtOH (1:1) in hexane at 1 mL/min); HPLC: 99% at 1.84 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 451.06 $[M+H]^+$ and 190 mg of the slower eluting enantiomer, compound 832ii (Chiral HPLC: 14.79 min; CHIRALPAK OJ 4.6×250 mm column; eluting with 20% MeOH/EtOH (1:1) in hexane at 1 mL/min); HPLC: 99% at 1.85 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 451.03 $[M+H]^+$. The absolute stereochemistry of compounds 832i & 832ii has not been established. Although each compound represents a single antipode, the nomenclature and structure shown does not reflect the absolute stereochemistry of the compound.

EXAMPLE 833

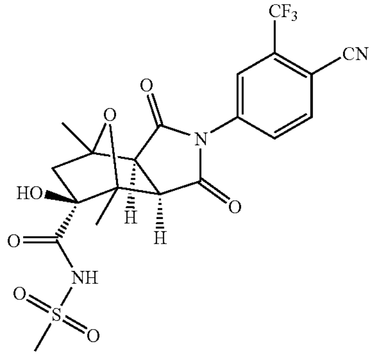

A solution of compound 792B (45 mg; 0.11 mmol), methane sulfonamide (27 mg; 0.28 mmol), 4-dimethylaminopyridine (34 mg; 0.28 mmol) and EDCI (24 mg; 0.12 mmol) in 1 mL of dichloromethane was stirred at rt for 18 hs. After partitioning the reaction mixture between EtOAc (25 mL) and water (25 mL), the organic layer was washed with saturated potassium bisulfate solution (25 mL), water (25 mL) and brine (25 mL). Drying ($MgSO_4$) and concentration gave an residue that was triturated with ethyl ether to afford compound 833 (29 mg, 55%) as an off-white powder. HPLC: 98% at 1.44 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 485.94 [M+H]$^+$. Compound 833 represents a racemic mixture of antipodes. The nomenclature and structure shown does not reflect the absolute stereochemistry of the compound.

EXAMPLE 834

3aα,4β,5α,7β,7aα)-2-(4-Cyano-3-(trifluoromethyl) phenyl)-hexahydro-4,7-dimethyl-1,3-dioxo-4,7-epoxy-1H-isoindole-5-carb (834)

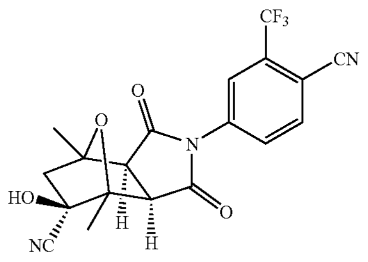

A mixture of compound 792B (100 mg; 0.24 mmol), (methoxycarbonylsulfamoyl)triethylammonium hydroxide, inner salt (125 mg; 0.5 mmol) and triethylamine (0.15 mL; 1 mmol) in 2.5 mL of THF was stirred at rt for 2 hs. After partitioning the reaction mixture between ethyl ether (30 mL) and water (30 mL), the organic layer was washed with saturated potassium bisulfate solution (30 mL), saturated sodium bicarbonate solution (30 mL) and brine (30 mL). Drying ($MgSO_4$) and concentration in vacuo afforded compound 834 (80 mg, 97%) as a white powder. HPLC: 99% at 1.51 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 390.03 [M+H]$^+$. Compound 834 represents a racemic mixture of antipodes. The nomenclature and structure shown does not reflect the absolute stereochemistry of the compound.

EXAMPLE 835

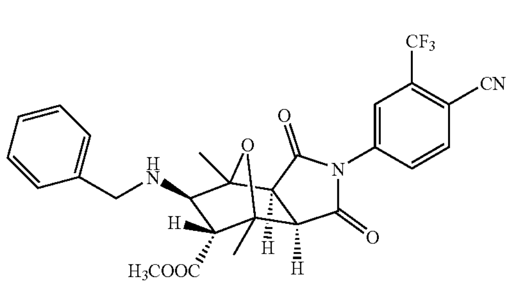

A mixture of compound 793A (121 mg; 0.29 mmol) and benzylamine (0.032 mL; 0.29 mmol) in 0.6 mL of THF was stirred at rt for 18 hs. After adding ~5 mL of hexane, the resulting suspension was filtered and dried to afford compound 835 (135 mg, 89%) as a white powder. HPLC: 99% at 1.42 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 528.39 [M+H]$^+$. Compound 835 represents a racemic mixture of antipodes. The nomenclature and structure shown does not reflect the absolute stereochemistry of the compound.

EXAMPLE 836

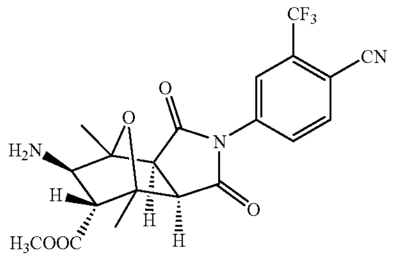

A mixture of compound 793A (190 mg; 0.45 mmol) and 2.0M ammonia in THF (0.3 mL; 0.6 mmol) in 0.7 mL of THF was stirred at rt. After 1 h, an additional amount of 2.0M ammonia in THF (0.7 mL; 1.4 mmol) was added and the reaction mixture was stirred at rt for 18 hs. The volatiles were removed in vacuo and the residue was triturated from hexane to afford compound 835 (145 mg, 74%) as an off-white powder. HPLC: 95.1% at 1.28 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 438.26 [M+H]$^+$. Compound 836 represents a racemic mixture of antipodes. The nomenclature and structure shown does not reflect the absolute stereochemistry of the compound.

EXAMPLE 837

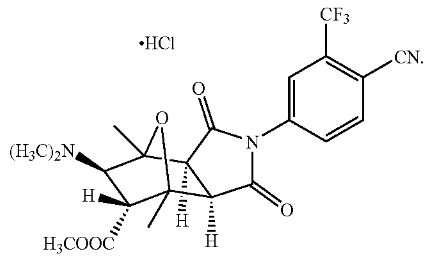

A mixture of compound 793A (42 mg; 0.1 mmol) and 2.0M dimethylamine in MeOH (0.1 mL; 0.1 mmol) in 0.5 mL of THF was stirred at rt for 18 h. The volatiles were removed in vacuo and the residue filtered though a 0.5×5 cm plug of silica gel, eluted with 50 mL of EtOAc. After concentration of the filtrate, the light yellow residue was dissolved in ethyl ether and 0.3 mL of 1M HCl in ethyl ether was added. The volatiles were removed in vacuo and the solid residue was triturated from ethyl ether to afford compound 837 (25 mg, 50%) as a cream colored powder. HPLC: 99% at 1.31 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 466.33 [M+H]$^+$. Compound 837 represents a racemic mixture of antipodes. The nomenclature and structure shown does not reflect the absolute stereochemistry of the compound.

EXAMPLE 838

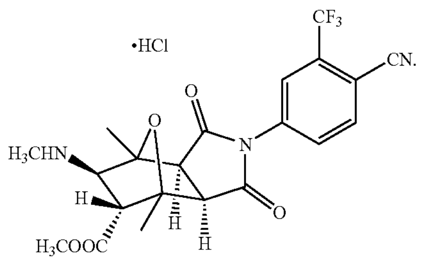

A mixture of compound 793A (42 mg; 0.1 mmol) and 2.0M dimethylamine in THF (0.1 mL; 0.1 mmol) in 0.5 mL of THF was stirred at rt for 18 h. The volatiles were removed in vacuo and the residue filtered though a 0.5×5 cm plug of silica gel, eluted with ~50 mL of EtOAc. After concentration of the filtrate, the yellow residue was dissolved in ethyl ether and 0.3 mL of 1M HCl in ethyl ether was added. The volatiles were removed in vacuo and the solid residue was triturated from ethyl ether to afford compound 838 (22 mg, 46%) as a yellow powder. HPLC: 99% at 1.28 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 452.31 $[M+H]^+$; Compound 838 represents a racemic mixture of antipodes. The nomenclature and structure shown does not reflect the absolute stereochemistry of the compound.

EXAMPLE 839

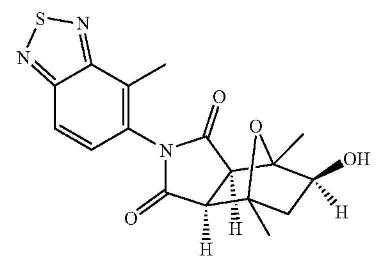

A. 4-Methyl-benzo[1,2,5]thiadiazole (839A)

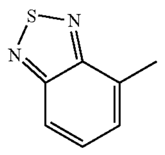

To a solution of 2,3-diaminotoluene (5.0 g, 40.9 mmol) in pyridine (40 mL) at 0° C. was added thionyl chloride (7.0 mL, 98.2 mmol) dropwise. The reaction mixture was stirred at 0° C. for 30 mins, then water (200 mL) was added. The solution was extracted with dicholomethane (2×250 mL). The combined organic layers were washed with brine, dried over $Na_2SO_4$ and concentrated in vacuo to give compound 839A (5.57 g) as a dark brown liquid.

B. 4-Methyl-5-nitro-benzo[1,2,5]thiadiazole (839B)

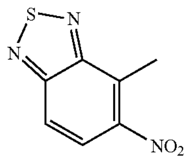

To a solution of 4-methyl-benzo[1,2,5]thiadiazole (5.57 g, 37.1 mmol) in conc. $H_2SO_4$ (14.5 mL) at 0° C. was slowly added $HNO_3/H_2SO_4$ (3.25 mL/4.25 mL). The reaction mixture was stirred at 0° C. for 20 min and then at rt for 30 min and then was poured into iced water (200 mL). The resulting precipitate was isolated by filtration, rinsed with water and purified by silica gel flash chromatography, eluting with $CHCl_3$ to give compound 839B (1.5 g) as a yellow solid and 4-methyl-7-nitrobenzo[1,2,5]thiadiazole (2.0 g) as a yellow solid.

C. 4-Methyl-benzo[1,2,5]thiadiazol-5-ylamine (839C)

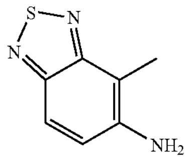

4-Methyl-5-nitro-benzo[1,2,5]thiadiazole (1.4 g, 7.18 mmol) was dissolved in THF (10 mL), acetic acid (1 mL) and water (21 mL) and iron powder (1.4 g, 25.0 mmol, 325 Mesh) was added. The reaction mixture was heated at 80° C. for 1.5 h, cooled to rt and filtered though celite to remove the iron powder. The solution was extracted with $CHCl_3$ (2×250 mL). The combined organic layers were washed with brine, dried over $Na_2SO_4$ and concentrated in vacuo to give compound 839C (1.1 g) as a light brown solid.

D. (839D)

4-Methyl-benzo[1,2,5]thiadiazol-5-ylamine (0.10 g, 0.610 mmol), 4A molecular sieve (0.46 g) and compound 752 (0.128 g, 0.610 mmol) were dissolved in DMA (0.60 mL) in a sealed tube. The reaction mixture was heated at 190° C. for 1 h and then was cooled to rt. The solution was filtered though celite to remove the sieves and then the filtrate was washed with saturated $NH_4Cl$ (10 mL) followed by brine (10 mL). The organic layer was then dried over $Na_2SO_4$ and concentrated in vacuo to yield a yellow oil. The resulting material was purified by preparative TLC ($SiO_2$), eluting with 20% acetone in $CHCl_3$ to give compound 839D (70 mg) as a light yellow solid. HPLC: 98% at 2.87 min (retention time) (YMC S-50DS-A column, 4.6×50 mm, eluting with 10-90% aqueous methanol over 4 mincontaining 0.2% phosphoric acid, 4 mL/min, monitoring at 220 nm). MS (ESI): m/z 360.19 [M+H]. The absolute stereochemistry of compound 752 is established by the known stereochemistry of the intermediate compound 839D and the retention of configuration therein. The absolute stereochemistry is as drawn in the above FIGURE and rendered by the nomenclature.

EXAMPLE 840

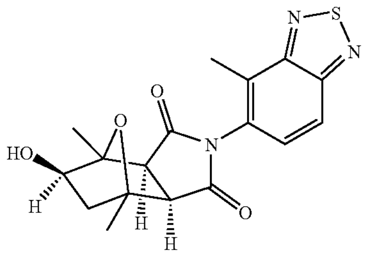

4-Methyl-benzo[1,2,5]thiadiazol-5-ylamine (0.078 g, 0.47 mmol), 4 Å molecular sieve (0.46 g) and compound 751 (0.100 g, 0.47 mmol) were dissolved in DMA (0.50 mL) in a sealed tube. The reaction mixture was heated at 190° C. for 1 h and then was cooled to rt. The solution was filtered though celite to remove the sieves and then the filtrate was washed with saturated $NH_4Cl$ (10 mL), followed by brine (10 mL). The organic layer was then dried over $Na_2SO_4$ and concentrated in vacuo to yield a yellow oil. The resulting material was purified by preparative TLC ($SiO_2$), eluting with 20% acetone in $CHCl_3$ to give compound 840 (20 mg) as a light yellow solid. HPLC: 97% at 2.87 min (retention time) (YMC S-50DS-A column, 4.6×50 mm, eluting with 10-90% aqueous methanol over 4 mincontaining 0.2% phosphoric acid, 4 mL/min, monitoring at 220 nm). MS (ESI): m/z 360.30 [M+H]. The absolute stereochemistry of compound 840 is established by the known stereochemistry of the intermediate compound 751 and the retention of configuration therein. The absolute stereochemistry is as drawn in the above FIGURE and rendered by the nomenclature.

EXAMPLE 841

[3aR-(3aα,4β,5β,7β,7aα)]-4-(Octahydro-5-hydroxy-4,7-dimethyl-1,3-dioxo-4,7-epoxy-2H-isoindol-2-yl)-3-methyl-2-(trifluoromethyl)benzonitrile (841E)

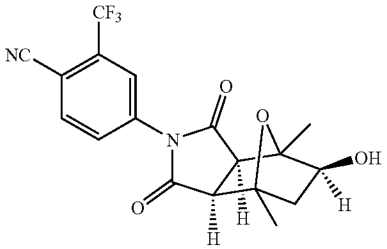

A. N-(4-Chloro-3-trifluoromethylphenyl)-2,2-dimethylpropionamide (841A)

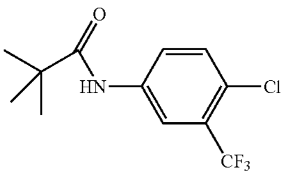

To a solution of commercially available 4-chloro-3-(trifluoromethyl)aniline (15.0 g, 76.7 mmol) in anhydrous THF (200 mL) cooled to 0-5° C. was added triethylamine (11.7 mL, 84.4 mmol) followed by pivaloyl chloride (10.4 mL, 84.4 mmol) over 30 min. The ice bath was removed and the mixture stirred at rt for 1 h. The mixture was diluted with ether and filtered. The filtrate was washed with water (2×) and brine, dried over $MgSO_4$, filtered and concentrated. The residue was triturated with hexanes and the solid was filtered and dried in vacuo to afford compound 841A (20.4 g, 95%). MS (ES): m/z=280 $[M+1]^+$.

B. N-(4-Chloro-2-methyl-3-trifluoromethylphenyl)-2,2-dimethylpropionamide (841B)

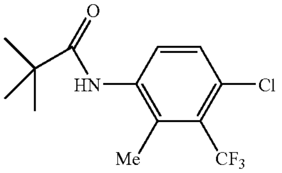

To a solution of N-(4-chloro-3-trifluoromethylphenyl)-2,2-dimethylpropionamide (2.29 g, 8.19 mmol) in anhydrous THF (25 mL) cooled to 0-5° C. was added a solution of 1.6 M n-butyllithium in hexanes (12.3 mL, 19.7 mmol), added slowly so that the reaction temperature was maintained below 5° C. The solution was stirred at 0-5° C. for 1.5 h. A solution of iodomethane (0.56 mL, 9.01 mmol) in petroleum ether (2 mL) was added over 20 min while maintaining the temperature below 5° C. The suspension was stirred at 0-5° C. for 1 h and diluted with water and ether. The aqueous layer was extracted with ether and the combined organic layers were washed with brine, dried over $MgSO_4$, filtered and concentrated in vacuo. The residue was chromatographed (silica gel), eluting with $CH_2Cl_2$ to afford compound 841B (1.60 g, 67%). MS (ES): m/z=294 $[M+1]^+$.

C. N-(4-Cyano-2-methyl-3-trifluoromethylphenyl)-2,2-dimethylpropionamide (841C)

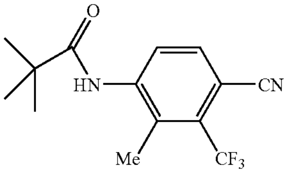

A suspension of N-(4-chloro-2-methyl-3-trifluoromethylphenyl)-2,2-dimethylpropionamide (8.36 g, 28.5 mmol) and CuCN (4.33 g, 65.5 mmol) in anhydrous N-methylpyrrolidinone (85 mL) was refluxed for 38 h. After cooling to rt, the suspension was poured into ice water with stirring. The resulting solid was filtered, washed with water and dried to yield an 85:15 mixture (7.55 g) of compound 841C and 841D. The resulting mixture was used in the next step.

D. 4-Amino-3-methyl-2-trifluoromethylbenzonitrile (841D)

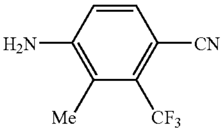

A solution of the mixed product from example 841C (7.53 g, 26.5 mmol) was dissolved in 120 mL of concentrated HCl/EtOH (1:1) and was refluxed for 14 h. After cooling to rt, the solution was concentrated in vacuo. The resulting residue was dissolved in EtOAc, washed with saturated aqueous $NaHCO_3$ (2×) and brine (1×), dried over $MgSO_4$, filtered and concentrated in vacuo. The residue was chromatographed (silica gel), eluting with chloroform/methanol (98:2) to furnish compound 841D (4.62 g, 87%). MS (ES): m/z=201 $[M+1]^+$.

E. [3aR-(3aα,4β,5β,7β,7aα)]-4-(Octahydro-5-hydroxy-4,7-dimethyl-1,3-dioxo-4,7-epoxy-2H-isoindol-2-yl)-3-methyl-2-(trifluoromethyl)benzonitrile (841E)

4-Amino-3-methyl-2-trifluoromethylbenzonitrile (0.051 g, 0.25 mmol), 4 Å molecular sieve (0.20 g) and compound 752 (0.059 g, 0.28 mmol) were dissolved in DMA (0.30 mL) in a sealed tube. The reaction mixture was heated at 175° C. for 30 min and then was cooled to rt. The solution was filtered though celite to remove the sieves and then the filtrate was washed with saturated $NH_4Cl$ (10 mL), followed by brine (10 mL). The organic layer was then dried over $Na_2SO_4$ and concentrated in vacuo to yield a yellow oil. The resulting material was purified by preparative TLC ($SiO_2$), eluting with 25% acetone in $CHCl_3$ to give compound 841E (40 mg) as a light brown solid. HPLC: 97% at 3.18 min (retention time) (YMC S-50DS-A column, 4.6×50 mm, eluting with 10-90% aqueous methanol over 4 mincontaining 0.2% phosphoric acid, 4 mL/min, monitoring at 220 nm). MS (ESI): m/z 393.18 $[M-H]^-$. The absolute stereochemistry of compound 841E is established by the known stereochemistry of the intermediate compound 752 and the retention of configuration therein. The absolute stereochemistry is as drawn in the above FIGURE and rendered by the nomenclature.

EXAMPLE 842

[3aS-(3aα,4β,5β,7β,7aα)]-5-(Octahydro-5-hydroxy-4,7-dimethyl-1,3-dioxo-4,7-epoxy-2H-isoindol-2-yl)-3-chloro-2-pyridinecarbonitrile (842)

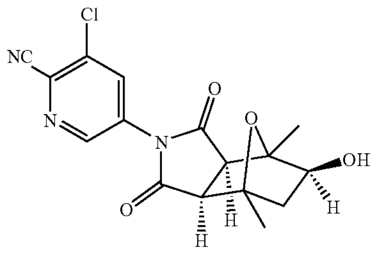

Compound 752 (500 mg, 2.36 mmol), 4 Å mol sieves (1.5 g), 5-amino-3-chloro-2-cyanopyridine (357 mg, 2.34 mmol) and DMA (2 mL) were combined in a sealed tube. The mixture was heated in a pre-heated oil-bath at 170° C. for 25 min, cooled and the sieve was removed by filtration, eluting with EtOAc. The organics were washed 3× with water, followed by brine. The resulting organics were dried over $MgSO_4$ and concentrated in vacuo. The residue was pre-adsorbed on Celite and purified by silica gel flash chromatography with 0 to 40% acetone in $CH_2Cl_2$ to give Compound 842 (480 mg, 63%) as a tan solid. HPLC: 97% at 2.66 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 348.30 $[M+H]^+$. The absolute stereochemistry of compound 842 is established by the known stereochemistry of the intermediate compound 752 and the retention of configuration there in. The absolute stereochemistry is as drawn in the above FIGURE and rendered by the nomenclature.

EXAMPLE 843

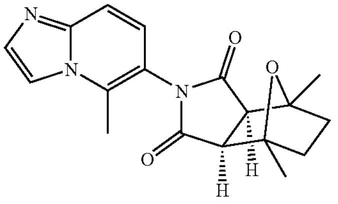

A. 5-Methyl-imidazo[1,2-a]pyridin-6-ylamine (843A)

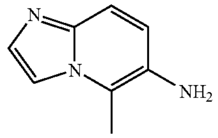

2-Methyl-3-nitro-6-amino pyridine (63 mg, 0.41 mmol) was suspended in 1.3 mL EtOH containing 0.3 mL conc. HCl. 2-Bromo-1,1-dimethoxy-ethane (73 μL, 0.62 mmol) was added and the resulting mixture was refluxed for 8 h, at which point additional 2-bromo-1,1-dimethoxy-ethane (0.1 mL, 0.85 mmol) was added. The mixture was stirred at reflux overnight, cooled and diluted with $CH_2Cl_2$. The organics were washed with sat. $NaHCO_3$ solution, dried over $MgSO_4$ and concentrated in vacuo. The residue was dissolved in 4 mL AcOH/EtOAc (1:1) and the resulting solution was heated to 75° C. Iron powder (46 mg, 0.82 mmol, 325 Mesh) was added and the mixture was stirred for 20 min. Additional iron powder (46 mg, 0.82 mmol, 325 Mesh) was added and stirring was continued for 30 min. The mixture was cooled to room temperature and concentrated. The resulting residue was purified by silica gel silica gel flash chromatography with 20% MeOH in $CH_2Cl_2$ to give compound 843A (51 mg, 85%) as a yellow-brown solid. HPLC: 72% at 0.18 min and 28% at 0.27 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 147.85 $[M+H]^+$.

C. (843B)

In a sealed tube was placed 5-methyl-imidazo[1,2-a]pyridin-6-ylamine (46 mg, 0.31 mmol), compound 20A (92 mg, 0.47 mmol), 250 mg 4 Å mol sieves and 0.3 mL DMA. The tube was sealed and heated in a pre-heated oil-bath to 170° C. for 30 min. The mixture was cooled and filtered eluting with EtOAc. The filtrate was washed 3× with water followed by brine. The organic layer was dried over $MgSO_4$, concentrated in vacuo and purified by preparative TLC ($SiO_2$) with 50% acetone in $CHCl_3$ to give Compound 843B (32 mg, 32%) as a pale yellow solid. HPLC: 99% at 1.47 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 326.39 $[M+H]^+$.

EXAMPLE 844

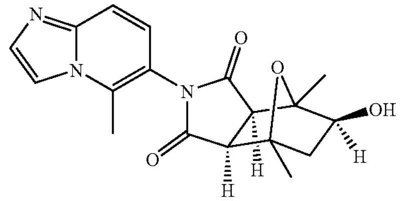

In a sealed tube were combined 5-methyl-imidazo[1,2-a]pyridin-6-ylamine (50 mg, 0.34 mmol), compound 752 (108 mg, 0.51 mmol), $MgSO_4$ (102 mg, 0.85 mmol), $Et_3N$ (0.24 mL, 1.7 mmol) and 0.3 mL 1,2-dimethoxy-ethane. The tube was sealed and heated to 135° C. for 14 h. The mixture was cooled to rt, filtered to remove the sieve, eluting with MeOH, and concentrated in vacuo. Purification of the resulting residue by silica gel flash chromatography with 0 to 10% MeOH in $CH_2Cl_2$ afforded compound 844 (86 mg, 74%) as a tan solid. HPLC: 100% at 0.85 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 342.20 $[M+H]^+$. The absolute stereochemistry of compound 844 is established by the known stereochemistry of the intermediate compound 752 and the retention of configuration therein. The absolute stereochemistry is as drawn in the above FIGURE and rendered by the nomenclature.

EXAMPLE 845

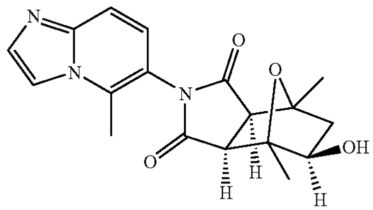

According to the procedure of Example 843, 5-methyl-imidazo[1,2-a]pyridin-6-ylamine (50 mg, 0.34 mmol), compound 751 (108 mg, 0.51 mmol), $MgSO_4$ (102 mg, 0.85 mmol), $Et_3N$ (0.24 mL, 1.7 mmol) were reacted in 0.3 mL 1,2-dimethoxyethane. Purification gave compound 845 (79 mg, 68%) as a tan solid. HPLC: 100% at 0.85 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 342.20 $[M+H]^+$. The absolute stereochemistry of compound 845 is established by the known stereochemistry of the intermediate compound 751 and the retention of configuration therein. The absolute stereochemistry is as drawn in the above FIGURE and rendered by the nomenclature.

EXAMPLE 846

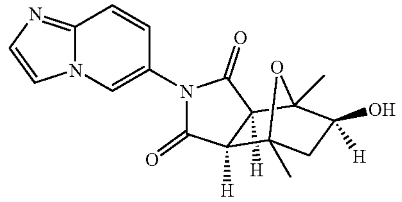

A. Imidazo[1,2-a]pyridin-6-ylamine (846A)

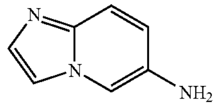

2-Amino-5-nitro pyridine was suspended in a 40 mL solution of EtOH/conc. HCl (3:1). To this suspension was added 2-bromo-1,1-dimethoxy-ethane (6.37 mL, 53.91 mmol) and the resulting mixture was heated to reflux for 8 h, after which additional 2-bromo-1,1-dimethoxy-ethane (6.37 mL, 53.91 mmol) was added. The mixture was heated at reflux overnight, cooled to rt and placed in a refrigerator for 24 h. The precipitates were collected, washed with ice-cold EtOH, air-dried and converted to the free-based using standard procedures to afford a yellow solid. The resulting crude yellow solid, (404 mg) was dissolved in 150 mL THF/MeOH (1:1) and the resulting solution was hydrogenated for 4 h over Pd/C (250 mg, 10%) using a hydrogen balloon. The mixture was filtered though Celite eluting with THF/MeOH (1:1) and the filtrate was concentrated. Purification was achieved using silica gel flash chromatography with 20% MeOH in $CH_2Cl_2$ to give Compound 846A (241 mg, 75%) as a colorless oil which turns dark upon standing.

B. (846B)

In a sealed tube were combined imidazo[1,2-a]pyridin-6-yl amine (64 mg, 0.48 mmol), compound 752 (148 mg, 0.71 mmol), $MgSO_4$ (146 mg, 1.21 mmol), $Et_3N$ (0.34 mL, 2.40 mmol) and 0.4 mL 1,2-dimethoxy-ethane. The tube was sealed and heated to 135° C. for 14 h. The mixture was cooled, filtered though Celite eluting with MeOH and concentrated. Purification was achieved by silica gel flash chromatography with 10% MeOH in $CH_2Cl_2$ to give compound 846B (107 mg, 64%) as a pale yellow solid. HPLC: 40% at 0.19 min and 60% at 0.38 min (retention time) (YMC S5 ODS-A column 4.6×50 mm Ballistic, 10-90% aqueous methanol over 4 minutes containing 0.2% $H_3PO_4$, 4 mL/min, monitoring at 220 mm). MS (ES): m/z 328.16 $[M+H]^+$. The absolute stereochemistry of compound 846B is established by the known stereochemistry of the intermediate compound 752 and the retention of configuration therein. The absolute stereochemistry is as drawn in the above FIGURE and rendered by the nomenclature.

EXAMPLE 847

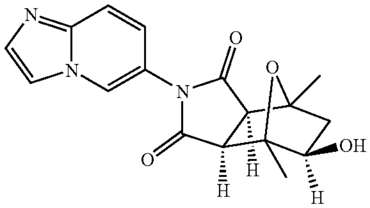

According to the procedure given in Example 846, imidazo [1,2-a]pyridin-6-ylamine (50 mg, 0.38 mmol), compound 751 (119 mg, 0.56 mmol), $MgSO_4$ (114 mg, 0.95 mmol), $Et_3N$ (0.26 mL, 1.9 mmol) were reacted in 0.35 mL 1,2-dimethoxyethane. Purification gave compound 847 (87 mg, 70%) as a white solid. HPLC: 32% at 0.20 min and 68% at 0.37 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 328.12 $[M+H]^+$. The absolute stereochemistry of compound 847 is established by the known stereochemistry of the intermediate compound 751 and the retention of configuration therein. The absolute stereochemistry is as drawn in the above FIGURE and rendered by the nomenclature.

EXAMPLE 848

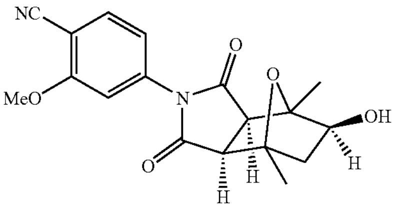

A. 4-Amino-2-methoxy-benzonitrile (848A)

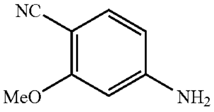

2-Methoxy-4-nitro-benzonitrile (500 mg, 2.81 mmol) was suspended into 4 mL AcOH/EtOAc (1:1) and the resulting mixture was heated to 75° C. to give a clear solution. Fe powder (313 mg, 5.61 mmol, 325 Mesh) was added and the mixture was stirred for 30 min, after which additional Fe powder (313 mg, 5.61 mmol, 325 Mesh) was introduced. The mixture was stirred at 75° C. for an additional 30 min, and then cooled to rt and filtered, eluting with EtOAc. The filtrate was concentrated in vacuo, re-dissolved in EtOAc, filtered (eluting with EtOAc) and concentrated. Purification was achieved by silica gel flash chromatography with 0 to 10% MeOH in $CH_2Cl_2$ to give compound 848A as a tan solid.

B. (848B)

In a sealed tube were combined 4-amino-2-methoxy-benzonitrile (40 mg, 0.27 mmol), compound 752 (86 mg, 0.41 mmol), $MgSO_4$ (81 mg, 0.68 mmol), $Et_3N$ (0.19 mL, 1.4 mmol) and 0.25 mL 1,2-dimethoxy-ethane. The tube was closed and heated to 135° C. for 14 h. The mixture was cooled to rt, filtered (eluting with MeOH) and concentrated in vacuo. Purification of the resulting residue by silica gel flash chromatography using 0 to 100% EtOAc in $CH_2Cl_2$ to afforded compound 848B (36 mg, 39%) as an off-white solid. HPLC: 100% at 2.36 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 341.23 $[M-H]^-$. The absolute stereochemistry of compound 848B is established by the known stereochemistry of the intermediate compound 752 and the retention of configuration therein. The absolute stereochemistry is as drawn in the above FIGURE and rendered by the nomenclature.

EXAMPLE 849

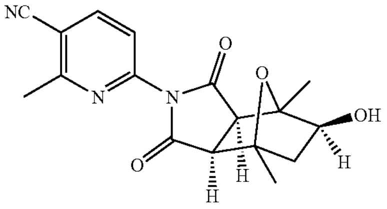

A. 6-Amino-2-methyl-nicotinonitrile (849A)

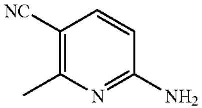

A mixture of 6-amino-2-methyl-nicotinonitrile (500 mg, 2.67 mmol), CuCN (478 mg, 5.34 mmol) and DMA (2 mL) was stirred under nitrogen for 20 h at 170° C. The reaction mixture was cooled and added to 50 mL of a 20% aqueous solution of ethane-1,2-diamine. The layers were separated and the aqueous layer was extracted 3× with EtOAc. The combined organics were washed with water followed by brine, dried over $MgSO_4$ and concentrated in vacuo. Purification by silica gel flash chromatography with 0 to 100% EtOAc in $CH_2Cl_2$ gave compound 849A (199 mg, 56%) as a white solid.

B. (849B)

In a sealed tube was placed 6-amino-2-methyl-nicotinonitrile (50 mg, 0.38 mmol), compound 752 (119 mg, 0.56 mmol), $MgSO_4$ (114 mg, 0.95 mmol), $Et_3N$ (0.26 mL, 1.9 mmol) and 0.3 mL 1,2-dimethoxy-ethane. The tube was sealed and heated to 135° C. for 14 h. The mixture was cooled to rt, filtered (eluting with MeOH) and concentrated in vacuo. The filtrate was concentrated and purified by silica gel flash chromatography with 0 to 100% EtOAc in $CH_2Cl_2$ to give compound 849B (36 mg, 29%) as a white solid. HPLC: 100% at 1.99 min (retention time) (YMC S5 ODSA column 4.6×50 mm Ballistic, 10-90% aqueous methanol over 4 mincontaining 0.2% $H_3PO_4$, 4 mL/min, monitoring at 220 nm). MS (ES): m/z 328.04 $[M+H]^+$. The absolute stereochemistry of compound 849B is established by the known stereochemistry of the intermediate compound 752 and the retention of configuration therein. The absolute stereochemistry is as drawn in the above FIGURE and rendered by the nomenclature.

EXAMPLE 850

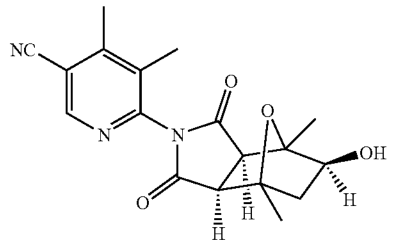

A. 6-Amino-4,5-dimethyl-nicotinonitrile (850A)

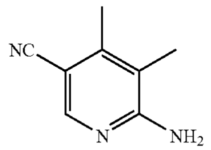

A mixture of 5-bromo-3,4-dimethyl-pyridin-2-ylamine (500 mg, 2.49 mmol), CuCN (445 mg, 4.97 mmol) and DMA (3.5 mL) was stirred under nitrogen for 20 h at 170° C. The reaction mixture was cooled and added to 50 mL of a 20% aqueous solution of ethane-1,2-diamine. The layers were separated and the aqueous layer was extracted 3× with EtOAc. The combined organics were washed with water, followed by brine and dried over $MgSO_4$. Concentration in vacuo afforded compound 850A (362 mg, 99%) as a white solid.

B. (850B)

In a sealed tube were combined 6-amino-4,5-dimethyl-nicotinonitrile (50 mg, 0.34 mmol), compound 752 (108 mg, 0.50 mmol), $MgSO_4$ (102 mg, 0.85 mmol), $Et_3N$ (0.24 mL, 1.7 mmol) and 0.3 mL 1,2-dimethoxy-ethane. The tube was closed and heated to 135° C. for 14 h. The mixture was cooled to rt, filtered (eluting with MeOH) and concentrated in vacuo. Purification of the resulting residue by silica gel flash chromatography with 0 to 100% EtOAc in $CH_2Cl_2$ afforded compound 850B (68 mg, 59%) as an off-white solid. HPLC: 10% at 2.15 min and 82% at 2.31 min (retention time) (YMC S5 ODS-A column 4.6x50 mm Ballistic, 10-90% aqueous methanol over 4 mincontaining 0.2% $H_3PO_4$, 4 mL/min, monitoring at 220 nm). MS (ES): m/z 342.06 $[M+H]^+$. The absolute stereochemistry of compound 850B is established by the known stereochemistry of the intermediate compound 752 and the retention of configuration therein. The absolute stereochemistry is as drawn in the above FIGURE and rendered by the nomenclature.

EXAMPLE 851

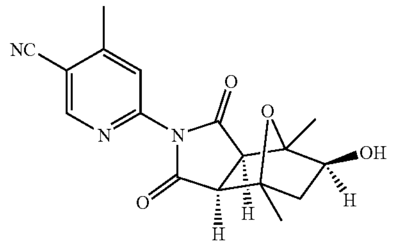

A. 6-Amino-4-methyl-nicotinonitrile (851A)

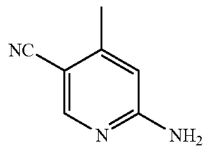

A mixture of 5-bromo-4-methyl-pyridin-2-ylamine (500 mg, 2.67 mmol), CuCN (478 mg, 5.34 mmol) and DMA (2 mL) was stirred under nitrogen for 20 h at 170° C. The reaction mixture was cooled and added to 50 mL of a 20% aqueous solution of ethane-1,2-diamine. The layers were separated and the aqueous layer was extracted 3× with EtOAc. The combined organics were washed with water followed by brine and dried over $MgSO_4$. Concentration in vacuo afforded compound 851A (309 mg, 87%) as a white solid.

B. (851B)

In a sealed tube was placed 6-amino-4-methyl-nicotinonitrile (50 mg, 0.38 mmol), compound 752 (119 mg, 0.56 mmol), $MgSO_4$ (114 mg, 0.95 mmol), $Et_3N$ (0.26 mL, 1.9 mmol) and 0.3 mL 1,2-dimethoxy-ethane. The tube was sealed and heated to 135° C. for 14 h. The mixture was allowed to cool to rt and filtered, eluting with MeOH. The filtrate was concentrated in vacuo and purified by silica gel flash chromatography with 0 to 100% EtOAc in $CH_2Cl_2$ to give compound 851B (67 mg, 54%) as a white solid. HPLC: 100% at 1.95 min (retention time) (YMC S5 ODS-A column 4.6x50 mm Ballistic, 10-90% aqueous methanol over 4 min-containing 0.2% $H_3PO_4$, 4 mL/min, monitoring at 220 nm). MS (ES): m/z 328.04 $[M+H]^+$. The absolute stereochemistry of compound 851B is established by the known stereochemistry of the intermediate compound 752 and the retention of configuration therein. The absolute stereochemistry is as drawn in the above FIGURE and rendered by the nomenclature.

EXAMPLE 852

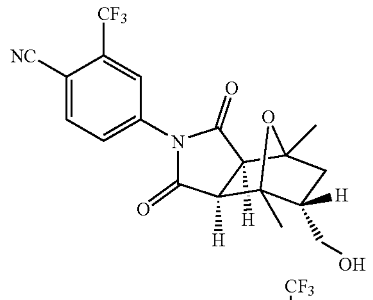

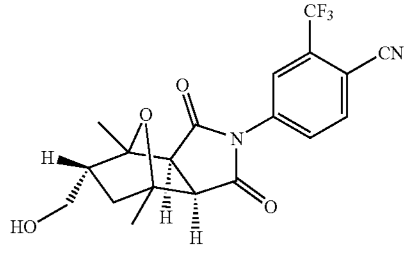

A. tert-Butyl-(2,5-dimethyl-furan-3-ylmethoxy)-dimethyl-silane (852A)

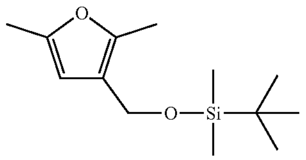

In a dry 100 mL round-bottom flask was prepared a solution of methyl 2,5-dimethyl-3-furoate (2.00 g, 13.0 mmol) in anhydrous $Et_2O$ (10 mL) under an inert atmosphere. To this solution was added dropwise a 1.0 M solution of $LiAlH_4$ in $Et_2O$ (13 mL, 13 mmol) at 0° C. The resulting suspension was stirred at 0° C. for 30 min and was then allowed to warm to rt, where it was kept for 4 h. The reaction was quenched by the careful addition of solid $Na_2SO_4.10H_2O$ (excess) and Celite (excess). To facilitate stirring, $Et_2O$ was added as necessary. The resulting mixture was stirred overnight, filtered and carefully concentrated in vacuo to yield the volatile alcohol which was dissolved in anhydrous DMF (5 mL) under an inert atmosphere. To this solution was added imidazole (1.32 g, 19.5 mmol) and TBSCl (2.05 g, 13.6 mmol) and the mixture was stirred for 6 h. The reaction mixture was diluted with EtOAc and water was added. The layers were separated and the organic layer was washed several times with water. The organics were dried over $MgSO_4$, concentrated in vacuo and purified by silica gel flash chromatography with 0 to 50% EtOAc in hexanes yielding compound 852A (3.08 g, 99%) as a colorless oil.

B. (852B)

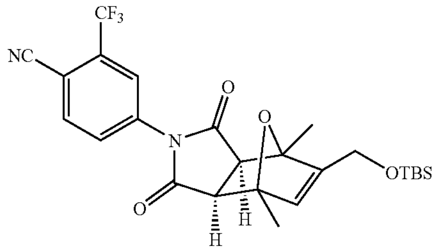

In a sealed-tube were combined tert-butyl-(2,5-dimethyl-furan-3-ylmethoxy)dimethyl-silane (2.60 g, 10.8 mmol), 4-(2,5-dihydro-2,5-2,5-dioxo-1H-pyrrol-1-yl)-2-trifluoromethylbenzonitrile (1.44 g, 5.41 g) and THF (1 mL). The tube was sealed and quickly heated to 95° C. to yield an almost clear solution. The mixture was then allowed to cool to rt and was stirred at rt overnight. Purification was achieved by silica gel flash chromatography with 0 to 100% EtOAc in hexanes to give compound 852B (2.37 g, 86%) as a white solid.

C. (852C)

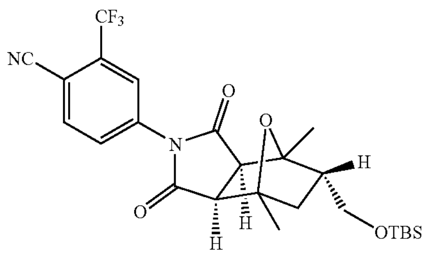

A solution Compound 852B of (1.4 g, 2.8 mmol) in EtOAc (50 mL) was hydrogenated over Pd/C (10%, 800 mg) for 6 h using a hydrogen balloon. The mixture was filtered, eluting with EtOAc, and concentrated in vacuo. Purification was achieved using silica gel flash chromatography with 0 to 100% EtOAc in hexanes to afford Compound 852C (0.9 g, 64%) as a white foam.

D

Compound 852C (0.9 g, 1.8 mmol) was dissolved in 7 mL EtOH containing 2% conc. HCl at rt and the resulting mixture was stirred for 2 h. The reaction mixture was carefully poured into sat. $NaHCO_3$ solution and the aqueous layer was extracted twice with EtOAc. The combined organics were dried over $MgSO_4$, concentrated in vacuo and purified by silica gel flash chromatography with 0 to 100% EtOAc in $CH_2Cl_2$ to afford a racemic mixture of compound 852Di & 852Dii (0.7 g, 100%) as a white solid. The racemic material was separated into its enantiomers by normal phase preparative chiral HPLC (CHIRALPAK OJ 5×50 cm column; eluting with 30% MeOH/EtOH (1:1) in heptane (isocratic) at 50 mL/min) to give the faster eluting enantiomer compound 852Di (Chiral HPLC: 5.56 min; CHIRALPAK OJ 4.6×250 mm column; eluting with 30% MeOH/EtOH (1:1) in heptane containing 0.1% DEA at 1 mL/min) and the slower eluting anantiomer compound 852Dii (Chiral HPLC: 7.01 min; CHIRALPAK OJ 4.6×250 mm column; eluting with 30% MeOH/EtOH (1:1) in heptane containing at 1 mL/min). The absolute stereochemistry of compounds 852Di & 852Dii has not been established. Although each compound represents a single antipode, the nomenclature and structure shown does not reflect the absolute stereochemistry of the compound.

EXAMPLE 853

(3aα,4β,5α,7β,7aα)-4-(Octahydro-5-[[[6-(trifluoromethyl)-4-pyrimidinyl]oxy]methyl]-4,7-dimethyl-1,3-dioxo-4,7-epoxy-2H-isoindol-2-yl)-2-(trifluoromethyl)benzonitrile (853)

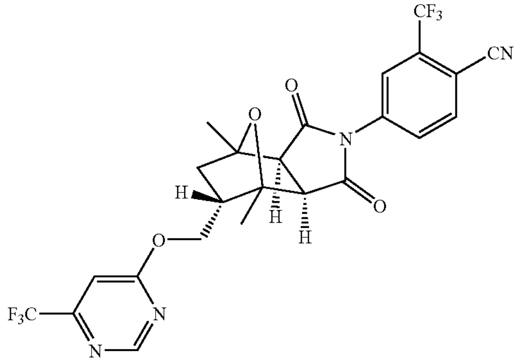

Triphenylphosphine (0.066 g, 0.254 mmol) and di-tert-butyl-azodicarboxylate (0.058 g, 0.254 mmol) in THF (0.5 mL) were stirred at rt under $N_2$ for 10 min, then 6-trifluoromethyl-4-pyrimidinol (0.042 g, 0.254 mmol) was added. The reaction mixture was stirred under $N_2$ for another 15 min, followed by the addition of a racemic mixture of compounds 852Di & 852Dii (0.050 g, 0.127 mmol). The reaction was allowed to proceed for 2 h, at which point $CH_2Cl_2$ (15 mL) was added. The organic layer was isolated and then washed consecutively with 1N NaOH (15 mL), brine (15 mL) and dried over $MgSO_4$ and concentrated in vacuo. The resulting solid was purified by silica gel chromatograph, eluting with EtOAc in Hexane from 0% to 100%, to give compound 853 (60 mg) as a white solid. HPLC: 99% at 4.083 min (retention time) (YMC S-50DS-A column, 4.6×50 mm, eluting with 10-90% aqueous methanol over 4 mincontaining 0.2% phosphoric acid, 4 mL/min, monitoring at 220 nm). MS (ESI): m/z 541.06 [M+H]. Compound 853 represents a racemic mixture of antipodes. The nomenclature and structure shown does not reflect the absolute stereochemistry of the compound.

EXAMPLE 854

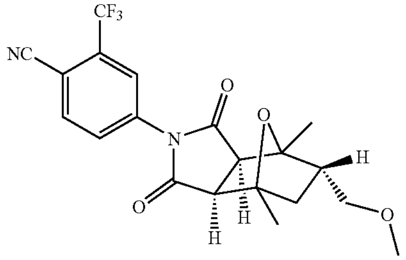

In a sealed tube was prepared a mixture of compound 852Di (150 mg, 0.38 mmol), MeI (0.24 mL, 3.8 mmol) and $Ag_2O$ (881 mg, 3.8 mmol) in 2 mL $CH_3CN$. The tube was sealed and heated to 80° C. overnight. The mixture was cooled to rt, filtered, eluting with EtOAc, and concentrated. Purification was achieved by silica gel flash chromatography with 0 to 100% EtOAc in hexanes to give compound 854 (49 mg, 32%) as a colorless oil. HPLC: 97% at 3.58 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 407.20 $[M+H]^+$. The absolute stereochemistry of compound 854 has not been established. Although the compound represents a single antipode, the nomenclature and structure shown does not reflect the absolute stereochemistry of the compound.

EXAMPLE 855

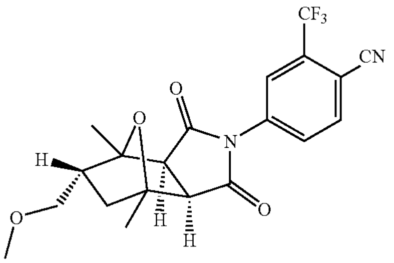

Compound 852Dii (150 mg, 0.38 mmol), MeI (0.24 mL, 3.8 mmol) and $Ag_2O$ (881 mg, 3.8 mmol) were reacted in 2 mL $CH_3CN$ and the reaction mixture purified as described for Example 854 to afford compound 855 (45 mg, 29%) as a colorless oil. HPLC: 98% at 3.58 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 407.19 $[M-H]^-$. The absolute stereochemistry of compound 855 has not been established. Although the compound represents a single antipode, the nomenclature and structure shown does not reflect the absolute stereochemistry of the compound.

EXAMPLE 856

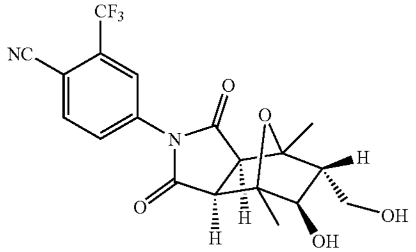

-continued

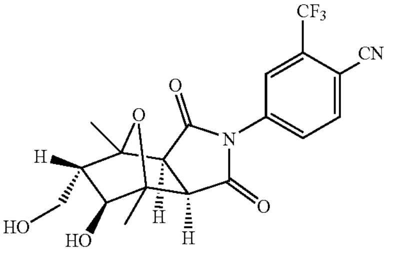

To a solution of compound 852B (835 mg, 1.65 mmol) in 10 mL THF was added a 1.0M solution of $BH_3$.THF (3.3 mL, 3.30 mmol) dropwise at 0° C. The resulting mixture was stirred at 0° C. for 2 h, after which 15 mL EtOH, 5 mL THF, 30 mL pH 7 phosphate buffer and 2.1 mL 30% $H_2O_2$ were added. The resulting mixture was stirred for 2 h at 0° C. after which water and EtOAc were added. The layers were separated and the aqueous layer was extracted again with EtOAc. The combined organic phases were washed with 10% $Na_2S_2O_3$-solution followed by brine. The organics were dried over $MgSO_4$, concentrated and purified by flash chromatography with 0 to 25% EtOAc in $CH_2Cl_2$. The material was dissolved in 8 mL EtOH containing 2% conc. HCl and the resulting mixture was stirred for 2 h. The reaction mixture was diluted with EtOAc and carefully poured into sat. $NaHCO_3$-solution. The layers were separated and the aqueous layer was extracted again with EtOAc. The combined organic layers were dried over $MgSO_4$ and concentrated in vacuo. The resulting racemic material was separated into its enantiomers by normal phase preparative chiral HPLC (CHIRALPAK OD 5×50 cm column; eluting with 15% MeOH/EtOH (1:1) in heptane (isocratic) at 50 mL/min) to give the faster eluting compound 856i (128 mg) (Chiral HPLC: 13.64 min; CHIRALPAK OD 4.6×250 mm column; eluting with 15% MeOH/EtOH (1:1) in heptane containing at 1 mL/min) and the slower eluting compound 856ii (137 mg, 39% combined yield) (Chiral HPLC: 16.31 min; CHIRALPAK OD 4.6×250 mm column; eluting with 15% MeOH/EtOH (1:1) in heptane at 1 mL/min).). MS (ES): m/z 411.01 $[M+H]^+$. The absolute stereochemistry of compounds 856i & 856ii has not been established. Although each compound represents a single antipode, the nomenclature and structure shown does not reflect the absolute stereochemistry of the compound.

EXAMPLE 857

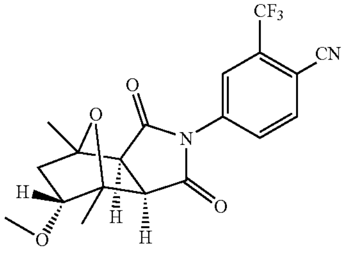

A. (857A)

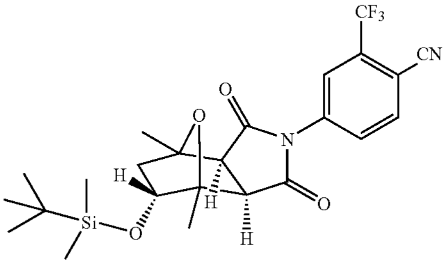

Compound 798i was converted to compound 857A by the procedure described in Example 774. HPLC: 95% at 4.307 min (retention time) (YMC S5 ODS-A column 4.6×50 mm eluting with 10-90% aqueous methanol over 4 mincontaining 0.2% phosphoric acid, 4 mL/min, monitoring at 220 nm).

B. (857B)

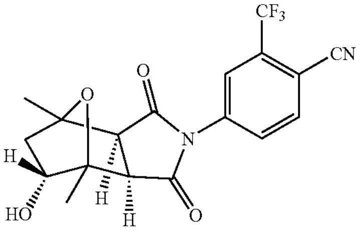

Compound 857A was converted to compound 857B by the procedure described in Example 774. HPLC: 100% at 2.89 min (retention time) (YMC S5 ODSA column 4.6×50 mm eluting with 10-90% aqueous methanol over 4 mincontaining 0.2% phosphoric acid, 4 mL/min, monitoring at 220 nm). MS (ES): m/z 381.16 $[M+H]^+$.

C. (857C)

Compound 857B (0.100 g, 0.26 mmol), MeI (0.163 mL, 2.6 mmol), $Ag_2O$ (0.603 g, 2.60 mmol) and acetonitrile (2.5 mL) were added to a high pressure reaction vessel. The vessel was sealed and heated to 75° C. After 16 h, the reaction was cooled to rt, diluted with EtOAc and filtered through celite, rinsing with EtOAc. The crude material was purified by flash chromatography on silica eluting with 0-5-8% acetone in chloroform to give compound 857C as a white solid. HPLC: 90% at 2.887 min (retention time) (YMC S5 ODS-A column 4.6×50 mm eluting with 10-90% aqueous methanol over 4 mincontaining 0.2% phosphoric acid, 4 mL/min, monitoring at 220 nm). MS (ES): m/z 395.07 $[M+H]^+$. The absolute stereochemistry of compound 857C has not been established. Although the compound represents a single antipode, the nomenclature and structure shown does not reflect the absolute stereochemistry of the compound.

EXAMPLE 858

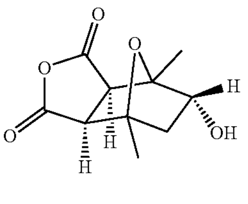

A. (858Ai & 858Aii)

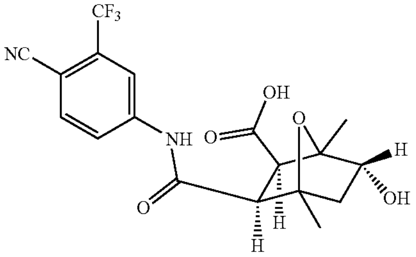

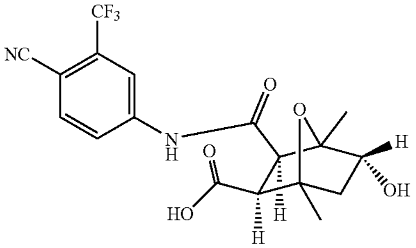

Compound 857B (2.50 g, 6.57 mmol) was dissolved in THF (10.0 mL) at 22° C. and 1 N NaOH (10.0 mL) was added. After 1 h, THF (10.0 mL), 1 N HCl (1.10 mL) and brine (10.0 mL) were added. The mixture was then extracted once with EtOAc (20.0 mL) and twice with 1:1 THF/EtOAc (20.0 mL). The combined organics were dried over anhydrous $MgSO_4$, filtered and concentrated in vacuo to give compounds 858Ai and 858Aii (1:1 by HPLC) as a white solid. No was purification necessary. HPLC: 100% at 2.383 and 2.573 min (retention time) (YMC S5 ODS-A column 4.6×50 mm eluting with 10-90% aqueous methanol over 4 mincontaining 0.2% phosphoric acid, 4 mL/min, monitoring at 220 nm).

B. (858B)

Compounds 858Ai and 858Aii were suspended in a mixture of THF (50.0 mL) and AcOH (20.0 mL) and heated to 60° C. for 16 h. The reaction became homogenous after 4 h. The reaction was cooled to 22° C. and concentrated in vacuo. Toluene (20.0 mL) was then added and mixture heated to 90° C. for 4 h until all product was dissolved. The mixture was then cooled to 22° C. and left standing for 20 h. Compound 858B precipitates from solution over the 20 h period. The product was filtered and rinsed with toluene followed by drying in vacuo. Compound 858B (1.10 g) was isolated as an off-white solid and used without further purification. $^1H$ NMR (DMSO-$d^6$): δ=4.91 (d, 1H, J=6.2 Hz), 3.97 (dd, 1H, J=3.9, 6.2 Hz), 3.82 (d, 1H, J=7.6 Hz), 3.31 (d, 1H, J=7.6 Hz), 2.27 (dd, 1H, J=10.2, 12.8 Hz), 1.77 (s, 3H), 1.49 (m, 1H) and 1.47 ppm (s, 3H). The absolute stereochemistry of compound 858B has not been established. Although the compound represents a single antipode, the nomenclature and structure shown does not reflect the absolute stereochemistry of the compound.

EXAMPLE 859

(3aα,4β,5α,6β,7β,7aα)-2-(4-Cyano-3-(trifluoromethyl)phenyl)hexahydro-6-cyano-4,7-dimethyl-1,3-dioxo-4,7-epoxy-1H-isoindole-5-carboxylic acid, methyl ester (859)

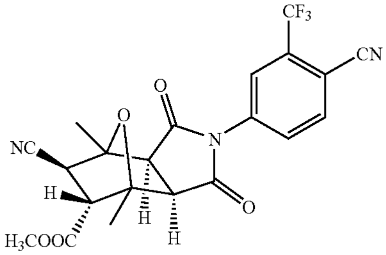

A mixture of compound 792A (84 mg; 0.2 mmol), KCN (15 mg; 0.22 mmol) and ammonium chloride (12 mg; 0.22 mmol) in 1 ml of DMF and 0.25 ml of water was stirred at rt for 18 hr. A precipitant formed on standing overnight. After adding an additional 10 ml of water, the suspension was filtered and the filter cake was washed with water. Drying and trituration with hexane afforded compound 859 (25 mg, 28%) as a tan powder. HPLC: 95% at 1.67 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 448.29 $[M+H]^+$. Compound 859 represents a racemic mixture of antipodes. The nomenclature and structure shown does not reflect the absolute stereochemistry of the compound.

EXAMPLE 860

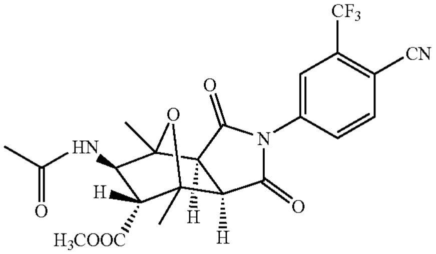

A mixture of compound 792A (44 mg; 0.1 mmol) and acetic anhydride (0.25 ml) was heated to 60° C. for 2 hr. The volatiles were removed in vacuo and the residue was co-evaporated from heptane (3×2 ml) to afford compound 860 (47 mg, 99%) as a white powder. HPLC: 95.8% at 1.49 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 480.35 $[M+H]^+$. Compound 860 represents a racemic mixture of antipodes. The nomenclature and structure shown does not reflect the absolute stereochemistry of the compound.

EXAMPLE 861

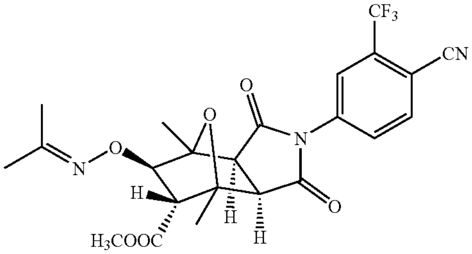

Sodium hydride, 60% in mineral oil (120 mg; 3 mmol) was added in portions over 10 min to a solution of compound 792A (1.9 g; 4.5 mmol) and acetone oxime (667 mg; 9 mmol) in THF at rt. After stirring 45 min, the reaction mixture was partitioned between brine (100 ml) and EtOAc (150 ml). The organic layer was washed with brine (50 ml), dried ($MgSO_4$) and concentrated in vacuo. The residue was chromatographed on a 5×20 cm silica gel column, eluting with 1000 ml of 25% EtOAc/hexane and 500 ml of 40% EtOAc/hexane. Concentration of the pure fractions in vacuo afforded compound 861 (1.75 g, 80%) as a white powder. HPLC: 98% at 1.82 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 494.05 $[M+H]^+$. Compound 861 represents a racemic mixture of antipodes. The nomenclature and structure shown does not reflect the absolute stereochemistry of the compound.

EXAMPLE 862

(3aα,4β,5α,6β,7β,7aα)]-2-(4-Cyano-3-(trifluoromethyl)phenyl)-hexahydro-6-hydroxy-4,7-dimethyl-1,3-dioxo-4,7-epoxy-1H-isoindole-5-carboxylic acid, methyl ester (862)

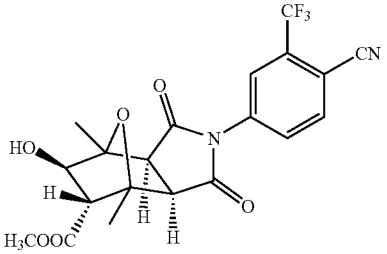

A mixture of compound 861 (1.75 g; 3.5 mmol) and zinc dust (6.07 g, 87.50 mA) in 19 ml of formic acid was refluxed for 20 min. After cooling to rt, the reaction mixture was diluted with ~50 ml of EtOAc and filtered though celite. The filtrate was diluted with ~200 ml of EtOAc and the organic layer was washed with water (200 ml), 0.5M NaOH (2×200 ml), water (200 ml) and brine (100 ml). Drying over $MgSO_4$ and concentration in vacuo gave a residue that was chromatographed on a 2.5×20 cm silica gel column, eluting with 1000 ml of 40% EtOAc/hexane and 500 ml of 50% EtOAc/hexane. Concentration of the pure fractions in vacuo afforded compound 862 (820 g, 54%) as a colorless foam. HPLC: 99% at 1.47 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 438.99 $[M+H]^+$. Compound 862 represents a racemic mixture of antipodes. The nomenclature and structure shown does not reflect the absolute stereochemistry of the compound.

EXAMPLE 863

[3aS-(3aα,4β,5α,6β,7β,7aα)]-2-(4-Cyano-3-(trifluoromethyl)phenyl)hexahydro-6-hydroxy-4,7-dimethyl-1,3-dioxo-4,7-epoxy-1H-isoindole-5-carboxylic acid, methyl ester (863i) & [3aS-(3aα,4β,5α,6β,7β,7aα)]-2-(4-Cyano-3-(trifluoromethyl)phenyl)-hexahydro-6-hydroxy-4,7-dimethyl-1,3-dioxo-4,7-epoxy-1H-isoindole-5-carboxylic acid, methyl ester (863ii)

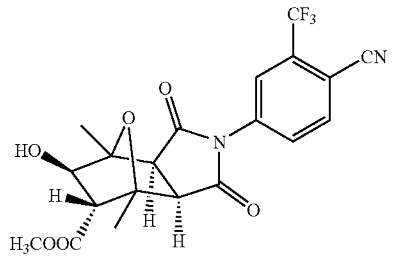

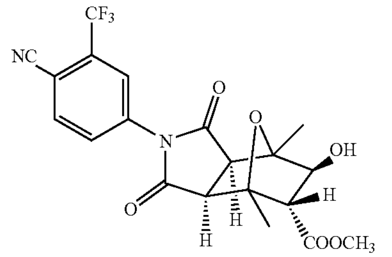

Racemic compound 862 (0.8 g) was separated into its enantiomers by normal phase preparative chiral HPLC (CHIRALPAK OD 5×50 cm column; eluting with 15% EtOH in hexanes (isocratic) at 50 mL/min) to give 355 mg of faster eluting compound 863i (Chiral HPLC: 8.89 min; CHIRALPAK OD 4.6×250 mm column; eluting with 15% EtOH in hexanes at 2 mL/min); HPLC: 99% at 2.91 min (retention time) (YMC S5 ODS column 4.6×50 mm eluting with 10-90% aqueous methanol over 2 mincontaining 0.2% phosphoric acid, 4 mL/min, monitoring at 220 nm); MS (ES): m/z 471.00 $[M+MeOH]^+$ and 330 mg of the slower eluting compound 863ii (Chiral HPLC: 12.30 min; CHIRALPAK OD 4.6×250 mm column; eluting with 15% EtOH in hexanes at 2 mL/min); HPLC: 99% at 2.89 min (retention time) (YMC S5 ODS column 4.6×50 mm eluting with 10-90% aqueous methanol over 2 mincontaining 0.2% phosphoric acid, 4 mL/min, monitoring at 220 nm); MS (ES): m/z 471.99 $[M+MeOH]^+$. The absolute stereochemistry of compounds 863i & 863ii has not been established. Although each compound represents a single antipode, the nomenclature and structure shown does not reflect the absolute stereochemistry of the compound.

EXAMPLE 864

(3aα,4β,5α,7β,7aα)-2-(4-Cyano-3-(trifluoromethyl)phenyl)-hexahydro-5-hydroxy-4,7-dimethyl-1,3-dioxo-4,7-epoxy-1H-isoindole-5-carboxylic acid, methyl ester (864)

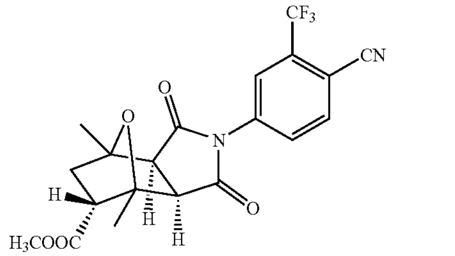

A mixture of compound 792A (210 mg; 0.5 mmol), phenylsilane (0.13 ml, 1 mmol) and $Mn(acac)_2$ (5 mg; 0.01 mmol) in 2.5 ml isopropanol and 0.25 ml of THF was stirred 3 days at rt in open air. After adding 5% sodium bisulfite solution (5 ml) and stirring 30 min, the reaction mixture was partitioned between EtOAc (30 ml) and water (30 ml). Washing the organic layer with brine (20 ml), followed by drying over $MgSO_4$ and concentration in vacuo, afforded a residue that was chromatographed on a 2.5×15 cm silica gel column, eluting with 50% EtOAc/hexane. Concentration of the pure fractions in vacuo, afforded compound 864 (109 mg, 50%) as a white powder. HPLC: 98.6% at 1.18 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 438.98 $[M+H]^+$. Compound 864 represents a racemic mixture of antipodes. The nomenclature and structure shown does not reflect the absolute stereochemistry of the compound.

EXAMPLE 865

(3aα,4β,5α,7β,7aα)-2-(4-Cyano-3-(trifluoromethyl)phenyl)hexahydro-5-hydroxy-4,7-dimethyl-1,3-dioxo-4,7-epoxy-1H-isoindole-5-carboxylic acids (1-methylethyl) ester (865C)

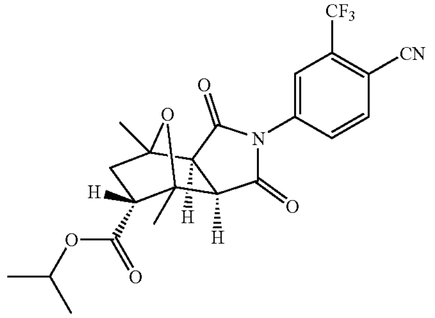

A. 2,5-Dimethyl-furan-3-carboxylic acid isopropyl ester (865A)

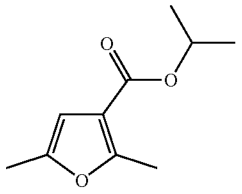

Isopropanol (5 ml) was added to a solution of 2,5-dimethylfuran-3-carbonylchloride (1.64 g; 10.3 mmol) in 15 ml of methylene chloride at rt. After allowing the reaction mixture to stand at rt for 30 mins, the volatiles were removed in vacuo and the residue was co-evaporated from isopropanol to afford compound 865A (1.8 g, 96%) as a light amber liquid. $^1$HNMR ($CDCl_3$): δ 1.30 (d, j=6.5 Hz, 6H), 2.23 (s, 3H), 2.52 (s, 3H), 5.14 (m, 1H), 6.21 (s, 1H).

B. (3aα,4β,7β,7aα)-2-(4-Cyano-3-(trifluoromethyl)phenyl)tetrahydro-4,7-dimethyl-1,3-dioxo-4,7-epoxy-1H-isoindole-5-carboxylic acid, (1-methylethyl) ester (865B)

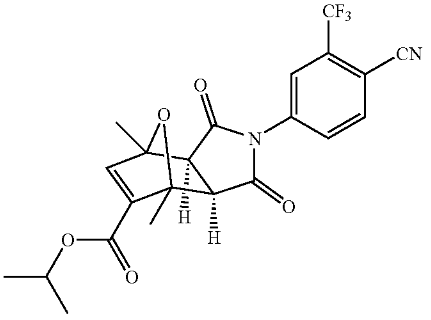

A mixture of 4-(2,5-dihydro-2,5-2,5-dioxo-1H-pyrrol-1-yl)-2-trifluoromethylbenzonitrile (851 mg; 3.2 mmol) and compound 865A (1.7 g; 9.4 mmol) was heated to 140° C. for 4 h. After allowing the mixture to cool to rt and stand 4 days, the reaction mixture was chromatographed on a 5×25 cm silica gel column, eluting with 25% EtOAc/hexane. Concentration of the pure fractions in vacuo afforded compound 865B (869 mg, 60%) as thick yellow oil. Due to the instability of this compound, it was stored at −20C and used promptly.

C. (3aα,4β,5α,7β,7aα)-2-(4-Cyano-3-(trifluoromethyl)phenyl)hexahydro-5-hydroxy-4,7-dimethyl-1,3-dioxo-4,7-epoxy-1H-isoindole-5-carboxylic acid, (1-methylethyl)ester (865C)

Compound 865B (224; 0.5 mmol) was converted to compound 865C using the procedure described in Example 791B to afford compound 865C (82 mg, 35%) as a white powder. HPLC: 98.4% at 1.18 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 466.98 [M+H]$^+$. Compound 865C represents a racemic mixture of antipodes. The nomenclature and structure shown does not reflect the absolute stereochemistry of the compound.

EXAMPLE 866

(3aα,4β,5α,7β,7aα)-2-(4-Cyano-3-(trifluoromethyl)phenyl)hexahydro-5-hydroxy-4,7-dimethyl-1,3-dioxo-4,7-epoxy-N,N-dimethyl-1H-isoindole-5-carboxamide (866C)

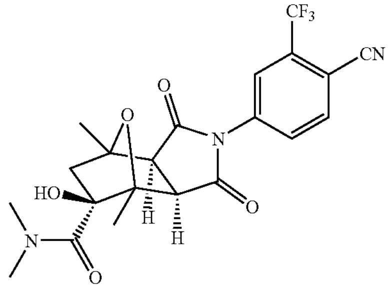

A. 2,5-Dimethyl-furan-3-carboxylic acid dimethylamide (866A)

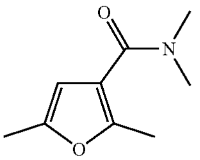

A solution of 2,5-dimethylfuran-3-carbonylchloride (2.19 g; 13.8 mmol) in 10 ml of THF was added to a 2M solution of dimethylamine in dioxane (21 ml; 42 mmol) in 80 ml of THF at rt. After stirring for 1 hr, the volatiles were removed in vacuo and the residue was partitioned between EtOAc (100 ml) and water (100 ml). The organic layer was washed with saturated potassium bisulfate solution (100 ml), 1N NaOH (50 ml) and brine (50 ml). Drying over $MgSO_4$ and concentration in vacuo afforded compound 866A (1.84 g, 80%) as an amber liquid. $^1$HNMR ($CDCl_3$): δ 2.23 (s, 3H), 2.33 (s, 3H), 3.04 (s, 6H), 5.96 (s, 1H).

B. (866B)

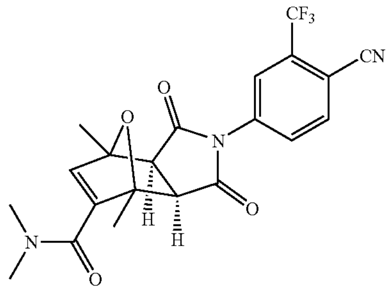

A mixture of 4-(2,5-dihydro-2,5-2,5-dioxo-1H-pyrrol-1-yl)-2-trifluoromethylbenzonitrile (1.45 mg; 5.4 mmol) and compound 866A (1.82 g; 10.9 mmol) was heated neat to 125° C. for 1 hr. After allowing the mixture to cool to rt overnight, the reaction mixture was dissolved in ~75 ml of EtOAc. Treatment with decolorizing carbon, filtration through celite and concentration in vacuo of the filtrate gave a residue that was dissolved in ~20 ml of ethyl ether. Addition of ~30 ml of hexane, followed by filtration and drying afforded compound 866B (1.89 g, 81%) as light pink solid.

C. (3aα,4β,5α,7β,7aα)-2-(4-Cyano-3-(trifluoromethyl)phenyl)hexahydro-5-hydroxy-4,7-dimethyl-1,3-dioxo-4,7-epoxy-N,N-dimethyl-1H-isoindole-5-carboxamide (866C)

Compound 866B (433; 1 mmol) was converted to compound 866C using the procedure described in Example 792B to afford compound 866C (85 mg, 18%) as a white powder. HPLC: 97.9% at 1.39 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 452.00 $[M+H]^+$. Compound 866C represents a racemic mixture of antipodes. The nomenclature and structure shown does not reflect the absolute stereochemistry of the compound.

EXAMPLE 867

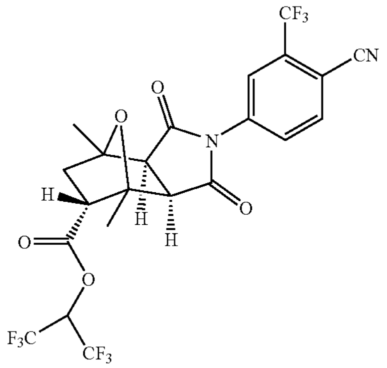

One drop of DMF was added to a solution of compound 792B (50 mg; 0.125 mmol) and oxalyl chloride (0.03 ml; 0.36 mmol) in methylene chloride (1 ml) at rt. After stirring 1.5 h at rt, the volatiles were removed in vacuo. The residue was treated with 1 ml of 1,3-hexafluoro-2-propanol, followed by 0.04 ml of pyridine and 2 mg of 4-dimethylpyridine. After stirring 18 h. at rt the reaction mixture was partitioned between EtOAc (20 ml) and saturated sodium bicarbonate solution (20 ml). The organic layer was washed with saturated potassium bisulfate solution (20 ml) and brine (20 ml). Drying over $MgSO_4$ and concentration in vacuo afforded a residue that was chromatographed on a 2.5×15 cm silica gel column, eluting with 25% EtOAc/hexane. Concentration of the pure fractions in vacuo afforded compound 867 (36 mg, 52%) as a white solid. HPLC: 99% at 1.96 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 558.00 $[M+H]^+$. Compound 867 represents a racemic mixture of antipodes. The nomenclature and structure shown does not reflect the absolute stereochemistry of the compound.

EXAMPLE 868

(3aα,4β,5α,7β,7aα)-2-(4-Cyano-3-(trifluoromethyl)phenyl)hexahydro-5-hydroxy-4,7-dimethyl-1,3-dioxo-4,7-epoxy-1H-isoindole-5-carboxylic acid, propyl ester (868B)

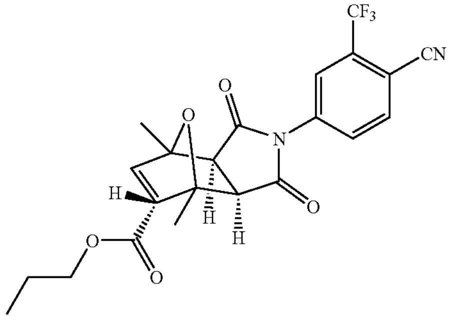

A (3aα,4β,5α,7β,7aα)-2-(4-Cyano-3-(trifluoromethyl)phenyl)hexahydro-5-hydroxy-4,7-dimethyl-1,3-dioxo-4,7-epoxy-1H-isoindole-5-carboxylic acid (868A)

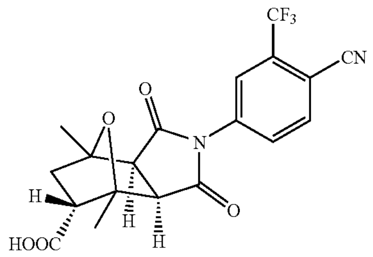

1N NaOH (2.2 ml; 2.2 mmol) was added to a solution of compound 867 (238 mg; 0.54 mmol) in 5 ml of methanol at rt. After stirring 5 h at rt, the volatiles were removed in vacuo and the residue was treated with 2 ml of trifluoroacetic acid for 18 hr. Concentration of the reaction mixture in vacuo, followed by co-evaporation from toluene (3×8 ml) gave a residue that was partitioned between EtOAc (40 ml) and brine (20 ml). Drying over $MgSO_4$ and concentration in vacuo afforded a solid that was triturated with hexane to afford compound 868A (120 mg, 53%) as a cream colored solid. HPLC: 93% at 1.35 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 425.08 $[M+H]^+$.

B. (3aα,4β,5α,7β,7aα)-2-(4-Cyano-3-(trifluoromethyl)phenyl)hexahydro-5-hydroxy-4,7-dimethyl-1,3-dioxo-4,7-epoxy-1H-isoindole-5-carboxylic acid, propyl ester (868B)

Oxalylchloride (0.18 ml, 2 mmol) was added to a solution of compound 868A (135 mg; 0.32 mmol) in 4 ml of THF at room rt. Bubbling was observed immediately. One drop of DMF was added and the reaction mixture was stirred 4 hrs. After adding 2 ml of n-propanol and stirring 18 h at rt, the reaction mixture was partitioned between EtOAc (30 ml) and water (30 ml). The organic layer was washed with saturated sodium bicarbonate solution (30 ml), dried over $MgSO_4$ and concentrated in vacuo. The residue was chromatographed on a 2.5×15 cm silica gel column, eluting with 25% EtOAc/hexane. The pure fractions were concentrated in vacuo to afford compound 868B (78 mg, 52%) as a white powder. HPLC: 95.4% at 1.63 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 467.10 $[M+H]^+$. Compound 868B represents a racemic mixture of antipodes. The nomenclature and structure shown does not reflect the absolute stereochemistry of the compound.

EXAMPLE 869

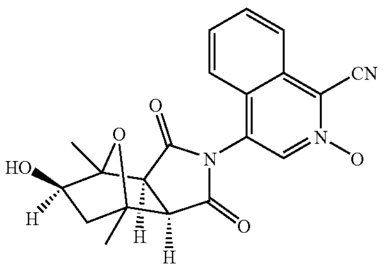

30% Hydrogen peroxide (0.1 ml) was added to a solution of compound 748 (36 mg; 0.1 mmol) in 1 ml of AcOH at 100 C. Four additional 0.1 ml aliquots of 30% hydrogen peroxide were added at 30 min intervals to the reaction mixture. Water (8 ml) was added to the reaction mixture 30 minutes after the last addition of 30% hydrogen peroxide. After cooling to rt and standing 2 days, the resulting suspension was filtered and the filter cake was washed with water. After drying, the solid was dissolved in ~2 ml of acetone and the solution was applied to a $SiO_2$ preparative thin layer chromatography plate. Elution with 30% acetone/chloroform, extraction of the more polar band, filtration and concentration afforded compound 869 (6 mg, 16%) as an off-white solid. HPLC: 99% at 1.06 min (retention time) (Phenominex S5 ODS column 4.6×50 mm eluting with 10-90% aqueous methanol over 2 mincontaining 0.1% TFA, 4 mL/min, monitoring at 254 nm); MS (ES): m/z 380.43 $[M+H]^+$. Compound 869 represents a racemic mixture of antipodes. The nomenclature and structure shown does not reflect the absolute stereochemistry of the compound.

EXAMPLE 870

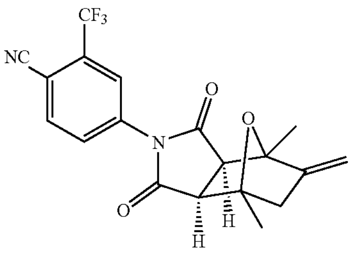

A racemic mixture of compound 852Di & 852Dii (150 mg, 0.38 mmol) was dissolved in THF (2 mL) under nitrogen and 2-nitrophenyl selenocyanate (202 mg, 0.89 mmol) followed by $PBu_3$ (0.22 mL, 0.89 mmol) was added. The resulting mixture was stirred for 20 h, concentrated and purified by flash chromatography with 0 to 100% EtOAc in hexanes. The resulting product was dissolved in THF (11 mL) and treated with 2 mL 30% $H_2O_2$ at 0° C. The reaction mixture was stirred for 10 min, then warmed to rt and stirred overnight. The reaction was quenched by the addition of 5% $Na_2S_2O_3$-solution and brine. The layers were separated and the aqueous layer was extracted 2× with $CH_2Cl_2$. The combined organic layers were dried over $MgSO_4$, concentrated in vacuo and purified by flash chromatography with 0 to 100% EtOAc in hexanes to give compound 870 (114 mg, 80%) as a yellow solid. HPLC: 100% at 3.67 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 375.23 $[M-H]^-$. Compound 870 represents a racemic mixture of antipodes. The nomenclature and structure shown does not reflect the absolute stereochemistry of the compound.

EXAMPLE 871

871Bi & 871Bii

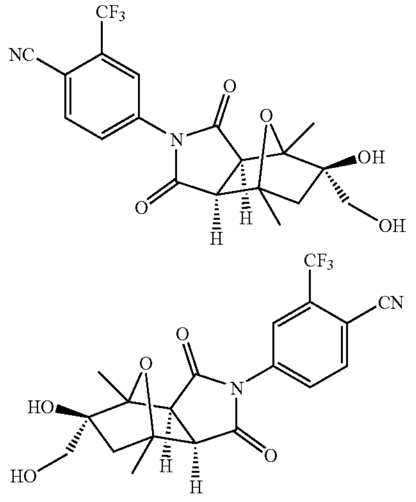

A. (871A)

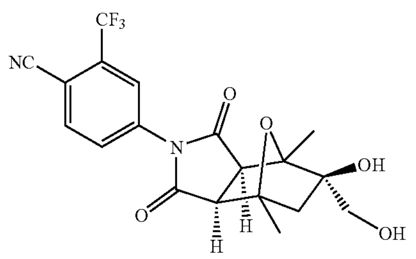

To a solution of a racemic mixture of compounds 852Di & 852Dii (33 mg, 0.09 mmol) in 0.5 mL acetone/0.4 mL water was added a 50% wt. solution of NMO in water (22 μL, 0.11 mmol) followed by a 4% wt. solution of $OsO_4$ in water (54 μL, 8.7 μmol). The resulting mixture was stirred for 12 h and the reaction was quenched by the addition of 5% $Na_2S_2O_3$-solution. $CH_2Cl_2$ was added, the layers were separated and the aqueous layer was extracted with $CH_2Cl_2$. The combined organic layers were dried over $MgSO_4$, concentrated in vacuo and purified by $SiO_2$ preparative TLC with 40% acetone in $CH_2Cl_2$ to give racemic compound 871A (30 mg, 83%) as a white solid. HPLC: 100% at 2.91 min (retention time) (YMC S5 ODSA column 4.6×50 mm Ballistic, 10-90% aqueous methanol over 4 mincontaining 0.2% $H_3PO_4$, 4 mL/min, monitoring at 220 nm). MS (ES): m/z 469.26 $[M+OAc]^-$. Compound 871A represents a racemic mixture of antipodes. The nomenclature and structure shown does not reflect the absolute stereochemistry of the compound.

B. (871Bi & 871Bii)

Racemic compound 871A was separated into its enantiomers by normal phase preparative chiral HPLC (CHIRALPAK OJ 5×50 cm column; eluting with 30% MeOH/EtOH (1:1) in heptane (isocratic) at 50 mL/min) to give the faster eluting antipode compound 871Bi (Chiral HPLC: 7.35 min; CHIRALPAK OJ 4.6×250 mm column; eluting with 30% MeOH/EtOH (1:1) in heptane at 1 mL/min) and the slower eluting antipode compound 871Bii (Chiral HPLC: 11.49 min; CHIRALPAK OJ 4.6×250 mm column; eluting with 30% MeOH/EtOH (1:1) in heptane at 1 mL/min). The absolute stereochemistry of compounds 871Bi & 871Bii has not been established. Although each compound represents a single antipode, the nomenclature and structure shown does not reflect the absolute stereochemistry of the compound.

EXAMPLE 872

(3aα,4β,5α,7β,7aα)-4-(Octahydro-5-[[[difluoromethyl]oxy]methyl]-4,7-dimethyl-1,3-dioxo-4,7-epoxy-2H-isoindol-2-yl)-2-(trifluoromethyl)benzonitrile (872)

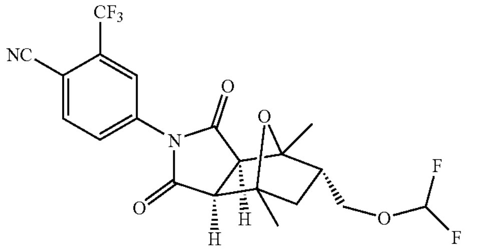

A racemic mixture of compounds 852Di & 852Dii (50 mg, 0.13 mmol) was dissolved under nitrogen in 1 mL $CH_3CN$ and CuI (2 mg, 8.9 μmol) was added. This mixture was heated to 45° C. and 2-(fluorosulfonyl)difluoroacetic acid (27 mg, 0.15 mmol) was added via syringe. The reaction mixture was stirred for 1.5 h at 45° C. and then allowed to cool to rt. The reaction was quenched by the addition of water and $CH_2Cl_2$. The layers were separated and the aqueous layer was extracted with $CH_2Cl_2$. The combined organic phases were dried over $MgSO_4$, concentrated in vacuo and purified twice by $SiO_2$ flash chromatography with 0 to 100% EtOAc in hexanes to afford compound 872 (10 mg, 18%) as a white foam. HPLC: 92% at 3.72 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 443.22 $[M-H]^-$. Compound 872 represents a racemic mixture of antipodes. The nomenclature and structure shown does not reflect the absolute stereochemistry of the compound.

EXAMPLE 873

873i & 8731i

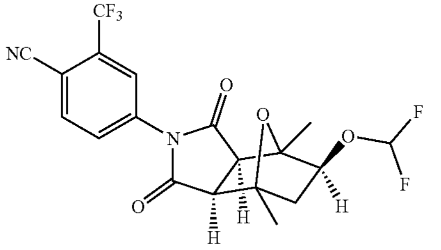

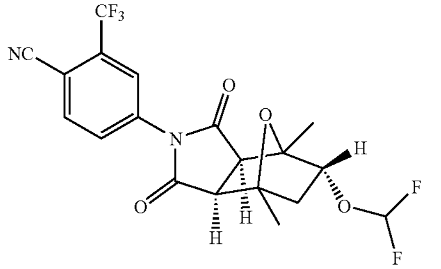

Compound 471Di (50 mg, 0.13 mmol), CuI (2 mg, 8.9 μmol) and 2-(fluorosulfonyl)difluoroacetic acid (28 mg, 0.16 mmol) were reacted in 1 mL $CH_3CN$ and purified as described in Example 872. Compounds 873i & 873ii (15 mg, 0.03 mmol) were obtained as a inseparable 6:1 mixture as determined by $^1$H-NMR. HPLC: 91% at 3.64 min (retention time) (YMC S5 ODS-A column 4.6×50 mm Ballistic, 10-90% aqueous methanol over 4 mincontaining 0.2% $H_3PO_4$, 4 mL/min, monitoring at 220 nm). MS (ES): m/z 489.22 $[M+OAc]^-$. Compounds 873i & 873ii each represent a racemic mixture of antipodes. The nomenclature and structure shown does not reflect the absolute stereochemistry of the compound.

EXAMPLE 874

874i & 874ii

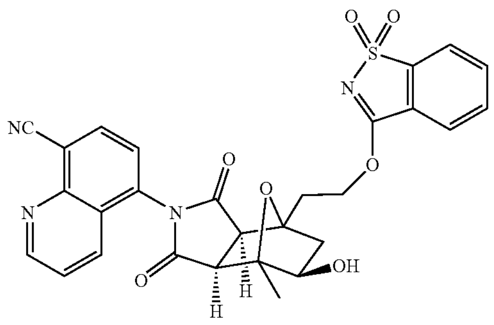

-continued

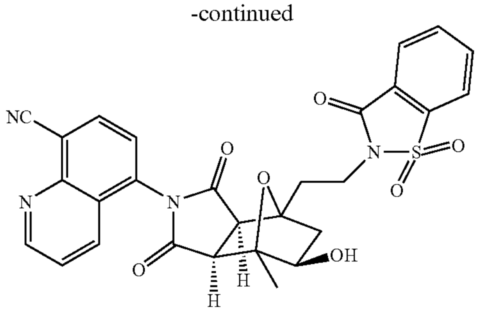

Triphenylphosphine (0.067 g, 0.254 mmol) and di-tert-butyl-azodicarboxylate (0.059 g, 0.254 mmol) in THF (1 mL) were stirred at rt under $N_2$ for 10 min, then saccharin (0.047 g, 0.254 mmol) was added. The reaction mixture was stirred under $N_2$ for another 15 min, followed by the addition of compound 429i (0.050 g, 0.127 mmol). The reaction was allowed to proceed for 24 h, at which point $CH_2Cl_2$ (15 mL) was added. The organic layer was isolated and then washed consecutively with 1N NaOH (15 mL), brine (15 mL) and dried over $MgSO_4$ and concentrated in vacuo. The resulting solid was purified by $SiO_2$ preparative TLC eluting with 25% acetone in $CHCl_3$, to give compound 874i (18 mg, 25%) as a white solid (HPLC: 91% at 2.96 min (retention time) (YMC S-50DS-A column, 4.6×50 mm, eluting with 10-90% aqueous methanol over 4 mincontaining 0.2% phosphoric acid, 4 mL/min, monitoring at 220 nm). MS (ESI): m/z 559.42 $[M+H]^+$) and compound 874ii (18 mg, 25%) as a white solid (HPLC: 93% at 2.85 min (retention time) (YMC S-50DS-A column, 4.6×50 mm, eluting with 10-90% aqueous methanol over 4 mincontaining 0.2% phosphoric acid, 4 mL/min, monitoring at 220 nm). MS (ESI): m/z 557.12 $[M-H]^-$). The absolute stereochemistry of compounds 874i & 874ii has not been established. Although each compound represents a single antipode, the nomenclature and structure shown does not reflect the absolute stereochemistry of the compound.

EXAMPLE 875

[3aR-(3aα,4β,5β,7β,7aα)]-4-(Octahydro-5-cyclopropyloxy-4,7-dimethyl-1,3-dioxo-4,7-epoxy-2H-isoindol-2-yl)-2-(trifluoromethyl)benzonitrile (875B)

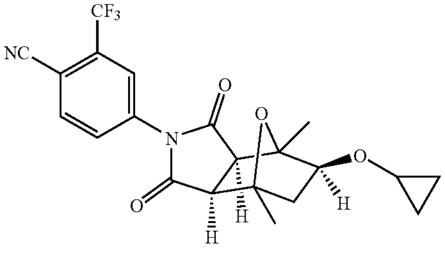

A. (875A)

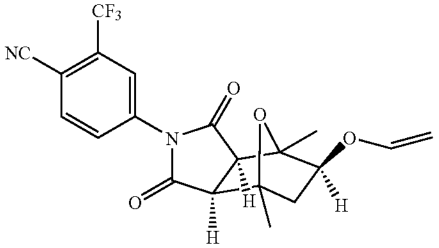

A solution of compound 471Di (300 mg, 0.79 mmol), mercuric trifluoroacetate (17 mg, 0.04 mmol) in tetrahydrofuran (THF, 1.5 mL) and ethyl vinyl ether (3 mL) in a thick-walled sealed tube was heated to 45° C. for 48 h. The tube was cooled, opened and the reaction mixture was concentrated in vacuo to give an oil. The crude material was purified by silica gel flash chromatography eluting with 1:4:4 EtOAc/methylene chloride/heptane to give compound 875A (115 mg, 36%) as a white solid. HPLC: 99% at 3.80 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 407.09 $[M+H]^+$. The absolute stereochemistry of compound 875A is established by the known stereochemistry of the intermediate compound 471Di and the retention of configuration therein. The absolute stereochemistry is as drawn in the above FIGURE and rendered by the nomenclature.

B. [3aR-(3aα,4β,5⊕,7β,7aα)]-4-(Octahydro-5-cyclopropyloxy-4,7-dimethyl-1,3-dioxo-4,7-epoxy-2H-isoindol-2-yl)-2-(trifluoromethyl)benzonitrile (875B)

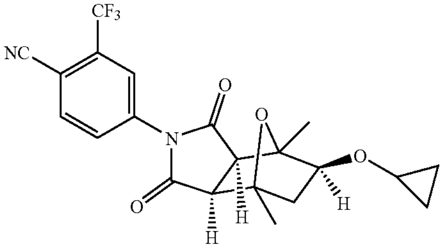

To a solution of compound 875A (100 mg, 0.25 mmol) in dry methylene chloride (5 mL) cooled to 5° C. was added, dropwise, diethylzinc solution (1.0M in hexanes, 1.4 mL, 1.4 mmol). The reaction mixture was warmed to rt, then diiodomethane (80 mL, 1.0 mmol) was introduced. After 3 h, HPLC indicated the reaction was ⅔ complete. Two additional portions of diethylzinc and diiodomethane were successively added then the reaction mixture cooled in an ice-bath, quenched with water, and partitioned between 1 M HCl solution (20 mL) and EtOAc (20 mL). The organic phase was separated, dried over sodium sulfate, concentrated in vacuo and purified by silica gel flash chromatography eluting with 2:3 EtOAc/heptane to give compound 875B as a white solid. HPLC: 100% at 3.72 min (retention time) (YMC S5 ODS column, 4.6×50 mm, eluting with 10-90% aqueous methanol over 4 min containing 0.2% phosphoric acid, 4 mL/min, monitoring at 220 nm). MS (ES): m/z 421.08 $[M+H]^+$. The absolute stereochemistry of compound 875B is established by the known stereochemistry of the intermediate compound 471Di and the retention of configuration therein. The absolute stereochemistry is as drawn in the above FIGURE and rendered by the nomenclature.

EXAMPLE 876

876

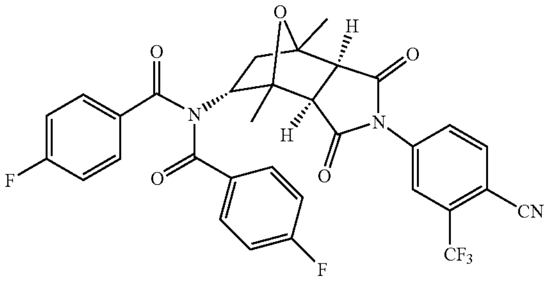

A racemic mixture of compounds 808& 809 (0.057 g, 0.15 mmol) was dissolved in 2 mL of $CH_2Cl_2$. Triethylamine (0.018 g, 0.18 mmol), a catalytic amount of DMAP, and 4-fluorobenzoyl chloride (0.075 g, 0.48 mmol) were added and the reaction was stirred for 6 h. The reaction mixture was diluted with $CH_2Cl_2$ and washed sequentially with 1N HCl, 10% $K_2CO_3$, and brine, dried over $MgSO_4$, filtered and concentrated in vacuo. The residue was purified by preparative TLC on silica gel using 2:1 EtOAc/hexanes as eluent. Removal of solvent gave compound 876 (0.066 g, 70%) as a white solid. HPLC: 100% at 3.94 min(YMC S5 ODS column) eluting with 10-90% aqueous methanol containing 0.2% phosphoric acid over a 4 min gradient monitoring at 220 nm. MS (ES): m/z 552.11 $[M+H]^+$.

EXAMPLE 877

877

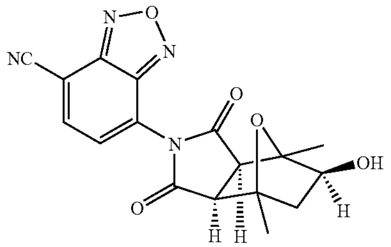

A. (877A)

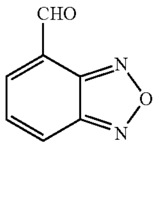

A 1.6 M solution of n-BuLi (54.6 mL, 87.4 mL) was added dropwise to a solution of diisopropylamine (12.8 mL, 91.6 mmol) in THF (40 mL) at −20° C. The reaction mixture was cooled to −78° C. and a solution of benzofurazan (10.0 g, 83.3 mmol) in THF (34 mL) was added dropwise. After stirring for 35 mins, the mixture was poured into a solution of DMF (10.3 mL, 133.2 mmol) in THF (34 mL) at −78° C. and a solution of 3:1 $H_2O$:AcOH (80 mL) was added. After stirring at rt for 12 h, toluene (150 mL) was added and the layers were separated. The organic layer was concentrated to ~30 mL and triturated with hexanes (150 mL). The resulting solid was filtered and rinsed with hexanes. Purification by flash chromatography on silica gel eluting with 50% EtOAc/hexanes gave compound 877A (7.77 g, 63%) as a tan solid. HPLC: 99% at 1.22 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 149.08 $[M+H]^+$.

B. (877B)

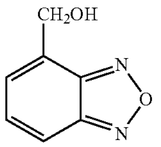

$NaBH_4$ (2.00 g, 52.5 mmol) was added portionwise to a solution of compound 877A (7.77 g, 52.5 mmol) in MeOH (100 mL) at 0° C. After 5 mins, the mixture was partitioned between $H_2O$ (100 mL) and $CH_2Cl_2$ (100 mL). The aqueous layer was extracted with EtOAc (2×100 mL) and the combined organic layers were dried ($MgSO_4$) and concentrated under reduced pressure to give crude compound 877B (7.55 g, 96%) which was taken on without purification. HPLC: 99% at 1.63 min (retention time) (YMC S5 ODS column, 4.6×50 mm, eluting with 10-90% aqueous methanol over 4 mincontaining 0.2% phosphoric acid, 4 mL/min, monitoring at 220 nm). MS (ES): m/z 133.05 $[M+H-H_2O]^+$.

C. (877C)

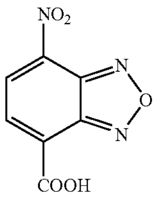

Fuming $HNO_3$ (4.25 mL, 100.58 mmol) was added dropwise to a solution of crude compound 877B (7.55 g, 50.29 mmol) in $H_2SO_4$ (50 mL) at 0° C. The mixture was, stirred at rt for 20 mins, poured onto ice (1 L), warmed to rt and then extracted with EtOAc (3×250 mL). The combined organic layers were dried ($MgSO_4$) and concentrated under reduced pressure. The resulting solid was washed with $H_2O$ and air-dried to give compound 877C (6.0 g) as an orange solid. An additional 2.7 g was recovered from the aqueous wash by extraction with EtOAc for a total yield of 8.7 g (83%). HPLC: 99% at 1.63 min (retention time) (YMC S5 ODS column, 4.6x50 mm, eluting with 10-90% aqueous methanol over 4 mincontaining 0.2% phosphoric acid, 4 mL/min, monitoring at 220 nm). MS (ES): m/z 210.18 $[M+H]^+$.

D. (877D)

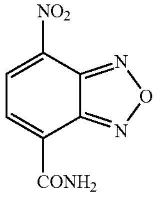

Urea (29.3 mg, 0.488 mmol) was added portionwise to a solution of compound 877C (100 mg, 0.488 mmol) in fuming $H_2SO_4$ (2 mL) at 50° C. with vigorous stirring. The mixture was then heated to 100° C. for 30 mins, cooled to rt and poured onto ice (100 mL). The resulting aqueous mixture was extracted with EtOAc (3x50 mL) and the combined organic layers were washed with $H_2O$ (1x100 mL), dried ($MgSO_4$) and concentrated under reduced pressure. Purification by flash chromatography on silica gel eluting with 50% EtOAc/hexanes gave compound 877D (76.3 mg, 77%) as a yellow-orange solid. HPLC: 96% at 1.39 min (retention time) (YMC S5 ODS column, 4.6x50 mm, eluting with 10-90% aqueous methanol over 4 mincontaining 0.2% phosphoric acid, 4 mL/min, monitoring at 220 nm). MS (ES): m/z 209.17 $[M+H]^+$.

E. (877E)

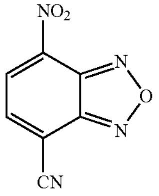

A mixture of compound 877D (1.01 mg, 4.85 mmol) and $P_2O_5$ (2.75 g, 9.70 mmol) in toluene (24 mL) was refluxed for 30 mins. $H_2O$ (50 mL) was added and the resulting mixture was extracted with EtOAc (3x100 mL). The combined organic layers were dried ($MgSO_4$) and concentrated under reduced pressure to give compound 877E (0.90 g, 98%) as a brown solid which was taken on without purification. HPLC: 90% at 1.78 min (retention time) (YMC S5 ODS column, 4.6x50 mm, eluting with 10-90% aqueous methanol over 4 mincontaining 0.2% phosphoric acid, 4 mL/min, monitoring at 220 nm).

F. (877F)

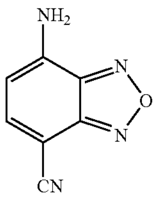

Iron powder (0.53 g, 9.47 mmol, 325 Mesh) was added in one portion to a solution of compound 877E (0.90 g, 4.73 mmol) in AcOH (24 mL) at 70° C. The reaction was complete after 30 mins, as judged by HPLC. The mixture was concentrated under reduced pressure, dissolved in EtOAC (50 mL) and washed with sat. $NaHCO_3$ (2x50 mL). The aqueous layer was extracted with EtOAc (4x20 mL) and the combined organic layers were dried ($Na_2SO_4$) and concentrated under reduced pressure. Purification by flash chromatography on silica gel eluting with 50% EtOAc/hexanes gave compound 877F (0.62 g, 82%) as a dark orange solid. HPLC: 94% at 1.94 min (retention time) (YMC S5 ODS column, 4.6x50 mm, eluting with 10-90% aqueous methanol over 4 mincontaining 0.2% phosphoric acid, 4 mL/min, monitoring at 220 nm). MS (ES): m/z 161.00 $[M+H]^+$.

G. (877G)

A small vial was charged with compound 752 (22.1 mg, 0.104 mmol compound 877F (11.1 mg, 0.069 mmol) and $MgSO_4$ (21 mg, 0.173 mmol). DME (0.07 mL) was added then $Et_3N$ (0.05 mL) and the vial was sealed with Teflon tape and heated at 135° C. for 18 h. Purification by preparative TLC ($SiO_2$) eluting with 30% acetone/$CHCl_3$ gave compound 877G (6.3 mg, 17%) as a brown solid. HPLC: 98% at 2.15 min (retention time) (YMC S5 ODS column, 4.6x50 mm, eluting with 10-90% aqueous methanol over 4 mincontaining 0.2% phosphoric acid, 4 mL/min, monitoring at 220 nm). MS (ES): m/z 337.16 $[M+H-H_2O]^+$. The absolute stereochemistry of compound 877G is established by the known stereochemistry of the intermediate compound 752 and the retention of configuration therein. The absolute stereochemistry is as drawn in the above FIGURE and rendered by the nomenclature.

EXAMPLE 878

[3aR-(3aα,4β,5β,7β,7aα)]-4-[Octahydro-5-hydroxy-4,7-dimethyl-1,3-dioxo-4,7-epoxy-2H-isoindol-2-yl]-2-chloro-3-methylbenzonitrile (878)

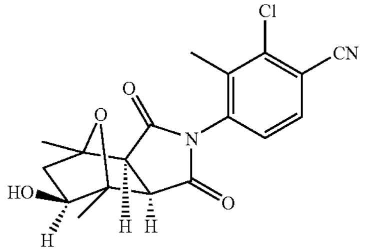

A mixture of 4-amino-2-chloro-3-methyl-benzonitrile (54.5 mg, 0.327 mmol), compound 752(104 mg, 0.491 mmol), $MgSO_4$ (98 mg, 0.818 mmol) and diisopropylethyl amine (0.28 mL, 1.64 mmol) in DME (0.33 mL) was heated at 150° C. in a sealed tube for 18 h. Purification by preparative TLC ($SiO_2$) eluting with 30% aetone/$CHCl_3$ gave 53.0 mg (45%) of compound 878 as a tan solid. HPLC: 95% at 2.63 min (retention time) (YMC S5 ODS column 4.6x50 mm eluting with 10-90% aqueous methanol over 4 minutes containing 0.2% phosphoric acid, 4 mL/min, monitoring at 220 nm). MS (ES): m/z 361.03 $[M+H]^+$. The absolute stereochemistry of compound 878 is established by the known stereochemistry of the intermediate compound 752 and the retention of configuration therein. The absolute stereochemistry is as drawn in the above FIGURE and rendered by the nomenclature.

EXAMPLES 879 TO 1020

Additional compounds of the present invention were prepared by procedures analogous to those described above. The compounds of Examples 879 to 1020 have the following structure (L is a bond):

where the structure, the compound name, retention time, molecular mass, and the procedure employed, are set forth in Table 18. The absolute configuration for designated compounds was not determined. Compounds having one or more optical centers are designated as being racemic or chiral. Racemic compounds represent a mixture of both possible antipodes. Chiral refers to a compound, which represents a single antipode of a possible pair. For compounds that are chiral but the absolute stereochemistry is not known, the structure does not reflect the absolute stereochemistry. For compounds which are chrial and the absolute stereochemistry is known by reference to a starting material, then the structure drawn reflects the absolute stereochemistry of the compound.

The chromatography techniques used to determine the compound retention times of Table 18 are as follows: LCMS=YMC S5 ODS column, 4.6x50 mm eluting with 10-90% $MeOH/H_2O$ over 4 minutes containing 0.1% TFA; 4 mL/min, monitoring at 220 nm. LCMS*=YMC S5 ODS column, 4.6x50 mm eluting with 10-90% $MeOH/H_2O$ over 2 minutes containing 0.1% TFA; 4 mL/min, monitoring at 220 nm. LC*=Hypersil C18 BDS column, 250x4.6 mm, 5 μm, a detection wavelength of 254 nm, and a flow rate of 1 mL/min. A linear gradient of 90% of 0.1% trifluoroacetic acid in water, 10% acetonitrile (start) to 100% acetonitrile over 15 min, then 100% acetonitrile for 5 min was used. LC=YMC S5 ODS column 4.6x50 mm eluting with 10-90% $MeOH/H_2O$ over 4 minutes containing 0.2% phosphoric acid, 4 mL/min, monitoring at 220 nm.

The molecular mass of the compounds listed in Table 18 were determined by MS (ES) by the formula m/z.

TABLE 18

| Ex. No | Structure | Compound Name/Comments | Retention Time Min./ Molecular Mass | Proc. of Ex. |
|---|---|---|---|---|
| 879 | 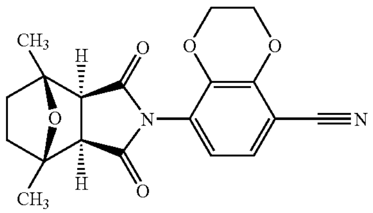 | | 2.34 LCMS $[M + H]^+$ = 355.23 | 470E |
| 880 | 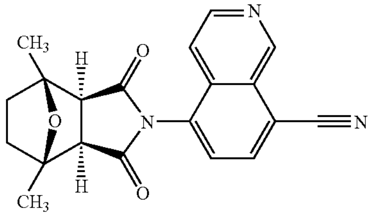 | | 2.44 LCMS $[M + H]^+$ = 348.24 | 470E |
| 881 | 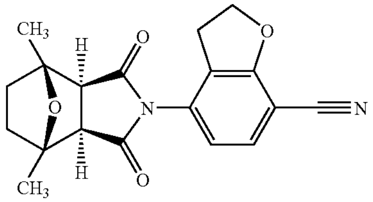 | | 3.21 LCMS $[M + H]^+$ = 339.24 | 470E |
| 882 | 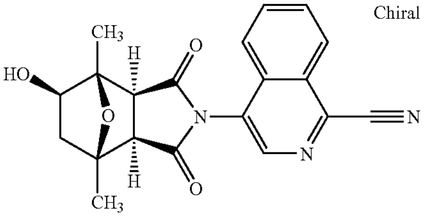 Chiral | Chiral, absolute stereochemistry not known | 1.2 LCMS $[M + H]^+$ = 364.15 | 754 |

TABLE 18-continued
| Ex. No | Structure | Compound Name/Comments | Retention Time Min./ Molecular Mass | Proc. of Ex. |
|---|---|---|---|---|
| 883 | 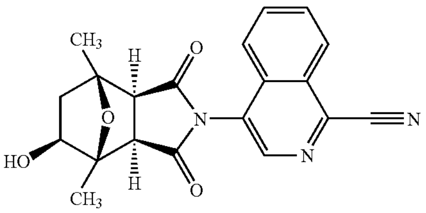 Chiral, absolute stereochem not known | Chiral, absolute stereochemistry not known | 1.20 LCMS $[M + H]^+$ = 364.15 | 761 |
| 884 | 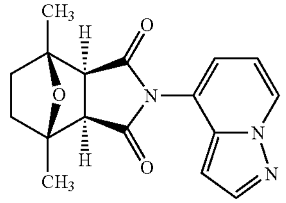 | | 2.72 LCMS $[M + H]^+$ = 312.18 | 470E |
| 885 | 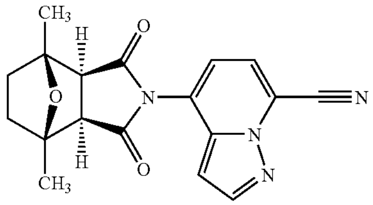 | | 2.95 LCMS $[M + H]^+$ = 337.09 | 470E, 777F |
| 886 | 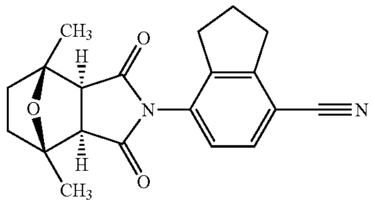 | | 2.93 LCMS $[M + H]^+$ = 337.23 | 470E |
| 887 | 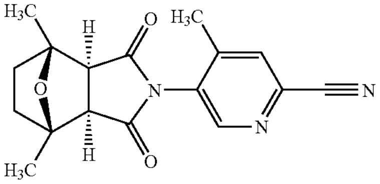 | | 2.69 LCMS $[M + H]^+$ = 312.06 | 470E |
| 888 | 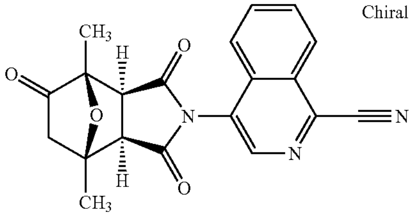 Chiral | Chiral, absolute stereochemistry not known | 1.46 LCMS $[M + H]^+$ = 362.15 | 795, 818 |

TABLE 18-continued
| Ex. No | Structure | Compound Name/Comments | Retention Time Min./ Molecular Mass | Proc. of Ex. |
|---|---|---|---|---|
| 889 | 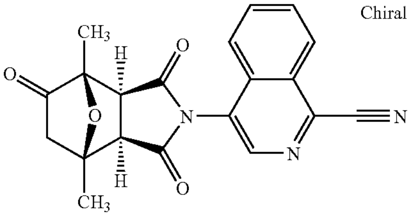 Chiral | Chiral, absolute stereochemistry not known | 1.48 LCMS $[M + H]^+$ = 362.15 | 795, 818 |
| 890 | 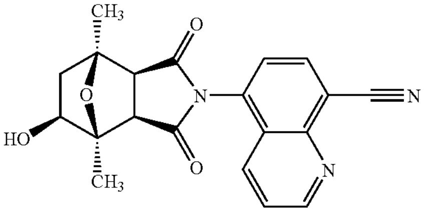 | Chiral, absolute stereochemistry as shown | 1.833 LCMS $[M + H]^+$ = 364.16 | 761 |
| 891 | 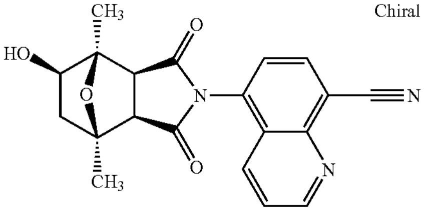 Chiral | Chiral, absolute stereochemistry as shown | 1.827 LCMS $[M + H]^+$ = 364.17 | 754 |
| 892 | 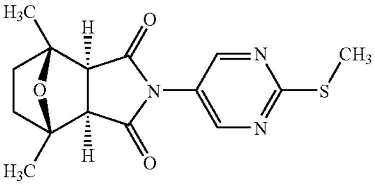 | | 3.09 LCMS $[M + H]^+$ = 319.93 | 470E |
| 893 | 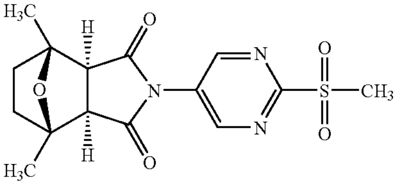 | | 2.30 LCMS $[M + H]^+$ = 351.96 | 470E |
| 894 | 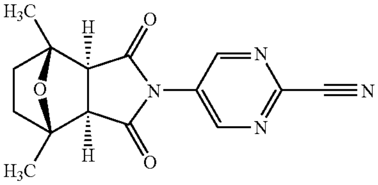 | | 2.88 LCMS $[M + H]^+$ = 299.02 | 470E |

TABLE 18-continued

| Ex. No | Structure | Compound Name/Comments | Retention Time Min./ Molecular Mass | Proc. of Ex. |
|---|---|---|---|---|
| 895 | 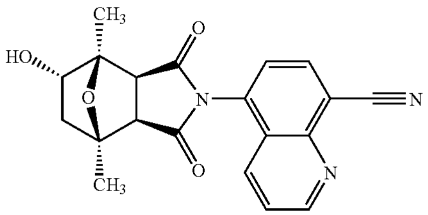 | Chiral, absolute stereochemistry as shown | 2.16 LCMS $[M + H]^+$ = 364.20 | 799 |
| 896 | 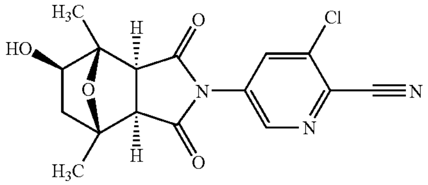 Chiral | Chiral, absolute stereochemistry as shown | 2.66 LCMS $[M + H]^+$ = 348.30 | 754 |
| 897 | 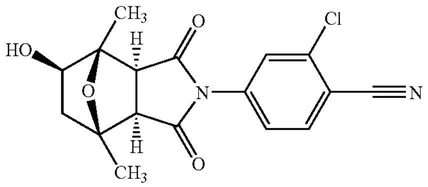 | Chiral, absolute stereochemistry as shown | 2.32 LCMS $[M + H]^+$ = 347.18 | 754 |
| 898 | 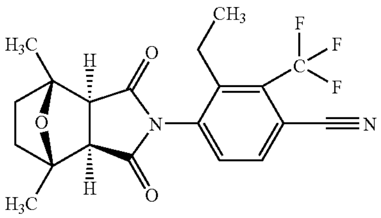 | | 3.47 LCMS $[M + H]^+$ = 393.19 | 470E |
| 899 | 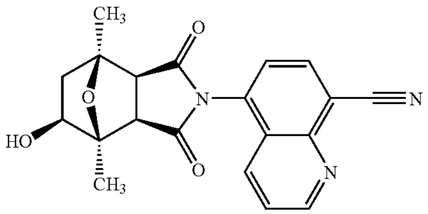 | Chiral, absolute stereochemistry as shown | 1.83 LCMS $[M + H]^+$ = 364.17 | 761 |
| 900 | 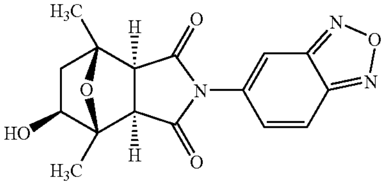 Chiral | Chiral, absolute stereochemistry as shown | 2.56 LCMS $[M + H]^+$ = 330.20 | 480A, 761 |

TABLE 18-continued

| Ex. No | Structure | Compound Name/Comments | Retention Time Min./ Molecular Mass | Proc. of Ex. |
|---|---|---|---|---|
| 901 | 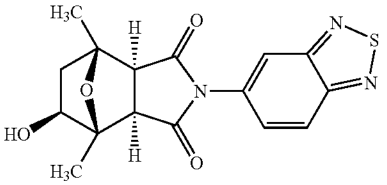 Chiral | Chiral, absolute stereochemistry as shown | 2.54 LCMS [M + H]$^+$ = 346.12 | 424A, 761 |
| 902 | 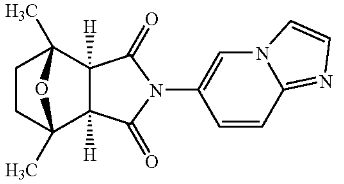 | | 1.48 LCMS [M + H]$^+$ = 312.14 | 470E, 844A |
| 903 | 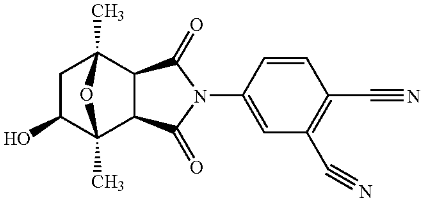 Chiral | Chiral, absolute stereochemistry as shown | 1.89 LCMS [M + H]$^+$ = 336.17 | 761 |
| 904 | 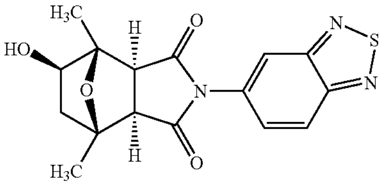 Chiral | Chiral, absolute stereochemistry as shown | 2.52 LCMS [M + H]$^+$ = 346.06 | 424A, 754 |
| 905 | 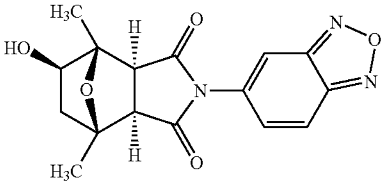 Chiral | Chiral, absolute stereochemistry as shown [3aS-(3aα,4β,5β,7β,7aα)]-2-(2,1,3-Benzoxadiazol-5-yl)hexahydro-5-hydroxy-4,7-dimethyl-4,7-epoxy-1H-isoindole-1,3(2H)-dione | 2.55 LCMS [M − H]$^-$ = 328.10 | 480A, 754 |
| 906 | 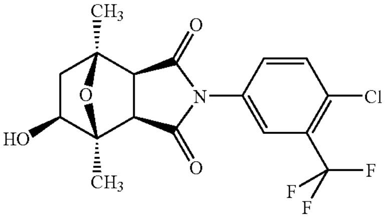 Chiral | Chiral, absolute stereochemistry as shown [3aR-(3aα,4β,5β,7β,7aα)]-2-(4-Chloro-3-(trifluoromethyl)phenyl)hexahydro-5-hydroxy-4,7-dimethyl-4,7-epoxy-1H-isoindole-1,3(2H)-dione | 3.06 LCMS [M + H]$^+$ = 390.20 | 761 |

TABLE 18-continued

| Ex. No | Structure | Compound Name/Comments | Retention Time Min./ Molecular Mass | Proc. of Ex. |
|---|---|---|---|---|
| 907 | 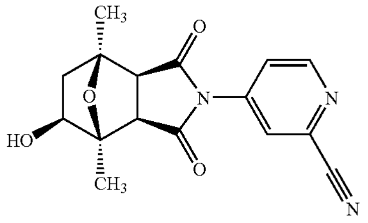 Chiral | Chiral, absolute stereochemistry as shown | 1.567 LCMS $[M + H]^+ =$ 314.16 | 761 |
| 908 | 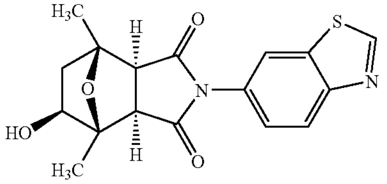 Chiral | Chiral, absolute stereochemistry as shown | 2.10 LCMS $[M + H]^+ =$ 345.14 | 761 |
| 909 | 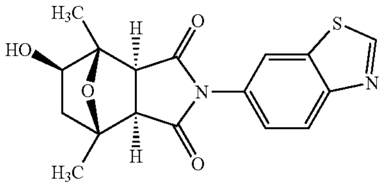 Chiral | Chiral, absolute stereochemistry as shown [3aS-(3aα,4β5β,7β,7aα)]-2-(6-Benzothiazolyl)hexahydro-5-hydroxy-4,7-dimethyl-4,7-epoxy-1H-isoindole-1,3(2H)-dione | 2.10 LCMS $[M + H]^+ =$ 345.14 | 754 |
| 910 | 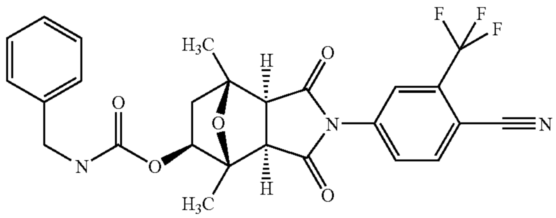 Chiral | Chiral, absolute stereochemistry as shown | 3.90 LCMS $[M + H]^+ =$ 514.36 | 756 |
| 911 | 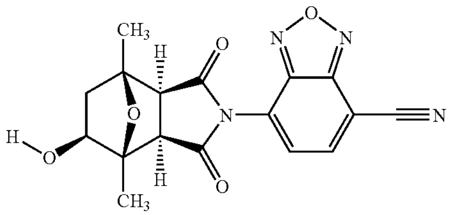 Chiral | Chiral, absolute stereochemistry as shown | 2.15 LCMS $[M + H]^+ =$ 337.16 | 761 |
| 912 | 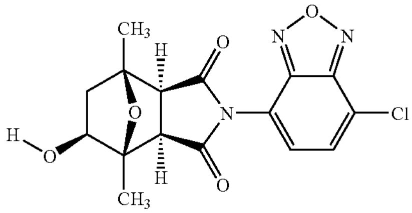 Chiral | Chiral, absolute stereochemistry as shown [3aR-(3aα,4β,5β,7β,7aα)]-2-(7-Chloro-2,1,3-benzoxadiazol-4-yl)hexahydro-5-hydroxy-4,7-dimethyl-4,7-epoxy-1H-isoindole-1,3(2H)-dione | 2.55 LCMS $[M + H]^+ =$ 364.18 | 761 |

TABLE 18-continued

| Ex. No | Structure | Compound Name/Comments | Retention Time Min./ Molecular Mass | Proc. of Ex. |
|---|---|---|---|---|
| 913 | 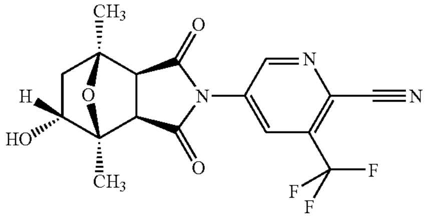 Chiral | Chiral, absolute stereochemistry not known [3aR-(3aα,4β,5α,7β,7aα)]-5-(Octahydro-5-hydroxy-4,7-dimethyl-1,3-dioxo-4,7-epoxy-2H-isoindol-2-yl)-3-(trifluoromethyl)-2-pyridinecarbonitrile | 2.933 LCMS $[M + H]^+$ = 382.26 | 763E, 799 |
| 914 | 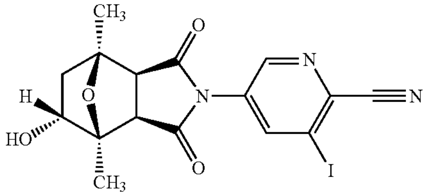 Chiral | Chiral, absolute stereochemistry not known [3aR-(3aα,4β,5α,7β,7aα)]-4-(Octahydro-5-hydroxy-4,7-dimethyl-1,3-dioxo-4,7-epoxy-2H-isoindol-2-yl)-2-iodobenzonitrile | 2.73 LCMS $[M + H]^+$ = 439.30 | 753F, 799 |
| 915 | 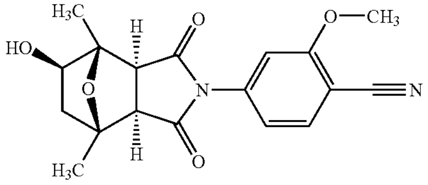 Chiral | Chiral, absolute stereochemistry as shown | 2.34 LCMS $[M + H]^+$ = 341.26 | 846 |
| 916 | 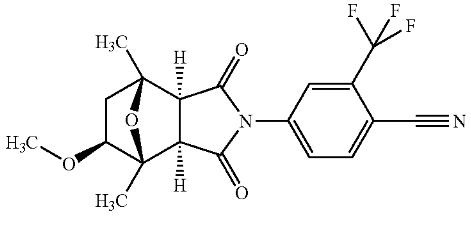 Chiral | Chiral, absolute stereochemistry as shown [3aR-(3aα,4I3,5β,7β,7aα)]-4-(Octahydro-5-methoxy-4,7-dimethyl-1,3-dioxo-4,7-epoxy-2H-isoindol-2-yl)-2-(trifluoromethyl)benzonitrile | 3.44 LCMS $[M + H]^+$ = 395.43 | 757A |
| 917 | 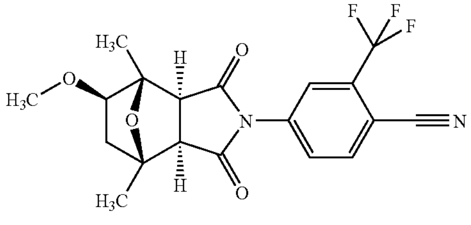 Chiral | Chiral, absolute stereochemistry as shown [3aS-(3aα,4β,5β,7β,7aα)]-4-(Octahydro-5-methoxy-4,7-dimethyl-1,3-dioxo-4,7-epoxy-2H-isoindol-2-yl)-2-(trifluoromethyl)benzonitrile | $[M + H]^+$ = 395.07 | 757A |
| 918 | 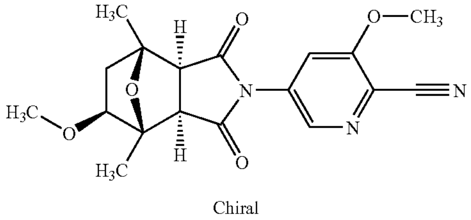 Chiral | Chiral, absolute stereochemistry as shown | 1.83 LCMS $[M + H]^+$ = 344.03 | 761 |

TABLE 18-continued

| Ex. No | Structure | Compound Name/Comments | Retention Time Min./ Molecular Mass | Proc. of Ex. |
|---|---|---|---|---|
| 919 | 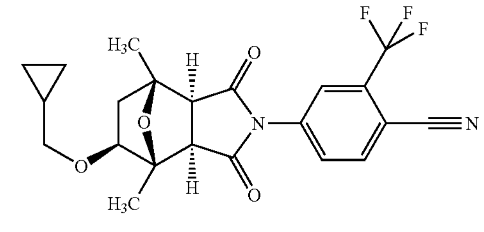 Chiral | Chiral, absolute stereochemistry as shown [3aR-(3aα,4β,5β,7β,7aα)]-4-(Octahydro-5-cyclopropylmethoxy-4,7-dimethyl-1,3-dioxo-4,7-epoxy-2H-isoindol-2-yl)-2-(trifluoromethyl)benzonitrile | 3.84 LCMS $[M + H]^+$ = 435.10 | 757A |
| 920 | 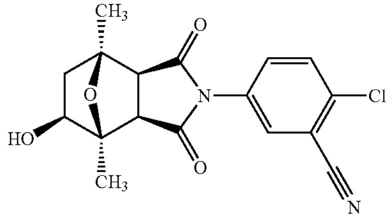 Chiral | Chiral, absolute stereochemistry as shown | 2.373 LCMS $[M + H]^+$ = 347.01 | 761 |
| 921 | 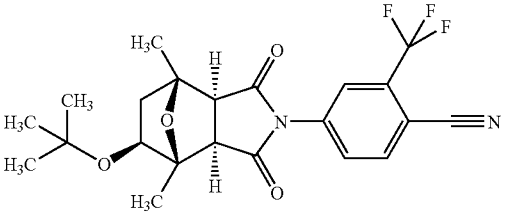 Chiral | Chiral, absolute stereochemistry as shown | 3.91 LCMS $[M + H]^+$ = 436 | 757A |
| 922 | 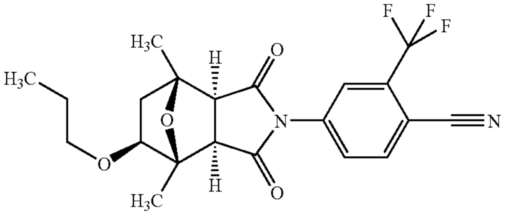 Chiral | Chiral, absolute stereochemistry as shown | 3.88 LCMS $[M + H]^+$ = 422.99 | 757A |
| 923 | 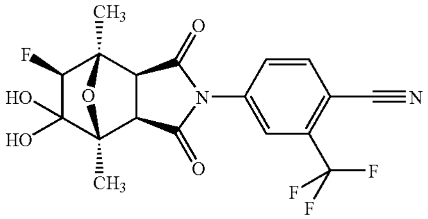 Chiral | Chiral, absolute stereochemistry as shown [3aR-(3aα,4β,6β,7β,7aα)]-4-(Octahydro-6-fluoro-5,5-dihydroxy-4,7-dimethyl-1,3-dioxo-4,7-epoxy-2H-isoindol-2-yl)-2-(trifluoromethyl)benzonitrile | 2.663 LCMS $[M + H]^+$ = 413.19 | 798 |

TABLE 18-continued

| Ex. No | Structure | Compound Name/Comments | Retention Time Min./ Molecular Mass | Proc. of Ex. |
|---|---|---|---|---|
| 924 | 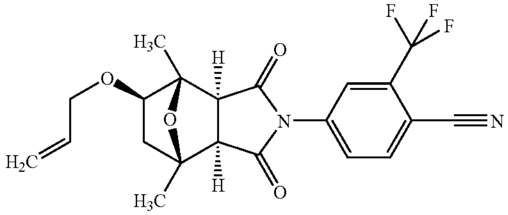 Chiral | Chiral, absolute stereochemistry as shown | 3.74 LCMS $[M + H]^+$ = 421.06 | 757A |
| 925 | 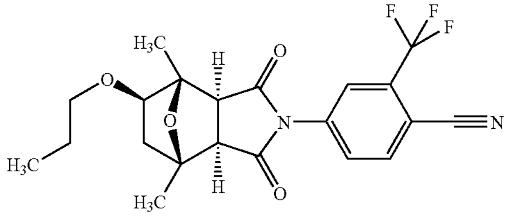 Chiral | Chiral, absolute stereochemistry as shown | 3.89 LCMS $[M + H]^+$ = 423.07 | 757A |
| 926 | 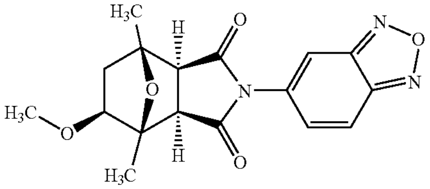 Chiral | Chiral, absolute stereochemistry as shown | 3.027 LCMS $[M + H]^+$ = 344.01 | 480A, 757A, 761 |
| 927 | 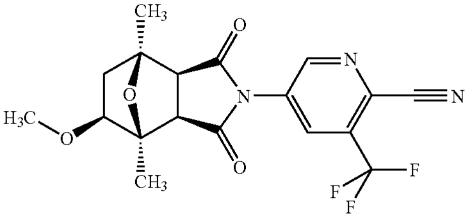 Chiral | Chiral, absolute stereochemistry as shown | 2.993 LCMS $[M + H]^+$ = 396.00 | 757A, 763F |
| 928 | 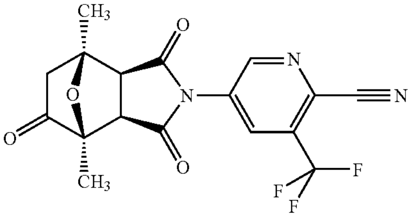 Chiral | Chiral, absolute stereochemistry as shown [3aR-(3aα,4β,7β,7aα)]-5-(Octahydro-4,7-dimethy-1,3,5-trioxo-4,7-epoxy-2H-isoindol-2-yl)-3-(trifluoromethyl)-2-pyridinecarbonitrile | 3.153 LCMS $[M + H]^+$ = 411.04 | 763E, 795 |
| 929 | 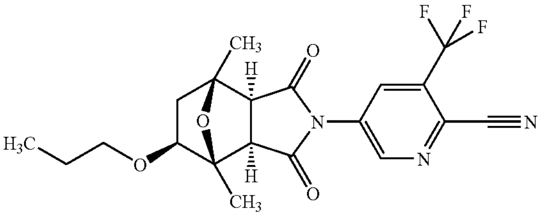 Chiral | Chiral, absolute stereochemistry as shown | 3.50 LCMS $[M + H]^+$ = 424.07 | 757A |

TABLE 18-continued

| Ex. No | Structure | Compound Name/Comments | Retention Time Min./ Molecular Mass | Proc. of Ex. |
|---|---|---|---|---|
| 930 | 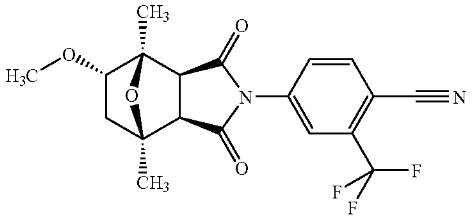 Chiral | Chiral, absolute stereochemistry as shown | 2.887 LCMS $[M + H]^+$ = 395.07 | 757A |
| 931 | 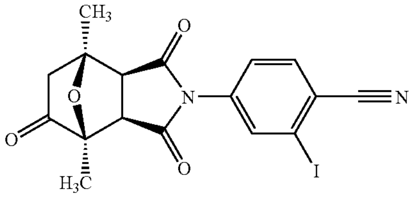 Chiral | Chiral, absolute stereochemistry as shown (3aα,4β,7β,7aα)-4-(Octahydro-4,7-dimethyl-1,3,5-trioxo-4,7-epoxy-2H-isoindol-2-yl)-2-iodobenzonitrile | 2.963 LCMS $[M + H]^+$ = 469.0 | 753F, 795 |
| 932 | 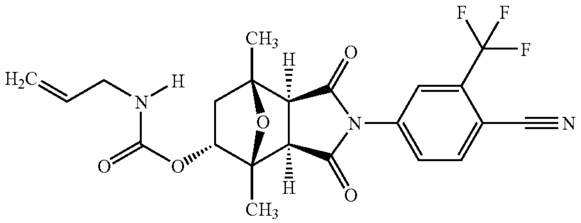 | Chiral, absolute stereochemistry as shown | 14.30 LC** $[M + H]^+$ = 464 | 810 |
| 933 | 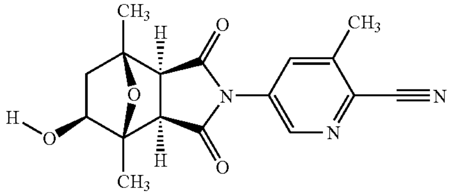 | Chiral, absolute stereochemistry as shown | 1.83 LCMS $[M + H]^+$ = 328.37 | 761 |
| 934 | 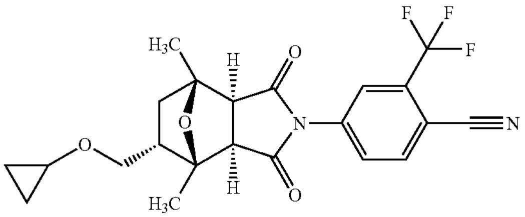 | Chiral, absolute stereochemistry not know | 3.85 LCMS $[M + H]^+$ = 433.27 | 852 |
| 935 | 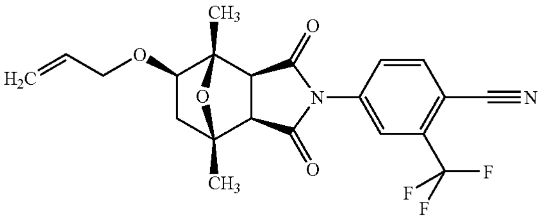 | Chiral, absolute stereochemistry as shown | 16.070 LC* $[M + H]^+$ = 421 | 757A |

TABLE 18-continued

| Ex. No | Structure | Compound Name/Comments | Retention Time Min./ Molecular Mass | Proc. of Ex. |
|---|---|---|---|---|
| 936 | 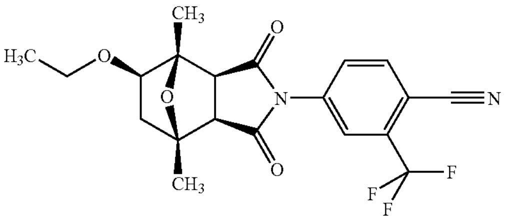 | Chiral, absolute stereochemistry as shown | 15.812 LC* $[M + H]^+$ = 409 | 757A |
| 937 | 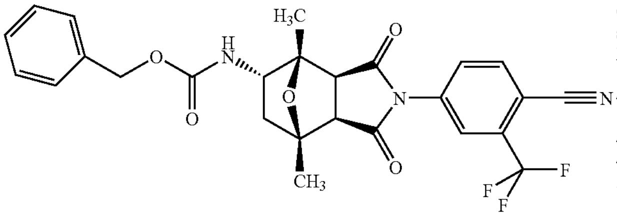 | Chiral, absolute stereochemistry not known (3aα,4β,5α,7β,7aα)-4-(Octahydro-5-[[phenylmethoxycarbonyl]amino]-4,7-dimethyl-1,3-dioxo-4,7-epoxy-2H-isoindol-2-yl)-2-(trifluoromethyl)benzonitrile | 15.627 LC* $[M + H]^+$ = 514 | 812 |
| 938 | 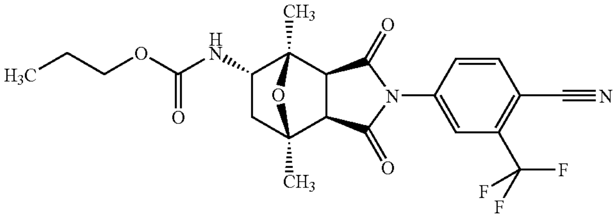 | Chiral, absolute stereochemistry not known (3aα,4β,5α,7β,7aα)-4-(Octahydro-5-[[propyloxycarbonyl]amino]-4,7-dimethyl-1,3-dioxo-4,7-epoxy-2H-isoindol-2-yl)-2-(trifluoromethyl)benzonitrile | 14.842 LC* $[M + H]^+$ = 416 | 812 |
| 939 | 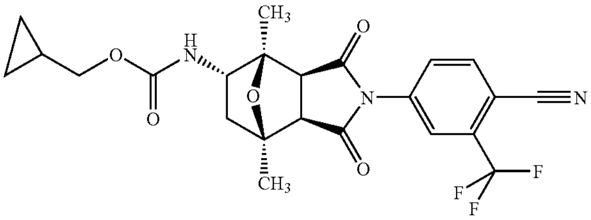 | Chiral, absolute stereochemistry not known (3aα,4β,5α,7β,7aα)-4-(Octahydro-5-[[[cyclopropyl-methyloxy]carbonyl]amino]-4,7-dimethyl-1,3-dioxo-4,7-epoxy-2H-isoindol-2-yl)-2-(trifluoromethyl)benzonitrile | 14.852 LC* $[M + H]^+$ = 478 | 812 |
| 940 | 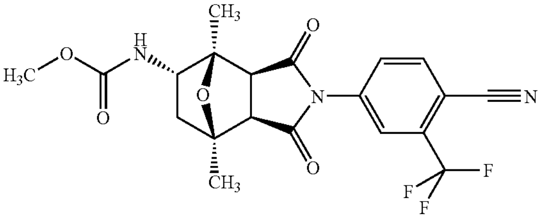 | Chiral, absolute stereochemistry not known (3aα,4β,5α,7β,7aα)-4-(Octahydro-5-[[methoxycarbonyl]amino]-4,7-dimethyl-1,3-dioxo-4,7-epoxy-2H-isoindol-2-yl)-2-(trifluoromethyl)benzonitrile | 13.241 LC* $[M + H]^+$ = 438 | 812 |
| 941 | 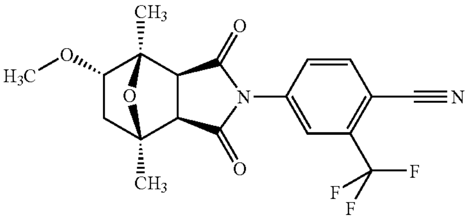 | Chiral, absolute stereochemistry not known | 14.671 LC* $[M + H]^+$ = 395.3 | 855 |

TABLE 18-continued

| Ex. No | Structure | Compound Name/Comments | Retention Time Min./ Molecular Mass | Proc. of Ex. |
|---|---|---|---|---|
| 942 | 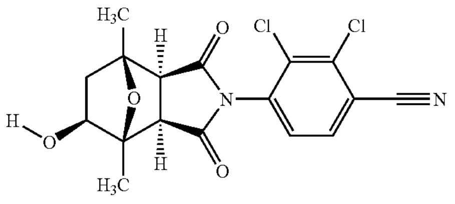 Chiral | Chiral, absolute stereochemistry as shown [3aR-(3aα,4β,5β,7β,7aα)]-4-(Octahydro-5-hydroxy-4,7-dimethyl-1,3-dioxo-4,7-epoxy-2H-isoindol-2-yl)-2,3-dichlorobenzonitrile | 2.63 LCMS $[M+H]^+ = 382.95$ | 761 |
| 943 | 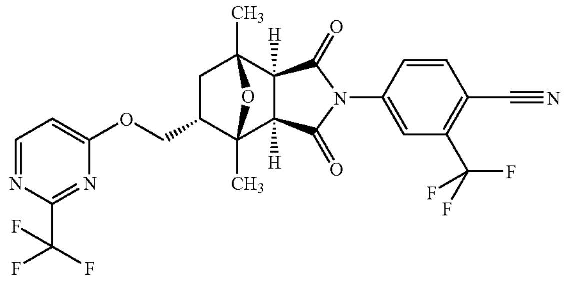 | Chiral, absolute stereochemistry not known | 3.987 LCMS $[M+H]^+ =$ 541.07 | 851 |
| 944 | 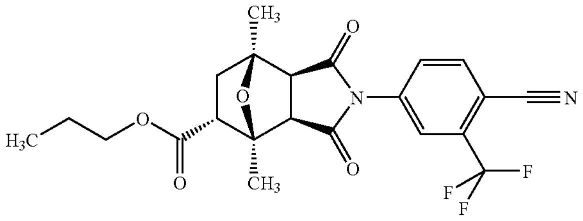 Chiral | Chiral, absolute stereochemistry not known | 16.595 LC* $[M+H]^+ =$ 451.3 | 830 |
| 945 | 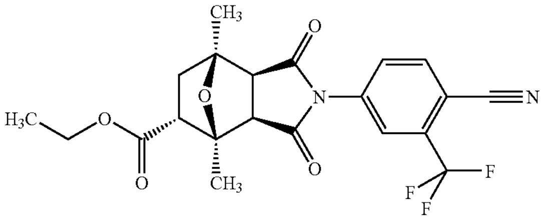 Chiral | Chiral, absolute stereochemistry not known | 16.294 LC* $[M+H]^+ =$ 437.3 | 830 |
| 946 | 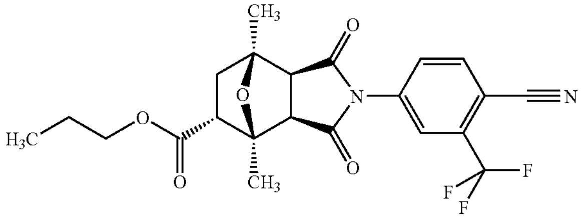 | Chiral, absolute stereochemistry not known | 17.077 LC* $[M+H]^+ =$ 451.2 | 830 |
| 947 | 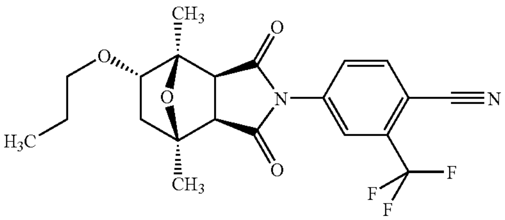 | Chiral, absolute stereochemistry not known | 16.970 LC* $[M+H]^+ =$ 423.7 | 757A |

TABLE 18-continued

| Ex. No | Structure | Compound Name/Comments | Retention Time Min./ Molecular Mass | Proc. of Ex. |
|---|---|---|---|---|
| 948 | 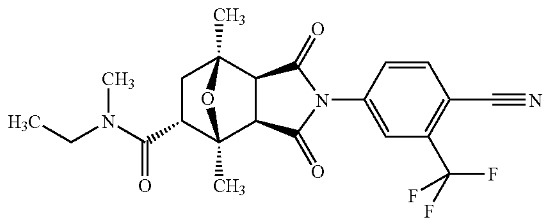 | Chiral, absolute stereochemistry not known | 14.750 LC* $[M + H]^+$ = 450.4 | 811 |
| 949 | 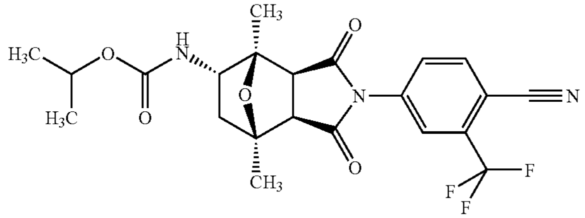 Chiral | Chiral, absolute stereochemistry not known [3aS-(3aα,4β,5α,7β,7aα)]-4-(Octahydro-5-[[(1-methylethoxy)carbonyl]amino]-4,7-dimethyl-1,3-dioxo-4,7-epoxy-2H-isoindol-2-yl)-2-(trifluoromethyl)benzonitrile | 15.314 LC* $[M + H]^+$ = 465 | 812 |
| 950 | 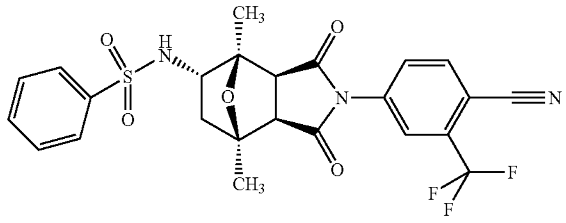 | Chiral, absolute stereochemistry not known (3aα,4β,5α,7β,7aα)-4-(Octahydro-5-benzenesulfonamido-4,7-dimethyl-1,3-dioxo-4,7-epoxy-2H-isoindol-2-yl)-2-(trifluoromethyl)benzonitrile | 15.394 LC* $[M + H]^+$ = 519 | 809 |
| 951 | 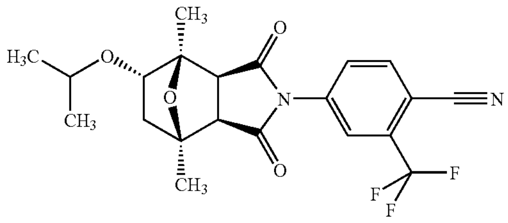 | Chiral, absolute stereochemistry not known | 16.902 LC* $[M + H]^+$ = 423 | 757A |
| 952 | 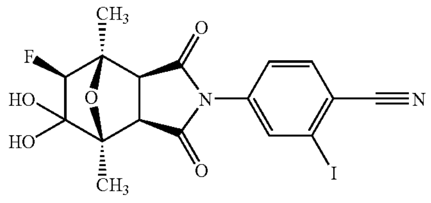 Chiral | Chiral, absolute stereochemistry as shown [3aR-(3aα,4β,6β,7β,7aα)]-4-(Octahydro-6-fluoro-5,5-dihydroxy-4,7-dimethyl-1,3-dioxo-4,7-epoxy-2H-isoindol-2-yl)-2-iodobenzonitrile | 2.497 LCMS $[M - H]^+$ = 471.07 | 753F, 798 |
| 953 | 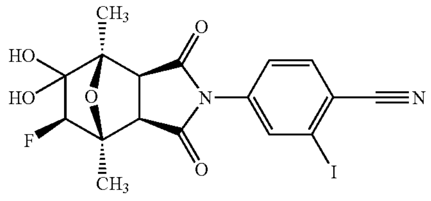 Chiral | Chiral, absolute stereochemistry as shown [3aS-(3aα,4β,6β,7β,7aα)]-4-(Octahydro-6-fluoro-5,5-dihydroxy-4,7-dimethyl-1,3-dioxo-4,7-epoxy-2H-isoindol-2-yl)-2-iodobenzonitrile | 2.497 LCMS $[M - H]^+$ = 471.07 | 753F, 798 |

TABLE 18-continued

| Ex. No | Structure | Compound Name/Comments | Retention Time Min./ Molecular Mass | Proc. of Ex. |
|---|---|---|---|---|
| 954 | 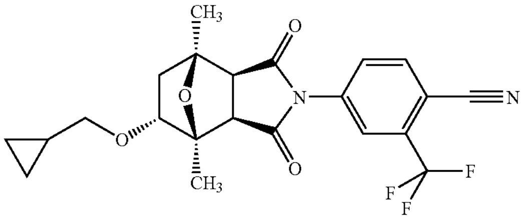 | Chiral, absolute stereochemistry not known | 17.119** MS $[M + H]^+$ = 435 | A. 757A |
| 955 | 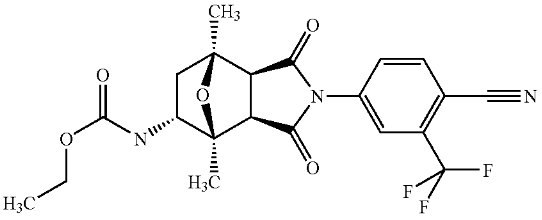 Chiral | Chiral, absolute stereochemistry not known [3aR-(3aα,4β,5α,7β,7aα)]-4-(Octahydro-5-[[ethoxycarbonyl]amino]-4,7-dimethyl-1,3-dioxo-4,7-epoxy-2H-isoindol-2-yl)-2-(trifluoromethyl)benzonitrile | 14.536 LC* $[M + H]^+$ = 452 | 812 |
| 956 | 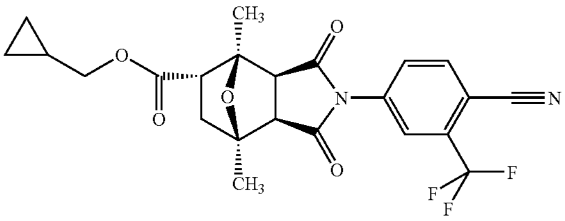 Chiral | Chiral, absolute stereochemistry not known | 18.043 LC* $[M + H]^+$ = 436.2 | 830 |
| 957 | 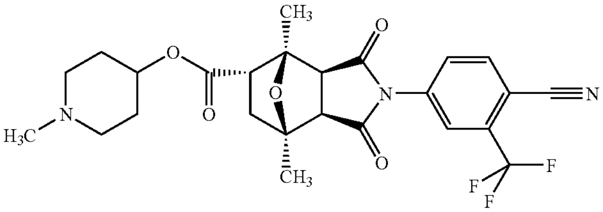 Chiral | Chiral, absolute stereochemistry not known | 13.764 LC* $[M + H]^+$ = 506.2 | 830 |
| 958 | 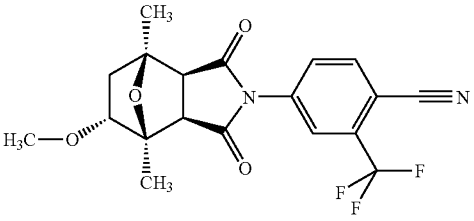 Chiral | Chiral, absolute stereochemistry not known [3aR-(3aα,4β,5α,7β,7aα)]-4-(Octahydro-5-methoxy-4,7-dimethyl-1,3-dioxo-4,7-epoxy-2H-isoindol-2-yl)-2-(trifluoromethyl)benzonitrile | 3.243 LCMS $[M + H]^+$ = 395.07 | 855 |
| 959 | 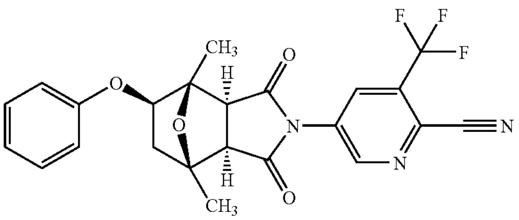 Chiral | Chiral, absolute stereochemistry as shown | 4.15 LCMS $[M + H]^+$ = 455.00 | 757 |

TABLE 18-continued

| Ex. No | Structure | Compound Name/Comments | Retention Time Min./ Molecular Mass | Proc. of Ex. |
|---|---|---|---|---|
| 960 | 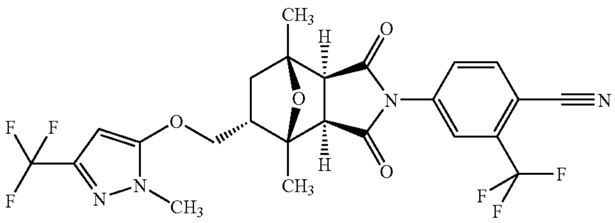 | Chiral, absolute stereochemistry as shown (3aα,4β,5α,7β,7aα)-4-(Octahydro-5-[[[2-methyl-5-(trifluoromethyl)-2H-pyrazol-3-yl]oxy]methyl]-4,7-dimethyl-1,3-dioxo-4,7-epoxy-2H-isoindol-2-yl)-2-(trifluoromethyl)benzonitrile | 3.933 LCMS $[M + H]^+$ = 543.00 | 851 |
| 961 | 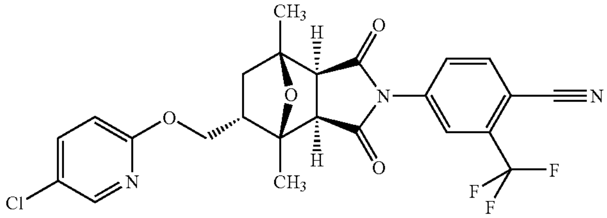 | Chiral, absolute stereochemistry as shown (3aα,4β,5α,7β,7aα)-4-(Octahydro-5-[[[5-chloro-2-pyridinyl]oxy]methyl]-4,7-dimethyl-1,3-dioxo-4,7-epoxy-2H-isoindol-2-yl)-2-(trifluoromethyl)benzonitrile | 4.46 LCMS $[M + H]^+$ = 505.92 | 851 |
| 962 | 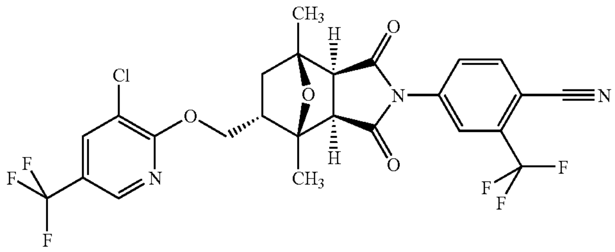 | Chiral, absolute stereochemistry as shown | 4.46 LCMS $[M + H]^+$ = 573.93 | 851 |
| 963 | 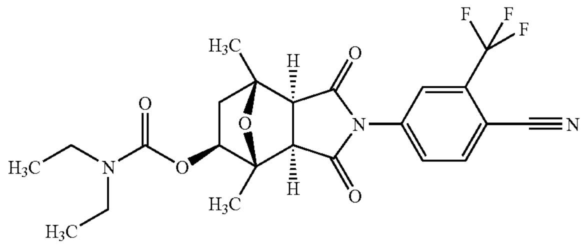 Chiral | Chiral, absolute stereochemistry as shown | 4.00 LCMS $[M + H]^+$ = 480.03 | 756 |
| 964 | 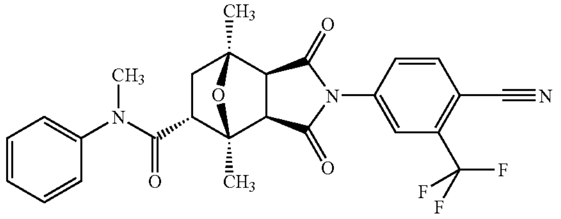 Chiral | Chiral, absolute stereochemistry not known [3aR-(3aα,4β,5α,7β,7aα)]-2-(4-Cyano-3-(trifluoromethyl)phenyl)hexahydro-4,7-dimethyl-1,3-dioxo-4,7-epoxy-N-methyl-N-phenyl-1H-isoindole-5-carboxamide | 18.695 LC* $[M + H]^+$ = 498.0 | 811 |

TABLE 18-continued

| Ex. No | Structure | Compound Name/Comments | Retention Time Min./ Molecular Mass | Proc. of Ex. |
|---|---|---|---|---|
| 965 | 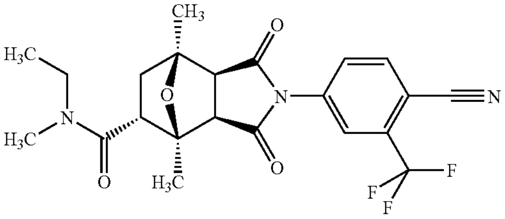 Chiral | Chiral, absolute stereochemistry not known | 17.025 LC* $[M + H]^+$ = 450.2 | 811 |
| 966 | 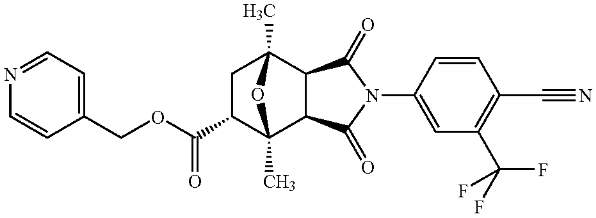 Chiral | Chiral, absolute stereochemistry not known | 15.425 LC* $[M + H]^+$ = 500.2 | 830 |
| 967 | 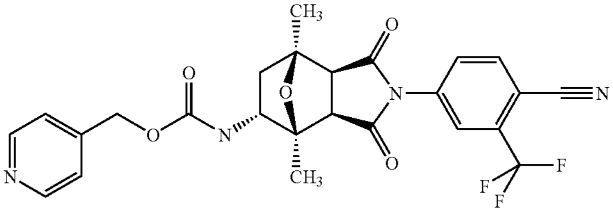 Chiral | Chiral, absolute stereochemistry not known | 14.375 LC* $[M + H]^+$ = 498 | 812 |
| 968 | 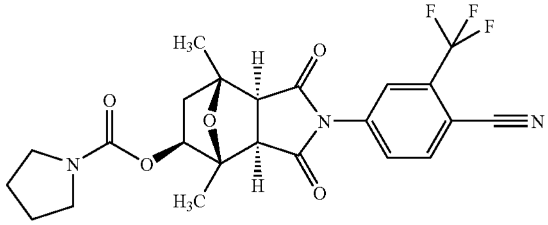 Chiral | Chiral, absolute stereochemistry as shown | 3.90 LCMS $[M + H]^+$ = 478.09 | 756 |
| 969 | 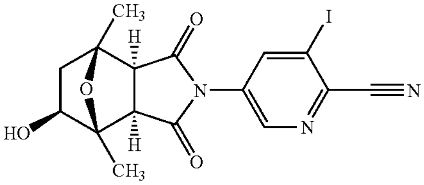 Chiral | Chiral, absolute stereochemistry as shown | 2.32 LCMS $[M + H]^+$ = 439.92 | 761 |
| 970 | 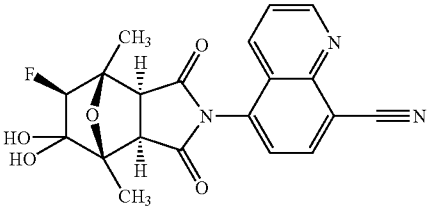 | Chiral, absolute stereochemistry as shown | 1.95 LCMS $[M + H]^+$ = 398.25 | 798 |

TABLE 18-continued

| Ex. No | Structure | Compound Name/Comments | Retention Time Min./ Molecular Mass | Proc. of Ex. |
|---|---|---|---|---|
| 971 | 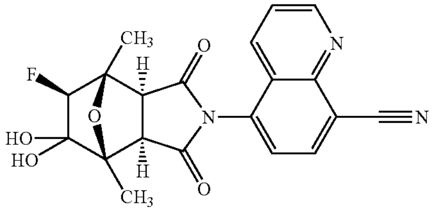 Chiral | Chiral, absolute stereochemistry as shown [3aR-(3aα,4β,5α,7β,7aα)]-4-(Octahydro-5-[[(4-fluorophenylamino)carbonyl]oxy]-4,7-dimethyl-1,3-dioxo-4,7-epoxy-2H-isoindol-2-yl)-2-(trifluoromethyl)benzonitrile | 3.757 LCMS $[M + H]^+$ = 516.31 | 798 |
| 972 | 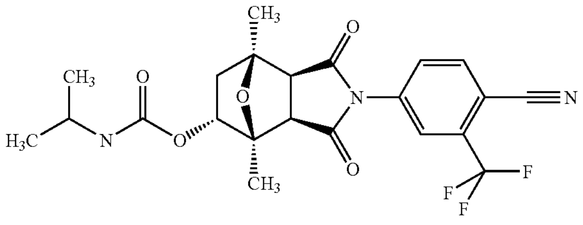 Chiral | Chiral, absolute stereochemistry not known [3aR-(3aα,4β,5α,7β,7aα)]-4-(Octahydro-5-[[( 1-methylethylamino)carbonyl]oxy]-4,7-dimethyl-1,3-dioxo-4,7-epoxy-2H-isoindol-2-yl)-2-(trifluoromethyl)benzonitrile | 3.367 LCMS $[M + H]^+$ = 464.32 | 810 |
| 973 | 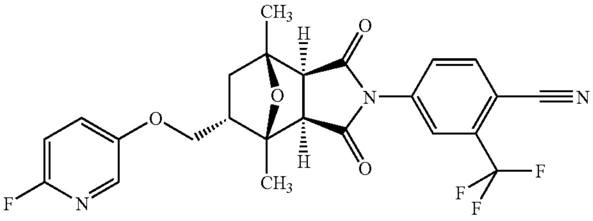 | Chiral, absolute stereochemistry not known | 3.80 LCMS $[M + H]^+$ = 490.04 | 851 |
| 974 | 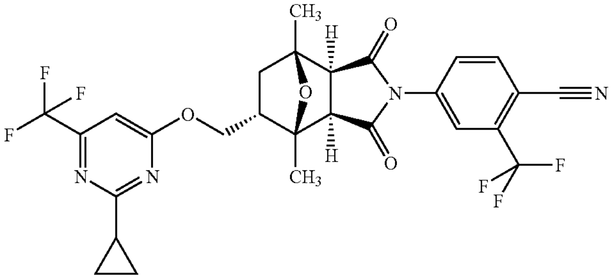 | Chiral, absolute stereochemistry not known | 4.383 LCMS $[M + H]^+$ = 581.10 | 851 |
| 975 | 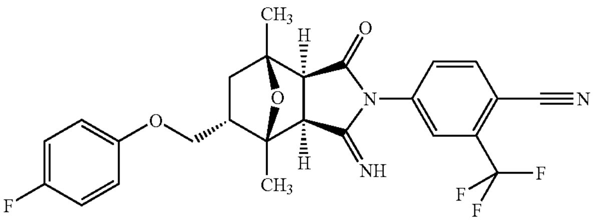 | Chiral, absolute stereochemistry not known | 4.147 LCMS $[M + H]^+$ = 489.01 | 851 |
| 976 | 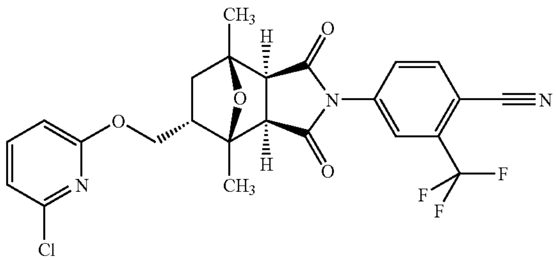 | Chiral, absolute stereochemistry not known | 4.173 LCMS $[M + H]^+$ = 507.99 | 851 |

TABLE 18-continued

| Ex. No | Structure | Compound Name/Comments | Retention Time Min./ Molecular Mass | Proc. of Ex. |
|---|---|---|---|---|
| 977 | 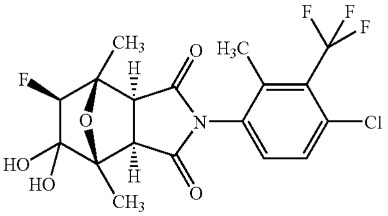 | Chiral, absolute stereochemistry as shown | 3.34 LCMS [M + H]+ = 436.26 | 798 |
| 978 | 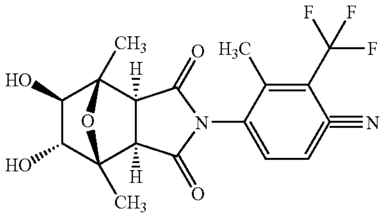 Chiral | Chiral, absolute stereochemistry not known [3aR-(3aα,4β,5β,6α,7β,7aα)]-4-(Octahydro-5,6-dihydroxy-4,7-dimethyl-1,3-dioxo-4,7-epoxy-2H-isoindol-2-yl)-3-methyl-2-(trifluoromethyl)benzonitrile | 3.28 LCMS [M + H]+ = 411.0 | 787 |
| 979 | 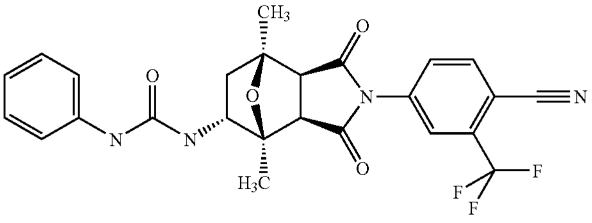 Chiral | Chiral, absolute stereochemistry not known [3aR-(3aα,4β,5α,7β,7aα)]-4-(Octahydro-5-[[[phenylamino]carbonyl]amino]-4,7-dimethyl-1,3-dioxo-4,7-epoxy-2H-isoindol-2-yl)-2-(trifluoromethyl)benzonitrile | 14.736 LC* [M + H]+ = 499.3 | 815 |
| 980 | 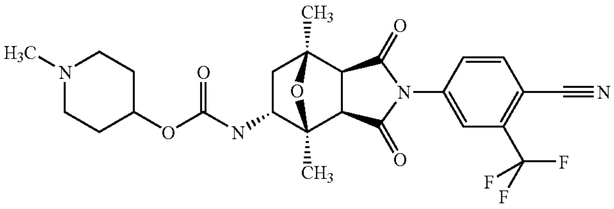 Chiral | Chiral, absolute stereochemistry not known | 15.370 LC* [M + H]+ = 521.4 | 812 |
| 981 | 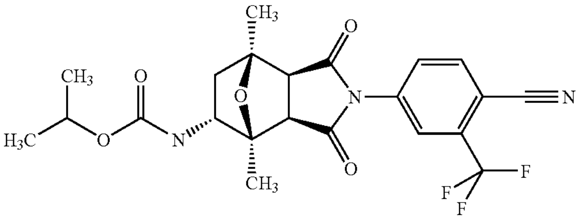 Chiral | Chiral, absolute stereochemistry not known [3aR-(3aα,4β,5α,7β,7aα)]-4-(Octahydro-5-[[(1-methylethyloxy)carbonyl]amino]-4,7-dimethyl-1,3-dioxo-4,7-epoxy-2H-isoindol-2-yl)-2-(trifluoromethyl)benzonitrile | 15.108 LC* [M + H]+ = 466 | 812 |
| 982 | 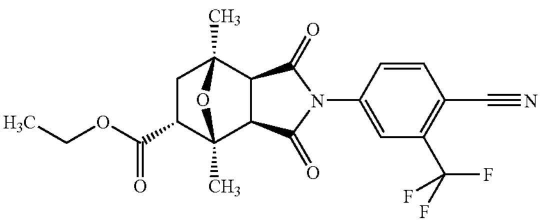 Chiral | Chiral, absolute stereochemistry not known | 16.235 LC* [M + H]+ = 437.0 | 830 |

TABLE 18-continued

| Ex. No | Structure | Compound Name/Comments | Retention Time Min./ Molecular Mass | Proc. of Ex. |
|---|---|---|---|---|
| 983 | 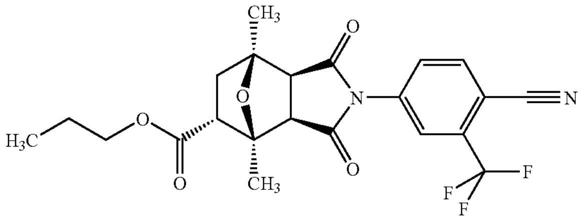 Chiral | Chiral, absolute stereochemistry not known | 17.195 LC* $[M + H]^+$ = 451.20 | 830 |
| 984 | 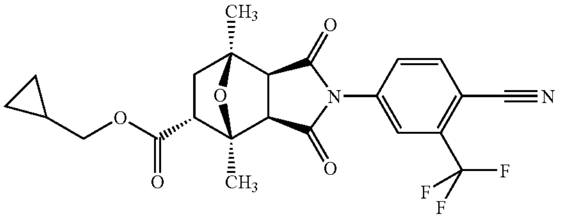 Chiral | Chiral, absolute stereochemistry not known | 16.851 LC* $[M + H]^+$ = 463.25 | 830 |
| 985 | 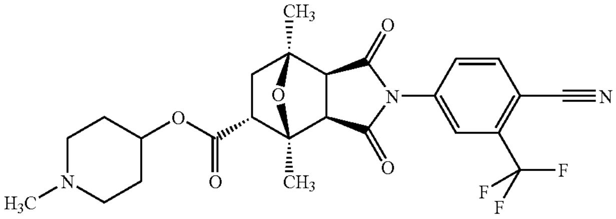 Chiral | Chiral, absolute stereochemistry not known | 12.530 LC* $[M + H]^+$ = 506.30 | 830 |
| 986 | 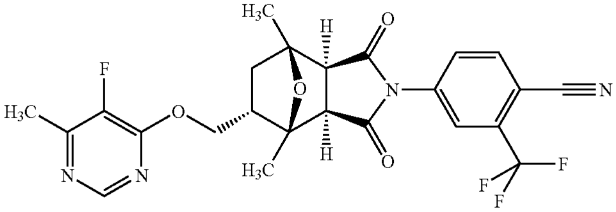 | Chiral, absolute stereochemistry not known | 3.947 LCMS $[M + H]^+$ = 505.27 | 851 |
| 987 | 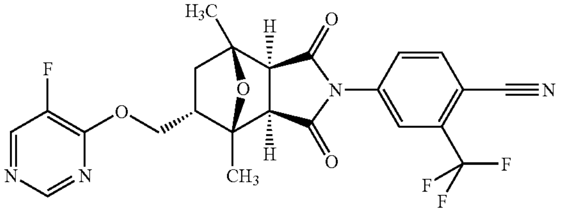 | Chiral, absolute stereochemistry not known (3aα,4β,5α,7β,7aα)-4-(Octahydro-5-[[[5-fluoro-4-pyrimidinyl]oxy]methyl]-4,7-dimethyl-1,3-dioxo-4,7-epoxy-2H-isoindol-2-yl)-2-(trifluoromethyl)benzonitrile | 3.80 LCMS $[M + H]^+$ = 491.08 | 851 |
| 988 | 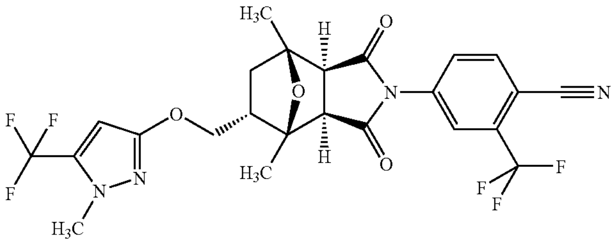 | Chiral, absolute stereochemistry not known | 3.80 LCMS $[M + H]^+$ = 543.07 | 851 |

TABLE 18-continued

| Ex. No | Structure | Compound Name/Comments | Retention Time Min./ Molecular Mass | Proc. of Ex. |
|---|---|---|---|---|
| 989 | 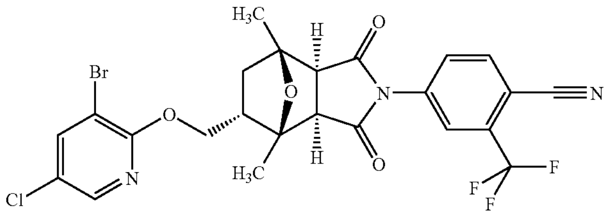 | Chiral, absolute stereochemistry not known | 4.50 LCMS $[M + H]^+$ = 585.96 | 851 |
| 990 | 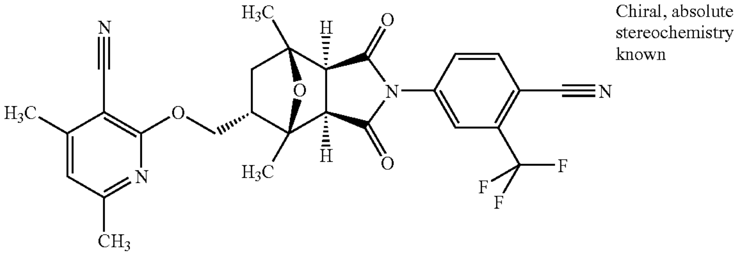 | Chiral, absolute stereochemistry not known | 4.09 LCMS $[M + H]^+$ = 525.12 | 851 |
| 991 | 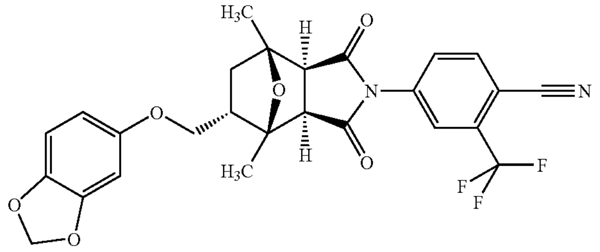 | Chiral, absolute stereochemistry not known | 4.12 LCMS $[M + H]^+$ = 515.05 | 851 |
| 992 | 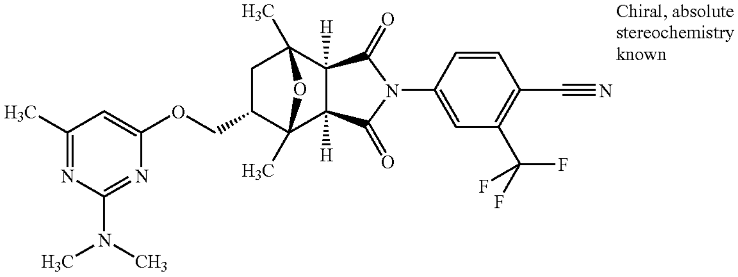 | Chiral, absolute stereochemistry not known | 3.10 LCMS $[M + H]^+$ = 530.13 | 851 |
| 993 | 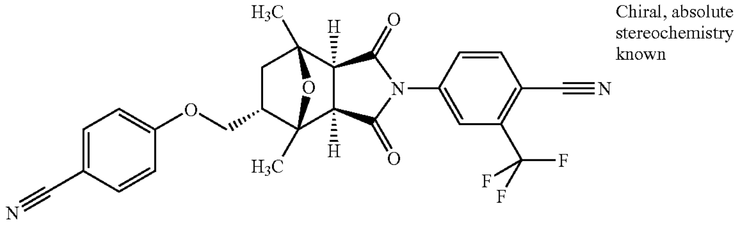 | Chiral, absolute stereochemistry not known | 3.95 LCMS $[M + H]^+$ = 496.05 | 851 |
| 994 | 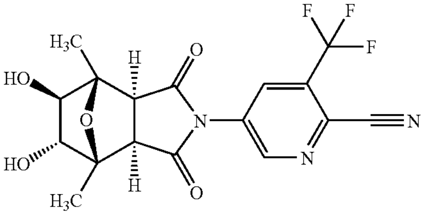 Chiral | Chiral, absolute stereochemistry not known | XXX LCMS $[M + H]^+$ = XXX | 797 |

TABLE 18-continued

| Ex. No | Structure | Compound Name/Comments | Retention Time Min./ Molecular Mass | Proc. of Ex. |
|---|---|---|---|---|
| 995 | 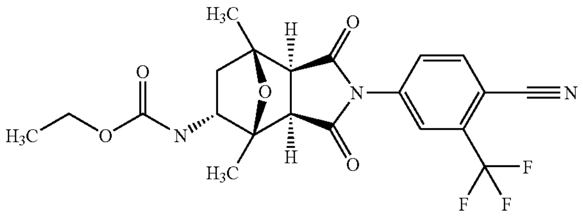 Chiral | Chiral, absolute stereochemistry not known [3aR-(3aα,4β,5α,7β,7aα)]-4-(Octahydro-5-[[ethyloxycarbonyl]amino]-4,7-dimethyl-1,3-dioxo-4,7-epoxy-2H-isoindol-2-yl)-2-(trifluoromethyl)benzonitrile | 14.522 LC* $[M + H]^+$ = 452 | 812 |
| 996 | 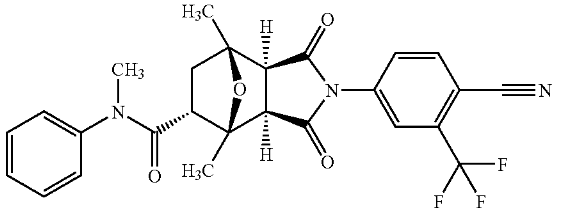 Chiral | Chiral, absolute stereochemistry not known | 16.068 LC* $[M + H]^+$ = 498.25 | 811 |
| 997 | 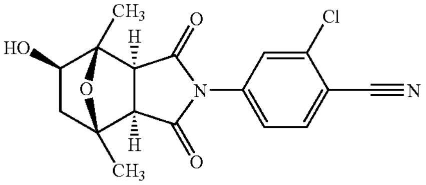 | Chiral, absolute stereochemistry not known | 14.076 LC* $[M + H]^+$ = 450.20 | 811 |
| 998 | 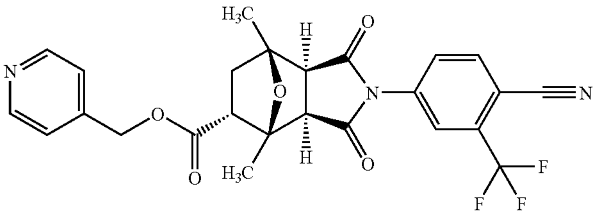 Chiral | Chiral, absolute stereochemistry not known [3aR-(3aα,4β,5α,7β,7aα)]-2-(4-Cyano-3-(trifluoromethyl)phenyl)-hexahydro-4,7-dimethyl-1,3-dioxo-4,7-epoxy-1H-isoindole-5-carboxylic acid, 4-pyridinylmethyl ester | 12.008 LC* $[M + H]^+$ = 500.2 | 830 |
| 999 | 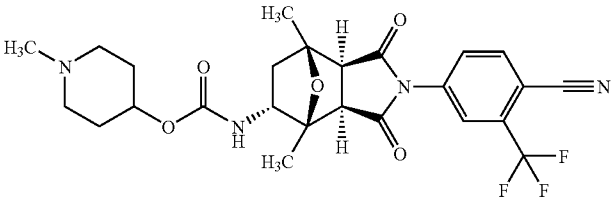 Chiral | Chiral, absolute stereochemistry not known | 11.196 LC* $[M + H]^+$ = 521.3 | 812 |
| 1000 | 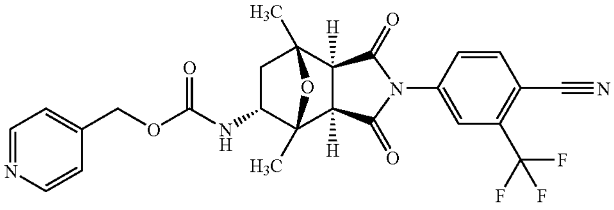 Chiral | Chiral, absolute stereochemistry not known [3aR-(3aα,4β,5α,7β,7aα)]-4-(Octahydro-5-[[4-pyridinylmethoxycarbonyl]amino]-4,7-dimethyl-1,3-dioxo-4,7-epoxy-2H-isoindol-2-yl)-2-(trifluoromethyl)benzonitrile | 11.342 LC* $[M + H]^+$ = 515.4 | 812 |

TABLE 18-continued

| Ex. No | Structure | Compound Name/Comments | Retention Time Min./ Molecular Mass | Proc. of Ex. |
|---|---|---|---|---|
| 1001 | 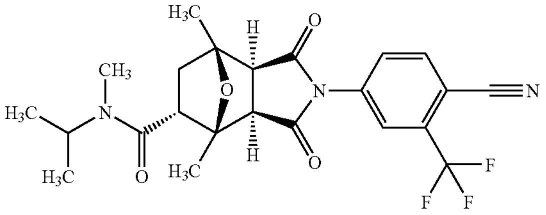 Chiral | Chiral, absolute stereochemistry not known | 14.897 LC* $[M + H]^+$ = 464.25 | 811 |
| 1002 | 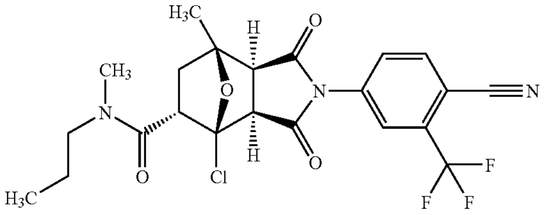 Chiral | Chiral, absolute stereochemistry not known | 14.905 LC* $[M + H]^+$ = 464.25 | 811 |
| 1003 | 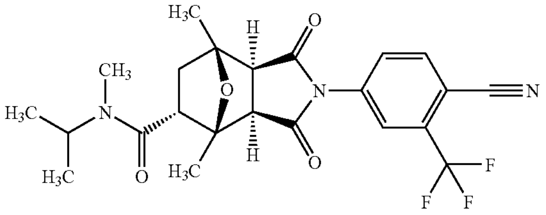 Chiral | Chiral, absolute stereochemistry not known | 14.692 LC* $[M + H]^+$ = 464.25 | 815 |
| 1004 | 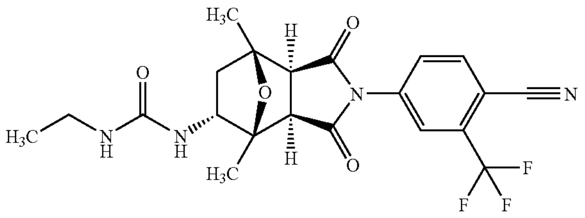 Chiral | Chiral, absolute stereochemistry not known | 11.93 LC* $[M + H]^+$ = 451.50 | 809 |
| 1005 | 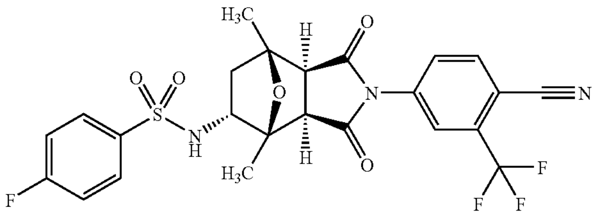 | Chiral, absolute stereochemistry not known | 15.325 LC* $[M + H]^+$ = 538.40 | 811 |
| 1006 | 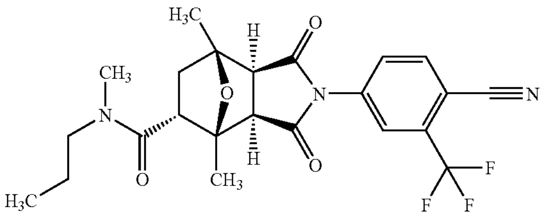 Chiral | Chiral, absolute stereochemistry not known | 14.724 LC* $[M + H]^+$ = 464.25 | 812 |

TABLE 18-continued

| Ex. No | Structure | Compound Name/Comments | Retention Time Min./ Molecular Mass | Proc. of Ex. |
|---|---|---|---|---|
| 1007 | 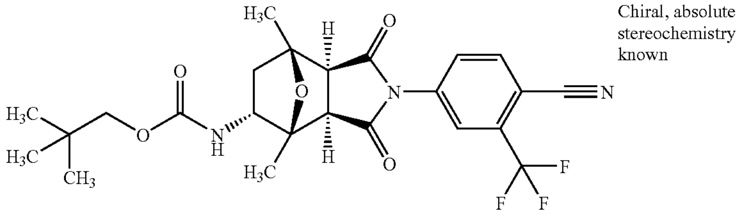 Chiral | Chiral, absolute stereochemistry not known | 16.123 LC* $[M + H]^+$ = 494.0 | 812 |
| 1008 | 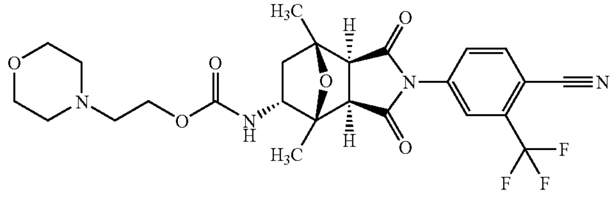 Chiral | Chiral, absolute stereochemistry not known | 11.187 LC* $[M + H]^+$ = 537.3 | 812 |
| 1009 | 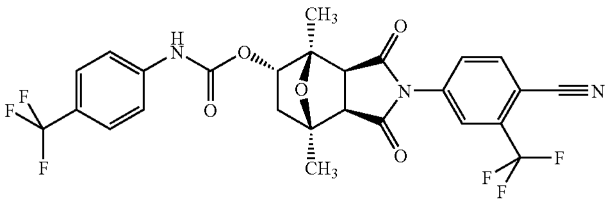 Chiral | Chiral, absolute stereochemistry not known | 4.02 LCMS $[M - H]^-$ = 566.18 | 812 |
| 1010 | 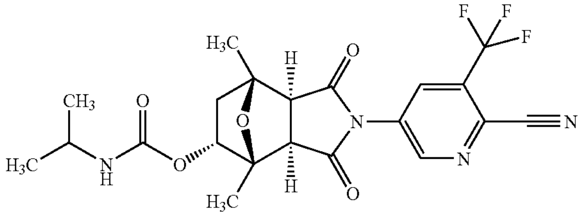 Chiral | Chiral, absolute stereochemistry not known | 3.35 LCMS $[M - H]^-$ = 464.19 | 810 |
| 1011 | 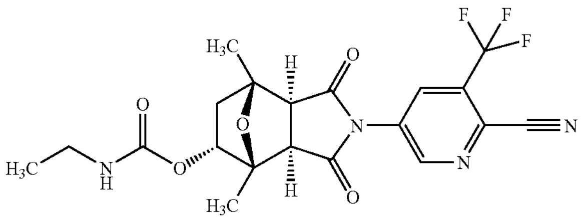 Chiral | Chiral, absolute stereochemistry not known | 3.23 LCMS | 814 |
| 1012 | 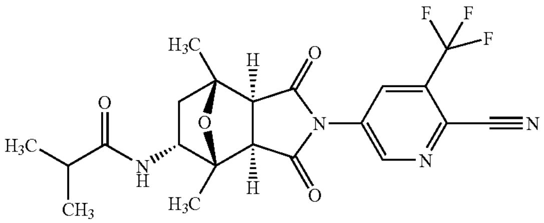 | Chiral, absolute stereochemistry not known | 3.12 LCMS $[M + H]^+$ = 450.12 | 812 |

TABLE 18-continued
| Ex. No | Structure | Compound Name/Comments | Retention Time Min./ Molecular Mass | Proc. of Ex. |
|---|---|---|---|---|
| 1013 | 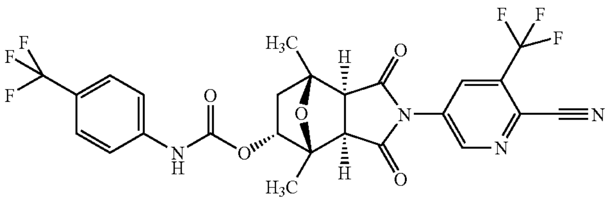 Chiral | Chiral, absolute stereochemistry not known | 4.04 LCMS | 810 |
| 1014 | 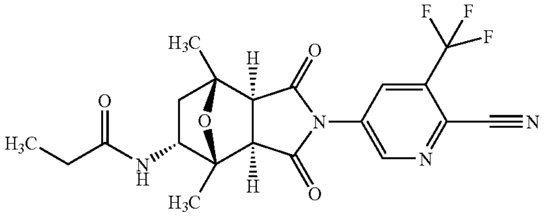 | Chiral, absolute stereochemistry not known | 3.02 LCMS $[M-H]^-$ = 436.1 | 814 |
| 1015 | 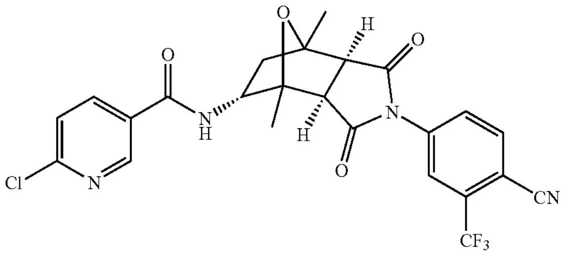 | Racemic | 3.32 LCMS $[M+H]^+$ = 519.05 | 812 |
| 1016 | 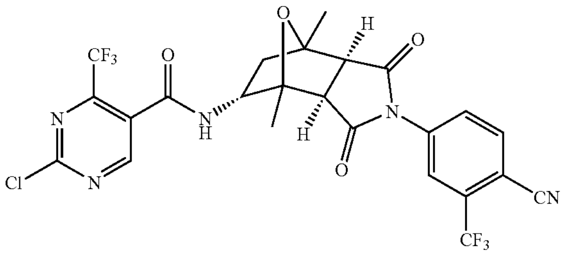 | Racemic | 3.56 LCMS $[M+H]^+$ = 587.97 | 812 |
| 1017 | 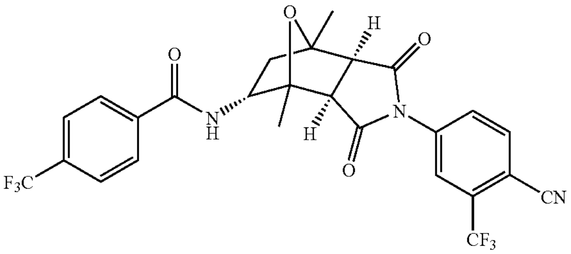 | Racemic | 3.65 LCMS $[M-H]^-$ = 552.11 | 812 |

TABLE 18-continued

| Ex. No | Structure | Compound Name/Comments | Retention Time Min./ Molecular Mass | Proc. of Ex. |
|---|---|---|---|---|
| 1018 | 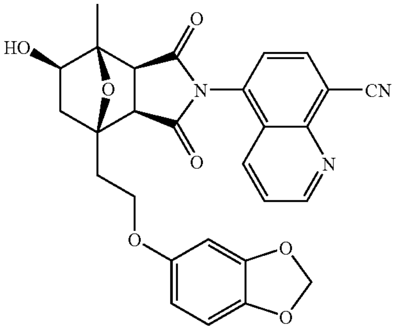 | [3aS-(3aα,4β,5β,7β,7aα)]-5-[7-[2-(1,3-Benzodioxol-5-yloxy)ethyl]octahydro-5-hydroxy-4-methyl-1,3-dioxo-4,7-epoxy-2H-isoindol-2-yl]-8-quinolinecarbonitrile | 2.86 LCMS $[M + H]^+$ = 514.16 | 485, 486, 487 & 488 |
| 1019 | 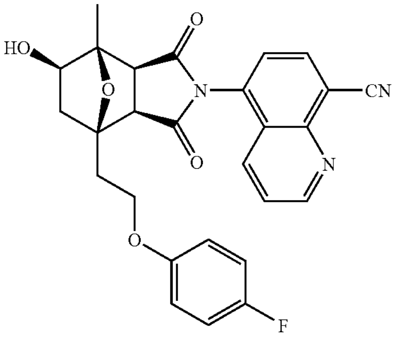 | [3aS-(3aα,4β,5β,7β,7aα)]-5-[7-[2-(4-Fluorophenoxy)ethyl]octahydro-5-hydroxy-4-methyl-1,3-dioxo-4,7-epoxy-2H-isoindol-2-yl]-8-quinolinecarbonitrile | 3.02 LCMS $[M + H]^+$ = 488.2 | 485, 486, 487 & 488 |
| 1020 | 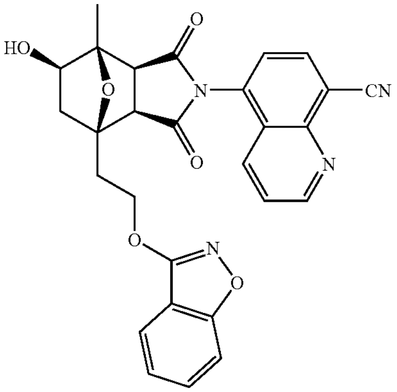 | [3aS-(3aα,4β,5β,7β,7aα)]-5-[7-[2-(1,2-Benzisoxazol-3-yloxy)ethyl]octahydro-5-hydroxy-4-methyl-1,3-dioxo-4,7-epoxy-2H-isoindol-2-yl]-8-quinolinecarbonitrile | 2.94 LCMS $[M + H]^+$ = 511.2 | 485, 486, 487 & 488 |

What we claimed is:

1. A compound of one of the following formulas:

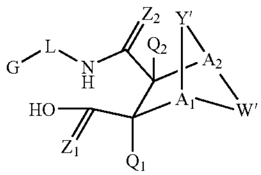

Ic or

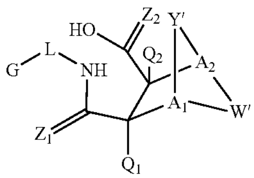

Id wherein the symbols have the following meanings:

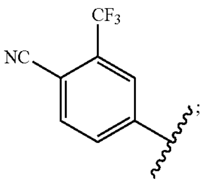

G is $Z_1$ is O;

$Z_2$ is O;

$A_1$ is $CCH_3$;

$A_2$ is $CCH_3$;

Y' is O;

W' is —CHR$^7$—CH$_2$— or —CH$_2$—C(═O)—;

R$^7$ is OH or NHSO$_2$(C$_{1-4}$alkyl);

Q$_1$ and Q$_2$ are each H; and

L is a bond;

or a pharmaceutically acceptable salt or stereoisomer thereof.

2. The compound according to claim 1, wherein:

W' is —CHR$^7$—CH$_2$— a pharmaceutically-acceptable salt or stereoisomer thereof.

3. The compound according to claim 2, wherein R$^7$ is NHSO$_2$(C$_{1-4}$alkyl), or a pharmaceutically-acceptable salt or stereoisomer thereof.

4. The compound according to claim 3, wherein R$^7$ is NHSO$_2$(ethyl), or a pharmaceutically-acceptable salt or stereoisomer thereof.

5. The compound according to claim 3 or stereoisomer thereof, wherein R$^7$ is NHSO$_2$(ethyl).

6. The compound according to claim 2 or a pharmaceutically-acceptable salt or stereoisomer thereof, wherein R$^7$ is OH.

7. The compound according to claim 2 or stereoisomer thereof, wherein R$^7$ is OH.

8. The compound according to claim 1 or a pharmaceutically-acceptable salt or stereoisomer thereof, wherein: W' is —CH$_2$—C(═O)—.

9. The compound according to claim 8 or stereoisomer thereof, having a formula:

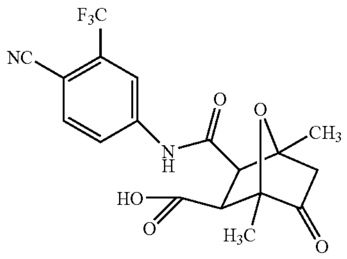

or

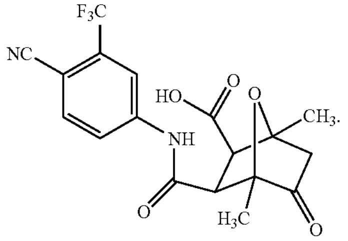

10. A pharmaceutical composition comprising one or more compounds according to claim 1, in a pharmaceutically-acceptable carrier or diluent.

11. A composition comprising one or more of the following compounds:

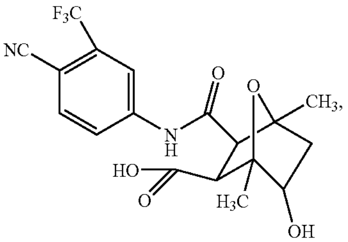

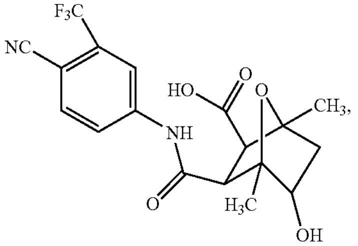

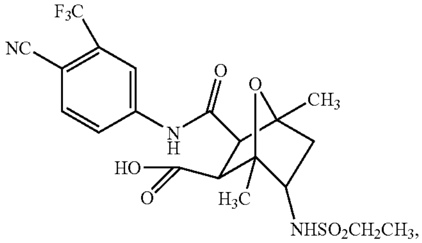

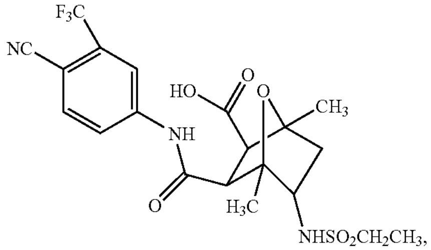

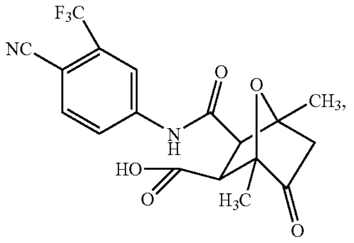

or

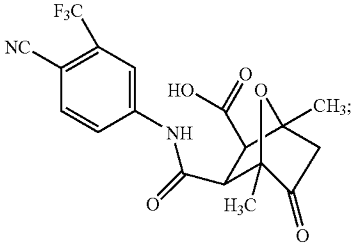

or stereoisomers thereof.

* * * * *

UNITED STATES PATENT AND TRADEMARK OFFICE

CERTIFICATE OF CORRECTION

PATENT NO. : 7,470,797 B2
APPLICATION NO. : 10/917031
DATED : December 30, 2008
INVENTOR(S) : Salvati et al.

It is certified that error appears in the above-identified patent and that said Letters Patent is hereby corrected as shown below:

In Column 659, Line 10,
"W' is $-CHR^7$—$CH_2-$;" should read
-- W' is $-CHR^7$—$CH_2-$; or --

Signed and Sealed this

Thirty-first Day of March, 2009

JOHN DOLL
*Acting Director of the United States Patent and Trademark Office*